US012467046B2

(12) United States Patent
Nonnenmacher et al.

(10) Patent No.: US 12,467,046 B2

(45) Date of Patent: Nov. 11, 2025

(54) REDIRECTION OF TROPISM OF AAV CAPSIDS

(71) Applicant: VOYAGER THERAPEUTICS, INC., Lexington, MA (US)

(72) Inventors: Mathieu E. Nonnenmacher, Boston, MA (US); Jinzhao Hou, Lexington, MA (US); Wei Wang, Lexington, MA (US)

(73) Assignee: VOYAGER THERAPEUTICS, INC., Lexington, MA (US)

(*) Notice: Subject to any disclaimer, the term of this patent is extended or adjusted under 35 U.S.C. 154(b) by 1259 days.

(21) Appl. No.: 17/282,479

(22) PCT Filed: Oct. 2, 2019

(86) PCT No.: PCT/US2019/054345

§ 371 (c)(1),
(2) Date: Apr. 2, 2021

(87) PCT Pub. No.: WO2020/072683

PCT Pub. Date: Apr. 9, 2020

(65) Prior Publication Data

US 2021/0380969 A1 Dec. 9, 2021

Related U.S. Application Data

(60) Provisional application No. 62/839,883, filed on Apr. 29, 2019, provisional application No. 62/740,310, filed on Oct. 2, 2018.

(51) Int. Cl.
*C12N 15/10* (2006.01)
*C07K 14/005* (2006.01)

(52) U.S. Cl.
CPC ........ *C12N 15/1037* (2013.01); *C07K 14/005* (2013.01); *C12N 2750/14122* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 9,409,953 | B2 | 8/2016 | Asokan et al. |
| 9,585,971 | B2 | 3/2017 | Deverman et al. |
| 9,644,205 | B2 | 5/2017 | Brunicardi et al. |
| 9,938,541 | B2 | 4/2018 | Nishie et al. |
| 10,081,659 | B2 | 9/2018 | Chiorini et al. |
| 10,265,417 | B2 | 4/2019 | Wilson et al. |
| 10,485,993 | B2 | 11/2019 | Goer et al. |
| 10,695,441 | B2 | 6/2020 | Wilson et al. |
| 10,973,928 | B2 | 4/2021 | Wilson et al. |
| 11,149,256 | B2 | 10/2021 | Gradinaru et al. |
| 11,459,558 | B2 | 10/2022 | Nakai et al. |
| 11,572,637 | B2 | 2/2023 | Nakai et al. |
| 11,821,009 | B2 | 11/2023 | Crystal et al. |
| 11,859,200 | B2 | 1/2024 | Nonnenmacher et al. |
| 11,981,967 | B2 | 5/2024 | McGovern et al. |
| 12,084,653 | B2 | 9/2024 | Nakai et al. |
| 12,084,654 | B2 | 9/2024 | Nakai et al. |
| 12,296,025 | B2 | 5/2025 | Nonnenmacher et al. |
| 2004/0132042 | A1 | 7/2004 | Frankard et al. |
| 2005/0148076 | A1 | 7/2005 | Allen |
| 2010/0186103 | A1 | 7/2010 | Gao et al. |
| 2013/0035472 | A1 | 2/2013 | Horlick et al. |
| 2013/0296409 | A1 | 11/2013 | Miller et al. |
| 2016/0333375 | A1 | 11/2016 | Chen |
| 2017/0166926 | A1 | 6/2017 | Deverman et al. |
| 2017/0204144 | A1 | 7/2017 | Deverman et al. |
| 2018/0230186 | A1 | 8/2018 | Deverman et al. |
| 2018/0265571 | A1 | 9/2018 | Esteves et al. |
| 2020/0165576 | A1 | 5/2020 | Gradinaru et al. |
| 2020/0237799 | A1 | 7/2020 | Sah et al. |
| 2020/0239912 | A1 | 7/2020 | Sah et al. |
| 2020/0316221 | A1 | 10/2020 | Gao et al. |
| 2021/0163985 | A1 | 6/2021 | Sah et al. |
| 2021/0207167 | A1 | 7/2021 | Hou et al. |
| 2021/0214749 | A1 | 7/2021 | Hou et al. |
| 2021/0230632 | A1 | 7/2021 | Sah et al. |
| 2021/0269825 | A1 | 9/2021 | Chamberlain |
| 2021/0277418 | A1 | 9/2021 | Sah et al. |
| 2021/0371470 | A1 | 12/2021 | Murlidharan et al. |
| 2021/0393713 | A1 | 12/2021 | Hordeaux et al. |
| 2022/0042044 | A1 | 2/2022 | Nonnenmacher et al. |
| 2022/0064675 | A1 | 3/2022 | McCoy et al. |
| 2022/0186256 | A1 | 6/2022 | Danos et al. |

(Continued)

FOREIGN PATENT DOCUMENTS

| | | |
|---|---|---|
| CN | 106032540 A | 10/2016 |
| CN | 106884014 A | 6/2017 |

(Continued)

OTHER PUBLICATIONS

Abeliovich, A. et al. "Gene Therapy for Parkinson's Disease Associated with GBA1 Mutations." Journal of Parkinson's Disease vol. 11,s2 (2021): S183-S188.

Adachi et al., "Drawing a high-resolution functional map of adeno-associated virus capsid by massively parallel sequencing," Nature Communications (2014) vol. 5, article 3075, 14 pages.

Adachi, M. et al. "A segment of the Mecp2 promoter is sufficient to drive expression in neurons." Human Molecular Genetics vol. 14,23 (2005): 3709-22.

Afione, S. et al. "Identification and mutagenesis of the adeno-associated virus 5 sialic acid binding region." Journal of Virology vol. 89,3 (2015): 1660-72.

(Continued)

*Primary Examiner* — Kaijiang Zhang
(74) *Attorney, Agent, or Firm* — K&L Gates LLP

(57) ABSTRACT

The disclosure relates to compositions, methods, and processes for the preparation, use, and/or formulation of adeno-associated virus capsid proteins, wherein the capsid proteins comprise targeting peptide inserts for enhanced tropism to a target tissue.

29 Claims, 85 Drawing Sheets

Specification includes a Sequence Listing.

(56) References Cited

U.S. PATENT DOCUMENTS

| | | | |
|---|---|---|---|
| 2023/0119163 | A1 | 4/2023 | Nakai et al. |
| 2023/0131352 | A1 | 4/2023 | Nonnenmacher et al. |
| 2023/0193315 | A1 | 6/2023 | Nakkai et al. |
| 2023/0203102 | A1 | 6/2023 | Nonnenmacher et al. |
| 2024/0141377 | A1 | 5/2024 | Nguyen et al. |
| 2024/0200097 | A1 | 6/2024 | Nonnenmacher et al. |
| 2024/0374756 | A1 | 11/2024 | Nonnenmacher et al. |
| 2024/0391988 | A1 | 11/2024 | Liu et al. |
| 2025/0001012 | A1 | 1/2025 | Nonnenmacher et al. |
| 2025/0011372 | A1 | 1/2025 | Nonnenmacher et al. |
| 2025/0034559 | A1 | 1/2025 | Nonnenmacher et al. |
| 2025/0049955 | A1 | 2/2025 | Nonnenmacher et al. |
| 2025/0161485 | A1 | 5/2025 | Nonnenmacher et al. |

FOREIGN PATENT DOCUMENTS

| | | | | |
|---|---|---|---|---|
| CN | 108330147 | A | 7/2018 | |
| WO | 2004096993 | A2 | 11/2004 | |
| WO | 2005/033321 | A2 | 4/2005 | |
| WO | 2010/138263 | A2 | 12/2010 | |
| WO | 2011/133890 | A1 | 10/2011 | |
| WO | 2012109570 | A1 | 8/2012 | |
| WO | 2012145601 | A2 | 10/2012 | |
| WO | 2015038958 | A1 | 3/2015 | |
| WO | 2015121501 | A1 | 8/2015 | |
| WO | 2015164757 | A1 | 10/2015 | |
| WO | 2016/065001 | A1 | 4/2016 | |
| WO | 2016073693 | A2 | 5/2016 | |
| WO | 2016081811 | A1 | 5/2016 | |
| WO | 2016126857 | A1 | 8/2016 | |
| WO | 2016164642 | A1 | 10/2016 | |
| WO | 2017058892 | A2 | 4/2017 | |
| WO | 2017100671 | A1 | 6/2017 | |
| WO | WO-2017143100 | A1 * | 8/2017 | ................ A61P 1/16 |
| WO | 2018022905 | A2 | 2/2018 | |
| WO | 2018035213 | A1 | 2/2018 | |
| WO | 2018119330 | A2 | 6/2018 | |
| WO | 2018226785 | A1 | 12/2018 | |
| WO | 2019006043 | A1 | 1/2019 | |
| WO | 2019006418 | A2 | 1/2019 | |
| WO | 2019/028306 | A2 | 2/2019 | |
| WO | 2019060454 | A2 | 3/2019 | |
| WO | 2019068854 | A1 | 4/2019 | |
| WO | 2019169132 | A1 | 9/2019 | |
| WO | 2019/222329 | A1 | 11/2019 | |
| WO | 2019/222441 | A1 | 11/2019 | |
| WO | 2019213668 | A1 | 11/2019 | |
| WO | 2019222444 | A2 | 11/2019 | |
| WO | 2020014471 | A1 | 1/2020 | |
| WO | 2020028751 | A2 | 2/2020 | |
| WO | 2020/068990 | A1 | 4/2020 | |
| WO | 2020/077165 | A1 | 4/2020 | |
| WO | 2020072683 | A1 | 4/2020 | |
| WO | 2020154324 | A1 | 7/2020 | |
| WO | 2020/160337 | A1 | 8/2020 | |
| WO | 2020160508 | A1 | 8/2020 | |
| WO | 2020191300 | A1 | 9/2020 | |
| WO | 2020193799 | A1 | 10/2020 | |
| WO | 2020205889 | A1 | 10/2020 | |
| WO | 2020206189 | A1 | 10/2020 | |
| WO | 2020210655 | A1 | 10/2020 | |
| WO | 2020219933 | A1 | 10/2020 | |
| WO | 2020219988 | A2 | 10/2020 | |
| WO | 2020/223280 | A1 | 11/2020 | |
| WO | 2021/025995 | A1 | 2/2021 | |
| WO | 2021073568 | A1 | 4/2021 | |
| WO | 2021113512 | A1 | 6/2021 | |
| WO | 2021202651 | A1 | 10/2021 | |
| WO | 2021216456 | A2 | 10/2021 | |
| WO | 2021222831 | A2 | 11/2021 | |
| WO | 2021226008 | A1 | 11/2021 | |
| WO | 2021230987 | A1 | 11/2021 | |
| WO | 2021242909 | A1 | 12/2021 | |
| WO | 2022040527 | A2 | 2/2022 | |
| WO | 2022076750 | A2 | 4/2022 | |
| WO | 2022187548 | A1 | 9/2022 | |
| WO | 2022/221400 | A2 | 10/2022 | |
| WO | 2022/221404 | A2 | 10/2022 | |
| WO | 2022/221420 | A2 | 10/2022 | |
| WO | 2022/221421 | A2 | 10/2022 | |
| WO | 2022/235702 | A1 | 11/2022 | |
| WO | 2023/004416 | A1 | 1/2023 | |
| WO | 2023/044306 | A1 | 3/2023 | |
| WO | 2023/049710 | A1 | 3/2023 | |
| WO | 2023044483 | A2 | 3/2023 | |
| WO | 2023/091934 | A1 | 5/2023 | |
| WO | 2023081648 | A1 | 5/2023 | |
| WO | 2023091948 | A1 | 5/2023 | |
| WO | 2023091949 | A2 | 5/2023 | |
| WO | 2023092002 | A2 | 5/2023 | |
| WO | 2023092004 | A1 | 5/2023 | |
| WO | 2023154693 | A1 | 8/2023 | |
| WO | 2023/168333 | A1 | 9/2023 | |
| WO | 2023/183582 | A2 | 9/2023 | |
| WO | 2023/183583 | A2 | 9/2023 | |
| WO | 2023201207 | A1 | 10/2023 | |
| WO | 2023/215546 | A2 | 11/2023 | |
| WO | 2023/225508 | A2 | 11/2023 | |
| WO | 2023220695 | A2 | 11/2023 | |
| WO | 2023/244919 | A1 | 12/2023 | |
| WO | 2023/244920 | A2 | 12/2023 | |
| WO | 2023235791 | A1 | 12/2023 | |
| WO | 2023240236 | A1 | 12/2023 | |
| WO | 2023250388 | A1 | 12/2023 | |
| WO | 2024006741 | A1 | 1/2024 | |
| WO | 2024011112 | A1 | 1/2024 | |
| WO | 2024030976 | A2 | 2/2024 | |
| WO | 2024059739 | A1 | 3/2024 | |
| WO | 2024/086628 | A2 | 4/2024 | |
| WO | 2024086747 | A1 | 4/2024 | |
| WO | 2024/092164 | A1 | 5/2024 | |
| WO | 2024100633 | A1 | 5/2024 | |
| WO | 2024191778 | A1 | 9/2024 | |
| WO | 2024226761 | A2 | 10/2024 | |
| WO | 2024226790 | A1 | 10/2024 | |
| WO | 2024228943 | A1 | 11/2024 | |
| WO | 2024229125 | A2 | 11/2024 | |
| WO | 2024229161 | A1 | 11/2024 | |
| WO | 2024229163 | A1 | 11/2024 | |
| WO | 2024229164 | A2 | 11/2024 | |
| WO | 2024229167 | A1 | 11/2024 | |
| WO | 2024229173 | A2 | 11/2024 | |
| WO | 2024229389 | A1 | 11/2024 | |
| WO | 2024229425 | A1 | 11/2024 | |
| WO | 2024238579 | A2 | 11/2024 | |
| WO | 2024238684 | A1 | 11/2024 | |
| WO | 2025038430 | A1 | 2/2025 | |
| WO | 2025038795 | A1 | 2/2025 | |
| WO | 2025038796 | A1 | 2/2025 | |
| WO | 2025038800 | A1 | 2/2025 | |
| WO | 2025038802 | A1 | 2/2025 | |
| WO | 2025038805 | A1 | 2/2025 | |

OTHER PUBLICATIONS

Albright et al. "Modulation of sialic acid dependence influences the central nervous system transduction profile of adeno-associated viruses," Journal of Virology, 2019, vol. 93, Issue 11, pp. 1-15.

Almeida, C F et al. "Promising AAV.U7snRNAs vectors targeting DMPK improve DM1 hallmarks in patient-derived cell lines." Frontiers in Cell and Developmental Biology vol. 11 1181040. Jun. 15, 2023.

Anonymous: "capsid-associated protein VP80 [Spodoptera littoralis nucleopolyhedrovirus]—Protein—NCBI", (Feb. 15, 2013), pp. 1-1, Retrieved from the Internet: URL:https://www.ncbi.nlm.nih.gov/protein/AGE89944 [retrieved on Mar. 6, 2023].

Anonymous: "toxin-antitoxin system YwqK family antitoxin [*Campylobacter* sp. CCUG 57310]—Protein—NCBI", (Jun. 7, 2020), Retrieved from the Internet: URL:https://www.ncbi.nlm.nih.gov/protein/WP_173030534 [retrieved on Mar. 7, 2023].

Bryant et al. "Deep diversification of an AAV capsid protein by machine learning," Nature Biotechnology, 2021, vol. 39, pp. 691-696.

(56) References Cited

OTHER PUBLICATIONS

Buning, H. & Srivastava, A. "Capsid Modifications for Targeting and Improving the Efficacy of AAV Vectors." Molecular Therapy—Methods & Clinical Development vol. 12 (2019): 248-265.
Child, M.A. et al. "High-resolution Quantitative Analysis of Multiple AAV Capsids in Rodent and Primate Models Using Multiplexed Reporter Protein Tagging Platform." Voyager Therapeutics. ASGCT 27th Annual Meeting 2024, May 7-11, 2024, Baltimore, MD, USA.
Choi et al., "AAV Hybrid Serotypes: Improved Vectors for Gene Delivery," Current Gene Therapy (2005) vol. 5, No. 3, pp. 209-210.
Davidsson et al. "A systematic capsid evolution approach performed in vivo for the design of AAV vectors with tailored properties and tropism," PNAS, 2019, vol. 116, No. 52, pp. 27053-27062.
Dimattia et al., "Structural Insight into the Unique Properties of Adeno-Associated Virus Serotype 9," J Virol (2012) vol. 86, No. 12, pp. 6947-6958.
Fischell, J.M. and Fishman, P.S. "A Multifaceted Approach to Optimizing AAV Delivery to the Brain for the Treatment of Neurodegenerative Diseases." Frontiers in Neuroscience vol. 15, article 747726 (2021).
Gao, G. et al. "Clades of Adeno-associated viruses are widely disseminated in human tissues," Journal of Virology vol. 78,12 (2004): 6381-8.
Gessler et al., "Intravenous infusion of AAV for widespread gene delivery to the nervous system," Methods Mol. Biol., 2019, vol. 1950, pp. 143-163.
Goertsen et al. "AAV capsid variants with brain-wide transgene expression and decreased liver targeting after intravenous delivery in mouse and marmoset," Nature Neuroscience, 2022, vol. 25, pp. 106-115.
Govindasamy, L. et al. "Structural insights into adeno-associated virus serotype 5." Journal of Virology vol. 87,20 (2013): 11187-99.
Grannan, M.D. et al. "Intravenous Delivery of AAV Gene Therapy for the Treatment of SOD1-ALS Provides Broad SOD1 Lowering in NHP." Molecular Therapy, vol. 32 No. 4S1 (2024): 769-770, Abstract 1647.
Grannan, M.D. et al. "Intravenous Delivery of AAV Gene Therapy for the Treatment of SOD1-ALS Provides Broad SOD1 Lowering in NHP." Voyager Therapeutics. ASGCT 27th Annual Meeting 2024, May 7-11, 2024, Baltimore, MD, USA.
Gray, S.J. et al. "Optimizing promoters for recombinant adeno-associated virus-mediated gene expression in the peripheral and central nervous system using self-complementary vectors." Human Gene Therapy vol. 22,9 (2011): 1143-53.
Hanlon et al. "Selection of an efficient AAV vector for robust CNS transgene expression," Molecular Therapy: Methods & Clinical Development, 2019, vol. 15, pp. 320-332.
Hida, K. et al. "Sites in the AAV5 capsid tolerant to deletions and tandem duplications." Archives of Biochemistry and Biophysics vol. 496, 1 (2010): 1-8.
Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Voyager Therapeutics. ASGCT 27th Annual Meeting 2024, May 7-11, 2024, Baltimore, MD, USA.
Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Molecular Therapy, vol. 32 No. 4S1 (2024): 475, Abstract 975.
Hoffman, B. et al. "Identification of a cell surface receptor utilized by an engineered BBB-penetrant capsid family with enhanced brain tropism in non-human primates and mice." Human Gene Therapy vol. 33: A2-A212 (Dec. 2022), A32, Abstract P024.
Hoffman, B.A. et al. "Discovery and Characterization of Novel Cross-Species BBB-Penetrant Capsids." Voyager Therapeutics. ASGCT 26th Annual Meeting 2023, May 16-20, 2023, Los Angeles, CA, USA.
Hoffman, B.A. et al. "Identification of a Cell Surface Receptor Utilized by an Engineered BBB-Penetrant Capsid Family with Enhanced Brain Tropism in Non-Human Primates and Mice." Voyager Therapeutics. ESGCT—29th Congress, Oct. 11-14, 2022, Edinburgh, Scotland, UK.
Ibe, M.et al. "Role of strong anchor residues in the effective binding of 10-mer and 11-mer peptides to HLA-A*2402 molecules," Immunogenetics vol. 44, 4, (1996): 233-241.
International Search Report and Written Opinion in International Patent Application No. PCT/US2022/079060 dated Mar. 6, 2023.
International Search Report and Written Opinion in International Patent Application No. PCT/US2022/079963 dated May 9, 2023.
International Search Report and Written Opinion in International Patent Application No. PCT/US2022/080035 dated Apr. 3, 2023.
International Search Report and Written Opinion in International Patent Application No. PCT/US2022/080040 dated Mar. 1, 2023.
International Search Report and Written Opinion in International Patent Application No. PCT/US2023/062101 dated Jul. 24, 2023.
International Search Report and Written Opinion in International Patent Application No. PCT/US2023/067749 dated Sep. 29, 2023.
International Search Report and Written Opinion in International Patent Application No. PCT/US2024/041668 dated Dec. 3, 2024.
International Search Report and Written Opinion in International Patent Application No. PCT/US2024/042395 dated Dec. 2, 2024.
International Search Report and Written Opinion in International Patent Application No. PCT/US2024/042397 dated Dec. 3, 2024.
International Search Report and Written Opinion in International Patent Application No. PCT/US2024/042405 dated Dec. 2, 2024.
International Search Report and Written Opinion in International Patent Application No. PCT/US2024/042407 dated Dec. 2, 2024.
International Search Report and Written Opinion in International Patent Application No. PCT/US2024/042411 dated Dec. 2, 2024.
International Search Report and Written Opinion of International Patent Application No. PCT/US2022/079964 dated Jun. 9, 2023.
Ishan, S. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.
Ising, C. et al. "AAV-mediated expression of anti-tau scFvs decreases tau accumulation in a mouse model of tauopathy." The Journal of Experimental Medicine vol. 214, 5 (2017): 1227-1238.
Jose, A. et al. "High-Resolution Structural Characterization of a New Adeno-associated Virus Serotype 5 Antibody Epitope toward Engineering Antibody-Resistant Recombinant Gene Delivery Vectors." Journal of Virology vol. 93,1 e01394-18. Dec. 10, 2018.
Khalid, A. et al. "Evaluation of Cross-species Expression Across Four Species and Cellular Tropism of VCAP-102, an Engineered Blood-brain Barrier-penetrating AAV Derived Capsid from TRACER Platform Screens." Voyager Therapeutics. ASGCT 27th Annual Meeting 2024, May 7-11, 2024, Baltimore, MD, USA.
Khalid, H. et al. "Evaluation of Cross-Species Expression Across Four Species and Cellular Tropism of VCAP-102, an Engineered Blood-Brain Barrier-Penetrating AAV." Molecular Therapy, vol. 32 No. 4S1 (2024): 685, Abstract 1452.
Kotchey, N. M. et al. "A potential role of distinctively delayed blood clearance of recombinant adeno-associated virus serotype 9 in robust cardiac transduction." Molecular Therapy : The Journal of the American Society of Gene Therapy vol. 19,6 (2011): 1079-89.
Kotterman et al. "4D-C102, a novel muscle-tropic AAV variant demonstrates superior gene delivery in cardiac and skeletal muscle tissues versus wild-type AAV in human cells and non-human primates."
Kotterman et al., "Directed evolution of AAV targeting lung epithelia using aerosol delivery identifies 4D-A101, a variant demonstrating robust gene delivery in non-human primates" Abstract 1336, 31 pages.
Kotterman et al., "Directed evolution of AAV targeting lung epithelia using aerosol delivery identifies 4D-A101, a variant demonstrating robust gene delivery in non-human primates."
Lin, J. et al. "An Evolved AAV Variant with Enhanced Brain and Spinal Cord Tropism and Translation across Primate Species," Molecular Therapy vol. 31 No. 4S1, Apr. 2023, Abstract 1393.

(56) References Cited

OTHER PUBLICATIONS

Lin, J. et al. "An Evolved AAV Variant with Enhanced Brain and Spinal Cord Tropism and Translation across Primate Species." Voyager Therapeutics. ASGCT Annual Meeting 2023, May 16-May 20, 2023, Los Angeles, CA, USA, (#1393).
Liu, W. et al. "AAV Gene Delivery of the Anti-Tau Antibody PHF1 Reduces Brain Tau Pathology in P301L Mice," Molecular Therapy vol. 23, Supplement 1 (2015): S237, Abstract 596.
Liu, W. et al. "Efficacy of a vectorized anti-tau antibody using systemic dosing of a blood brain barrier penetrant AAV capsid in mouse models of tauopathies." Alzheimer's & Dementia vol. 17, No. S9 (2021): e053341.
Marsic et al. "High-accuracy biodistribution analysis of adeno-associated virus variants by double barcode sequencing," Molecular Therapy—Methods & Clinical Development (2015) vol. 2, 15041.
Marsic, D. et al. "Vector design Tour de Force: integrating combinatorial and rational approaches to derive novel adeno-associated virus variants." Molecular Therapy : The Journal of the American Society of Gene Therapy vol. 22,11 (2014): 1900-9.
Maura, D. et al. "Discovery of TRACER AAV Capsids Escaping Pre-Existing Neutralizing Antibodies." Molecular Therapy, vol. 32 No. 4S1 (2024): 475, Abstract 973.
Maura, D. et al. "Discovery of TRACER AAV Capsids Escaping Pre-existing Neutralizing Antibodies." Voyager Therapeutics. ASGCT 27th Annual Meeting 2024, May 7-11, 2024, Baltimore, MD, USA.
Maura, D. et al. "Stepwise Evolution of the AAV5-Derived Capsid VCAP-100 Identifies Novel Variants with Improved CNS Transduction and Liver Detargeting Following Systemic Injection," Molecular Therapy vol. 31 No. 4S1, Apr. 2023, Abstract 464.
Maura, D. et al. "Stepwise evolution of the AAV5-derived capsid VCAP-100 identifies novel variants with improved CNS transduction and liver detargeting following systemic injection." Voyager Therapeutics. ASGCT Annual Meeting 2023, May 16-May 20, 2023, Los Angeles, CA, USA, (#464).
Medici, G. et al., "Expression of a Secretable, Cell-Penetrating CDKL5 Protein Enhances the Efficacy of AAV Vector-Mediated Gene Therapy for CDKL5 Deficiency Disorder," Dec. 17, 2021 (Dec. 17, 2021), p. 1-25, Retrieved from the Internet: URL:https://www.biorxiv.org/content/10.1101/2021.07.26.453746v2.full.pdf.
Moyer, T. "Continued directed evolution of VCAP-101 and VCAP-102 identifies second generation capsids with increased brain tropism in non-human primates and mice (#119)." Voyager Therapeutics. ASGCT 27th Annual Meeting. ASGCT 27th Annual Meeting 2024, May 7-11, 2024, Baltimore, MD, USA. Breaking Barriers to the CNS via AAV Capsid Engineering, Wednesday May 8, 2024.
Moyer, T. "Directed Evolution of AAV9 Peptide Display Libraries Identifies a Family of Cross-Species Variants With Enhanced Brain Tropism in Non-Human Primates and Mice Following Systemic Administration." Voyager Therapeutics. SGCT 2022—Novel AAV Capsids for the Brain, Eye, and Kidney, May 19, 2022.
Moyer, T. "Directed Evolution of an AAV9 Library Identifies a Capsid Variant with Enhanced Brain Tropism and Liver Detargeting in Non-Human Primates and Mice Following Systemic Administration." Voyager Therapeutics. AAV Engineering for CNS Targeting, Thursday, May 18, 2023, Abstract #105.
Moyer, T. et al. "Continued Directed Evolution of VCAP-101 and VCAP-102 Identifies Second Generation Capsid Variants with Increased Brain Tropism and in Non-Human Primates and Mice." Molecular Therapy, vol. 32 No. 4S1 (2024): 64, Abstract 119.
Moyer, T. et al. "Directed Evolution of AAV9 Peptide Display Libraries Identifies a Family of Cross-Species Variants with Enhanced Brain Tropism in Non-Human Primates and Mice Following Systemic Administration." Molecular Therapy, vol. 30 No. 4S1 (2022): 556, Abstract 1198.
Moyer, T. et al. "Directed Evolution of an AAV9 Library Identifies a Capsid Variant with Enhanced Brain Tropism and Liver De-Targeting in Non-Human Primates and Mice Following Systemic Administration." Molecular Therapy, vol. 31 No. 4S1 (2023): 57, Abstract 105.
Moyer, T.C. et al. "Highly conserved brain vascular receptor ALPL mediates transport of engineered viral vectors across the blood-brain barrier," bioRxiv 2024.03.12.584703.
Nonnenmacher et al., "Dose-response evaluation of 9P801, an engineered AAV capsid with high BBB penetration and CNS transduction in non-human primates," ESGCT 29th Annual Congress In collaboration with BSGCT Edinburgh, UK Oct. 11-14, 2022 Abstract P015.Human Gene Therapy. Dec. 2022.
Nonnenmacher, M. "Iterative Evolution of Cross-Species BBB-Penetrant Capsids." Voyager Therapeutics. In Vivo Gene Therapy & Genome Editing Summit, Oct. 30-Nov. 2, 2023, Miami, FL, USA, talk was on Oct. 31, 2023.
Nonnenmacher, M. "TracerTM capsid discovery platform." Voyager Therapeutics. In Vivo Gene Therapy & Genome Editing Summit, Oct. 31-Nov. 2, 2022, Miami, FL, USA.
Nonnenmacher, M. et al. "Directed Evolution of an AAV5 Capsid Library Identifies a Variant with Enhanced Transduction in Non-Human Primate and Rodent Brain Following Systemic Administration," Molecular Therapy vol. 30 No. 4S1, Apr. 2022, Abstract 129.
Nonnenmacher, M. et al. "Directed Evolution of an AAV5 Capsid Library Identifies a Variant with Enhanced Transduction in Non-Human Primate and Rodent Brain Following Systemic Administration." Voyager Therapeutics. ASGCT 2022 Annual Meeting, May 16-19, 2022, Washington, DC, USA (#129).
Ogden et al. "Comprehensive AAV capsid fitness landscape reveals a viral gene and enables machine-guided design," Science, 2019, 366(6469), pp. 1139-1143.
Puglisi, M. et al. "Targeting astrocytes by non-invasive viral vectors and probing the influence of age and inducibile expression of the reprogramming factors in vivo." Presented at Cell State Conversions, Cold Spring Harbor Laboratory, New York, USA, Oct. 10-14, 2023.
Qian, R. et al. "Directed Evolution of AAV Serotype 5 for Increased Hepatocyte Transduction and Retained Low Humoral Seroreactivity." Molecular Therapy. Methods & Clinical Development vol. 20 122-132. Oct. 20, 2020.
Qiao, C. et al. "Liver-specific microRNA-122 target sequences incorporated in AAV vectors efficiently inhibits transgene expression in the liver." Gene Therapy vol. 18,4 (2011): 403-10.
Rees, H. A. and Liu, D. R. "Base editing: precision chemistry on the genome and transcriptome of living cells." Nature Reviews. Genetics vol. 19,12 (2018): 770-788.
Ren, X. et al. "Establishment of a Predictive Transcytosis Model to Recapitulate Capsid-Receptor Interaction and Phenotype of BBB Penetrant AAV Variants." Molecular Therapy, vol. 32 No. 4S1 (2024): 476, Abstract 976.
Shah, I. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.
Stanton, A. C. et al. "Systemic administration of novel engineered AAV capsids facilitates enhanced transgene expression in the macaque CNS." Med vol. 4, 1 (2023): 31-50.e8. Epub: Nov. 22, 2022.
Stoica, L. and Sena-Esteves, M. "Adeno Associated Viral Vector Delivered RNAi for Gene Therapy of SOD1 Amyotrophic Lateral Sclerosis." Frontiers in Molecular Neuroscience vol. 9 article 56 (2016).
Voyager Therapeutics, "Intravenous Delivery of Novel AAV Capsids", Oct. 20, 2017, Retrieved from the Internet: URL:https://www.voyagertherapeutics.com/wp-content/uploads/2017/10/ESGCT_slides.pdf [retrieved on Oct. 9, 2019].
Walters, R. W. et al. "Structure of adeno-associated virus serotype 5." Journal of Virology vol. 78,7 (2004): 3361-71.
Wang et al. "Adeno-associated virus vector as a platform for gene therapy delivery," Nat Rev Drug Discov., 2019, vol. 18, 5, pp. 358-378.
Yan et al., "Two-Amino Acid Molecular Switch in an Epithelial Morphogen That Regulates Binding to Two Distinct Receptors," Science (2000) vol. 290, pp. 523-527.
Yin, Z. et al., "Research Advances on Increasing the Transduction Efficiency of Recombinant Adeno-associated Viral Vectors." Biotechnology Bulletin vol. 31, 9 (2015): 49-59.

(56) References Cited

OTHER PUBLICATIONS

Adachi et al. "A new recombinant adeno-associated virus (AAV)-based random peptide display library system: Infection-defective AAV1.9-3 as a novel detargeted platform for vector evolution" Gene Therapy and Regulation (2010) vol. 5, pp. 31-55.
Challis et al. "Systemic AAV vectors for widespread and targeted gene delivery in rodents" Nature Protocols (2019) vol. 14, pp. 379-414.
Chen et al. "Targeting the Rodent Peripheral Nervous System Efficiently and with Greater Specificity through Intravenous Delivery of AAV Capsids Evolved by Multiplexed-CREATE" Molecular Therapy (2020) vol. 28, No. 4S1, pp. 252-253, Abstract 571.
Deverman et al. "Cre-dependent selection yields AAV variants for widespread gene transfer to the adult brain" Nat Biotechnol. (2016) vol. 34, No. 2, pp. 204-209.
Flytzanis et al. "Broad gene expression throughout the mouse and marmoset brain after intravenous delivery of engineered AAV capsids" bioRxiv Preprint Server (2020) Doi: https://doi.org/10.1101/2020.06.16.152975, 21 pages.
Goertsen et al. "Transduction Profiles of Engineered Adeno-Associated Viral Capsids in Mouse and Marmoset" Molecular Therapy (2020) vol. 28, No. 4S1, pp. 269-270, Abstract 609.
Huang et al. "Cell Type-Specific TRAnscriptionDependent Directed Evolution (TRADE) Identifies Novel AAV Capsids Capable of Enhanced Neuronal Transduction in Mice and Non-Human Primates" Molecular Therapy (2019) vol. 27, No. 4S1, pp. 24-25, Abstract 44.
Huang et al. "Delivering genes across the blood-brain barrier: LY6A, a novel cellular receptor for AAV-PHP.B capsids" PLOS One (2019) vol. 14, No. 11, e0225206, pp. 1-17.
International Search Report and Written Opinion for International Application No. PCT/US2021/025061 dated Sep. 20, 2021.
International Search Report and Written Opinion for International Application No. PCT/US2021/025072 dated Jul. 26, 2021.
Invitation to Pay Additional Fees and Partial Search Report from International Application No. PCT/US2021/025061 dated Jul. 27, 2021.
Kotterman et al. "Engineering adeno-associated viruses for clinical gene therapy" Nature Reviews Genetics (2014) vol. 15, pp. 445-451.
Kumar et al. "Evolution and Investigation of Engineered AAV Capsids Exhibiting Enhanced Transduction of the Central Nervous System with or without Murine Strain Specificity" Molecular Therapy (2020) vol. 28, No. 4S1, pp. 11-12, Abstract 22.
Kumar et al. "Multiplexed Cre-dependent selection yields systemic AAVs for targeting distinct brain cell types" Nature Methods (2020) vol. 17, No. 5, pp. 541-550.
Li et al. "A Novel AAV Capsid with a Potential of Crossing NHP Blood-Brain Barrier" Molecular Therapy (2020) vol. 28, No. 4S1, p. 253, Abstract 572.
Nonnenmacher et al. "Rapid evolution of blood-brain barrier-penetrating MV capsids by RNA-driven biopanning" Molecular Therapy (2021) vol. 20, pp. 366-378.
Nonnenmacher et al. "RNA-Driven Evolution of AAV Capsid Libraries Identifies Variants with High Transduction Efficiency in Non-Human Primate Central Nervous System" Molecular Therapy (2021) vol. 29, No. 4S1, pp. 25-26, Abstract 51.
Nonnenmacher et al. "Targeted In Vivo Biopanning of AAV Capsid Libraries Using Cell Type-Specific RNA Expression" Molecular Therapy (2019) vol. 27, No. 4S1, p. 27, Abstract 48.
Nonnenmacher, "RNA-driven Evolution of AAV Capsid Libraries Identifies Variants with High Transduction Efficiency in Non-Human Primate Central Nervous System," American Society of Cell + Gene Therapy Annual Meeting 2021, 17 pages.
Eike Christoph Keinle: "Secrets to finding the ideal mate: New insights into parametes that govern successful Adeno-associated virus (AAV) vector evolution", Dissertation, University Heidelberg, Jan. 1, 2014 (Jan. 1, 2014), pp. 1-194.
Zhen Song et al: "98. Strong Alpha Cell Preference of the AAV Strains That Best Transduce Human Pancreatic slets in Vitro", Molecular Therapy, vol. 25, No. 5S1, May 1, 2017 (May 1, 2017), p. 47.
Min Chen et al: "Efficient Gene Delivery and Expression in Pancreas and Pancreatic Tumors by Capsid-Optimized AAV8 Vectors", Human Gene Therapy Methods, vol. 28, No. 1, Feb. 1, 2017 Feb. 1, (2017), pp. 49-59.
Katja Pekrun et al: 82. Screening of Barcoded Capsid Shuffled AAV Libraries Results in the Selection of Capsids with Enhances Transduction Efficiency for Human Islets, Molecular Therapy, vol. 26, No. 5S1, May 1, 2018 (May 1, 2018), p. 41.
International Search Report & Written Opinion issued Jan. 24, 2020 in co-pending application No. PCT/US2019/054345, entitled Redirection of Tropism of AAV Capsids.
Bremel, R. et al. "Bioinformatic Processes for Determination of Peptide Binding", GS_PROT_ALERT:WO20130401421 Mar. 2013 (Mar. 21, 2013), retrieved from WO2013040142, Database Accession No. GS_PROT_ALERT:WO2013040142.974324.
Choudhury, S. et al. "Peptide Grafting Yields Novel AAV Vectors Capable of Enhanced Neuronal Transduction in Adult Mouse Brain." Molecular Therapy vol. 22, Supplement 1 (2014): S109-S110, Abstract 285.
International Search Report and Written Opinion in International Patent Application No. PCT/US2023/069146 dated Nov. 9, 2023.
International Search Report and Written Opinion in International Patent Application No. PCT/US2023/069621 dated Oct. 16, 2023.
Zhang, X. et al. "Blood-brain barrier shuttle peptides enhance AAV transduction in the brain after systemic administration." Biomaterials vol. 176 (2018): 71-83.

* cited by examiner

GloSpliceF4 ccgtgccaagagtgacctcc
GloSpliceF6 gtgccaagagtgacctcctg

FIG. 6
Promoter Activity in TRACER Vectors
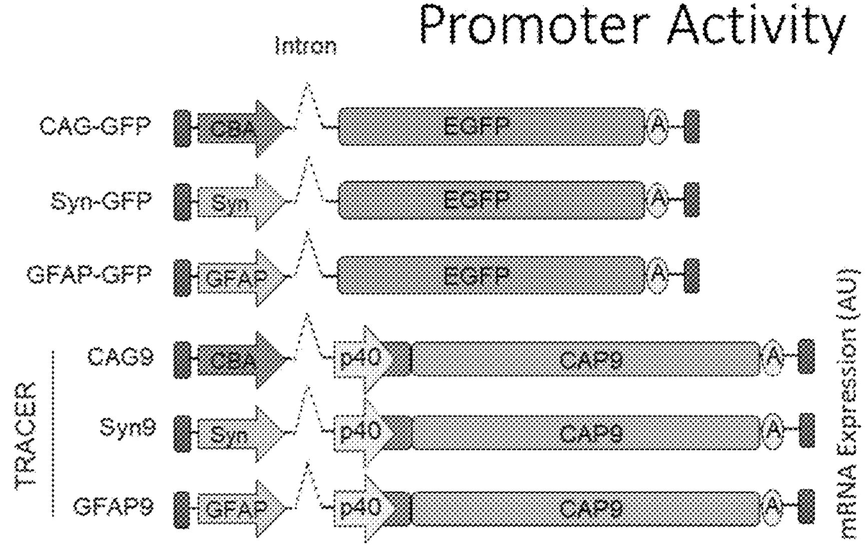
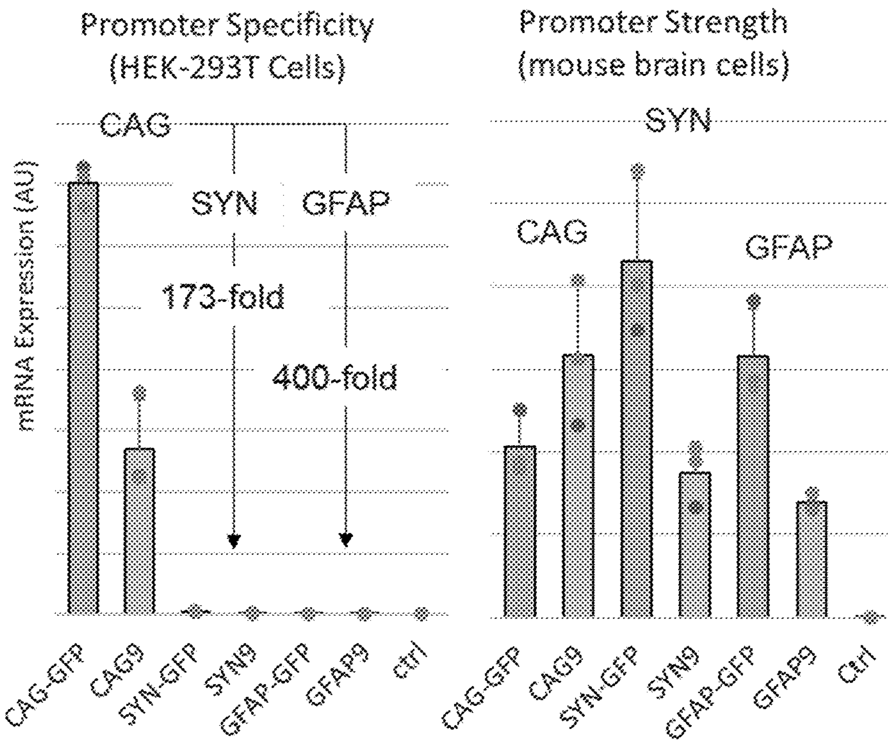
| | EGFP AVG | EGFP SD | CAP9 AVG | CAP9 SD | EGFP fold | CAP9 fold |
|---|---|---|---|---|---|---|
| CAG | 7.0E-03 | 3.3E-04 | 2.7E-03 | 8.0E-04 | 1.0E+00 | 1.0E+00 |
| SYN | 5.2E-05 | 5.7E-06 | 1.6E-05 | 4.4E-06 | 1.3E+02 | 1.7E+02 |
| GFAP | 4.1E-06 | 1.9E-06 | 6.9E-06 | 1.6E-06 | 1.7E+03 | 3.9E+02 |
| Ctrl | 9.2E-08 | 1.5E-07 | 8.3E-09 | 1.2E-09 | N/A | 3.2E+05 |

Tropism Redirection of AAV by Cell type-specific Expression of RNA (TRACER)

- Platform requirements:
  - Transduction-restricted
  - Cell type-restricted
  - Applicable in NHP
- NGS analysis of RNA-derived peptide pool (variant enrichment)
  - Transduction potential
  - Cell type specificity

```
                                        BsrGI                  polyA
AAV5     : GCCACCAACAACCAGAGCTCT/GTAC/Atcgattgttaatcaataaa
AAV6     : GTGGCAGTCAATCTCCAGAGT/GTAC/Atcgattgttaatcaataaa
AAV-DJ8  : TCTACCAACCTCCAGCAAGGT/GTAC/Atcgattgttaatcaataaa
AAV9     : GTGGCCACAAACCACCAGAGT/GTAC/Atcgattgttaatcaataaa
```

AAV9 wt
...CACCAGAGTGCCCAA//GCACAGGCGCAGACC...
...H Q S A Q //A Q A Q T...

CAAGTGGCCACAAACCACCAGAGTgcccaaNNKNNKNNKNNKNNKNNKNNKGCACAGGCGCAGACCGGCTG original
Q V A T N H Q S A Q X X X X X X X A Q A Q T G...
CAgGTcGCtACcAAtCAtCAatccGCaCAgNNKNNKNNKNNKNNKNNKNNKGCtCAaGCaCAaACaGGa Codon mutant CAAGTGGCCACAAACCACCAGAGT
CAgGTcGCtACcAAtCAtCAa
Recovery primer NNK machine mix:
P0 virus NNK machine mix:
P1 virus

| Study VE0-142-2017-Ms | | | | | | | |
|---|---|---|---|---|---|---|---|
| Peptide Libraries | Titer (VG/ml) | Endotoxin | Mouse group | Number of animals | route | volume/ mouse (ul) | **VG/mouse** |
| NEUR-P3-300 | 4.45E+13* | <0.5 | SYN9P3 | 3 | IV | 50 | **2.00E+12** |
| ASTR-P3-300 | 4.85E+13* | <0.5 | GFAP9P3 | 3 | IV | 50 | **2.00E+12** |

FIG. 31A

| NEU-LIB | | Brain1 | Brain2 | Brain3 | **mean of brain** |
|---|---|---|---|---|---|
| wtAAV9 - NNM codon | AGTGCCCAAGCACAGGCGCAGACC | 14,012 | 9,198 | 9,473 | **10894.3** |
| wtAAV9 - NNK codon | AGTGCTCAGGCACAGGCGCAGACC | 10,407 | 8,116 | 7,768 | **8763.7** |
| PHP.N - NNM codon | GACGGAACACTCGCAGTCCCATTCAAA | **58,553** | **203,200** | **95,929** | **119227.3** |
| PHP.N - NNK codon | GATGGGACTTTGGCGGTGCCTTTTAAG | **4,827** | **13,936** | **7,507** | **8756.7** |
| PHP.B - NNM codon | GCACAAACACTCGCAGTCCCATTCAAA | 15,971 | 6,970 | 32,396 | **18445.7** |
| PHP.B - NNK codon | GCCCAAACTTTGGCGGTGCCTTTTAAG | 8,002 | 2,259 | 14,051 | **8104.0** |

| NEU-LIB | | Virus Stock | **Brain/Virus** | **Brain/Virus (depth adjusted)** | Brain/Virus average of two codons | **Brain/virus vs. wtAAV9** |
|---|---|---|---|---|---|---|
| wtAAV9 - NNM codon | AGTGCCCAAGCACAGGCGCAGACC | 86423 | **0.1** | **0.11** | | |
| wtAAV9 - NNK codon | AGTGCTCAGGCACAGGCGCAGACC | 67395 | **0.1** | **0.12** | 0.116 | |
| PHP.N - NNM codon | GACGGAACACTCGCAGTCCCATTCAAA | 36898 | **3.2** | **2.9** | | |
| PHP.N - NNK codon | GATGGGACTTTGGCGGTGCCTTTTAAG | 2802 | **3.1** | **2.8** | 2.889 | **24.8** |
| PHP.B - NNM codon | GCACAAACACTCGCAGTCCCATTCAAA | 17813 | **1.0** | **0.9** | | |
| PHP.B - NNK codon | GCCCAAACTTTGGCGGTGCCTTTTAAG | 8206 | **1.0** | **0.9** | 0.920 | **7.9** |

FIG. 32A

Neuron synthesis library-NGS-P3

| pepSeq | Brain1 | Brain2 | Brain3 | mean of brain | virus stock | Brain/ Virus | Br1/vi rus | Br2/vir us | Br3/vi rus |
|---|---|---|---|---|---|---|---|---|---|
| DGTSSYYDS_1 | 61531 | 48295 | 24838 | 44888 | 9427 | 4.76 | 6.53 | 5.12 | 2.63 |
| AQPEGSARW_1 | 106764 | 59048 | 72175 | 79329 | 16862 | 4.70 | 6.33 | 3.50 | 4.28 |
| DGTSSYYDS_2 | 84784 | 69506 | 32611 | 62300 | 13416 | 4.64 | 6.32 | 5.18 | 2.43 |
| AQPEGSARW_2 | 129187 | 72820 | 85144 | 95717 | 21279 | 4.50 | 6.07 | 3.42 | 4.00 |
| DGTASYYDS_1 | 90508 | 82418 | 24663 | 65863 | 15547 | 4.24 | 5.82 | 5.30 | 1.59 |
| DGTASYYDS_2 | 98081 | 96707 | 30517 | 75102 | 18088 | 4.15 | 5.42 | 5.35 | 1.69 |
| AQWPTSYDA_1 | 206147 | 5013 | 61696 | 90952 | 22049 | 4.12 | 9.35 | 0.23 | 2.80 |
| DGTADKPFR_1 | 114140 | 219057 | 192943 | 175380 | 44512 | 3.94 | 2.56 | 4.92 | 4.33 |
| AQWPTSYDA_2 | 231396 | 5433 | 71311 | 102713 | 26944 | 3.81 | 8.59 | 0.20 | 2.65 |
| DGSSSYYDA_2 | 62708 | 56941 | 26771 | 48807 | 13289 | 3.67 | 4.72 | 4.28 | 2.01 |
| DGSSSYYDA_1 | 19195 | 16367 | 8397 | 14653 | 4105 | 3.57 | 4.68 | 3.99 | 2.05 |
| DGTADKPFR_2 | 111033 | 217899 | 191385 | 173439 | 49321 | 3.52 | 2.25 | 4.42 | 3.88 |
| DGTLSQPFR_1 | 23175 | 99366 | 115373 | 79305 | 23204 | 3.42 | 1.00 | 4.28 | 4.97 |
| AQFPTNYDS_2 | 141935 | 3078 | 47247 | 64087 | 18860 | 3.40 | 7.53 | 0.16 | 2.51 |
| DGTAIHLSS_2 | 150492 | 89416 | 65976 | 101961 | 30112 | 3.39 | 5.00 | 2.97 | 2.19 |
| DGTAIHLSS_1 | 91896 | 59070 | 42010 | 64325 | 19081 | 3.37 | 4.82 | 3.10 | 2.20 |
| DGTLSQPFR_2 | 30944 | 145129 | 167147 | 114407 | 34444 | 3.32 | 0.90 | 4.21 | 4.85 |
| DGTGQVTGW_1 | 104223 | 66451 | 46346 | 72340 | 21828 | 3.31 | 4.77 | 3.04 | 2.12 |
| AQFPTNYDS_1 | 110378 | 2154 | 33870 | 48801 | 14732 | 3.31 | 7.49 | 0.15 | 2.30 |
| DGTGNVTGW_1 | 98253 | 66566 | 50174 | 71664 | 21878 | 3.28 | 4.49 | 3.04 | 2.29 |
| DGTMDKPFR_1 | 31800 | 126945 | 90386 | 83044 | 25950 | 3.20 | 1.23 | 4.89 | 3.48 |
| DGTLAVPFK_2 | 60273 | 208417 | 99023 | 122571 | 38435 | 3.19 | 1.57 | 5.42 | 2.58 |
| DGTMDKPFR_2 | 44872 | 160645 | 113192 | 106236 | 33416 | 3.18 | 1.34 | 4.81 | 3.39 |
| DGTLAVPFK_1 | 5079 | 14812 | 8024 | 9305 | 2983 | 3.12 | 1.70 | 4.97 | 2.69 |
| DGTGNTHGW_1 | 133298 | 88815 | 71161 | 97758 | 31834 | 3.07 | 4.19 | 2.79 | 2.24 |
| DGTVIHLSS_2 | 118419 | 57659 | 37350 | 71143 | 23256 | 3.06 | 5.09 | 2.48 | 1.61 |
| DGTGTTVGW_1 | 84623 | 70422 | 50121 | 68389 | 22452 | 3.05 | 3.77 | 3.14 | 2.23 |

FIG. 33

Astrocyte synthesis library-P3

| GFAP-LIB | | Brain1 | Brain2 | Liver1 | Liver2 | mean of brain | mean of liver | Virus Stock | Brain/Virus | Brain/Liver |
|---|---|---|---|---|---|---|---|---|---|---|
| wtAAV9 - NNM codon | AGT**GCCCAA**GCACAGGCGCAGACC | **12,798** | **9,282** | 530,908 | 637,731 | 11,040 | 584,320 | 83,439 | **0.132** | 0.019 |
| wtAAV9 - NNK codon | AGT**GCTCAG**GCACAGGCGCAGACC | **11,667** | **8,417** | 389,373 | 452,574 | 10,042 | 420,974 | 66,967 | **0.150** | 0.024 |
| **PHP.N - NNM codon** | **GACGGAACACTCGCAGTCCCATTCAAA** | 6,756 | 90,000 | 5,078 | 12,075 | 48,378 | 8,577 | 36,976 | **1.308** | 5.641 |
| **PHP.N - NNK codon** | **GATGGGACTTTGGCGGTGCCTTTTAAG** | 457 | 5,815 | 207 | 778 | 3,136 | 493 | 2,593 | **1.209** | 6.368 |
| PHP.B - NNM codon | GCACAAACACTCGCAGTCCCATTCAAA | 3,701 | 43,200 | 4,331 | 23,858 | 23,451 | 14,095 | 19,812 | **1.184** | 1.664 |
| PHP.B - NNK codon | GCCCAAACTTTGGCGGTGCCTTTTAAG | 1,452 | 19,963 | 1,264 | 11,801 | 10,708 | 6,533 | 8,982 | **1.192** | 1.639 |

| AST mouse 1 | | Brain mouse 1 | Liver mouse 1 | virus stock | Brain/virus mouse 1 | Brain/liver mouse 1 | Liver/virus mouse 1 | Brain vs. AAV9 | Liver vs. AAV9 |
|---|---|---|---|---|---|---|---|---|---|
| wtAAV9 - NNM codon | AGT**GCCCAA**GCACAGGCGCAGACC | 12,798 | 530,908 | 83,439 | 0.15 | 0.02 | 6.36 | **1.00** | 1.00 |
| wtAAV9 - NNK codon | AGT**GCTCAG**GCACAGGCGCAGACC | 11,667 | 389,373 | 66,967 | 0.17 | 0.03 | 5.81 | **1.00** | 1.00 |
| PHP.N - NNM codon | GACGGAACACTCGCAGTCCCATTCAAA | 6,756 | 5,078 | 36,976 | **0.18** | 1.33 | 0.14 | **1.59** | **0.02** |
| PHP.N - NNK codon | GATGGGACTTTGGCGGTGCCTTTTAAG | 457 | 207 | 2,593 | **0.18** | 2.21 | 0.08 | **1.53** | **0.01** |
| PHP.B - NNM codon | GCACAAACACTCGCAGTCCCATTCAAA | 3,701 | 4,331 | 19,812 | **0.19** | 0.85 | 0.22 | **1.62** | 0.03 |
| PHP.B - NNK codon | GCCCAAACTTTGGCGGTGCCTTTTAAG | 1,452 | 1,264 | 8,982 | **0.16** | 1.15 | 0.14 | **1.41** | 0.02 |

| GFAP mouse 2 | | Brain mouse 2 | Liver mouse 2 | virus stock | Brain/virus mouse 2 | Brain/liver mouse 2 | Liver/virus mouse 2 | Brain vs. AAV9 | Liver vs. AAV9 |
|---|---|---|---|---|---|---|---|---|---|
| wtAAV9 - NNM codon | AGT**GCCCAA**GCACAGGCGCAGACC | 9,282 | 637,731 | 83,439 | 0.11 | 0.01 | 7.64 | **1.00** | 1.00 |
| wtAAV9 - NNK codon | AGT**GCTCAG**GCACAGGCGCAGACC | 8,417 | 452,574 | 66,967 | 0.13 | 0.02 | 6.76 | **1.00** | 1.00 |
| PHP.N - NNM codon | GACGGAACACTCGCAGTCCCATTCAAA | 90,000 | 12,075 | 36,976 | **2.43** | 7.45 | 0.33 | **21.17** | **0.05** |
| PHP.N - NNK codon | GATGGGACTTTGGCGGTGCCTTTTAAG | 5,815 | 778 | 2,593 | **2.24** | 7.47 | 0.30 | **19.50** | **0.04** |
| PHP.B - NNM codon | GCACAAACACTCGCAGTCCCATTCAAA | 43,200 | 23,858 | 19,812 | **2.18** | 1.81 | 1.20 | **18.96** | 0.17 |
| PHP.B - NNK codon | GCCCAAACTTTGGCGGTGCCTTTTAAG | 19,963 | 11,801 | 8,982 | **2.22** | 1.69 | 1.31 | **19.33** | 0.19 |

FIG. 37A

Peptide Phylogeny

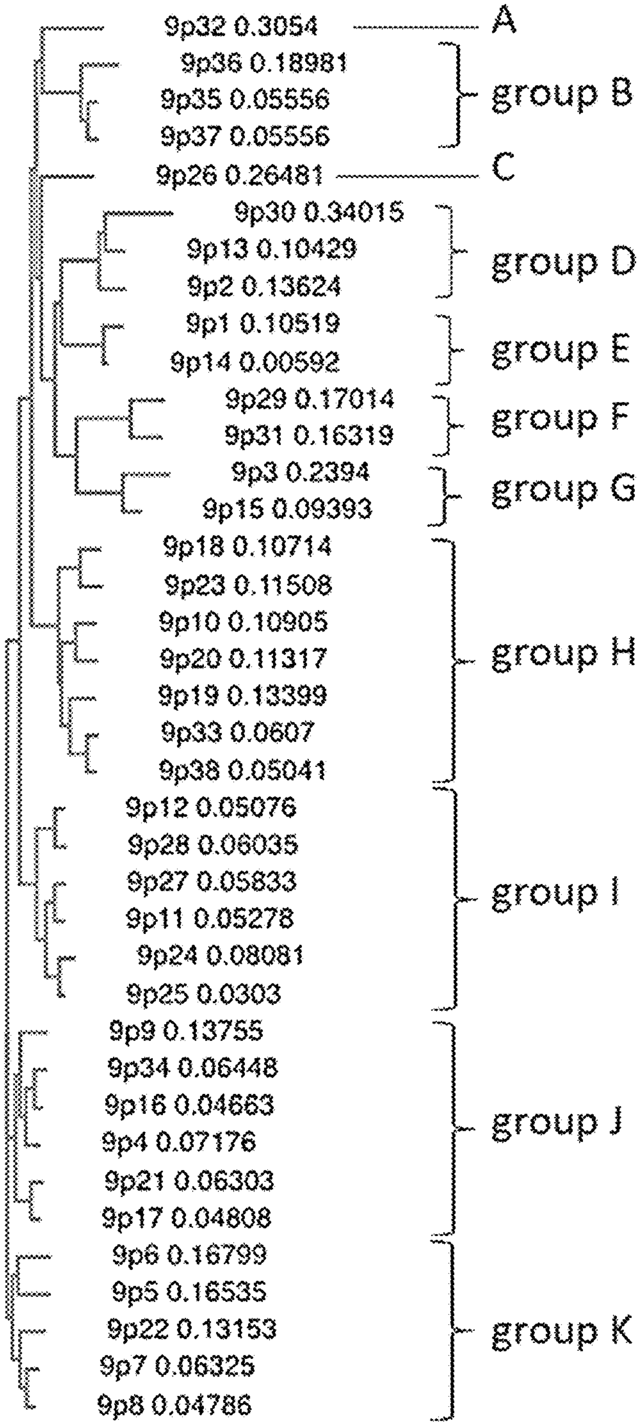

Top Variants from P3 enrichment

| Group | variant | peptide |
|---|---|---|
| A | 9p32 | DGTAIHLSS |
| B | 9p35 | DGTSSYYDS |
| | 9p36 | DGSSSYYDA |
| | 9p37 | DGTASYYDS |
| C | 9p26 | DGTTTYGAR |
| D | 9p2 | AQNGNPGRW |
| | 9p13 | AQGENPGRW |
| | 9p30 | AQPEGSARW |
| E | 9p1 | AQGSWNPFA |
| | 9p14 | AQGTWNPPA |
| F | 9p29 | AQFPTNYDS |
| | 9p31 | AQWPTSYDA |
| G | 9p3 | AQTTEKPWL |
| | 9p15 | AQTTDRPFL |
| H | 9p10 | DGTRTTTGW |
| | 9p18 | DGTGGIKGW |
| | 9p19 | DGTGNTRGW |
| | 9p20 | DGTRTRTGW |
| | 9p23 | DGTNGLKGW |
| | 9p33 | DGTGQVTGW |
| | 9p38 | DGTGNVTGW |
| I | 9p11 | DGTTFTPPR |
| | 9p12 | DGTTYVPPR |
| | 9p24 | DGTSFTPPR |
| | 9p25 | DGTSFTPPR |
| | 9p27 | DGTTWTPPR |
| | 9p28 | DGTSYVPPR |
| J | 9p4 | DGTADRPFR |
| | 9p9 | DGTMDRPFK |
| | 9p16 | DGTADKPFR |
| | 9p17 | DGTAERPFR |
| | 9p21 | DGTIERPFR |
| | 9p34 | DGTMDRPFR |
| K | 9p5 | DGTISQPFK |
| | 9p6 | DGTLAAPFK |
| | 9p7 | DGTLQQPFR |
| | 9p8 | DGTLSQPFR |
| | 9p22 | DGTLNNPFR |

TRIM/NNK Peptide Cloning

FIG. 41

```
Illumina Adapter-TGGCCACAAACCACCAGAGT                                    Illumina adapter-CAGCCGGTCTGCGCCTGT
          CAAGTGGCCACAAACCACCAGAGTGCCCAANNKNNKNNKNNKNNKNNKNNKGCACAGGCGCAGACCGGCTG
          Q  V  A  T  N  H  Q  S  A  Q  X  X  X  X  X  X  X  A  Q  A  Q  T  G
```

| peptide diversity statistics from sample plasmidNNK.v2 | |
|---|---|
| Forward strand left primer trim: CTATGGACAAGTGGCCACAAACCACCAGAGTGCCCAA | |
| Forward strand right primer trim: GCACAGGCGCAG | |
| | |
| stats | Forward |
| input_reads: | 81,363,292 |
| withLeftPrimer_reads: | 28674037 (35.24%) |
| withRightPrimer_reads: | 19914669 (69.45%) |
| sequence_species: | 12,031,556 |
| sequence_reads | 19,914,669 |
| species_wCount1: | 7,296,999 |
| | |
| peptide_species: | 11,670,656 |
| peptide_reads: | 19,914,669 |
| species_wCount1: | 6,865,289 |
| peptideCount1SpeciesR: | 59 |
| peptideCount1ReadsR: | 34 |
| species_wStopCodon: | 2,493,961 |
| peptideStopSpeciesR: | 21 |
| reads_wStopCodon: | 4,135,553 |
| peptideStopReadsR: | 21 |

- 30 million bacterial transformants
- 81 million sequence reads
- 12 million sequence variants

NNK Library Data

BEST AVAILABLE IMAGE

FIG. 48B
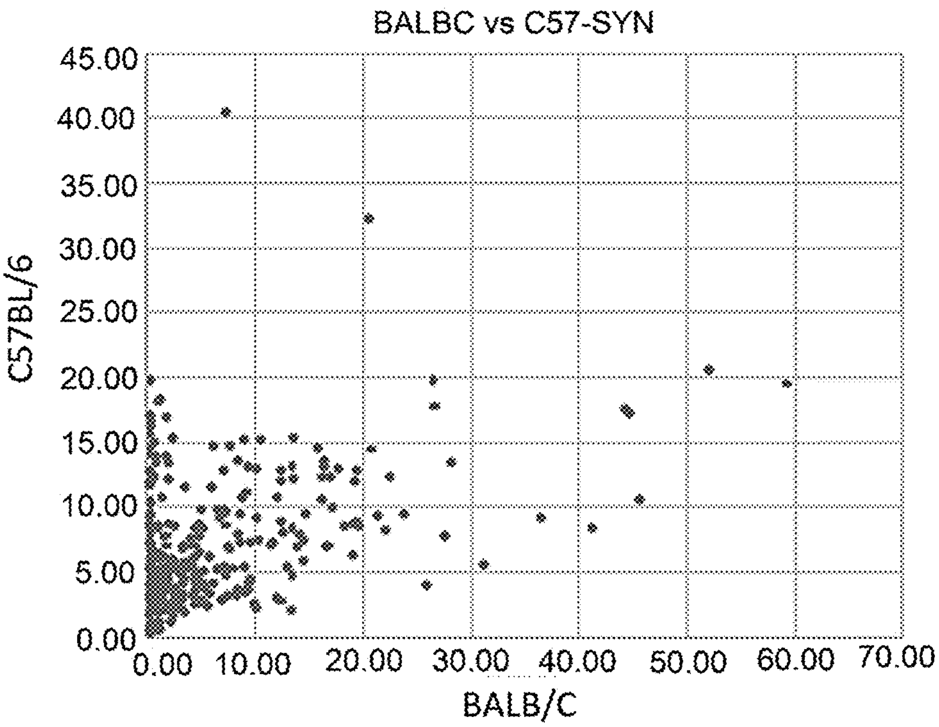
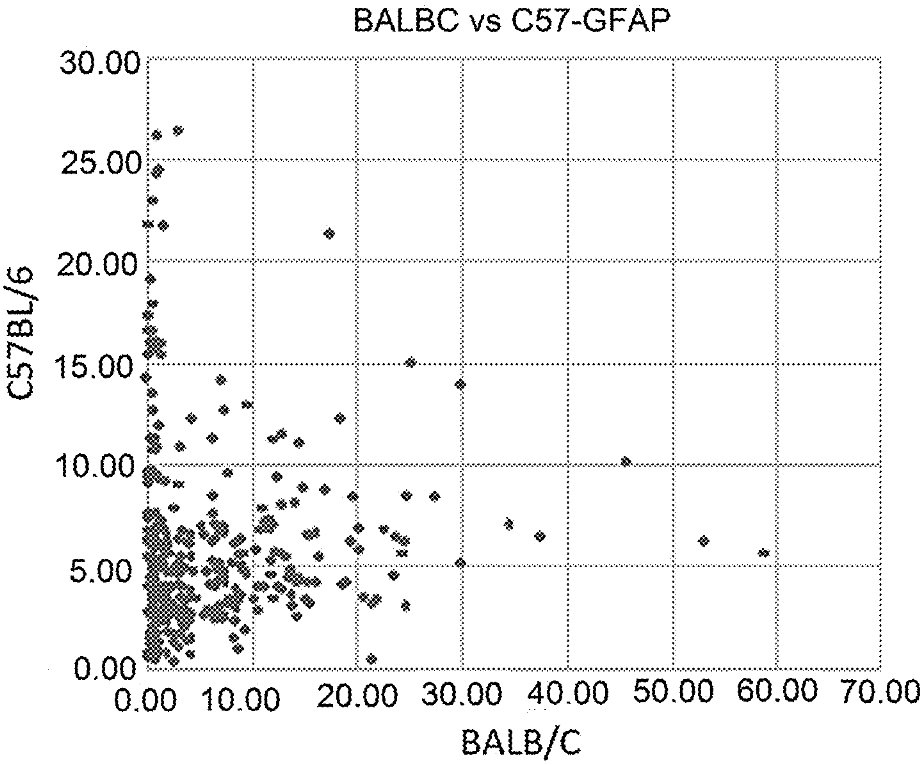

| Variant | Translate |
|---|---|
| 9p8 | TNHQSDGTLSQPFRAQAQTG |
| 9p12 | TNHQSDGTTYVPPRAQAQTG |
| 9p16 | TNHQSDGTADKPFRAQAQTG |
| 9p23 | TNHQSDGTNGLKGWAQAQTG |
| 9p30 | TNHQSAQPEGSARWAQAQTG |
| 9p31 | TNHQSAQWPTSYDAAQAQTG |
| 9p35 | TNHQSDGTSSYYDSAQAQTG |
| PHPN | TNHQSDGTLAVPFKAQAQTG |
| PHPB | TNHQSAQTLAVPFKAQAQTG |
| AAV9 | TNHQSAQ-------AQAQTG |

FIG. 49C
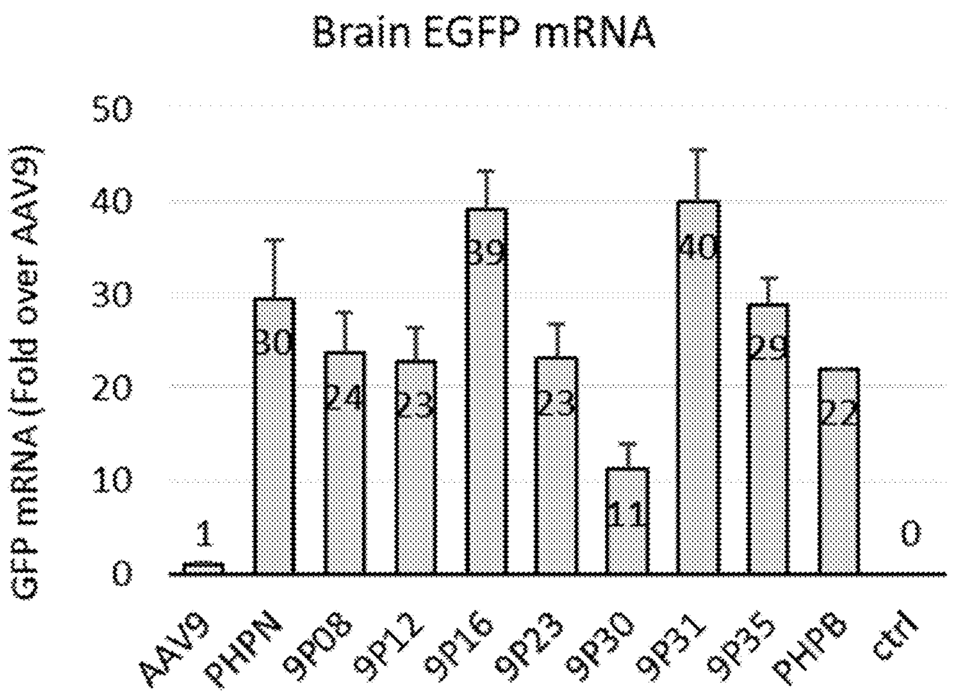
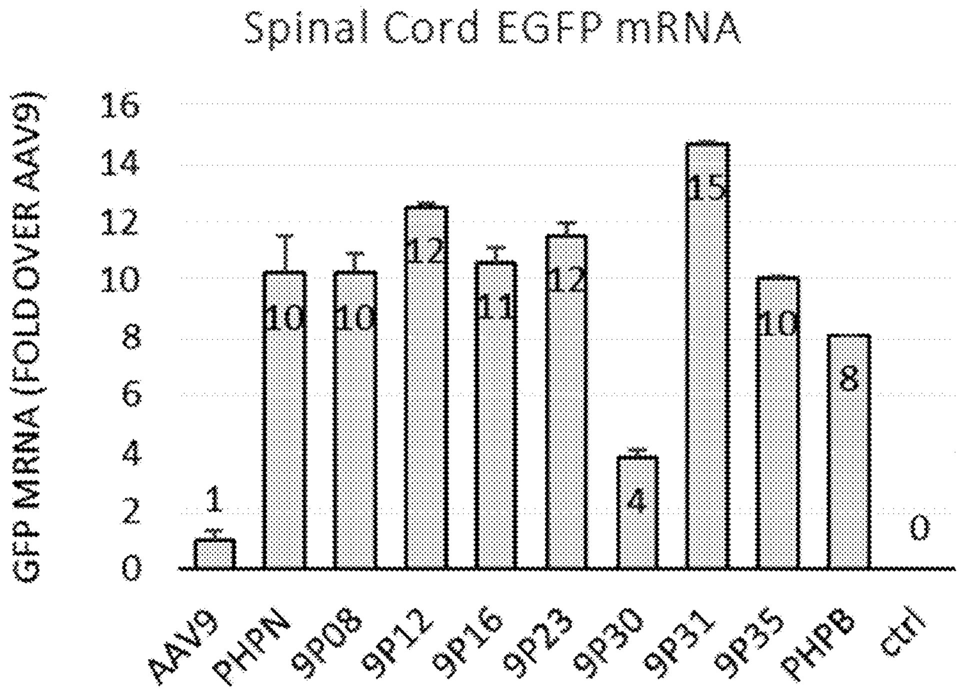

Individual Capsid test – Whole Brain Transduction

Individual Capsid test – Whole Brain Transduction

Individual Capsid test – Cerebellum Transduction

REDIRECTION OF TROPISM OF AAV CAPSIDS

CROSS REFERENCE TO RELATED APPLICATIONS

This application is a 35 U.S.C. § 371 U.S. National Stage Entry of International Application No. PCT/US2019/054345, filed Oct. 2, 2019 and entitled REDIRECTION OF TROPISM OF AAV CAPSIDS; which claims priority to U.S. Provisional Patent Application No. 62/740,310, filed Oct. 2, 2018, entitled AAV CAPSID LIBRARIES AND TISSUE TARGETING PEPTIDE INSERTS; U.S. Provisional Patent Application No. 62/839,883, filed Apr. 29, 2019 entitled REDIRECTION OF TROPISM OF AAV CAPSIDS; the contents of which are each incorporated herein by reference in their entirety.

REFERENCE TO SEQUENCE LISTING

The present application is being filed along with a Sequence Listing in electronic format. The Sequence Listing is provided as a file entitled 20571060US371_SL.txt, created on Apr. 2, 2021, which is 401,885 bytes in size. The information in the electronic format of the sequence listing is incorporated herein by reference in its entirety.

FIELD OF THE DISCLOSURE

The disclosure relates to compositions, methods, and processes for the preparation, use, and/or formulation of adeno-associated virus capsid proteins, wherein the capsid proteins comprise targeting peptide inserts for enhanced tropism to a target tissue.

BACKGROUND

Gene delivery to the adult central nervous system (CNS) remains a major challenge in gene therapy, and engineered AAV capsids with improved brain tropism represent an attractive solution.

Adeno-associated virus (AAV)-derived vectors are promising tools for clinical gene transfer because of their non-pathogenic nature, their low immunogenic profile, low rate of integration into the host genome and long-term transgene expression in non-dividing cells. However, the transduction efficiency of AAV natural variants in certain organs is too low for clinical applications, and capsid neutralization by pre-existing neutralizing antibodies may prevent treatment of a large proportion of patients. For these reasons, major efforts have been devoted to obtaining novel capsid variants with enhanced properties. Of many approaches tested so far, the most significant advances have resulted from directed evolution of AAV capsids using in vitro or in vivo selection of capsid variants created by capsid sequence randomization using either error-prone PCR, shuffling of various parent serotypes or insertion of fully randomized short peptides at defined positions.

In order to perform directed evolution of AAV capsids, the sequence encoding the viral capsid is itself flanked by inverted terminal repeats (ITR) so it can be packaged into its own capsid shell. Following infection of cultured cells or animals by the mixed population of capsids, the DNA encoding capsids variants that have successfully homed into the tissue of interest is recovered by PCR for further rounds of selection. In this approach, all viral DNA species present in a given tissue are recovered, with no discrimination for specific cell types or for vectors able to perform complete transduction (cell surface binding, endocytosis, trafficking, nuclear import, uncoating, second-strand synthesis, transcription). For example, in the case of highly complex tissues containing multiple cell types, such as the central nervous system (CNS), it would be highly preferable to apply a more stringent selective pressure aimed at recovering capsid variants capable of transducing neuron and/or astrocyte rather than microglia or blood vessel endothelial cells.

Attempts at improving the CNS tropism of AAV capsids upon systemic administration have been met with limited success.

Two previous approaches have been used to address this issue. The first strategy used co-infection of cultured cells (Grimm et al., 2008) or in situ animal tissue (Lisowski et al., 2014) with adenovirus, in order to trigger exponential replication of infectious AAV DNA. Another successful approach involved the use of cell-specific CRE transgenic mice (Deverman et al., 2016) allowing viral DNA recombination specifically in astrocytes, followed by recovery of CRE-recombined capsid variants. Both approaches proved successful, allowing the isolation of several capsid variants with enhanced transduction of target cell populations.

This finding suggested that cell type-specific library selection could improve the outcome of directed evolution. However, the transgenic CRE system used by Deverman et al. is not tractable in other animal species and AAV variants selected by directed evolution in mouse tissue do not show similar properties in large animals. Therefore, it would be necessary to perform the entire directed evolution process directly in non-human primates to increase the probability of translatability in human subjects. None of the previously described transduction-specific approaches are amenable to large animal studies because: 1) many tissues of interest (e.g. CNS) are not readily accessible to adenovirus co-infection, 2) the specific Ad tropism itself would bias the library distribution, and 3) large animals are typically not amenable to transgenesis and cannot be genetically engineered to express CRE recombinase in defined cell types.

To address this problem, we have developed a broadly-applicable functional AAV capsid library screening platform for cell type-specific biopanning in non-transgenic animals. In the TRACER (Tropism Redirection of AAV by Cell type-specific Expression of RNA) platform system, the capsid gene is placed under the control of a cell type-specific promoter to drive capsid mRNA expression in the absence of helper virus co-infection. This RNA-driven screen increases the selective pressure in favor of capsid variants which transduce a specific cell type.

The TRACER platform allows generation of AAV capsid libraries whereby specific recovery and subcloning of capsid mRNA expressed in transduced cells is achieved with no need for transgenic animals or helper virus co-infection. Since mRNA transcription is a hallmark of full transduction, these methods will allow identification of fully infectious AAV capsid mutants. In addition to its higher stringency, this method allows identification of capsids with high tropism for particular cell types using libraries designed to express CAP mRNA under the control of any cell-specific promoter such as, but not limited to, synapsin-1 promoter (neurons), GFAP promoter (astrocytes), TBG promoter (liver), CAMK promoter (skeletal muscle), MYH6 promoter (cardiomyocytes).

SUMMARY OF THE DISCLOSURE

The present disclosure provides compositions and methods for the engineering and/or redirecting the tropism of AAV capsids. Also provided herein are peptides which may be inserted into AAV capsid sequences to increase the tropism of the capsid for a particular tissue. In one aspect, the peptides may be used to target the capsids to brain or regions of the brain or the spinal cord.

The present disclosure presents methods for generating one or more variant AAV capsid polypeptides. In certain embodiments, the variant AAV capsid polypeptides exhibit at least one of improved transduction or increased cell or tissue specificity, relative to a parental AAV capsid polypeptide. In certain embodiments, the method includes: (a) generating a library of variant AAV capsid polypeptides, wherein said library includes (i) a plurality of capsid polypeptides having a region of randomized sequence of 2, 3, 4, 5, 6, 7, 8, or 9 consecutive amino acids, or (ii) a plurality of capsid polypeptides from more than one parental AAV capsid polypeptide; (b) generating an AAV vector library by cloning the capsid polypeptides of libraries (a)(i) or (a)(ii) into AAV vectors, wherein the AAV vectors include a first promoter and a second promoter, wherein said second promoter drives capsid mRNA expression in the absence of helper virus co-infection.

In certain embodiments, the first promoter is AAV2 P40. In certain embodiments, the second promoter is a ubiquitous promoter. In certain embodiments, the first promoter is AAV2 P40 and the second promoter is a ubiquitous promoter.

In certain embodiments, the first promoter is AAV2 P40. In certain embodiments, the second promoter is a cell-type-specific promoter. In certain embodiments, the first promoter is AAV2 P40 and the second promoter is a cell-type-specific promoter.

In certain embodiments, the promoter is selected from any promoter listed in Table 3. In certain embodiments, the ubiquitous or cell-specific promoter allows the expression of RNA encoding the capsid polypeptides.

In certain embodiments, the method includes recovery of the RNA encoding the capsid polypeptides. In certain embodiments, the method includes determining the sequence of the capsid polypeptides. In certain embodiments, the capsid polypeptides recovered exhibit increased target cell transduction or target cell specificity (tropism) as compared to a parental capsid polypeptide.

In certain embodiments, the target cell is a neuronal cell, a neural stem cell, an astrocyte, an oligodendrocyte, a microglia cell, a retinal cell, a tumor cell, a hematopoietic stem cell, an insulin producing beta cell, a lung epithelium cell, an endothelial cell, a liver cell, a skeletal muscle cell, a muscle stem cell, a muscle satellite cell, or a cardiac muscle cell.

In certain embodiments, the AAV vectors comprise a first promoter and a second promoter, wherein the second promoter is located the downstream of the capsid gene and drives its anti-sense RNA expression in the absence of helper virus co-infection.

In certain embodiments, the first promoter is AAV2 P40 and the second promoter is a ubiquitous promoter. In certain embodiments, the first promoter is AAV2 P40 and the second promoter is a cell-specific promoter. In certain embodiments, the ubiquitous or cell-specific promoter allows the expression of gene encoding the capsid polypeptide of variant AAV in an anti-sense direction, resulting in the anti-sense RNA. In certain embodiments, the method included the recovery of the anti-sense RNA that can be converted to RNA encoding the variant AAV capsid polypeptide that is used to determine the sequence of the variant AAV capsid polypeptides.

In certain embodiments, the variant AAV capsid polypeptide exhibits increased target cell transduction or target cell specificity (tropism) as compared to a parental capsid polypeptide.

BRIEF DESCRIPTION OF THE DRAWINGS

The foregoing and other objects, features, and advantages will be apparent from the following description of particular embodiments of the disclosure, as illustrated in the accompanying drawings. The drawings are not necessarily to scale, emphasis instead being placed upon illustrating the principles of various embodiments of the disclosure.

FIG. 1A shows transcription of VP1, VP2 and VP3 AAV transcripts from wildtype AAV genome. Transcription start sites of each viral promoter are indicated. SD, splice donor, SA, splice acceptor. Sequence of start codons for each reading frame is indicated. Translation of AAP and VP3 is performed by leaky scanning of the major mRNA. FIG. 1B shows the structure of the CMV-p40 dual promoter vectors used to determine the minimal regulatory sequences necessary for efficient virus production. The pREP2ΔCAP vector shown at the bottom is obtained by deletion of most CAP reading frame and is used to provide the REP protein in trans.

FIG. 2A shows average yield of AAV9 produced in HEK-293T cells using the constructs described in FIG. 1, co-transfected with an Ad Helper vector. Wild-type AAV9 plasmid (pAV9) is used as a positive control. Y-axis values indicate AAV DNA copies per ul from each 15-cm plate (~1000 ul total, left panel) or the percentage of wtAAV9 (right panel). FIG. 2B shows evidence for expression of CAP transcripts in transfected cells. mRNA from transfected 293T cells was subjected to RT-PCR using primers specific for the major spliced CAP transcript. Note the lack of p40-driven transcription in the absence of Ad Helper vector (lane 2).

FIG. 3A shows the design of improved pREP helper vectors. The MscI fragment deletion removes the C-terminal part of VP proteins, which is necessary for capsid formation. Asterisks represent early stop codons introduced to disrupt the coding potential of VP1, VP2 and VP3 reading frames. FIG. 3B shows the yield of Synapsin-p40-CAP9 AAV produced with various REP plasmid architectures. Values on the Y-axis represent the percentage of VG relative to wild-type AAV9. FIG. 3C shows the quantification of recombination and/or illegitimate packaging of full-length REP from the pREP plasmids. Virus stocks produced were subjected to qPCR using Taqman probes located in the N-terminal part of REP absent from the ITR-containing vectors.

FIG. 4A shows the design of Pro9 vectors. Architecture of all three vectors is based on the BstEII construct. AAV9 capsid RNA is placed under control of P40 and CMV, hSyn1 or GFAP promoters, respectively. FIG. 4B shows the silver stain of SDS-PAGE gel obtained by running 1e10 VG of each vector, after double iodixanol purification. FIG. 4C shows the biodistribution of viral DNA in mouse brain (cortex), liver and heart following tail-vein injection of 1e12 VG per mouse. AAV9 VP3 DNA is quantified by Taqman PCR and normalized to mouse transferrin receptor gene. FIG. 4D shows the capsid RNA recovery from mouse tissues. Total RNA was reverse transcribed and Taqman PCR was performed with capsid-specific Taqman primers and probe. Values represent VP3 cDNA copies normalized to TBP housekeeping gene.

FIG. 5A shows the design of intronic Pro9 vectors harboring a hybrid CMV/Globin intron. AAV9 capsid RNA is placed under control of P40 and CBA, hSyn1 or GFAP promoters in a tandem configuration (top) or in an inverted configuration (bottom). In the inverted promoter vectors, an extra SV40 polyadenylation site (orange) is added at the 3' extremity to allow polyadenylation of antisense CAPS transcripts. FIG. 5B shows the AAV9 CAP cDNA amplification. All vectors depicted were produced using triple transfection with pHelper and pREP-3stops and resulting viruses were used to infect HEK-293T cells at a MOI of 1e4 VG per cell. RNA was extracted 48 hours post-infection and subjected to RT-PCR with primers amplifying full capsid (top) or a C-terminal fragment (bottom). FIG. 5C shows the AAV9 VP3 cDNA from cells infected with intronless or intronic viruses with tandem promoters in forward orientation was quantified by Taqman PCR and normalized to GAPDH housekeeping gene. Values indicate the ratio of VP3 to GAPDH cDNA. FIG. 5D shows the mapping of capsid RNA recovery from cells infected with tandem or inverted constructs. Total RNA was reverse transcribed and PCR was performed with primers flanking the entire capsid gene. White arrowheads represent VP3 size variants resulting from aberrant splicing of antisense CAP mRNA. FIG. 5E shows the analysis of Globin intron splicing. CAG9 plasmid (left) or cDNA from HEK-293T cells transduced by CAG9 virus was submitted to PCR with forward primers located before (Glo ex1) or within (GloSpliceF4 (SEQ ID NO: 26) and GloSpliceF6 (SEQ ID NO: 13)) the Globin exon-exon junction. Primers spanning junction between exon 1 (no underline) and exon 2 (underline) are described at the bottom.

FIG. 6 provides in vitro evidence that the presence of the P40 promoter downstream of Synapsin or Gfabc1D promoters does not relieve the repression of either promoter in HEK-293T cells.

FIG. 15A shows the sequence of the insertion site used to introduce random libraries (SEQ ID NOS 43-46, respectively, in order of appearance). FIG. 15B provides a description of the assembly procedure.

FIG. 21A describes RNA library evolution. FIG. 21B and FIG. 21C show the amino acid distribution of NNK machine mix preparations for P0 and P1 virus.

FIG. 31A, FIG. 31B, FIG. 31C and FIG. 31D provide results of control capsids from the Syn-driven synthetic library NGS analysis. FIG. 31A shows the enrichment analysis of internal AAV9, PHP.B and PHP.eB controls (SEQ ID NOS 53-58 and 53-58, respectively, in order of appearance). FIG. 31B, FIG. 31C and FIG. 31D show the NNK/NNM codon distribution in mRNA from mouse brain tissue.

FIG. 32A and FIG. 32B provide the results of the neuron synthetic library NGS analysis (SEQ ID NOS 59-60, 59-61, 61-63, 62, 64, 64, 63, 65-67, 67, 65, 68, 66, 69, 70-71, and 70-74, respectively, in order of appearance).

FIG. 33 provides the results of the astrocyte synthetic library NGS analysis (SEQ ID NOS 53-58, 53-58, and 53-58, respectively, in order of appearance).

FIG. 37A and FIG. 37B provides the top 38 variants from the synthetic library screen. FIG. 37A shows the phylogenetic analysis of 9-mer peptide sequences, and also shows the sequence of the peptide variants (SEQ ID NOS 67, 59, 64, 61, 77, 84, 96, 60, 80, 82, 66, 62, 83, 85, 106, 131, 94, 90, 76, 68-69, 79, 75, 81, 88, 139, 78, 155, 102, 63, 140, 87, 70, 105, 120, 89, 65, and 109, respectively, in order of appearance). Highlighted sequences represent the peptides that were selected for individual transduction assay. FIG. 37B shows the graphic representation of the neuron and astrocyte tropism of each peptide, both axis indicate the inverted rank in Synapsin and GFAP screen.

FIG. 41 provides peptide diversity statistics from a study using the Illumina adapter having 42 million bacterial transformants, 81 million sequence reads and 12 million sequence variants (SEQ ID NOS 172-173, 48-49, and 174-175, respectively, in order of appearance).

FIG. 46A shows the ranking of capsids using SYN or GFAP promoters; FIG. 46B shows the scatter plot showing the correlation of Syn-versus GFAP-driven libraries.

FIG. 48A, FIG. 48B and FIG. 48C provide results from a multi-strain/species comparison of 333 capsid variants. FIG. 48A shows the ranking of 333 capsids by brain RNA enrichment score in C57BL/6 mice, BALB/C mice and rats. Capsids are ranked according to Syn-driven brain enrichment score in C57BL/6 mice. FIG. 48B shows the scatter plots showing the correlation between C57BL/6 and BALB/C enrichment scores from Syn- and GFAP-driven pools. FIG. 48C shows the Venn diagram showing the intersection and consensus sequence of capsids with a brain enrichment score>10-fold higher than AAV9 (either Syn- or GFAP-driven) in C57BL/6 and BALB/C strains. In rats, no capsid showed an enrichment score>10-fold versus AAV9.

FIG. 49A, FIG. 49B, FIG. 49C and FIG. 49D provide transduction (RNA) and biodistribution (DNA) analysis of 10 capsid variants indicated in FIG. 49A (SEQ ID NOS 179-188, respectively, in order of appearance). Individual capsids were used to package self-complementary CBA-EGFP genomes (FIG. 49B) and injected intravenously to C57BL/6 mice. FIG. 49C shows the RNA expression in brain and spinal cord samples. FIG. 49D shows the DNA distribution in brain and spinal cord samples.

FIG. 59A, FIG. 59B and FIG. 57C provide diagrams of external barcoding for NGS analysis and recovery of full-length capsid variants. A general barcode pair is shown (FIG. 59C). Full ITR-to-ITR constructs are shown with the barcode pair 5' of the CAP sequence (FIG. 59A) and 3' of the CAP sequence (FIG. 59B).

DETAILED DESCRIPTION OF THE DISCLOSURE

Figure 1A:
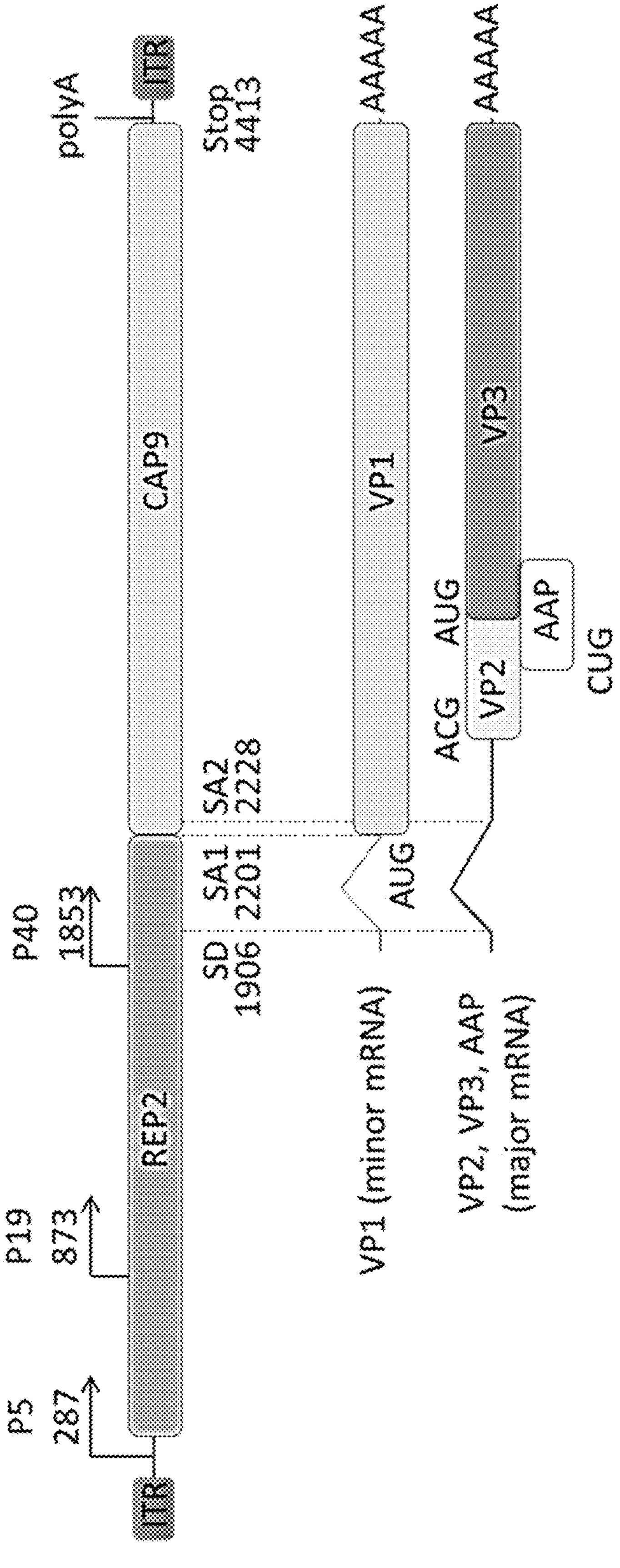
FIG. 1A and FIG. 1B are maps of wild-type AAV capsid gene transcription and CMV-CAP vectors.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

According to the present disclosure, AAV particles with enhanced tropism for a target tissue (e.g., CNS) are provided, as well as associated processes for their targeting, preparation, formulation and use. Targeting peptides and nucleic acid sequences encoding the targeting peptides are provided. These targeting peptides may be inserted into an AAV capsid protein sequence to alter tropism to a particular cell-type, tissue, organ or organism, in vivo, ex vivo or in vitro.

As used herein, an "AAV particle" or "AAV vector" comprises a capsid protein and a viral genome, wherein the viral genome comprises at least one payload region and at least one inverted terminal repeat (ITR). The AAV particle and/or its component capsid and viral genome may be engineered to alter tropism to a particular cell-type, tissue, organ or organism.

As used herein, "viral genome" or "vector genome" refers to the nucleic acid sequence(s) encapsulated in an AAV particle. A viral genome comprises a nucleic acid sequence with at least one payload region encoding a payload and at least one ITR.

As used herein, a "payload region" is any nucleic acid molecule which encodes one or more "payloads" of the disclosure. As non-limiting examples, a payload region may be a nucleic acid sequence encoding a payload comprising an RNAi agent or a polypeptide.

As used herein, a "targeting peptide" refers to a peptide of 3-20 amino acids in length. These targeting peptides may be inserted into, or attached to, a parent amino acid sequence to alter the characteristics (e.g., tropism) of the parent protein. As a non-limiting example, the targeting peptide can be inserted into an AAV capsid sequence for enhanced targeting to a desired cell-type, tissue, organ or organism.

The AAV particles and payloads of the disclosure may be delivered to one or more target cells, tissues, organs, or organisms. In a preferred embodiment, the AAV particles of the disclosure demonstrate enhanced tropism for a target cell type, tissue or organ. As a non-limiting example, the AAV particle may have enhanced tropism for cells and tissues of the central or peripheral nervous systems (CNS and PNS, respectively). The AAV particles of the disclosure may, in addition, or alternatively, have decreased tropism for an undesired target cell-type, tissue or organ.

Adeno-associated viruses (AAV) are small non-enveloped icosahedral capsid viruses of the Parvoviridae family characterized by a single stranded DNA viral genome. Parvoviridae family viruses consist of two subfamilies: Parvovirinae, which infect vertebrates, and Densovirinae, which infect invertebrates. The Parvoviridae family comprises the *Dependovirus* genus which includes AAV, capable of replication in vertebrate hosts including, but not limited to, human, primate, bovine, canine, equine, and ovine species.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

AAV have proven to be useful as a biological tool due to their relatively simple structure, their ability to infect a wide range of cells (including quiescent and dividing cells) without integration into the host genome and without replicating, and their relatively benign immunogenic profile. The genome of the virus may be manipulated to contain a minimum of components for the assembly of a functional recombinant virus, or viral particle, which is loaded with or engineered to target a particular tissue and express or deliver a desired payload.

The wild-type AAV vector genome is a linear, single-stranded DNA (ssDNA) molecule approximately 5,000 nucleotides (nt) in length. Inverted terminal repeats (ITRs) traditionally cap the viral genome at both the 5' and the 3' end, providing origins of replication for the viral genome. While not wishing to be bound by theory, an AAV viral genome typically comprises two ITR sequences. These ITRs have a characteristic T-shaped hairpin structure defined by a self-complementary region (145 nt in wild-type AAV) at the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

The wild-type AAV viral genome further comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are important for replication and packaging, while the capsid proteins are assembled to create the protein shell of the AAV, or AAV capsid. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu.14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In other words, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically comprises a molar ratio of 1:1:10 of VP1:VP2:VP3. As used herein, an "AAV serotype" is defined primarily by the AAV capsid. In some instances, the ITRs are also specifically described by the AAV serotype (e.g., AAV2/9).

AAV vectors of the present disclosure may be produced recombinantly and may be based on adeno-associated virus (AAV) parent or reference sequences. As used herein, a "vector" is any molecule or moiety which transports, transduces, or otherwise acts as a carrier of a heterologous molecule such as the nucleic acids described herein.

In addition to single stranded AAV viral genomes (e.g., ssAAVs), the present disclosure also provides for self-complementary AAV (scAAVs) viral genomes. scAAV vector genomes contain DNA strands which anneal together to form double stranded DNA. By skipping second strand synthesis, scAAVs allow for rapid expression in the transduced cell.

In one embodiment, the AAV particle of the present disclosure is an scAAV.

In one embodiment, the AAV particle of the present disclosure is an ssAAV.

Methods for producing and/or modifying AAV particles are disclosed in the art such as pseudotyped AAV vectors (PCT Patent Publication Nos. WO200028004; WO200123001; WO2004112727; WO2005005610; and WO2005072364, the content of each of which is incorporated herein by reference in its entirety).

In one embodiment, the AAV particles of the disclosure comprising a capsid with an inserted targeting peptide and a viral genome, may have enhanced tropism for a cell-type or tissue of the human CNS.

AAV Capsids

AAV particles of the present disclosure may comprise or be derived from any natural or recombinant AAV serotype. AAV serotypes may differ in characteristics such as, but not limited to, packaging, tropism, transduction and immunogenic profiles. While not wishing to be bound by theory, the AAV capsid protein is often considered to be the driver of AAV particle tropism to a particular tissue.

In one embodiment, an AAV particle may have a capsid protein and ITR sequences derived from the same parent serotype (e.g., AAV2 capsid and AAV2 ITRs). In another embodiment, the AAV particle may be a pseudo-typed AAV particle, wherein the capsid protein and ITR sequences are derived from different parent serotypes (e.g., AAV9 capsid and AAV2 ITRs; AAV2/9).

The AAV particles of the present disclosure may comprise an AAV capsid protein with a targeting peptide inserted into the parent sequence. The parent capsid or serotype may comprise or be derived from any natural or recombinant AAV serotype. As used herein, a "parent" sequence is a nucleotide or amino acid sequence into which a targeting sequence is inserted (i.e., nucleotide insertion into nucleic acid sequence or amino acid sequence insertion into amino acid sequence).

In a preferred embodiment, the parent AAV capsid nucleotide sequence is as set forth in SEQ ID NO: 1.

In another embodiment, the parent AAV capsid nucleotide sequence is a K449R variant of SEQ ID NO: 1, wherein the codon encoding a lysine (e.g., AAA or AAG) at position 449 in the amino acid sequence (nucleotides 1345-1347) is exchanged for one encoding an arginine (CGT, CGC, CGA, CGG, AGA, AGG). The K449R variant has the same function as wild-type AAV9.

In one embodiment, the parent AAV capsid amino acid sequence is as set forth in SEQ ID NO: 2.

In another embodiment, the parent AAV capsid amino acid sequence is as set forth in SEQ ID NO: 3.

In one embodiment the parent AAV capsid sequence is any of those shown in Table 1.

TABLE 1

AAV Capsid Sequences

| Serotype | SEQ ID NO | Reference Information |
|---|---|---|
| AAV9/hu.14 (nt) | 1 | U.S. Pat. No. 7,906,111 SEQ ID NO: 3; WO2015038958 SEQ ID NO: 11 |
| AAV9/hu.14 (aa) | 2 | U.S. Pat. No. 7,906,111 SEQ ID NO: 123; WO2015038958 SEQ ID NO: 2 |
| AAV9/hu.14 K449R (aa) | 3 | WO2017100671 SEQ ID NO: 45 |

Each of the patents, applications and or publications listed in Table 1 are hereby incorporated by reference in their entirety.

The parent AAV serotype and associated capsid sequence may be any of those known in the art. Non-limiting examples of such AAV serotypes include, AAV9, AAV9 K449R (or K449R AAV9), AAV1, AAVrh10, AAV-DJ, AAV-DJ8, AAV5, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV2, AAV2G9, AAV3, AAV3a, AAV3b, AAV3-3, AAV4, AAV4-4, AAV6, AAV6.1, AAV6.2, AAV6.1.2, AAV7, AAV7.2, AAV8, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu. 15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVCS, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, the serotype may be AAVDJ or a variant thereof, such as AAVDJ8 (or AAV-DJ8), as described by Grimm et al. (Journal of Virology 82(12): 5887-5911 (2008), US Publication US20140359799 and U.S. Pat. No. 7,588,772, each of which is herein incorporated by reference in its entirety). The amino acid sequence of AAVDJ8 may comprise two or more mutations in order to remove the heparin binding domain (HBD). As a non-limiting example, the AAV-DJ sequence is as described by SEQ ID NO: 1 in U.S. Pat. No. 7,588,772, the contents of which are herein incorporated by reference in their entirety, and the AAVDJ8 sequence may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, the AAVDJ8 sequence may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In one embodiment, the parent AAV capsid sequence comprises an AAV9 sequence.

In one embodiment, the parent AAV capsid sequence comprises an K449R AAV9 sequence.

In one embodiment, the parent AAV capsid sequence comprises an AAVDJ sequence.

In one embodiment, the parent AAV capsid sequence comprises an AAVDJ8 sequence.

In one embodiment, the parent AAV capsid sequence comprises an AAVrh10 sequence.

In one embodiment, the parent AAV capsid sequence comprises an AAV1 sequence.

In one embodiment, the parent AAV capsid sequence comprises an AAV5 sequence.

While not wishing to be bound by theory, it is understood that a parent AAV capsid sequence comprises a VP1 region. In one embodiment, a parent AAV capsid sequence comprises a VP1, VP2 and/or VP3 region, or any combination thereof. A parent VP1 sequence may be considered synonymous with a parent AAV capsid sequence.

The present disclosure refers to structural capsid proteins (including VP1, VP2 and VP3) which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins comprising the viral capsid may be produced, some of which may include a Met1/AA1 amino acid (Met+/AA+) and some of which may lack a Met1/AA1 amino acid as a result of Met/AA-clipping (Met−/AA−). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. *Science.* 2010 Feb. 19. 327(5968): 973-977; the contents of which are each incorporated herein by reference in its entirety.

According to the present disclosure, references to capsid proteins is not limited to either clipped (Met−/AA−) or unclipped (Met+/AA+) and may, in context, refer to independent capsid proteins, viral capsids comprised of a mixture of capsid proteins, and/or polynucleotide sequences (or fragments thereof) which encode, describe, produce or result in capsid proteins of the present disclosure. A direct reference to a "capsid protein" or "capsid polypeptide" (such as VP1, VP2 or VP2) may also comprise VP capsid proteins which include a Met1/AA1 amino acid (Met+/AA+) as well as corresponding VP capsid proteins which lack the Met1/AA1 amino acid as a result of Met/AA-clipping (Met−/AA−).

Further according to the present disclosure, a reference to a specific SEQ ID NO: (whether a protein or nucleic acid) which comprises or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

As a non-limiting example, reference to a VP1 polypeptide sequence which is 736 amino acids in length and which includes a "Met1" amino acid (Met+) encoded by the AUG/ATG start codon may also be understood to teach a VP1 polypeptide sequence which is 735 amino acids in length and which does not include the "Met1" amino acid (Met−) of the 736 amino acid Met+ sequence. As a second non-limiting example, reference to a VP1 polypeptide sequence which is 736 amino acids in length and which includes an "AA1" amino acid (AA1+) encoded by any NNN initiator codon may also be understood to teach a VP1 polypeptide sequence which is 735 amino acids in length and which does not include the "AA1" amino acid (AA1−) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met−/AA1−), and combinations thereof (Met+/AA1+ and Met−/AA1−).

As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+) and VP3 (Met−/AA1−); and can also include similar optional combinations of VP2 (Met+/AA1) and VP2 (Met−/AA1−).

In one embodiment, the parent AAV capsid sequence may comprise an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

In one embodiment, the parent AAV capsid sequence may be encoded by a nucleotide sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described above.

In one embodiment, the parent sequence is not an AAV capsid sequence and is instead a different vector (e.g., lentivirus, plasmid, etc.). In another embodiment, the parent sequence is a delivery vehicle (e.g., a nanoparticle) and the targeting peptide is attached thereto.

Targeting Peptides

Disclosed herein are targeting peptides and associated AAV particles comprising a capsid protein with one or more targeting peptide inserts, for enhanced or improved transduction of a target tissue (e.g., cells of the CNS or PNS).

In one embodiment, the targeting peptide may direct an AAV particle to a cell or tissue of the CNS. The cell of the CNS may be, but is not limited to, neurons (e.g., excitatory, inhibitory, motor, sensory, autonomic, sympathetic, parasympathetic, Purkinje, Betz, etc.), glial cells (e.g., microglia, astrocytes, oligodendrocytes) and/or supporting cells of the brain such as immune cells (e.g., T cells). The tissue of the CNS may be, but is not limited to, the cortex (e.g., frontal, parietal, occipital, temporal), thalamus, hypothalamus, striatum, putamen, caudate nucleus, hippocampus, entorhinal cortex, basal ganglia, or deep cerebellar nuclei.

In one embodiment, the targeting peptide may direct an AAV particle to a cell or tissue of the PNS. The cell or tissue of the PNS may be, but is not limited to, a dorsal root ganglion (DRG).

The targeting peptide may direct an AAV particle to the CNS (e.g., the cortex) after intravenous administration.

The targeting peptide may direct and AAV particle to the PNS (e.g., DRG) after intravenous administration.

A targeting peptide may vary in length. In one embodiment, the targeting peptide is 3-20 amino acids in length. As non-limiting examples, the targeting peptide may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length.

Targeting peptides of the present disclosure may be identified and/or designed by any method known in the art. As a non-limiting example, the CREATE system as described in Deverman et al., (Nature Biotechnology 34(2):204-209 (2016)), Chan et al., (Nature Neuroscience 20(8):1172-1179 (2017)), and in International Patent Application Publication Nos. WO2015038958 and WO2017100671, the contents of each of which are herein incorporated by reference in their entirety, may be used as a means of identifying targeting peptides, in either mice or other research animals, such as, but not limited to, non-human primates.

Targeting peptides and associated AAV particles may be identified from libraries of AAV capsids comprised of targeting peptide variants. In one embodiment, the targeting peptides may be 7 amino acid sequences (7-mers). In another embodiment, the targeting peptides may be 9 amino acid sequences (9-mers). The targeting peptides may also differ in their method of creation or design, with non-limiting examples including, random peptide selection, site saturation mutagenesis, and/or optimization of a particular region of the peptide (e.g., flanking regions or central core).

In one embodiment, a targeting peptide library comprises targeting peptides of 7 amino acids (7-mer) in length randomly generated by PCR.

In one embodiment, a targeting peptide library comprises targeting peptides with 3 mutated amino acids. In one embodiment, these 3 mutated amino acids are consecutive amino acids. In another embodiment, these 3 mutated amino acids are not consecutive amino acids. In one embodiment, the parent targeting peptide is a 7-mer. In another embodiment, the parent peptide is a 9-mer.

In one embodiment, a targeting peptide library comprises 7-mer targeting peptides, wherein the amino acids of the targeting peptide and/or the flanking sequences are evolved through site saturation mutagenesis of 3 consecutive amino acids. In one embodiment, NNK (N=any base; K=G or T) codons are used to generate the site saturated mutation sequences.

AAV particles comprising capsid proteins with targeting peptide inserts are generated and viral genomes encoding a reporter (e.g., GFP) encapsulated within. These AAV particles (or AAV capsid library) are then administered to a transgenic mouse by intravenous delivery to the tail vein. Administration of these capsid libraries to cre-expressing mice results in expression of the reporter payload in the target tissue, due to the expression of Cre.

AAV particles and/or viral genomes may be recovered from the target tissue for identification of targeting peptides and associated AAV particles that are enriched, indicating enhanced transduction of target tissue. Standard methods in the art, such as, but not limited to next generation sequencing (NGS), viral genome quantification, biochemical assays, immunohistochemistry and/or imaging of target tissue samples may be used to determine enrichment.

A target tissue may be any cell, tissue or organ of a subject. As non-limiting examples, samples may be collected from brain, spinal cord, dorsal root ganglia and associated roots, liver, heart, gastrocnemius muscle, soleus muscle, pancreas, kidney, spleen, lung, adrenal glands, stomach, sciatic nerve, saphenous nerve, thyroid gland, eyes (with or without optic nerve), pituitary gland, skeletal muscle (rectus femoris), colon, duodenum, ileum, jejunum, skin of the leg, superior cervical ganglia, urinary bladder, ovaries, uterus, prostate gland, testes, and/or any sites identified as having a lesion, or being of interest.

Targeting Peptide Sequences

In one embodiment the targeting peptide may comprise a sequence as set forth in Table 2. In Table 2, "_1" refers to NNM codons where A or C is in the third position and "_2" refers to NNK codons where G or T is in the third position. Additionally, the NNM codons cannot cover the entire repertoire of amino acids since Met or Trp can only be encoded by codons ATG and TGG, respectively. Therefore, some "NNM" sequences also contain some codons ending in G.

TABLE 2

| Peptides | | | |
|---|---|---|---|
| Peptide Sequence_ID | SEQ ID NO: | Peptide Sequence_ID | SEQ ID NO: |
| AQAGAGSER_1 | 194 | DGTGQVTGW_1 | 68 |
| AQAGAGSER_2 | 194 | DGTGQVTGW_2 | 68 |
| AQDQNPGRW_1 | 195 | DGTGRLTGW_1 | 159 |
| AQDQNPGRW_2 | 195 | DGTGRLTGW_2 | 159 |
| AQELTRPFL_1 | 144 | DGTGRTVGW_1 | 117 |
| AQELTRPFL_2 | 144 | DGTGRTVGW_2 | 117 |
| AQEVPGYRW_1 | 196 | DGTGSGMMT_1 | 306 |
| AQEVPGYRW_2 | 196 | DGTGSGMMT_2 | 306 |
| AQFPTNYDS_1 | 66 | DGTGSISGW_1 | 307 |
| AQFPTNYDS_2 | 66 | DGTGSISGW_2 | 307 |
| AQFVVGQQY_1 | 95 | DGTGSLAGW_1 | 308 |
| AQFVVGQQY_2 | 95 | DGTGSLAGW_2 | 308 |
| AQGASPGRW_1 | 149 | DGTGSLNGW_1 | 309 |
| AQGASPGRW_2 | 149 | DGTGSLNGW_2 | 309 |
| AQGENPGRW_1 | 96 | DGTGSLQGW_1 | 310 |
| AQGENPGRW_2 | 96 | DGTGSLQGW_2 | 310 |
| AQGGNPGRW_1 | 91 | DGTGSLSGW_1 | 311 |
| AQGGNPGRW_2 | 91 | DGTGSLSGW_2 | 311 |
| AQGGSTGSN_1 | 197 | DGTGSLVGW_1 | 312 |
| AQGGSTGSN_2 | 197 | DGTGSLVGW_2 | 312 |
| AQGPTRPFL_1 | 125 | DGTGSTHGW_1 | 119 |
| AQGPTRPFL_2 | 125 | DGTGSTHGW_2 | 119 |
| AQGRDGWAA_1 | 198 | DGTGSTKGW_1 | 313 |
| AQGRDGWAA_2 | 198 | DGTGSTKGW_2 | 313 |
| AQGRMTDSQ_1 | 199 | DGTGSTMGW_1 | 314 |
| AQGRMTDSQ_2 | 199 | DGTGSTMGW_2 | 314 |
| AQGSDVGRW_1 | 128 | DGTGSTQGW_1 | 315 |
| AQGSDVGRW_2 | 128 | DGTGSTQGW_2 | 315 |
| AQGSNPGRW_1 | 103 | DGTGSTSGW_1 | 316 |
| AQGSNPGRW_2 | 103 | DGTGSTSGW_2 | 316 |
| AQGSNSPQV_1 | 200 | DGTGSTTGW_1 | 134 |
| AQGSNSPQV_2 | 200 | DGTGSTTGW_2 | 134 |
| AQGSWNPPA_1 | 80 | DGTGSVMGW_1 | 317 |
| AQGSWNPPA_2 | 80 | DGTGSVMGW_2 | 317 |
| AQGTWNPPA_1 | 82 | DGTGSVTGW_1 | 318 |
| AQGTWNPPA_2 | 82 | DGTGSVTGW_2 | 318 |
| AQGVFIPPK_1 | 201 | DGTGTLAGW_1 | 319 |
| AQGVFIPPK_2 | 201 | DGTGTLAGW_2 | 319 |
| AQHVNASQS_1 | 202 | DGTGTLHGW_1 | 320 |
| AQHVNASQS_2 | 202 | DGTGTLHGW_2 | 320 |
| AQIKAGWAQ_1 | 203 | DGTGTLKGW_1 | 321 |

TABLE 2-continued

Peptides

| Peptide Sequence_ID | SEQ ID NO: | Peptide Sequence_ID | SEQ ID NO: |
|---|---|---|---|
| AQIKAGWAQ_2 | 203 | DGTGTLKGW_2 | 321 |
| AQIMSGYAQ_1 | 204 | DGTGTLSGW_1 | 322 |
| AQIMSGYAQ_2 | 204 | DGTGTLSGW_2 | 322 |
| AQKSVGSVY_1 | 205 | DGTGTTLGW_1 | 323 |
| AQKSVGSVY_2 | 205 | DGTGTTLGW_2 | 323 |
| AQLEHGFAQ_1 | 206 | DGTGTTMGW_1 | 324 |
| AQLEHGFAQ_2 | 206 | DGTGTTMGW_2 | 324 |
| AQLGGVLSA_1 | 207 | DGTGTTTGW_1 | 130 |
| AQLGGVLSA_2 | 207 | DGTGTTTGW_2 | 130 |
| AQLGLSQGR_1 | 208 | DGTGTTVGW_1 | 74 |
| AQLGLSQGR_2 | 208 | DGTGTTVGW_2 | 74 |
| AQLGYGFAQ_1 | 209 | DGTGTTYGW_1 | 325 |
| AQLGYGFAQ_2 | 209 | DGTGTTYGW_2 | 325 |
| AQLKYGLAQ_1 | 115 | DGTGTVHGW_1 | 326 |
| AQLKYGLAQ_2 | 115 | DGTGTVHGW_2 | 326 |
| AQLRIGFAQ_1 | 210 | DGTGTVQGW_1 | 327 |
| AQLRIGFAQ_2 | 210 | DGTGTVQGW_2 | 327 |
| AQLRMGYSQ_1 | 211 | DGTGTVSGW_1 | 328 |
| AQLRMGYSQ_2 | 211 | DGTGTVSGW_2 | 328 |
| AQLRQGYAQ_1 | 212 | DGTGTVTGW_1 | 329 |
| AQLRQGYAQ_2 | 212 | DGTGTVTGW_2 | 329 |
| AQLRVGFAQ_1 | 123 | DGTHARLSS_1 | 330 |
| AQLRVGFAQ_2 | 123 | DGTHARLSS_2 | 330 |
| AQLSCRSQM_1 | 213 | DGTHAYMAS_1 | 153 |
| AQLSCRSQM_2 | 213 | DGTHAYMAS_2 | 153 |
| AQLTYSQSL_1 | 214 | DGTHFAPPR_1 | 112 |
| AQLTYSQSL_2 | 214 | DGTHFAPPR_2 | 112 |
| AQLYKGYSQ_1 | 215 | DGTHIHLSS_1 | 162 |
| AQLYKGYSQ_2 | 215 | DGTHIHLSS_2 | 162 |
| AQMPQRPFL_1 | 216 | DGTHIRALS_1 | 331 |
| AQMPQRPFL_2 | 216 | DGTHIRALS_2 | 331 |
| AQNGNPGRW_1 | 84 | DGTHIRLAS_1 | 332 |
| AQNGNPGRW_2 | 84 | DGTHIRLAS_2 | 332 |
| AQPEGSARW_1 | 60 | DGTHLQPFR_1 | 333 |
| AQPEGSARW_2 | 60 | DGTHLQPFR_2 | 333 |
| AQPLAVYGA_1 | 217 | DGTHSFYDA_1 | 334 |
| AQPLAVYGA_2 | 217 | DGTHSFYDA_2 | 334 |
| AQPQSSSMS_1 | 218 | DGTHSTTGW_1 | 145 |
| AQPQSSSMS_2 | 218 | DGTHSTTGW_2 | 145 |
| AQPSVGGYW_1 | 219 | DGTHTRTGW_1 | 90 |
| AQPSVGGYW_2 | 219 | DGTHTRTGW_2 | 90 |
| AQQAVGQSW_1 | 220 | DGTHVRALS_1 | 335 |
| AQQAVGQSW_2 | 220 | DGTHVRALS_2 | 335 |
| AQQRSLASG_1 | 221 | DGTHVYMAS_1 | 336 |
| AQQRSLASG_2 | 221 | DGTHVYMAS_2 | 336 |
| AQQVMNSQG_1 | 222 | DGTHVYMSS_1 | 337 |
| AQQVMNSQG_2 | 222 | DGTHVYMSS_2 | 337 |
| AQRGVGLSQ_1 | 223 | DGTIALPFK_1 | 338 |
| AQRGVGLSQ_2 | 223 | DGTIALPFK_2 | 338 |
| AQRHDAEGS_1 | 224 | DGTIALPFR_1 | 339 |
| AQRHDAEGS_2 | 224 | DGTIALPFR_2 | 339 |
| AQRKGEPHY_1 | 225 | DGTIATRYV_1 | 340 |
| AQRKGEPHY_2 | 225 | DGTIATRYV_2 | 340 |
| AQRYTGDSS_1 | 138 | DGTIERPFR_1 | 87 |
| AQRYTGDSS_2 | 138 | DGTIERPFR_2 | 87 |
| AQSAMAAKG_1 | 226 | DGTIGYAYV_1 | 341 |
| AQSAMAAKG_2 | 226 | DGTIGYAYV_2 | 341 |
| AQSGGLTGS_1 | 227 | DGTIQAPFK_1 | 342 |
| AQSGGLTGS_2 | 227 | DGTIQAPFK_2 | 342 |
| AQSGGVGQV_1 | 228 | DGTIRLPFK_1 | 343 |
| AQSGGVGQV_2 | 228 | DGTIRLPFK_2 | 343 |
| AQSLATPFR_1 | 169 | DGTISKEVG_1 | 344 |
| AQSLATPFR_2 | 169 | DGTISKEVG_2 | 344 |
| AQSMSRPFL_1 | 229 | DGTISQPFK_1 | 105 |
| AQSMSRPFL_2 | 229 | DGTISQPFK_2 | 105 |
| AQSQLRPFL_1 | 230 | DGTKIQLSS_1 | 146 |
| AQSQLRPFL_2 | 230 | DGTKIQLSS_2 | 146 |
| AQSVAKPFL_1 | 231 | DGTKIRLSS_1 | 111 |
| AQSVAKPFL_2 | 231 | DGTKIRLSS_2 | 111 |
| AQSVSQPFR_1 | 232 | DGTKLMLSS_1 | 157 |
| AQSVSQPFR_2 | 232 | DGTKLMLSS_2 | 157 |
| AQSVVRPFL_1 | 233 | DGTKLRLSS_1 | 118 |
| AQSVVRPFL_2 | 233 | DGTKLRLSS_2 | 118 |
| AQTALSSST_1 | 234 | DGTKMVLQL_1 | 142 |
| AQTALSSST_2 | 234 | DGTKMVLQL_2 | 142 |

TABLE 2-continued

Peptides

| Peptide Sequence_ID | SEQ ID NO: | Peptide Sequence_ID | SEQ ID NO: |
|---|---|---|---|
| AQTEMGGRC_1 | 235 | DGTKSLVQL_1 | 345 |
| AQTEMGGRC_2 | 235 | DGTKSLVQL_2 | 345 |
| AQTGFAPPR_1 | 161 | DGTKVLVQL_1 | 122 |
| AQTGFAPPR_2 | 161 | DGTKVLVQL_2 | 122 |
| AQTIRGYSS_1 | 236 | DGTLAAPFK_1 | 120 |
| AQTIRGYSS_2 | 236 | DGTLAAPFK_2 | 120 |
| AQTISNYHT_1 | 237 | DGTLAVNFK_1 | 346 |
| AQTISNYHT_2 | 237 | DGTLAVNFK_2 | 346 |
| AQTLARPFV_1 | 98 | DGTLAVPFK_1 | 71 |
| AQTLARPFV_2 | 98 | DGTLAVPFK_2 | 71 |
| AQTLAVPFK_1 | 168 | DGTLAYPFK_1 | 347 |
| AQTLAVPFK_2 | 168 | DGTLAYPFK_2 | 347 |
| AQTPDRPWL_1 | 238 | DGTLERPFR_1 | 156 |
| AQTPDRPWL_2 | 238 | DGTLERPFR_2 | 156 |
| AQTRAGYAQ_1 | 126 | DGTLEVHFK_1 | 348 |
| AQTRAGYAQ_2 | 126 | DGTLEVHFK_2 | 348 |
| AQTRAGYSQ_1 | 141 | DGTLLRLSS_1 | 121 |
| AQTRAGYSQ_2 | 141 | DGTLLRLSS_2 | 121 |
| AQTREYLLG_1 | 93 | DGTLNNPFR_1 | 109 |
| AQTREYLLG_2 | 93 | DGTLNNPFR_2 | 109 |
| AQTSAKPFL_1 | 163 | DGTLQQPFR_1 | 89 |
| AQTSAKPFL_2 | 163 | DGTLQQPFR_2 | 89 |
| AQTSARPFL_1 | 100 | DGTLSQPFR_1 | 65 |
| AQTSARPFL_2 | 100 | DGTLSQPFR_2 | 65 |
| AQTTDRPFL_1 | 85 | DGTLSRTLW_1 | 349 |
| AQTTDRPFL_2 | 85 | DGTLSRTLW_2 | 349 |
| AQTTEKPWL_1 | 83 | DGTLSSPFR_1 | 350 |
| AQTTEKPWL_2 | 83 | DGTLSSPFR_2 | 350 |
| AQTVARPFY_1 | 239 | DGTLTVPFR_1 | 351 |
| AQTVARPFY_2 | 239 | DGTLTVPFR_2 | 351 |
| AQTVATPFR_1 | 240 | DGTLVAPFR_1 | 352 |
| AQTVATPFR_2 | 240 | DGTLVAPFR_2 | 352 |
| AQTVTQLFK_1 | 241 | DGTMDKPFR_1 | 70 |
| AQTVTQLFK_2 | 241 | DGTMDKPFR_2 | 70 |
| AQVHVGSVY_1 | 165 | DGTMDRPFK_1 | 102 |
| AQVHVGSVY_2 | 165 | DGTMDRPFK_2 | 102 |
| AQVLAGYNM_1 | 242 | DGTMLRLSS_1 | 148 |

TABLE 2-continued

Peptides

| Peptide Sequence_ID | SEQ ID NO: | Peptide Sequence_ID | SEQ ID NO: |
|---|---|---|---|
| AQVLAGYNM_2 | 242 | DGTMLRLSS_2 | 148 |
| AQVSEARVR_1 | 243 | DGTMQLTGW_1 | 353 |
| AQVSEARVR_2 | 243 | DGTMQLTGW_2 | 353 |
| AQVVVGYSQ_1 | 244 | DGTNGLKGW_1 | 76 |
| AQVVVGYSQ_2 | 244 | DGTNGLKGW_2 | 76 |
| AQWAAGYNV_1 | 245 | DGTNSISGW_1 | 354 |
| AQWAAGYNV_2 | 245 | DGTNSISGW_2 | 354 |
| AQWELSNGY_1 | 246 | DGTNSLSGW_1 | 355 |
| AQWELSNGY_2 | 246 | DGTNSLSGW_2 | 355 |
| AQWEVKGGY_1 | 247 | DGTNSTTGW_1 | 143 |
| AQWEVKGGY_2 | 247 | DGTNSTTGW_2 | 143 |
| AQWEVKRGY_1 | 248 | DGTNSVTGW_1 | 356 |
| AQWEVKRGY_2 | 248 | DGTNSVTGW_2 | 356 |
| AQWEVQSGF_1 | 249 | DGTNTINGW_1 | 124 |
| AQWEVQSGF_2 | 249 | DGTNTINGW_2 | 124 |
| AQWEVRGGY_1 | 250 | DGTNTLGGW_1 | 357 |
| AQWEVRGGY_2 | 250 | DGTNTLGGW_2 | 357 |
| AQWEVTSGW_1 | 251 | DGTNTTHGW_1 | 113 |
| AQWEVTSGW_2 | 251 | DGTNTTHGW_2 | 113 |
| AQWGAPSHG_1 | 252 | DGTNYRLSS_1 | 358 |
| AQWGAPSHG_2 | 252 | DGTNYRLSS_2 | 358 |
| AQWMELGSS_1 | 253 | DGTQALSGW_1 | 359 |
| AQWMELGSS_2 | 253 | DGTQALSGW_2 | 359 |
| AQWMFGGSG_1 | 254 | DGTQFRLSS_1 | 129 |
| AQWMFGGSG_2 | 254 | DGTQFRLSS_2 | 129 |
| AQWMLGGAQ_1 | 255 | DGTQFSPPR_1 | 108 |
| AQWMLGGAQ_2 | 255 | DGTQFSPPR_2 | 108 |
| AQWPTAYDA_1 | 256 | DGTQGLKGW_1 | 158 |
| AQWPTAYDA_2 | 256 | DGTQGLKGW_2 | 158 |
| AQWPTSYDA_1 | 62 | DGTQTTSGW_1 | 360 |
| AQWPTSYDA_2 | 62 | DGTQTTSGW_2 | 360 |
| AQWQVQTGF_1 | 257 | DGTRALTGW_1 | 361 |
| AQWQVQTGF_2 | 257 | DGTRALTGW_2 | 361 |
| AQWSTEGGY_1 | 258 | DGTRFSLSS_1 | 362 |
| AQWSTEGGY_2 | 258 | DGTRFSLSS_2 | 362 |
| AQWTAAGGY_1 | 259 | DGTRGLSGW_1 | 363 |
| AQWTAAGGY_2 | 259 | DGTRGLSGW_2 | 363 |
| AQWTTESGY_1 | 260 | DGTRIGLSS_1 | 364 |

TABLE 2-continued

| Peptides | | | |
|---|---|---|---|
| Peptide Sequence_ID | SEQ ID NO: | Peptide Sequence_ID | SEQ ID NO: |
| AQWTTESGY_2 | 260 | DGTRIGLSS_2 | 364 |
| AQWVYGSSH_1 | 261 | DGTRLHLAS_1 | 365 |
| AQWVYGSSH_2 | 261 | DGTRLHLAS_2 | 365 |
| AQYLAGYTV_1 | 262 | DGTRLHLSS_1 | 366 |
| AQYLAGYTV_2 | 262 | DGTRLHLSS_2 | 366 |
| AQYLKGYSV_1 | 152 | DGTRLLLSS_1 | 367 |
| AQYLKGYSV_2 | 152 | DGTRLLLSS_2 | 367 |
| AQYLSGYNT_1 | 263 | DGTRLMLSS_1 | 368 |
| AQYLSGYNT_2 | 263 | DGTRLMLSS_2 | 368 |
| DGAAATTGW_1 | 264 | DGTRLNLSS_1 | 369 |
| DGAAATTGW_2 | 264 | DGTRLNLSS_2 | 369 |
| DGAGGTSGW_1 | 151 | DGTRMVVQL_1 | 370 |
| DGAGGTSGW_2 | 151 | DGTRMVVQL_2 | 370 |
| DGAGTTSGW_1 | 265 | DGTRNMYEG_1 | 135 |
| DGAGTTSGW_2 | 265 | DGTRNMYEG_2 | 135 |
| DGAHGLSGW_1 | 266 | DGTRSITGW_1 | 371 |
| DGAHGLSGW_2 | 266 | DGTRSITGW_2 | 371 |
| DGAHVGLSS_1 | 267 | DGTRSLHGW_1 | 372 |
| DGAHVGLSS_2 | 267 | DGTRSLHGW_2 | 372 |
| DGARTVLQL_1 | 268 | DGTRSTTGW_1 | 373 |
| DGARTVLQL_2 | 268 | DGTRSTTGW_2 | 373 |
| DGEYQKPFR_1 | 269 | DGTRTTTGW_1 | 106 |
| DGEYQKPFR_2 | 269 | DGTRTTTGW_2 | 106 |
| DGGGTTTGW_1 | 270 | DGTRTVTGW_1 | 374 |
| DGGGTTTGW_2 | 270 | DGTRTVTGW_2 | 374 |
| DGHATSMGW_1 | 271 | DGTRTVVQL_1 | 375 |
| DGHATSMGW_2 | 271 | DGTRTVVQL_2 | 375 |
| DGKGSTQGW_1 | 272 | DGTRVHLSS_1 | 376 |
| DGKGSTQGW_2 | 272 | DGTRVHLSS_2 | 376 |
| DGKQYQLSS_1 | 92 | DGTSFPYAR_1 | 86 |
| DGKQYQLSS_2 | 92 | DGTSFPYAR_2 | 86 |
| DGNGGLKGW_1 | 167 | DGTSFTPPK_1 | 81 |
| DGNGGLKGW_2 | 167 | DGTSFTPPK_2 | 81 |
| DGQGGLSGW_1 | 273 | DGTSFTPPR_1 | 88 |
| DGQGGLSGW_2 | 273 | DGTSFTPPR_2 | 88 |
| DGQHFAPPR_1 | 110 | DGTSGLHGW_1 | 377 |
| DGQHFAPPR_2 | 110 | DGTSGLHGW_2 | 377 |

TABLE 2-continued

| Peptides | | | |
|---|---|---|---|
| Peptide Sequence_ID | SEQ ID NO: | Peptide Sequence_ID | SEQ ID NO: |
| DGRATKTLY_1 | 274 | DGTSGLKGW_1 | 101 |
| DGRATKTLY_2 | 274 | DGTSGLKGW_2 | 101 |
| DGRNALTGW_1 | 275 | DGTSIHLSS_1 | 378 |
| DGRNALTGW_2 | 275 | DGTSIHLSS_2 | 378 |
| DGRRQVIQL_1 | 276 | DGTSIMLSS_1 | 379 |
| DGRRQVIQL_2 | 276 | DGTSIMLSS_2 | 379 |
| DGRVYGLSS_1 | 277 | DGTSLRLSS_1 | 166 |
| DGRVYGLSS_2 | 277 | DGTSLRLSS_2 | 166 |
| DGSGRTTGW_1 | 147 | DGTSNYGAR_1 | 380 |
| DGSGRTTGW_2 | 147 | DGTSNYGAR_2 | 380 |
| DGSGTTRGW_1 | 114 | DGTSSYYDA_1 | 381 |
| DGSGTTRGW_2 | 114 | DGTSSYYDA_2 | 381 |
| DGSGTVSGW_1 | 278 | DGTSSYYDS_1 | 59 |
| DGSGTVSGW_2 | 278 | DGTSSYYDS_2 | 59 |
| DGSPEKPFR_1 | 160 | DGTSTISGW_1 | 382 |
| DGSPEKPFR_2 | 160 | DGTSTISGW_2 | 382 |
| DGSQSTTGW_1 | 136 | DGTSTITGW_1 | 383 |
| DGSQSTTGW_2 | 136 | DGTSTITGW_2 | 383 |
| DGSSFYPPK_1 | 127 | DGTSTLHGW_1 | 384 |
| DGSSFYPPK_2 | 127 | DGTSTLHGW_2 | 384 |
| DGSSSYYDA_1 | 64 | DGTSTLRGW_1 | 385 |
| DGSSSYYDA_2 | 64 | DGTSTLRGW_2 | 385 |
| DGSIERPFR_1 | 99 | DGTSTLSGW_1 | 386 |
| DGSIERPFR_2 | 99 | DGTSTLSGW_2 | 386 |
| DGTAARLSS_1 | 132 | DGTSYVPPK_1 | 97 |
| DGTAARLSS_2 | 132 | DGTSYVPPK_2 | 97 |
| DGTADKPFR_1 | 63 | DGTSYVPPR_1 | 78 |
| DGTADKPFR_2 | 63 | DGTSYVPPR_2 | 78 |
| DGTADRPFR_1 | 155 | DGTTATYYK_1 | 387 |
| DGTADRPFR_2 | 155 | DGTTATYYK_2 | 387 |
| DGTAERPFR_1 | 140 | DGTTFTPPR_1 | 79 |
| DGTAERPFR_2 | 140 | DGTTFTPPR_2 | 79 |
| DGTAIHLSS_1 | 67 | DGTTLAPFR_1 | 388 |
| DGTAIHLSS_2 | 67 | DGTTLAPFR_2 | 388 |
| DGTAIYLSS_1 | 279 | DGTTLVPPR_1 | 116 |
| DGTAIYLSS_2 | 279 | DGTTLVPPR_2 | 116 |
| DGTALMLSS_1 | 280 | DGTTSKTLW_1 | 389 |
| DGTALMLSS_2 | 280 | DGTTSKTLW_2 | 389 |

TABLE 2-continued

| Peptide Sequence_ID | SEQ ID NO: | Peptide Sequence_ID | SEQ ID NO: |
|---|---|---|---|
| DGTASISGW_1 | 281 | DGTTSRTLW_1 | 390 |
| DGTASISGW_2 | 281 | DGTTSRTLW_2 | 390 |
| DGTASTSGW_1 | 282 | DGTTTRSLY_1 | 391 |
| DGTASTSGW_2 | 282 | DGTTTRSLY_2 | 391 |
| DGTASVTGW_1 | 283 | DGTTTTTGW_1 | 392 |
| DGTASVTGW_2 | 283 | DGTTTTTGW_2 | 392 |
| DGTASYYDS_1 | 61 | DGTTTYGAR_1 | 77 |
| DGTASYYDS_2 | 61 | DGTTTYGAR_2 | 77 |
| DGTATTMGW_1 | 284 | DGTTWTPPR_1 | 139 |
| DGTATTMGW_2 | 284 | DGTTWTPPR_2 | 139 |
| DGTATTTGW_1 | 285 | DGTTYMLSS_1 | 393 |
| DGTATTTGW_2 | 285 | DGTTYMLSS_2 | 393 |
| DGTAYRLSS_1 | 286 | DGTTYVPPR_1 | 75 |
| DGTAYRLSS_2 | 286 | DGTTYVPPR_2 | 75 |
| DGTDKMWSL_1 | 287 | DGTVANPFR_1 | 394 |
| DGTDKMWSL_2 | 287 | DGTVANPFR_2 | 394 |
| DGTGGIKGW_1 | 131 | DGTVDRPFK_1 | 395 |
| DGTGGIKGW_2 | 131 | DGTVDRPFK_2 | 395 |
| DGTGGIMGW_1 | 288 | DGTVIHLSS_1 | 73 |
| DGTGGIMGW_2 | 288 | DGTVIHLSS_2 | 73 |
| DGTGGISGW_1 | 289 | DGTVILLSS_1 | 396 |
| DGTGGISGW_2 | 289 | DGTVILLSS_2 | 396 |
| DGTGGLAGW_1 | 290 | DGTVIMLSS_1 | 397 |
| DGTGGLAGW_2 | 290 | DGTVIMLSS_2 | 397 |
| DGTGGLHGW_1 | 291 | DGTVLHLSS_1 | 398 |
| DGTGGLHGW_2 | 291 | DGTVLHLSS_2 | 398 |
| DGTGGLQGW_1 | 292 | DGTVLMLSS_1 | 399 |
| DGTGGLQGW_2 | 292 | DGTVLMLSS_2 | 399 |
| DGTGGLRGW_1 | 154 | DGTVLVPFR_1 | 150 |
| DGTGGLRGW_2 | 154 | DGTVLVPFR_2 | 150 |
| DGTGGLSGW_1 | 293 | DGTVPYLAS_1 | 400 |
| DGTGGLSGW_2 | 293 | DGTVPYLAS_2 | 400 |
| DGTGGLTGW_1 | 294 | DGTVPYLSS_1 | 401 |
| DGTGGLTGW_2 | 294 | DGTVPYLSS_2 | 401 |
| DGTGGTKGW_1 | 107 | DGTVRVPFR_1 | 164 |
| DGTGGTKGW_2 | 107 | DGTVRVPFR_2 | 164 |
| DGTGGTSGW_1 | 295 | DGTVSMPFK_1 | 402 |

TABLE 2-continued

| Peptide Sequence_ID | SEQ ID NO: | Peptide Sequence_ID | SEQ ID NO: |
|---|---|---|---|
| DGTGGTSGW_2 | 295 | DGTVSMPFK_2 | 402 |
| DGTGGVHGW_1 | 296 | DGTVSNPFR_1 | 403 |
| DGTGGVHGW_2 | 296 | DGTVSNPFR_2 | 403 |
| DGTGGVMGW_1 | 297 | DGTVSTRWV_1 | 404 |
| DGTGGVMGW_2 | 297 | DGTVSTRWV_2 | 404 |
| DGTGGVSGW_1 | 298 | DGTVTTTGW_1 | 405 |
| DGTGGVSGW_2 | 298 | DGTVTTTGW_2 | 405 |
| DGTGGVTGW_1 | 299 | DGTVTVTGW_1 | 406 |
| DGTGGVTGW_2 | 299 | DGTVTVTGW_2 | 406 |
| DGTGGVYGW_1 | 300 | DGTVWVPPR_1 | 407 |
| DGTGGVYGW_2 | 300 | DGTVWVPPR_2 | 407 |
| DGTGNLQGW_1 | 301 | DGTVYRLSS_1 | 408 |
| DGTGNLQGW_2 | 301 | DGTVYRLSS_2 | 408 |
| DGTGNLRGW_1 | 133 | DGTYARLSS_1 | 409 |
| DGTGNLRGW_2 | 133 | DGTYARLSS_2 | 409 |
| DGTGNLSGW_1 | 302 | DGTYGNKLW_1 | 410 |
| DGTGNLSGW_2 | 302 | DGTYGNKLW_2 | 410 |
| DGTGNTHGW_1 | 72 | DGTYIHLSS_1 | 411 |
| DGTGNTHGW_2 | 72 | DGTYIHLSS_2 | 411 |
| DGTGNTRGW_1 | 94 | DGTYSTSGW_1 | 412 |
| DGTGNTRGW_2 | 94 | DGTYSTSGW_2 | 412 |
| DGTGNTSGW_1 | 137 | DGVHPGLSS_1 | 104 |
| DGTGNTSGW_2 | 137 | DGVHPGLSS_2 | 104 |
| DGTGNVSGW_1 | 303 | DGVVALLAS_1 | 413 |
| DGTGNVSGW_2 | 303 | DGVVALLAS_2 | 413 |
| DGTGNVTGW_1 | 69 | DGYVGVGSL_1 | 414 |
| DGTGNVTGW_2 | 69 | DGYVGVGSL_2 | 414 |
| DGTGQLVGW_1 | 304 | control (wtAAV9-NNM) | |
| DGTGQLVGW_2 | 304 | control (wtAAV9-NNK) | |
| DGTGQTIGW_1 | 305 | | |
| DGTGQTIGW_2 | 305 | | |

In one embodiment, the targeting peptide may comprise an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the sequences shown in Table 2.

In one embodiment, a targeting peptide may comprise 4 or more contiguous amino acids of any of the targeting peptides disclosed herein. In one embodiment the targeting peptide may comprise 4 contiguous amino acids of any of the sequences as set forth in Table 2. In one embodiment the targeting peptide may comprise 5 contiguous amino acids of any of the sequences as set forth in Table 2. In one embodiment the targeting peptide may comprise 6 contiguous amino acids of any of the sequences as set forth in Table 2.

In one embodiment, the AAV particle of the disclosure comprises an AAV capsid with a targeting peptide insert, wherein the targeting peptide has an amino acid sequence as set forth in any of Table 2.

In one embodiment, the AAV particle of the disclosure comprises an AAV capsid with a targeting peptide insert, wherein the targeting peptide has an amino acid sequence comprising at least 4 contiguous amino acids of any of the sequences as set forth in any of Table 2.

In one embodiment, the AAV particle of the disclosure comprises an AAV capsid with a targeting peptide insert, wherein the targeting peptide has an amino acid sequence substantially comprising any of the sequences as set forth in any of Table 2.

In one embodiment, the AAV particle of the disclosure comprises an AAV capsid polynucleotide with a targeting nucleic acid insert, wherein the targeting nucleic acid insert has a nucleotide sequence substantially comprising any of those set forth as Table 2.

The AAV particle of the disclosure comprising a targeting nucleic acid insert, may have a polynucleotide sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, identity to the parent capsid sequence.

The AAV particle of the disclosure comprising a targeting peptide insert, may have an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, identity to the parent capsid sequence.

In any of the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

Use of Targeting Peptides in AAV Particles

Targeting peptides may be stand-alone peptides or may be inserted into or conjugated to a parent sequence. In one embodiment, the targeting peptides are inserted into the capsid protein of an AAV particle.

One or more targeting peptides may be inserted into a parent AAV capsid sequence to generate the AAV particles of the disclosure.

Targeting peptides may be inserted into a parent AAV capsid sequence in any location that results in fully functional AAV particles. The targeting peptide may be inserted in VP1, VP2 and/or VP3. Numbering of the amino acid residues differs across AAV serotypes, and so the exact amino acid position of the targeting peptide insertion may not be critical. As used herein, amino acid positions of the parent AAV capsid sequence are described using AAV9 (SEQ ID NO: 2) as reference.

In one embodiment, the targeting peptides are inserted in a hypervariable region of the AAV capsid sequence. Non-limiting examples of such hypervariable regions include Loop IV and Loop VIII of the parent AAV capsid. While not wishing to be bound by theory, these surface exposed loops are unstructured and poorly conserved, making them ideal regions for insertion of targeting peptides.

In one embodiment, the targeting peptide is inserted into Loop IV. In another embodiment, the targeting peptide is used to replace a portion, or all of Loop IV. As a non-limiting example, addition of the targeting peptide to the parent AAV capsid sequence may result in the replacement or mutation of at least one amino acid of the parent AAV capsid.

In one embodiment, the targeting peptide is inserted into Loop VIII. In another embodiment, the targeting peptide is used to replace a portion, or all of Loop VIII. As a non-limiting example, addition of the targeting peptide to the parent AAV capsid sequence may result in the replacement or mutation of at least one amino acid of the parent AAV capsid.

In one embodiment, more than one targeting peptide is inserted into a parent AAV capsid sequence. As a non-limiting example, targeting peptides may be inserted at both Loop IV and Loop VIII in the same parent AAV capsid sequence.

Targeting peptides may be inserted at any amino acid position of the parent AAV capsid sequence, such as, but not limited to, between amino acids at positions 586-592, 588-589, 586-589, 452-458, 262-269, 464-473, 491-495, 546-557 and/or 659-668.

In a preferred embodiment, the targeting peptides are inserted into a parent AAV capsid sequence between amino acids at positions 588 and 589 (Loop VIII). In one embodiment, the parent AAV capsid is AAV9 (SEQ ID NO: 2). In a second embodiment, the parent AAV capsid is K449R AAV9 (SEQ ID NO: 3).

The targeting peptides described herein may increase the transduction of the AAV particles of the disclosure to a target tissue as compared to the parent AAV particle lacking a targeting peptide insert. In one embodiment, the targeting peptide increases the transduction of an AAV particle to a target tissue by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a targeting peptide insert.

In one embodiment, the targeting peptide increases the transduction of an AAV particle to a cell or tissue of the CNS by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a targeting peptide insert.

In one embodiment, the targeting peptide increases the transduction of an AAV particle to a cell or tissue of the PNS by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a targeting peptide insert.

In one embodiment, the targeting peptide increases the transduction of an AAV particle to a cell or tissue of the DRG by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500%, or more as compared to a parent AAV particle lacking a targeting peptide insert.

AAV Production

Viral production disclosed herein describes processes and methods for producing AAV particles (with enhanced, improved and/or increased tropism for a target tissue) that may be used to contact a target cell to deliver a payload.

The present disclosure provides methods for the generation of AAV particles comprising targeting peptides. In one embodiment, the AAV particles are prepared by viral genome replication in a viral replication cell. Any method known in the art may be used for the preparation of AAV particles. In one embodiment, AAV particles are produced in mammalian cells (e.g., HEK293). In another embodiment, AAV particles are produced in insect cells (e.g., Sf9)

Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.,* 219:37-44 (1996); Zhao et al., *Vir.* 272:382-93 (2000); the contents of each of which are herein incorporated by reference in their entirety. In one embodiment, the AAV particles are made using the methods described in International Patent Publication WO2015191508, the contents of which are herein incorporated by reference in their entirety.

Therapeutic Applications

The present disclosure provides a method for treating a disease, disorder and/or condition in a mammalian subject, including a human subject, comprising administering to the subject an AAV particle described herein where the AAV particle comprises the novel capsids ("TRACER AAV particles") defined by the present disclosure or administering to the subject any of the described compositions, including pharmaceutical compositions, described herein.

In one embodiment, the TRACER AAV particles of the present disclosure are administered to a subject prophylactically, to prevent on-set of disease. In another embodiment, the TRACER AAV particles of the present disclosure are administered to treat (lessen the effects of) a disease or symptoms thereof. In yet another embodiment, the TRACER AAV particles of the present disclosure are administered to cure (eliminate) a disease. In another embodiment, the TRACER AAV particles of the present disclosure are administered to prevent or slow progression of disease. In yet another embodiment, the TRACER AAV particles of the present disclosure are used to reverse the deleterious effects of a disease. Disease status and/or progression may be determined or monitored by standard methods known in the art.

In some embodiments, the TRACER AAV particles of the disclosure are useful in the field of medicine for the treatment, prophylaxis, palliation or amelioration of neurological diseases and/or disorders.

In some embodiments, the TRACER AAV particles of the disclosure are useful in the field of medicine for the treatment, prophylaxis, palliation or amelioration of tauopathy.

In some embodiments, the TRACER AAV particles of the disclosure are useful in the field of medicine for the treatment, prophylaxis, palliation or amelioration of Alzheimer's Disease.

In some embodiments, the TRACER AAV particles of the disclosure are useful in the field of medicine for the treatment, prophylaxis, palliation or amelioration of Friedreich's ataxia, or any disease stemming from a loss or partial loss of frataxin protein.

In some embodiments, the TRACER AAV particles of the disclosure are useful in the field of medicine for the treatment, prophylaxis, palliation or amelioration of Parkinson's Disease.

In some embodiments, the TRACER AAV particles of the disclosure are useful in the field of medicine for the treatment, prophylaxis, palliation or amelioration of Amyotrophic lateral sclerosis.

In some embodiments, the TRACER AAV particles of the disclosure are useful in the field of medicine for the treatment, prophylaxis, palliation or amelioration of Huntington's Disease.

In some embodiments, the TRACER AAV particles of the disclosure are useful in the field of medicine for the treatment, prophylaxis, palliation or amelioration of chronic or neuropathic pain.

In some embodiments, the TRACER AAV particles of the disclosure are useful in the field of medicine for treatment, prophylaxis, palliation or amelioration of a disease associated with the central nervous system.

In some embodiments, the TRACER AAV particles of the disclosure are useful in the field of medicine for treatment, prophylaxis, palliation or amelioration of a disease associated with the peripheral nervous system.

In one embodiment, the TRACER AAV particles of the present disclosure are administered to a subject having at least one of the diseases or symptoms described herein.

As used herein, any disease associated with the central or peripheral nervous system and components thereof (e.g., neurons) may be considered a "neurological disease".

Any neurological disease may be treated with the TRACER AAV particles of the disclosure, or pharmaceutical compositions thereof, including but not limited to, Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Bechet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbar palsy, Bulbospinal Muscular Atrophy, Cerebral Autosomal Dominant Arteriopathy with Sub-cortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Concentric sclerosis (Balo's sclerosis), Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Chronic progressive external ophtalmoplegia, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia—Multi-Infarct, Dementia—Semantic, Dementia—Subcortical, Dementia With Lewy Bodies, Demyelination diseases, Dentate Cerebellar Ataxia, Dentatorubral Atrophy, Dermatomyositis, Developmental Dyspraxia, Devic's Syndrome, Diabetic Neuropathy, Diffuse Sclerosis, Distal hereditary motor neuronopathies, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalomyelitis, Encephalopathy, Encephalopathy (familial infantile), Encephalotrigeminal Angiomatosis, Epilepsy, Epileptic Hemiplegia, Episodic ataxia, Erb's Palsy, Erb-Duchenne and Dejerine-Klumpke Palsies, Essential Tremor, Extrapontine Myelinolysis, Faber's disease, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses (GM1, GM2), Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hurler syndrome, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kluver-Bucy Syndrome, Korsakoff s Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lichtheim's disease, Lipid Storage Diseases, Lipoid Proteinosis, Lissencephaly, Locked-In Syndrome, Lou Gehrig's Disease, Lupus—Neurological Sequelae, Lyme Disease—Neurological Complications, Lysosomal storage disorders, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Mitochondrial DNA depletion syndromes, Moebius Syndrome, Monomelic Amyotrophy, Morvan Syndrome, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myelitis, Myoclonic Encephalopathy of Infants, Myoclonus, Myoclonus epilepsy, Myopathy, Myopathy—Congenital, Myopathy—Thyrotoxic, Myotonia, Myotonia Congenita, Narcolepsy, NARP (neuropathy, ataxia and retinitis pigmentosa), Neuroacanthocytosis, Neurodegeneration with Brain Iron Accumulation, Neurodegenerative disease, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathic pain, Neuropathy—Hereditary, Neuropathy, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Peroneal muscular atrophy, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive bulbar palsy, Progressive Hemifacial Atrophy, Progressive Locomotor Ataxia, Progressive Multifocal Leukoencephalopathy, Progressive Muscular Atrophy, Progressive Sclerosing Poliodystrophy, Progressive Supranuclear Palsy, Prosopagnosia, Pseudobulbar palsy, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Ataxia, Spinocerebellar Atrophy, Spinocerebellar Degeneration, Sporadic ataxia, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Vitamin B12 deficiency, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, X-Linked Spinal and Bulbar Muscular Atrophy.

Methods of Treatment of Neurological Disease

TRACER AAV Particles Encoding Protein Payloads

Provided in the present disclosure are methods for introducing the TRACER AAV particles of the present disclosure into cells, the method comprising introducing into said cells any of the vectors in an amount sufficient for an increase in the production of target mRNA and protein to occur. In some aspects, the cells may be neurons such as but not limited to, motor, hippocampal, entorhinal, thalamic, cortical, sensory, sympathetic, or parasympathetic neurons, and glial cells such as astrocytes, microglia, and/or oligodendrocytes.

Disclosed in the present disclosure are methods for treating neurological disease associated with insufficient function/presence of a target protein (e.g., ApoE, FXN) in a subject in need of treatment. The method optionally comprises administering to the subject a therapeutically effective amount of a composition comprising TRACER AAV particles of the present disclosure. As a non-limiting example, the TRACER AAV particles can increase target gene expression, increase target protein production, and thus reduce one or more symptoms of neurological disease in the subject such that the subject is therapeutically treated.

In one embodiment, the composition comprising the TRACER AAV particles of the present disclosure is administered to the central nervous system of the subject via systemic administration. In one embodiment, the systemic administration is intravenous injection.

In some embodiments, the composition comprising the TRACER AAV particles of the present disclosure is administered to the central nervous system of the subject. In other embodiments, the composition comprising the TRACER AAV particles of the present disclosure is administered to a CNS tissue of a subject (e.g., putamen, thalamus or cortex of the subject).

In one embodiment, the composition comprising the TRACER AAV particles of the present disclosure is administered to the central nervous system of the subject via intraparenchymal injection. Non-limiting examples of intraparenchymal injections include intraputamenal, intracortical, intrathalamic, intrastriatal, intrahippocampal or into the entorhinal cortex.

In one embodiment, the composition comprising the TRACER AAV particles of the present disclosure is administered to the central nervous system of the subject via intraparenchymal injection and intravenous injection.

In one embodiment, the TRACER AAV particles of the present disclosure may be delivered into specific types of targeted cells, including, but not limited to, thalamic, hippocampal, entorhinal, cortical, motor, sensory, excitatory, inhibitory, sympathetic, or parasympathetic neurons; glial cells including oligodendrocytes, astrocytes and microglia; and/or other cells surrounding neurons such as T cells.

In one embodiment, the TRACER AAV particles of the present disclosure may be delivered to neurons in the putamen, thalamus and/or cortex.

In some embodiments, the TRACER AAV particles of the present disclosure may be used as a therapy for neurological disease.

In some embodiments, the TRACER AAV particles of the present disclosure may be used as a therapy for tauopathies.

In some embodiments, the TRACER AAV particles of the present disclosure may be used as a therapy for Alzheimer's Disease.

In some embodiments, the TRACER AAV particles of the present disclosure may be used as a therapy for Amyotrophic Lateral Sclerosis.

In some embodiments, the TRACER AAV particles of the present disclosure may be used as a therapy for Huntington's Disease.

In some embodiments, the TRACER AAV particles of the present disclosure may be used as a therapy for Parkinson's Disease.

In some embodiments, the TRACER AAV particles of the present disclosure may be used as a therapy for Friedreich's Ataxia.

In some embodiments, the TRACER AAV particles of the present disclosure may be used as a therapy for chronic or neuropathic pain.

In one embodiment, administration of the TRACER AAV particles described herein to a subject may increase target protein levels in a subject. The target protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may increase the protein levels of a target protein by at least 50%. As a non-limiting example, the TRACER AAV particles may increase the proteins levels of a target protein by at least 40%. As a non-limiting example, a subject may have an increase of 10% of target protein. As a non-limiting example, the TRACER AAV particles may increase the protein levels of a target protein by fold increases over baseline. In one embodiment, TRACER AAV particles lead to 5-6 times higher levels of a target protein.

In one embodiment, administration of the TRACER AAV particles described herein to a subject may increase the expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may increase the expression of a target protein by at least 50%. As a non-limiting example, the TRACER AAV particles may increase the expression of a target protein by at least 40%.

In one embodiment, intravenous administration of the TRACER AAV particles described herein to a subject may increase the CNS expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may increase the expression of a target protein in the CNS by at least 50%. As a non-limiting example, the TRACER AAV particles may increase the expression of a target protein in the CNS by at least 40%.

In some embodiments, the TRACER AAV particles of the present disclosure may be used to increase target protein expression in astrocytes in order to treat a neurological disease. Target protein in astrocytes may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles may be used to increase target protein in microglia. The increase of target protein in microglia may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles may be used to increase target protein in cortical neurons. The increase of target protein in the cortical neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles may be used to increase target protein in hippocampal neurons. The increase of target protein in the hippocampal neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles may be used to increase target protein in DRG and/or sympathetic neurons. The increase of target protein in the DRG and/or sympathetic neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles of the present disclosure may be used to increase target protein in sensory neurons in order to treat neurological disease. Target protein in sensory neurons may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the TRACER AAV particles of the present disclosure may be used to increase target protein and reduce symptoms of neurological disease in a subject. The increase of target protein and/or the reduction of symptoms of neurological disease may be, independently, altered (increased for the production of target protein and reduced for the symptoms of neurological disease) by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles of the present disclosure may be used to reduce the decline of functional capacity and activities of daily living as measured by a standard evaluation system such as, but not limited to, the total functional capacity (TFC) scale.

In one embodiment, the TRACER AAV particles of the present disclosure may be used to improve performance on any assessment used to measure symptoms of neurological disease. Such assessments include, but are not limited to ADAS-cog (Alzheimer Disease Assessment Scale—cognitive), MNISE (Mini-Mental State Examination), GDS (Geriatric Depression Scale), FAQ (Functional Activities Questionnaire), ADL (Activities of Daily Living), GPCOG (General Practitioner Assessment of Cognition), Mini-Cog, AMTS (Abbreviated Mental Test Score), Clock-drawing test, 6-CIT (6-item Cognitive Impairment Test), TYM (Test Your Memory), MoCa (Montreal Cognitive Assessment), ACE-R (Addenbrookes Cognitive Assessment), MIS (Memory Impairment Screen), BADLS (Bristol Activities of Daily Living Scale), Barthel Index, Functional Independence Measure, Instrumental Activities of Daily Living, IQCODE (Informant Questionnaire on Cognitive Decline in the Elderly), Neuropsychiatric Inventory, The Cohen-Mansfield Agitation Inventory, BEHAVE-AD, EuroQol, Short Form-36 and/or MBR Caregiver Strain Instrument, or any of the other tests as described in Sheehan B (Ther Adv Neurol Disord. 5(6):349-358 (2012)), the contents of which are herein incorporated by reference in their entirety.

In some embodiments, the present composition is administered as a solo therapeutic or as combination therapeutic for the treatment of neurological disease.

The TRACER AAV particles encoding the target protein may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the TRACER AAV particles of the present disclosure can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation. As a non-limiting example, the combination therapy may be in combination with one or more neuroprotective agents such as small molecule compounds, growth factors and hormones which have been tested for their neuroprotective effect on motor neuron degeneration.

Compounds tested for treating neurological disease which may be used in combination with the TRACER AAV particles described herein include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3 (3 (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the TRACER AAV particles of the present disclosure for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the TRACER AAV particle described herein may be co-administered with TRACER AAV particles expressing neurotrophic factors such as AAV-IGF-I (See e.g., Vincent et al., *Neuromolecular medicine,* 2004, 6, 79-85; the contents of which are incorporated herein by reference in their entirety) and AAV-GDNF (See e.g., Wang et al., *J Neurosci.,* 2002, 22, 6920-6928; the contents of which are incorporated herein by reference in their entirety).

In one embodiment, administration of the TRACER AAV particles to a subject will increase the expression of a target protein in a subject and the increase of the expression of the target protein will reduce the effects and/or symptoms of neurological disease in a subject.

As a non-limiting example, the target protein may be an antibody, or fragment thereof.

TRACER AAV Particles Comprising RNAi Agents or Modulatory Polynucleotides

Provided in the present disclosure are methods for introducing the TRACER AAV particles of the disclosure, comprising a viral genome with a nucleic acid sequence encoding one or more siRNA molecules into cells, the method comprising introducing into said cells any of the vectors in an amount sufficient for degradation of a target mRNA to occur, thereby activating target-specific RNAi in the cells. In some aspects, the cells may be neurons such as but not limited to, motor, hippocampal, entorhinal, thalamic, cortical, sensory, sympathetic, or parasympathetic neurons, and glial cells such as astrocytes, microglia, and/or oligodendrocytes.

Disclosed in the present disclosure are methods for treating neurological diseases associated with dysfunction of a target protein in a subject in need of treatment. The method optionally comprises administering to the subject a therapeutically effective amount of a composition comprising TRACER AAV particles comprising a viral genome with a nucleic acid sequence encoding one or more siRNA molecules. As a non-limiting example, the siRNA molecules can silence target gene expression, inhibit target protein production, and reduce one or more symptoms of neurological disease in the subject such that the subject is therapeutically treated.

In some embodiments, the composition comprising the TRACER AAV particles of the present disclosure comprising a viral genome encoding one or more siRNA molecules comprise an AAV capsid that allows for enhanced transduction of CNS and/or PNS cells after intravenous administration.

In some embodiments, the composition comprising the TRACER AAV particles of the present disclosure with a viral genome encoding at least one siRNA molecule is administered to the central nervous system of the subject. In other embodiments, the composition comprising the TRACER AAV particles of the present disclosure is administered to a tissue of a subject (e.g., putamen, thalamus or cortex of the subject).

In one embodiment, the composition comprising the TRACER AAV particles of the disclosure, comprising a viral genome with a nucleic acid sequence encoding one or more siRNA molecules is administered to the central nervous system of the subject via systemic administration. In one embodiment, the systemic administration is intravenous injection.

In one embodiment, the composition comprising the TRACER AAV particles of the disclosure comprising a viral genome with a nucleic acid sequence encoding one or more siRNA molecules is administered to the central nervous system of the subject via intraparenchymal injection. Non-limiting examples of intraparenchymal injections include intraputamenal, intracortical, intrathalamic, intrastriatal, intrahippocampal or into the entorhinal cortex.

In one embodiment, the composition comprising the TRACER AAV particles comprising a viral genome with a nucleic acid sequence encoding one or more siRNA molecules is administered to the central nervous system of the subject via intraparenchymal injection and intravenous injection.

In one embodiment, the TRACER AAV particles comprising a viral genome with a nucleic acid sequence encoding one or more siRNA molecules may be delivered into specific types or targeted cells, including, but not limited to, thalamic, hippocampal, entorhinal, cortical, motor, sensory, excitatory, inhibitory, sympathetic, or parasympathetic neurons; glial cells including oligodendrocytes, astrocytes and microglia; and/or other cells surrounding neurons such as T cells.

In one embodiment, the TRACER AAV particles comprising a viral genome with a nucleic acid sequence encoding one or more siRNA molecules may be delivered to neurons in the putamen, thalamus, and/or cortex.

In one embodiment, the TRACER AAV particles comprising a viral genome with a nucleic acid sequence encoding one or more siRNA molecules may be used as a therapy for neurological disease.

In one embodiment, the TRACER AAV particles comprising a viral genome with a nucleic acid sequence encoding one or more siRNA molecules may be used as a therapy for tauopathies.

In one embodiment, the TRACER AAV particles comprising a viral genome with a nucleic acid sequence encoding one or more siRNA molecules may be used as a therapy for Alzheimer's Disease.

In one embodiment, the TRACER AAV particles comprising a viral genome with a nucleic acid sequence encoding one or more siRNA molecules may be used as a therapy for Amyotrophic Lateral Sclerosis.

In one embodiment, the TRACER AAV particles comprising a viral genome with a nucleic acid sequence encoding one or more siRNA molecules may be used as a therapy for Huntington's Disease.

In one embodiment, the TRACER AAV particles comprising a viral genome with a nucleic acid sequence encoding one or more siRNA molecules may be used as a therapy for Parkinson's Disease.

In one embodiment, the TRACER AAV particles comprising a viral genome with a nucleic acid sequence encoding one or more siRNA molecules may be used as a therapy for Friedreich's Ataxia.

In one embodiment, the administration of TRACER AAV particles comprising a viral genome with a nucleic acid sequence encoding one or more siRNA molecules to a subject may lower target protein levels in a subject. The target protein levels may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may lower the protein levels of a target protein by at least 50%. As a non-limiting example, the TRACER AAV particles may lower the proteins levels of a target protein by at least 40%.

In one embodiment, the administration of TRACER AAV particles comprising a viral genome with a nucleic acid sequence encoding one or more siRNA molecules to a subject may lower the expression of a target protein in a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may lower the expression of a target protein by at least 50%. As a non-limiting example, the TRACER AAV particles may lower the expression of a target protein by at least 40%.

In one embodiment, the administration of TRACER AAV particles comprising a viral genome with a nucleic acid sequence encoding one or more siRNA molecules to a subject may lower the expression of a target protein in the CNS of a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the TRACER AAV particles may lower the expression of a target protein by at least 50%. As a non-limiting example, the TRACER AAV particles may lower the expression of a target protein by at least 40%.

In one embodiment, the TRACER AAV particles comprising a viral genome with a nucleic acid sequence encoding one or more siRNA molecules may be used to suppress a target protein in astrocytes in order to treat neurological disease. Target protein in astrocytes may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in astrocytes may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress a target protein in microglia. The suppression of the target protein in microglia may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress target protein in cortical neurons. The suppression of a target protein in cortical neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress a target protein in hippocampal neurons. The suppression of a target protein in the hippocampal neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress a target protein in DRG and/or sympathetic neurons. The suppression of a target protein in the DRG and/or sympathetic neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5- 70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5- 70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress a target protein in sensory neurons in order to treat neurological disease. Target protein in sensory neurons may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in the sensory neurons may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5- 70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to suppress a target protein and reduce symptoms of neurological disease in a subject. The suppression of target protein and/or the reduction of symptoms of neurological disease may be, independently, reduced or suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the TRACER AAV particles comprising a viral genome with a nucleic acid sequence encoding one or more siRNA molecules may be used to reduce the decline of functional capacity and activities of daily living as measured by a standard evaluation system such as, but not limited to, the total functional capacity (TFC) scale.

In some embodiments, the present composition is administered as a solo therapeutic or as combination therapeutic for the treatment of neurological disease.

The TRACER AAV particles comprising a viral genome with a nucleic acid sequence encoding one or more siRNA molecules may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the TRACER AAV particles comprising a viral genome with a nucleic acid sequence encoding one or more siRNA molecules can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation.

Compounds tested for treating neurological disease which may be used in combination with the TRACER AAV particles comprising a viral genome with a nucleic acid sequence encoding one or more siRNA molecules include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the TRACER AAV particles comprising a viral genome with a nucleic acid sequence encoding one or more siRNA molecules for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the TRACER AAV particle encoding the nucleic acid sequence for the at least one siRNA duplex targeting the gene of interest may be co-administered with TRACER AAV particles expressing neurotrophic factors such as AAV-IGF-I (See e.g., Vincent et al., *Neuromolecular medicine,* 2004, 6, 79-85; the content of which is incorporated herein by reference in its entirety) and AAV-GDNF (See e.g., Wang et al., *J Neurosci.,* 2002, 22, 6920-6928; the contents of which are incorporated herein by reference in their entirety).

In one embodiment, administration of the TRACER AAV particles to a subject will reduce the expression of a target protein in a subject and the reduction of expression of the target protein will reduce the effects and/or symptoms of neurological disease in a subject.

Definitions

Adeno-associated virus: As used herein, the term "adeno-associated virus" or "AAV" refers to members of the *Dependovirus* genus comprising any particle, sequence, gene, protein, or component derived therefrom.

AAV Particle: As used herein, an "AAV particle" is a virus which comprises a capsid and a viral genome with at least one payload region and at least one ITR. As used herein "AAV particles of the disclosure" are AAV particles comprising a parent capsid sequence with at least one targeting peptide insert. AAV particles of the present disclosure may be produced recombinantly and may be based on adeno-associated virus (AAV) parent or reference sequences. AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted. In one embodiment, the AAV particle may have a targeting peptide inserted into the capsid to enhance tropism for a desired target tissue. It is to be understood that reference to the AAV particles of the disclosure also includes pharmaceutical compositions thereof, even if not explicitly recited.

Administering: As used herein, the term "administering" refers to providing a pharmaceutical agent or composition to a subject.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of a gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Capsid: As used herein, the term "capsid" refers to the protein shell of a virus particle.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenine. However, when a U is denoted in the context of the present disclosure, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form a hydrogen bond with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Control Elements: As used herein, "control elements", "regulatory control elements" or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Delivery: As used herein, "delivery" refers to the act or manner of delivering an AAV particle, a compound, substance, entity, moiety, cargo or payload.

Element: As used herein, the term "element" refers to a distinct portion of an entity. In some embodiments, an element may be a polynucleotide sequence with a specific purpose, incorporated into a longer polynucleotide sequence.

Encapsulate: As used herein, the term "encapsulate" means to enclose, surround or encase. As an example, a capsid protein often encapsulates a viral genome.

Engineered: As used herein, embodiments of the disclosure are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least one AAV particle (active ingredient) and an excipient, and/or an inactive ingredient.

Fragment: A "fragment," as used herein, refers to a portion. For example, an antibody fragment may comprise a CDR, or a heavy chain variable region, or a scFv, etc.

Functional: As used herein, a "functional" biological molecule is a biological molecule in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; the contents of each of which are incorporated herein by reference in their entirety. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

Insert: As used herein the term "insert" may refer to the addition of a targeting peptide sequence to a parent AAV capsid sequence. An "insertion" may result in the replacement of one or more amino acids of the parent AAV capsid sequence. Alternatively, an insertion may result in no changes to the parent AAV capsid sequence beyond the addition of the targeting peptide sequence.

Inverted terminal repeat: As used herein, the term "inverted terminal repeat" or "ITR" refers to a cis-regulatory element for the packaging of polynucleotide sequences into viral capsids.

Library: As used herein, the term "library" refers to a diverse collection of linear polypeptides, polynucleotides, viral particles, or viral vectors. As examples, a library may be a DNA library or an AAV capsid library.

Neurological disease: As used herein, a "neurological disease" is any disease associated with the central or peripheral nervous system and components thereof (e.g., neurons).

Naturally Occurring: As used herein, "naturally occurring" or "wild-type" means existing in nature without artificial aid, or involvement of the hand of man.

Open reading frame: As used herein, "open reading frame" or "ORF" refers to a sequence which does not contain a stop codon in a given reading frame.

Parent sequence: As used herein, a "parent sequence" is a nucleic acid or amino acid sequence from which a variant is derived. In one embodiment, a parent sequence is a sequence into which a heterologous sequence is inserted. In other words, a parent sequence may be considered an acceptor or recipient sequence. In one embodiment, a parent sequence is an AAV capsid sequence into which a targeting sequence is inserted.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition.

Payload region: As used herein, a "payload region" is any nucleic acid sequence (e.g., within the viral genome) which encodes one or more "payloads" of the disclosure. As non-limiting examples, a payload region may be a nucleic acid sequence within the viral genome of an AAV particle, which encodes a payload, wherein the payload is an RNAi agent or a polypeptide. Payloads of the present disclosure may be, but are not limited to, peptides, polypeptides, proteins, antibodies, RNAi agents, etc.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preventing: As used herein, the term "preventing" or "prevention" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini.

In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and/or 3' termini.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interfering or RNAi: As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

RNAi agent: As used herein, the term "RNAi agent" refers to an RNA molecule, or its derivative, that can induce inhibition, interfering, or "silencing" of the expression of a target gene and/or its protein product. An RNAi agent may knock-out (virtually eliminate or eliminate) expression, or knock-down (lessen or decrease) expression. The RNAi agent may be, but is not limited to, dsRNA, siRNA, shRNA, pre-miRNA, pri-miRNA, miRNA, stRNA, lncRNA, piRNA, or snoRNA.

Sample: As used herein, the term "sample" or "biological sample" refers to a subset of its tissues, cells or component parts (e.g. body fluids, including but not limited to blood, serum, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Self-complementary viral particle: As used herein, a "self-complementary viral particle" is a particle comprised of at least two components, a protein capsid and a self-complementary viral genome enclosed within the capsid.

Sense Strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Short interfering RNA or siRNA: As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called an siRNA duplex.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Targeting peptide: As used herein, a "targeting peptide" refers to a peptide of 3-20 amino acids in length. These targeting peptides may be inserted into, or attached to, a parent amino acid sequence to alter the characteristics (e.g., tropism) of the parent protein. As a non-limiting example, the targeting peptide can be inserted into an AAV capsid sequence for enhanced targeting to a desired cell-type, tissue, organ or organism. It is to be understood that a targeting peptide is encoded by a targeting polynucleotide which may similarly be inserted into a parent polynucleotide sequence. Therefore, a "targeting sequence" refers to a peptide or polynucleotide sequence for insertion into an appropriate parent sequence (amino acid or polynucleotide, respectively).

Target Cells: As used herein, "target cells" or "target tissue" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Vector: As used herein, the term "vector" refers to any molecule or moiety which transports, transduces or otherwise acts as a carrier of a heterologous molecule. In some embodiments, vectors may be plasmids. In some embodiments, vectors may be viruses. An AAV particle is an example of a vector. Vectors of the present disclosure may be produced recombinantly and may be based on and/or may comprise adeno-associated virus (AAV) parent or reference sequences. The heterologous molecule may be a polynucleotide and/or a polypeptide.

Viral Genome: As used herein, the terms "viral genome" or "vector genome" refer to the nucleic acid sequence(s) encapsulated in an AAV particle. A viral genome comprises a nucleic acid sequence with at least one payload region encoding a payload and at least one ITR.

Equivalents and Scope

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

The present disclosure is further illustrated by the following non-limiting examples.

EXAMPLES

Example 1. TRACER Proof of Concept: Promoter Selection

Proof-of-concept experiments were conducted by placing the genes encoding an AAV9 peptide display capsid library under the control of either the neuron-specific synapsin promoter (SYN) or the astrocyte-specific GFAP promoter. Following intravenous administration to C57BL/6 mice, RNA was recovered from brain tissue and used for further library evolution. Next-generation sequencing (NGS) showed sequence convergence between animals after only two rounds of selection. Interestingly, several variants highly similar to the PHP.eB capsid were recovered, suggesting that our method allowed a rapid selection of high-performance capsids. A subset of capsids having peptide sequences with high CNS enrichment was selected for further study. It is understood that any promoter may be selected depending on the desired tropism. Examples of such promoters are found in Table 3.

TABLE 3

Promoters, tissue and cell type

| Promoter name | Tissue | Cell type |
|---|---|---|
| B29 promoter | Blood | B cells |
| Immunoglobulin heavy chain promoter | Blood | B cells |
| CD45 promoter | Blood | Hematopoietic |
| Mouse INF-β promoter | Blood | Hematopoietic |
| CD45 SV40/CD45 promoter | Blood | Hematopoietic |
| WASP promoter | Blood | Hematopoietic |
| CD43 promoter | Blood | Leuko & Platelets |
| CD43 SV40/CD43 promoter | Blood | Leuko & Platelets |
| CD68 promoter | Blood | Macrophages |
| GPIIb promoter | Blood | Megakaryocyte |
| CD14 promoter | Blood | Monocytes |
| CD2 promoter | Blood | T cells |
| Osteocalcin | Bone | Osteoblasts |
| Bone sialoprotein | Bone | Osteoblasts |
| OG-2 promoter | Bone | Osteoblasts, odontoblasts |
| GFAP promoter | Brain | Astrocytes |
| Vga | Brain | GABAergic neurons |
| Vglut2 | Brain | glutamatergic neurons |
| NSE/RU5' promoter | Brain | Neurons |
| SYN1 promoter | Brain | Neurons |
| Neurofilament light chain | Brain | Neurons |
| VGF | Brain | Neurons |
| Nestin | Brain | NSC |
| Chx10 | Eye | All retinal neurons |
| PrP | Eye | All retinal neurons |
| Dkk3 | Eye | All retinal neurons |

TABLE 3-continued

| Promoters, tissue and cell type | | |
|---|---|---|
| Promoter name | Tissue | Cell type |
| Math5 | Eye | Amacrine and horizontal cells |
| Ptf1a | Eye | Amacrine and horizontal cells |
| Pcp2 | Eye | Bipolar cells |
| Nefh | Eye | Ganglion cells |
| gamma-synuclein gene (SNCG) | Eye | ganglion cells |
| Grik4 | Eye | GC |
| Pdgfra | Eye | GC and ONL Müller cells |
| Chat | Eye | GC/Amacrine cells |
| Thy 1.2 | Eye | GC/neural retina |
| hVmd2 | Eye | INL Müller cells |
| Thy 1 | Eye | INL Müller cells |
| Modified αA-crystallin | Eye | Lens/neural retina |
| hRgp | Eye | M- and S-cone |
| mMo | Eye | M-cone |
| Opn4 | Eye | Melanopsin-expressing GC |
| RLBP1 | Eye | Muller cells |
| Glast | Eye | Müller cells |
| Foxg1 | Eye | Müller cells |
| hVmd2 | Eye | Müller cells/optic nerve/ INL |
| Trp1 | Eye | Neural retina |
| Six3 | Eye | Neural retina |
| cx36 | Eye | Neurons |
| Grm6 - SV40 eukaryotic promoter | Eye | ON bipolar |
| hVmd2 | Eye | Optic nerve |
| Dct | Eye | Pigmented cells |
| Rpe65 | Eye | Retinal pigment epithelium |
| mRho | Eye | Rod |
| Irbp | Eye | Rod |
| hRho | Eye | Rod |
| Pcp2 | Eye | Rod bipolar cells |
| Rhodopsin | Eye | Rod Photoreceptors |
| mSo | Eye | S-cone |
| MLC2v promoter | Heart | Cardiomyocyte |
| αMHC promoter | Heart | Cardiomyocyte |
| rat troponin T (Tnnt2) | Heart | Cardiomyocyte |
| Tie2 | Heart | Endothelial |
| Tcf21 | Heart | Fibroblasts |
| ECAD | Kidney | Collecting duct |
| NKCC2 | Kidney | Loop of Henle |
| KSPC | Kidney | Nephron |
| NPHS1 | Kidney | Podocyte |
| SGLT2 | Kidney | Proximal tubular cells |
| SV40/bAlb promoter | Liver | hepatocytes |
| SV40/hAlb promoter | Liver | hepatocytes |
| Hepatitis B virus core promoter | Liver | hepatocytes |
| Alpha fetoprotein | Liver | hepatocytes |
| Surfactant protein B promoter | Lung | AT II cells and Clara cells |
| Surfactant protein C promoter | Lung | AT II cells and Clara cells |
| Desmin | Muscle | Muscle stem cells + Myocytes |
| Mb promoter | Muscle | Myocyte |
| Myosin | Muscle | Myocyte |
| Dystrophin | Muscle | Myocyte |
| dMCK and tMCK | Muscle | Myocytes |
| Elastase-1 promoter | Pancreas | Acinar cells |
| PDX1 promoter | Pancreas | Beta cells |
| Insulin promoter | Pancreas | langherans |
| Slco1c1 | Vasculature | BBB Endothelial |
| tie | Vasculature | Endothelial |
| cadherin | Vasculature | Endothelial |
| ICAM-2 | Vasculature | Endothelial |
| claudin 1 | Vasculature | Endothelial |
| Cldn5 | Vasculature | Endothelial |
| Flt-1 promoter | Vasculature | Endothelial |
| Endoglin promoter | Vasculature | Endothelial |

Capsid pools were injected to three rodent species, followed by RNA enrichment analysis for characterization of transduction efficiency in neurons or astrocytes and cross-species performance. Top-ranking capsids were then individually tested and several variants showed CNS transduction similar to or higher than the PHP.eB benchmark. These results suggest that the TRACER platform allows rapid in vivo evolution of AAV capsids in non-transgenic animals with a high degree of tropism improvement. The following examples illustrate the findings in more detail.

Figure 1B:
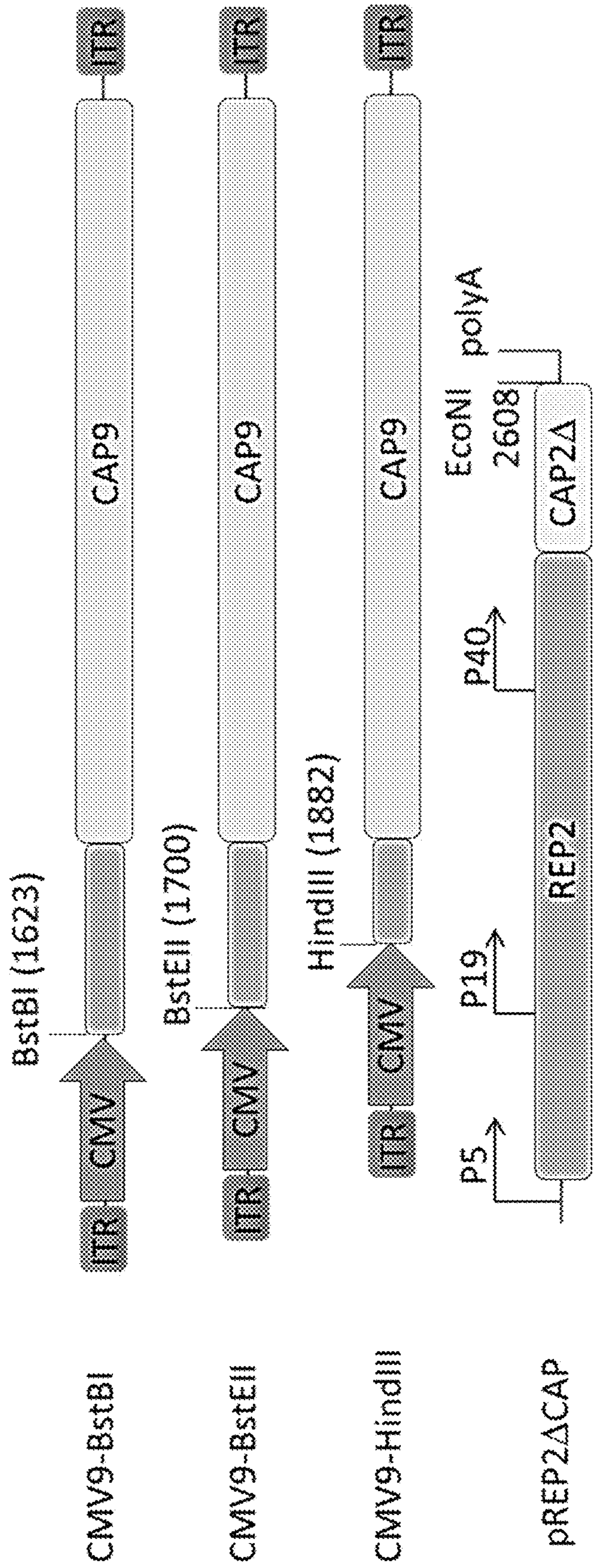
Figure 2A:
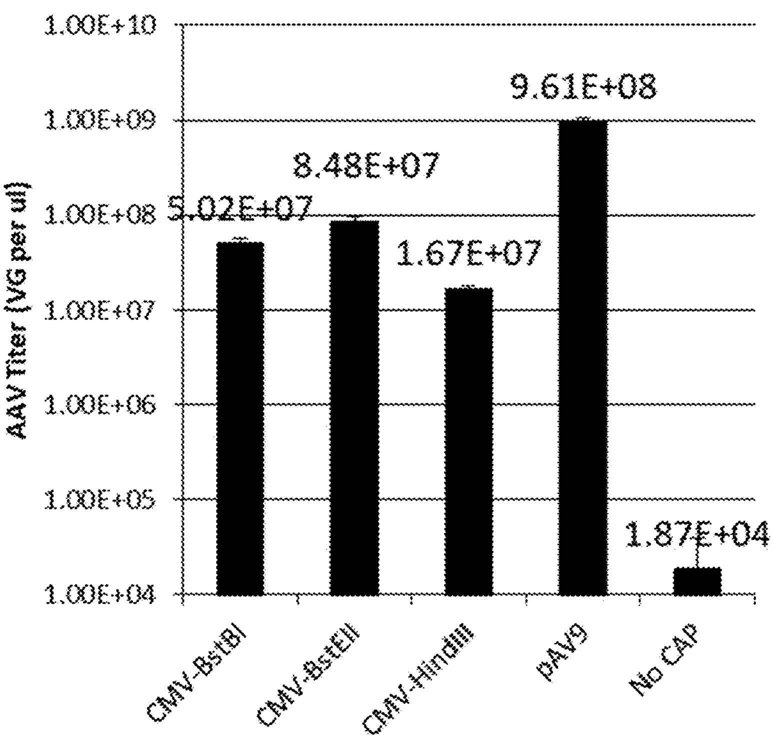
FIG. 2A and FIG. 2B are histogram representations of the data and show the effect of CMV promoter position on virus yield and CAP mRNA splicing.
Figure 2B:
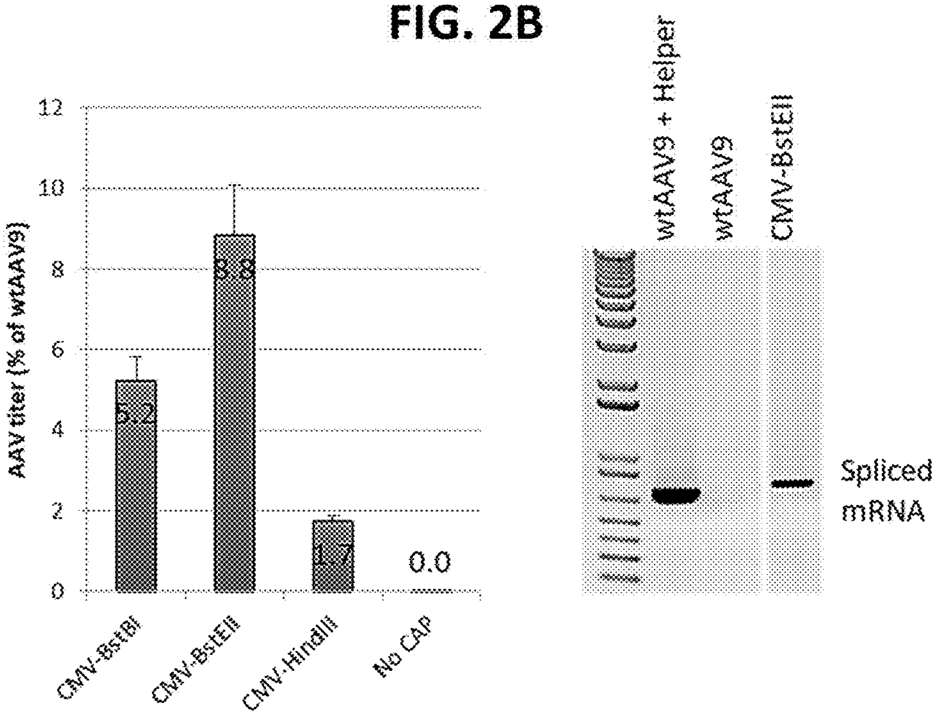

Example 2. Generation of an AAV Vectors Capable of Capsid mRNA Expression in the Absence of Helper Virus In order to perform cell type- and transduction-restricted in vivo evolution of AAV capsid libraries, a capsid library system was engineered in which the capsid mutant gene can be transcribed in the absence of a helper virus, in a specific cell type. In the wild-type AAV virus, the mRNA encoding the capsid proteins VP1, VP2 and VP3, as well as the AAP accessory protein, are expressed by the P40 promoter located in the 3' region of the REP gene (FIG. 1A), that is only active in the presence of the REP protein as well as the helper virus functions (Berns et al., 1996). In order to allow expression of the capsid mRNA in animal tissue or in cultured cells, another promoter must be inserted upstream or downstream of the CAP gene. Because of the limited packaging capacity of the AAV capsid, a portion of the REP gene must be deleted to accommodate the extra promoter insertion, and the REP gene has to be provided in trans by another plasmid to allow virus production. The minimal viral sequence required for high titer AAV production was determined by introducing a CMV promoter at various locations upstream of the CAP gene of AAV9 (FIG. 1B). The REP protein was provided in trans by the pREP2 plasmid obtained by deleting the CAP gene from a REP2-CAP2 packaging vector using EcoNI and ClaI (SEQ. ID NO:4). For small-scale virus production test, HEK-293T cells grown in DMEM supplemented with 5% FBS and 1× pen/strep were plated in 15-cm dishes and co-transfected with 15 ug of pHelper (pFdelta6) plasmid, 10 ug pREP2 plasmid and 1 ug ITR-CMV-CAP plasmid using calcium phosphate transfection. After 72 hours, cells were harvested by scraping, pelleted by a brief centrifugation and suspended in 1 ml of a buffer containing 10 mM Tris and 2 mM MgCl2. Cells were lysed by addition of triton X-100 to 0.1% final concentration and treated with 50U of benzonase for 1 hour. Virus from the supernatants was precipitated with 8% polyethylene glycol and 0.5M NaCl, suspended in 1 ml of 10 mM TRIS-2 mM MgCl2 and combined with the cell lysate. The pooled virus was adjusted to 0.5M NaCl, cleared by centrifugation for 15 minutes at 4,000×g and fractionated on a step iodixanol gradient of 15%, 25%, 40% and 60% for 3 hours at 40,000 prm (Zolotukhin et al., 1999). The 40% fraction containing the purified AAV particles was harvested and viral titers were measured by real-time PCR using a Taqman primer/probe mix specific for the 3'-end of REP, shared by all the constructs. Virus yields were significantly lower than the fully wild-type ITR-REP2-CAP9-ITR used as a reference (1.7% to 8.8%), but the CMV-BstEII construct allowed the highest yields of all three CMV constructs. See FIG. 2. The CMV-HindIII construct, in which most of the P40 promoter sequence is deleted, generated the lowest yield (1.7% of wtAAV9), indicating that even the potent CMV promoter cannot replace the P40 promoter without a severe drop in virus yields. Following these observations, the BstEII architecture (SEQ. ID NO:5), which preserves the minimal P40 sequence and the CAP mRNA splice donor, was used in all further experiments.

The REP-expressing plasmid was then improved by preserving the AAP reading frame together with a large portion of the capsid gene from the REP2-CAP9 helper vector, which may contain sequences necessary for the regulation of CAP transcription and/or splicing. In order to eliminate the capsid coding potential of the vector, a C-terminus fragment of the capsid gene was deleted by a triple cut with the MscI restriction enzyme followed by self-ligation, in order to obtain the pREP-AAP plasmid (FIG. 3A, SEQ. ID NO:6).

Figure 3A:
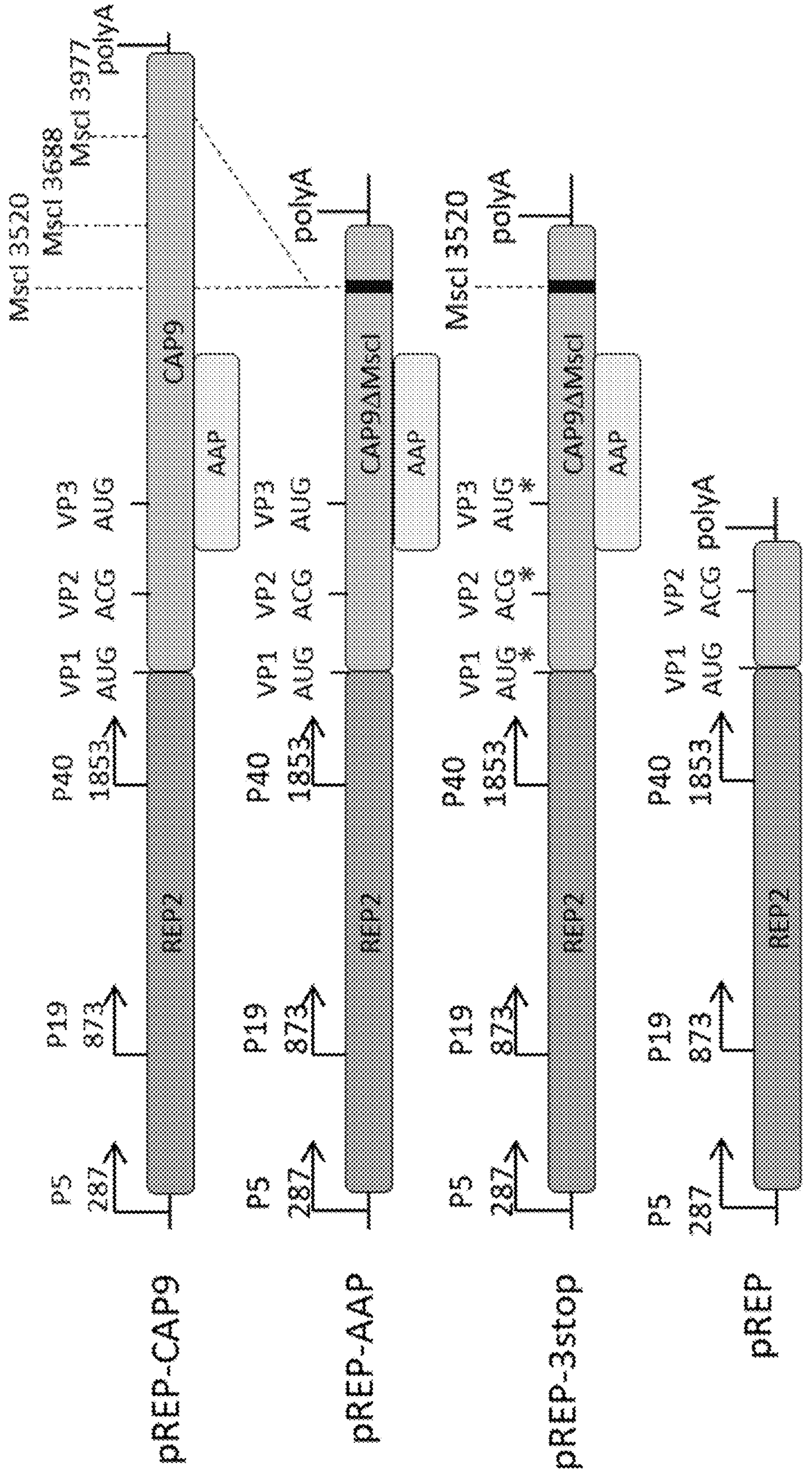
FIG. 3A, FIG. 3B and FIG. 3C show the effect of REP helper plasmid optimization on virus yield.

An iteration of this construct was engineered by introducing premature stop codons immediately after the start codons of VP1, VP2 and VP3, without perturbing the amino acid sequence of the colinear AAP reading frame (FIG. 3A). This construct was named pREP-3stop (SEQ. ID NO:7). A neuron-specific syn-CAPS vector (SEQ. ID NO:8) was derived from the CMV9-BstEII plasmid by swapping the CMV promoter with the neuron-specific human synapsin 1 promoter.

Figure 3B:
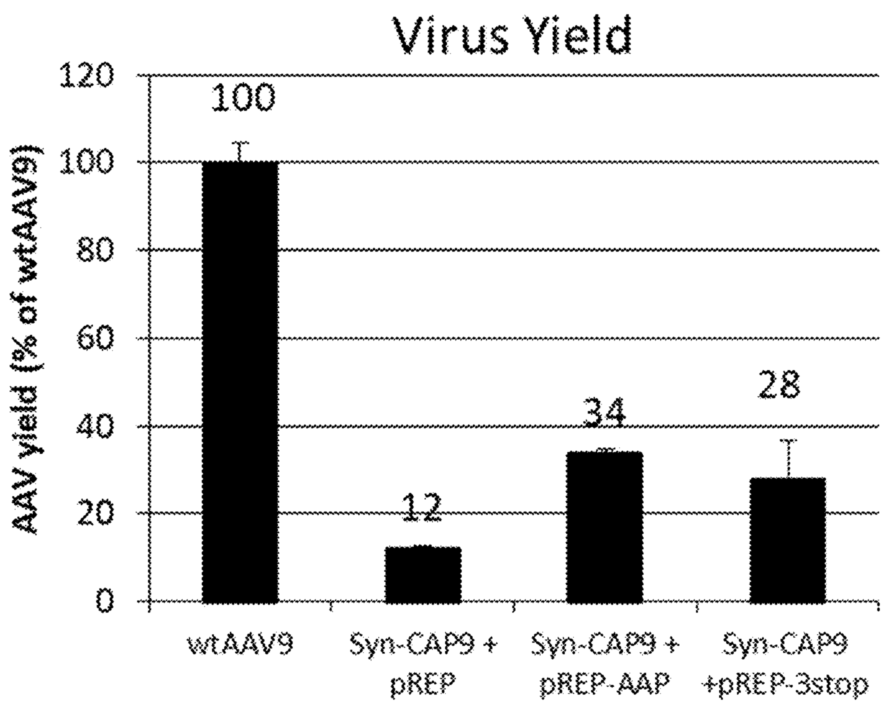

Production efficiency of this Syn-CAPS was tested as described previously using pREP, pREP-AAP or pREP-3stop plasmid to supply REP in trans. As shown in FIG. 3B, the REP plasmids harboring a longer capsid sequence as well as AAP increased virus yields by approximately 3-fold compared to the pREP plasmid. Virus titers obtained with the pREP-AAP or pREP-3stop vectors reached ~30% of wild-type AAV9. An important concern with plasmids harboring long homologous regions is the potential for unwanted recombination with the ITR-CAP vector, that would reconstitute a wild-type ITR-REP-CAP vector and contaminate combinatorial libraries.

Figure 3C:
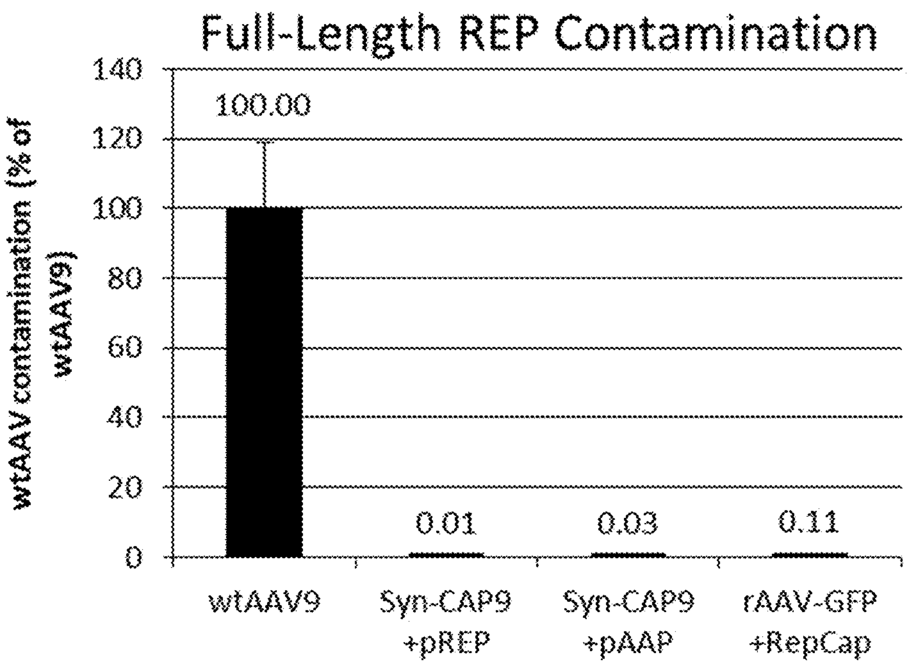

To evaluate the risk of wild-type virus reconstitution, the viral preparations obtained in FIG. 3B were subjected to real-time PCR with a Taqman probe located in the N terminus of REP. The percentage of capsids containing a detectable full-length REP was less than 0.03% of wild-type virus (FIG. 3C), which was even lower than the routinely detected 0.1% illegitimate REP-CAP packaging occurring in most recombinant AAV preparations obtained from 293T cell transfection (FIG. 3C, our unpublished observations). Because the premature stop codons of the pREP-3 stop vector offer an extra layer of safety against potential reconstitution of wild-type capsids and prevents the translation of truncated capsid proteins, the 3stop plasmid was used for all subsequent studies.

Figure 4A:
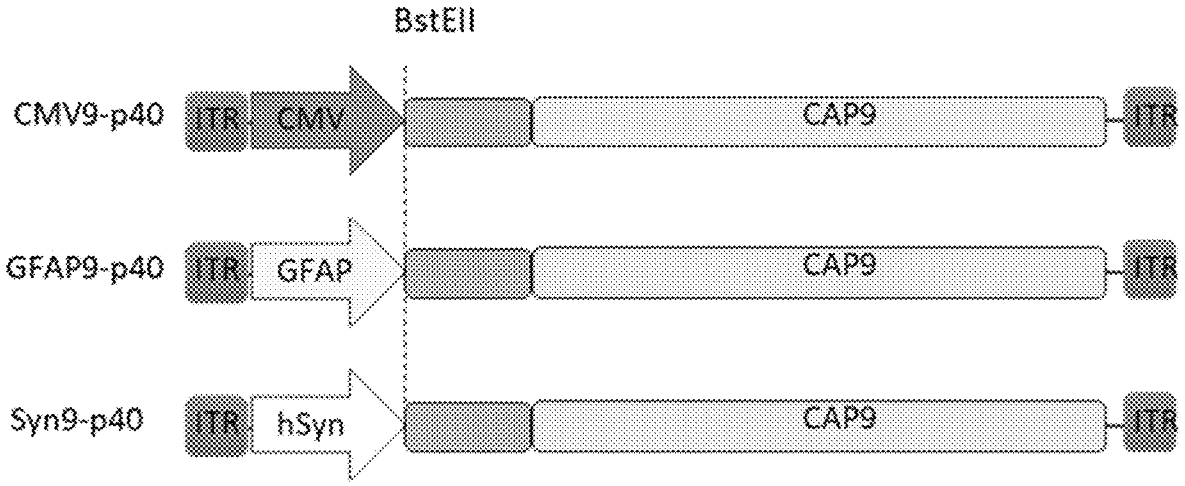
FIG. 4A, FIG. 4B, FIG. 4C and FIG. 4D describe the in vivo analysis of the second-generation vectors.
Figure 4B:
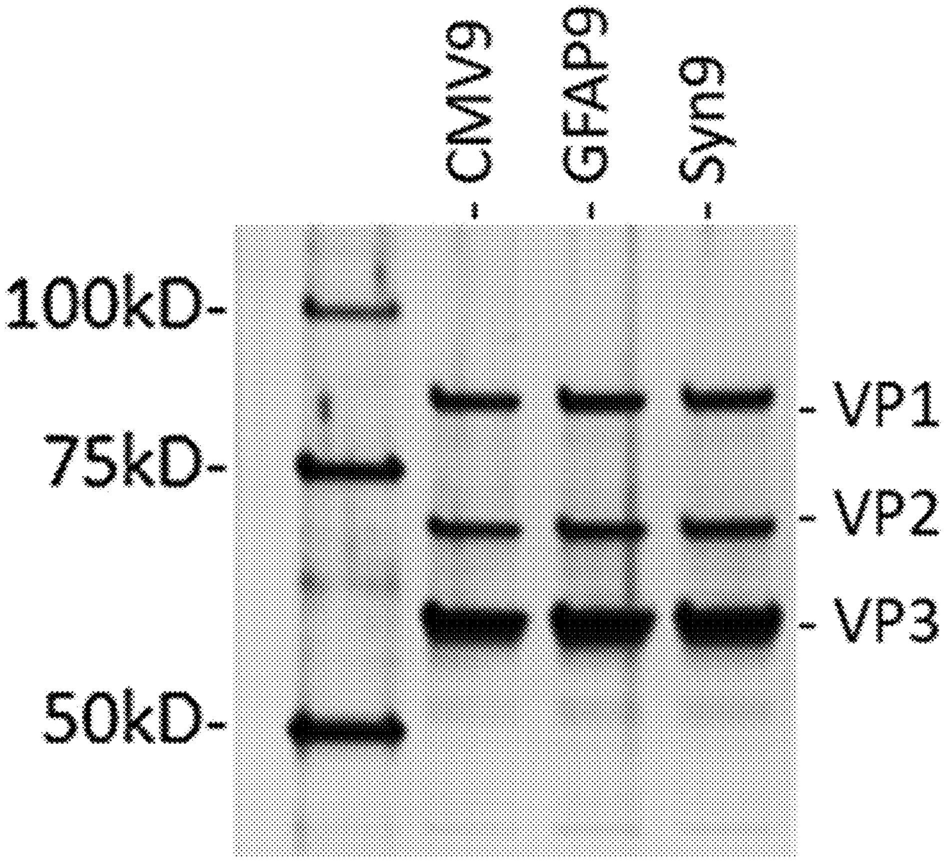

Following this, the feasibility of RNA-driven biopanning in C57BL/6 mice using AAV9-packaged vectors where the AAV9 capsid gene is driven by the CMV promoter, the Synapsin promoter or the astrocyte-specific GFabc1D promoter (SEQ. ID NO:9), thereafter referred to as GFAP promoter (Brenner et al., 2008) was tested (FIG. 4A). The three vectors were produced in HEK-293T cells as previously described and analyzed by PAGE-silver stain. As shown in FIG. 4B, all vectors showed a normal ratio of VP1, VP2 and VP3 capsid proteins, indicating that the particular promoter architecture does not disrupt the balance of capsid protein expression. Six-week old male C57BL/6 mice were injected intravenously with 1e12 VG per mouse and sacrificed after 28 days. DNA biodistribution and capsid mRNA expression were tested in the brain, liver and heart tissues.

Figure 4C:
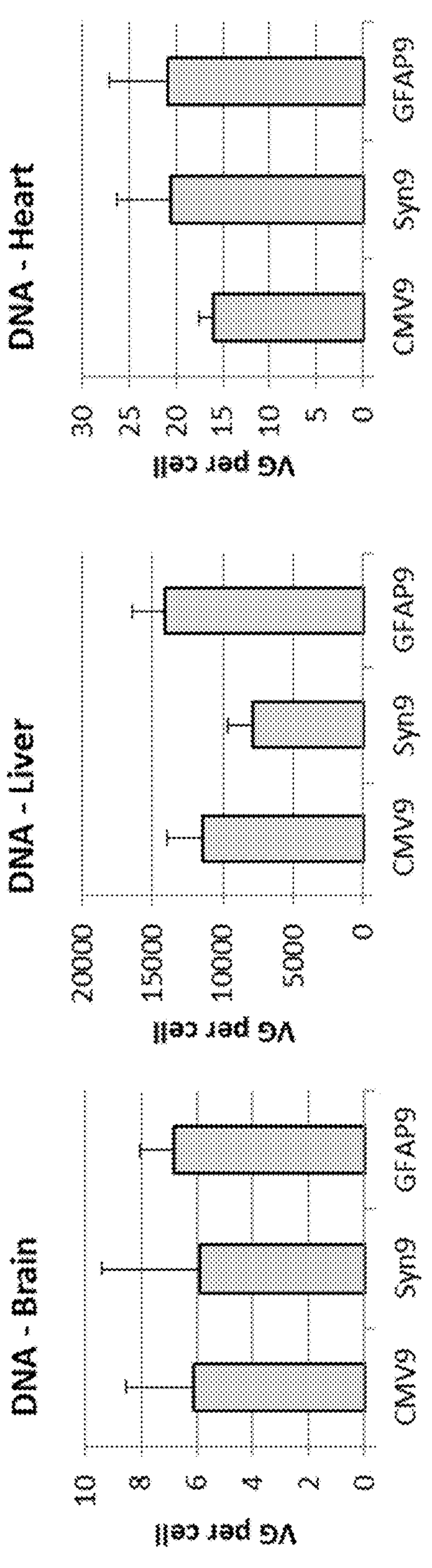

Total DNA was extracted from brain, liver and heart tissues using Qiagen DNeasy Blood and Tissue columns, and viral DNA was quantified by real-time PCR using a Taqman probe located in the VP3 N-terminal region. DNA abundance was normalized using a pre-designed probe detecting the single-copy transferrin receptor gene (Life Technologies ref. 4458366). Viral DNA was highly abundant in the liver and to a lower extent in the heart. The DNA distribution did not show any noticeable difference between the three vectors (FIG. 4C). RNA was extracted with Qiagen RNeasy plus universal kit following manufacturer's instructions, then treated with ezDNAse (Qiagen) to remove residual DNA, and reverse transcribed with Superscript IV (Life technologies).

Figure 4D:
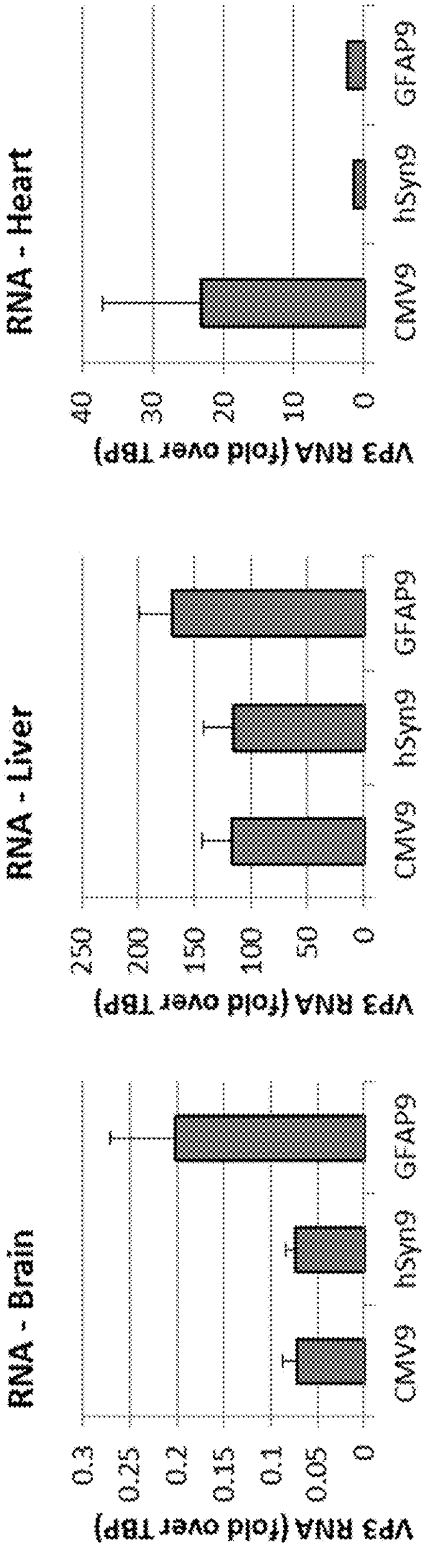

RNA expression was evaluated using the same VP3 probe used to quantify viral DNA and normalized using TBP as a reference RNA (Life technologies Mm01277042 m1). In the brain, the GFAP promoter allowed the strongest expression level, and the Synapsin promoter allowed a comparable expression as the potent CMV promoter. In the liver, all promoters resulted in a similar expression level, which could be the result of a leaky expression at very high copy number (FIG. 4D). In the heart, the cell type specificity of the Syn and GFAP promoters was evident, since they allowed only ~3 and 10% of CMV expression, respectively despite of a similar DNA biodistribution.

Overall the experiment showed that mRNA from transduction-competent capsids could be recovered from various animal organs, including weakly transduced tissues such as the brain.

Example 3. AAV Vector Configuration

Various vector configurations were explored toward increasing RNA expression to maximize library recovery. The CMV promoter was replaced by a hybrid CMV enhancer/Chicken beta-actin promoter sequence (Niwa et al., 1991) and a potent cytomegalovirus-beta-globin hybrid intron derived from the AAV-MCS cloning vector (Stratagene) was inserted between the promoter sequence and the capsid gene, as introns have been shown to increase mRNA processing and stability (Powell et al., 2015). This resulted in the constructs CAG9 (SEQ. ID NO:10), SYNG9 (SEQ. ID NO:11) and GFAPG (SEQ. ID NO:12).

Figure 5A:
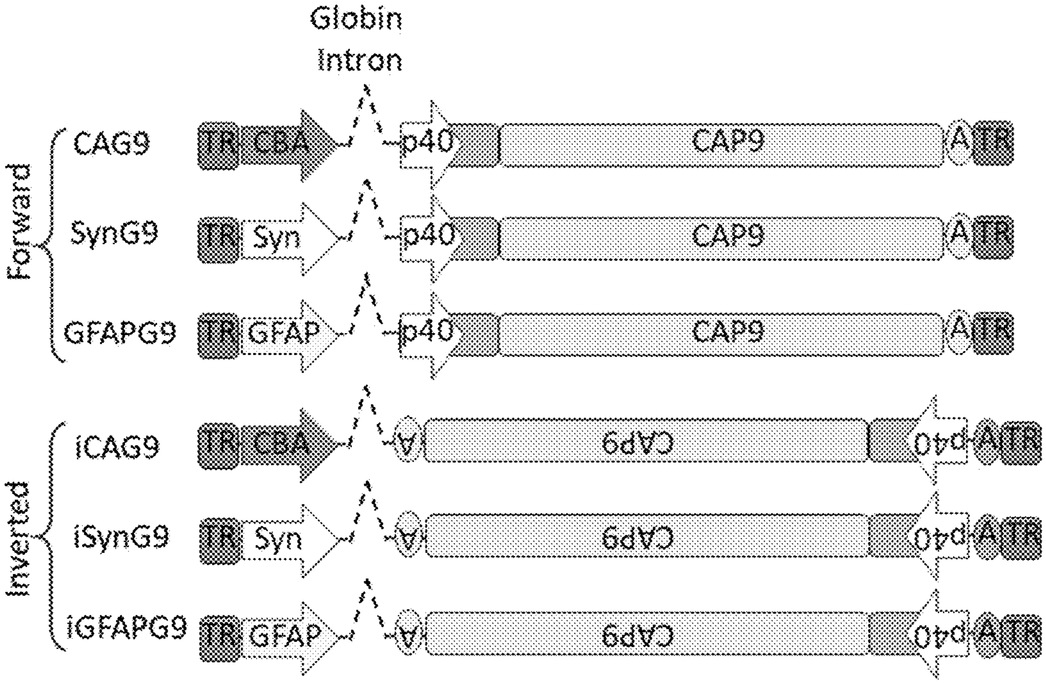
FIG. 5A, FIG. 5B, FIG. 5C, FIG. 5D and FIG. 5E describes in vitro analysis of intronic second generation vectors.

An inverted vector configuration was also tested where the helper-independent promoter was placed downstream of the capsid gene in reverse orientation, in order to avoid potential interference with the P40 promoter (FIG. 5A). This configuration allows the expression of an antisense capsid transcript in animal tissue. Because most polyadenylation signals (AATAAA) are orientation-dependent, it was hypothesized that the natural AAV capsid polyA would not prematurely terminate transcription when placed in reverse orientation. All constructs were co-transfected with pHelper and pREP-3 stop plasmids to generate AAV9-packaged virions that were used to transduce HEK-293T cells at a MOI of 1e4 VG per cell. RNA was extracted 48 hours post-transfection and reverse transcribed using the Quantitect kit (Qiagen).

Figure 5B:
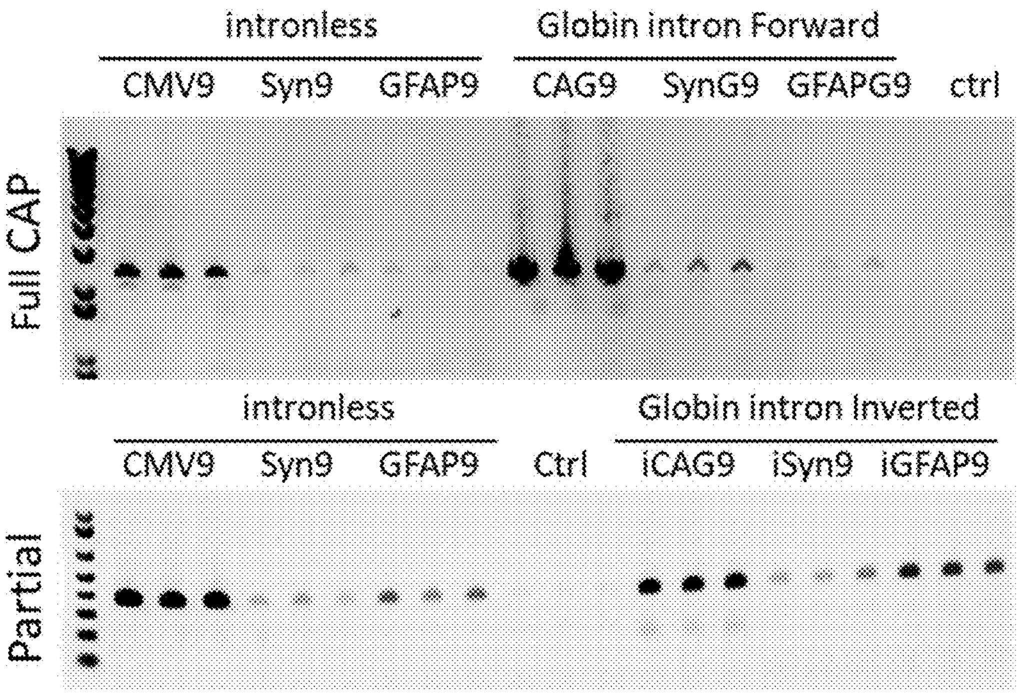
Figure 5C:
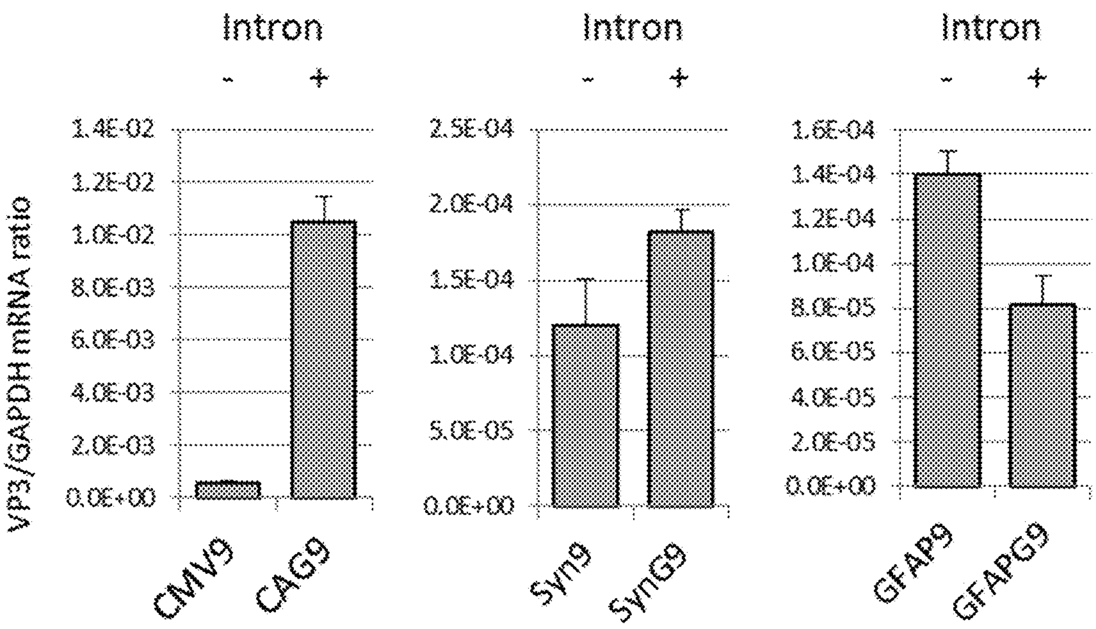

PCR was performed with primers allowing amplification of the full-length capsid or a partial sequence localized close to the C-terminus (FIG. 5B). Overall, the presence of an intron had little influence on the expression from low-activity promoters Syn and GFAP, which indicates that mRNA splicing did not alleviate promoter repression in nonpermissive cells. The combination of the CMV enhancer with a Chicken beta-actin promoter and the hybrid intron allowed a significantly higher (>10-fold) mRNA expression compared to CMV promoter alone (FIGS. 5B, C).

Figure 5D:
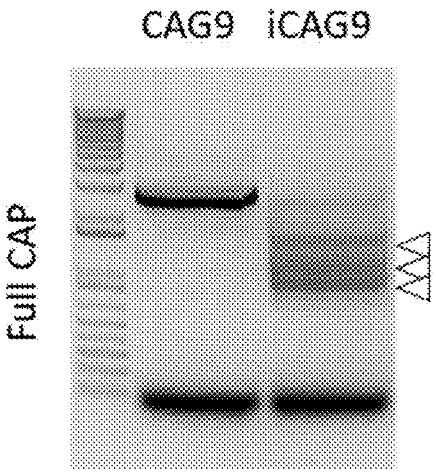

When comparing endpoint PCR amplification between forward and inverted intronic vectors, a discrepancy was obvious between full-length and partial capsid amplicons (FIG. 5B, right-hand lanes), which led us to question the integrity of capsid RNA. When cDNA from inverted iCAG9 genome was amplified using primers flanking the full-length capsid, multiple low-molecular weight bands were detected, whereas the forward orientation vector allowed amplification of a single product with the expected length (FIG. 5D). Sanger sequencing of low-molecular weight amplicons showed that each band corresponded to an illegitimate splicing product from the antisense capsid RNA.

In light of these results, the forward tandem promoter architecture for subsequent experiments.

Figure 5E:
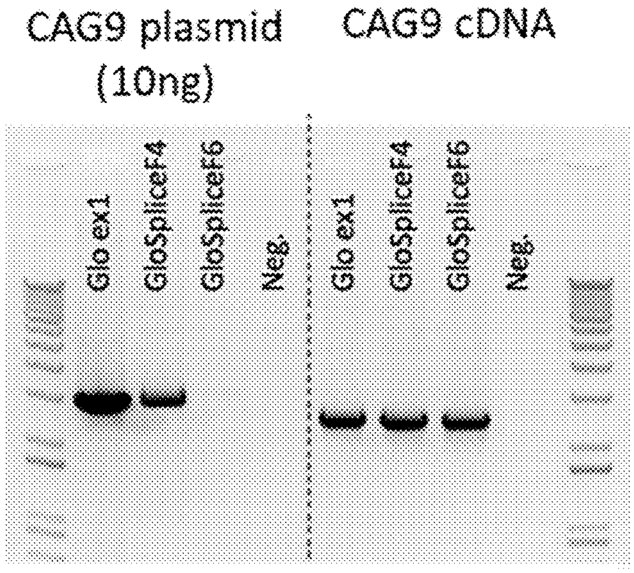

Splice-specific PCR amplification was tested to avoid amplification of residual DNA present in RNA preparations. Two candidate PCR primers overlapping the CMV/Globin exon-exon junction were designed and tested them for amplification of cDNA (spliced) or plasmid DNA (still containing the intron sequence). As shown in FIG. 5E, the GloSpliceF6 primer (SEQ. ID NO:13) allowed a fully specific amplification from cDNA without producing a detectable amplicon from the plasmid DNA sequence. This primer was used in subsequent assays to ascertain the absence of amplification from contaminating DNA.

Tandem constructs were then tested for potential interference of the P40 promoter with the cell-specific promoter placed upstream. For this, two series of AAV genomes were tested for transgene mRNA expression in HEK-293T cells. A series of transgenes where the GFP gene was placed immediately downstream of the CAG, SYNG or GFAPG promoter without P40 sequence were tested, and compared to the library constructs where AAV9 capsid was placed downstream of the P40 promoter (FIG. 6A). All genomes were packaged into the AAV9 capsid and used to infect HEK-293T at a MOI of 1e4 VG per cell. RNA was extracted 48 hours post-infection and transgene RNA was quantified by using a Taqman primer/probe mix specific for the spliced globin exon-exon junction. As shown in FIG. 6B, the expression from the CAG promoter was similar between the GFP and the P40-CAP9 constructs (2-fold lower in p40-CAP9, within the error margin of AAV titration). Expression from the synapsin promoter was drastically lower with both constructs and even lower for GFAP-driven mRNA (FIG. 6B). This was expected since HEK-293T cells are not permissive to Synapsin or GFAP promoter expression. Overall, this experiment confirmed that the presence of the P40 sequence did not alter the cell type specificity of synapsin or GFAP promoters.

Figure 7:
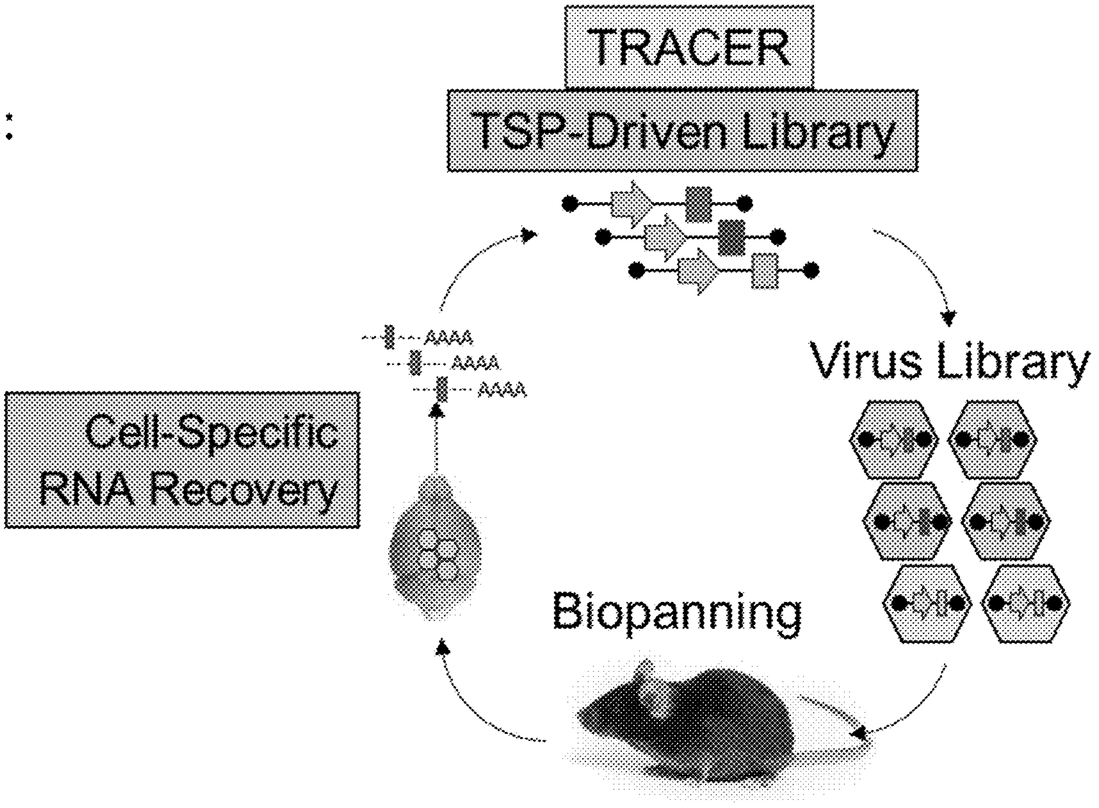
FIG. 7 illustrates the basic tenets of the TRACER platform.
Figure 8:
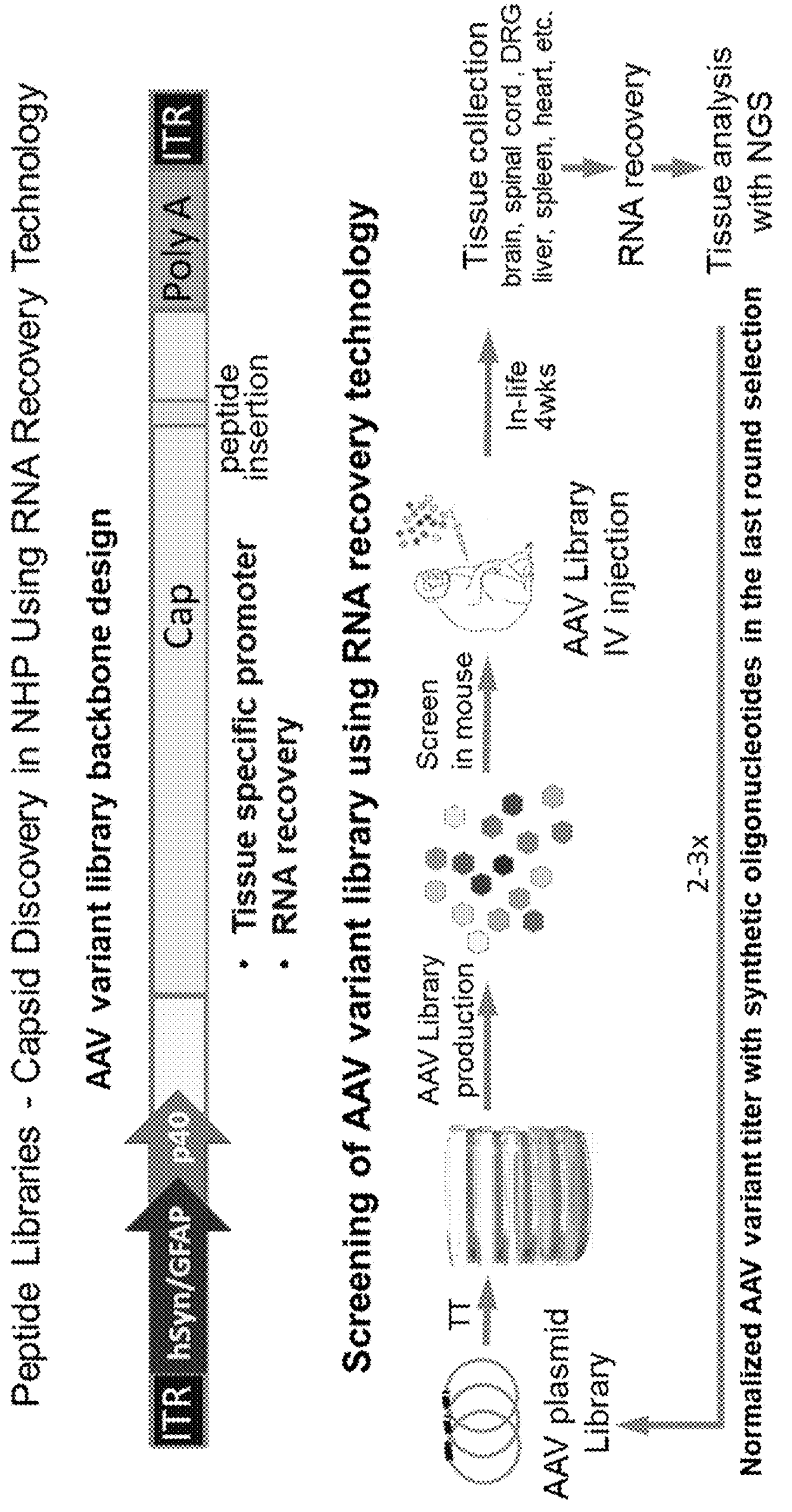
FIG. 8 illustrates features of the TRACER platform including the use of a tissue specific promoter and RNA recovery.

This novel platform was termed TRACER (Tropism Redirection of AAV by Cell type-specific Expression of RNA). The TRACER platform solves the problems of standard methods including transduction and cell-type restrictions. (FIG. 7). Use of the TRACER system is well suited to capsid discovery where targeting peptide libraries are utilized. Screening of such a library may be conducted as outlined in FIG. 8.

Figure 9:
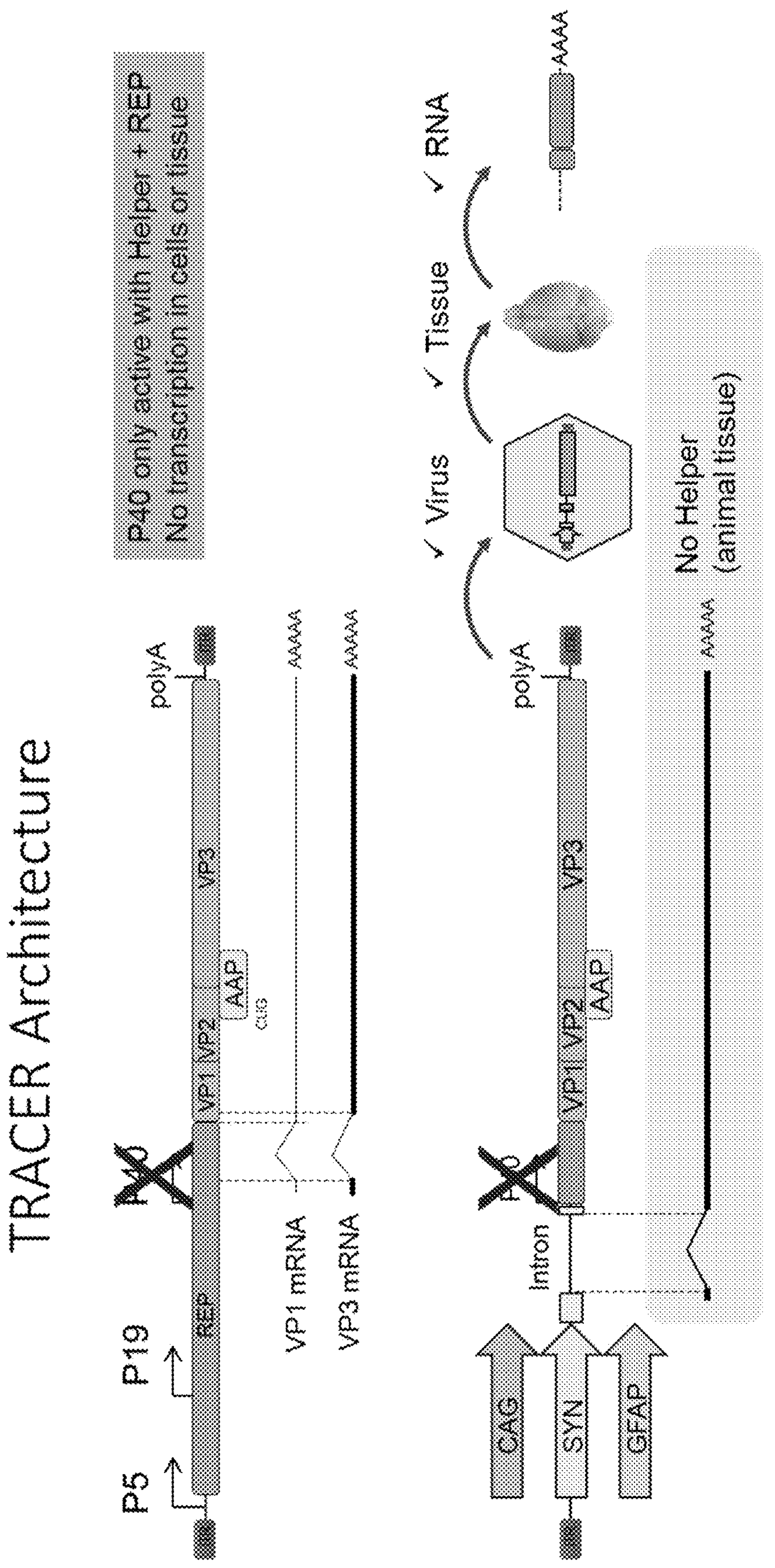
FIG. 9 provides one embodiment of the TRACER production architecture.
Figure 12A:
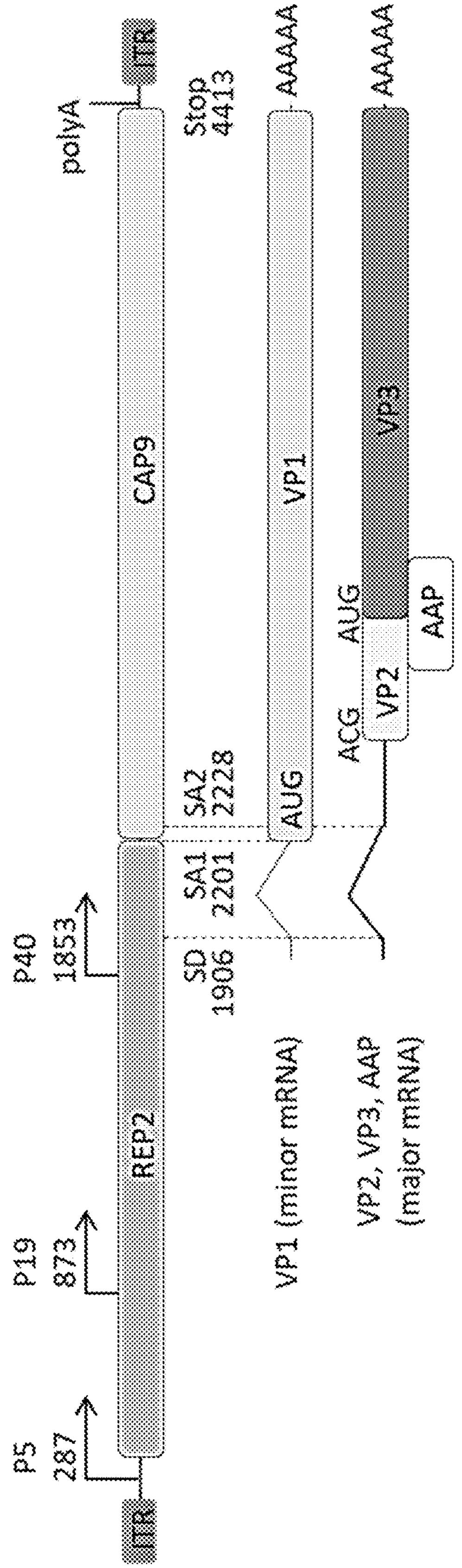
FIG. 12A and FIG. 12B provide diagrams representing capsid gene transcription of natural AAV (FIG. 12A) and TRACER libraries (FIG. 12B).
Figure 12B:
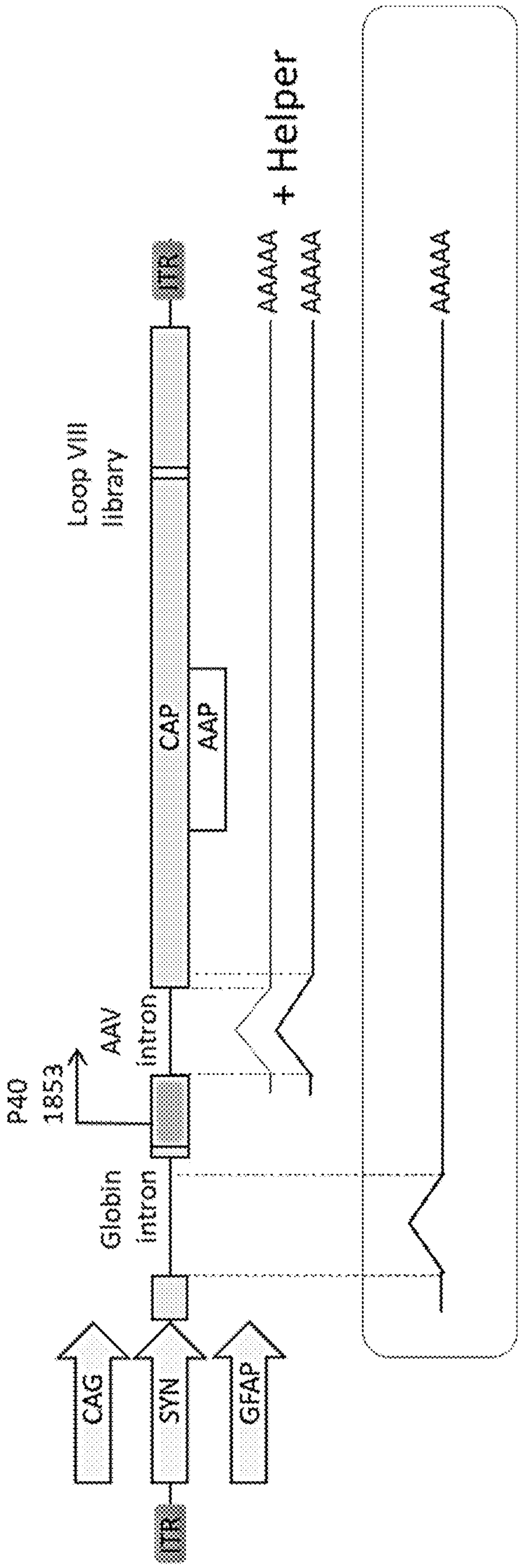

While several variations of the AAV vectors which encode the capsids as payloads are taught herein, one canonical design is shown in FIG. 9B and in FIG. 12A and FIG. 12B.

Figure 10:
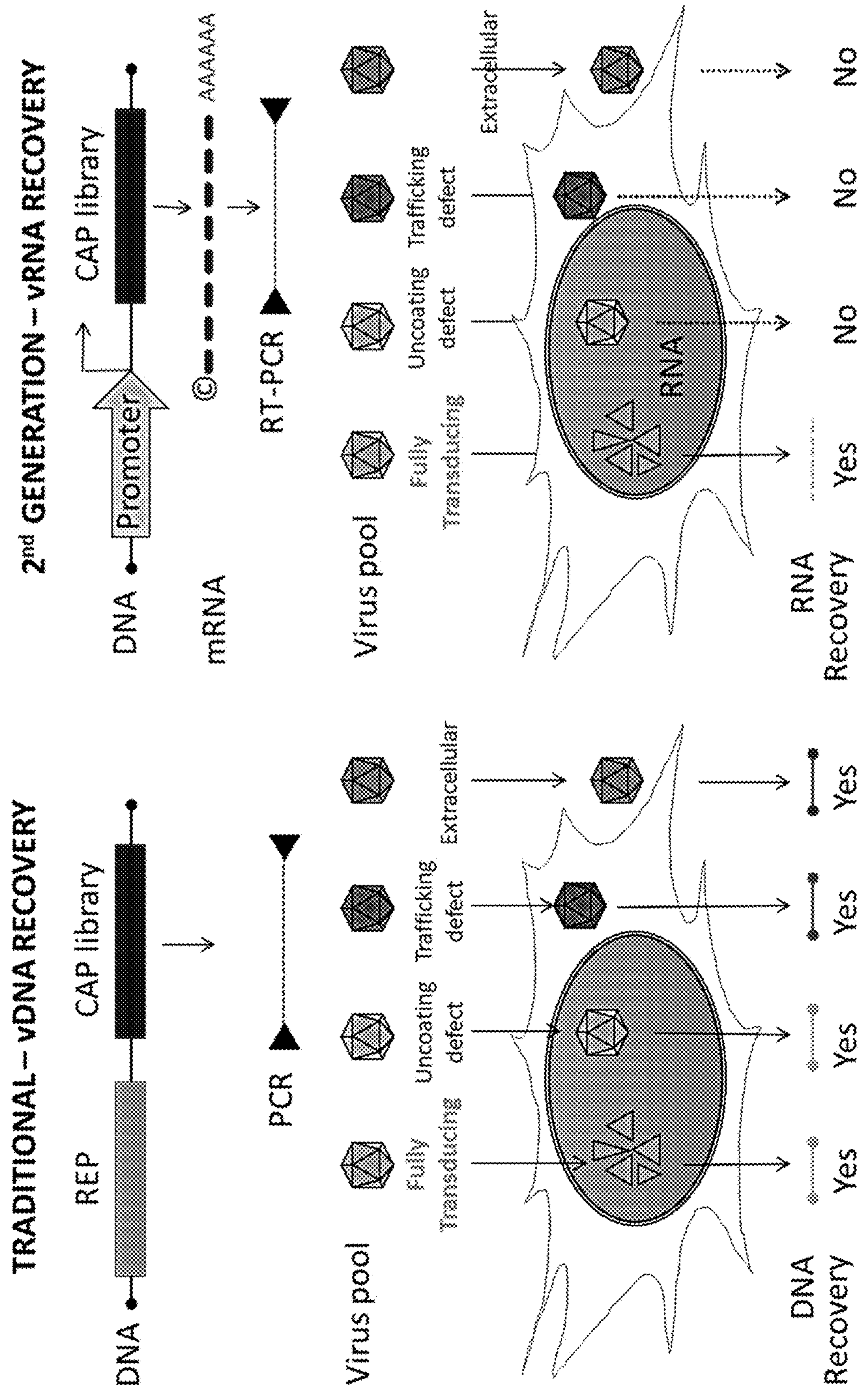
FIG. 10 provides a comparison between traditional vDNA recovery and $2^{nd}$ generation vRNA recovery.
Figure 11:
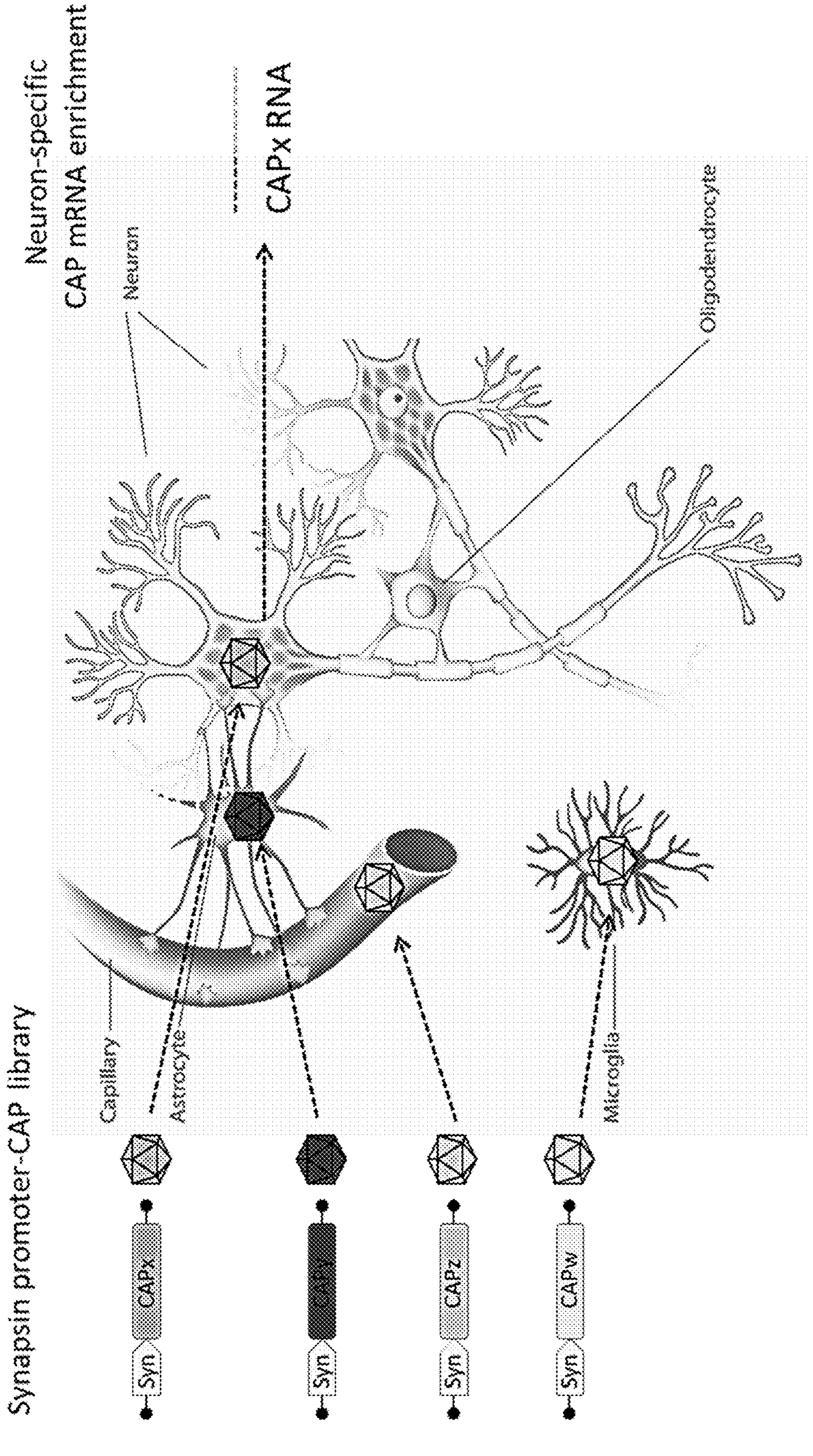
FIG. 11 provides an overview of the use of cell-specific RNA expression for targeted evolution.

Further advantages of the TRACER platform relate to the nature of the virus pool and the recovery of RNA only from fully transduced cells (FIG. 10). Consequently, capsid discovery can be accelerated in a manner that results in cell and/or tissue specific tropism (FIG. 11).

Figure 13:
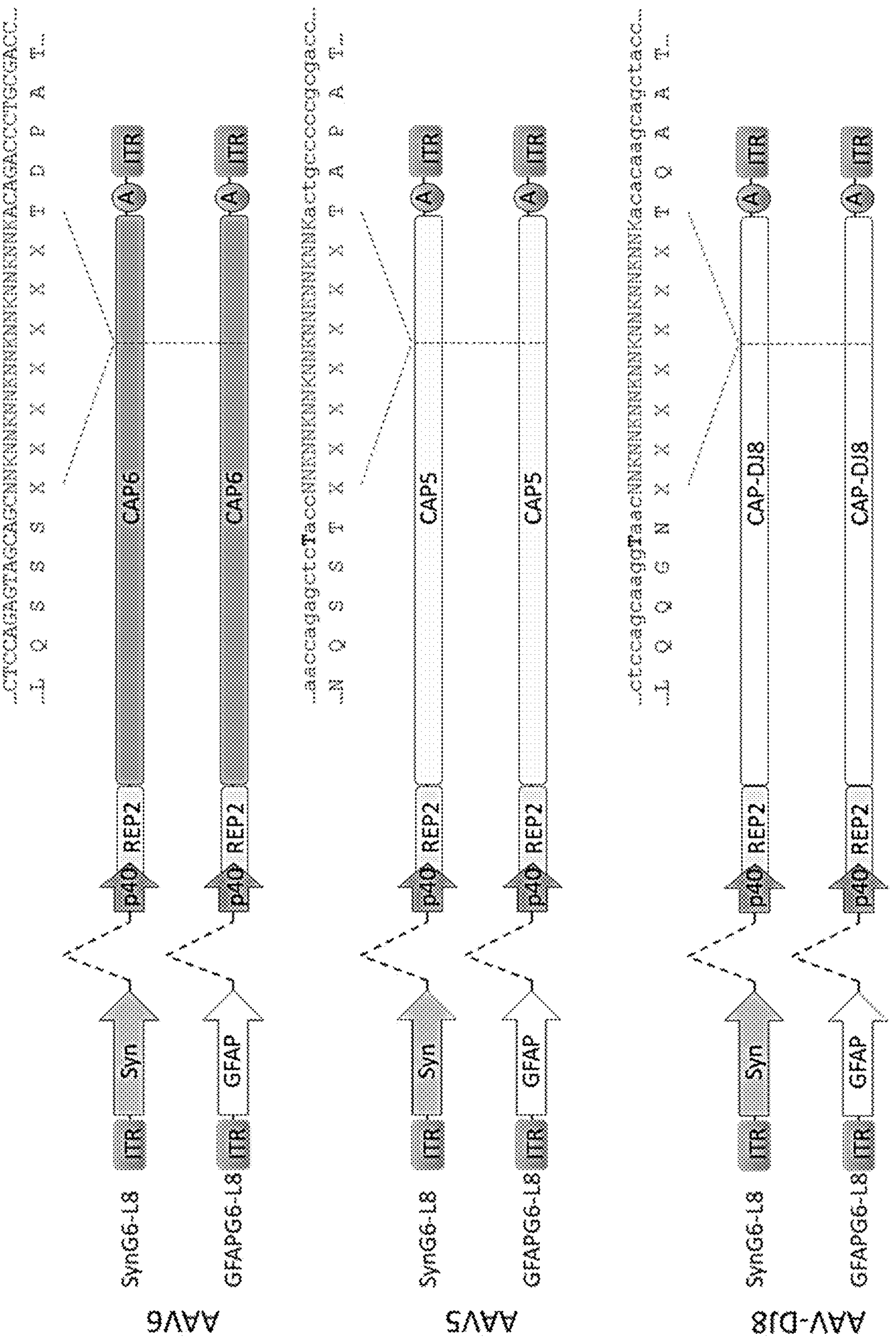
FIG. 13 is a diagram of the AAV6, AAV5 and AAV-DJ capsid peptide display libraries used for in vivo evolution (SEQ ID NOS 27-32, respectively, in order of appearance).
Figure 14:
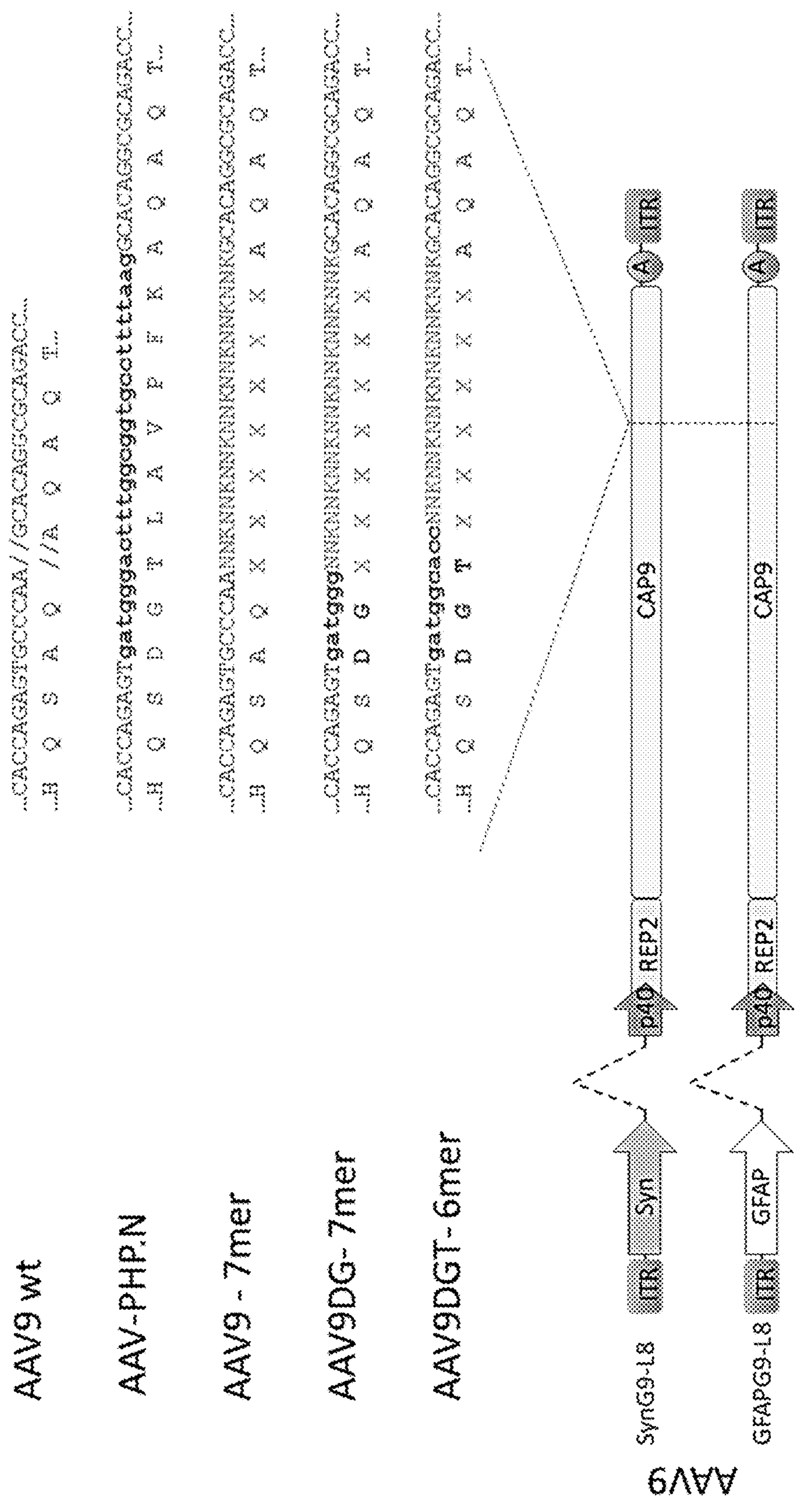
FIG. 14 is a diagram of the AAV9 capsid peptide display libraries used for in vivo evolution (SEQ ID NOS 33-42, respectively, in order of appearance).
Figures 15A, 15B:
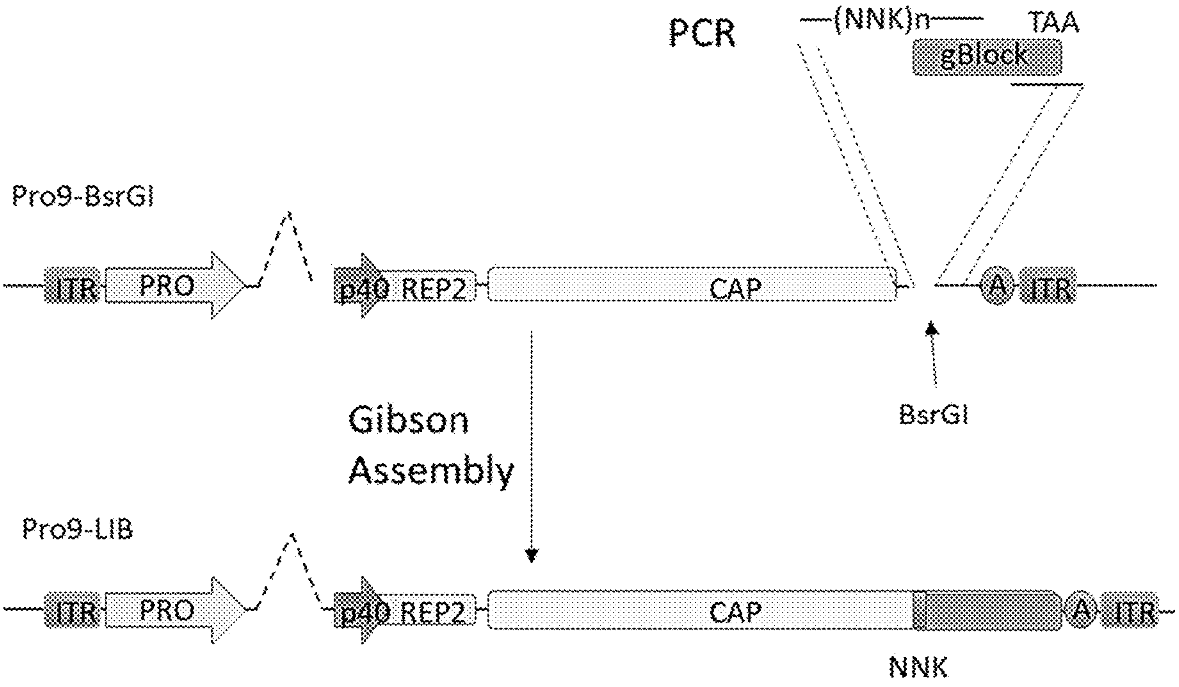
FIG. 15A and FIG. 15B present the method used for library construction.
Figure 39:
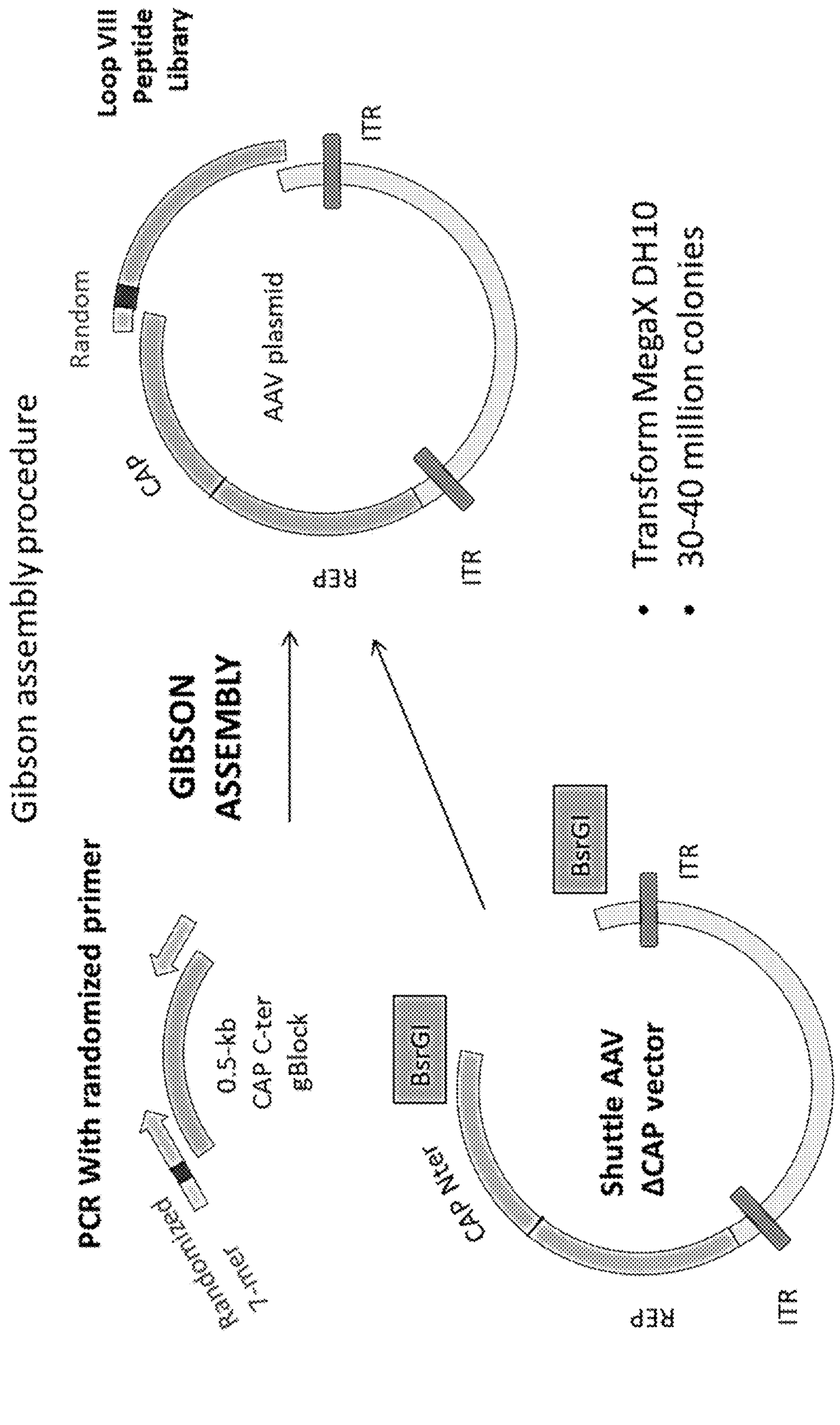
FIG. 39 is a diagram of the Gibson assembly library cloning procedure.
Figure 40:
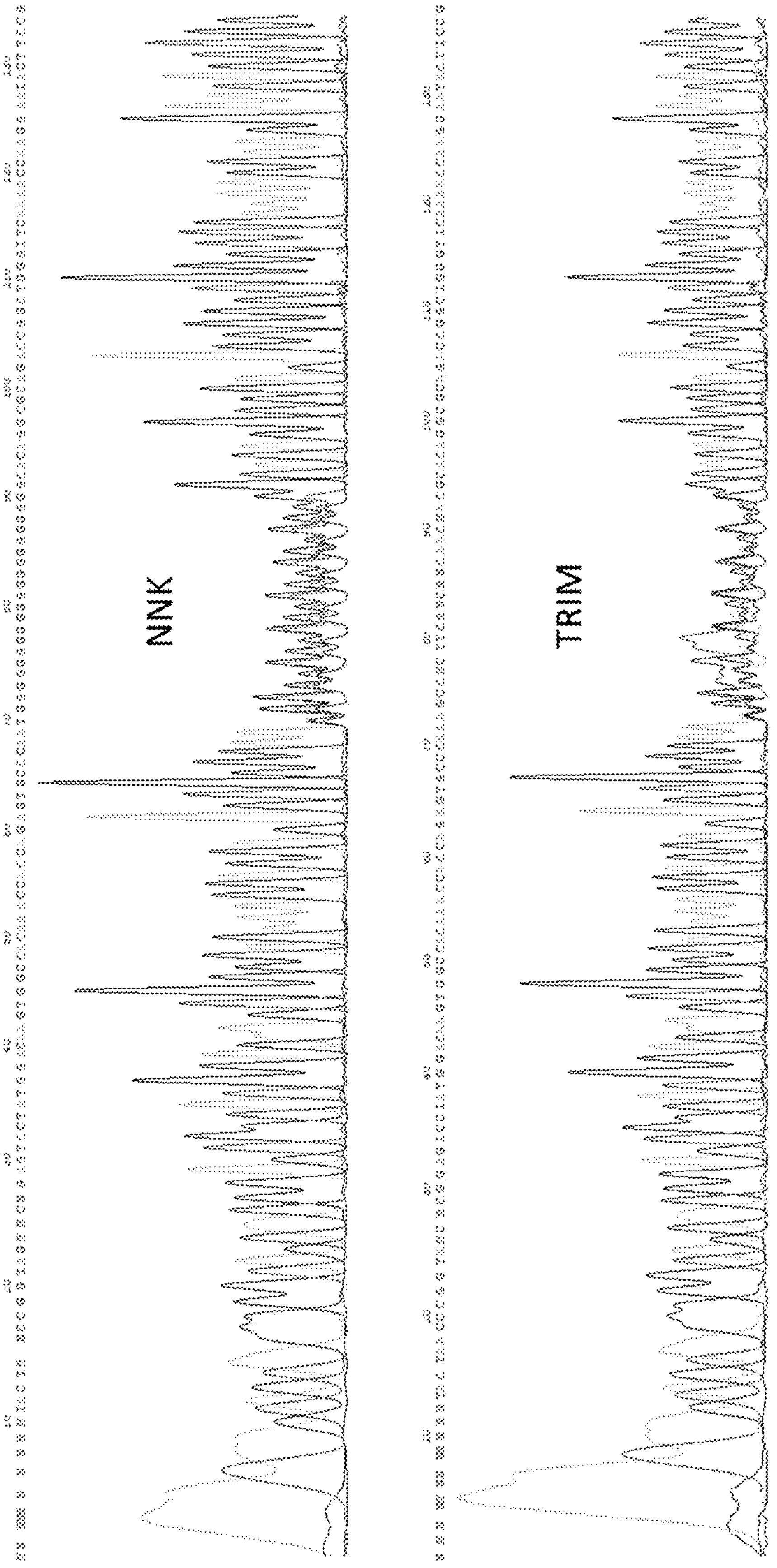
FIG. 40 provides an example of TRIM/NNK peptide prevalence (SEQ ID NOS 170-171, respectively, in order of appearance).
Figure 42:
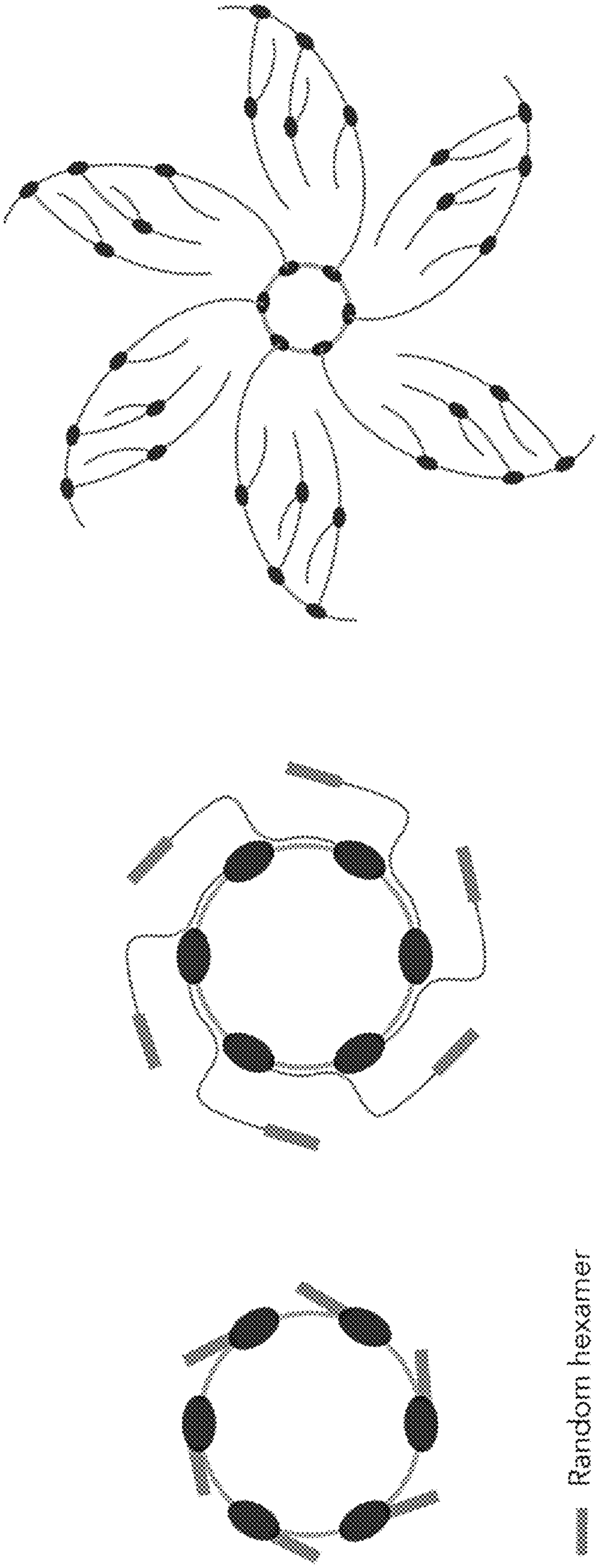
FIG. 42 provides an exemplary diagram of cloning-free DNA amplification by rolling circle amplification.
Figure 43:
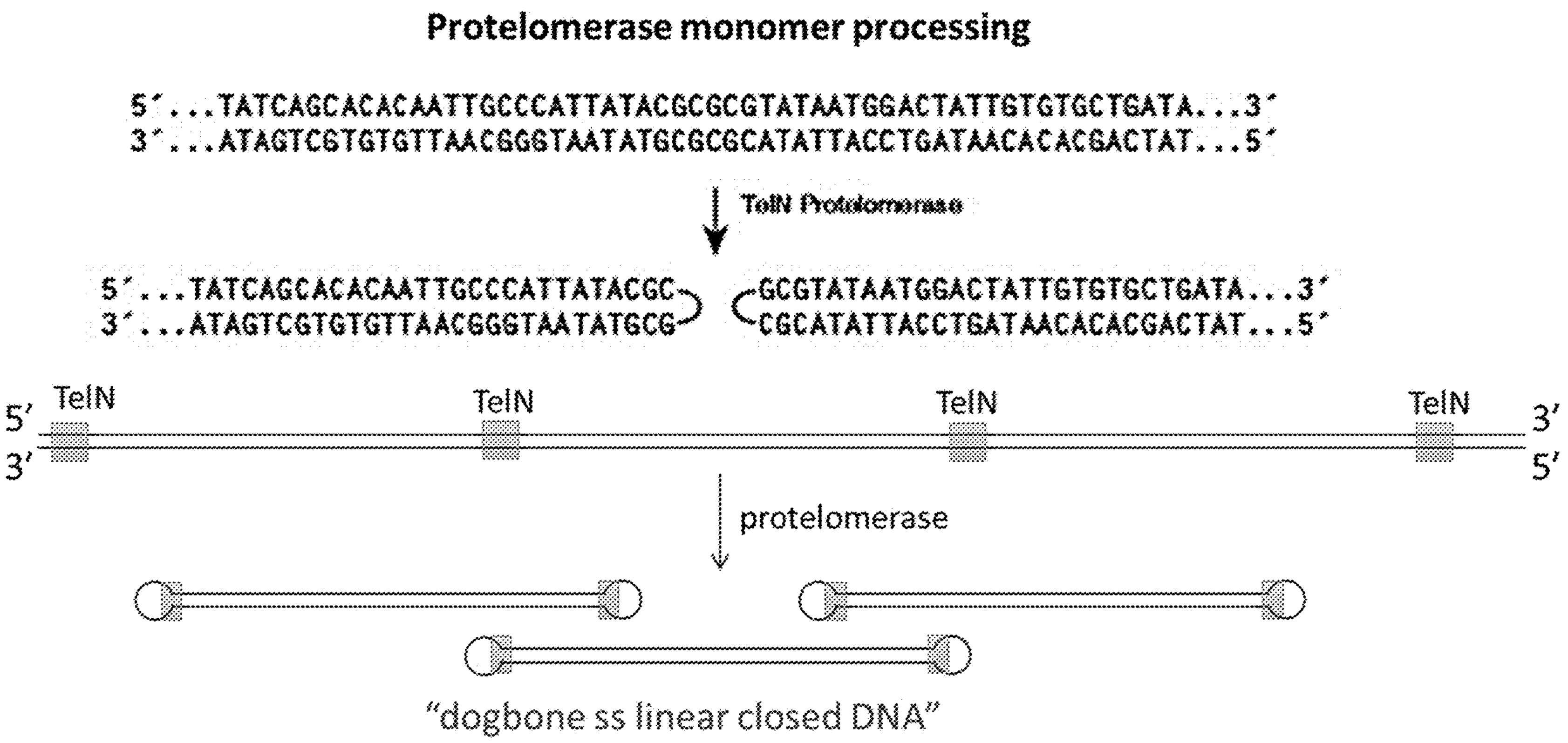
FIG. 43 provides a diagram of protelomerase monomer processing (SEQ ID NOS 176-178, respectively, in order of appearance).
Figure 44:
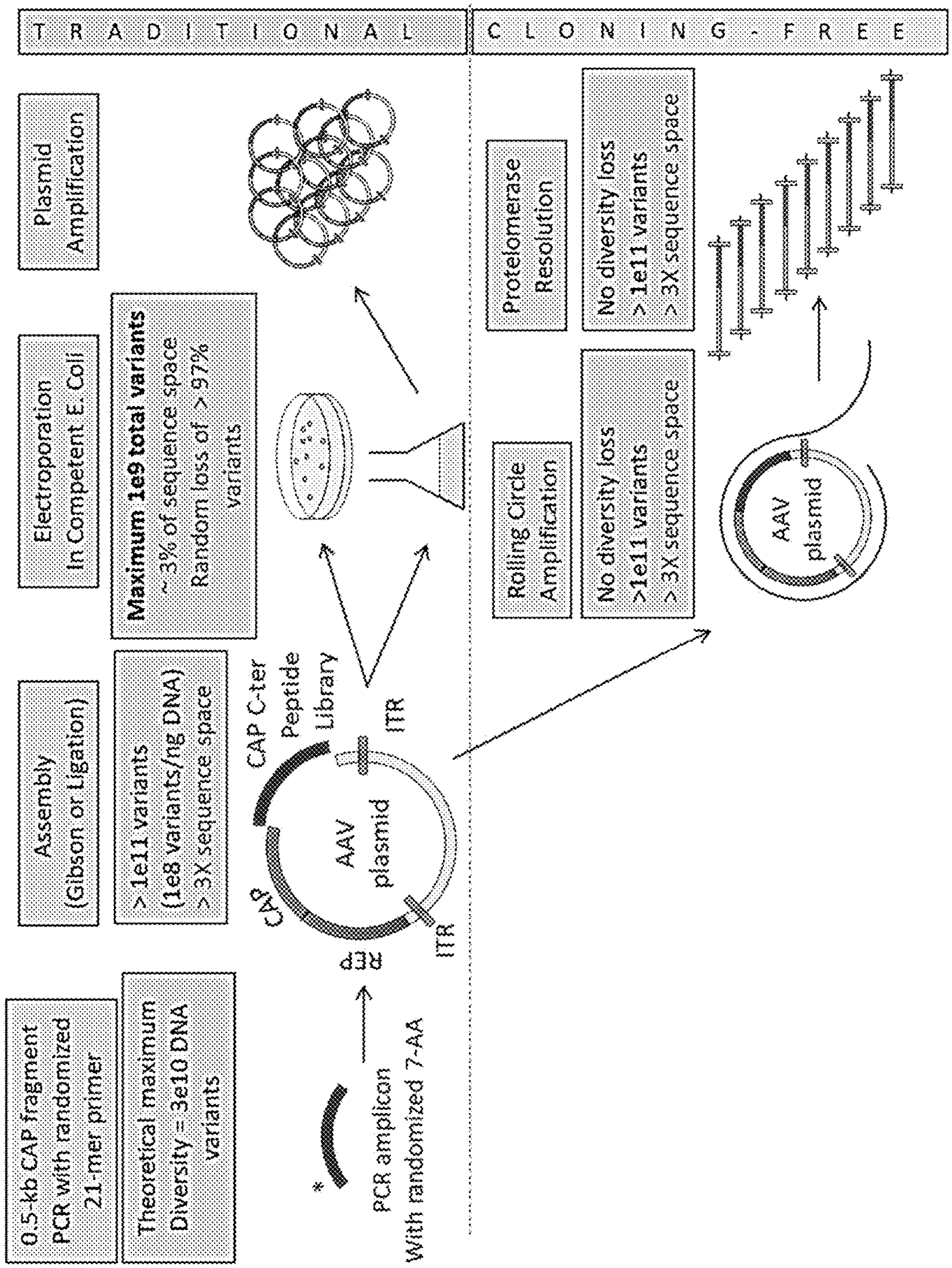
FIG. 44 provides a diagram comparing the traditional and cloning-free methods.
Figure 45A:
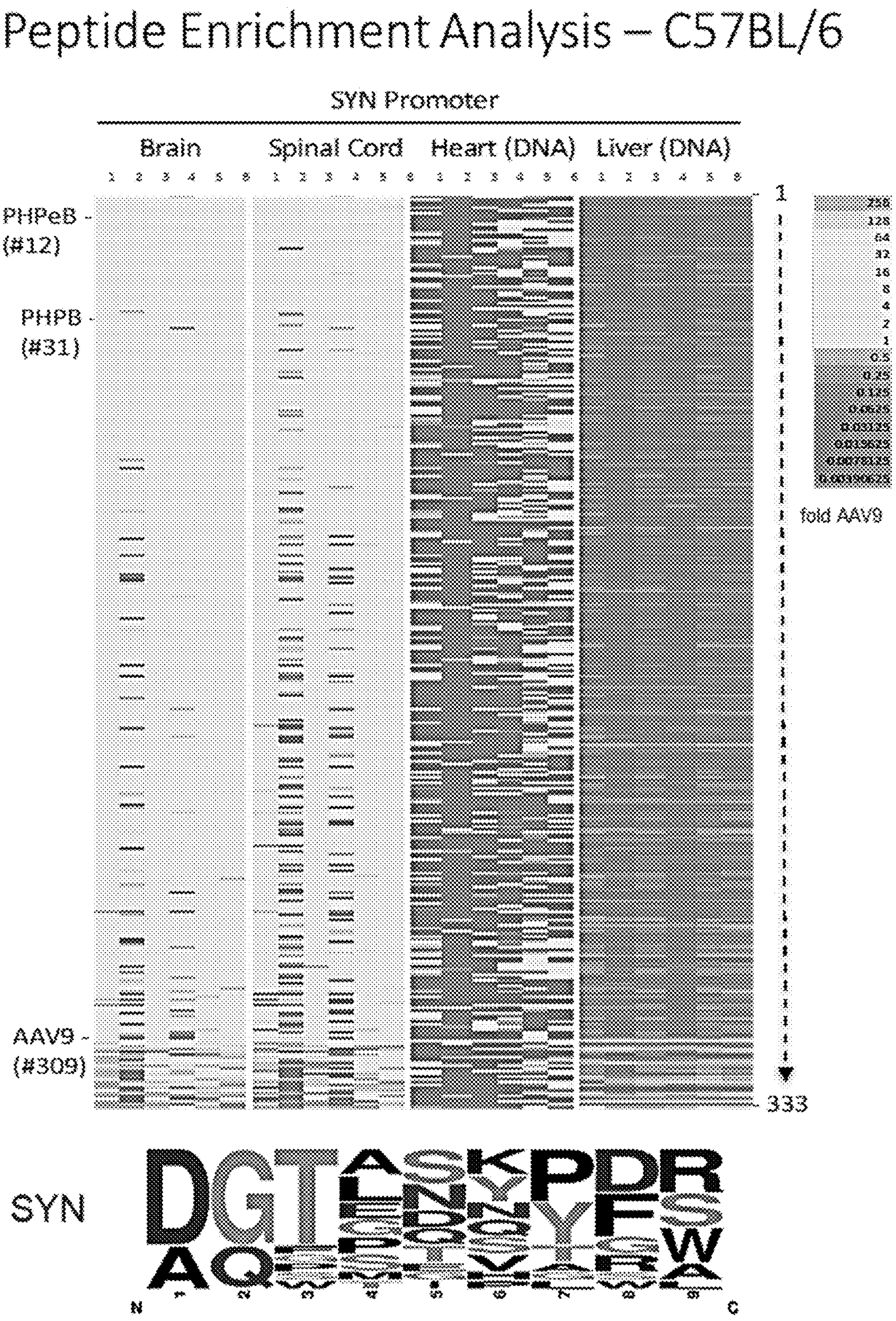
FIG. 45A and FIG. 45C provide the full ranking of Syn-driven (FIG. 45A) and GFAP-driven (FIG. 45B) 333 variants in the brain, spinal cord, liver and heart tissues. Capsid variants are ranked by their average brain RNA enrichment score (average of NNK and NNM codons). The rank of internal control capsids PHP.B, PHP.eB and AAV9 is indicated (FIG. 45A and FIG. 45B). A comparison of combined Syn-driven results and GFAP-driven results is provided (FIG. 45C). Only 4 animals were represented for the GFAP-driven libraries because 2/6 mice showed a very different ranking profile and were considered as outliers.
Figure 45B:
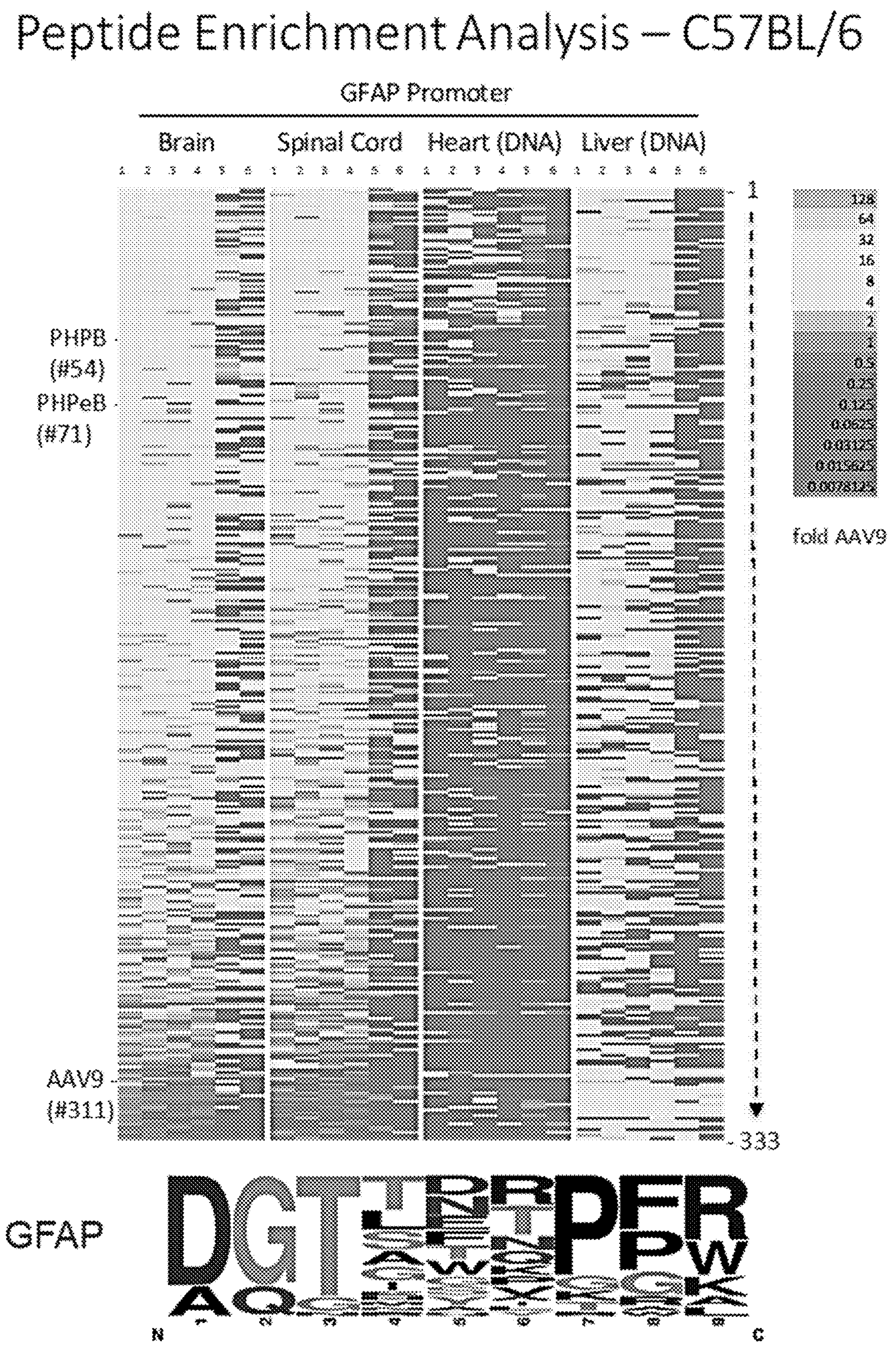
Figure 45C:
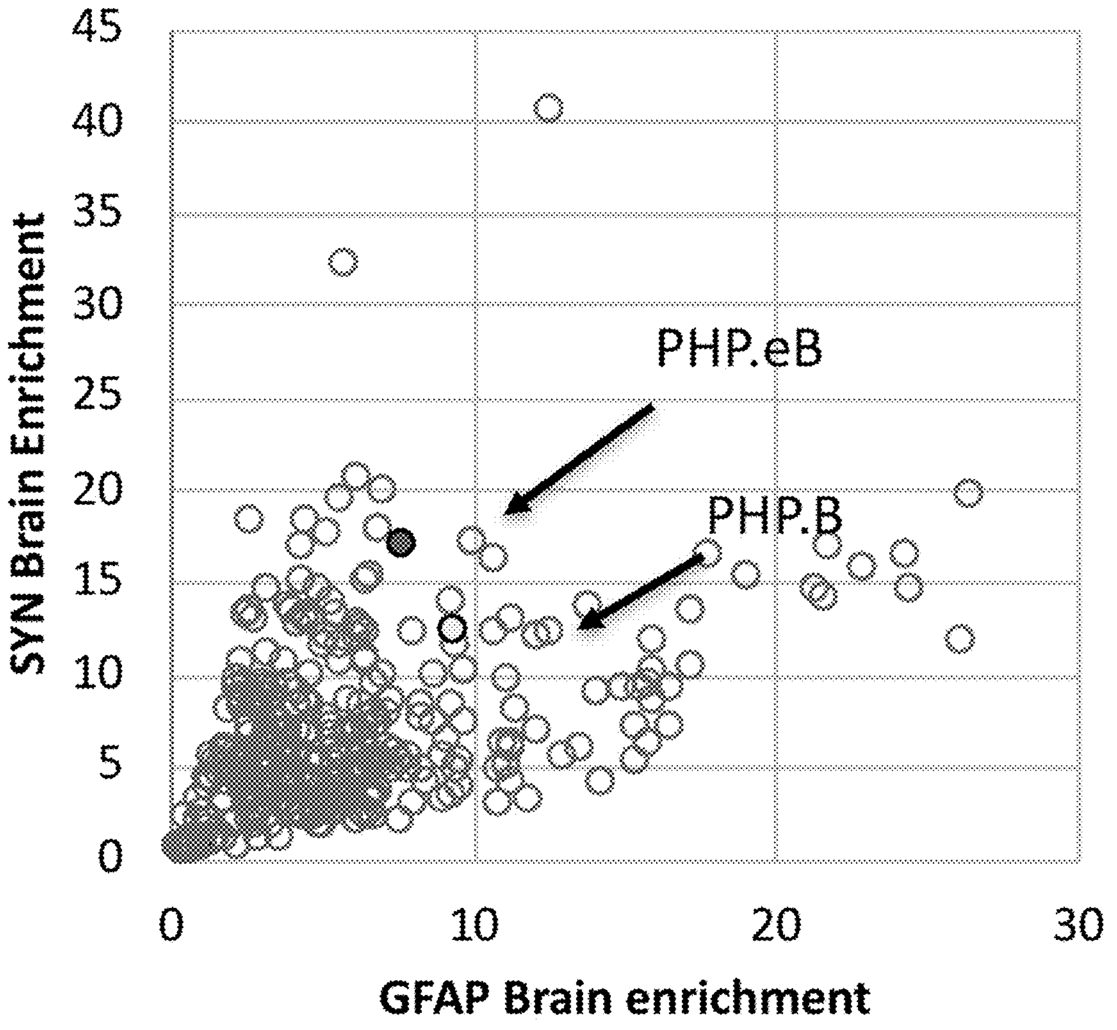
Figure 46A:
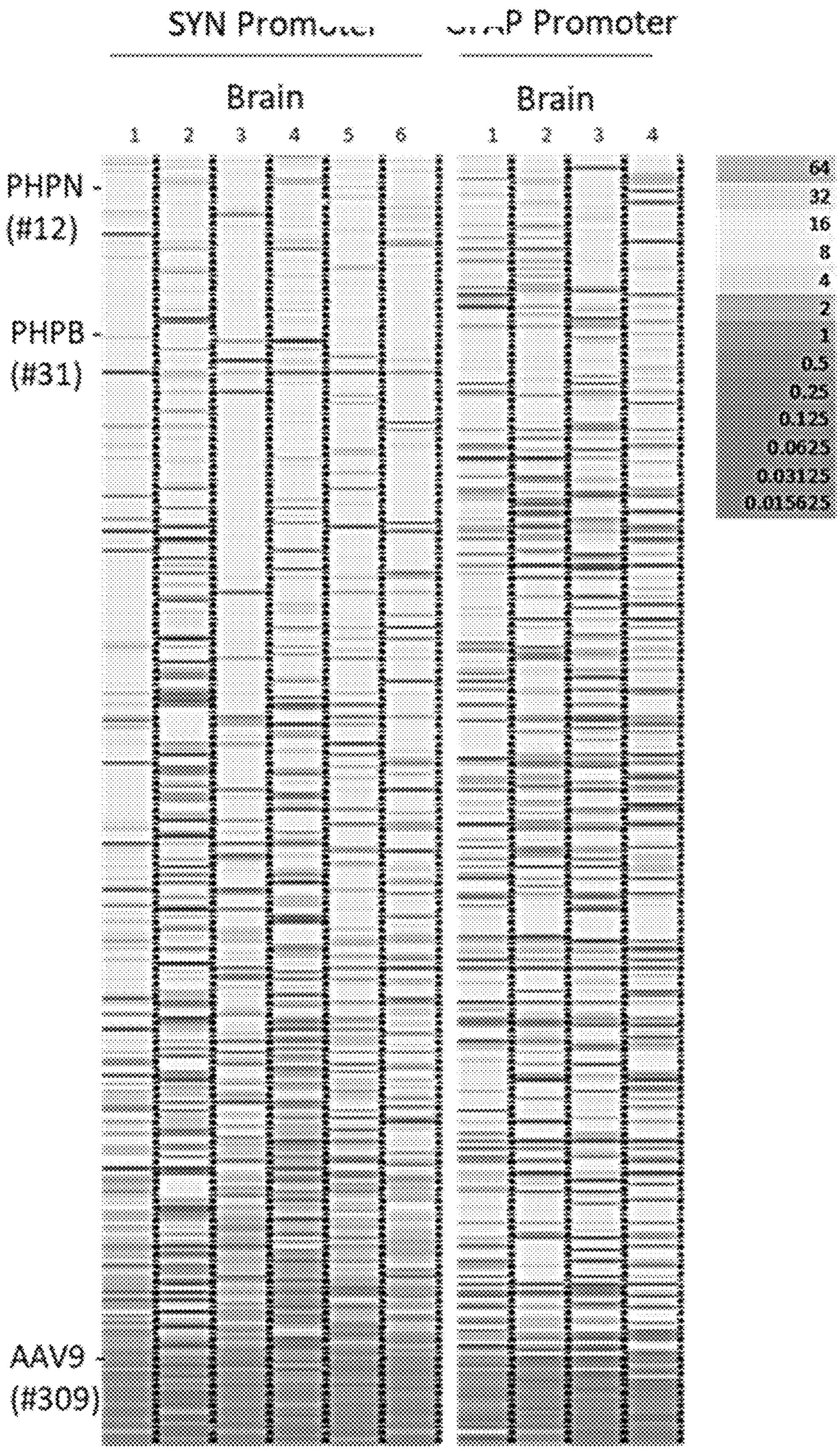
FIG. 46A and FIG. 46B provide the comparison of results of the neuron and astrocyte synthetic library NGS analysis.
Figure 46B:
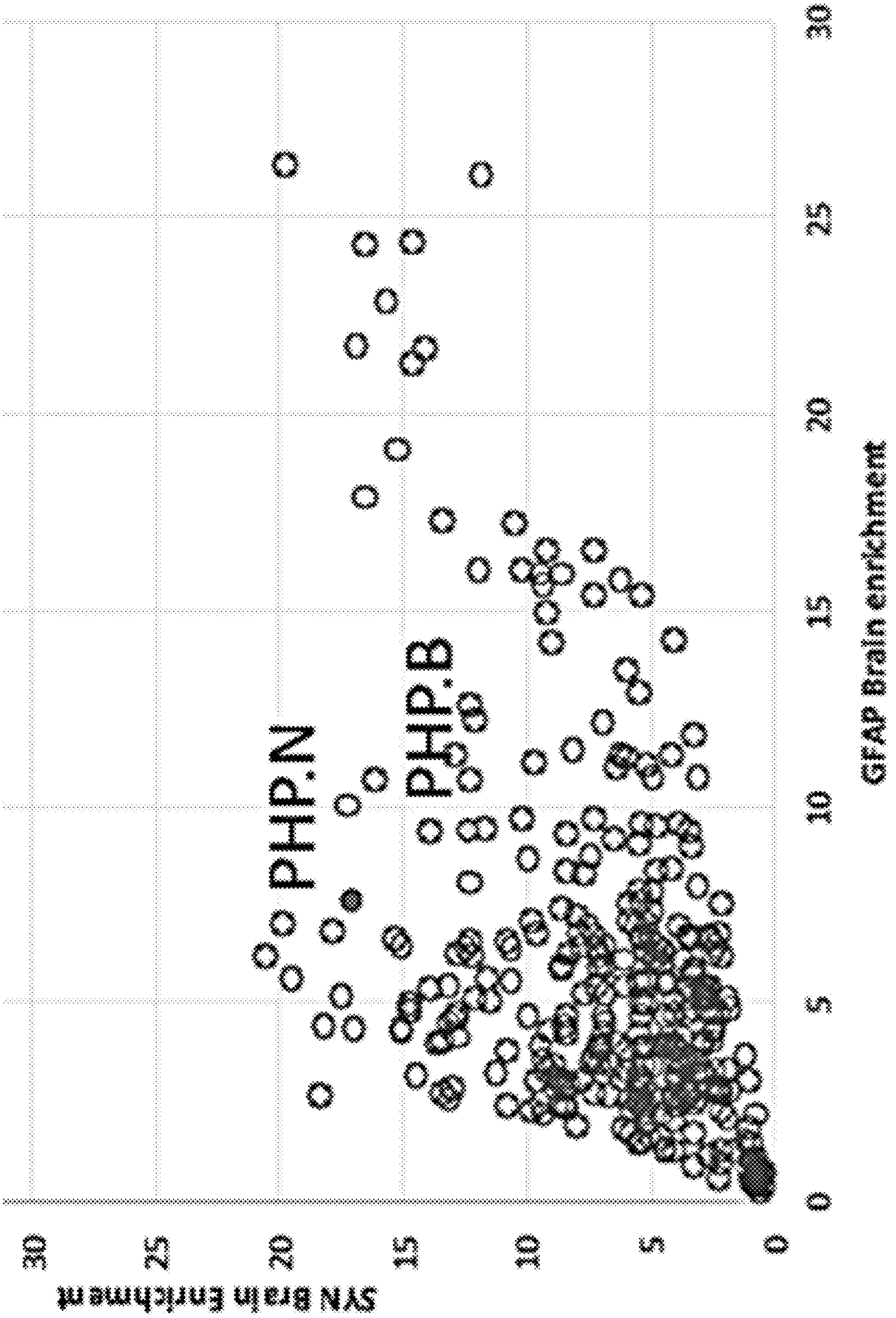

Example 4. Generation of Peptide Display Libraries and Cloning-Free Amplification Several peptide display capsid libraries were generated by insertion of seven contiguous randomized amino acids into the surface-exposed hypervariable loop VIII region of AAV5, AAV6, or AAV-DJ8 capsids (FIG. 13 and FIG. 39) as well as AAV9 (FIG. 14). For AAV9 libraries, two extra libraries by modifying residues at positions −2, −1 and +1 of the insertion to match the flanking sequence of the highly neurotrophic PHP.eB vector (Chan et al., 2018). In order to facilitate the insertion of various loops and to prevent contamination by wild-type capsids, defective shuttle vectors were generated in which the C-terminal region of the capsid gene comprised between the loop VIII and the stop codon was deleted and replaced by a unique BsrGI restriction site (FIGS. 15A, B). Degenerate primers containing randomized NNK (K=T or G) sequences able to encode all amino acids were synthesized by IDT and used to amplify the missing capsid fragment using gBlock (IDT) double-stranded linear DNA as templates (SEQ. ID NO 14, 15, 16, 17). Linear PCR templates were preferred to plasmids in order to completely prevent the possibility of plasmid carryover in the PCR reaction. Amplicons containing the random library sequence (500 ng) were inserted in the shuttle plasmid linearized by BsrGI (2 ug) using 100 ul of NEBuilder HiFi DNA assembly master mix (NEB) during 30 minutes at 50° C. Unassembled linear templates were eliminated by addition of 5 ul of T5 exonuclease to the reaction and digestion for 30 minutes at 37° C. The entire reaction was purified with DNA Clean and Concentrator-5 and quantified with a nanodrop to estimate the efficiency of assembly. This method routinely allows the recovery of 0.5-1 ug assembled material.

gBlock templates were engineered by introducing silent mutations to remove unique restriction sites, to allow selective elimination of wild-type virus contaminants from the libraries by restriction enzyme treatment. As an example, AAV9 gBlock was engineered to remove BamHI and AfeI sites present in the parental sequence (SEQ. ID NO 17).

Example 5. Cloning Free Amplification

Figure 16:
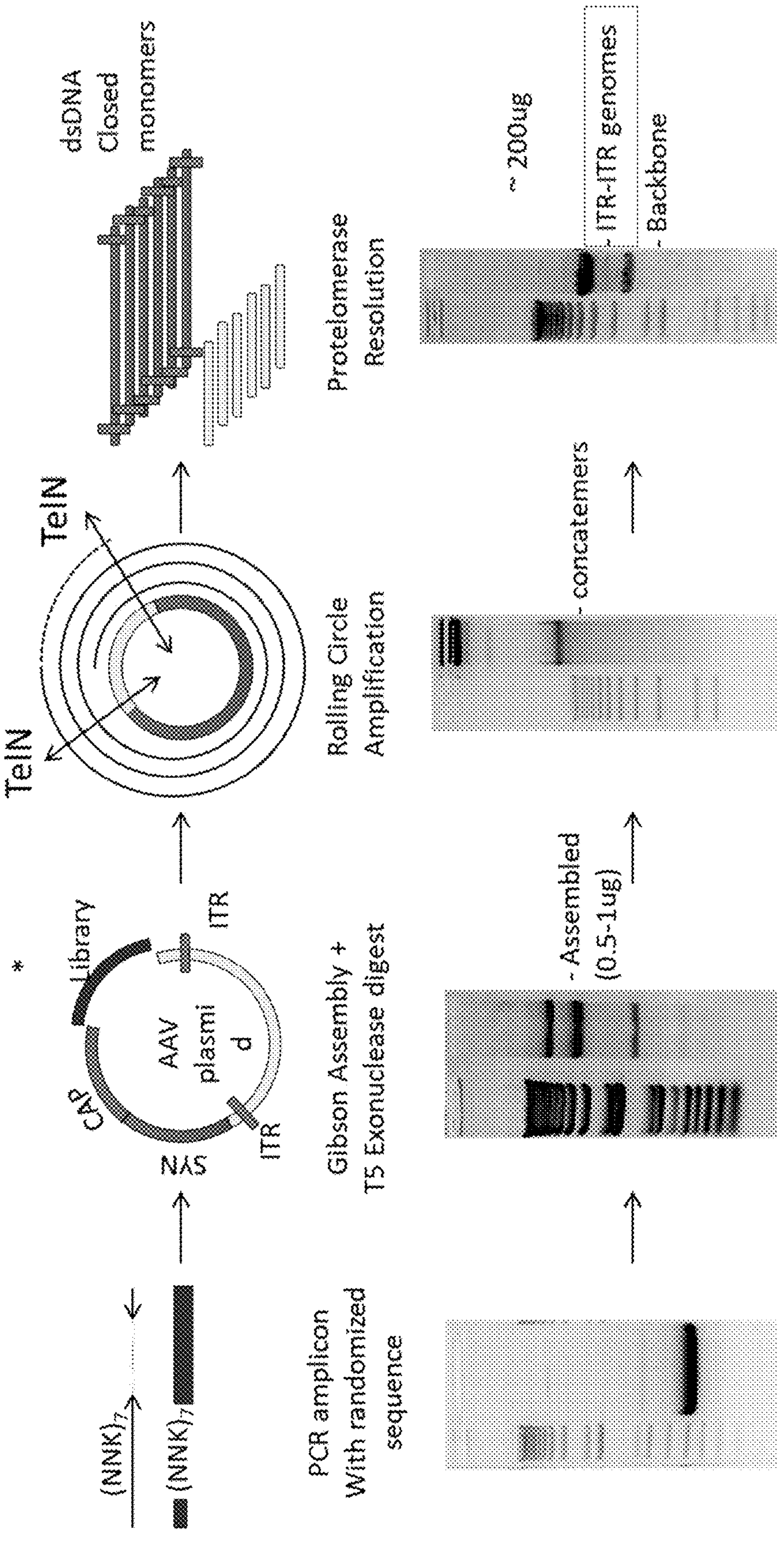
FIG. 16 provides an exemplary diagram of cloning-free rolling circle procedure used for library amplification (SEQ ID NO 47; $NNK_7$).

Transformation of assembled library DNA into competent bacteria represents a major bottleneck in library diversity, since even highly competent strains rarely exceed 1e7-1e8 colonies per transformation. By comparison, 100 nanograms of a 6-kilobase plasmid contain 1.5e10 DNA molecules. Therefore, bacterial transformation arbitrarily eliminates more than 99% of DNA species in a given pool. A cloning-free method was therefore created that allows >100-fold amplification of Gibson-assembled DNA while bypassing the bacterial transformation bottleneck (FIG. 16). A protocol based on rolling-circle amplification was optimized, which allows unbiased exponential amplification of circular DNA templates with an extremely low error rate (Hutchinson et al., 2005). One issue with rolling circle amplification is that it produces very large (~70 kilobases on average) heavily branched concatemers that have to be cleaved into monomers for efficient cell transfection. This process can be accomplished by several methods, for example by using restriction enzymes to generate open-ended linear templates (Hutchinson et al., 2005, Huovinen, 2012), or CRE-Lox recombination to generates self-ligated circular templates (Huovinen et al., 2011). However, open-ended DNA is sensitive to degradation by cytoplasmic exonucleases, and the CRE recombination method showed relatively low efficiency (our unpublished observations). Therefore, an alternative monomer resolution method was chosen based on the use of TelN protelomerase (Rybchin et al., 1999), an enzyme that catalyzes the formation of closed-ended linear "dog-bone" DNA monomers that are highly suitable for mammalian cell transfection (Heinrich et al., 2002).

To that end, the protelomerase recognition sequence TATCAGCACACAATTGCCCATTATACGC*GCGT ATAATGGACTATTGTGTGCTGATA (SEQ ID NO: 176) was introduced outside both ITRs in all the BsrGI shuttle vectors used for capsid library insertion (the asterisk depicts the position were the two complementary strands get covalently linked to each other), in order to obtain the following plasmids: TelN-Syn9-BsrGI (SEQ ID NO 18), TelN-GFAP9-BsrGI (SEQ ID NO 19), TelN-Syn5-BsrGI (SEQ ID NO 20), TelN-GFAP5-BsrGI (SEQ ID NO 21), TelN-Syn6-BsrGI (SEQ ID NO 22), TelN-GFAP6-BsrGI (SEQ ID NO 23), TelN-SynDJ8-BsrGI (SEQ ID NO 24), TelN-GFAPDJ8-BsrGI (SEQ ID NO 25). Several methods for rolling circle amplification were tested, and the best results (high yield and low non-specific amplification) were obtained with the TruePrime technology (Expedeon), which relies on primerless amplification (Picher et al., 2016).

Briefly, the entire column-purified assembly reaction was used in a 900-ul TruePrime reaction following the manufacturer's instructions and incubated overnight at 30° C. The following day, the rolling circle reaction product was incubated 10 minutes at 65° C. to inactivate the enzymes and was diluted 5-fold in 1× thermoPol buffer with 50 ul protelomerase (NEB) in a 4.5-ml reaction. After 1 hour at 30° C., the reaction was heat-treated for 10 minutes at 70° C. to inactivate the protelomerase, and a 4.5-ul aliquot was run on an agarose gel. The entire reaction was then purified on multiple (10-12) Qiagen QiaPrep 2.0 columns following manufacturer's instructions. The typical yield obtained with this method was 160-180 ug DNA, which indicates >100-fold amplification of the starting material (typically 0.5-1 ug) and provides enough DNA for transfection of 200 cell culture dishes (FIG. 16).

The composition of all libraries was tested by next-gen sequencing with an Illumina NextSeq sequencing platform to estimate the number of variants and the eventual contamination by wild-type viruses. Amplicons were generated by PCR with Q5 polymerase (NEB) using primers containing Illumina TruSeq adapters and index barcodes. Amplicons were obtained by low-cycle PCR amplification (15 cycles), ran on 3% agarose gels and purified using Zymo gel extraction reagents. Libraries were quantified using a nanodrop, pooled into equimolar mixes and re-quantified with a KAPA library quantification kit following manufacturer's instruction. Libraries were mixed with 20-40% of PhiX control library to increase sequence diversity.

All DNA libraries generated by rolling circle showed a high sequence diversity (typically >1e8 unique variants, beyond the limits of NextSeq sequencing). By comparison, plasmid libraries generated by bacterial transformation rarely exceeded 1-2e7 variants.

Example 6. Prevention and/or Reduction of Contamination

Figure 17:
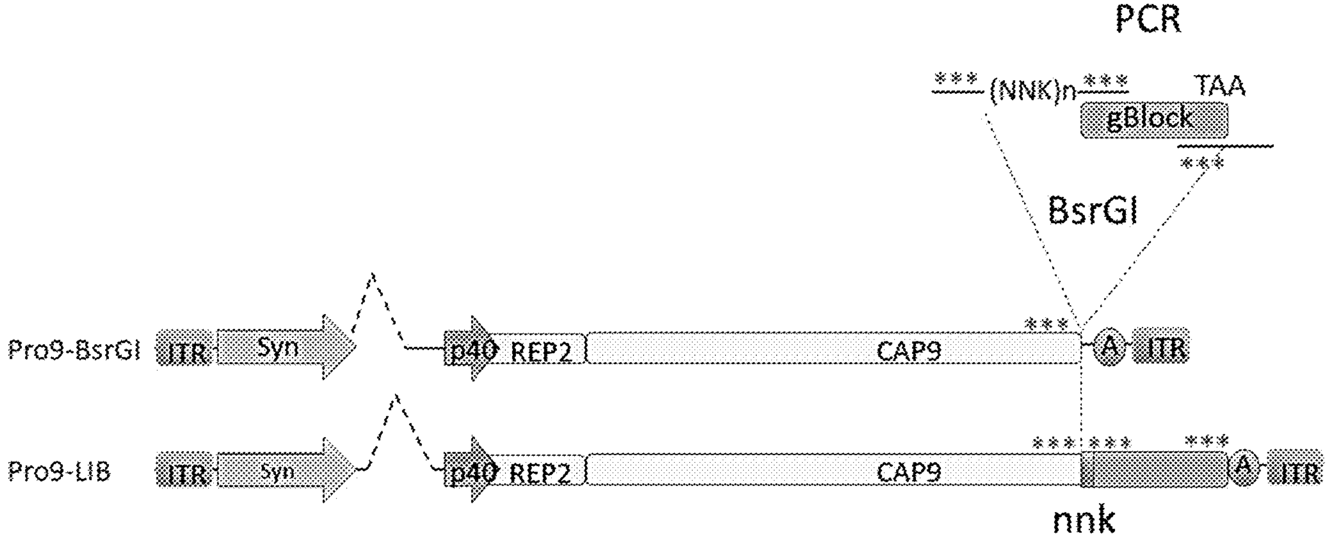
FIG. 17 provides the sequence of the codon-mutant AAV9 library shuttle designed to minimize wild-type contamination (SEQ ID NOS 33-34 and 48-52, respectively, in order of appearance).

In another embodiment, a primer/vector system aimed at completely preventing contamination of AAV9 libraries by wild-type virus possibly recovered from environmental contamination or from naturally infected primate animal tissues was created. This was achieved by introducing a maximum number of silent mutations in the sequences surrounding the library insertion site, as well as the sequence immediately before the CAP stop codon, used for PCR amplification (FIG. 17). These libraries showed an extremely low number of wild-type AAV9 detection by NGS (<2 AAV9 reads per 5e7 total reads), suggesting that the alteration of codons surrounding the library amplification and cloning sites is a very efficient way to preserve libraries from environmental or experimental contaminations.

Libraries were produced as described previously by calcium phosphate transfection of HEK-293T cells, dual iodixanol gradient fractionation and membrane ultrafiltration using 100,000 Da MWCO Amicon-15 membranes (Millipore), quantified by real-time PCR and an aliquot was used for NGS amplicon generation and NextSeq sequencing. The diversity of viral libraries was significantly lower than that of DNA libraries (typically ~1-2e7 unique variants) and showed a very strong counter-selection of variants containing stop codons (from 20% in DNA libraries to ~1% in virus libraries), evincing a very high rate of cis-packaging, as observed in previous studies (Nonnenmacher et al., 2014).

Example 7. In Vivo Selection of AAV9 Libraries for Mouse Brain Transduction

Figure 18:
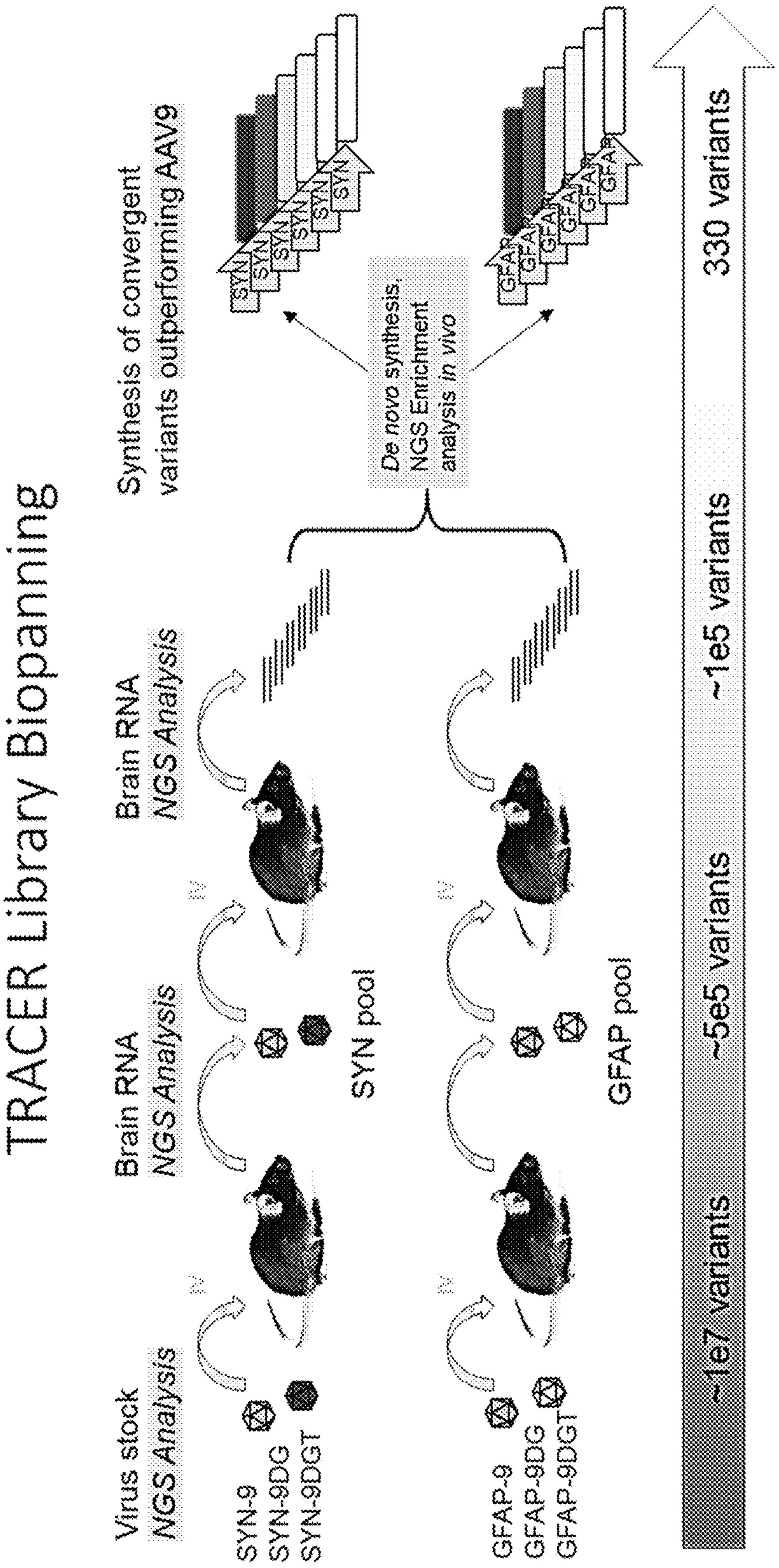
FIG. 18 provides a description of AAV9 peptide libraries biopanning.
Figure 19:
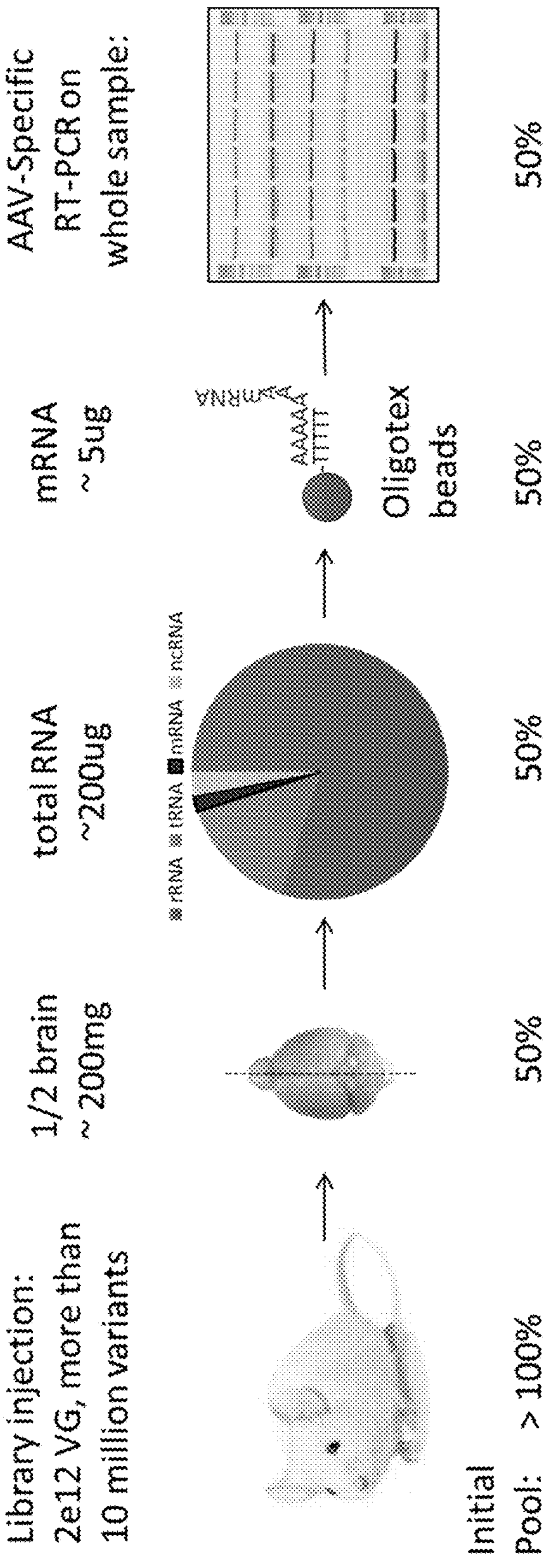
FIG. 19 illustrates the recovery process from an initial pool with recovery at 50%.
Figure 20:
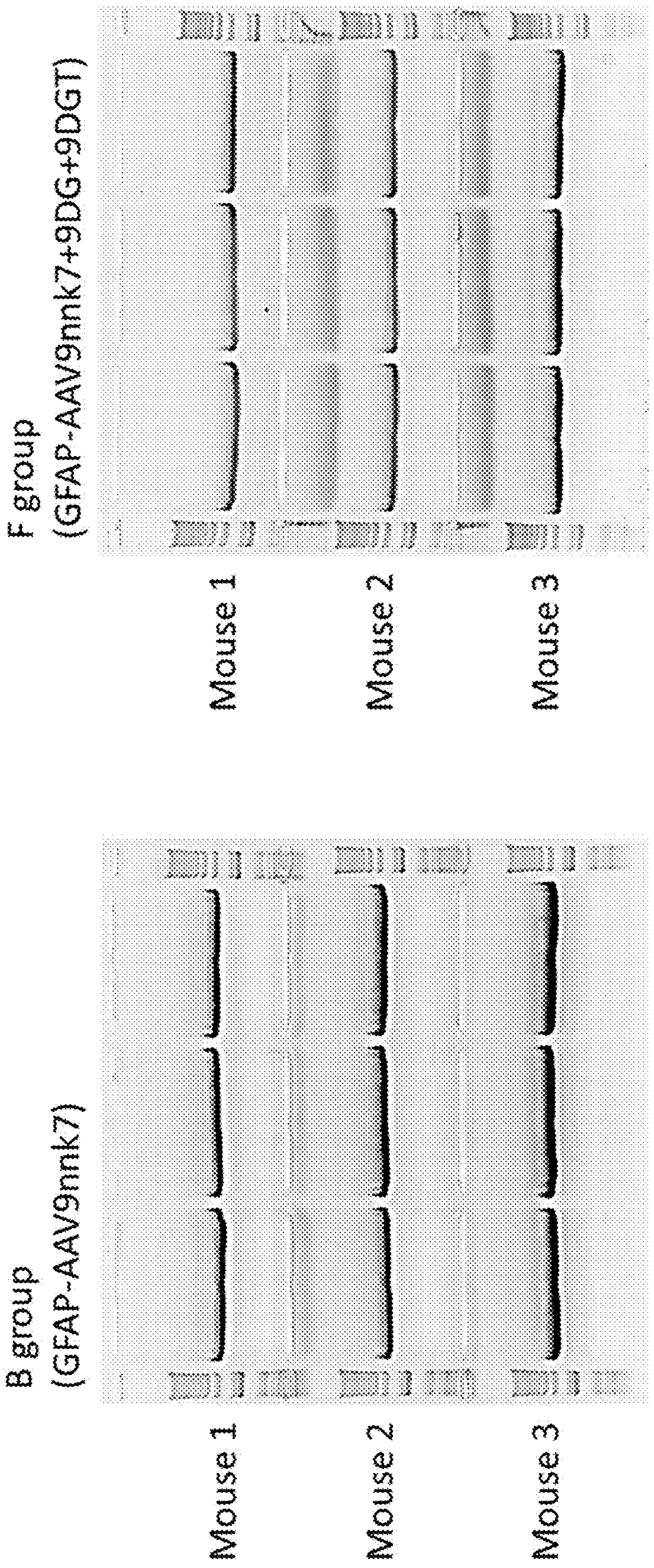
FIG. 20 provides an example of the cDNA recovery and amplification from GFAP-driven libraries (B group and F group).

An RNA-driven library selection for increased brain transduction in a murine model was then developed. AAV9 libraries generated as described above were intravenously injected to male C57BL/6 mice at a dose 2e12 VG per mouse. Two groups of mice were injected with a single SYN-driven or GFAP-driven libraries derived from wild-type AAV9 flanking sequences, and two other groups received pooled libraries containing wild-type and PHP.eB-derived flanking sequences (FIG. 18). After one month, RNA was extracted from 200 mg of brain tissue corresponding to a whole hemisphere using RNeasy Universal Plus procedure (Qiagen). In order to minimize the possibility of RNA under sampling, the entire RNA preparation (~200 ug) was subjected to mRNA enrichment using Oligotex beads (Qiagen) as recommended by the manufacturer. The entire preparation of enriched mRNA (~5 ug, equivalent to 2% of total RNA) was then reverse transcribed in a 40-ul Superscript IV reaction (Life Technologies) using a library-specific primer with the following sequence: 5'-GAAACGAATTAAACGGTTTATTGATTAACAATCGATTA-3' (SEQ ID NO: 415) (CAP stop codon is underlined) (FIG. 19). The entire pool of cDNA was then amplified 30 cycles with 55° C. annealing temperature and 2 minutes elongation in a 500-ul PCR reaction assembled with Q5 master mix, GloSpliceF6 forward primer and a CAP9-specific reverse primer: 5'-CGGTTTATTGATTAACAATCGATTACAGATTACGAGTCAGGTATC-3' (SEQ ID NO: 416) (CAP stop codon is underlined). This method allowed recovery of abundant amplicons from all brain samples (FIG. 20).

Figure 21A:
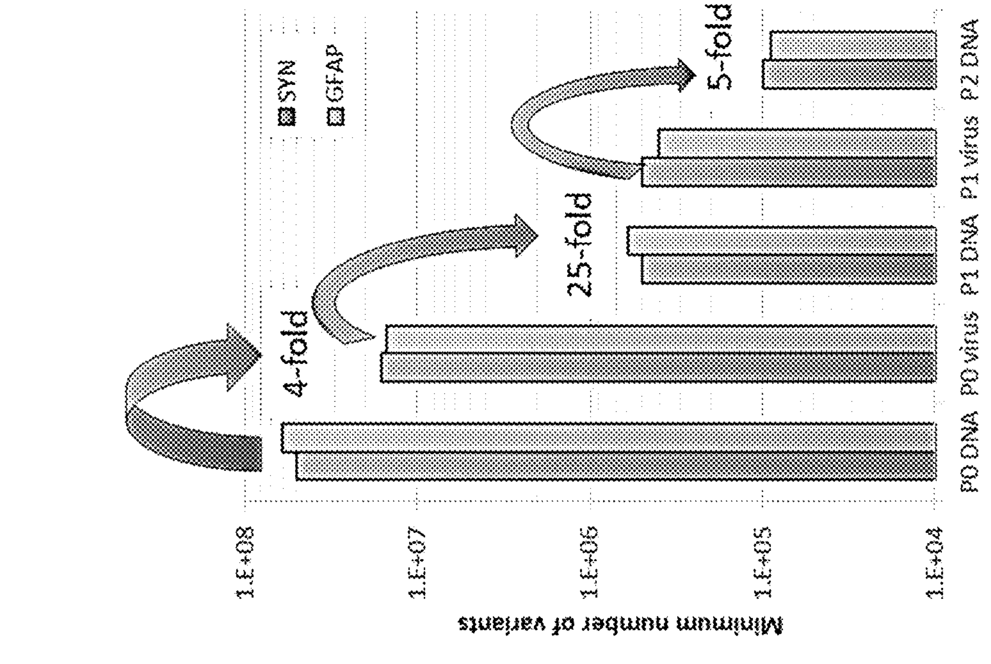
FIG. 21A, FIG. 21B and FIG. 21C show the progression of AAV9 peptide library diversity throughout the biopanning process.
Figure 21B:
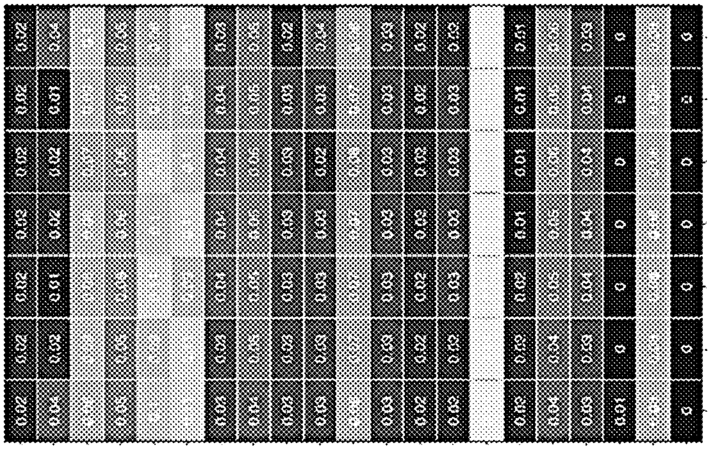
Figure 21C:
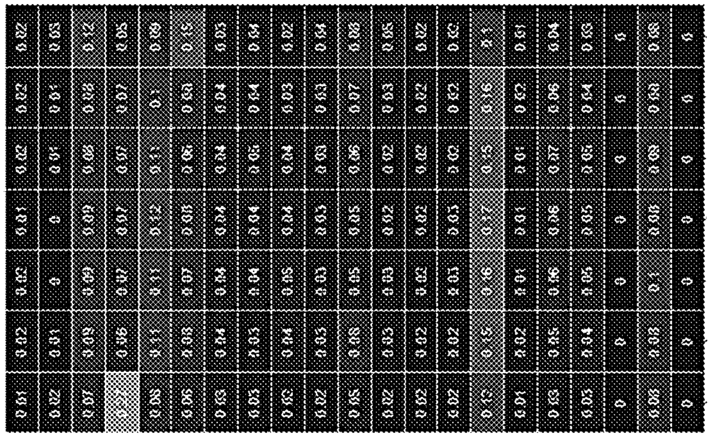

Full-length capsid amplicons were then used as templates for NGS library generation, as well as cloning into a P1 DNA library for the next round of biopanning, using the exact same assembly and cloning-free procedure. NGS analysis performed on PCR amplicons indicated that the library diversity dropped ~25-fold (from 1e7 to 4e5) after the first round of biopanning for both Syn-driven and GFAP-driven libraries (FIG. 21). The number of 1$^{st}$ pass variants (P1) recovered was too high to show any significant sequence convergence at this point, and there was very little overlap between the composition of pools recovered from individual animals. Therefore, a second round of selection was performed. After the second biopanning (P2), the total number of unique variants further dropped by 4-5-fold, down to <1e5 peptides. Importantly, some libraries recovered after the first round of biopanning showed significant counts of wild-type AAV9 and AAV-PHP.eB sequences, presumably from environmental contamination. These later became useful benchmarks in the second round of enrichment.

Figure 22:
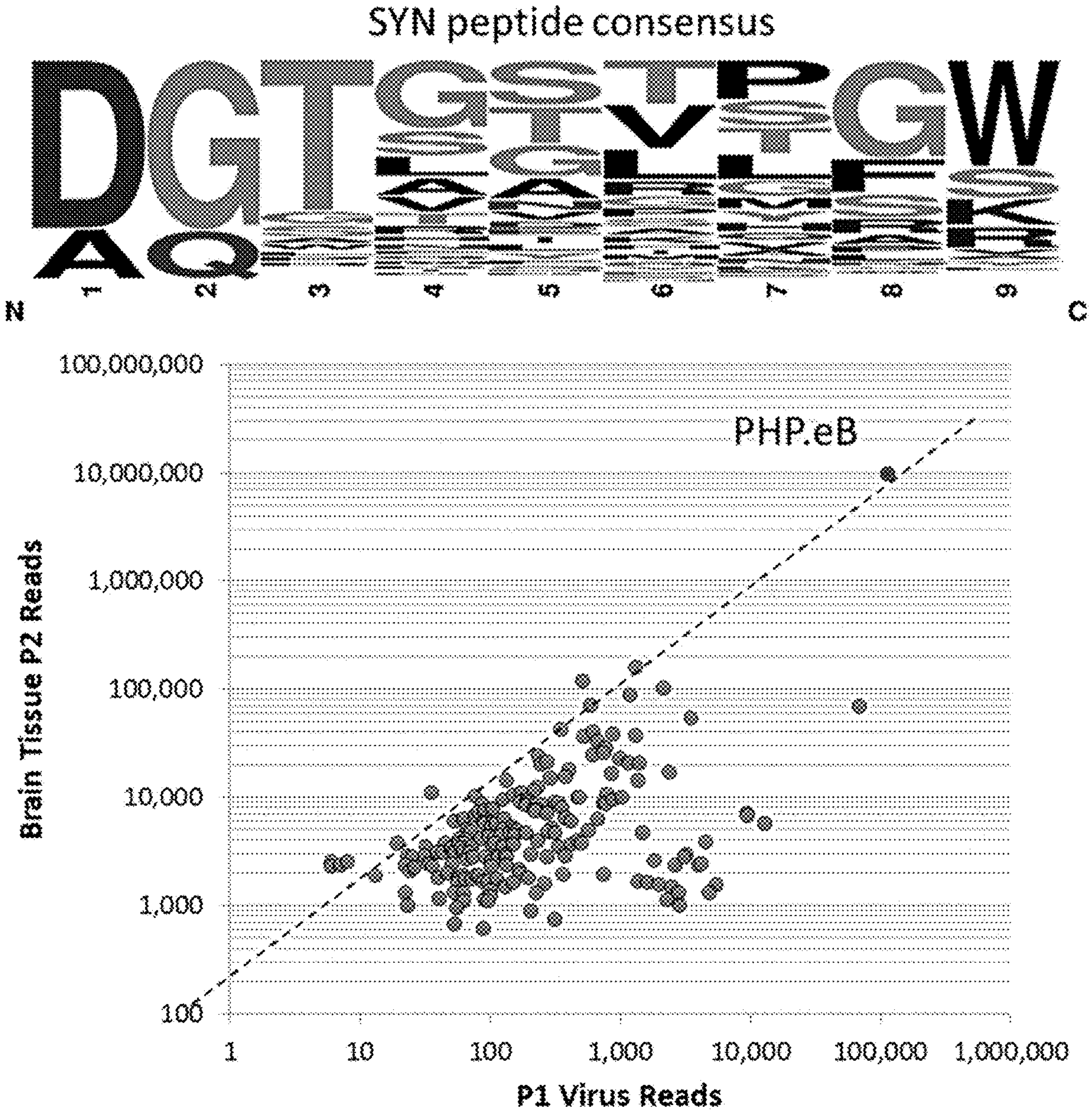
FIG. 22 provides neuron (SYN)-AAV9 Peptide Libraries Composition at P2.
Figure 23:
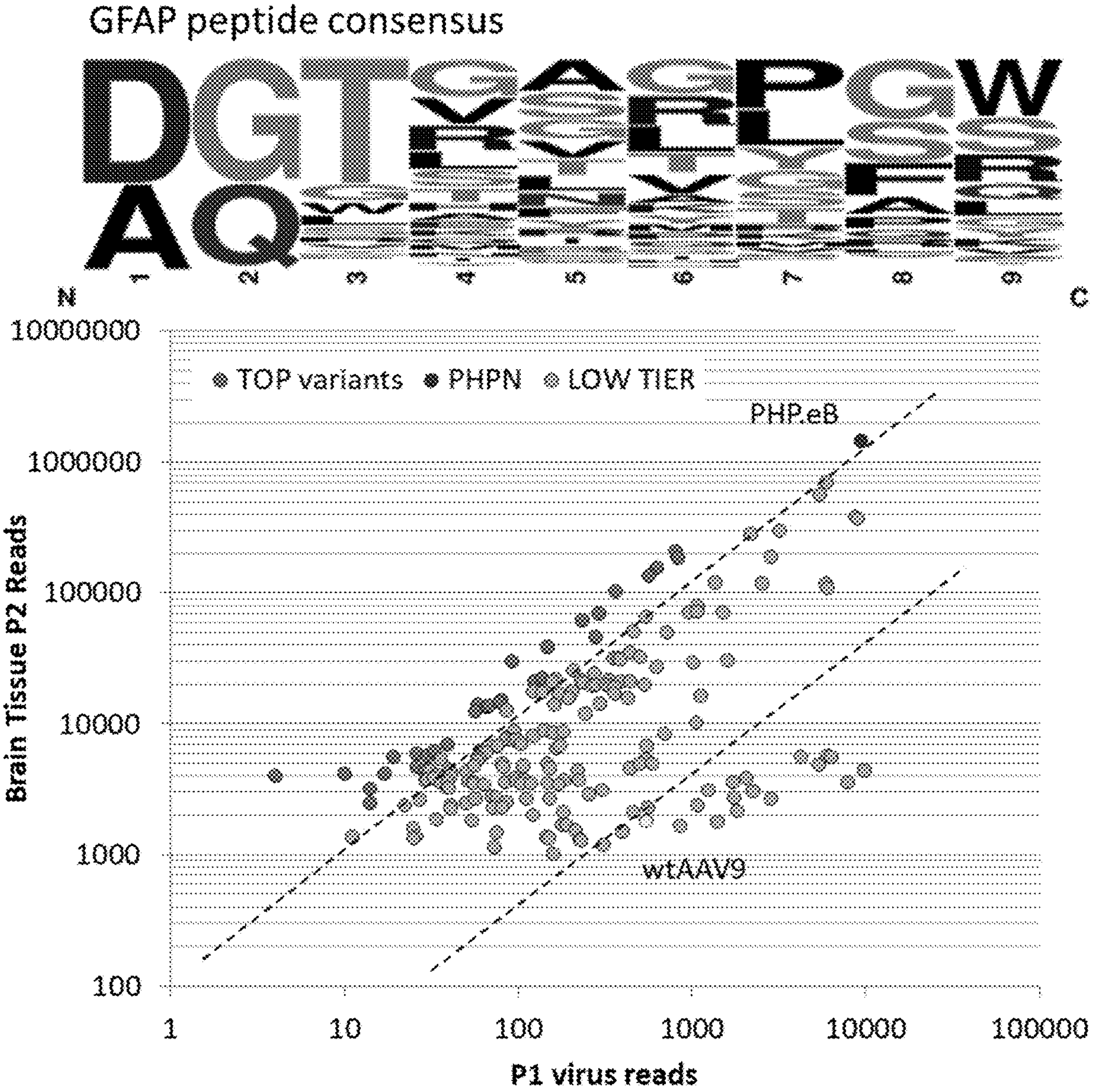
FIG. 23 provides astrocyte (GFAP)-AAV9 Peptide Libraries Composition at P2.

Following RNA recovery and PCR amplification, a systematic enrichment analysis by NGS was performed by calculating the ratio of P2/P1 reads and comparing it to AAV9 or PHP.eB P2/P1 ratio. As shown in FIG. 22, Table 4, FIG. 23 and Table 5, several capsids showed a higher enrichment ratio than the benchmark PHP.eB in both Syn-driven and GFAP-driven libraries, and sequence convergence was obvious, as represented by consensus sequence generation.

TABLE 4

Capsid analysis results

| Rank (enrichment factor) | Ranking (count) | Peptide | SEQ ID NO | Average of brain | P1 AEvirus_S11 | Brain/ virus stock |
|---|---|---|---|---|---|---|
| 1 | 136 | DGTLAVHFK | 417 | 2546.3 | 6 | 254.6 |
| 2 | 153 | DGTFAVPFK | 418 | 2321.7 | 6 | 232.2 |
| 3 | 155 | EGTLAVPFK | 419 | 2351.0 | 7 | 201.5 |
| 4 | 147 | DGTMAVPFK | 420 | 2547.0 | 8 | 191.0 |
| 5 | 32 | DGTGGTKGW | 107 | 11116.0 | 35 | 190.6 |
| 6 | 3 | AQWPTSYDA | 62 | 119359.7 | 512 | 139.9 |
| 7 | 99 | DGTLAVTFK | 421 | 3779.7 | 19 | 119.4 |
| 8 | 176 | DGTLAVPIK | 422 | 1882.0 | 13 | 86.9 |
| 9 | 36 | AQTTEKPWL | 83 | 10192.0 | 76 | 80.5 |
| 10 | 165 | DGTAIHLSS | 67 | 2885.0 | 23 | 75.3 |
| 11 | 13 | DGTLSQPFR | 65 | 42145.7 | 344 | 73.5 |
| 12 | 2 | DGTLAAPFK | 120 | 157129.3 | 1,300 | 72.5 |
| 13 | 8 | AQPEGSARW | 60 | 70884.0 | 594 | 71.6 |
| 14 | 48 | AQWPTAYDA | 256 | 5934.0 | 53 | 67.2 |
| 15 | 198 | DGTLQQPFR | 89 | 2793.3 | 25 | 67.0 |
| 16 | 104 | DGTLAVNFK | 346 | 3511.0 | 32 | 65.8 |
| 17 | 31 | DGTGNLSGW | 302 | 14521.3 | 133 | 65.5 |
| 18 | 158 | DGTLEVTFK | 423 | 2337.7 | 22 | 63.8 |
| 19 | 51 | DGTMDKPFR | 70 | 23962.3 | 234 | 61.4 |
| 20 | 80 | DGTGQVTGW | 68 | 6242.7 | 62 | 60.4 |
| 21 | 42 | AQFPTNYDS | 66 | 8640.0 | 86 | 60.3 |
| 22 | 127 | ERTLAVPFK | 424 | 2873.3 | 31 | 55.6 |
| 23 | 1 | DGTLAVPFK | 71 | 9885065.7 | 110,785 | 53.5 |
| 24 | 61 | DGTGTTMGW | 324 | 6753.0 | 76 | 53.3 |
| 25 | 69 | DGSQSTTGW | 136 | 7227.7 | 82 | 52.9 |
| 26 | 186 | DGTVSNPFR | 403 | 2074.3 | 24 | 51.9 |
| 27 | 160 | DGTLEVHFK | 348 | 2245.0 | 26 | 51.8 |
| 28 | 29 | DGTISQPFK | 105 | 20505.7 | 243 | 50.6 |
| 29 | 102 | AQGSWNPPA | 80 | 3746.0 | 45 | 49.9 |
| 30 | 59 | DGTHSTTGW | 145 | 7499.0 | 91 | 49.4 |

TABLE 4-continued

| Capsid analysis results | | | | | | |
|---|---|---|---|---|---|---|
| Rank (enrichment factor) | Ranking (count) | Peptide | SEQ ID NO | Average of brain | P1 AEvirus_S11 | Brain/ virus stock |
| 31 | 23 | DGTGSTTGW | 134 | 21582.0 | 272 | 47.6 |
| 32 | 142 | DGTGTTTGW | 130 | 3077.3 | 39 | 47.3 |
| 33 | 74 | DGTVTTTGW | 405 | 5088.7 | 66 | 46.3 |
| 34 | 35 | DGTTYVPPR | 75 | 9614.7 | 126 | 45.8 |
| 35 | 40 | DGTMDRPFK | 102 | 7868.3 | 104 | 45.4 |
| 36 | 4 | DGTGTTLGW | 323 | 88397.3 | 1,169 | 45.4 |
| 37 | 156 | DGTALMLSS | 280 | 2444.0 | 34 | 43.1 |
| 38 | 116 | DGTNTTHGW | 113 | 3065.0 | 43 | 42.8 |
| 39 | 98 | SGSLAVPFK | 425 | 4107.3 | 58 | 42.5 |
| 40 | 38 | DGTATTTGW | 285 | 10529.7 | 150 | 42.1 |
| 41 | 11 | DGTSYVPPR | 78 | 36293.3 | 526 | 41.4 |
| 42 | 89 | DGTGNTHGW | 72 | 3399.3 | 50 | 40.8 |
| 43 | 129 | DGTASVTGW | 283 | 4824.3 | 71 | 40.8 |
| 44 | 12 | AQWELSNGY | 246 | 40837.0 | 611 | 40.1 |
| 45 | 115 | DGTGNTSGW | 137 | 3405.0 | 51 | 40.1 |
| 46 | 67 | DGKGSTQGW | 272 | 5818.0 | 88 | 39.7 |
| 47 | 137 | DGTVIMLSS | 397 | 3781.0 | 58 | 39.1 |
| 48 | 119 | DGTGGVMGW | 297 | 2302.3 | 36 | 38.4 |
| 49 | 58 | DGGGTTTGW | 270 | 11174.3 | 175 | 38.3 |
| 50 | 71 | DGTSIHLSS | 378 | 5703.7 | 90 | 38.0 |

TABLE 5

| Capsid analysis results | | | | | | |
|---|---|---|---|---|---|---|
| Rank (enrichment factor) | Ranking (count) | Peptide | SEQ ID NO | Average of brain | p1 AEvirus_S11 | Brain/ virus stock |
| 1 | 106 | DGTGGTKGW | 107 | 3620.7 | 0 | NA |
| 2 | 264 | GGTRNTAPM | 426 | 831.0 | 0 | NA |
| 3 | 295 | AQGRMTDSQ | 199 | 716.0 | 0 | NA |
| 4 | 677 | DGNSYVPPR | 427 | 474.3 | 0 | NA |
| 5 | 700 | AQAGVSGQR | 428 | 456.0 | 0 | NA |
| 6 | 731 | AQAGNSNAV | 429 | 844.0 | 0 | NA |
| 7 | 181 | DGTGGLTGW | 294 | 4044.3 | 4 | 606.7 |
| 8 | 558 | AQWVYGQTV | 430 | 977.7 | 1 | 586.6 |
| 9 | 123 | DGTSFSPPK | 431 | 4227.3 | 10 | 253.6 |
| 10 | 35 | DGTIERPFR | 87 | 29872.0 | 92 | 194.8 |
| 11 | 105 | DGTTLVPPR | 116 | 5597.3 | 19 | 176.8 |

TABLE 5-continued

Capsid analysis results

| Rank (enrichment factor) | Ranking (count) | Peptide | SEQ ID NO | Average of brain | p1 AEvirus_S11 | Brain/ virus stock |
|---|---|---|---|---|---|---|
| 12 | 18 | DGTADKPFR | 63 | 103305.3 | 363 | 170.8 |
| 13 | 22 | DGTASYYDS | 61 | 61841.3 | 233 | 159.2 |
| 14 | 26 | AQTTDRPFL | 85 | 38893.7 | 147 | 158.7 |
| 15 | 8 | DGTQFSPPR | 108 | 206660.7 | 801 | 154.8 |
| 16 | 169 | DGTTTYGAR | 77 | 4237.3 | 17 | 149.6 |
| 17 | 11 | AQFVVGQQY | 95 | 152965.0 | 625 | 146.8 |
| 18 | 61 | DGTSYVPPR | 78 | 13968.0 | 58 | 144.5 |
| 19 | 16 | DGTAERPFR | 140 | 134132.7 | 565 | 142.4 |
| 20 | 21 | AQGENPGRW | 96 | 68919.7 | 292 | 141.6 |
| 21 | 157 | DGTSFTPPR | 88 | 3210.0 | 14 | 137.6 |
| 22 | 73 | AQTLARPFV | 98 | 5947.7 | 26 | 137.3 |
| 23 | 9 | DGTTWTPPR | 139 | 184936.7 | 825 | 134.5 |
| 24 | 721 | DGTATTMGW | 284 | 5562.3 | 25 | 133.5 |
| 25 | 129 | AQGTWNPPA | 82 | 12379.3 | 57 | 130.3 |
| 26 | 215 | DGTRLMLSS | 368 | 2505.0 | 12 | 125.3 |
| 27 | 60 | AQPLAVYGA | 217 | 13419.3 | 66 | 122.0 |
| 28 | 909 | AQGLDLGRW | 432 | 405.0 | 2 | 121.5 |
| 29 | 53 | DGTSFTPPK | 81 | 13673.3 | 68 | 120.6 |
| 30 | 412 | AQVMSGVGQ | 433 | 583.0 | 3 | 116.6 |
| 31 | 390 | AQKSVGSVY | 205 | 4415.7 | 23 | 115.2 |
| 32 | 70 | AQTREYLLG | 93 | 5752.7 | 30 | 115.1 |
| 33 | 43 | DGTNGLKGW | 76 | 15068.7 | 79 | 114.4 |
| 34 | 93 | AQYLAGYTV | 262 | 6223.3 | 33 | 113.2 |
| 35 | 54 | AQTGFAPPR | 161 | 14611.3 | 78 | 112.4 |
| 36 | 115 | DGTLNNPFR | 109 | 4719.7 | 26 | 108.9 |
| 37 | 968 | DGNGGLKGW | 167 | 3199.0 | 18 | 106.6 |
| 38 | 120 | AQSVAKPFL | 231 | 6929.7 | 39 | 106.6 |
| 39 | 544 | DGTHGLRGW | 434 | 528.0 | 3 | 105.6 |
| 40 | 159 | AQSVVRPFL | 233 | 2457.3 | 14 | 105.3 |
| 41 | 65 | DGTRNMYEG | 135 | 21086.3 | 124 | 102.0 |
| 42 | 556 | AQRWAADSS | 435 | 500.7 | 3 | 100.1 |
| 43 | 30 | AQGPTRPFL | 125 | 46225.3 | 279 | 99.4 |
| 44 | 64 | DGTVPYLSS | 401 | 22384.3 | 137 | 98.0 |
| 45 | 870 | AQTGASGAT | 436 | 473.7 | 3 | 94.7 |
| 46 | 341 | AQLVAGYSQ | 437 | 1240.0 | 8 | 93.0 |
| 47 | 375 | AQSGGVGQV | 228 | 768.3 | 5 | 92.2 |
| 48 | 145 | AQSLARLFP | 438 | 4435.3 | 29 | 91.8 |

TABLE 5-continued

Capsid analysis results

| Rank (enrichment factor) | Ranking (count) | Peptide | SEQ ID NO | Average of brain | p1 AEvirus_S11 | Brain/ virus stock |
|---|---|---|---|---|---|---|
| 49 | 1 | DGTLAVPFK | 71 | 1445517.0 | 9453 | 91.7 |
| 50 | 124 | DGTGNVTGW | 69 | 5424.3 | 36 | 90.4 |

Figure 24:
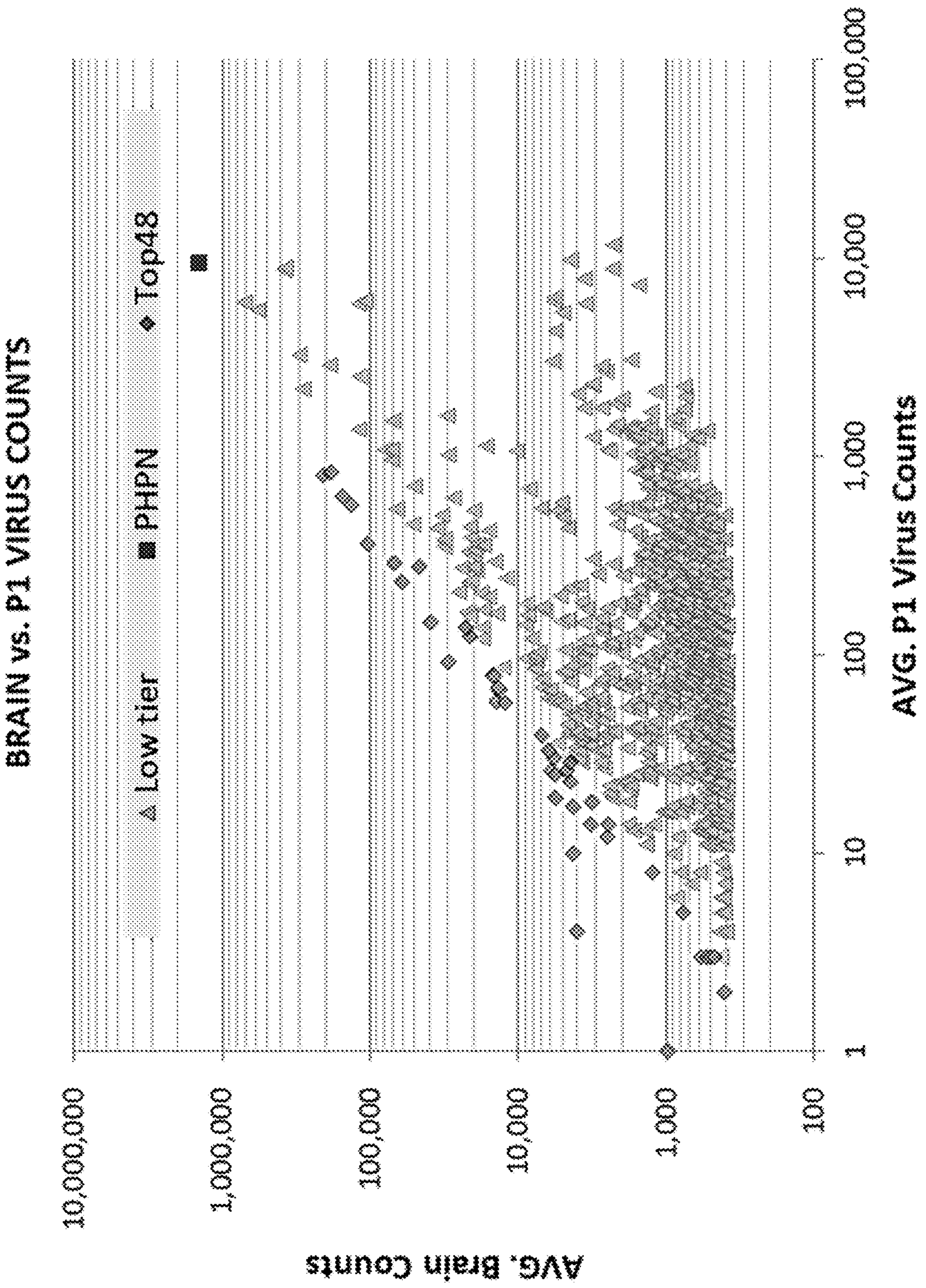
FIG. 24 provides an estimation of brain/liver specificity in GFAP-AAV9 peptide library candidates.
Figure 25:
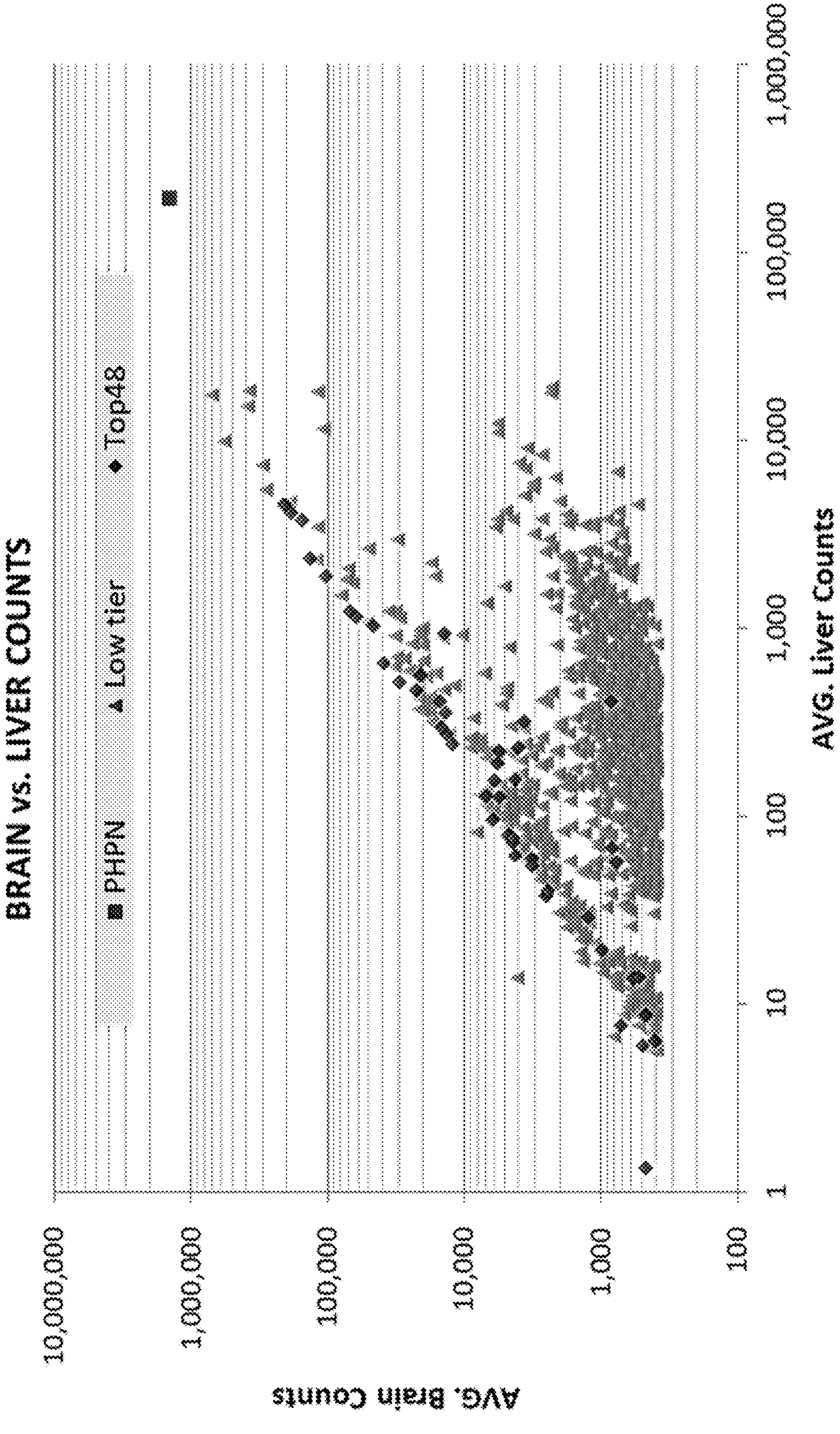
FIG. 25 provides an estimation of brain/liver specificity in GFAP-AAV9 peptide library candidates.

Importantly, there was also a strong sequence convergence between different animals, suggesting an efficient selection after only two passages. FIG. 24 and FIG. 25 provide an estimation of brain/liver specificity in GFAP-AAV9 peptide library candidates.

Example 8. Multiplexing Selections

Figure 26:
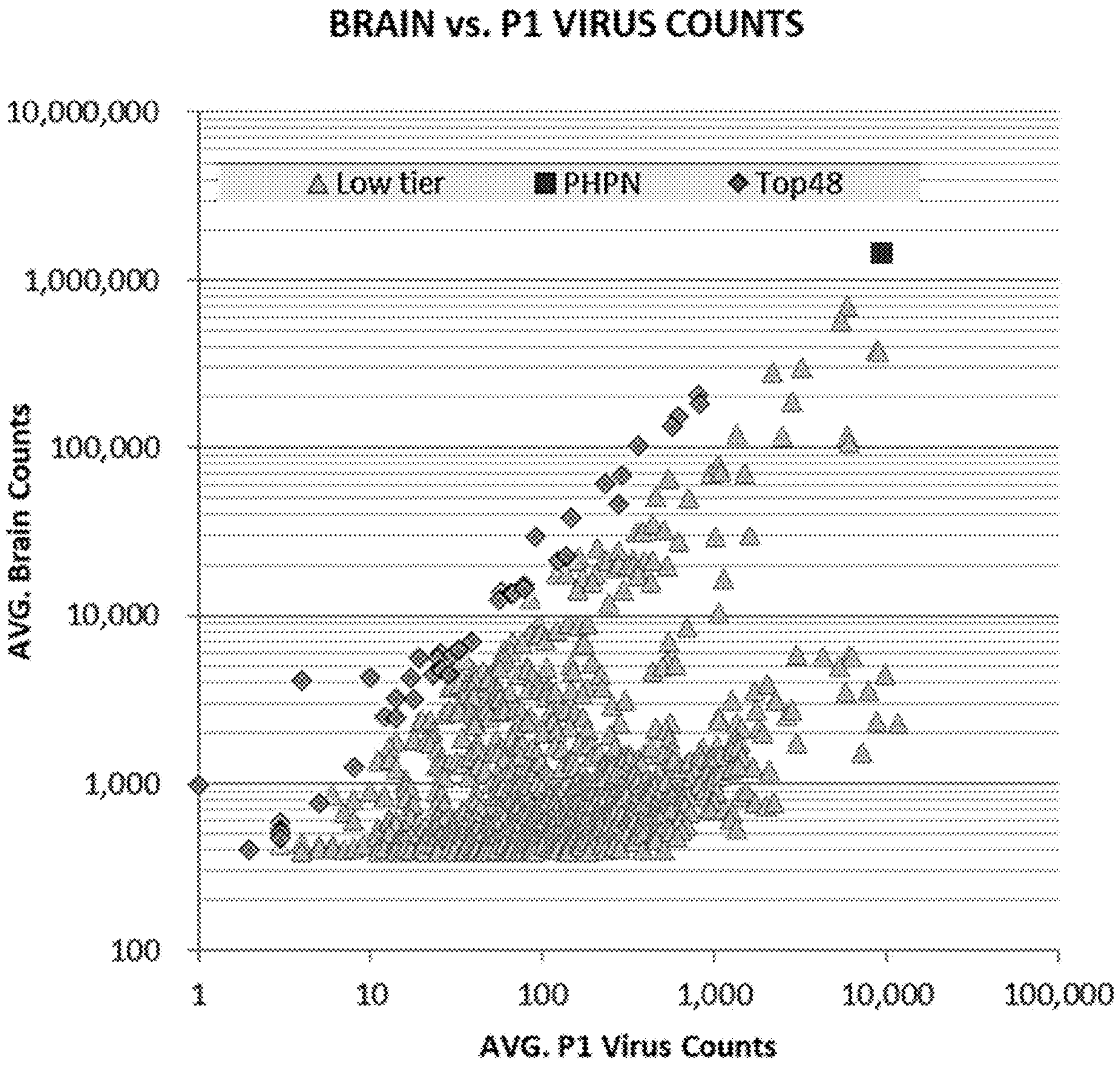
FIG. 26 provide an example subpopulation selection of variants.

For the final multiplex in vivo screen by individual variant pooling in equimolar library, a subpopulation of variants with promising properties (such as, but not limited to, enrichment factor, liver detargeting, high counts in more than one mouse, etc.) may be selected as shown in FIG. 26 and then an equimolar pool of primers encoding all the 7-mers (microchip solid-phase synthesis, up to 3,800 primers per chip) can be synthesized. The limited diversity library may be produced including internal controls such as, but not limited to, PHP.N, PHP.B, wild-type AAV9 (wtAAV9) and/or any other serotype including those taught herein. The mice are injected and then the RNA enrichment is compared to internal controls in a similar manner to a barcoding study, which is known in the art and described herein.

Example 9. Codon Optimization

Codon variants may be used to improve data strength when using synthesized libraries. A listing of NNK codons, NNM codons and the most favorable NNM codons in mammals for various amino acids is provided in Table 6. In Table 6, * means that no NNM codon was available and ** means "avoid homopolymeric stretches if possible."

TABLE 6

Codon Variants

| Amino acid | NNK codon | NNM codons | Most favorable NNM codon in mammals |
|---|---|---|---|
| F | TTT | TTC | TTC |
| L | TTG, CTT, CTG | TTA, CTC, CTA | CTC |
| S | TCT, TCG, AGT | TCC, TCA, AGC | AGC |
| Y | TAT | TAC | TAC |
| C | TGT | TGC | TGC |
| W | TGG | | TGG* |
| P | CCT, CCG | CCC, CCA | CCA** |
| H | CAT | CAC | CAC |
| Q | CAG | CAA | CAA |
| R | CGT, CGG, AGG | CGC, CGA, AGA | AGA |
| I | ATT | ATC, ATA | ATC |
| M | ATG | | ATT* |
| T | ACT, ACG | ACC, ACA | ACC |
| N | AAT | AAC | AAC |
| K | AAG | AAA | AAA |
| V | GTT, GTG | GTC, GTA | GTC |
| A | GCT, GCG | GCC, GCA | GCC |
| D | GAT | GAC | GAC |
| E | GAG | GAA | GAA |
| G | GGT, GGG | GGC, GGA | GGC |
| stop | TAG | TAC, TAA | n/a |

*no NNM codon available
**avoid homopolymeric stretches if possible

In order to have a balanced library it is recommended to establish a list of potential candidates. Then, using Table 6, a pooled primer library containing every peptide variant with encoded by NNK codons (original from library) and non-NNK codons (maximum variation). If similar behavior is seen between the two variants of the same peptide, this would strengthen the analysis of that peptide. Additionally, it is recommended to choose the most favorable NNM codons (M=A or C).

Example 10. Library Generation

The top-ranking 330 peptide variants from SYN-driven and GFAP-driven libraries that showed enhanced performance relative to the parental AAV9 were selected. A de novo library by pooled primer synthesis of all 330 peptide sequences plus AAV9, AAV-PHP.B and AAV-PHP.eB controls was generated (Table 7). In order to exclude potential artifacts due to the DNA sequence and to increase the robustness of the assay, each peptide variant was encoded by two different DNA sequences, one where all amino acids were encoded by NNK codons (identical to the original library) and another one where NNM codons were used whenever possible (M=C or A, Table 6).

TABLE 7

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQ (AAV9)** | | CAGAGTGCTCAG GCACAG | 439 | CAGAGTGCCCAA GCACAG | 772 |
| **AQAGAGSER** | 194 | CAGAGTGCCCAA GCGGGTGCGGGG TCGGAGCGGGCA CAG | 440 | CAGAGTGCACAA GCAGGAGCAGGA AGCGAAAGAGCA CAG | 773 |
| **AQDQNPGRW** | 195 | CAGAGTGCCCAA GATCAGAATCCG GGGCGTTGGGCA CAG | 441 | CAGAGTGCACAA GACCAAAACCCA GGAAGATGGGCA CAG | 774 |
| **AQELTRPFL** | 144 | CAGAGTGCCCAA GAGTTGACGCGT CCGTTTTTGGCAC AG | 442 | CAGAGTGCACAA GAACTCACAAGA CCATTCCTCGCAC AG | 775 |
| **AQEVPGYRW** | 196 | CAGAGTGCCCAA GAGGTGCCTGGG TATAGGTGGGCA CAG | 443 | CAGAGTGCACAA GAAGTCCCAGGA TACAGATGGGCA CAG | 776 |
| **AQFPTNYDS** | 66 | CAGAGTGCCCAA TTTCCTACGAATT ATGATTCTGCACA G | 444 | CAGAGTGCACAA TTCCCAACAAACT ACGACAGCGCAC AG | 777 |
| **AQFVVGQQY** | 95 | CAGAGTGCCCAA TTTGTGGTTGGTC AGCAGTATGCAC AG | 445 | CAGAGTGCACAA TTCGTCGTCGGAC AACAATACGCAC AG | 778 |
| **AQGASPGRW** | 149 | CAGAGTGCCCAA GGGGCTAGTCCG GGGCGGTGGGCA CAG | 446 | CAGAGTGCACAA GGAGCAAGCCCA GGAAGATGGGCA CAG | 779 |
| **AQGENPGRW** | 96 | CAGAGTGCCCAA GGGGAGAATCCG GGTAGGTGGGCA CAG | 447 | CAGAGTGCACAA GGAGAAAACCCA GGAAGATGGGCA CAG | 780 |
| **AQGGNPGRW** | 91 | CAGAGTGCCCAA GGGGGGAATCCG GGTCGGTGGGCA CAG | 448 | CAGAGTGCACAA GGAGGAAACCCA GGAAGATGGGCA CAG | 781 |
| **AQGGSTGSN** | 197 | CAGAGTGCCCAA GGTGGTTCTACG GGGTCGAATGCA CAG | 449 | CAGAGTGCACAA GGAGGAAGCACA GGAAGCAACGCA CAG | 782 |
| **AQGPTRPFL** | 125 | CAGAGTGCCCAA GGGCCGACTAGG CCGTTTTTGGCAC AG | 450 | CAGAGTGCACAA GGACCAACAAGA CCATTCCTCGCAC AG | 783 |
| **AQGRDGWAA** | 198 | CAGAGTGCCCAA GGTCGGGATGGT TGGGCGGCGGCA CAG | 451 | CAGAGTGCACAA GGAAGAGACGGA TGGGCAGCAGCA CAG | 784 |
| **AQGRMTDSQ** | 199 | CAGAGTGCCCAA GGTCGTATGACT GATTCGCAGGCA CAG | 452 | CAGAGTGCACAA GGAAGAATGACA GACAGCCAAGCA CAG | 785 |
| **AQGSDVGRW** | 128 | CAGAGTGCCCAA GGTAGTGATGTG GGGCGGTGGGCA CAG | 453 | CAGAGTGCACAA GGAAGCGACGTC GGAAGATGGGCA CAG | 786 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQGSNPGRW** | 103 | CAGAGTGCCCAA GGTAGTAATCCG GGGAGGTGGGCA CAG | 454 | CAGAGTGCACAA GGAAGCAACCCA GGAAGATGGGCA CAG | 787 |
| **AQGSNSPQV** | 200 | CAGAGTGCCCAA GGGTCTAATTCGC CTCAGGTGGCAC AG | 455 | CAGAGTGCACAA GGAAGCAACAGC CCACAAGTCGCA CAG | 788 |
| **AQGSWNPPA** | 80 | CAGAGTGCCCAA GGTTCGTGGAAT CCGCCGGCGGCA CAG | 456 | CAGAGTGCACAA GGAAGCTGGAAC CCACCAGCAGCA CAG | 789 |
| **AQGTWNPPA** | 82 | CAGAGTGCCCAA GGTACTTGGAAT CCGCCGGCTGCA CAG | 457 | CAGAGTGCACAA GGAACATGGAAC CCACCAGCAGCA CAG | 790 |
| **AQGVFIPPK** | 201 | CAGAGTGCCCAA GGTGTTTTTATTC CGCCGAAGGCAC AG | 458 | CAGAGTGCACAA GGAGTCTTCATCC CACCAAAAGCAC AG | 791 |
| **AQHVNASQS** | 202 | CAGAGTGCCCAA CATGTGAATGCTT CTCAGTCTGCACA G | 459 | CAGAGTGCACAA CACGTCAACGCA AGCCAAAGCGCA CAG | 792 |
| **AQIKAGWAQ** | 203 | CAGAGTGCCCAA ATTAAGGCGGGG TGGGCGCAGGCA CAG | 460 | CAGAGTGCACAA ATCAAAGCAGGA TGGGCACAAGCA CAG | 793 |
| **AQIMSGYAQ** | 204 | CAGAGTGCCCAA ATTATGAGTGGG TATGCTCAGGCA CAG | 461 | CAGAGTGCACAA ATCATGAGCGGA TACGCACAAGCA CAG | 794 |
| **AQKSVGSVY** | 205 | CAGAGTGCCCAA AAGAGTGTGGGT AGTGTTTATGCAC AG | 462 | CAGAGTGCACAA AAAAGCGTCGGA AGCGTCTACGCA CAG | 795 |
| **AQLEHGFAQ** | 206 | CAGAGTGCCCAA CTTGAGCATGGG TTTGCTCAGGCAC AG | 463 | CAGAGTGCACAA CTCGAACACGGA TTCGCACAAGCA CAG | 796 |
| **AQLGGVLSA** | 207 | CAGAGTGCCCAA CTGGGTGGGGTG TTGAGTGCTGCAC AG | 464 | CAGAGTGCACAA CTCGGAGGAGTC CTCAGCGCAGCA CAG | 797 |
| **AQLGLSQGR** | 208 | CAGAGTGCCCAA CTGGGGCTTTCGC AGGGGCGGGCAC AG | 465 | CAGAGTGCACAA CTCGGACTCAGC CAAGGAAGAGCA CAG | 798 |
| **AQLGYGFAQ** | 209 | CAGAGTGCCCAA TTGGGGTATGGG TTTGCTCAGGCAC AG | 466 | CAGAGTGCACAA CTCGGATACGGA TTCGCACAAGCA CAG | 799 |
| **AQLKYGLAQ** | 115 | CAGAGTGCCCAA TTGAAGTATGGTC TTGCGCAGGCAC AG | 467 | CAGAGTGCACAA CTCAAATACGGA CTCGCACAAGCA CAG | 800 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQLRIGFAQ** | 210 | CAGAGTGCCCAACTTCGGATTGGTTTTGCTCAGGCACAG | 468 | CAGAGTGCACAACTCAGAATCGGATTCGCACAAGCACAG | 801 |
| **AQLRMGYSQ** | 211 | CAGAGTGCCCAATTGCGTATGGGTTATAGTCAGGCACAG | 469 | CAGAGTGCACAACTCAGAATGGGATACAGCCAAGCACAG | 802 |
| **AQLRQGYAQ** | 212 | CAGAGTGCCCAACTGAGGCAGGGGTATGCTCAGGCACAG | 470 | CAGAGTGCACAACTCAGACAAGGATACGCACAAGCACAG | 803 |
| **AQLRVGFAQ** | 123 | CAGAGTGCCCAATTGCGTGTTGGTTTTGCGCAGGCACAG | 471 | CAGAGTGCACAACTCAGAGTCGGATTCGCACAAGCACAG | 804 |
| **AQLSCRSQM** | 213 | CAGAGTGCCCAACTGTCGTGTCGGAGTCAGATGGCACAG | 472 | CAGAGTGCACAACTCAGCTGCAGAAGCCAAATGGCACAG | 805 |
| **AQLTYSQSL** | 214 | CAGAGTGCCCAATTGACGTATAGTCAGTCGCTGGCACAG | 473 | CAGAGTGCACAACTCACATACAGCCAAAGCCTCGCACAG | 806 |
| **AQLYKGYSQ** | 215 | CAGAGTGCCCAACTGTATAAGGGTTATAGTCAGGCACAG | 474 | CAGAGTGCACAACTCTACAAAGGATACAGCCAAGCACAG | 807 |
| **AQMPQRPFL** | 216 | CAGAGTGCCCAAATGCCTCAGCGGCCGTTTTTGGCACAG | 475 | CAGAGTGCACAAATGCCACAAAGACCATTCCTCGCACAG | 808 |
| **AQNGNPGRW** | 84 | CAGAGTGCCCAAAATGGTAATCCGGGGCGGTGGGCACAG | 476 | CAGAGTGCACAAAACGGAAACCCAGGAAGATGGGCACAG | 809 |
| **AQPEGSARW** | 60 | CAGAGTGCCCAACCTGAGGGTAGTGCGAGGTGGGCACAG | 477 | CAGAGTGCACAACCAGAAGGAAGCGCAAGATGGGCACAG | 810 |
| **AQPLAVYGA** | 217 | CAGAGTGCCCAACCGTTGGCTGTTTATGGGGCGGCACAG | 478 | CAGAGTGCACAACCACTCGCAGTCTACGGAGCAGCACAG | 811 |
| **AQPQSSSMS** | 218 | CAGAGTGCCCAACCGCAGTCGTCGTCGATGAGTGCACAG | 479 | CAGAGTGCACAACCACAAAGCAGCAGCATGAGCGCACAG | 812 |
| **AQPSVGGYW** | 219 | CAGAGTGCCCAACCGAGTGTGGGTGGGTATTGGGCACAG | 480 | CAGAGTGCACAACCAAGCGTCGGAGGATACTGGGCACAG | 813 |
| **AQQAVGQSW** | 220 | CAGAGTGCCCAACAGGCTGTGGGTCAGTCTTGGGCACAG | 481 | CAGAGTGCACAACAAGCAGTCGGACAAAGCTGGGCACAG | 814 |
| **AQQRSLASG** | 221 | CAGAGTGCCCAACAGCGTTCGCTGGCTTCGGGTGCACAG | 482 | CAGAGTGCACAACAAAGAAGCCTCGCAAGCGGAGCACAG | 815 |
| **AQQVMNSQG** | 222 | CAGAGTGCCCAACAGGTGATGAATAGTCAGGGGGCACAG | 483 | CAGAGTGCACAACAAGTCATGAACAGCCAAGGAGCACAG | 816 |
| **AQRGVGLSQ** | 223 | CAGAGTGCCCAACGTGGGGTTGGGTTGAGTCAGGCACAG | 484 | CAGAGTGCACAAAGAGGAGTCGGACTCAGCCAAGCACAG | 817 |
| **AQRHDAEGS** | 224 | CAGAGTGCCCAAAGGCATGATGCGGAGGGTAGTGCACAG | 485 | CAGAGTGCACAAAGACACGACGCAGAAGGAAGCGCACAG | 818 |
| **AQRKGEPHY** | 225 | CAGAGTGCCCAACGTAAGGGGGAGCCTCATTATGCACAG | 486 | CAGAGTGCACAAAGAAAAGGAGAACCACACTACGCACAG | 819 |
| **AQRYTGDSS** | 138 | CAGAGTGCCCAAAGGTATACGGGGGATTCTAGTGCACAG | 487 | CAGAGTGCACAAAGATACACAGGAGACAGCAGCGCACAG | 820 |
| **AQSAMAAKG** | 226 | CAGAGTGCCCAATCGGCGATGGCTGCGAAGGGTGCACAG | 488 | CAGAGTGCACAAAGCGCAATGGCAGCAAAAGGAGCACAG | 821 |
| **AQSGGLTGS** | 227 | CAGAGTGCCCAATCTGGGGGTCTTACGGGGAGTGCACAG | 489 | CAGAGTGCACAAAGCGGAGGACTCACAGGAAGCGCACAG | 822 |
| **AQSGGVGQV** | 228 | CAGAGTGCCCAATCGGGTGGGGTGGGGCAGGTGGCACAG | 490 | CAGAGTGCACAAAGCGGAGGAGTCGGACAAGTCGCACAG | 823 |
| **AQSLATPFR** | 169 | CAGAGTGCCCAATCTCTGGCGACGCCTTTTCGTGCACAG | 491 | CAGAGTGCACAAAGCCTCGCAACACCATTCAGAGCACAG | 824 |
| **AQSMSRPFL** | 229 | CAGAGTGCCCAAAGTATGTCGCGTCCGTTTCTGGCACAG | 492 | CAGAGTGCACAAAGCATGAGCAGACCATTCCTCGCACAG | 825 |
| **AQSQLRPFL** | 230 | CAGAGTGCCCAAAGTCAGCTTAGGCCGTTTCTTGCACAG | 493 | CAGAGTGCACAAAGCCAACTCAGACCATTCCTCGCACAG | 826 |
| **AQSVAKPFL** | 231 | CAGAGTGCCCAATCTGTGGCTAAGCCTTTTTTGGCACAG | 494 | CAGAGTGCACAAAGCGTCGCAAAACCATTCCTCGCACAG | 827 |
| **AQSVSQPFR** | 232 | CAGAGTGCCCAATCGGTTTCGCAGCCGTTTAGGGCACAG | 495 | CAGAGTGCACAAAGCGTCAGCCAACCATTCAGAGCACAG | 828 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQSVVRPFL** | 233 | CAGAGTGCCCAATCTGTGGTGCGTCCTTTTCTGGCACAG | 496 | CAGAGTGCACAAAGCGTCGTCAGACCATTCCTCGCACAG | 829 |
| **AQTALSSST** | 234 | CAGAGTGCCCAAACTGCGCTTTCGTCGTCGACGGCACAG | 497 | CAGAGTGCACAAACAGCACTCAGCAGCAGCACAGCACAG | 830 |
| **AQTEMGGRC** | 235 | CAGAGTGCCCAAACGGAGATGGGTGGGAGGTGTGCACAG | 498 | CAGAGTGCACAAACAGAAATGGGAGGAAGATGCGCACAG | 831 |
| **AQTGFAPPR** | 161 | CAGAGTGCCCAAACGGGGTTTGCTCCGCCGCGTGCACAG | 499 | CAGAGTGCACAAACAGGATTCGCACCACCAAGAGCACAG | 832 |
| **AQTIRGYSS** | 236 | CAGAGTGCCCAAACGATTCGGGGGTATTCGTCTGCACAG | 500 | CAGAGTGCACAAACAATCAGAGGATACAGCAGCGCACAG | 833 |
| **AQTISNYHT** | 237 | CAGAGTGCCCAAACTATTTCTAATTATCATACGGCACAG | 501 | CAGAGTGCACAAACAATCAGCAACTACCACACAGCACAG | 834 |
| **AQTLARPFV** | 98 | CAGAGTGCCCAAACTTTGGCGCGTCCGTTTGTGGCACAG | 502 | CAGAGTGCACAAACACTCGCAAGACCATTCGTCGCACAG | 835 |
| **AQTLAVPFK (PHP.B)** | 168 | CAGAGTGCCCAAACTTTGGCGGTGCCTTTTAAGGCACAG | 503 | CAGAGTGCACAAACACTCGCAGTCCCATTCAAAGCACAG | 836 |
| **AQTPDRPWL** | 238 | CAGAGTGCCCAAACTCCTGATCGTCCTTGGTTGGCACAG | 504 | CAGAGTGCACAAACACCAGACAGACCATGGCTCGCACAG | 837 |
| **AQTRAGYAQ** | 126 | CAGAGTGCCCAAACTCGGGCTGGGTATGCTCAGGCACAG | 505 | CAGAGTGCACAAACAAGAGCAGGATACGCACAAGCACAG | 838 |
| **AQTRAGYSQ** | 141 | CAGAGTGCCCAAACTAGGGCGGGGTATTCTCAGGCACAG | 506 | CAGAGTGCACAAACAAGAGCAGGATACAGCCAAGCACAG | 839 |
| **AQTREYLLG** | 93 | CAGAGTGCCCAAACGCGTGAGTATCTGCTGGGGGCACAG | 507 | CAGAGTGCACAAACAAGAGAATACCTCCTCGGAGCACAG | 840 |
| **AQTSAKPFL** | 163 | CAGAGTGCCCAAACTTCTGCGAAGCCGTTTCTTGCACAG | 508 | CAGAGTGCACAAACAAGCGCAAAACCATTCCTCGCACAG | 841 |
| **AQTSARPFL** | 100 | CAGAGTGCCCAAACTTCTGCTAGGCCTTTTCTGGCACAG | 509 | CAGAGTGCACAAACAAGCGCAAGACCATTCCTCGCACAG | 842 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQTTDRPFL** | 85 | CAGAGTGCCCAAACTACTGATAGGCCTTTTTTGGCACAG | 510 | CAGAGTGCACAAACAACAGACAGACCATTCCTCGCACAG | 843 |
| **AQTTEKPWL** | 83 | CAGAGTGCCCAAACGACTGAGAAGCCGTGGCTGGCACAG | 511 | CAGAGTGCACAAACAACAGAAAAACCATGGCTCGCACAG | 844 |
| **AQTVARPFY** | 239 | CAGAGTGCCCAAACGGTTGCGCGGCCTTTTTATGCACAG | 512 | CAGAGTGCACAAACAGTCGCAAGACCATTCTACGCACAG | 845 |
| **AQTVATPFR** | 240 | CAGAGTGCCCAAACTGTTGCTACGCCGTTTAGGGCACAG | 513 | CAGAGTGCACAAACAGTCGCAACACCATTCAGAGCACAG | 846 |
| **AQTVTQLFK** | 241 | CAGAGTGCCCAAACGGTGACGCAGTTGTTTAAGGCACAG | 514 | CAGAGTGCACAAACAGTCACACAACTCTTCAAAGCACAG | 847 |
| **AQVHVGSVY** | 165 | CAGAGTGCCCAAGTTCATGTTGGGAGTGTTTATGCACAG | 515 | CAGAGTGCACAAGTCCACGTCGGAAGCGTCTACGCACAG | 848 |
| **AQVLAGYNM** | 242 | CAGAGTGCCCAAGTTCTTGCTGGGTATAATATGGCACAG | 516 | CAGAGTGCACAAGTCCTCGCAGGATACAACATGGCACAG | 849 |
| **AQVSEARVR** | 243 | CAGAGTGCCCAAGTTTCTGAGGCGAGGGTTAGGGCACAG | 517 | CAGAGTGCACAAGTCAGCGAAGCAAGAGTCAGAGCACAG | 850 |
| **AQVVVGYSQ** | 244 | CAGAGTGCCCAAGTTGTGGTGGGTTATAGTCAGGCACAG | 518 | CAGAGTGCACAAGTCGTCGTCGGATACAGCCAAGCACAG | 851 |
| **AQWAAGYNV** | 245 | CAGAGTGCCCAATGGGCTGCTGGGTATAATGTGGCACAG | 519 | CAGAGTGCACAATGGGCAGCAGGATACAACGTCGCACAG | 852 |
| **AQWELSNGY** | 246 | CAGAGTGCCCAATGGGAGCTGAGTAATGGGTATGCACAG | 520 | CAGAGTGCACAATGGGAACTCAGCAACGGATACGCACAG | 853 |
| **AQWEVKGGY** | 247 | CAGAGTGCCCAATGGGAGGTGAAGGGGGGTTATGCACAG | 521 | CAGAGTGCACAATGGGAAGTCAAAGGAGGATACGCACAG | 854 |
| **AQWEVKRGY** | 248 | CAGAGTGCCCAATGGGAGGTGAAGCGGGGGTATGCACAG | 522 | CAGAGTGCACAATGGGAAGTCAAAAGAGGATACGCACAG | 855 |
| **AQWEVQSGF** | 249 | CAGAGTGCCCAATGGGAGGTTCAGTCTGGGTTTGCACAG | 523 | CAGAGTGCACAATGGGAAGTCCAAAGCGGATTCGCACAG | 856 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **AQWEVRGGY** | 250 | CAGAGTGCCCAATGGGAGGTTCGTGGTGGTTATGCACAG | 524 | CAGAGTGCACAATGGGAAGTCAGAGGAGGATACGCACAG | 857 |
| **AQWEVTSGW** | 251 | CAGAGTGCCCAATGGGAGGTGACGAGTGGTTGGGCACAG | 525 | CAGAGTGCACAATGGGAAGTCACAAGCGGATGGGCACAG | 858 |
| **AQWGAPSHG** | 252 | CAGAGTGCCCAATGGGGGGCGCCGAGTCATGGGGCACAG | 526 | CAGAGTGCACAATGGGGAGCACCAAGCCACGGAGCACAG | 859 |
| **AQWMELGSS** | 253 | CAGAGTGCCCAATGGATGGAGCTTGGTAGTTCGGCACAG | 527 | CAGAGTGCACAATGGATGGAACTCGGAAGCAGCGCACAG | 860 |
| **AQWMFGGSG** | 254 | CAGAGTGCCCAATGGATGTTTGGGGGTAGTGGGGCACAG | 528 | CAGAGTGCACAATGGATGTTCGGAGGAAGCGGAGCACAG | 861 |
| **AQWMLGGAQ** | 255 | CAGAGTGCCCAATGGATGCTGGGGGGGGCGCAGGCACAG | 529 | CAGAGTGCACAATGGATGCTCGGAGGAGCACAAGCACAG | 862 |
| **AQWPTAYDA** | 256 | CAGAGTGCCCAATGGCCGACTGCTTATGATGCGGCACAG | 530 | CAGAGTGCACAATGGCCAACAGCATACGACGCAGCACAG | 863 |
| **AQWPTSYDA** | 62 | CAGAGTGCCCAATGGCCTACGAGTTATGATGCTGCACAG | 531 | CAGAGTGCACAATGGCCAACAAGCTACGACGCAGCACAG | 864 |
| **AQWQVQTGF** | 257 | CAGAGTGCCCAATGGCAGGTTCAGACGGGGTTTGCACAG | 532 | CAGAGTGCACAATGGCAAGTCCAAACAGGATTCGCACAG | 865 |
| **AQWSTEGGY** | 258 | CAGAGTGCCCAATGGTCGACTGAGGGTGGGTATGCACAG | 533 | CAGAGTGCACAATGGAGCACAGAAGGAGGATACGCACAG | 866 |
| **AQWTAAGGY** | 259 | CAGAGTGCCCAATGGACTGCTGCGGGTGGTTATGCACAG | 534 | CAGAGTGCACAATGGACAGCAGCAGGAGGATACGCACAG | 867 |
| **AQWTTESGY** | 260 | CAGAGTGCCCAATGGACGACGGAGTCGGGTTATGCACAG | 535 | CAGAGTGCACAATGGACAACAGAAAGCGGATACGCACAG | 868 |
| **AQWVYGSSH** | 261 | CAGAGTGCCCAATGGGTTTATGGGAGTTCGCATGCACAG | 536 | CAGAGTGCACAATGGGTCTACGGAAGCAGCCACGCACAG | 869 |
| **AQYLAGYTV** | 262 | CAGAGTGCCCAATATTTGGCGGGGTATACGGTGGCACAG | 537 | CAGAGTGCACAATACCTCGCAGGATACACAGTCGCACAG | 870 |
| **AQYLKGYSV** | 152 | CAGAGTGCCCAATATCTGAAGGGGTATTCTGTGGCACAG | 538 | CAGAGTGCACAATACCTCAAAGGATACAGCGTCGCACAG | 871 |
| **AQYLSGYNT** | 263 | CAGAGTGCCCAATATTTGTCGGGTTATAATACGGCACAG | 539 | CAGAGTGCACAATACCTCAGCGGATACAACACAGCACAG | 872 |
| **DGAAATTGW** | 264 | CAGAGTGATGGCGCTGCGGCGACTACTGGGTGGGCACAG | 540 | CAGAGTGACGGAGCAGCAGCAACAACAGGATGGGCACAG | 873 |
| **DGAGGTSGW** | 151 | CAGAGTGATGGCGCGGGTGGGACGAGTGGTTGGGCACAG | 541 | CAGAGTGACGGAGCAGGAGGAACAAGCGGATGGGCACAG | 874 |
| **DGAGTTSGW** | 265 | CAGAGTGATGGCGCGGGTACTACTTCGGGTTGGGCACAG | 542 | CAGAGTGACGGAGCAGGAACAACAAGCGGATGGGCACAG | 875 |
| **DGAHGLSGW** | 266 | CAGAGTGATGGCGCTCATGGGCTGTCGGGGTGGGCACAG | 543 | CAGAGTGACGGAGCACACGGACTCAGCGGATGGGCACAG | 876 |
| **DGAHVGLSS** | 267 | CAGAGTGATGGCGCTCATGTTGGGCTGTCGTCGGCACAG | 544 | CAGAGTGACGGAGCACACGTCGGACTCAGCAGCGCACAG | 877 |
| **DGARTVLQL** | 268 | CAGAGTGATGGCGCTCGGACGGTGCTTCAGTTGGCACAG | 545 | CAGAGTGACGGAGCAAGAACAGTCCTCCAACTCGCACAG | 878 |
| **DGEYQKPFR** | 269 | CAGAGTGATGGCGAGTATCAGAAGCCGTTTAGGGCACAG | 546 | CAGAGTGACGGAGAATACCAAAAACCATTCAGAGCACAG | 879 |
| **DGGGTTTGW** | 270 | CAGAGTGATGGCGGTGGGACTACGACGGGGTGGGCACAG | 547 | CAGAGTGACGGAGGAGGAACAACAACAGGATGGGCACAG | 880 |
| **DGHATSMGW** | 271 | CAGAGTGATGGCCATGCGACGAGTATGGGTTGGGCACAG | 548 | CAGAGTGACGGACACGCAACAAGCATGGGATGGGCACAG | 881 |
| **DGKGSTQGW** | 272 | CAGAGTGATGGCAAGGGTTCGACGCAGGGGTGGGCACAG | 549 | CAGAGTGACGGAAAAGGAAGCACACAAGGATGGGCACAG | 882 |
| **DGKQYQLSS** | 92 | CAGAGTGATGGCAAGCAGTATCAGCTGTCTTCGGCACAG | 550 | CAGAGTGACGGAAAACAATACCAACTCAGCAGCGCACAG | 883 |
| **DGNGGLKGW** | 167 | CAGAGTGATGGCAATGGTGGGTTGAAGGGGTGGGCACAG | 551 | CAGAGTGACGGAAACGGAGGACTCAAAGGATGGGCACAG | 884 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGQQGLSGW** | 273 | CAGAGTGATGGCCAGGGGGGTTTGTCTGGGTGGGCACAG | 552 | CAGAGTGACGGACAAGGAGGACTCAGCGGATGGGCACAG | 885 |
| **DGQHFAPPR** | 110 | CAGAGTGATGGCCAGCATTTTGCTCCGCCGCGGGCACAG | 553 | CAGAGTGACGGACAACACTTCGCACCACCAAGAGCACAG | 886 |
| **DGRATKTLY** | 274 | CAGAGTGATGGCCGTGCGACTAAGACGCTTTATGCACAG | 554 | CAGAGTGACGGAAGAGCAACAAAAACACTCTACGCACAG | 887 |
| **DGRNALTGW** | 275 | CAGAGTGATGGCCGTAATGCGTTGACGGGGTGGGCACAG | 555 | CAGAGTGACGGAAGAAACGCACTCACAGGATGGGCACAG | 888 |
| **DGRRQVIQL** | 276 | CAGAGTGATGGCAGGAGGCAGGTGATTCAGCTGGCACAG | 556 | CAGAGTGACGGAAGAAGACAAGTCATCCAACTCGCACAG | 889 |
| **DGRVYGLSS** | 277 | CAGAGTGATGGCAGGGTTTATGGTCTTTCGTCGGCACAG | 557 | CAGAGTGACGGAAGAGTCTACGGACTCAGCAGCGCACAG | 890 |
| **DGSGRTTGW** | 147 | CAGAGTGATGGCAGTGGGCGTACGACGGGTTGGGCACAG | 558 | CAGAGTGACGGAAGCGGAAGAACAACAGGATGGGCACAG | 891 |
| **DGSGTTRGW** | 114 | CAGAGTGATGGCTCTGGTACGACGCGGGGTTGGGCACAG | 559 | CAGAGTGACGGAAGCGGAACAACAAGAGGATGGGCACAG | 892 |
| **DGSGTVSGW** | 278 | CAGAGTGATGGCTCGGGTACGGTTAGTGGGTGGGCACAG | 560 | CAGAGTGACGGAAGCGGAACAGTCAGCGGATGGGCACAG | 893 |
| **DGSPEKPFR** | 160 | CAGAGTGATGGCAGTCCGGAGAAGCCGTTTCGGGCACAG | 561 | CAGAGTGACGGAAGCCCAGAAAAACCATTCAGAGCACAG | 894 |
| **DGSQSTTGW** | 136 | CAGAGTGATGGCAGTCAGTCTACTACGGGGTGGGCACAG | 562 | CAGAGTGACGGAAGCCAAAGCACAACAGGATGGGCACAG | 895 |
| **DGSSFYPPK** | 127 | CAGAGTGATGGCAGTAGTTTTTATCCTCCTAAGGCACAG | 563 | CAGAGTGACGGAAGCAGCTTCTACCCACCAAAAGCACAG | 896 |
| **DGSSSYYDA** | 64 | CAGAGTGATGGCAGTAGTTCTTATTATGATGCGGCACAG | 564 | CAGAGTGACGGAAGCAGCAGCTACTACGACGCAGCACAG | 897 |
| **DGSTERPFR** | 99 | CAGAGTGATGGCTCTACGGAGAGGCCGTTTAGGGCACAG | 565 | CAGAGTGACGGAAGCACAGAAAGACCATTCAGAGCACAG | 898 |
| **DGTAARLSS** | 132 | CAGAGTGATGGCACCGCGGCTCGGCTGTCGTCGGCACAG | 566 | CAGAGTGACGGAACAGCAGCAAGACTCAGCAGCGCACAG | 899 |
| **DGTADKPFR** | 63 | CAGAGTGATGGCACCGCTGATAAGCCGTTTCGGGCACAG | 567 | CAGAGTGACGGAACAGCAGACAAACCATTCAGAGCACAG | 900 |
| **DGTADRPFR** | 155 | CAGAGTGATGGCACGGCGGATCGTCCTTTTCGGGCACAG | 568 | CAGAGTGACGGAACAGCAGACAGACCATTCAGAGCACAG | 901 |
| **DGTAERPFR** | 140 | CAGAGTGATGGCACCGCGGAGAGGCCTTTTAGGGCACAG | 569 | CAGAGTGACGGAACAGCAGAAAGACCATTCAGAGCACAG | 902 |
| **DGTAIHLSS** | 67 | CAGAGTGATGGCACCGCGATTCATCTTTCGTCTGCACAG | 570 | CAGAGTGACGGAACAGCAATCCACCTCAGCAGCGCACAG | 903 |
| **DGTAIYLSS** | 279 | CAGAGTGATGGCACCGCGATTTATCTGTCTTCTGCACAG | 571 | CAGAGTGACGGAACAGCAATCTACCTCAGCAGCGCACAG | 904 |
| **DGTALMLSS** | 280 | CAGAGTGATGGCACCGCTCTTATGTTGTCGTCTGCACAG | 572 | CAGAGTGACGGAACAGCACTCATGCTCAGCAGCGCACAG | 905 |
| **DGTASISGW** | 281 | CAGAGTGATGGCACCGCGAGTATTAGTGGTTGGGCACAG | 573 | CAGAGTGACGGAACAGCAAGCATCAGCGGATGGGCACAG | 906 |
| **DGTASTSGW** | 282 | CAGAGTGATGGCACCGCGTCGACGAGTGGGTGGGCACAG | 574 | CAGAGTGACGGAACAGCAAGCACAAGCGGATGGGCACAG | 907 |
| **DGTASVTGW** | 283 | CAGAGTGATGGCACCGCGTCGGTGACGGGGTGGGCACAG | 575 | CAGAGTGACGGAACAGCAAGCGTCACAGGATGGGCACAG | 908 |
| **DGTASYYDS** | 61 | CAGAGTGATGGCACCGCGAGTTATTATGATTCTGCACAG | 576 | CAGAGTGACGGAACAGCAAGCTACTACGACAGCGCACAG | 909 |
| **DGTATTMGW** | 284 | CAGAGTGATGGCACCGCGACGACGATGGGGTGGGCACAG | 577 | CAGAGTGACGGAACAGCAACAACAATGGGATGGGCACAG | 910 |
| **DGTATTTGW** | 285 | CAGAGTGATGGCACCGCGACGACGACGGGTTGGGCACAG | 578 | CAGAGTGACGGAACAGCAACAACAACAGGATGGGCACAG | 911 |
| **DGTAYRLSS** | 286 | CAGAGTGATGGCACCGCGTATCGTTTGTCGTCTGCACAG | 579 | CAGAGTGACGGAACAGCATACAGACTCAGCAGCGCACAG | 912 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTDKMWSI** | 287 | CAGAGTGATGGCACCGATAAGATGTGGAGTATTGCACAG | 580 | CAGAGTGACGGAACAGACAAAATGTGGAGCATCGCACAG | 913 |
| **DGTGGIKGW** | 131 | CAGAGTGATGGCACCGGTGGTATTAAGGGGTGGGCACAG | 581 | CAGAGTGACGGAACAGGAGGAATCAAAGGATGGGCACAG | 914 |
| **DGTGGIMGW** | 288 | CAGAGTGATGGCACCGGGGGGATTATGGGTTGGGCACAG | 582 | CAGAGTGACGGAACAGGAGGAATCATGGGATGGGCACAG | 915 |
| **DGTGGISGW** | 289 | CAGAGTGATGGCACCGGTGGGATTTCGGGGTGGGCACAG | 583 | CAGAGTGACGGAACAGGAGGAATCAGCGGATGGGCACAG | 916 |
| **DGTGGLAGW** | 290 | CAGAGTGATGGCACCGGGGGTCTTGCTGGTTGGGCACAG | 584 | CAGAGTGACGGAACAGGAGGACTCGCAGGATGGGCACAG | 917 |
| **DGTGGLHGW** | 291 | CAGAGTGATGGCACCGGGGGGTTGCATGGTTGGGCACAG | 585 | CAGAGTGACGGAACAGGAGGACTCCACGGATGGGCACAG | 918 |
| **DGTGGLQGW** | 292 | CAGAGTGATGGCACCGGGGGTTTGCAGGGTTGGGCACAG | 586 | CAGAGTGACGGAACAGGAGGACTCCAAGGATGGGCACAG | 919 |
| **DGTGGLRGW** | 154 | CAGAGTGATGGCACCGGGGGTTTGCGTGGTTGGGCACAG | 587 | CAGAGTGACGGAACAGGAGGACTCAGAGGATGGGCACAG | 920 |
| **DGTGGLSGW** | 293 | CAGAGTGATGGCACCGGTGGGTTGTCGGGTTGGGCACAG | 588 | CAGAGTGACGGAACAGGAGGACTCAGCGGATGGGCACAG | 921 |
| **DGTGGLTGW** | 294 | CAGAGTGATGGCACCGGGGGGTTGACGGGTTGGGCACAG | 589 | CAGAGTGACGGAACAGGAGGACTCACAGGATGGGCACAG | 922 |
| **DGTGGTKGW** | 107 | CAGAGTGATGGCACCGGTGGGACTAAGGGTTGGGCACAG | 590 | CAGAGTGACGGAACAGGAGGAACAAAAGGATGGGCACAG | 923 |
| **DGTGGTSGW** | 295 | CAGAGTGATGGCACCGGGGGGACGAGTGGTTGGGCACAG | 591 | CAGAGTGACGGAACAGGAGGAACAAGCGGATGGGCACAG | 924 |
| **DGTGGVHGW** | 296 | CAGAGTGATGGCACCGGTGGGGTGCATGGTTGGGCACAG | 592 | CAGAGTGACGGAACAGGAGGAGTCCACGGATGGGCACAG | 925 |
| **DGTGGVMGW** | 297 | CAGAGTGATGGCACCGGTGGTGTTATGGGGTGGGCACAG | 593 | CAGAGTGACGGAACAGGAGGAGTCATGGGATGGGCACAG | 926 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTGGVSGW** | 298 | CAGAGTGATGGCACCGGGGGGGTGTCTGGTTGGGCACAG | 594 | CAGAGTGACGGAACAGGAGGAGTCAGCGGATGGGCACAG | 927 |
| **DGTGGVTGW** | 299 | CAGAGTGATGGCACCGGTGGTGTGACGGGGTGGGCACAG | 595 | CAGAGTGACGGAACAGGAGGAGTCACAGGATGGGCACAG | 928 |
| **DGTGGVYGW** | 300 | CAGAGTGATGGCACCGGTGGTGTGTATGGGTGGGCACAG | 596 | CAGAGTGACGGAACAGGAGGAGTCTACGGATGGGCACAG | 929 |
| **DGTGNLQGW** | 301 | CAGAGTGATGGCACCGGTAATTTGCAGGGTTGGGCACAG | 597 | CAGAGTGACGGAACAGGAAACCTCCAAGGATGGGCACAG | 930 |
| **DGTGNLRGW** | 133 | CAGAGTGATGGCACCGGGAATCTTAGGGGGTGGGCACAG | 598 | CAGAGTGACGGAACAGGAAACCTCAGAGGATGGGCACAG | 931 |
| **DGTGNLSGW** | 302 | CAGAGTGATGGCACCGGGAATTTGAGTGGGTGGGCACAG | 599 | CAGAGTGACGGAACAGGAAACCTCAGCGGATGGGCACAG | 932 |
| **DGTGNTHGW** | 72 | CAGAGTGATGGCACCGGGAATACTCATGGGTGGGCACAG | 600 | CAGAGTGACGGAACAGGAAACACACACGGATGGGCACAG | 933 |
| **DGTGNTRGW** | 94 | CAGAGTGATGGCACCGGGAATACTCGGGGGTGGGCACAG | 601 | CAGAGTGACGGAACAGGAAACACAAGAGGATGGGCACAG | 934 |
| **DGTGNTSGW** | 137 | CAGAGTGATGGCACCGGTAATACTAGTGGTTGGGCACAG | 602 | CAGAGTGACGGAACAGGAAACACAAGCGGATGGGCACAG | 935 |
| **DGTGNVSGW** | 303 | CAGAGTGATGGCACCGGGAATGTGTCGGGGTGGGCACAG | 603 | CAGAGTGACGGAACAGGAAACGTCAGCGGATGGGCACAG | 936 |
| **DGTGNVTGW** | 69 | CAGAGTGATGGCACCGGTAATGTGACGGGGTGGGCACAG | 604 | CAGAGTGACGGAACAGGAAACGTCACAGGATGGGCACAG | 937 |
| **DGTGQLVGW** | 304 | CAGAGTGATGGCACCGGGCAGCTTGTGGGTTGGGCACAG | 605 | CAGAGTGACGGAACAGGACAACTCGTCGGATGGGCACAG | 938 |
| **DGTGQTIGW** | 305 | CAGAGTGATGGCACCGGTCAGACGATTGGTTGGGCACAG | 606 | CAGAGTGACGGAACAGGACAAACAATCGGATGGGCACAG | 939 |
| **DGTGQVTGW** | 68 | CAGAGTGATGGCACCGGGCAGGTGACTGGGTGGGCACAG | 607 | CAGAGTGACGGAACAGGACAAGTCACAGGATGGGCACAG | 940 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTGRLTGW** | 159 | CAGAGTGATGGCACCGGTCGGTTGACGGGTTGGGCACAG | 608 | CAGAGTGACGGAACAGGAAGACTCACAGGATGGGCACAG | 941 |
| **DGTGRTVGW** | 117 | CAGAGTGATGGCACCGGTCGGACTGTTGGGTGGGCACAG | 609 | CAGAGTGACGGAACAGGAAGAACAGTCGGATGGGCACAG | 942 |
| **DGTGSGMMT** | 306 | CAGAGTGATGGCACCGGTTCGGGTATGATGACGGCACAG | 610 | CAGAGTGACGGAACAGGAAGCGGAATGATGACAGCACAG | 943 |
| **DGTGSISGW** | 307 | CAGAGTGATGGCACCGGGTCGATTAGTGGGTGGGCACAG | 611 | CAGAGTGACGGAACAGGAAGCATCAGCGGATGGGCACAG | 944 |
| **DGTGSLAGW** | 308 | CAGAGTGATGGCACCGGTTCTTTGGCGGGGTGGGCACAG | 612 | CAGAGTGACGGAACAGGAAGCCTCGCAGGATGGGCACAG | 945 |
| **DGTGSLNGW** | 309 | CAGAGTGATGGCACCGGGTCTTTGAATGGGTGGGCACAG | 613 | CAGAGTGACGGAACAGGAAGCCTCAACGGATGGGCACAG | 946 |
| **DGTGSLQGW** | 310 | CAGAGTGATGGCACCGGGTCGCTGCAGGGTTGGGCACAG | 614 | CAGAGTGACGGAACAGGAAGCCTCCAAGGATGGGCACAG | 947 |
| **DGTGSLSGW** | 311 | CAGAGTGATGGCACCGGGAGTCTGTCGGGGTGGGCACAG | 615 | CAGAGTGACGGAACAGGAAGCCTCAGCGGATGGGCACAG | 948 |
| **DGTGSLVGW** | 312 | CAGAGTGATGGCACCGGGTCGTTGGTGGGTTGGGCACAG | 616 | CAGAGTGACGGAACAGGAAGCCTCGTCGGATGGGCACAG | 949 |
| **DGTGSTHGW** | 119 | CAGAGTGATGGCACCGGGAGTACGCATGGGTGGGCACAG | 617 | CAGAGTGACGGAACAGGAAGCACACACGGATGGGCACAG | 950 |
| **DGTGSTKGW** | 313 | CAGAGTGATGGCACCGGGAGTACTAAGGGGTGGGCACAG | 618 | CAGAGTGACGGAACAGGAAGCACAAAAGGATGGGCACAG | 951 |
| **DGTGSTMGW** | 314 | CAGAGTGATGGCACCGGTTCTACTATGGGTTGGGCACAG | 619 | CAGAGTGACGGAACAGGAAGCACAATGGGATGGGCACAG | 952 |
| **DGTGSTQGW** | 315 | CAGAGTGATGGCACCGGTAGTACGCAGGGTTGGGCACAG | 620 | CAGAGTGACGGAACAGGAAGCACACAAGGATGGGCACAG | 953 |
| **DGTGSTSGW** | 316 | CAGAGTGATGGCACCGGGAGTACTTCGGGGTGGGCACAG | 621 | CAGAGTGACGGAACAGGAAGCACAAGCGGATGGGCACAG | 954 |
| **DGTGSTTGW** | 134 | CAGAGTGATGGCACCGGGAGTACGACGGGGTGGGCACAG | 622 | CAGAGTGACGGAACAGGAAGCACAACAGGATGGGCACAG | 955 |
| **DGTGSVMGW** | 317 | CAGAGTGATGGCACCGGTTCGGTTATGGGGTGGGCACAG | 623 | CAGAGTGACGGAACAGGAAGCGTCATGGGATGGGCACAG | 956 |
| **DGTGSVTGW** | 318 | CAGAGTGATGGCACCGGGTCTGTGACTGGGTGGGCACAG | 624 | CAGAGTGACGGAACAGGAAGCGTCACAGGATGGGCACAG | 957 |
| **DGTGTLAGW** | 319 | CAGAGTGATGGCACCGGGACGCTTGCGGGGTGGGCACAG | 625 | CAGAGTGACGGAACAGGAACACTCGCAGGATGGGCACAG | 958 |
| **DGTGTLHGW** | 320 | CAGAGTGATGGCACCGGTACTTTGCATGGTTGGGCACAG | 626 | CAGAGTGACGGAACAGGAACACTCCACGGATGGGCACAG | 959 |
| **DGTGTLKGW** | 321 | CAGAGTGATGGCACCGGTACTCTTAAGGGTTGGGCACAG | 627 | CAGAGTGACGGAACAGGAACACTCAAAGGATGGGCACAG | 960 |
| **DGTGTLSGW** | 322 | CAGAGTGATGGCACCGGGACTCTGTCGGGTTGGGCACAG | 628 | CAGAGTGACGGAACAGGAACACTCAGCGGATGGGCACAG | 961 |
| **DGTGTTLGW** | 323 | CAGAGTGATGGCACCGGGACTACGCTGGGGTGGGCACAG | 629 | CAGAGTGACGGAACAGGAACAACACTCGGATGGGCACAG | 962 |
| **DGTGTTMGW** | 324 | CAGAGTGATGGCACCGGGACTACTATGGGTTGGGCACAG | 630 | CAGAGTGACGGAACAGGAACAACAATGGGATGGGCACAG | 963 |
| **DGTGTTTGW** | 130 | CAGAGTGATGGCACCGGGACTACTACGGGGTGGGCACAG | 631 | CAGAGTGACGGAACAGGAACAACAACAGGATGGGCACAG | 964 |
| **DGTGTTVGW** | 74 | CAGAGTGATGGCACCGGTACTACGGTGGGGTGGGCACAG | 632 | CAGAGTGACGGAACAGGAACAACAGTCGGATGGGCACAG | 965 |
| **DGTGTTYGW** | 325 | CAGAGTGATGGCACCGGGACGACGTATGGTTGGGCACAG | 633 | CAGAGTGACGGAACAGGAACAACATACGGATGGGCACAG | 966 |
| **DGTGTVHGW** | 326 | CAGAGTGATGGCACCGGTACGGTTCATGGTTGGGCACAG | 634 | CAGAGTGACGGAACAGGAACAGTCCACGGATGGGCACAG | 967 |
| **DGTGTVQGW** | 327 | CAGAGTGATGGCACCGGGACTGTGCAGGGGTGGGCACAG | 635 | CAGAGTGACGGAACAGGAACAGTCCAAGGATGGGCACAG | 968 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTGTVSGW** | 328 | CAGAGTGATGGCACCGGTACTGTTTCTGGTTGGGCACAG | 636 | CAGAGTGACGGAACAGGAACAGTCAGCGGATGGGCACAG | 969 |
| **DGTGTVTGW** | 329 | CAGAGTGATGGCACCGGTACTGTTACTGGGTGGGCACAG | 637 | CAGAGTGACGGAACAGGAACAGTCACAGGATGGGCACAG | 970 |
| **DGTHARLSS** | 330 | CAGAGTGATGGCACCCATGCGAGGTTGTCTTCGGCACAG | 638 | CAGAGTGACGGAACACACGCAAGACTCAGCAGCGCACAG | 971 |
| **DGTHAYMAS** | 153 | CAGAGTGATGGCACCCATGCTTATATGGCGTCTGCACAG | 639 | CAGAGTGACGGAACACACGCATACATGGCAAGCGCACAG | 972 |
| **DGTHFAPPR** | 112 | CAGAGTGATGGCACCCATTTTGCGCCGCCGCGTGCACAG | 640 | CAGAGTGACGGAACACACTTCGCACCACCAAGAGCACAG | 973 |
| **DGTHIHLSS** | 162 | CAGAGTGATGGCACCCATATTCATCTGAGTAGTGCACAG | 641 | CAGAGTGACGGAACACACATCCACCTCAGCAGCGCACAG | 974 |
| **DGTHIRALS** | 331 | CAGAGTGATGGCACCCATATTAGGGCTCTGAGTGCACAG | 642 | CAGAGTGACGGAACACACATCAGAGCACTCAGCGCACAG | 975 |
| **DGTHIRLAS** | 332 | CAGAGTGATGGCACCCATATTCGTTTGGCGAGTGCACAG | 643 | CAGAGTGACGGAACACACATCAGACTCGCAAGCGCACAG | 976 |
| **DGTHLQPFR** | 333 | CAGAGTGATGGCACCCATCTGCAGCCGTTTAGGGCACAG | 644 | CAGAGTGACGGAACACACCTCCAACCATTCAGAGCACAG | 977 |
| **DGTHSFYDA** | 334 | CAGAGTGATGGCACCCATAGTTTTTATGATGCGGCACAG | 645 | CAGAGTGACGGAACACACAGCTTCTACGACGCAGCACAG | 978 |
| **DGTHSTTGW** | 145 | CAGAGTGATGGCACCCATTCTACTACGGGTTGGGCACAG | 646 | CAGAGTGACGGAACACACAGCACAACAGGATGGGCACAG | 979 |
| **DGTHTRTGW** | 90 | CAGAGTGATGGCACCCATACGCGGACGGGTTGGGCACAG | 647 | CAGAGTGACGGAACACACACAAGAACAGGATGGGCACAG | 980 |
| **DGTHVRALS** | 335 | CAGAGTGATGGCACCCATGTTAGGGCGTTGTCGGCACAG | 648 | CAGAGTGACGGAACACACGTCAGAGCACTCAGCGCACAG | 981 |
| **DGTHVYMAS** | 336 | CAGAGTGATGGCACCCATGTTTATATGGCTAGTGCACAG | 649 | CAGAGTGACGGAACACACGTCTACATGGCAAGCGCACAG | 982 |
| **DGTHVYMSS** | 337 | CAGAGTGATGGCACCCATGTGTATATGTCTAGTGCACAG | 650 | CAGAGTGACGGAACACACGTCTACATGAGCAGCGCACAG | 983 |
| **DGTIALPFK** | 338 | CAGAGTGATGGCACCATTGCGCTTCCGTTTAAGGCACAG | 651 | CAGAGTGACGGAACAATCGCACTCCCATTCAAAGCACAG | 984 |
| **DGTIALPFR** | 339 | CAGAGTGATGGCACCATTGCTTTGCCGTTTAGGGCACAG | 652 | CAGAGTGACGGAACAATCGCACTCCCATTCAGAGCACAG | 985 |
| **DGTIATRYV** | 340 | CAGAGTGATGGCACCATTGCGACGCGGTATGTGGCACAG | 653 | CAGAGTGACGGAACAATCGCAACAAGATACGTCGCACAG | 986 |
| **DGTIERPFR** | 87 | CAGAGTGATGGCACCATTGAGCGGCCTTTTCGTGCACAG | 654 | CAGAGTGACGGAACAATCGAAAGACCATTCAGAGCACAG | 987 |
| **DGTIGYAYV** | 341 | CAGAGTGATGGCACCATTGGTTATGCGTATGTTGCACAG | 655 | CAGAGTGACGGAACAATCGGATACGCATACGTCGCACAG | 988 |
| **DGTIQAPFK** | 342 | CAGAGTGATGGCACCATTCAGGCTCCGTTTAAGGCACAG | 656 | CAGAGTGACGGAACAATCCAAGCACCATTCAAAGCACAG | 989 |
| **DGTIRLPFK** | 343 | CAGAGTGATGGCACCATTCGTCTTCCTTTTAAGGCACAG | 657 | CAGAGTGACGGAACAATCAGACTCCCATTCAAAGCACAG | 990 |
| **DGTISKEVG** | 344 | CAGAGTGATGGCACCATTTCTAAGGAGGTGGGGGCACAG | 658 | CAGAGTGACGGAACAATCAGCAAAGAAGTCGGAGCACAG | 991 |
| **DGTISQPFK** | 105 | CAGAGTGATGGCACCATTTCGCAGCCTTTTAAGGCACAG | 659 | CAGAGTGACGGAACAATCAGCCAACCATTCAAAGCACAG | 992 |
| **DGTKIQLSS** | 146 | CAGAGTGATGGCACCAAGATTCAGCTGTCTAGTGCACAG | 660 | CAGAGTGACGGAACAAAAATCCAACTCAGCAGCGCACAG | 993 |
| **DGTKIRLSS** | 111 | CAGAGTGATGGCACCAAGATTCGGTTGTCGTCTGCACAG | 661 | CAGAGTGACGGAACAAAAATCAGACTCAGCAGCGCACAG | 994 |
| **DGTKLMLSS** | 157 | CAGAGTGATGGCACCAAGCTGATGTTGAGTAGTGCACAG | 662 | CAGAGTGACGGAACAAAACTCATGCTCAGCAGCGCACAG | 995 |
| **DGTKLRLSS** | 118 | CAGAGTGATGGCACCAAGTTGAGGCTTAGTTCTGCACAG | 663 | CAGAGTGACGGAACAAAACTCAGACTCAGCAGCGCACAG | 996 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTKMVLQL** | 142 | CAGAGTGATGGCACCAAGATGGTGTTGCAGCTGGCACAG | 664 | CAGAGTGACGGAACAAAAATGGTCCTCCAACTCGCACAG | 997 |
| **DGTKSLVQL** | 345 | CAGAGTGATGGCACCAAGAGTCTTGTGCAGCTTGCACAG | 665 | CAGAGTGACGGAACAAAAAGCCTCGTCCAACTCGCACAG | 998 |
| **DGTKVLVQL** | 122 | CAGAGTGATGGCACCAAGGTGCTGGTGCAGTTGGCACAG | 666 | CAGAGTGACGGAACAAAAGTCCTCGTCCAACTCGCACAG | 999 |
| **DGTLAAPFK** | 120 | CAGAGTGATGGCACCTTGGCTGCTCCTTTTAAGGCACAG | 667 | CAGAGTGACGGAACACTCGCAGCACCATTCAAAGCACAG | 1000 |
| **DGTLAVNFK** | 346 | CAGAGTGATGGGACTTTGGCGGTGAATTTTAAGGCACAG | 668 | CAGAGTGACGGAACACTCGCAGTCAACTTCAAAGCACAG | 1001 |
| **DGTLAVPFK (PHP.eB)** | 71 | CAGAGTGATGGGACTTTGGCGGTGCCTTTTAAGGCACAG | 669 | CAGAGTGACGGAACACTCGCAGTCCCATTCAAAGCACAG | 1002 |
| **DGTLAYPFK** | 347 | CAGAGTGATGGCACCCTTGCGTATCCTTTTAAGGCACAG | 670 | CAGAGTGACGGAACACTCGCATACCCATTCAAAGCACAG | 1003 |
| **DGTLERPFR** | 156 | CAGAGTGATGGCACCCTGGAGAGGCCGTTTCGGGCACAG | 671 | CAGAGTGACGGAACACTCGAAAGACCATTCAGAGCACAG | 1004 |
| **DGTLEVHFK** | 348 | CAGAGTGATGGGACTTTGGAGGTGCATTTTAAGGCACAG | 672 | CAGAGTGACGGAACACTCGAAGTCCACTTCAAAGCACAG | 1005 |
| **DGTLLRLSS** | 121 | CAGAGTGATGGCACCTTGCTGAGGCTGAGTAGTGCACAG | 673 | CAGAGTGACGGAACACTCCTCAGACTCAGCAGCGCACAG | 1006 |
| **DGTLNNPFR** | 109 | CAGAGTGATGGCACCTTGAATAATCCGTTTAGGGCACAG | 674 | CAGAGTGACGGAACACTCAACAACCCATTCAGAGCACAG | 1007 |
| **DGTLQQPFR** | 89 | CAGAGTGATGGCACCTTGCAGCAGCCGTTTCGGGCACAG | 675 | CAGAGTGACGGAACACTCCAACAACCATTCAGAGCACAG | 1008 |
| **DGTLSQPFR** | 65 | CAGAGTGATGGCACCCTGTCTCAGCCTTTTAGGGCACAG | 676 | CAGAGTGACGGAACACTCAGCCAACCATTCAGAGCACAG | 1009 |
| **DGTLSRTLW** | 349 | CAGAGTGATGGCACCTTGTCGCGTACGCTTTGGGCACAG | 677 | CAGAGTGACGGAACACTCAGCAGAACACTCTGGGCACAG | 1010 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTLSSPFR** | 350 | CAGAGTGATGGCACCCTGTCTAGTCCGTTTAGGGCACAG | 678 | CAGAGTGACGGAACACTCAGCAGCCCATTCAGAGCACAG | 1011 |
| **DGTLTVPFR** | 351 | CAGAGTGATGGCACCTTGACGGTTCCTTTTCGGGCACAG | 679 | CAGAGTGACGGAACACTCACAGTCCCATTCAGAGCACAG | 1012 |
| **DGTLVAPFR** | 352 | CAGAGTGATGGCACCCTTGTTGCGCCGTTTAGGGCACAG | 680 | CAGAGTGACGGAACACTCGTCGCACCATTCAGAGCACAG | 1013 |
| **DGTMDKPFR** | 70 | CAGAGTGATGGCACGATGGATAAGCCTTTTAGGGCACAG | 681 | CAGAGTGACGGAACAATGGACAAACCATTCAGAGCACAG | 1014 |
| **DGTMDRPFK** | 102 | CAGAGTGATGGCACCATGGATAGGCCGTTTAAGGCACAG | 682 | CAGAGTGACGGAACAATGGACAGACCATTCAAAGCACAG | 1015 |
| **DGTMLRLSS** | 148 | CAGAGTGATGGCACCATGTTGCGTCTTAGTTCGGCACAG | 683 | CAGAGTGACGGAACAATGCTCAGACTCAGCAGCGCACAG | 1016 |
| **DGTMQLTGW** | 353 | CAGAGTGATGGCACCATGCAGCTTACGGGGTGGGCACAG | 684 | CAGAGTGACGGAACAATGCAACTCACAGGATGGGCACAG | 1017 |
| **DGTNGLKGW** | 76 | CAGAGTGATGGCACCAATGGTCTGAAGGGGTGGGCACAG | 685 | CAGAGTGACGGAACAAACGGACTCAAAGGATGGGCACAG | 1018 |
| **DGTNSISGW** | 354 | CAGAGTGATGGCACCAATAGTATTAGTGGGTGGGCACAG | 686 | CAGAGTGACGGAACAAACAGCATCAGCGGATGGGCACAG | 1019 |
| **DGTNSLSGW** | 355 | CAGAGTGATGGCACCAATTCTCTGTCGGGTTGGGCACAG | 687 | CAGAGTGACGGAACAAACAGCCTCAGCGGATGGGCACAG | 1020 |
| **DGTNSTTGW** | 143 | CAGAGTGATGGCACCAATTCTACGACGGGTTGGGCACAG | 688 | CAGAGTGACGGAACAAACAGCACAACAGGATGGGCACAG | 1021 |
| **DGTNSVTGW** | 356 | CAGAGTGATGGCACCAATAGTGTTACGGGTTGGGCACAG | 689 | CAGAGTGACGGAACAAACAGCGTCACAGGATGGGCACAG | 1022 |
| **DGTNTINGW** | 124 | CAGAGTGATGGCACCAATACTATTAATGGGTGGGCACAG | 690 | CAGAGTGACGGAACAAACACAATCAACGGATGGGCACAG | 1023 |
| **DGTNTLGGW** | 357 | CAGAGTGATGGCACCAATACGTTGGGGGGGTGGGCACAG | 691 | CAGAGTGACGGAACAAACACACTCGGAGGATGGGCACAG | 1024 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTNTTHGW** | 113 | CAGAGTGATGGCACCAATACTACTCATGGGTGGGCACAG | 692 | CAGAGTGACGGAACAAACACAACACACGGATGGGCACAG | 1025 |
| **DGTNYRLSS** | 358 | CAGAGTGATGGCACCAATTATAGGCTGTCGAGTGCACAG | 693 | CAGAGTGACGGAACAAACTACAGACTCAGCAGCGCACAG | 1026 |
| **DGTQALSGW** | 359 | CAGAGTGATGGCACCCAGGCGCTGTCGGGGTGGGCACAG | 694 | CAGAGTGACGGAACACAAGCACTCAGCGGATGGGCACAG | 1027 |
| **DGTQFRLSS** | 129 | CAGAGTGATGGCACCCAGTTTAGGTTGTCTTCGGCACAG | 695 | CAGAGTGACGGAACACAATTCAGACTCAGCAGCGCACAG | 1028 |
| **DGTQFSPPR** | 108 | CAGAGTGATGGCACCCAGTTTAGTCCTCCGCGTGCACAG | 696 | CAGAGTGACGGAACACAATTCAGCCCACCAAGAGCACAG | 1029 |
| **DGTQGLKGW** | 158 | CAGAGTGATGGCACCCAGGGGCTGAAGGGGTGGGCACAG | 697 | CAGAGTGACGGAACACAAGGACTCAAAGGATGGGCACAG | 1030 |
| **DGTQTTSGW** | 360 | CAGAGTGATGGCACCCAGACTACGAGTGGGTGGGCACAG | 698 | CAGAGTGACGGAACACAAACAACAAGCGGATGGGCACAG | 1031 |
| **DGTRALTGW** | 361 | CAGAGTGATGGCACCAGGGCTCTTACGGGTTGGGCACAG | 699 | CAGAGTGACGGAACAAGAGCACTCACAGGATGGGCACAG | 1032 |
| **DGTRFSLSS** | 362 | CAGAGTGATGGCACCCGGTTTTCGCTTTCGAGTGCACAG | 700 | CAGAGTGACGGAACAAGATTCAGCCTCAGCAGCGCACAG | 1033 |
| **DGTRGLSGW** | 363 | CAGAGTGATGGCACCAGGGGGTTGTCGGGGTGGGCACAG | 701 | CAGAGTGACGGAACAAGAGGACTCAGCGGATGGGCACAG | 1034 |
| **DGTRIGLSS** | 364 | CAGAGTGATGGCACCAGGATTGGGCTGAGTAGTGCACAG | 702 | CAGAGTGACGGAACAAGAATCGGACTCAGCAGCGCACAG | 1035 |
| **DGTRLHLAS** | 365 | CAGAGTGATGGCACCAGGCTTCATCTGGCGAGTGCACAG | 703 | CAGAGTGACGGAACAAGACTCCACCTCGCAAGCGCACAG | 1036 |
| **DGTRLHLSS** | 366 | CAGAGTGATGGCACCAGGCTTCATCTGTCGTCGGCACAG | 704 | CAGAGTGACGGAACAAGACTCCACCTCAGCAGCGCACAG | 1037 |
| **DGTRLLLSS** | 367 | CAGAGTGATGGCACCCGTTTGCTGCTGTCGAGTGCACAG | 705 | CAGAGTGACGGAACAAGACTCCTCCTCAGCAGCGCACAG | 1038 |
| **DGTRLMLSS** | 368 | CAGAGTGATGGCACCCGTTTGATGCTTTCTAGTGCACAG | 706 | CAGAGTGACGGAACAAGACTCATGCTCAGCAGCGCACAG | 1039 |
| **DGTRLNLSS** | 369 | CAGAGTGATGGCACCCGTTTGAATCTTAGTTCGGCACAG | 707 | CAGAGTGACGGAACAAGACTCAACCTCAGCAGCGCACAG | 1040 |
| **DGTRMVVQL** | 370 | CAGAGTGATGGCACCCGGATGGTTGTTCAGCTTGCACAG | 708 | CAGAGTGACGGAACAAGAATGGTCGTCCAACTCGCACAG | 1041 |
| **DGTRNMYEG** | 135 | CAGAGTGATGGCACCCGTAATATGTATGAGGGGGCACAG | 709 | CAGAGTGACGGAACAAGAAACATGTACGAAGGAGCACAG | 1042 |
| **DGTRSITGW** | 371 | CAGAGTGATGGCACCAGGAGTATTACGGGGTGGGCACAG | 710 | CAGAGTGACGGAACAAGAAGCATCACAGGATGGGCACAG | 1043 |
| **DGTRSLHGW** | 372 | CAGAGTGATGGCACCAGGAGTTTGCATGGGTGGGCACAG | 711 | CAGAGTGACGGAACAAGAAGCCTCCACGGATGGGCACAG | 1044 |
| **DGTRSTTGW** | 373 | CAGAGTGATGGCACCCGGAGTACTACGGGTTGGGCACAG | 712 | CAGAGTGACGGAACAAGAAGCACAACAGGATGGGCACAG | 1045 |
| **DGTRTTTGW** | 106 | CAGAGTGATGGCACCCGTACTACGACGGGTTGGGCACAG | 713 | CAGAGTGACGGAACAAGAACAACAACAGGATGGGCACAG | 1046 |
| **DGTRTVTGW** | 374 | CAGAGTGATGGCACCCGGACGGTGACTGGTTGGGCACAG | 714 | CAGAGTGACGGAACAAGAACAGTCACAGGATGGGCACAG | 1047 |
| **DGTRTVVQL** | 375 | CAGAGTGATGGCACCCGTACTGTGGTGCAGTTGGCACAG | 715 | CAGAGTGACGGAACAAGAACAGTCGTCCAACTCGCACAG | 1048 |
| **DGTRVHLSS** | 376 | CAGAGTGATGGCACCCGGGTGCATCTTTCTAGTGCACAG | 716 | CAGAGTGACGGAACAAGAGTCCACCTCAGCAGCGCACAG | 1049 |
| **DGTSFPYAR** | 86 | CAGAGTGATGGCACCTCGTTTCCGTATGCTCGGGCACAG | 717 | CAGAGTGACGGAACAAGCTTCCCATACGCAAGAGCACAG | 1050 |
| **DGTSFTPPK** | 81 | CAGAGTGATGGCACCTCGTTTACGCCGCCTAAGGCACAG | 718 | CAGAGTGACGGAACAAGCTTCACACCACCAAAAGCACAG | 1051 |
| **DGTSFTPPR** | 88 | CAGAGTGATGGCACCTCGTTTACTCCGCCGCGGGCACAG | 719 | CAGAGTGACGGAACAAGCTTCACACCACCAAGAGCACAG | 1052 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTSGLHGW** | 377 | CAGAGTGATGGCACCTCTGGGTTGCATGGGTGGGCACAG | 720 | CAGAGTGACGGAACAAGCGGACTCCACGGATGGGCACAG | 1053 |
| **DGTSGLKGW** | 101 | CAGAGTGATGGCACCAGTGGGCTTAAGGGGTGGGCACAG | 721 | CAGAGTGACGGAACAAGCGGACTCAAAGGATGGGCACAG | 1054 |
| **DGTSIHLSS** | 378 | CAGAGTGATGGCACCTCGATTCATTTGAGTAGTGCACAG | 722 | CAGAGTGACGGAACAAGCATCCACCTCAGCAGCGCACAG | 1055 |
| **DGTSIMLSS** | 379 | CAGAGTGATGGCACCTCGATTATGTTGAGTTCTGCACAG | 723 | CAGAGTGACGGAACAAGCATCATGCTCAGCAGCGCACAG | 1056 |
| **DGTSLRLSS** | 166 | CAGAGTGATGGCACCTCTTTGCGGCTTTCTTCTGCACAG | 724 | CAGAGTGACGGAACAAGCCTCAGACTCAGCAGCGCACAG | 1057 |
| **DGTSNYGAR** | 380 | CAGAGTGATGGCACCTCTAATTATGGGCGCGGGCACAG | 725 | CAGAGTGACGGAACAAGCAACTACGGAGCAAGAGCACAG | 1058 |
| **DGTSSYYDA** | 381 | CAGAGTGATGGCACCAGTTCGTATTATGATGCGGCACAG | 726 | CAGAGTGACGGAACAAGCAGCTACTACGACGCAGCACAG | 1059 |
| **DGTSSYYDS** | 59 | CAGAGTGATGGCACCTCGAGTTATTATGATTCTGCACAG | 727 | CAGAGTGACGGAACAAGCAGCTACTACGACAGCGCACAG | 1060 |
| **DGTSTISGW** | 382 | CAGAGTGATGGCACCTCTACGATTTCTGGTTGGGCACAG | 728 | CAGAGTGACGGAACAAGCACAATCAGCGGATGGGCACAG | 1061 |
| **DGTSTITGW** | 383 | CAGAGTGATGGCACCAGTACTATTACGGGTTGGGCACAG | 729 | CAGAGTGACGGAACAAGCACAATCACAGGATGGGCACAG | 1062 |
| **DGTSTLHGW** | 384 | CAGAGTGATGGCACCTCGACGTTGCATGGGTGGGCACAG | 730 | CAGAGTGACGGAACAAGCACACTCCACGGATGGGCACAG | 1063 |
| **DGTSTLRGW** | 385 | CAGAGTGATGGCACCTCTACTCTGCGTGGGTGGGCACAG | 731 | CAGAGTGACGGAACAAGCACACTCAGAGGATGGGCACAG | 1064 |
| **DGTSTLSGW** | 386 | CAGAGTGATGGCACCTCGACGCTGTCGGGGTGGGCACAG | 732 | CAGAGTGACGGAACAAGCACACTCAGCGGATGGGCACAG | 1065 |
| **DGTSYVPPK** | 97 | CAGAGTGATGGCACCTCTTATGTGCCGCCGAAGGCACAG | 733 | CAGAGTGACGGAACAAGCTACGTCCCACCAAAAGCACAG | 1066 |
| **DGTSYVPPR** | 78 | CAGAGTGATGGCACCAGTTATGTGCCGCCTCGGGCACAG | 734 | CAGAGTGACGGAACAAGCTACGTCCCACCAAGAGCACAG | 1067 |
| **DGTTATYYK** | 387 | CAGAGTGATGGCACCACGGCGACTTATTATAAGGCACAG | 735 | CAGAGTGACGGAACAACAGCAACATACTACAAAGCACAG | 1068 |
| **DGTTFTPPR** | 79 | CAGAGTGATGGCACCACTTTTACTCCTCCTCGGGCACAG | 736 | CAGAGTGACGGAACAACATTCACACCACCAAGAGCACAG | 1069 |
| **DGTTLAPFR** | 388 | CAGAGTGATGGCACCACTCTGGCTCCTTTTAGGGCACAG | 737 | CAGAGTGACGGAACAACACTCGCACCATTCAGAGCACAG | 1070 |
| **DGTTLVPPR** | 116 | CAGAGTGATGGCACCACTTTGGTTCCGCCGCGTGCACAG | 738 | CAGAGTGACGGAACAACACTCGTCCCACCAAGAGCACAG | 1071 |
| **DGTTSKTLW** | 389 | CAGAGTGATGGCACCACGAGTAAGACGCTTTGGGCACAG | 739 | CAGAGTGACGGAACAACAAGCAAAACACTCTGGGCACAG | 1072 |
| **DGTTSRTLW** | 390 | CAGAGTGATGGCACCACTTCTAGGACTTTGTGGGCACAG | 740 | CAGAGTGACGGAACAACAAGCAGAACACTCTGGGCACAG | 1073 |
| **DGTTTRSLY** | 391 | CAGAGTGATGGCACCACGACTCGTAGTTTGTATGCACAG | 741 | CAGAGTGACGGAACAACAACAAGAAGCCTCTACGCACAG | 1074 |
| **DGTTTTTGW** | 392 | CAGAGTGATGGCACCACTACGACTACGGGTTGGGCACAG | 742 | CAGAGTGACGGAACAACAACAACAACAGGATGGGCACAG | 1075 |
| **DGTTTYGAR** | 77 | CAGAGTGATGGCACCACTACGTATGGGGCTCGTGCACAG | 743 | CAGAGTGACGGAACAACAACATACGGAGCAAGAGCACAG | 1076 |
| **DGTTWTPPR** | 139 | CAGAGTGATGGCACCACTTGGACGCCGCCGCGTGCACAG | 744 | CAGAGTGACGGAACAACATGGACACCACCAAGAGCACAG | 1077 |
| **DGTTYMLSS** | 393 | CAGAGTGATGGCACCACGTATATGCTTAGTAGTGCACAG | 745 | CAGAGTGACGGAACAACATACATGCTCAGCAGCGCACAG | 1078 |
| **DGTTYVPPR** | 75 | CAGAGTGATGGCACCACGTATGTTCCTCCGCGGGCACAG | 746 | CAGAGTGACGGAACAACATACGTCCCACCAAGAGCACAG | 1079 |
| **DGTVANPFR** | 394 | CAGAGTGATGGCACCGTGGCGAATCCTTTTCGGGCACAG | 747 | CAGAGTGACGGAACAGTCGCAAACCCATTCAGAGCACAG | 1080 |

TABLE 7-continued

Peptide variants selected after 2 rounds of RNA-driven mouse brain biopanning

| Peptide Sequence | SEQ ID NO: | Nucleotide sequence (NNK codons) | SEQ ID NO: | Nucleotide sequence (NNM codons) | SEQ ID NO: |
|---|---|---|---|---|---|
| **DGTVDRPFK** | 395 | CAGAGTGATGGCACCGTGGATCGGCCTTTTAAGGCACAG | 748 | CAGAGTGACGGAACAGTCGACAGACCATTCAAAGCACAG | 1081 |
| **DGTVIHLSS** | 73 | CAGAGTGATGGCACCGTTATTCATCTGAGTAGTGCACAG | 749 | CAGAGTGACGGAACAGTCATCCACCTCAGCAGCGCACAG | 1082 |
| **DGTVILLSS** | 396 | CAGAGTGATGGCACCGTTATTCTGTTGTCGAGTGCACAG | 750 | CAGAGTGACGGAACAGTCATCCTCCTCAGCAGCGCACAG | 1083 |
| **DGTVIMLSS** | 397 | CAGAGTGATGGCACCGTGATTATGCTGTCGAGTGCACAG | 751 | CAGAGTGACGGAACAGTCATCATGCTCAGCAGCGCACAG | 1084 |
| **DGTVLHLSS** | 398 | CAGAGTGATGGCACCGTGCTTCATTTGTCGTCTGCACAG | 752 | CAGAGTGACGGAACAGTCCTCCACCTCAGCAGCGCACAG | 1085 |
| **DGTVLMLSS** | 399 | CAGAGTGATGGCACCGTTTTGATGCTGAGTAGTGCACAG | 753 | CAGAGTGACGGAACAGTCCTCATGCTCAGCAGCGCACAG | 1086 |
| **DGTVLVPFR** | 150 | CAGAGTGATGGCACCGTGTTGGTGCCGTTTAGGGCACAG | 754 | CAGAGTGACGGAACAGTCCTCGTCCCATTCAGAGCACAG | 1087 |
| **DGTVPYLAS** | 400 | CAGAGTGATGGCACCGTTCCGTATCTTGCTTCTGCACAG | 755 | CAGAGTGACGGAACAGTCCCATACCTCGCAAGCGCACAG | 1088 |
| **DGTVPYLSS** | 401 | CAGAGTGATGGCACCGTGCCGTATTTGTCTTCGGCACAG | 756 | CAGAGTGACGGAACAGTCCCATACCTCAGCAGCGCACAG | 1089 |
| **DGTVRVPFR** | 164 | CAGAGTGATGGCACCGTTCGTGTGCCGTTTAGGGCACAG | 757 | CAGAGTGACGGAACAGTCAGAGTCCCATTCAGAGCACAG | 1090 |
| **DGTVSMPFK** | 402 | CAGAGTGATGGCACCGTGTCGATGCCGTTTAAGGCACAG | 758 | CAGAGTGACGGAACAGTCAGCATGCCATTCAAAGCACAG | 1091 |
| **DGTVSNPFR** | 403 | CAGAGTGATGGCACCGTGTCTAATCCGTTTAGGGCACAG | 759 | CAGAGTGACGGAACAGTCAGCAACCCATTCAGAGCACAG | 1092 |
| **DGTVSTRWV** | 404 | CAGAGTGATGGCACCGTTTCTACGCGTTGGGTGGCACAG | 760 | CAGAGTGACGGAACAGTCAGCACAAGATGGGTCGCACAG | 1093 |
| **DGTVTTGW** | 405 | CAGAGTGATGGCACCGTGACGACGACTGGGTGGGCACAG | 761 | CAGAGTGACGGAACAGTCACAACAACAGGATGGGCACAG | 1094 |
| **DGTVTVTGW** | 406 | CAGAGTGATGGCACCGTGACGGTTACGGGGTGGGCACAG | 762 | CAGAGTGACGGAACAGTCACAGTCACAGGATGGGCACAG | 1095 |
| **DGTVWVPPR** | 407 | CAGAGTGATGGCACCGTTTGGGTGCCTCCTAGGGCACAG | 763 | CAGAGTGACGGAACAGTCTGGGTCCCACCAAGAGCACAG | 1096 |
| **DGTVYRLSS** | 408 | CAGAGTGATGGCACCGTTTATAGGTTGTCGAGTGCACAG | 764 | CAGAGTGACGGAACAGTCTACAGACTCAGCAGCGCACAG | 1097 |
| **DGTYARLSS** | 409 | CAGAGTGATGGCACCTATGCGCGTTTGTCTTCTGCACAG | 765 | CAGAGTGACGGAACATACGCAAGACTCAGCAGCGCACAG | 1098 |
| **DGTYGNKLW** | 410 | CAGAGTGATGGCACCTATGGTAATAAGTTGTGGGCACAG | 766 | CAGAGTGACGGAACATACGGAAACAAACTCTGGGCACAG | 1099 |
| **DGTYIHLSS** | 411 | CAGAGTGATGGCACCTATATTCATCTGTCTTCGGCACAG | 767 | CAGAGTGACGGAACATACATCCACCTCAGCAGCGCACAG | 1100 |
| **DGTYSTSGW** | 412 | CAGAGTGATGGCACCTATTCGACGAGTGGGTGGGCACAG | 768 | CAGAGTGACGGAACATACAGCACAAGCGGATGGGCACAG | 1101 |
| **DGVHPGLSS** | 104 | CAGAGTGATGGCGTGCATCCTGGGCTTTCGAGTGCACAG | 769 | CAGAGTGACGGAGTCCACCCAGGACTCAGCAGCGCACAG | 1102 |
| **DGVVALLAS** | 413 | CAGAGTGATGGCGTGGTTGCGTTGCTTGCTAGTGCACAG | 770 | CAGAGTGACGGAGTCGTCGCACTCCTCGCAAGCGCACAG | 1103 |
| **DGYVGVGSL** | 414 | CAGAGTGATGGCTATGTGGGTGTTGGTAGTTTGGCACAG | 771 | CAGAGTGACGGATACGTCGGAGTCGGAAGCCTCGCACAG | 1104 |

Figure 27:
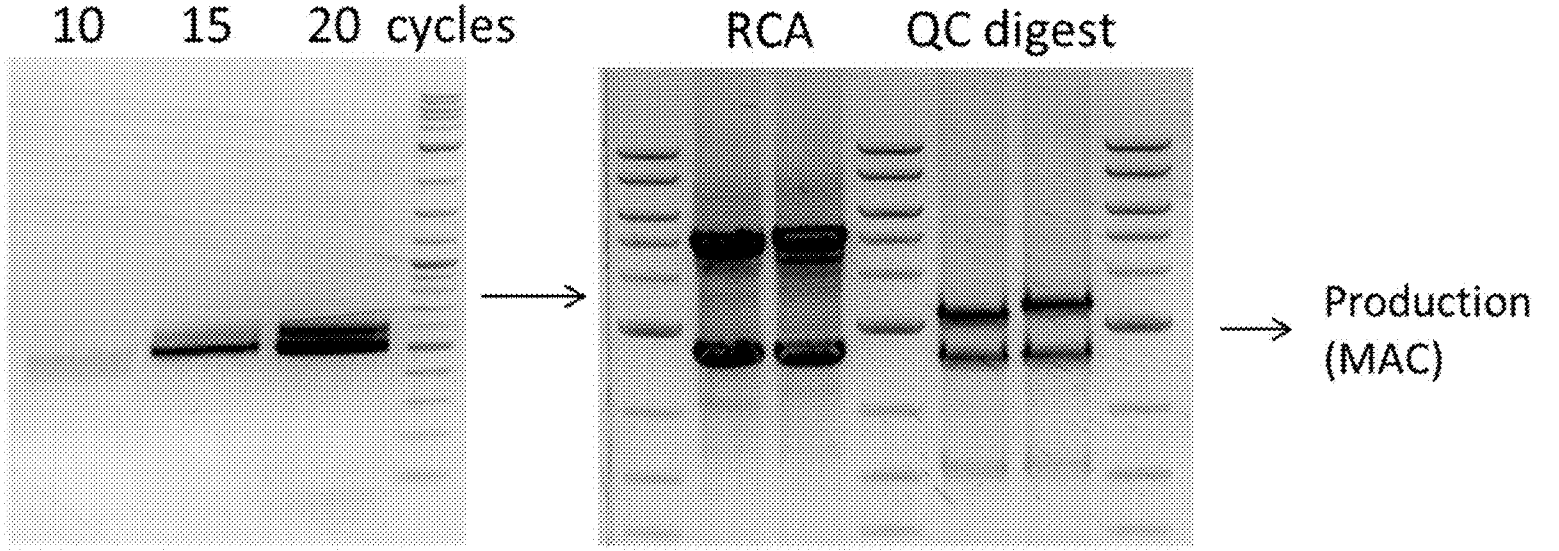
FIG. 27 provides an exemplary design of a library generation and cloning procedure.

Primer pools were produced by Twist biosciences using solid-phase synthesis and were used to generate a balanced library of 666 nucleotide variants by PCR amplification of CAP C-terminus and Gibson assembly as described in FIG. 27. 666 primers were provided a 1 fmole each, resulting in 0.6 pmole (regular PCR requires ~25 pmole of primer). Primerless amplification on capsid gBlock template was performed over 10 cycles. Forward and reverse primers were added, followed by an additional 10, 15 or 20 PCR cycles. Constructs were then cloned into AAV9 backbone plasmids by Gibson/RCA (like regular libraries).

Figure 28:
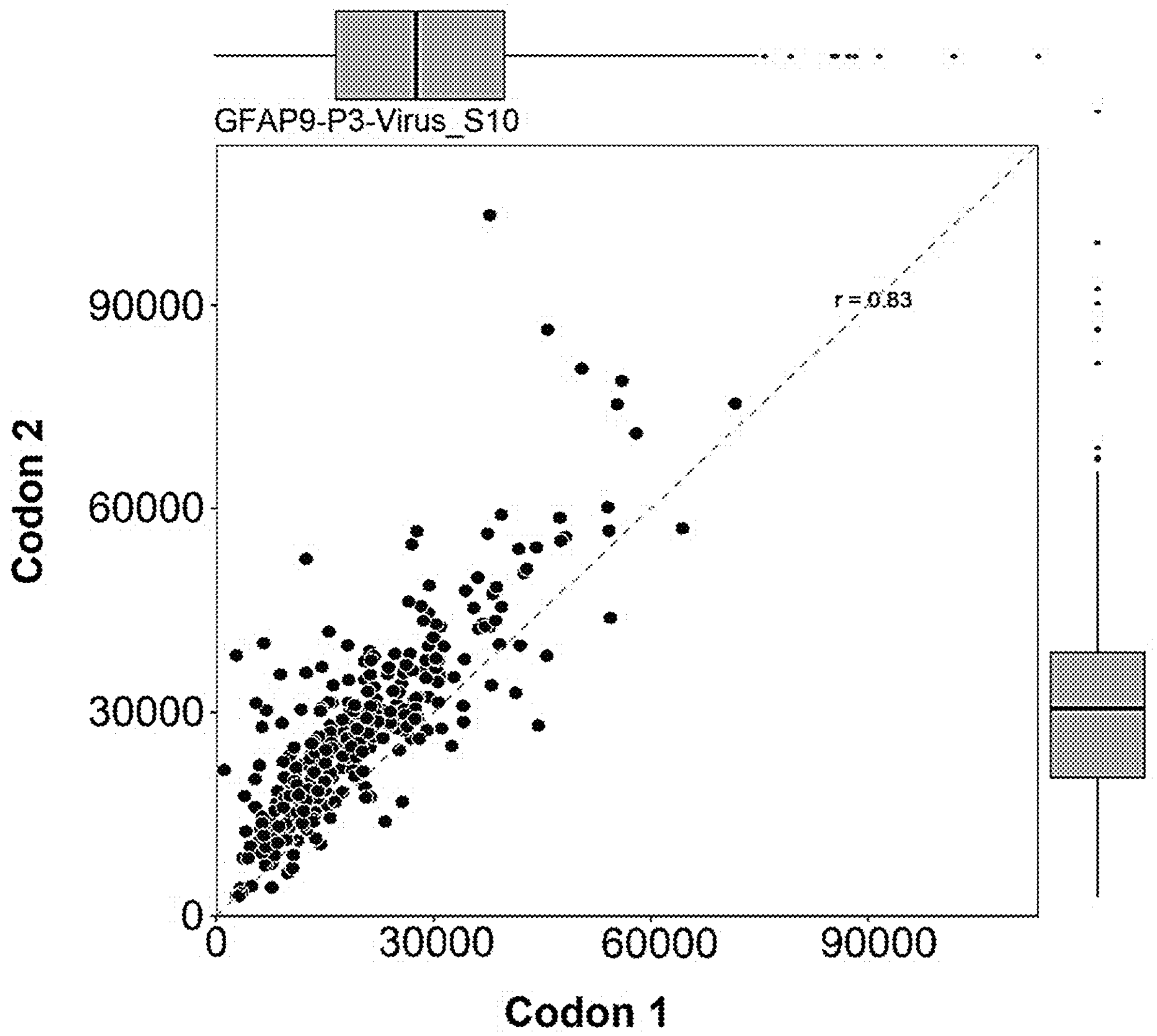
FIG. 28 provides the NNK/NNM codon distribution (covariance of codon mutants) of AAV produced with a synthetic library of 666 sequence variants (GFAP promoter).
Figure 29:
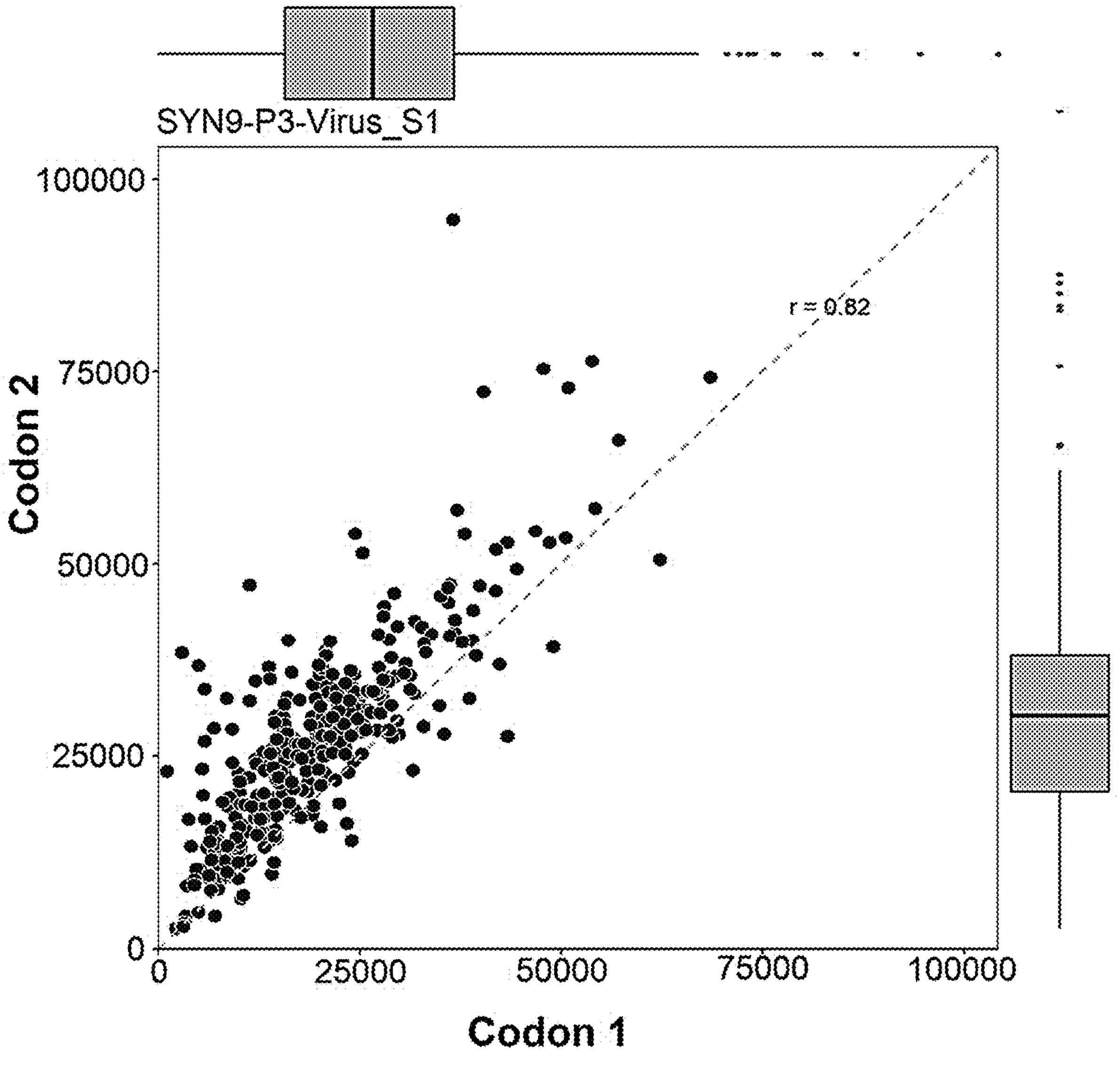
FIG. 29 provides the NNK/NNM codon distribution (covariance of codon mutants) of AAV produced with a synthetic library of 666 sequence variants (SYN9 promoter).
Figure 30:
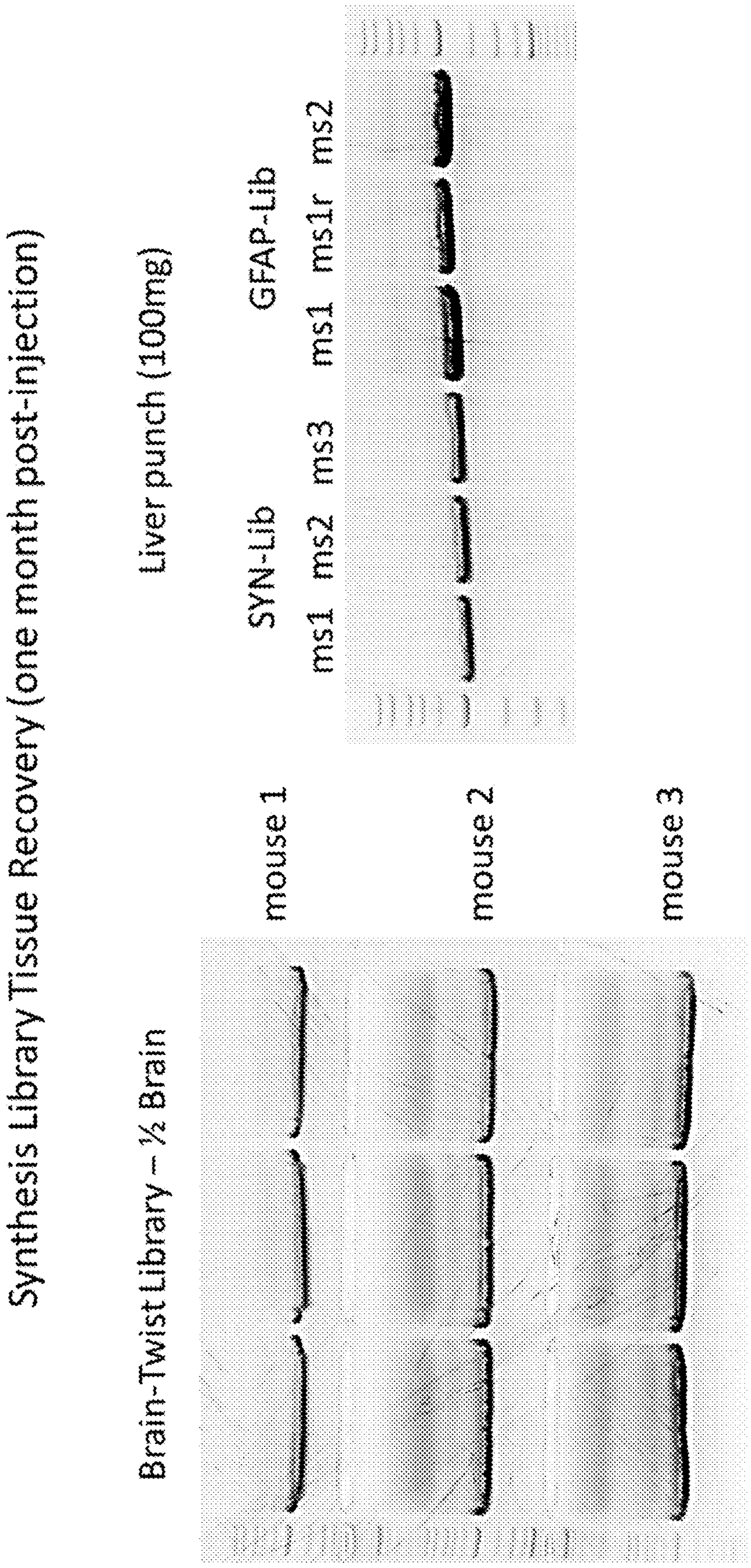
FIG. 30 provides the data from the tissue recovery, one-month post injection, from brain and a liver punch.

NGS analysis of SYN- and GFAP-driven AAV libraries produced with the pooled DNA showed a good correlation between the codon variants of each peptide, suggesting that the DNA sequence itself had little influence on virus production (FIG. 28 and FIG. 29). The pooled synthetic library was injected intravenously to C57BL/6 mice (5e11 VG per mouse, N=9), BALB/C mice (5e11 VG per mouse, N=6) and to rats (5e12 VG per rat, N=6), and after one month in-life RNA was extracted from the brain and spinal cord, and DNA was extracted from liver and heart tissue samples for bio-distribution analysis (FIG. 30). Because the Synapsin and GFAP promoters are not fully active in non-CNS tissue, DNA was analyzed instead of RNA in peripheral organs. The initial focus was on the C57BL/6 mouse analysis because this is the mouse strain in which library evolution was performed.

Figure 31B:
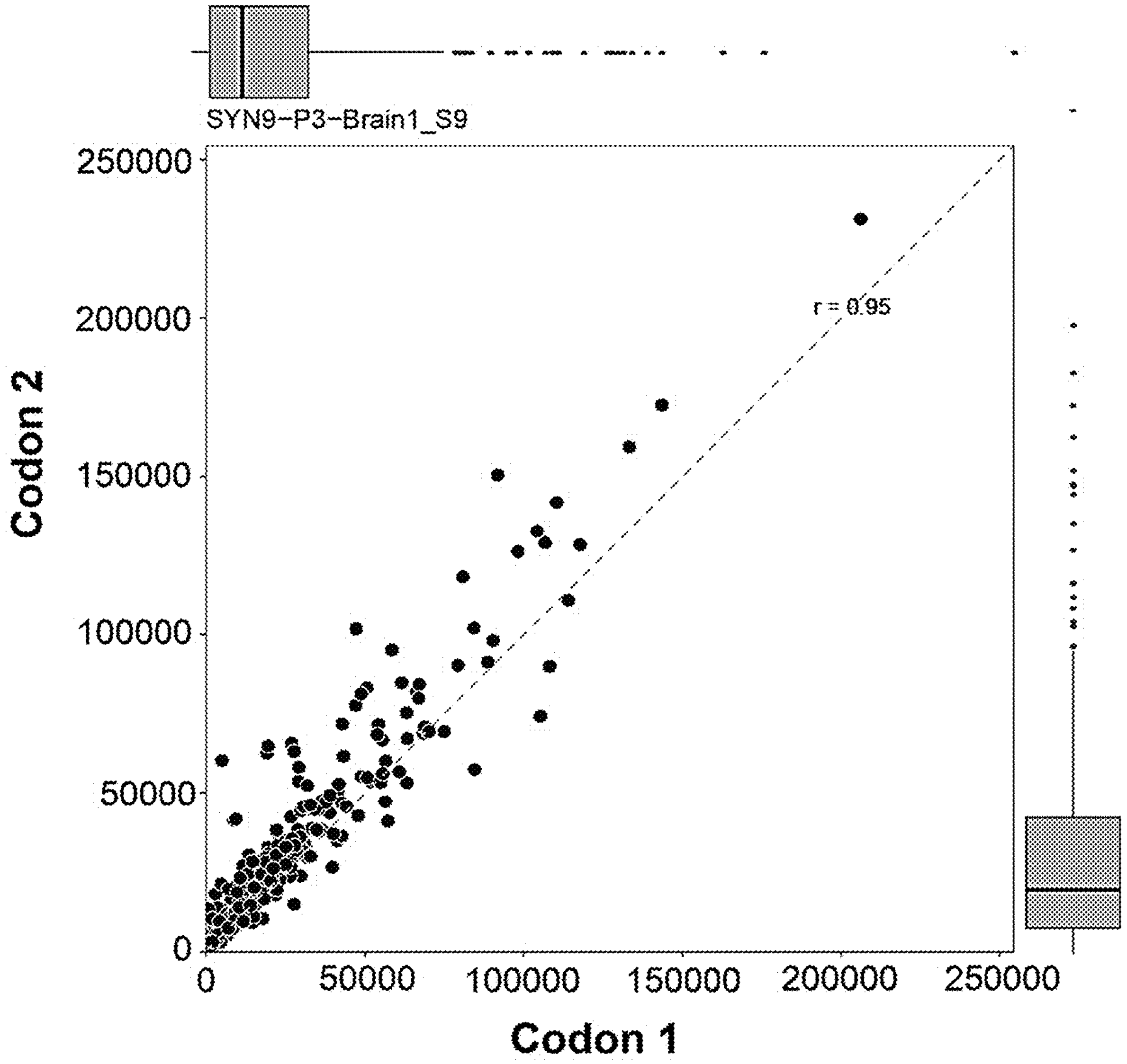
Figure 31C:
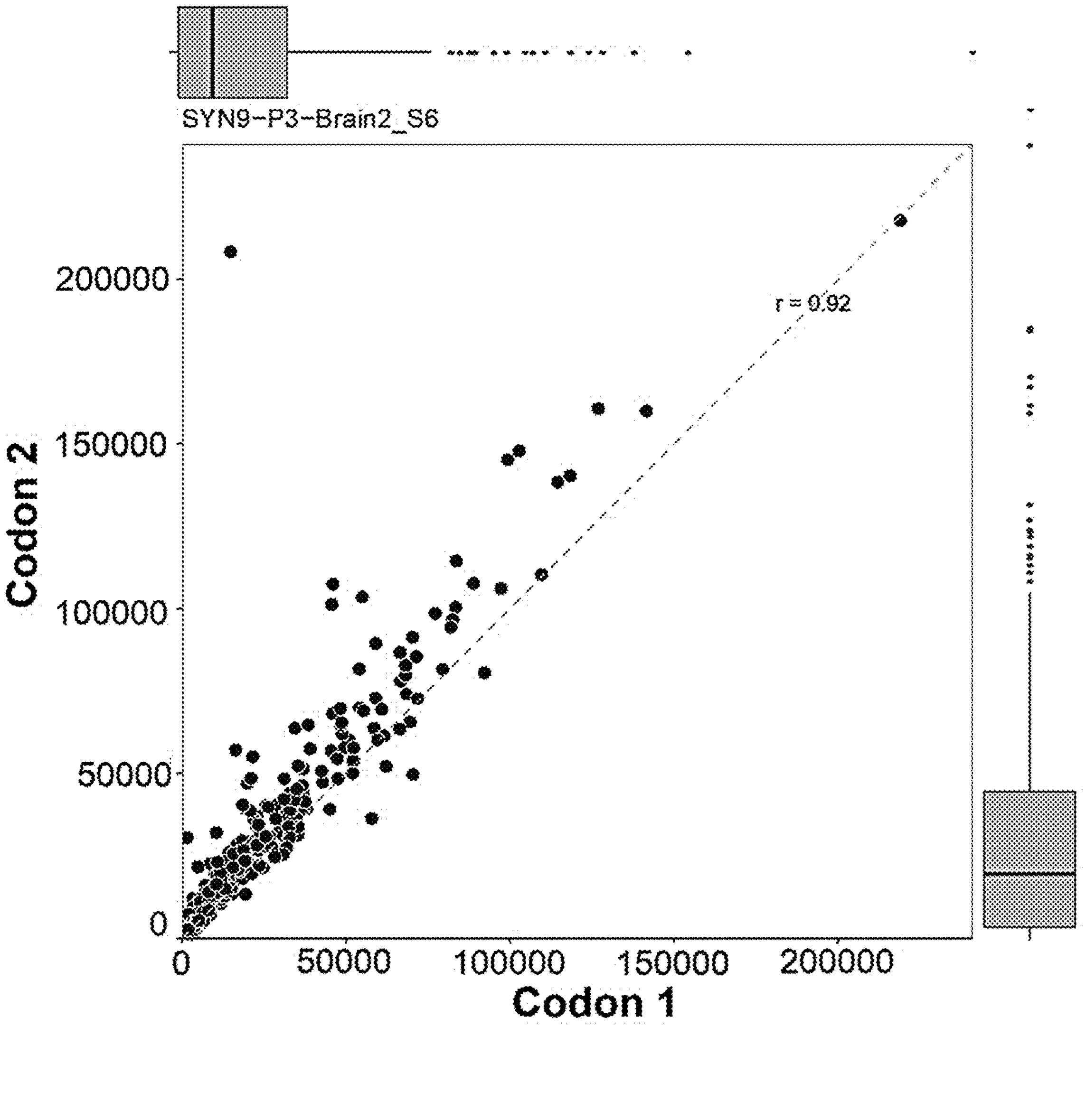
Figure 31D:
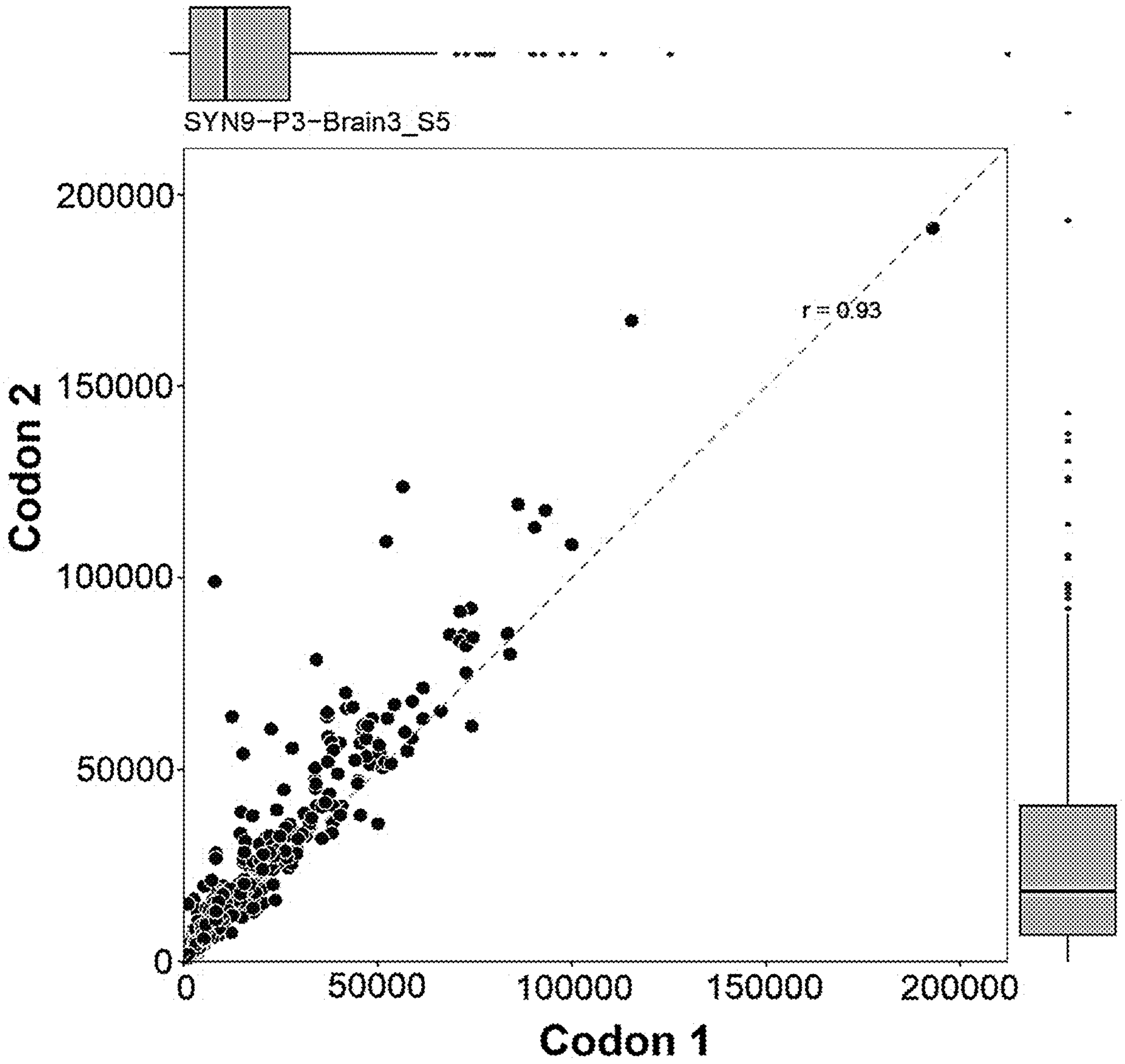
Figure 32B:
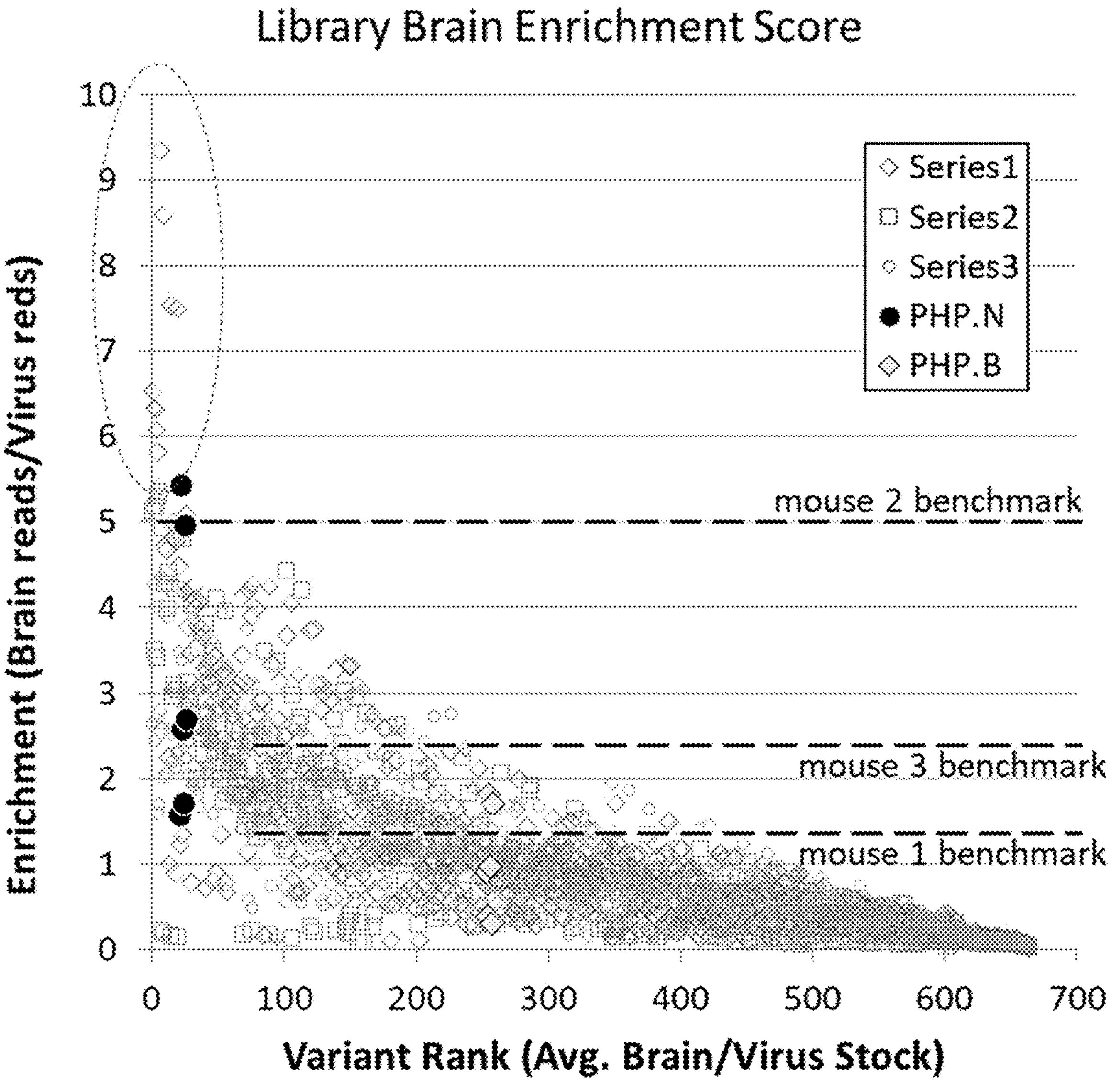
Figure 34A:
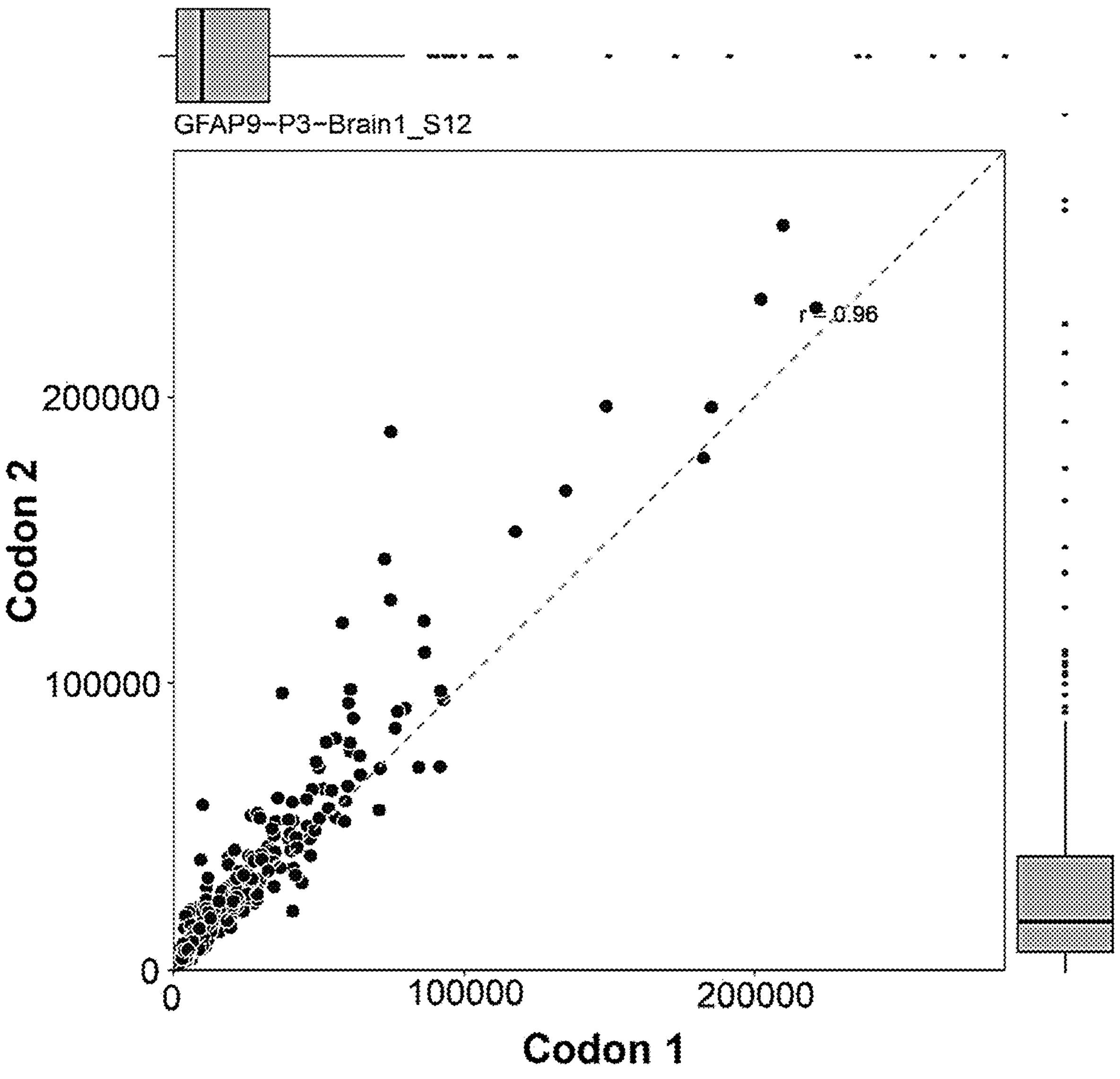
FIG. 34A and FIG. 34B provide astrocyte synthetic library codon mutants covariance.
Figure 34B:
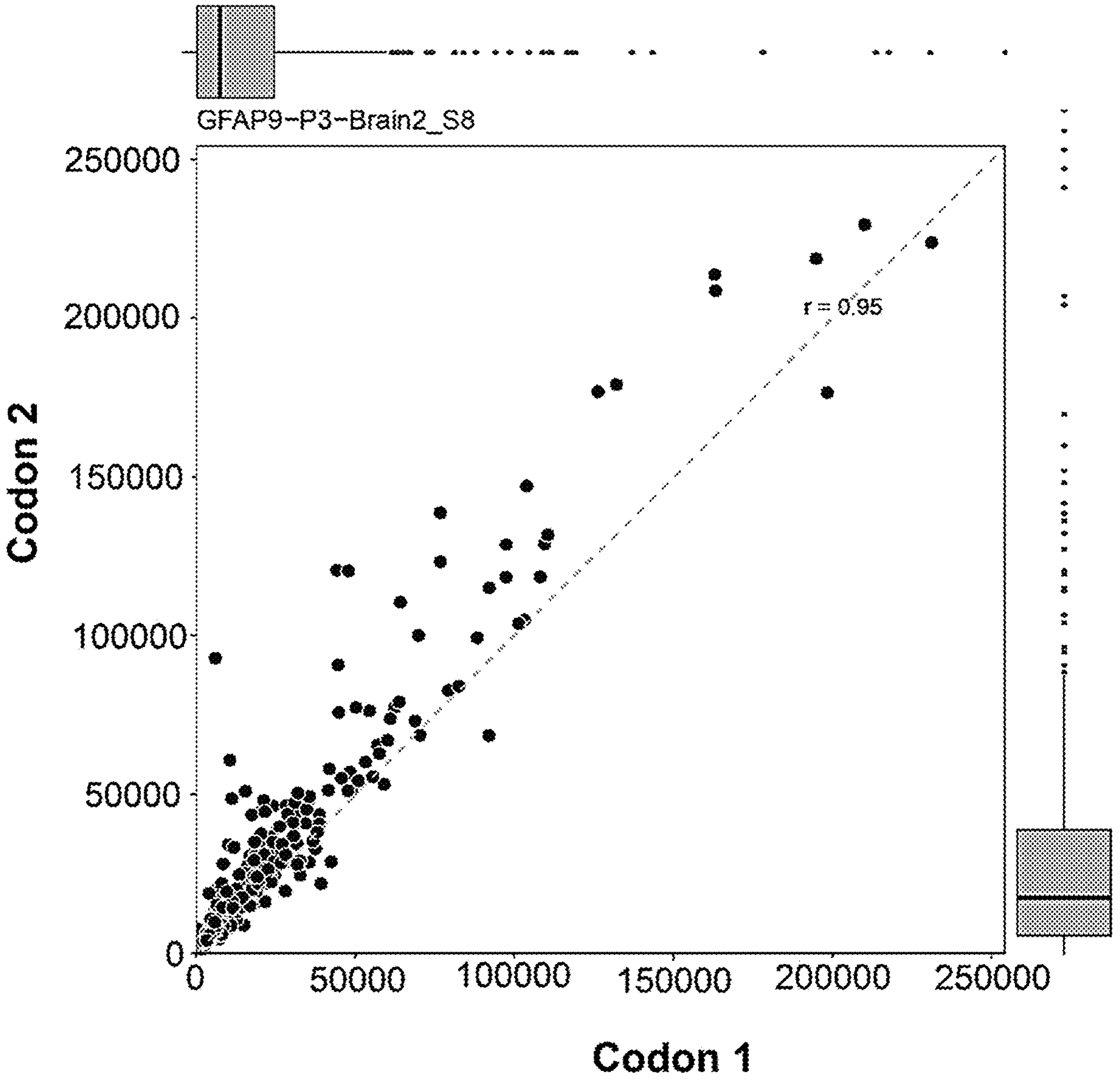
Figure 35:
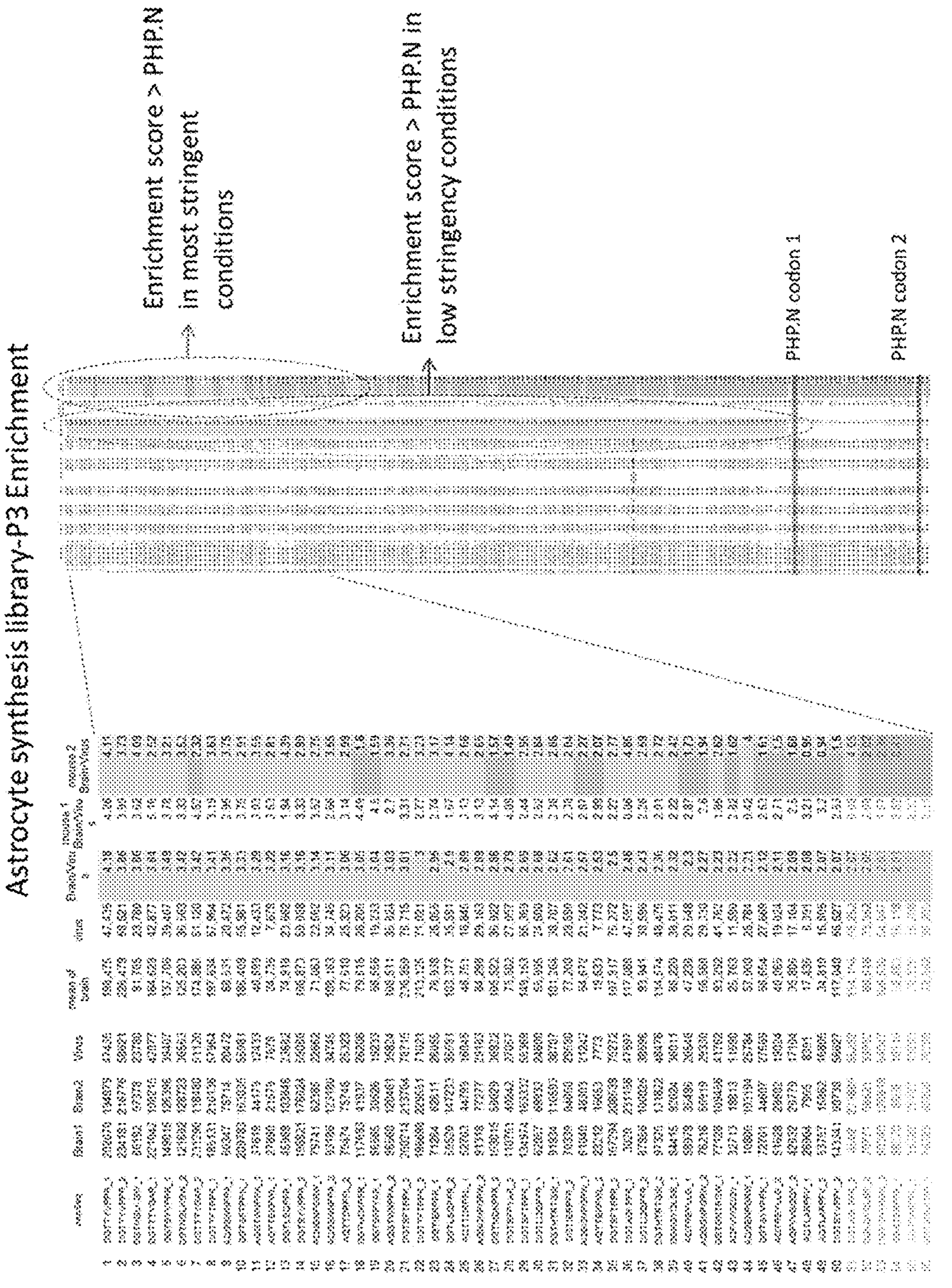
FIG. 35 provides the results of the astrocyte synthetic library NGS analysis (SEQ ID NOS 75, 75-78, 76-77, 79-83, 65, 78, 84, 80, 85, 70, 86, 82, 81, 79, 87, 65, 85, 84, 70, 86, 88-90, 87, 91, 83, 88, 63, 89-90, 92-93, 91, 94-97, 93, 95, 98, 98, 97, 63, 92, 94, 99-101, 75, 75-78, 76-77, 79-83, 65, 78, 84, 80, 85, 70, 86, 82, 81, 79, 87, 65, 85, 84, 70, 86, 88-90, 87, 91, 83, 88, 63, 89-90, 92-93, 91, 94-97, 93, 95, 98, 98, 97, 63, 92, 94, 99-102, 99, 103, 103-104, 96, 105-106, 101, 100, 102, 107, 104-105, 108-113, 106, 60, 66, 114-117, 109, 113, 72, 108, 110, 67, 118-119, 116, 120, 120, 107, 112, 121-123, 66, 124-125, 115, 118, 126, 121, 127-128, 60, 129, 119, 130-132, 72, 133, 123, 125, 69, 134-139, 62, 124, 67, 111, 114, 126, 140-141, 122, 142, 128-129, 143, 138, 144, 134, 62, 136, 145, 141, 146-153, 127, 154, 69, 144, 155, 71, 156, 133, 132, 137, 147, 157-158, 135, 159, 140, 117, 160, 139, 161-162, 130, 163, 143, 164, 152, 151, 165-167, 155, 168, 71, 169, and 146, respectively, in order of appearance).
Figure 36:
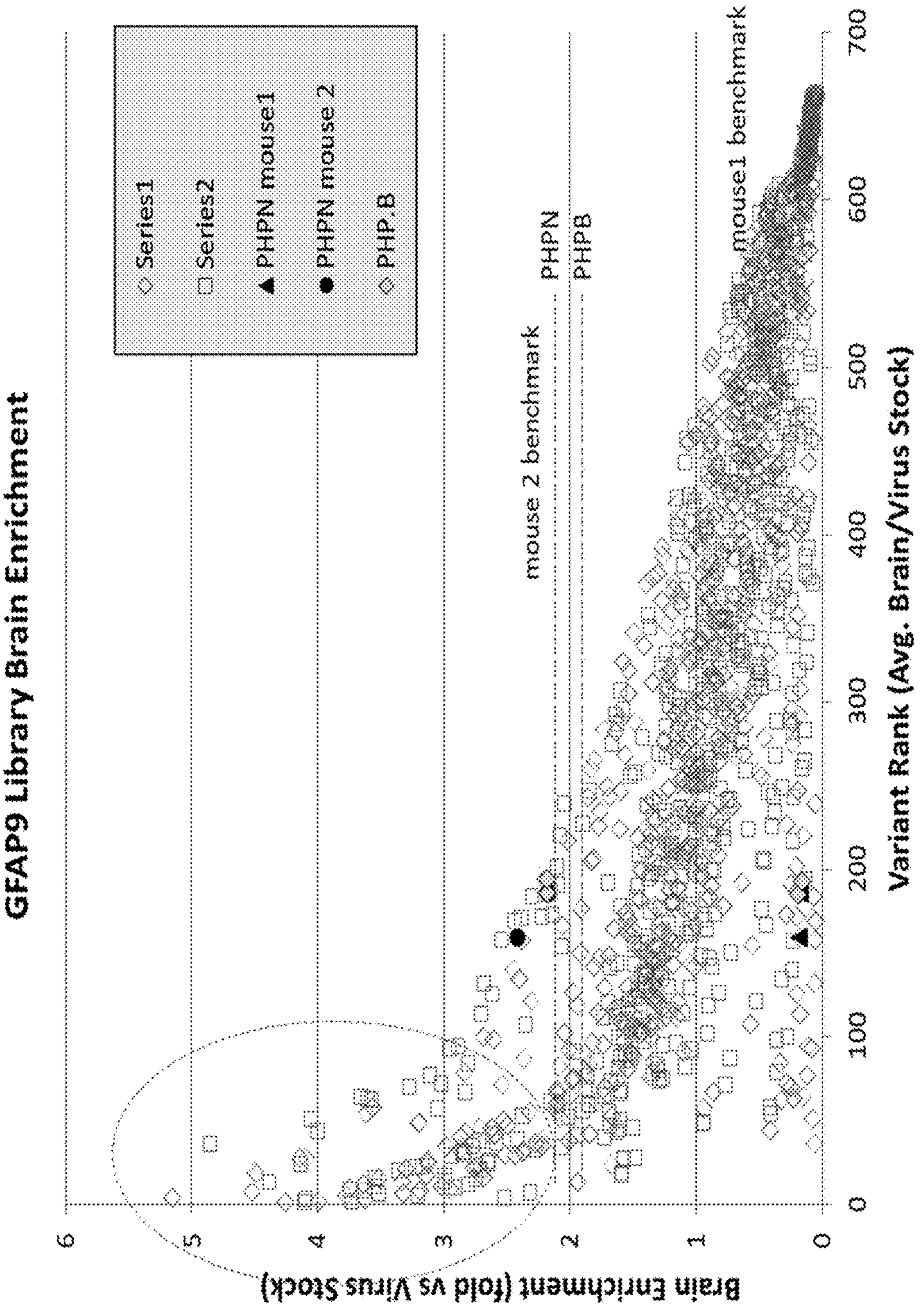
FIG. 36 provides the GFAP synthetic library NGS analysis.

The enrichment score of each capsid was determined by NGS analysis and defined as the ratio of reads per million (RPM) in the target tissue versus RPM in the inoculum. An example of analysis performed on the control capsids is shown in FIG. 31A. As expected from the published data, the PHP.B and PHP.eB (aka, PHP.N) capsids allowed significantly higher RNA expression in neurons compared to the AAV9 parental capsid (8-fold and 25-fold, respectively). There was a very high correlation between the codon variants of each peptide species in each animal (r=0.92, 0.93 and 0.95), confirming the robustness of the NGS assay (FIG. 31B-FIG. 31D).

An example of enrichment analysis is presented in FIG. 32A-FIG. 36. The 333 capsid variants are ranked by average brain enrichment score from all animals, and the individual enrichment values are indicated by a color scale. As indicated by the position of the reference capsids, a group of novel variants showed a higher enrichment score than the PHP.eB benchmark capsid in both neurons (Syn-driven) and astrocytes (GFAP-driven). Interestingly, many variants showed a different enrichment score in neurons vs. astrocytes, as indicated by the medium level of correlation between Syn- and GFAP-driven RNA. This suggests that certain capsids display an enhanced tropism for neurons, and others for astrocytes (FIG. 33).

Figure 38:
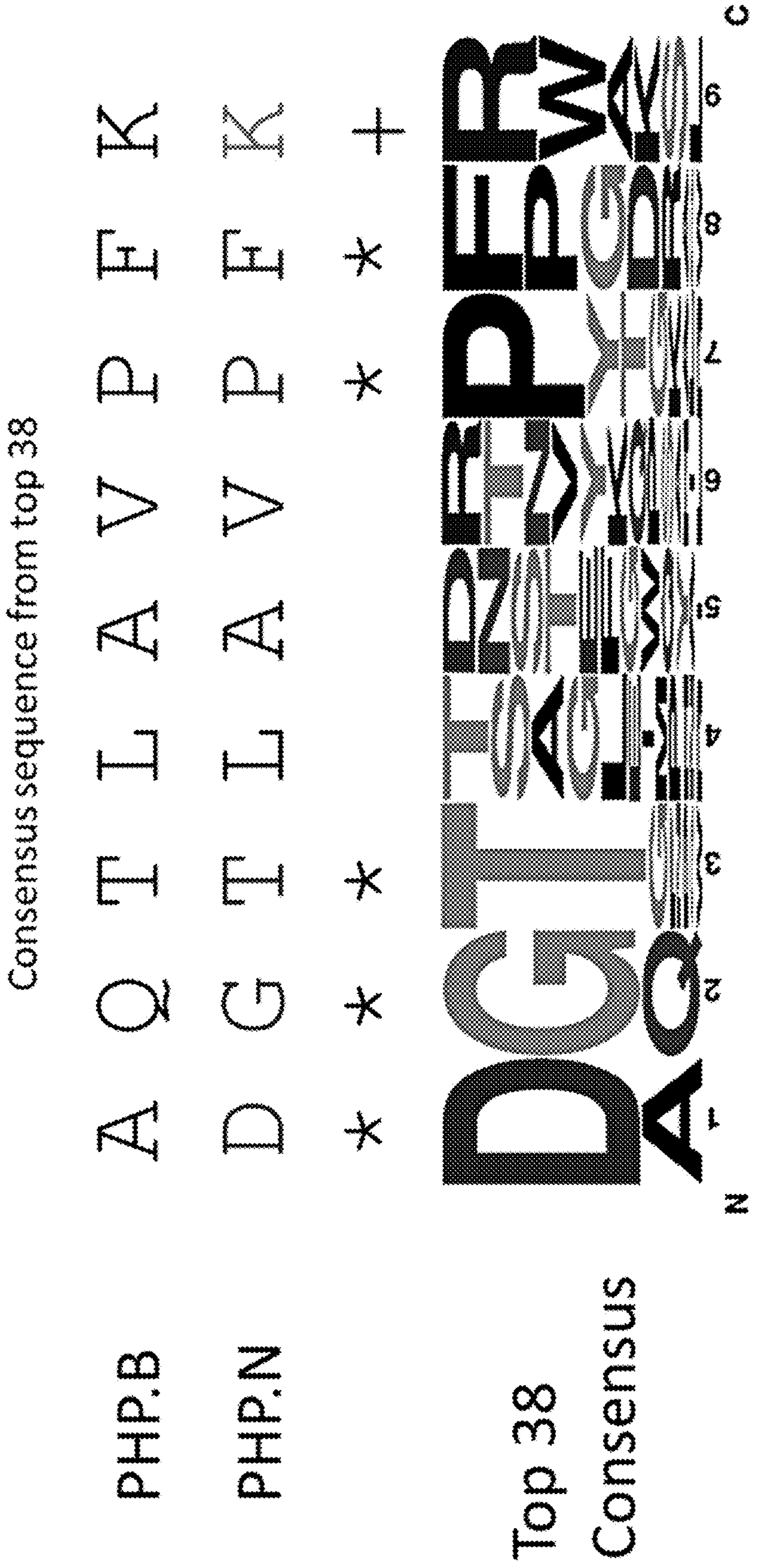
FIG. 38 provides the top consensus sequences as compared to PHP.N and PHP.B (SEQ ID NOS 168 and 71, respectively, in order of appearance).

A group of 38 capsids showed potentially interesting properties based on their tropism for neurons, astrocytes or both (Table 8A and Table 8B) (FIG. 38) and showed a strong consensus peptide sequence similarity, different between neuron- and astrocyte-targeting variants (FIG. 45A-FIG. 45C and FIG. 46A-FIG. 46B).

TABLE 8A

TOP 38 candidates from C57BL/6 screen #1 (N =3)

| Groups | variant | peptide | SEQ ID NO: | SYN ranking | GFAP ranking |
|---|---|---|---|---|---|
| A | 9p32 | DGTAIHLSS | 67 | 15, 16 | 113, 133 |
| | 9p35 | DGTSSYYDS | 59 | 1, 3 | 565, 581 |
| B | 9p36 | DGSSSYYDA | 64 | 10, 11 | 591, 594 |
| | 9p37 | DGTASYYDS | 61 | 5, 6 | 553, 560 |
| C | 9p26 | DGTTTYGAR | 77 | 225, 262 | 49, 56 |
| D | 9p2 | AQNGNPGRW | 84 | 156, 160 | 38, 44 |
| | 9p13 | AQGENPGRW | 96 | 77, 87 | 7, 13 |
| | 9p30 | AQPEGSARW | 60 | 2, 4 | 154, 160 |
| E | 9p1 | AQGSWNPPA | 80 | 348, 361 | 8, 15 |
| | 9p14 | AQGTWNPPA | 82 | 448, 467 | 14, 17 |
| F | 9p29 | AQFPTNYDS | 66 | 14, 19 | 490, 537 |
| | 9p31 | AQWPTSYDA | 62 | 7, 9 | 290, 304 |
| G | 9p3 | AQTTEKPWL | 83 | 53, 72 | 35, 70 |
| | 9p15 | AQTTDRPFL | 85 | 206, 219 | 26, 43 |
| H | 9p10 | DGTRTTTGW | 106 | 161, 220 | 10, 22 |
| | 9p18 | DGTGGIKGW | 131 | 346, 388 | 41, 68 |
| | 9p19 | DGTGNTRGW | 94 | 322, 340 | 45, 54 |
| | 9p20 | DGTHTRTGW | 90 | 380, 427 | 31, 39 |
| | 9p23 | DGTNGLKGW | 76 | 132, 153 | 5, 16 |
| | 9p33 | DGTGQVTGW | 68 | 18, 33 | 172, 213 |
| | 9p38 | DGTGNVTGW | 69 | 20, 31 | 117, 137 |
| I | 9p11 | DGTTFTPPR | 79 | 183, 199 | 11, 19 |
| | 9p12 | DGTTYVPPR | 75 | 146, 154 | 4, 9 |
| | 9p24 | DGTSFTPPK | 81 | 210, 243 | 29, 40 |
| | 9p25 | DGTSFTPPR | 88 | 250, 273 | 28, 37 |
| | 9p27 | DGTTWTPPR | 139 | 567, 570 | 46, 59 |
| | 9p28 | DGTSYVPPR | 78 | 162, 179 | 20, 25 |
| J | 9p4 | DGTADRPFR | 155 | 109, 118 | 48, 57 |
| | 9p9 | DGTMDRPFK | 102 | 102, 113 | 23 ,34 |
| | 9p16 | DGTADKPFR | 63 | 8, 12 | 1, 6 |
| | 9p17 | DGTAERPFR | 140 | 106, 138 | 42, 50 |
| | 9p21 | DGTIERPFR | 87 | 186, 235 | 21, 33 |
| | 9p34 | DGTMDKPFR | 70 | 21, 23 | 107, 112 |
| K | 9p5 | DGTISQPFK | 105 | 184, 193 | 12, 18 |
| | 9p6 | DGTLAAPFK | 120 | 110, 112 | 27, 30 |
| | 9p7 | DGTLQQPFR | 89 | 46, 57 | 32, 47 |
| | 9p8 | DGTLSQPFR | 65 | 13, 17 | 2, 3 |
| | 9p22 | DGTLNNPFR | 109 | 30, 41 | 24, 36 |

TABLE 8A-continued

| TOP 38 candidates from C57BL/6 screen #1 (N =3) | | | | | |
|---|---|---|---|---|---|
| Groups | variant | peptide | SEQ ID NO: | SYN ranking | GFAP ranking |
| Ref. | PHPN | DGTLAVPFK | 71 | 22, 24 | 51, 60 |
| | PHPB | AQTLAVPFK | 168 | 253, 261 | 61, 62 |
| | wtAAV9 | AQ | | 630, 631 | 611, 620 |

TABLE 8B

| Variant 9mer and encoding sequences | | | | | | |
|---|---|---|---|---|---|---|
| variant | 9mer peptide | SEQ ID NO: | NNK nucleotide sequences | SEQ ID NO: | NNM nucleotide sequences | SEQ ID NO: |
| 9p1 | AQGSWNPPA | 80 | GCCCAAGGTT<br>CGTGGAATCC<br>GCCGGCG | 1105 | GCACAAGGAAG<br>CTGGAACCCACC<br>AGCA | 1143 |
| 9p2 | AQNGNPGRW | 84 | GCCCAAAATG<br>GTAATCCGGG<br>GCGGTGG | 1106 | GCACAAAACGG<br>AAACCCAGGAA<br>GATGG | 1144 |
| 9p3 | AQTIEKPWL | 83 | GCCCAAACGA<br>CTGAGAAGCC<br>GTGGCTG | 1107 | GCACAAACAAC<br>AGAAAAACCAT<br>GGCTC | 1145 |
| 9p4 | DGTADRPFR | 155 | GATGGCACGG<br>CGGATCGTCCT<br>TTTCGG | 1108 | GACGGAACAGC<br>AGACAGACCATT<br>CAGA | 1146 |
| 9p5 | DGTISQPFK | 105 | GATGGCACCA<br>TTTCGCAGCCT<br>TTTAAG | 1109 | GACGGAACAAT<br>CAGCCAACCATT<br>CAAA | 1147 |
| 9p6 | DGTLAAPFK | 120 | GATGGCACCTT<br>GGCTGCTCCTT<br>TTAAG | 1110 | GACGGAACACTC<br>GCAGCACCATTC<br>AAA | 1148 |
| 9p7 | DGTLQQPFR | 89 | GATGGCACCTT<br>GCAGCAGCCG<br>TTTCGG | 1111 | GACGGAACACTC<br>CAACAACCATTC<br>AGA | 1149 |
| 9p8 | DGTLSQPFR | 65 | GATGGCACCC<br>TGTCTCAGCCT<br>TTTAGG | 1112 | GACGGAACACTC<br>AGCCAACCATTC<br>AGA | 1150 |
| 9p9 | DGTMDRPFK | 102 | GATGGCACCA<br>TGGATAGGCC<br>GTTTAAG | 1113 | GACGGAACAAT<br>GGACAGACCATT<br>CAAA | 1151 |
| 9p10 | DGTRTTTGW | 106 | GATGGCACCC<br>GTACTACGAC<br>GGGTTGG | 1114 | GACGGAACAAG<br>AACAACAACAG<br>GATGG | 1152 |
| 9p11 | DGTTFTPPR | 79 | GATGGCACCA<br>CTTTTACTCCT<br>CCTCGG | 1115 | GACGGAACAAC<br>ATTCACACCACC<br>AAGA | 1153 |
| 9p12 | DGTTYVPPR | 75 | GATGGCACCA<br>CGTATGTTCCT<br>CCGCGG | 1116 | GACGGAACAAC<br>ATACGTCCCACC<br>AAGA | 1154 |
| 9p13 | AQGENPGRW | 96 | GCCCAAGGGG<br>AGAATCCGGG<br>TAGGTGG | 1117 | GCACAAGGAGA<br>AAACCCAGGAA<br>GATGG | 1155 |
| 9p14 | AQGTWNPPA | 82 | GCCCAAGGTA<br>CTTGGAATCCG<br>CCGGCT | 1118 | GCACAAGGAAC<br>ATGGAACCCACC<br>AGCA | 1156 |
| 9p15 | AQTTDRPFL | 85 | GCCCAAACTA<br>CTGATAGGCCT<br>TTTTTG | 1119 | GCACAAACAAC<br>AGACAGACCATT<br>CCTC | 1157 |

TABLE 8B-continued

Variant 9mer and encoding sequences

| variant | 9mer peptide | SEQ ID NO: | NNK nucleotide sequences | SEQ ID NO: | NNM nucleotide sequences | SEQ ID NO: |
|---|---|---|---|---|---|---|
| 9p16 | DGTADKPFR | 63 | GATGGCACCG CTGATAAGCC GTTTCGG | 1120 | GACGGAACAGC AGACAAACCATT CAGA | 1158 |
| 9p17 | DGTAERPFR | 140 | GATGGCACCG CGGAGAGGCC TTTTAGG | 1121 | GACGGAACAGC AGAAAGACCATT CAGA | 1159 |
| 9p18 | DGTGGIKGW | 131 | GATGGCACCG GTGGTATTAA GGGGTGG | 1122 | GACGGAACAGG AGGAATCAAAG GATGG | 1160 |
| 9p19 | DGTGNTRGW | 94 | GATGGCACCG GGAATACTCG GGGGTGG | 1123 | GACGGAACAGG AAACACAAGAG GATGG | 1161 |
| 9p20 | DGTHTRTGW | 90 | GATGGCACCC ATACGCGGAC GGGTTGG | 1124 | GACGGAACACA CACAAGAACAG GATGG | 1162 |
| 9p21 | DGTIERPFR | 87 | GATGGCACCA TTGAGCGGCCT TTTCGT | 1125 | GACGGAACAAT CGAAAGACCATT CAGA | 1163 |
| 9p22 | DGTLNNPFR | 109 | GATGGCACCTT GAATAATCCG TTTAGG | 1126 | GACGGAACACTC AACAACCCATTC AGA | 1164 |
| 9p23 | DGTNGLKGW | 76 | GATGGCACCA ATGGTCTGAA GGGGTGG | 1127 | GACGGAACAAA CGGACTCAAAG GATGG | 1165 |
| 9p24 | DGTSFTPPK | 81 | GATGGCACCT CGTTTACGCCG CCTAAG | 1128 | GACGGAACAAG CTTCACACCACC AAAA | 1166 |
| 9p25 | DGTSFTPPR | 88 | GATGGCACCT CGTTTACTCCG CCGCGG | 1129 | GACGGAACAAG CTTCACACCACC AAGA | 1167 |
| 9p26 | DGTTTYGAR | 77 | GATGGCACCA CTACGTATGG GGCTCGT | 1130 | GACGGAACAAC AACATACGGAG CAAGA | 1168 |
| 9p27 | DGTTWTPPR | 139 | GATGGCACCA CTTGGACGCC GCCGCGT | 1131 | GACGGAACAAC ATGGACACCACC AAGA | 1169 |
| 9p28 | DGTSYVPPR | 78 | GATGGCACCA GTTATGTTCCT CCGAGG | 1132 | GACGGAACAAG CTACGTCCCACC AAGA | 1170 |
| 9p29 | AQFPTNYDS | 66 | GCCCAATTTCC TACGAATTATG ATTCT | 1133 | GCACAATTCCCA ACAAACTACGAC AGC | 1171 |
| 9p30 | AQPEGSARW | 60 | GCCCAACCTG AGGGTAGTGC GAGGTGG | 1134 | GCACAACCAGA AGGAAGCGCAA GATGG | 1172 |
| 9p31 | AQWPTSYDA | 62 | GCCCAATGGC CTACGAGTTAT GATGCT | 1135 | GCACAATGGCCA ACAAGCTACGAC GCA | 1173 |
| 9p32 | DGTAIHLSS | 67 | GATGGCACCG CGATTCATCTT TCGTCT | 1136 | GACGGAACAGC AATCCACCTCAG CAGC | 1174 |
| 9p33 | DGTGQVTGW | 68 | GATGGCACCG GGCAGGTGAC TGGGTGG | 1137 | GACGGAACAGG ACAAGTCACAG GATGG | 1175 |

TABLE 8B-continued

| Variant 9mer and encoding sequences | | | | | | |
|---|---|---|---|---|---|---|
| variant | 9mer peptide | SEQ ID NO: | NNK nucleotide sequences | SEQ ID NO: | NNM nucleotide sequences | SEQ ID NO: |
| 9p34 | DGTMDKPFR | 70 | GATGGCACGA TGGATAAGCC TTTTAGG | 1138 | GACGGAACAAT GGACAAACCATT CAGA | 1176 |
| 9p35 | DGTSSYYDS | 59 | GATGGCACCT CGAGTTATTAT GATTCT | 1139 | GACGGAACAAG CAGCTACTACGA CAGC | 1177 |
| 9p36 | DGSSSYYDA | 64 | GATGGCAGTA GTTCTTATTAT GATGCG | 1140 | GACGGAAGCAG CAGCTACTACGA CGCA | 1178 |
| 9p37 | DGTASYYDS | 61 | GATGGCACCG CGAGTTATTAT GATTCT | 1141 | GACGGAACAGC AAGCTACTACGA CAGC | 1179 |
| 9p38 | DGTGNVTGW | 69 | GATGGCACCG GTAATGTGAC GGGGTGG | 1142 | GACGGAACAGG AAACGTCACAG GATGG | 1180 |
| AAV9 | AQ | | AGTGCTCAGG CACAGGCGCA GACC | 54 | AGTGCCCAAGCA CAGGCGCAGAC C | 53 |
| PHPN | DGTLAVPFK | 71 | GATGGGACTTT GGCGGTGCCTT TTAAG | 56 | GACGGAACACTC GCAGTCCCATTC AAA | 55 |
| PHPB | AQTLAVPFK | 168 | GCCCAAACTTT GGCGGTGCCTT TTAAG | 58 | GCACAAACACTC GCAGTCCCATTC AAA | 57 |

Example 11. Phylogenetic Grouping

Figure 37B:
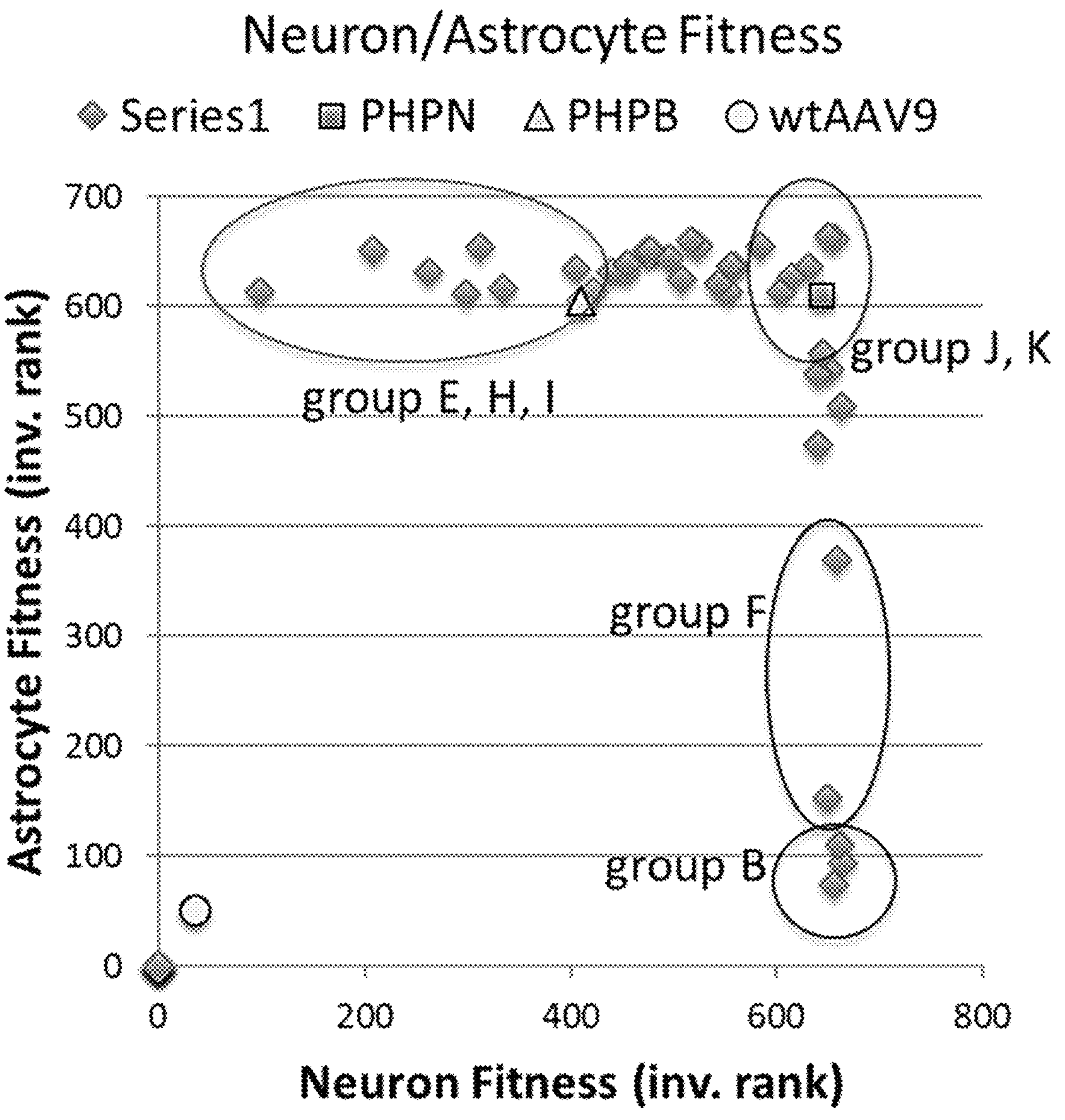

Phylogenetic grouping of peptide sequences showed an evident correlation between sequence homology clusters and capsid phenotypes (FIG. 37). For example, 9-mer variants with the sequence DGTxxxPFK/R (SEQ ID NO: 1181) presented a similar behavior as PHP.eB capsid (high transduction of both neurons and astrocytes), whereas variants harboring the sequence DGTxxxYDS/A (SEQ ID NO: 1182) showed a preference for neuron transduction. By contrast, peptides with the consensus DGTxxxxGW (SEQ ID NO: 1183) or CGTxxxPPR/K (SEQ ID NO: 1184) presented a higher tropism for astrocytes.

Example 12. Capsid Testing

Figures 49A, 49B:
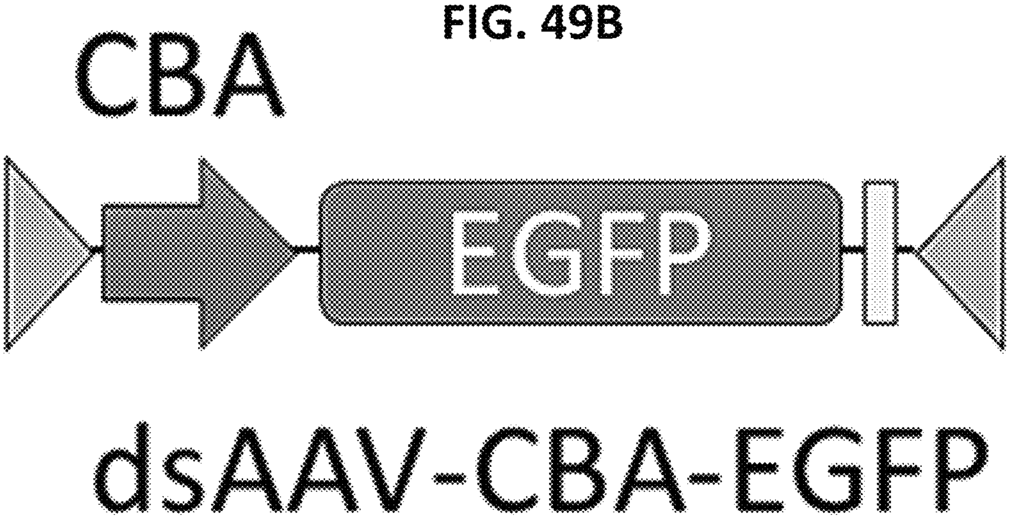
Figure 49D:
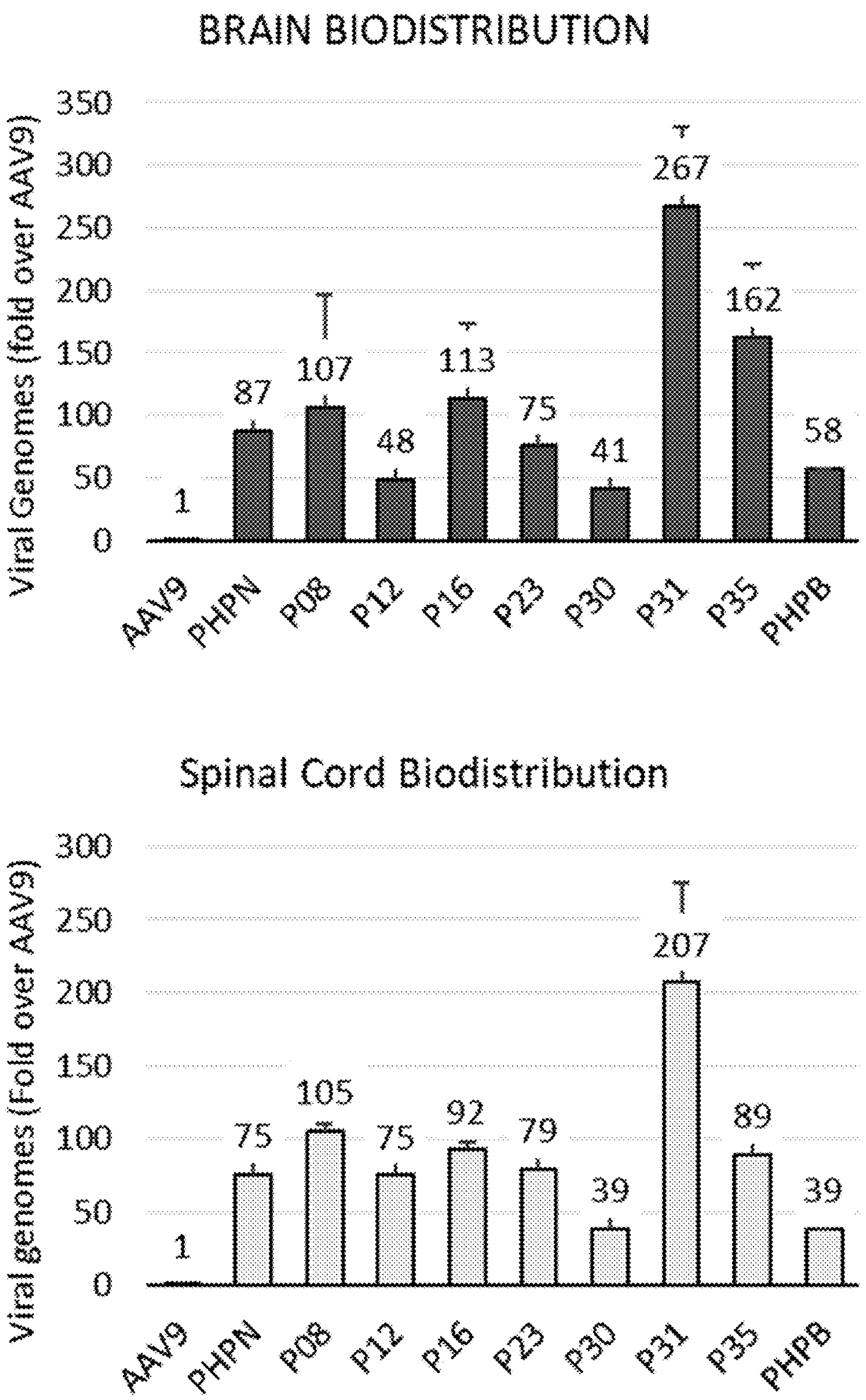
Figure 50A:
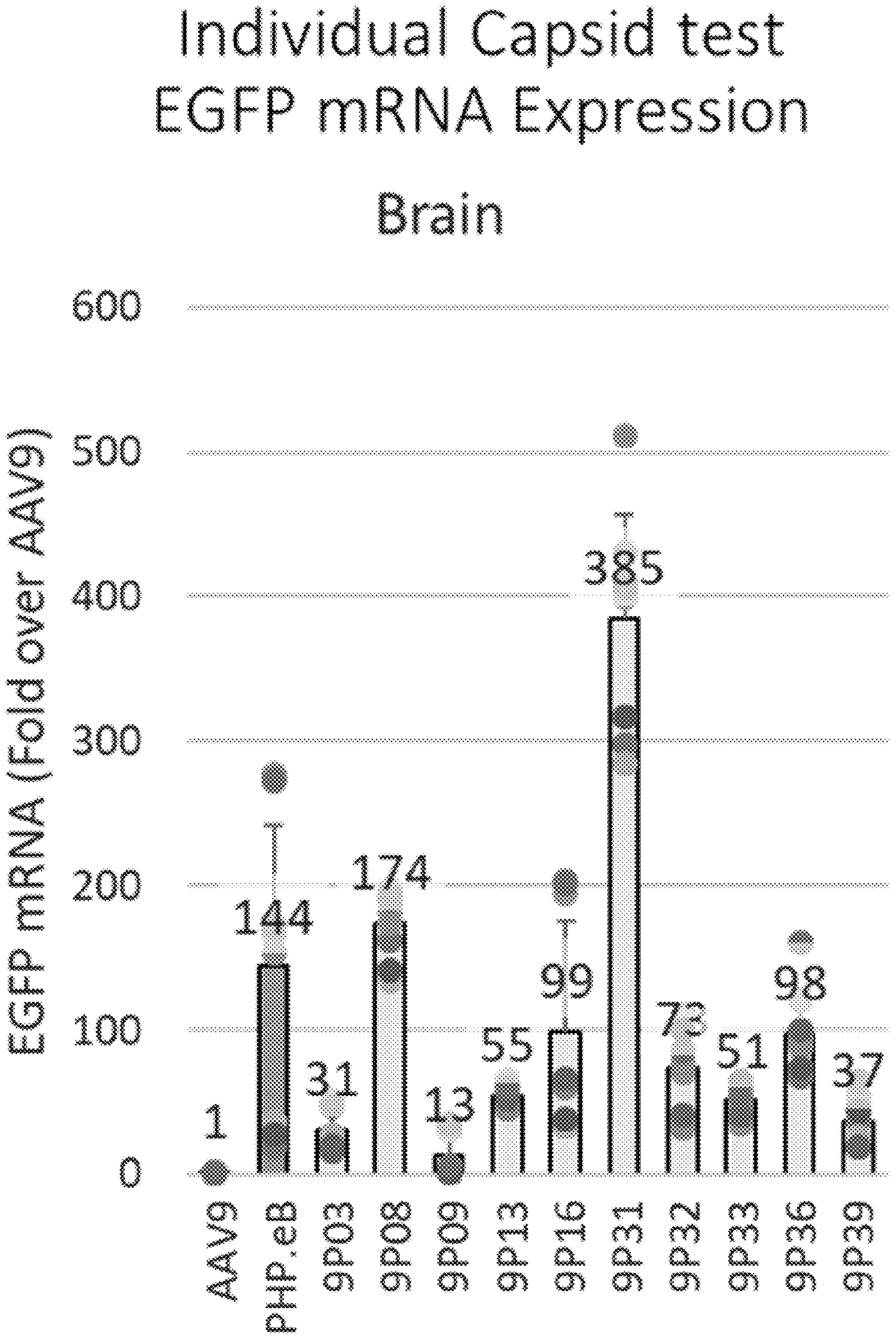
FIG. 50A, FIG. 50B and FIG. 50C provide the results of testing of individual capsids and their mRNA expression in brain, spinal cord and liver. EGFP mRNA expression results are shown for the brain (FIG. 50A), the spinal cord (FIG. 50B) and the liver (FIG. 50C).
Figure 50B:
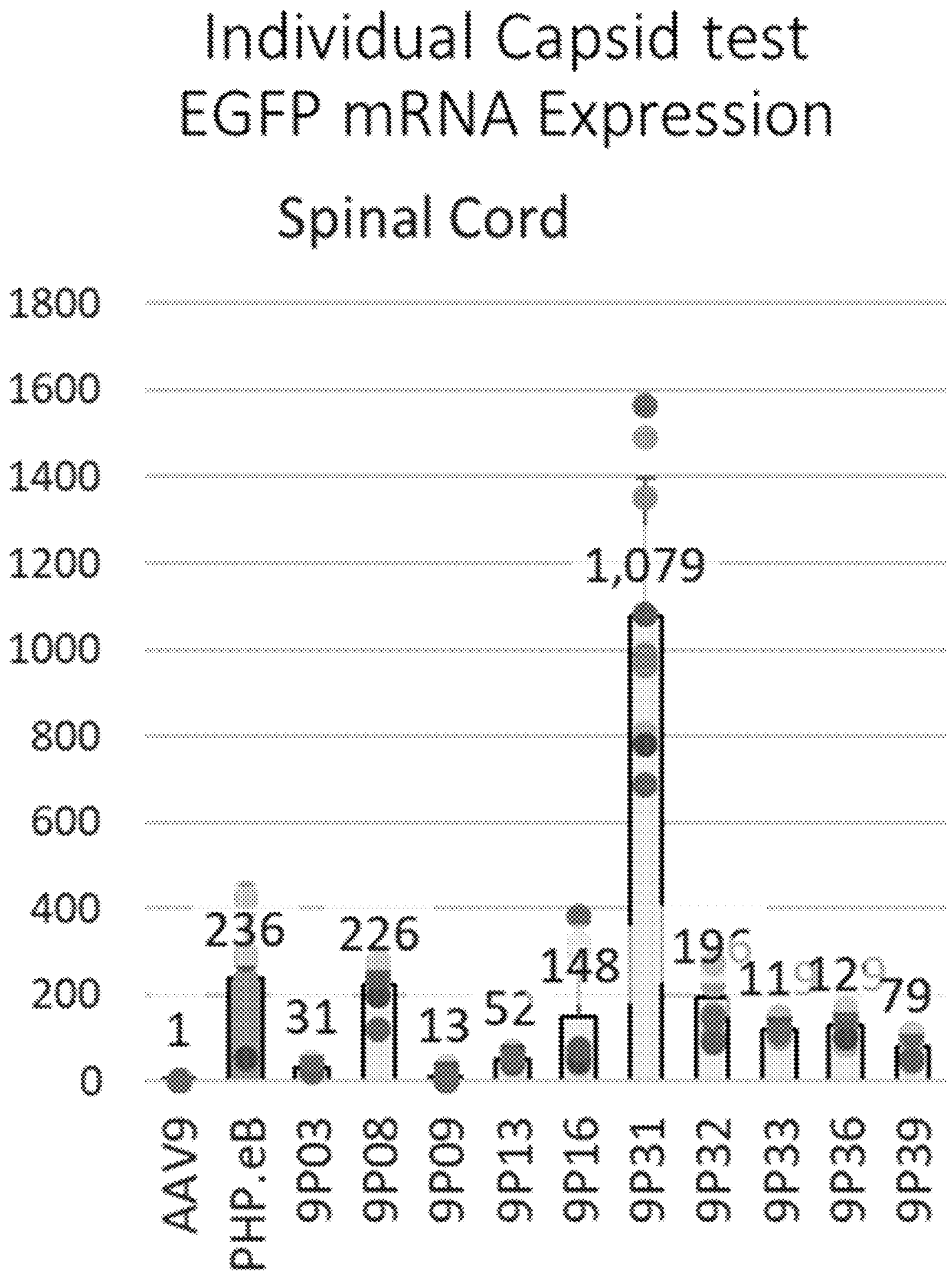
Figure 50C:
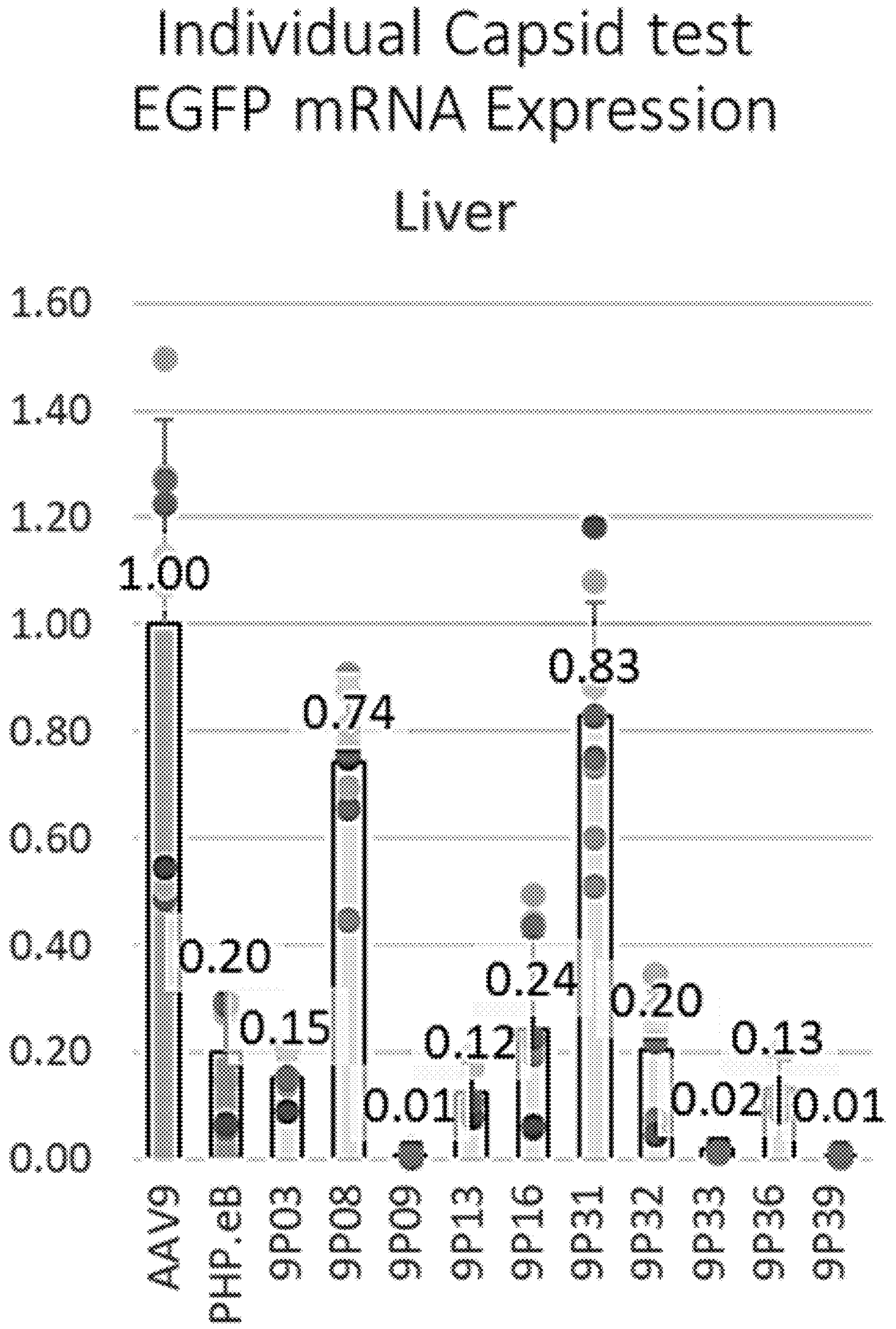

Capsid variants representative of distinct sequence clusters (highlighted in FIG. 37B) were chosen for individual transduction analysis in C57BL/6 mice. Each capsid was produced as a recombinant AAV packaging a self-complementary EGFP transgene driven by the ubiquitous promoter (FIGS. 49A, B). Mouse groups (N=3) were injected intravenously with 6e10 VG and transduction efficiency was assessed after 1 month by quantifying EGFP mRNA in the brain, spinal cord, and liver tissue. EGFP mRNA expression was normalized using mouse TBP as a housekeeping gene, and DNA biodistribution was normalized to the single-copy mouse TfR gene (FIG. 50A-FIG. 50C). Reverse transcription was performed with the Quantitect kit and included a DNA removal treatment. All capsid variants showed a significant improvement in brain and spinal cord mRNA expression by comparison to the parent AAV9 capsid, and 3 out of 7 variants (9P16, 9P31 and 9P35) showed similar or higher transduction than the PHP.eB benchmark capsid (FIG. 49C, Table 10). The viral DNA biodistribution showed a very strong tropism of 9P31 and 9P35 for the brain and spinal cord, but all the variants showed a 40- to 260-fold increase of biodistribution compared to AAV9 (FIG. 49D, Table 10).

Figure 51:
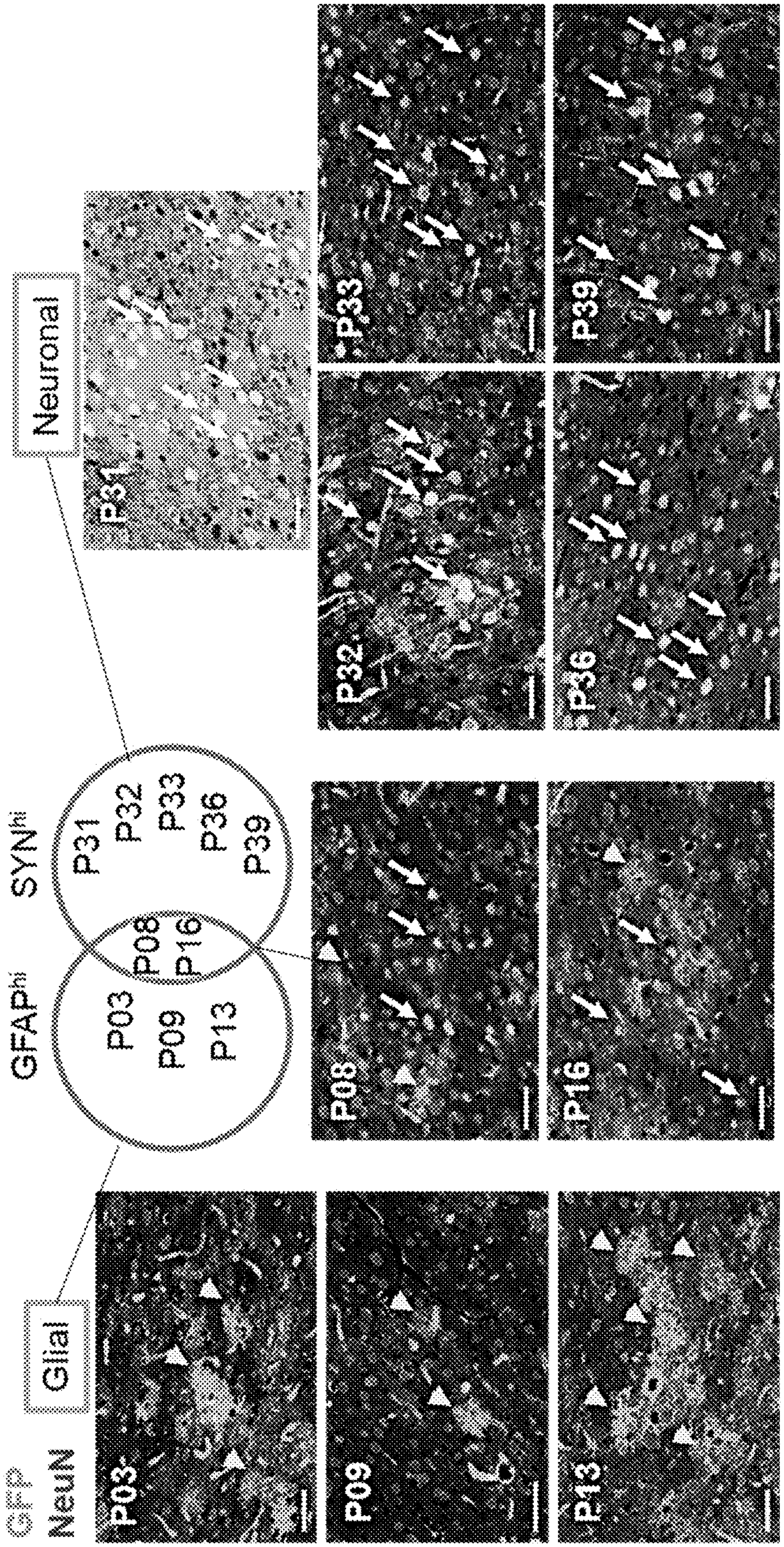
FIG. 51 provides results for NGS screening using neuronal NeuN marker (FIG. 51) for both GFAP screening and SYN screening.
Figure 52:
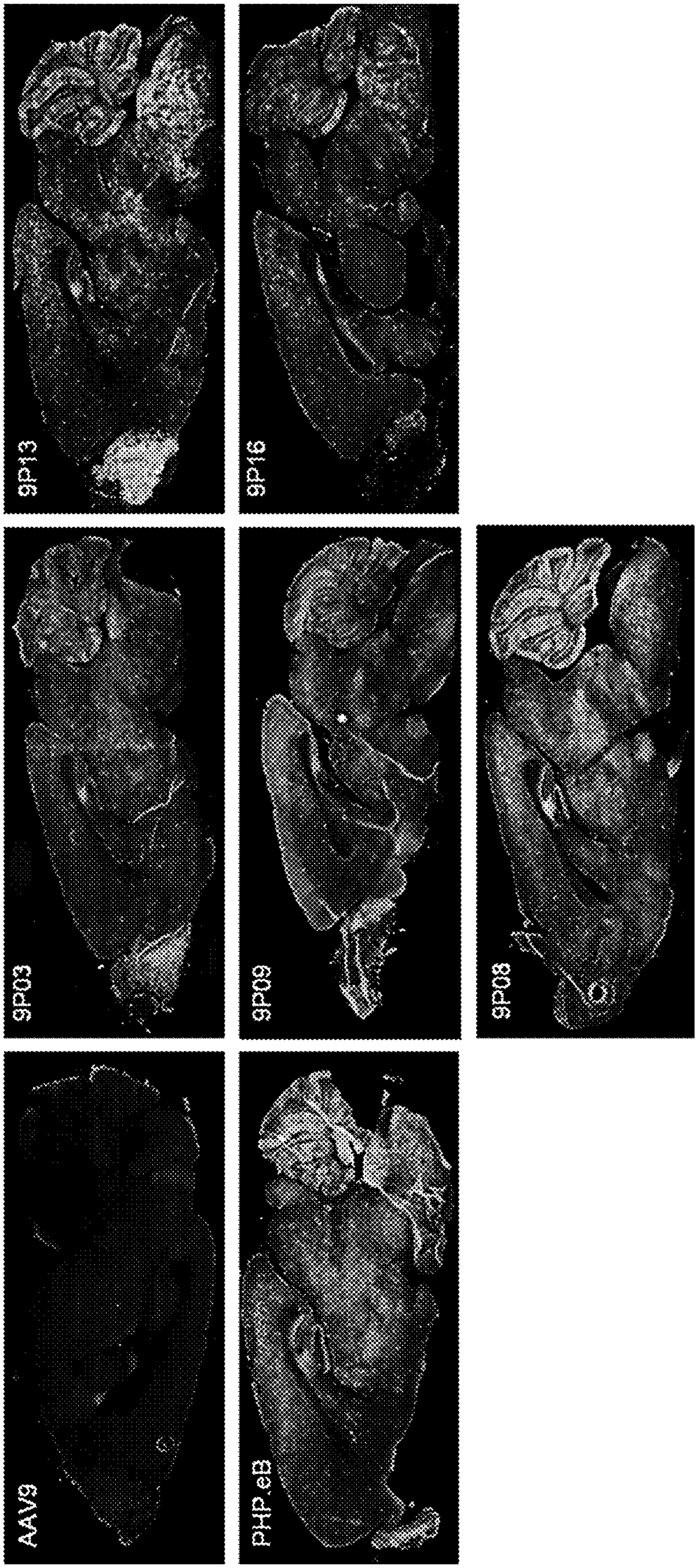
FIG. 52 provides the results of testing of individual capsids in whole brain.
Figure 53:
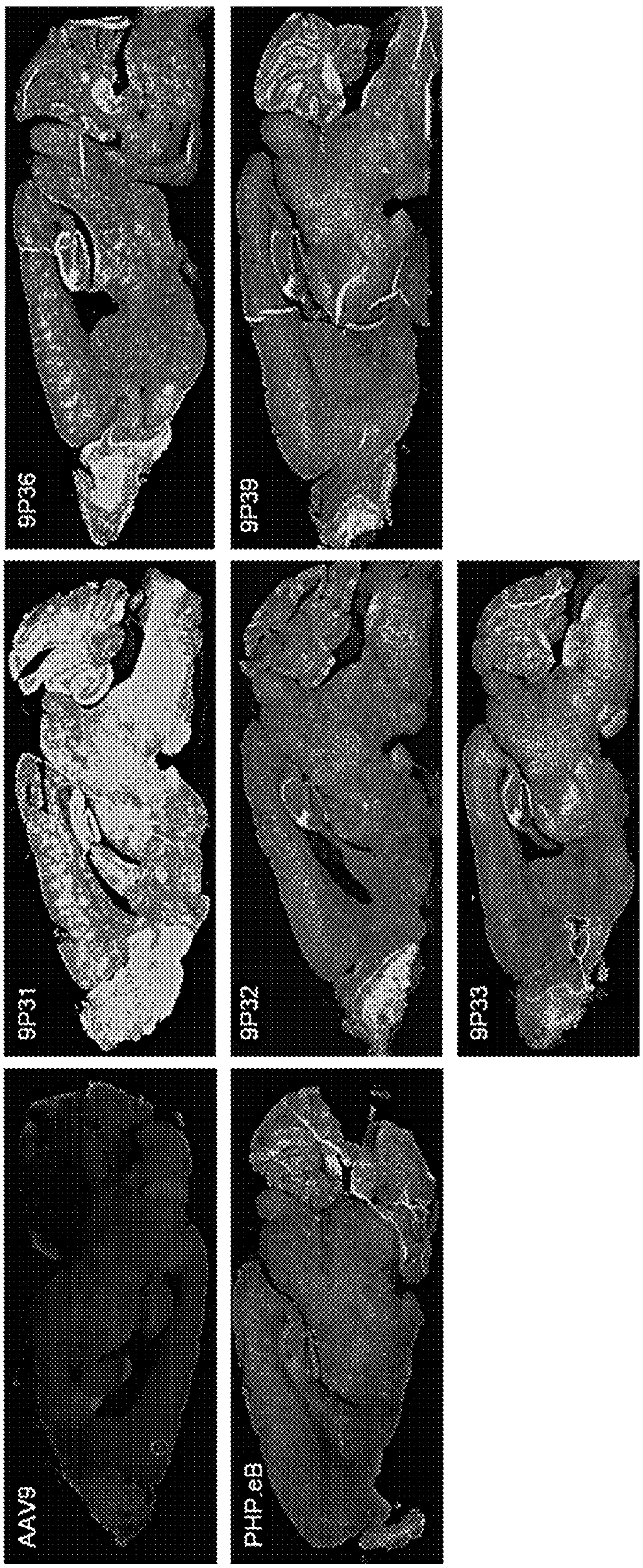
FIG. 53 provides the results of testing of additional individual capsids in whole brain.
Figure 54:
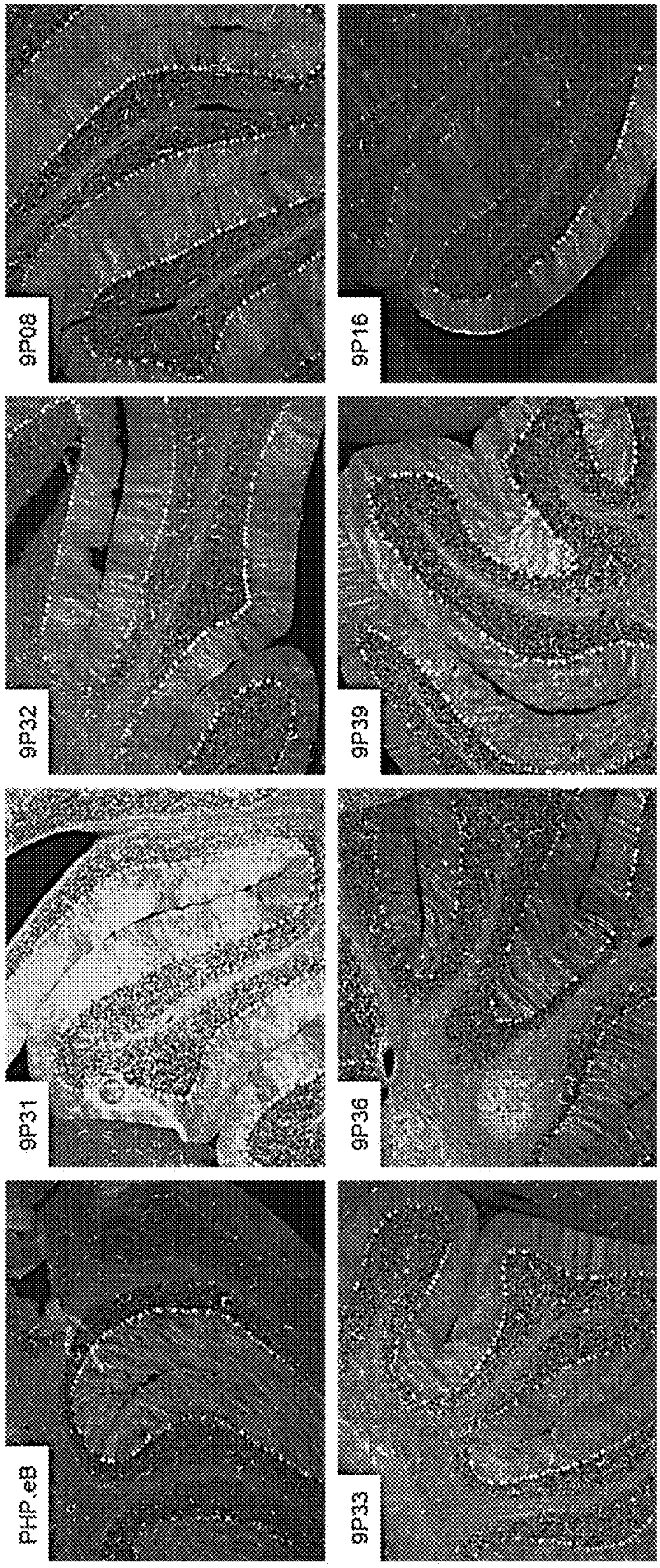
FIG. 54 provides the results of testing of individual capsids in cerebellum.
Figure 55:
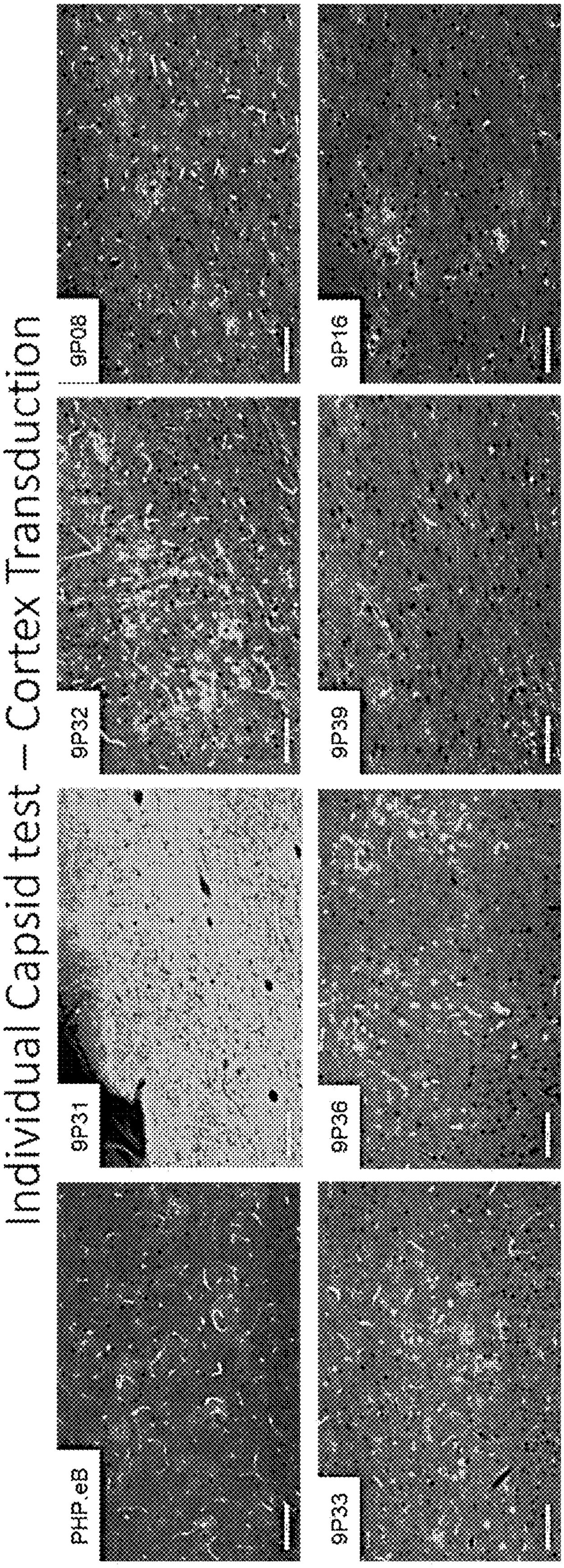
FIG. 55 provides the results of testing of individual capsids in cortex.
Figure 56:
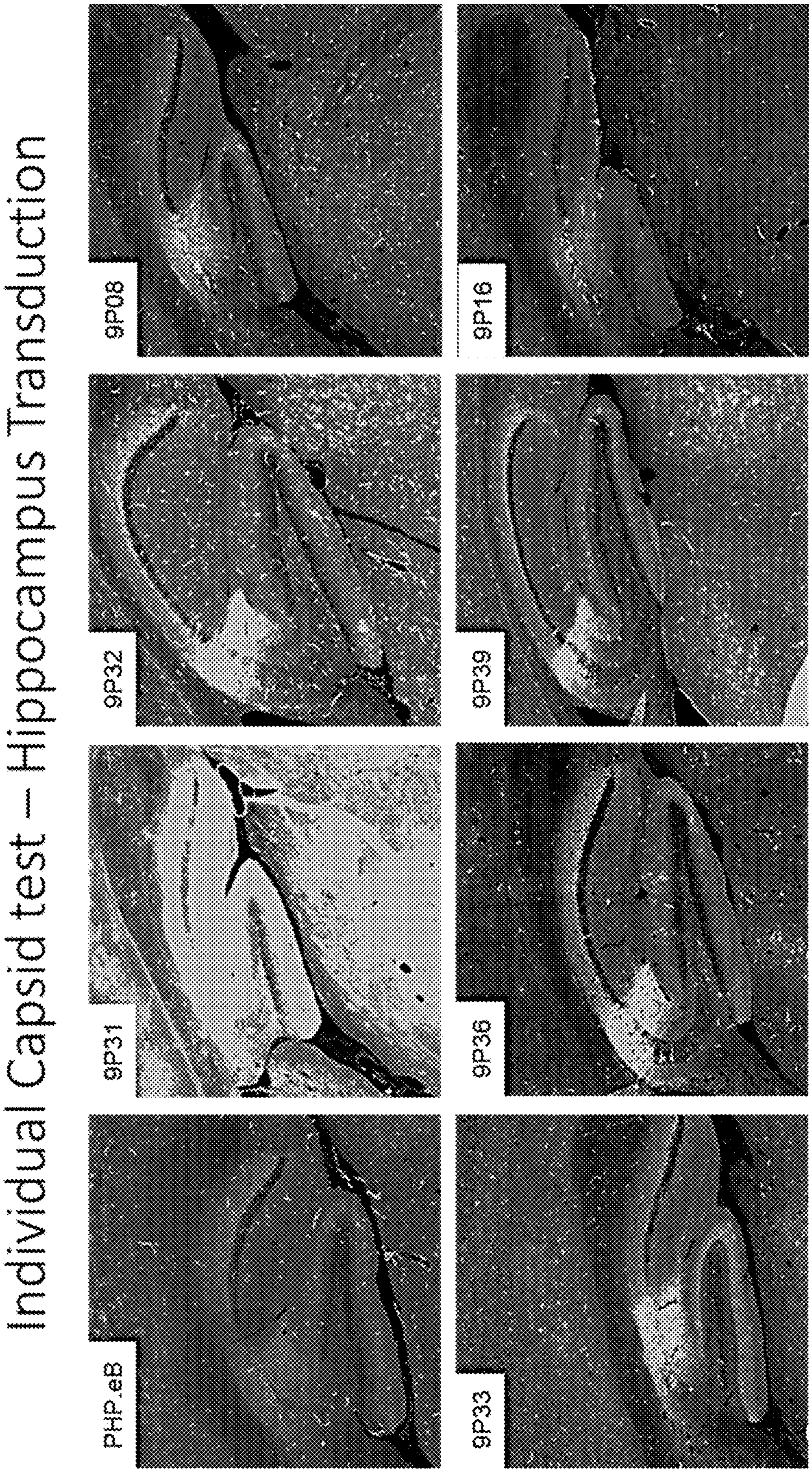
FIG. 56 provides the results of testing of individual capsids in hippocampus.

Expected cellular tropism was tested using an NGS screen by labeling the neuronal NeuN marker (FIG. 51). Within the cortex, the top capsids in the GFAP screen showed mostly GFP expression in NeuN-negative cells with glial morphology. Conversely, top capsids in the SYN screen showed a very high transduction of NeuN-positive cells, and the dual-specificity capsids 9P08 and 9P16—ranking high in both assays—showed mixed cell preference with multiple NeuN+ cells and glial cells.

Cellular tropism was also tested using mouse brain microvascular EC (mBMVEC) binding relative to AAV9. Results are shown in Table 9.

TABLE 9

| mBMVEC binding results | | | |
|---|---|---|---|
| PEPTIDE | SEQUENCE | SEQUENCE ID | BINDING TO mBMVEC (fold over AAV9) |
| AAV9 | AQ | | 1 |
| PHP.eB | DGTLAVPFK | 71 | 153 |
| 9P03 | AQTTEKPWL | 83 | 170 |
| 9P08 | DGTLSQPFR | 65 | 349 |

TABLE 9-continued mBMVEC binding results

| PEPTIDE | SEQUENCE | SEQUENCE ID | BINDING TO mBMVEC (fold over AAV9) |
|---|---|---|---|
| 9P09 | DGTMDRPFK | 102 | 222 |
| 9P13 | AQGENPGRW | 96 | 2.5 |
| 9P16 | DGTADKPFR | 63 | 176 |
| 9P31 | AQWPTSYDA | 62 | 2 |
| 9P32 | DGTAIHLSS | 67 | 16 |
| 9P33 | DGTGQVTGW | 68 | 5 |

TABLE 9-continued mBMVEC binding results

| PEPTIDE | SEQUENCE | SEQUENCE ID | BINDING TO mBMVEC (fold over AAV9) |
|---|---|---|---|
| 9P36 | DGSSSYYDA | 64 | 0 |
| 9P39 | DGTGSTTGW | 134 | 2 |

Fluorescent EGFP expression in tissues of whole brain, cerebellum, cortex, and hippocampus revealed transduction patterns across a spectrum and demonstrate the identification of tissue-specific capsids (FIG. 52-FIG. 56).

Figure 57A:
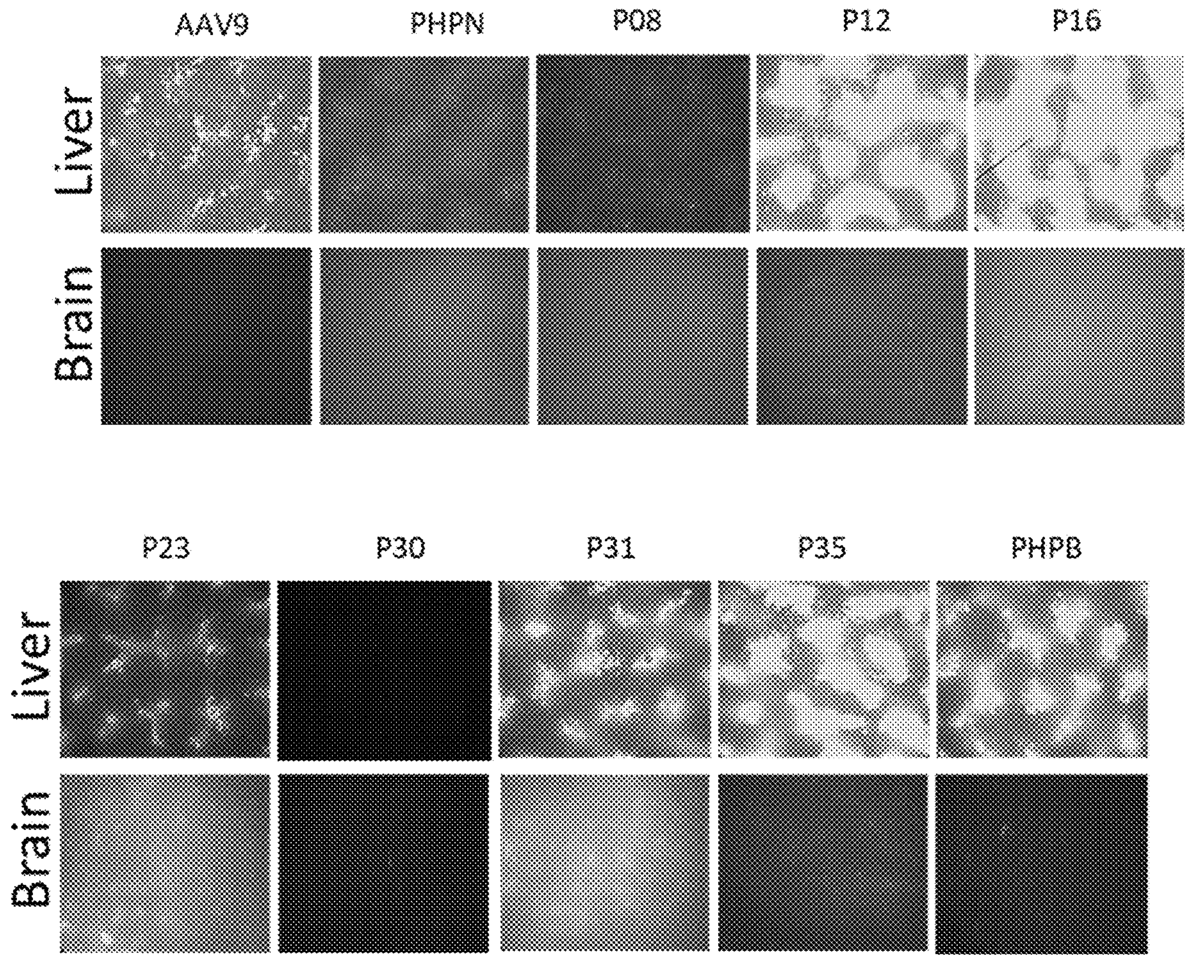
FIG. 57A and FIG. 57B provide transduction data of 10 capsid variants in mouse liver (FIG. 57B), analyzed by EGFP RNA expression and whole tissue fluorescence (FIG. 57A).
Figure 57B:
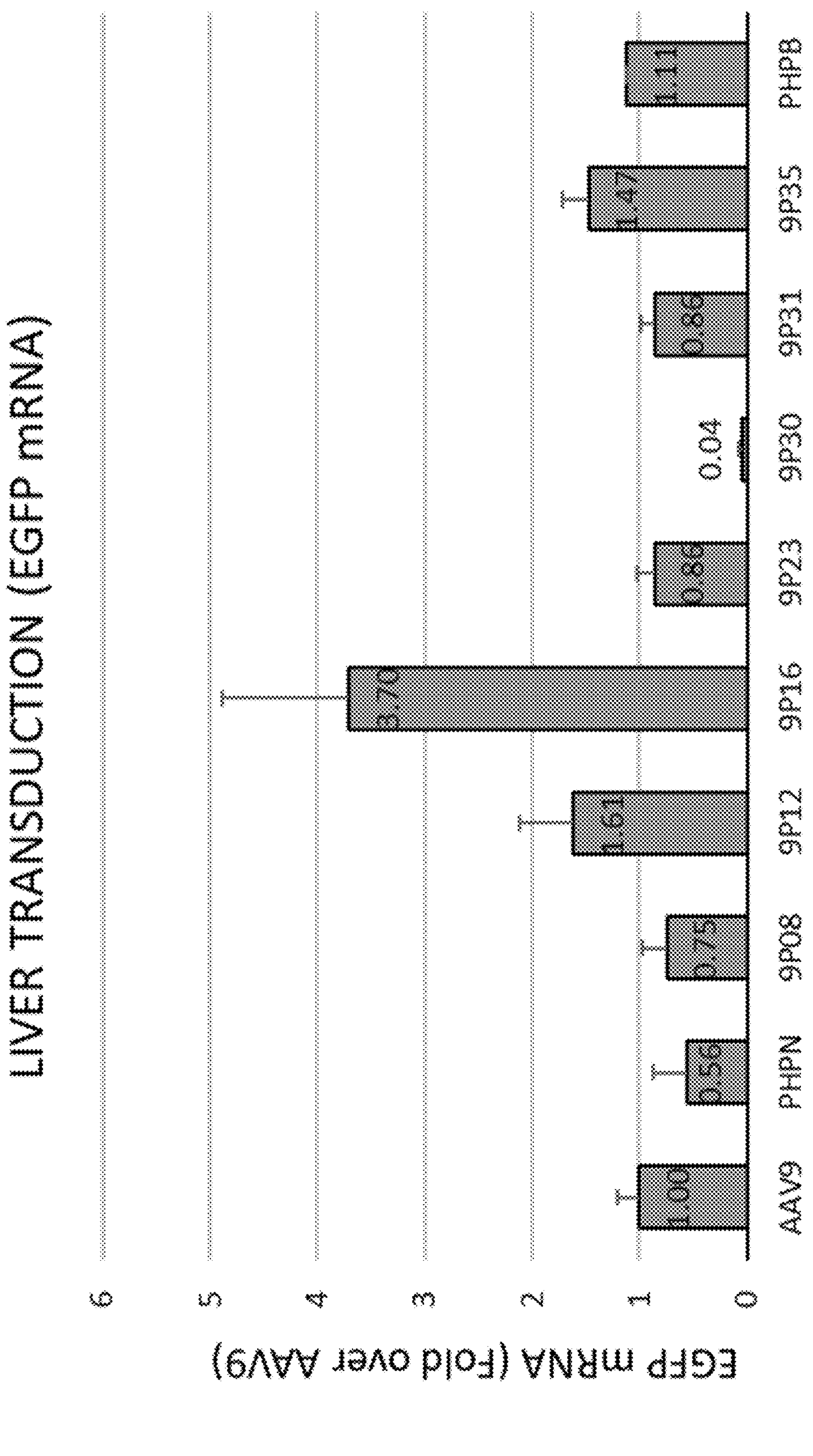

The liver transduction, measured by mRNA expression and by whole tissue GFP expression, showed that several variants outperformed AAV9, which was unexpected in light of the NGS results. Some variants, such as 9P08 or 9P23, showed a relative liver detargeting by comparison with AAV9 (FIG. 57A-FIG. 57B).

TABLE 10

Brain and Spinal cord tropism

| | BRAIN EGFP mRNA* | | | | | | |
|---|---|---|---|---|---|---|---|
| CAPSID | EGFP/TBP m1 | EGFP/TBP m2 | EGFP/TBP m3 | group mean | group SD | Mean Fold over AAV9 | Fold SDEV |
| AAV9 | 0.11 | 0.1 | 0.15 | 0.12 | 0.03 | 1 | 0.21 |
| PHPN | 2.94 | 4.44 | 3.42 | 3.6 | 0.77 | 30 | 6.38 |
| 9P08 | 2.46 | 3.47 | 2.73 | 2.89 | 0.53 | 24 | 4.38 |
| 9P12 | 3.07 | 2.27 | 2.98 | 2.77 | 0.44 | 23 | 3.65 |
| 9P16 | 4.31 | 4.75 | 5.28 | 4.78 | 0.49 | 39 | 4.06 |
| 9P23 | 3.28 | 2.37 | 2.79 | 2.81 | 0.46 | 23 | 3.79 |
| 9P30 | 1.06 | 1.7 | 1.32 | 1.36 | 0.32 | 11 | 2.66 |
| 9P31 | 4.87 | 5.53 | 4.2 | 4.87 | 0.66 | 40 | 5.54 |
| 9P35 | 3.9 | 3.24 | 3.45 | 3.53 | 0.33 | 29 | 2.78 |
| PHPB*** | 2.68 | 2.68 | 2.68 | 2.68 | 0 | 22 | 0 |
| ctrl | 0 | 0 | 0 | 0 | 0 | 0 | 0 |

| | SPINAL CORD EGFP mRNA* | | | | | | |
|---|---|---|---|---|---|---|---|
| CAPSID | EGFP/TBP m1 | EGFP/TBP m2 | EGFP/TBP m3 | group mean | group SD | Mean Fold over AAV9 | Fold SD |
| AAV9 | 0.84 | 0.29 | 0.3 | 0.48 | 0.31 | 1 | 0.66 |
| PHPN | 3.36 | 5.8 | 5.4 | 4.86 | 1.31 | 10.22 | 2.75 |
| 9P08 | 4.3 | 5.62 | 4.65 | 4.86 | 0.68 | 10.22 | 1.43 |
| 9P12 | 6.09 | 5.94 | 5.78 | 5.94 | 0.16 | 12.49 | 0.33 |
| 9P16 | 4.42 | 5.31 | 5.37 | 5.04 | 0.53 | 10.6 | 1.12 |
| 9P23 | 5.41 | 5.95 | 5.04 | 5.47 | 0.46 | 11.5 | 0.96 |
| 9P30 | 1.53 | 1.83 | 2.11 | 1.82 | 0.29 | 3.84 | 0.61 |
| 9P31 | 6.92 | 7.06 | 6.94 | 6.98 | 0.08 | 14.68 | 0.16 |
| 9P35 | 4.68 | 4.81 | 4.79 | 4.76 | 0.07 | 10.02 | 0.15 |
| PHPB | 3.84 | 3.84 | 3.84 | 3.84 | 0 | 8.09 | 0 |
| ctrl | 0 | 0 | 0 | 0 | 0 | 0 | 0 |

| | BRAIN EGFP DNA** (VG/Cell) | | | | | | |
|---|---|---|---|---|---|---|---|
| CAPSID | EGFP/TERT m1 | EGFP/TERT m2 | EGFP/TERT m3 | Group mean | Group SD | Mean Fold over AAV9 | Fold SDEV |
| AAV9 | 0.03 | 0.04 | 0.01 | 0.03 | 0.01 | 1 | 0 |
| PHPN | 2.07 | 2.79 | 1.94 | 2.27 | 0.46 | 87 | 18 |
| P08 | 1.25 | 1.62 | 5.47 | 2.78 | 2.34 | 107 | 90 |
| P12 | 1.43 | 0.94 | 1.41 | 1.26 | 0.27 | 48 | 10 |
| P16 | 4.13 | 1.15 | 3.56 | 2.95 | 1.58 | 113 | 60 |
| P23 | 1.34 | 2.68 | 1.87 | 1.96 | 0.68 | 75 | 26 |
| P30 | 0.59 | 1.42 | 1.21 | 1.08 | 0.43 | 41 | 17 |
| P31 | 6.47 | 5.6 | 8.81 | 6.96 | 1.66 | 267 | 64 |

TABLE 10-continued

| Brain and Spinal cord tropism | | | | | | | |
|---|---|---|---|---|---|---|---|
| P35 | 4.62 | 5.55 | 2.52 | 4.23 | 1.55 | 162 | 59 |
| PHPB | 1.5 | 1.5 | 1.5 | 1.5 | 0 | 58 | 0 |
| ctrl | 0 | 0 | 0 | 0 | 0 | 0 | 0 |
| | SPINAL CORD EGFP DNA** (VG/Cell) | | | | | | |
| CAPSID | EGFP/TERT m 1 | EGFP/TERT m 2 | EGFP/TERT m 3 | Group AVG | Group SD | Mean Fold over AAV9 | Fold SDEV |
| AAV9 | 0.03 | 0.04 | 0.04 | 0.03 | 0.007 | 1 | 0.2 |
| PHPN | 1.75 | 2.96 | 3.14 | 2.62 | 0.752 | 75 | 21.7 |
| P08 | 3.81 | 3.47 | 3.66 | 3.65 | 0.174 | 105 | 5 |
| P12 | 1.62 | 3.31 | 2.87 | 2.6 | 0.873 | 75 | 25.2 |
| P16 | 3.3 | 3.34 | 2.96 | 3.2 | 0.211 | 92 | 6.1 |
| P23 | 2.63 | 2.47 | 3.1 | 2.73 | 0.322 | 79 | 9.3 |
| P30 | 0.8 | 1.8 | 1.43 | 1.34 | 0.507 | 39 | 14.6 |
| P31 | 9.88 | 6.19 | 5.47 | 7.18 | 2.366 | 207 | 68.2 |
| P35 | 2.95 | 3.92 | 2.41 | 3.1 | 0.765 | 89 | 22 |
| PHPB | 1.34 | 1.34 | 1.34 | 1.34 | 0 | 39 | 0 |
| ctrl | 0 | 0 | 0 | 0 | 0 | 0 | 0 |

*EGFP mRNA expression was normalized to TBP as a housekeeping marker
**GFP DNA was normalized to single-copy TfR DNA
***N = 1

Example 13. Multi-Rodent Testing (Cross Species)

Figure 47:
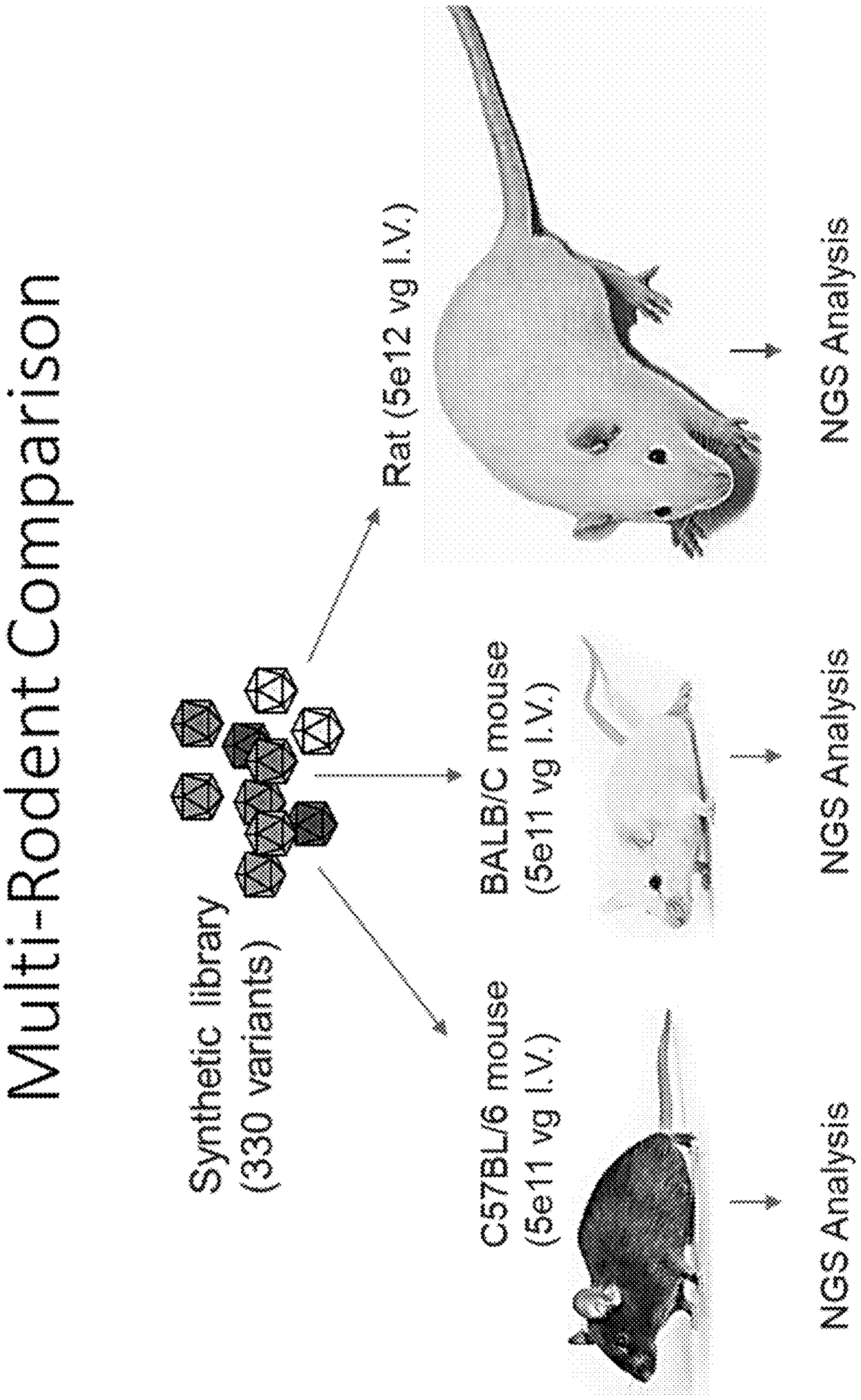
FIG. 47 illustrates one embodiment of a multi-species (e.g., rodent) study followed by next generation sequencing (NGS).
Figure 48A:
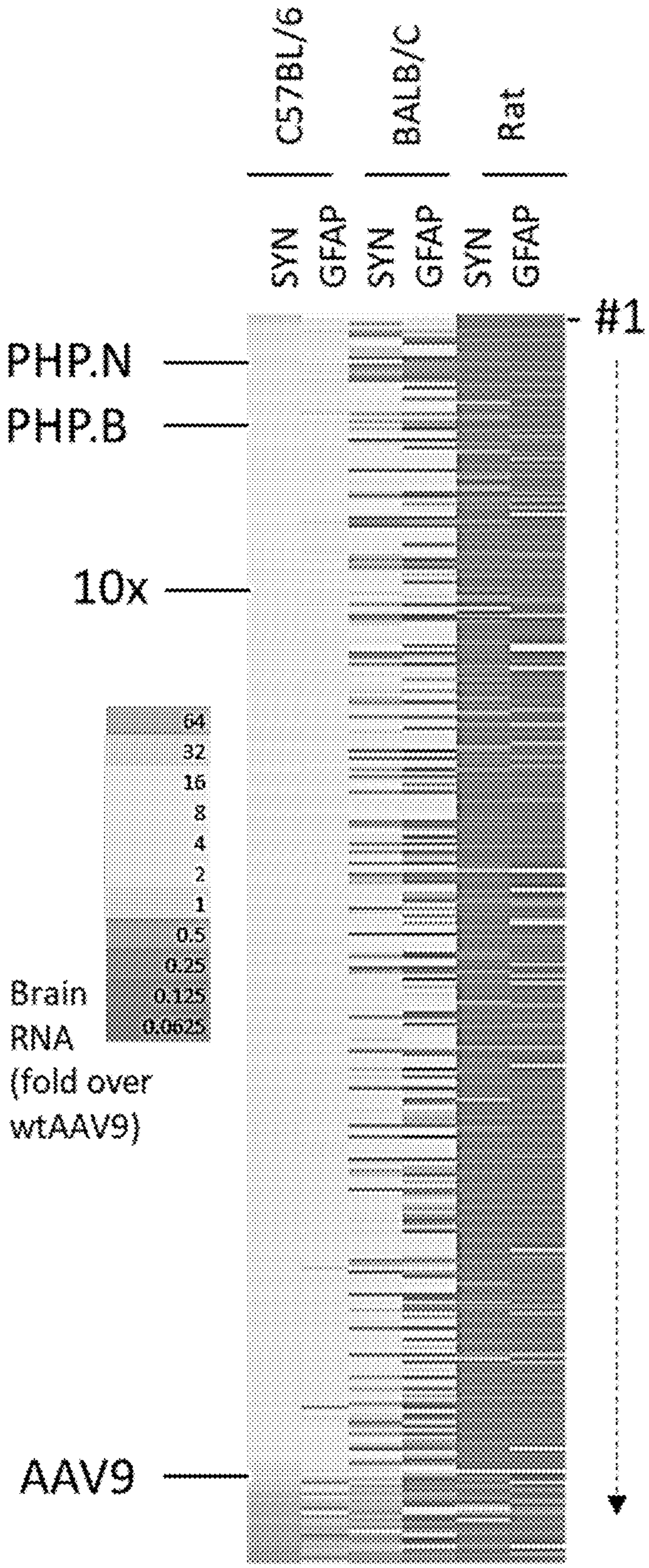
Figure 48C:
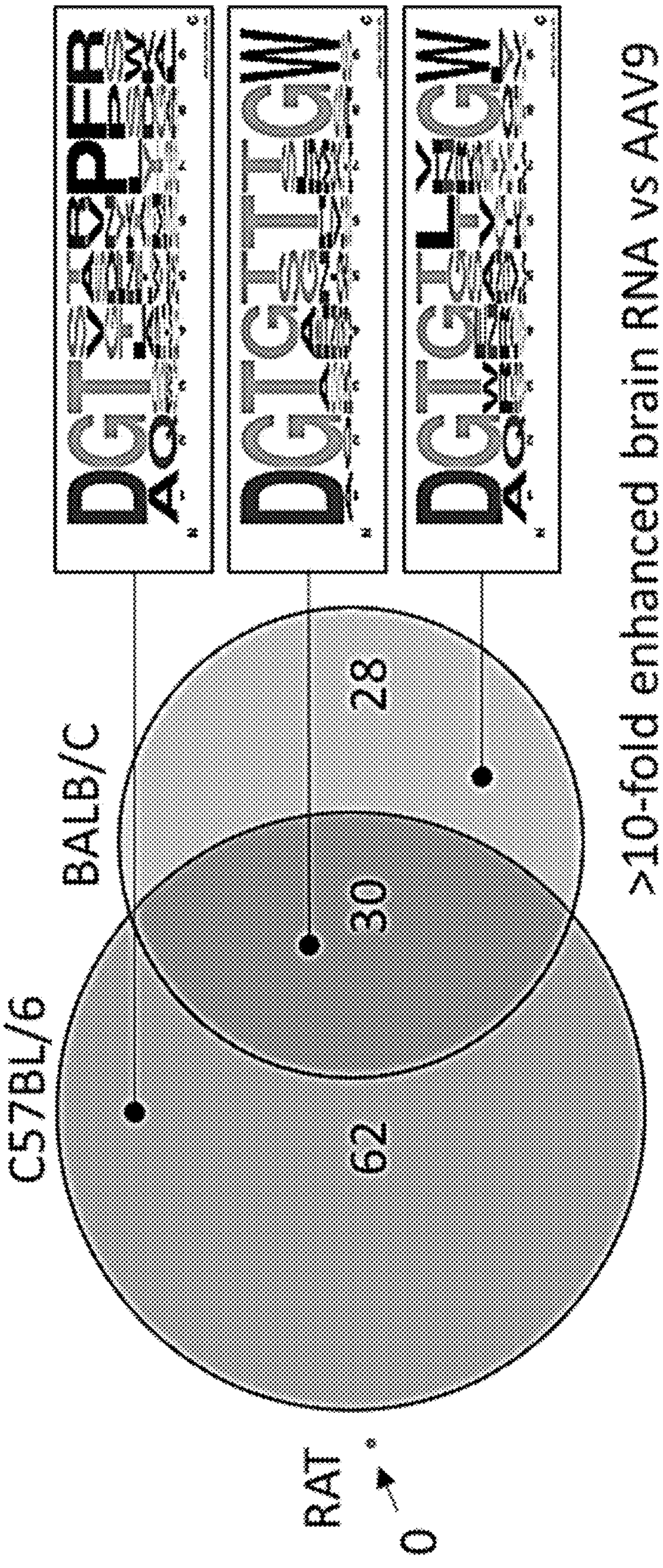

The efficacy of the 333 capsid variants to transduce CNS was tested in other rodent strains or species (FIG. 47). Side-by-side comparison of neuron and astrocyte transduction in C57BL/6 mice, BALB/C mice and rats showed major differences in the enrichment scores of multiple variants between the two mouse strains, and even more pronounced differences between mice and rats (FIG. 48A-FIG. 48C). Strikingly, the most efficient capsid for rat brain transduction was the parental AAV9, which suggests that directed evolution "bottlenecks" capsid variants that are highly performant in one given species, as opposed to the versatility of wild-type AAV capsids.

Correlation analysis showed that some capsids shared high CNS transduction between C57BL/6 and BALB/C mice, whereas others were restricted to only one strain (FIG. 48B).

Interestingly, the PHP.B and PHP.eB capsid showed poor brain transduction in BALB/C mice, in line with a recent publication (Hordeaux et al., 2018). When focusing on the capsids that showed >10-fold increase in brain transduction, 62 variants were improved only in C57BL/6 mice, 28 variants were improved only in BALB/C mice and 30 variants showed improved brain transduction in both strains (Table 11). Consensus sequence analysis showed a "C57BL/6 signature" closely resembling the PHP.eB peptide (DGTxxxPFR (SEQ ID NO: 1185)) whereas the BALB/C signature showed a different consensus (DGTxxxxGW (SEQ ID NO: 1183)), suggesting the use of a different cellular receptor (FIG. 48C).

TABLE 11

| TOP 30 candidates from C57BL/6 and BALB/C mouse screen | | | | | |
|---|---|---|---|---|---|
| SYNAPSIN PROMOTER | | | | | |
| C57BL/6 | | | | BALB/C | |
| REPLICATE 1 (N = 3) | | REPLICATE 2 (N = 6) | | REPLICATE 1 (N = 6) | |
| 9-mer peptide insert | Brain Enrichment Factor (fold over AAV9) | 9-mer peptide insert | Brain Enrichment Factor (fold over AAV9) | 9-mer peptide insert | Brain Enrichment Factor (fold over AAV9) |
| DGTSSYYDS (SEQ ID NO: 59) | 36.40 | AQWPTSYDA (SEQ ID NO: 62) | 39.97 | DGTGSTTGW (SEQ ID NO: 134) | 57.05 |
| AQPEGSARW (SEQ ID NO: 60) | 35.95 | AQPEGSARW (SEQ ID NO: 60) | 31.83 | DGTGQVTGW (SEQ ID NO: 68) | 49.87 |
| DGTASYYDS (SEQ ID NO: 61) | 32.34 | DGTGQVTGW (SEQ ID NO: 68) | 20.35 | DGTGSTHGW (SEQ ID NO: 119) | 43.08 |

TABLE 11-continued

| TOP 30 candidates from C57BL/6 and BALB/C mouse screen | | | | | |
|---|---|---|---|---|---|
| AQWPTSYDA (SEQ ID NO: 62) | 30.81 | DGTAIHLSS (SEQ ID NO: 67) | 19.55 | DGTGSTQGW (SEQ ID NO: 315) | 38.31 |
| DGTADKPFR (SEQ ID NO: 63) | 29.30 | DGTMDRPFK (SEQ ID NO: 102) | 19.48 | DGTGTTTGW (SEQ ID NO: 130) | 37.29 |
| DGSSSYYDA (SEQ ID NO: 64) | 28.05 | DGTGSTTGW (SEQ ID NO: 134) | 19.20 | AQWAAGYNV (SEQ ID NO: 245) | 34.57 |
| DGTLSQPFR (SEQ ID NO: 65) | 26.73 | DGSSSYYDA (SEQ ID NO: 64) | 18.08 | DGTGGTKGW (SEQ ID NO: 107) | 33.59 |
| DGTAIHLSS (SEQ ID NO: 67) | 26.23 | DGTSSYYDA (SEQ ID NO: 381) | 17.93 | DGTGSTKGW (SEQ ID NO: 313) | 29.64 |
| AQFPTNYDS (SEQ ID NO: 66) | 26.07 | DGSQSTTGW (SEQ ID NO: 136) | 17.59 | DGSQSTTGW (SEQ ID NO: 136) | 25.19 |
| DGTMDKPFR (SEQ ID NO: 70) | 25.05 | DGTGSTQGW (SEQ ID NO: 315) | 17.24 | AQWEVKGGY (SEQ ID NO: 247) | 23.44 |
| **DGTLAVPFK** (SEQ ID NO: 71) | 24.62 | DGTGTTTGW (SEQ ID NO: 130) | 17.00 | DGTAIHLSS (SEQ ID NO: 67) | 22.81 |
| DGTGNVTGW (SEQ ID NO: 69) | 24.05 | **DGTLAVPFK** (SEQ ID NO: 71) | 16.84 | DGGGTTTGW (SEQ ID NO: 270) | 22.62 |
| DGTGQVTGW (SEQ ID NO: 68) | 23.83 | DGTASYYDS (SEQ ID NO: 61) | 16.68 | DGTGGLTGW (SEQ ID NO: 294) | 22.42 |
| DGTHIHLSS (SEQ ID NO: 162) | 22.93 | DGTMDKPFR (SEQ ID NO: 70) | 16.68 | DGTNTINGW (SEQ ID NO: 124) | 20.76 |
| DGTGNTHGW (SEQ ID NO: 72) | 22.63 | DGTVANPFR (SEQ ID NO: 394) | 16.32 | DGAGGTSGW (SEQ ID NO: 151) | 19.55 |
| DGTVIHLSS (SEQ ID NO: 73) | 22.62 | DGTLNNPFR (SEQ ID NO: 109) | 16.24 | DGTNTTHGW (SEQ ID NO: 113) | 18.99 |
| DGTLNNPFR (SEQ ID NO: 109) | 22.33 | DGTLAAPFK (SEQ ID NO: 120) | 15.96 | DGTGTVQGW (SEQ ID NO: 327) | 18.84 |
| DGTGNTSGW (SEQ ID NO: 137) | 22.10 | DGTLSQPFR (SEQ ID NO: 65) | 15.43 | DGTGQTIGW (SEQ ID NO: 305) | 18.55 |
| DGTGTTVGW (SEQ ID NO: 74) | 21.72 | DGTHIHLSS (SEQ ID NO: 162) | 15.11 | AQWELSNGY (SEQ ID NO: 246) | 18.13 |
| DGTSSYYDA (SEQ ID NO: 381) | 20.94 | AQTTEKPWL (SEQ ID NO: 83) | 15.00 | DGTGSLNGW (SEQ ID NO: 309) | 17.93 |
| DGAGTTSGW (SEQ ID NO: 265) | 20.42 | DGTGNVTGW (SEQ ID NO: 69) | 14.90 | DGTGTTLGW (SEQ ID NO: 323) | 17.48 |
| DGGGTTTGW (SEQ ID NO: 270) | 20.27 | DGTGGVTGW (SEQ ID NO: 299) | 14.89 | AQPEGSARW (SEQ ID NO: 60) | 17.11 |

TABLE 11-continued

| TOP 30 candidates from C57BL/6 and BALB/C mouse screen | | | | | |
|---|---|---|---|---|---|
| DGTLQQPFR (SEQ ID NO: 89) | 19.88 | DGTSSYYDS (SEQ ID NO: 59) | 14.80 | DGTGSTMGW (SEQ ID NO: 314) | 16.91 |
| DGTGQTIGW (SEQ ID NO: 305) | 19.52 | DGTGNTSGW (SEQ ID NO: 137) | 14.48 | DGTGNTHGW (SEQ ID NO: 72) | 16.47 |
| DGTVTTTGW (SEQ ID NO: 405) | 19.49 | AQWPTAYDA (SEQ ID NO: 256) | 14.48 | DGSGTTRGW (SEQ ID NO: 114) | 15.83 |
| DGTSIHLSS (SEQ ID NO: 378) | 19.45 | AQGENPGRW (SEQ ID NO: 96) | 14.41 | DGTNSTTGW (SEQ ID NO: 143) | 15.48 |
| DGTGSTTGW (SEQ ID NO: 134) | 19.45 | DGTADKPFR (SEQ ID NO: 63) | 14.32 | DGRNALTGW (SEQ ID NO: 275) | 15.13 |
| DGTGGVTGW (SEQ ID NO: 299) | 19.44 | DGTGQTIGW (SEQ ID NO: 305) | 14.27 | DGAAATTGW (SEQ ID NO: 264) | 15.02 |
| DGTVANPFR (SEQ ID NO: 394) | 19.42 | DGTISQPFK (SEQ ID NO: 105) | 13.84 | DGTATTMGW (SEQ ID NO: 284) | 14.54 |
| DGTGTTTGW (SEQ ID NO: 130) | 19.16 | DGTKLMLSS (SEQ ID NO: 157) | 13.71 | AQRYTGDSS (SEQ ID NO: 138) | 14.35 |
| DGAGGTSGW (SEQ ID NO: 151) | 18.99 | **AQTLAVPFK** (SEQ ID NO: 168) | 13.69 | DGAGTTSGW (SEQ ID NO: 265) | 14.29 |

| GFAP PROMOTER | | | | | |
|---|---|---|---|---|---|
| C57BL/6 | | | | BALB/C | |
| REPLICATE 1 (N = 2) | | REPLICATE 2 (N = 6) | | REPLICATE 1 (N = 6) | |
| 9-mer peptide insert | Brain Enrichment Factor (fold over AAV9) | 9-mer peptide insert | Brain Enrichment Factor (fold over AAV9) | 9-mer peptide insert | Brain Enrichment Factor (fold over AAV9) |
| DGTADKPFR (SEQ ID NO: 63) | 37.60 | DGTMDRPFK (SEQ ID NO: 102) | 24.89 | DGTGSTTGW (SEQ ID NO: 134) | 21.03 |
| DGTLSQPFR (SEQ ID NO: 65) | 35.97 | DGTAERPFR (SEQ ID NO: 140) | 24.66 | DGTGQVTGW (SEQ ID NO: 68) | 19.24 |
| DGTTYVPPR (SEQ ID NO: 75) | 33.09 | DGTADKPFR (SEQ ID NO: 63) | 23.03 | DGTGTTTGW (SEQ ID NO: 130) | 15.56 |
| DGTNGLKGW (SEQ ID NO: 76) | 32.14 | DGTLNNPFR (SEQ ID NO: 109) | 22.91 | DGTGSTHGW (SEQ ID NO: 119) | 14.45 |
| AQGENPGRW (SEQ ID NO: 96) | 31.99 | DGTLSQPFR (SEQ ID NO: 65) | 21.60 | DGTAIHLSS (SEQ ID NO: 67) | 11.74 |
| AQGSWNPPA (SEQ ID NO: 80) | 30.78 | DGTMDKPFR (SEQ ID NO: 70) | 20.52 | DGTGSTQGW (SEQ ID NO: 315) | 11.40 |
| AQGTWNPPA (SEQ ID NO: 82) | 29.19 | DGTISQPFK (SEQ ID NO: 105) | 20.47 | DGTGGLTGW (SEQ ID NO: 294) | 8.87 |
| DGTISQPFK (SEQ ID NO: 105) | 29.01 | AQGENPGRW (SEQ ID NO: 96) | 20.09 | AQNGNPGRW (SEQ ID NO: 84) | 8.82 |

TABLE 11-continued

| TOP 30 candidates from C57BL/6 and BALB/C mouse screen | | | | | |
|---|---|---|---|---|---|
| DGTTFTPPR (SEQ ID NO: 79) | 28.94 | AQTTEKPWL (SEQ ID NO: 83) | 18.04 | DGTGGIKGW (SEQ ID NO: 131) | 8.62 |
| DGTRTTTGW (SEQ ID NO: 106) | 28.59 | DGTVANPFR (SEQ ID NO: 394) | 16.87 | DGRNALTGW (SEQ ID NO: 275) | 8.39 |
| DGTSYVPPR (SEQ ID NO: 78) | 26.17 | DGTTYVPPR (SEQ ID NO: 75) | 16.31 | DGTGSTKGW (SEQ ID NO: 313) | 8.38 |
| DGTIERPFR (SEQ ID NO: 87) | 25.37 | AQTTDRPFL (SEQ ID NO: 85) | 16.27 | AQRYTGDSS (SEQ ID NO: 138) | 8.13 |
| DGTMDRPFK (SEQ ID NO: 102) | 24.85 | DGTTTYGAR (SEQ ID NO: 77) | 15.62 | DGTGGTKGW (SEQ ID NO: 107) | 8.06 |
| DGTLAAPFK (SEQ ID NO: 120) | 24.67 | DGTADRPFR (SEQ ID NO: 155) | 15.60 | DGTATTTGW (SEQ ID NO: 285) | 8.04 |
| DGTLNNPFR (SEQ ID NO: 109) | 24.62 | DGTIERPFR (SEQ ID NO: 87) | 15.11 | DGTKMVLQL (SEQ ID NO: 142) | 7.87 |
| DGTSFTPPR (SEQ ID NO: 88) | 24.14 | AQGSWNPPA (SEQ ID NO: 80) | 15.11 | DGTGSLNGW (SEQ ID NO: 309) | 7.71 |
| AQTTDRPFL (SEQ ID NO: 85) | 23.85 | AQGTWNPPA (SEQ ID NO: 82) | 15.03 | DGTNTINGW (SEQ ID NO: 124) | 7.59 |
| DGTSFTPPK (SEQ ID NO: 81) | 23.75 | DGSTERPFR (SEQ ID NO: 99) | 15.01 | AQWELSNGY (SEQ ID NO: 246) | 7.57 |
| DGTHTRTGW (SEQ ID NO: 90) | 23.54 | AQSVAKPFL (SEQ ID NO: 231) | 14.90 | DGTNGLKGW (SEQ ID NO: 76) | 7.50 |
| DGTLQQPFR (SEQ ID NO: 89) | 22.94 | DGTVDRPFK (SEQ ID NO: 395) | 14.74 | DGTNTTHGW (SEQ ID NO: 113) | 7.25 |
| AQNGNPGRW (SEQ ID NO: 84) | 22.80 | DGTTFTPPR (SEQ ID NO: 79) | 14.56 | DGTRMVVQL (SEQ ID NO: 370) | 7.25 |
| DGTAERPFR (SEQ ID NO: 140) | 21.65 | AQTLARPFV (SEQ ID NO: 98) | 14.51 | DGTNSTTGW (SEQ ID NO: 143) | 6.41 |
| DGTGNTRGW (SEQ ID NO: 94) | 21.12 | DGTGGTKGW (SEQ ID NO: 107) | 14.13 | DGSQSTTGW (SEQ ID NO: 136) | 6.29 |
| AQTTEKPWL (SEQ ID NO: 83) | 20.58 | AQGPTRPFL (SEQ ID NO: 125) | 13.47 | AQPEGSARW (SEQ ID NO: 60) | 6.23 |
| DGTADRPFR (SEQ ID NO: 155) | 20.49 | DGTRTTTGW (SEQ ID NO: 106) | 13.39 | DGTGQTIGW (SEQ ID NO: 305) | 6.16 |
| DGTTWTPPR (SEQ ID NO: 139) | 20.44 | AQNGNPGRW (SEQ ID NO: 84) | 13.09 | DGTGGVTGW (SEQ ID NO: 299) | 6.07 |
| DGTTTYGAR (SEQ ID NO: 77) | 20.43 | DGTVSNPFR (SEQ ID NO: 403) | 12.77 | DGTVTTTGW (SEQ ID NO: 405) | 6.04 |

TABLE 11-continued

| TOP 30 candidates from C57BL/6 and BALB/C mouse screen | | | | | |
|---|---|---|---|---|---|
| DGTGGIKGW (SEQ ID NO: 131) | 20.20 | AQGGNPGRW (SEQ ID NO: 91) | 12.21 | DGKGSTQGW (SEQ ID NO: 272) | 5.97 |
| **DGTLAVPFK** (SEQ ID NO: 71) | 19.43 | AQWPTSYDA (SEQ ID NO: 62) | 11.93 | AQGENPGRW (SEQ ID NO: 96) | 5.88 |
| DGKQYQLSS (SEQ ID NO: 92) | 18.74 | DGTLQQPFR (SEQ ID NO: 89) | 11.92 | DGNGGLKGW (SEQ ID NO: 167) | 5.82 |
| DGSPEKPFR (SEQ ID NO: 160) | 18.73 | DGTNGLKGW (SEQ ID NO: 76) | 11.53 | DGTGTVHGW (SEQ ID NO: 326) | 5.82 |

Figure 58A:
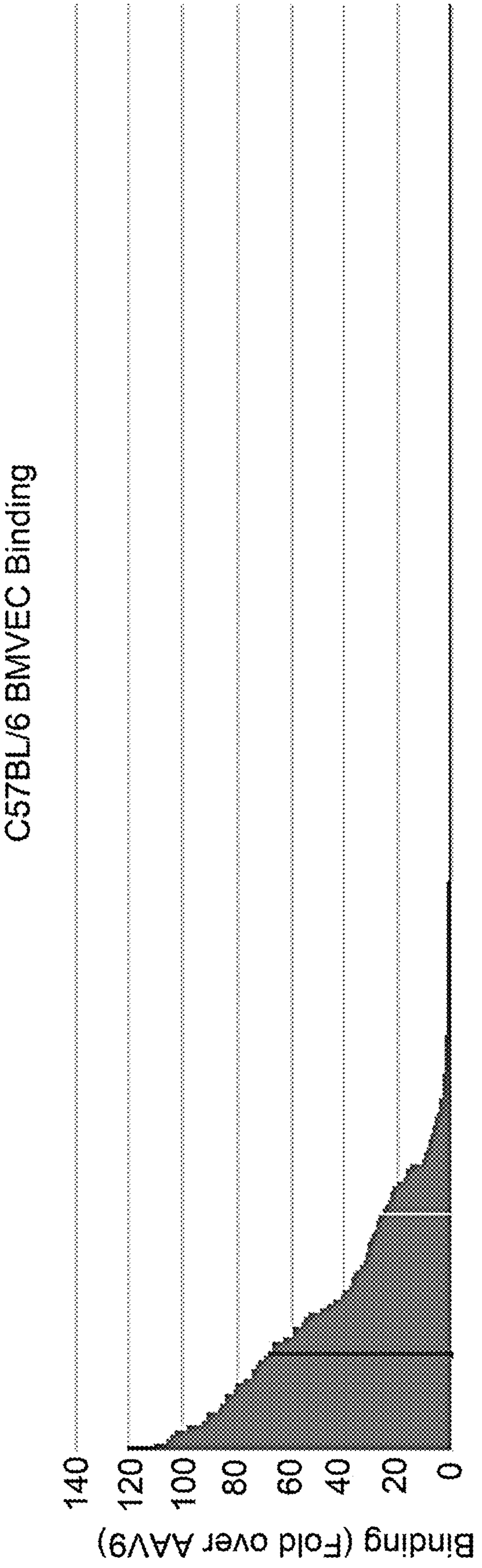
FIG. 58A and FIG. 58B provide results for comparison studies on the efficacy of the 333 capsid variants to transduce CNS for C57BL/6 mice BMVEC (FIG. 58A) and Human BMVEC (FIG. 58B).
Figure 58B:
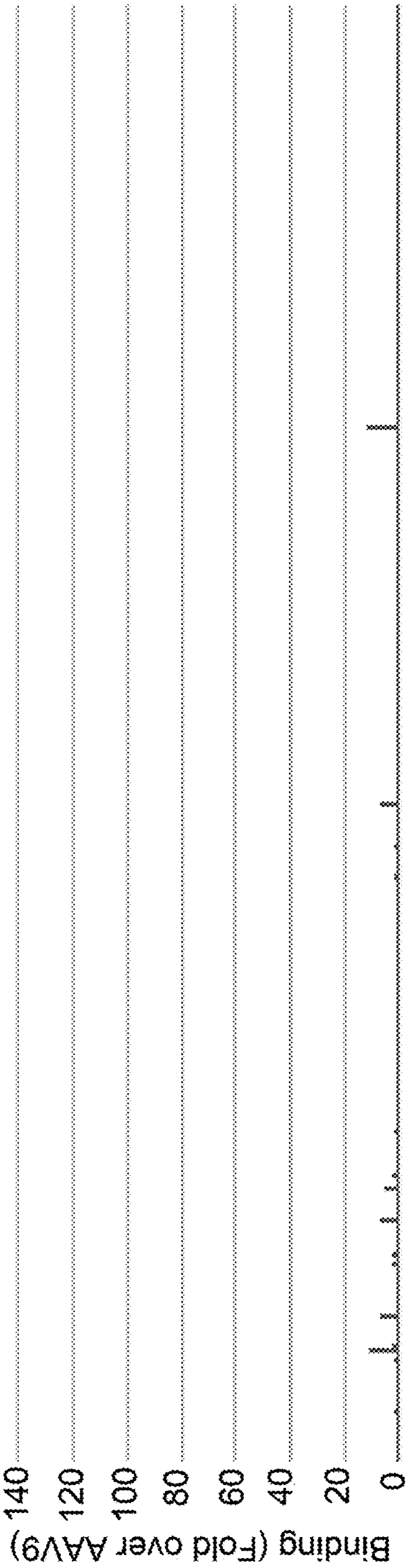

The efficacy of the 333 capsid variants to transduce CNS was also compared for C57BL/6 mice BMVEC and Human BMVEC (FIG. 58A and FIG. 58B).

Example 14. Engineering of a NGS-Driven Selection System for Full-Length Capsid Variants A barcode system was engineered to allow enrichment studies with full capsid length modifications. While the TRACER platform described here was initially developed for the use of peptide display libraries, where the randomized peptide sequence itself can be used for Illumina NGS analysis due to its short size, the Illumina sequencing technology does not typically allow sequencing of more than 300 contiguous bases, and therefore our platform cannot be used for NGS analysis of full-length capsid variants, such as those generated by DNA shuffling technology or error-prone PCR.

Figure 59A:
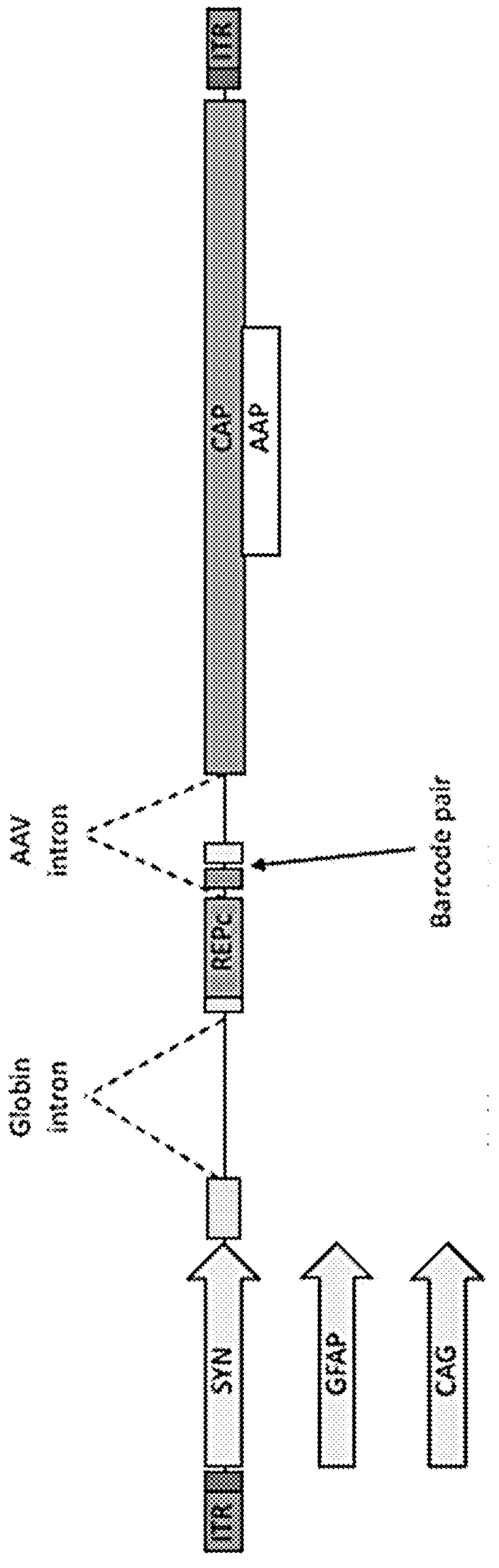
Figure 59B:
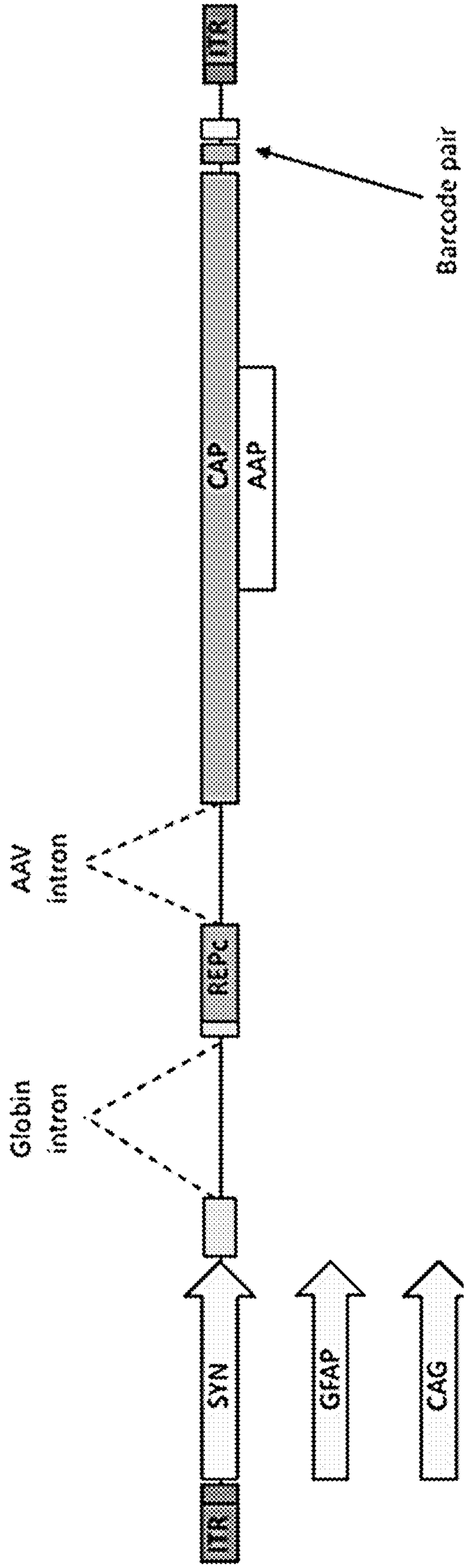
Figure 59C:
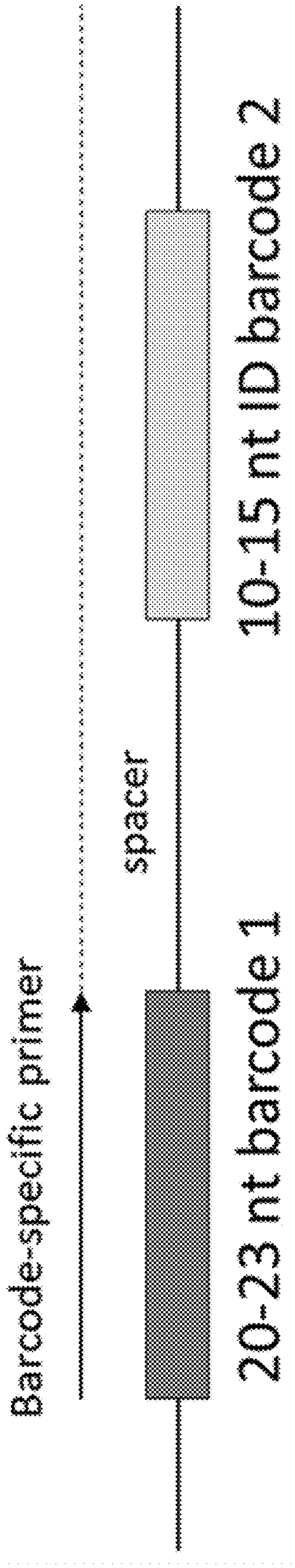

An alternative RNA-driven platform for full-length capsid libraries in which a unique molecular identified (UMI) is placed outside the capsid gene and can be used for NGS enrichment analysis was designed (FIG. 59A-FIG. 59C). Once the variants with desired properties are identified by UMI enrichment analysis from animal tissue, the UMI sequence must allow highly specific recovery of the full-length capsid from the starting material with a minimal error rate. The system should have one or more of the following properties to be effective: 1) the UMI should be transcribed under control of a cell type-specific promoter, 2) the UMI should not interfere with capsid expression or splicing during virus production, 3) the UMI should be short enough for Illumina NGS sequencing (typically less than 60 nt for standard single-end 75 nt sequencing), and 4) the UMI should allow sequence-specific recovery of full-length capsids of interest from the starting DNA/virus library with a minimal error rate.

To address these properties: 1) the UMI was placed in the transcribed region of capsid library (i.e., anywhere between the transcription start site and the polyadenylation signal), 2) the UMI was placed either in various locations of the AAV intron (which mostly unspliced in the absence of helper functions) or between the capsid stop codon and the polyadenylation signal, 3) the UMI cassette was composed of two randomized 21-nt sequences separated by a 15-nt spacer, for a total length of 57 nt, which allows 18 extra nucleotides for primer annealing, and 4) the UMI randomized sequences were formed of NSW triplets (N=A, T, G, C; S=G, C; W=A, T) to prevent large variations in annealing temperature with amplification primers, avoid homopolymeric stretches and prevent the formation of a premature polyA signal (AATAAA).

Importantly, the UMI cassette contained two random sequences in tandem. The first sequence (outermost) is used to design a matching capsid recovery primer, and the second sequence (innermost) to confirm the identity of the capsid amplicon after cloning. This method should allow to eliminate all clones containing non-specific amplification products. In an alternative embodiment, the innermost sequence can also be used to design a nested PCR primer in order to increase the specificity of amplification (FIG. 59A-FIG. 59C).

Figure 60A:
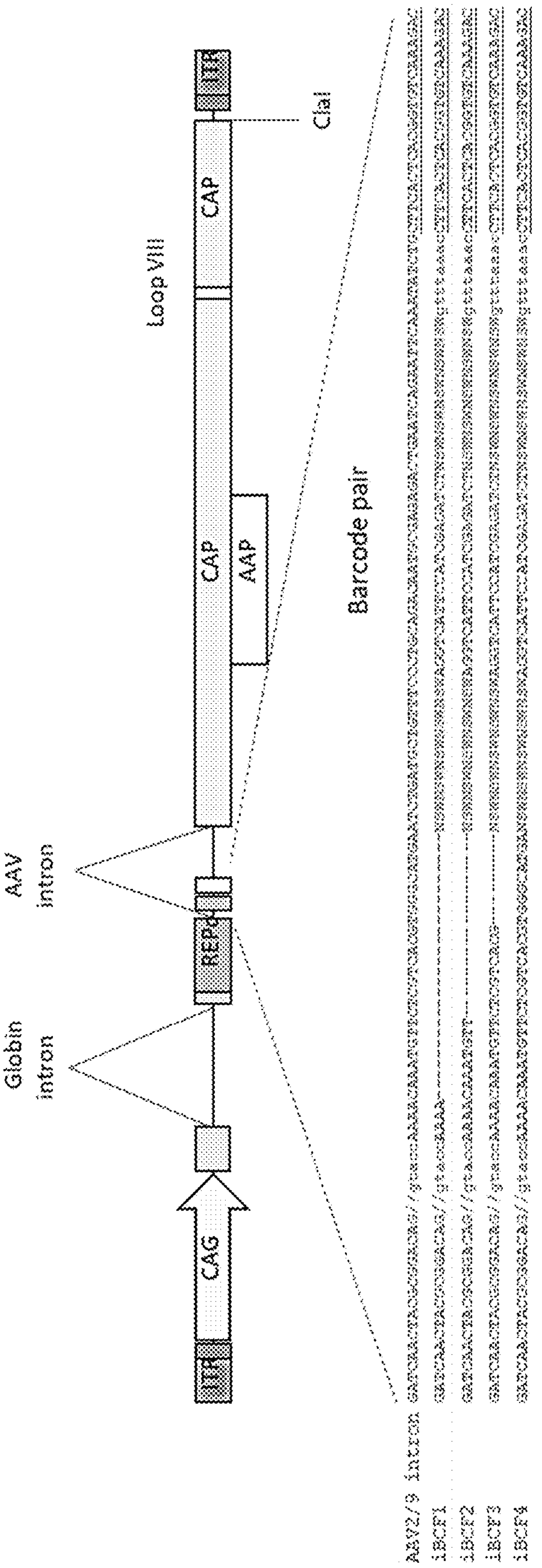
FIG. 60A, FIG. 60B and FIG. 60C provide detailed analysis of virus production and RNA splicing with several configurations of intronic barcoded platforms. A general ITR-to-ITR construct is shown in FIG. 60A (SEQ ID NOS 189-193, respectively, in order of appearance), with intronic barcode yields (FIG. 60B) and gel columns showing AAV intron splicing and Globin intron splicing results (FIG. 60C).
Figure 60B:
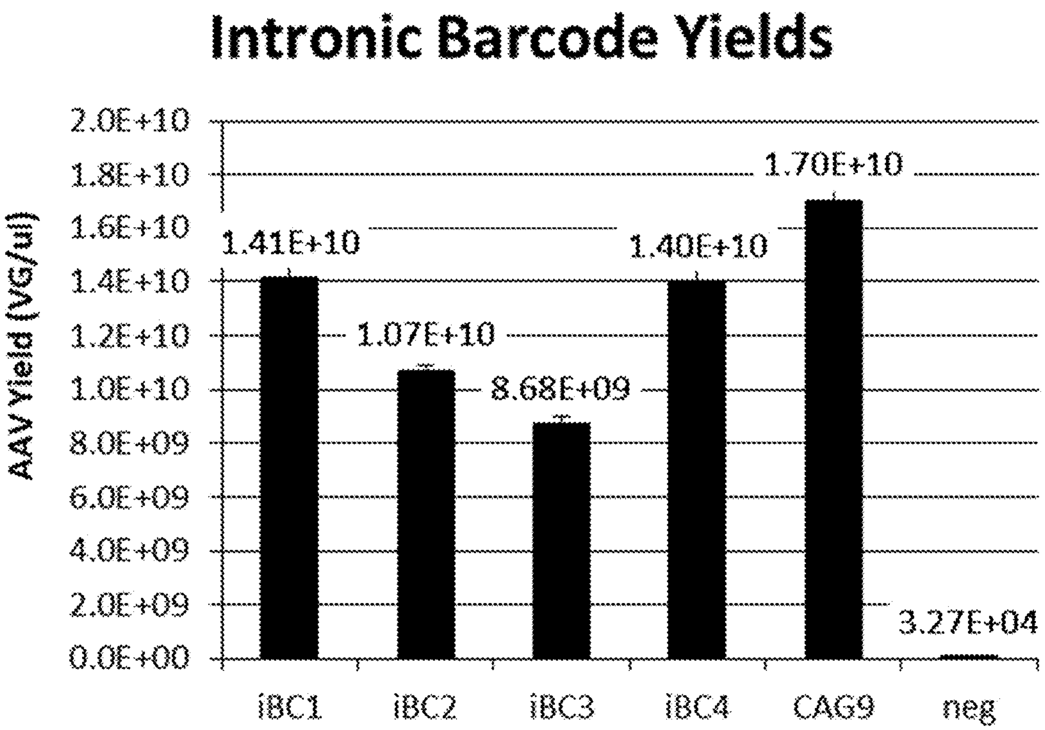

Several insertion sites of the tandem barcode to test the impact on virus viability and titers were explored. A series of constructs were engineered with the barcode inserted in the AAV intron of the CAG9 plasmid (FIG. 60A). Since AAV intron is spliced during virus production, the presence of the barcode should have only a minimal impact on the yields. Conversely, the AAV splicing is very ineffective in the absence of helper functions (Mouw et al., 2000), therefore the barcode sequence will be preserved in the RNA recovered from animal tissue. All intronic barcode constructs were tested for their ability to produce high titer AAV progeny by cotransfecting them with pHelper and pREP3 stop plasmids. All constructs allowed high titer AAV production going from 50% to 80% of non-barcoded CAG9 virus (FIG. 60B).

RNA splicing analysis from transfected cells showed that the rate of AAV intron splicing was slightly different between constructs and was more efficient when the intronic barcode was inserted after a conserved intervening sequence downstream of the splice donor (FIG. 58C, upper panel).

Figure 60C:
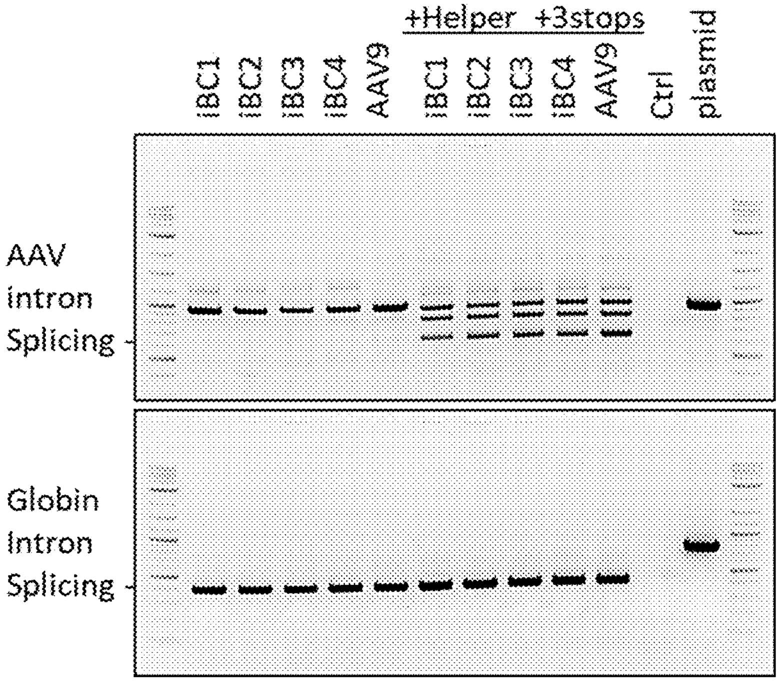

Globin intron splicing was 100% effective in all tested conditions (FIG. 60C, lower panel). As expected, AAV intron splicing was almost undetectable in the absence of helper functions.

An alternative platform was tested where the tandem barcode was placed between the capsid stop codon and the polyadenylation signal (FIG. 59B). Titers produced by the 3'-barcoded constructs were identical to the non-barcoded CAG9 construct.

Overall, external barcoding of full-length capsid allows highly efficient AAV production, and the novel tandem barcode platform allows NGS-driven sequence-specific recovery from library preparations with high confidence.

TABLE 12

| Sequences | |
|---|---|
| DESCRIPTION SEQ ID NO: | NUCLEIC ACID SEQUENCE |
| PREP2 SEQ ID NO: 4 | CGCAGGGTCTCCATTTTGAAGCGGGAGGTTTGAACGCGCAGCCGCCATGCCGGGGTTTTA<br>CGAGATTGTGATTAAGGTCCCCAGCGACCTTGACGAGCATCTGCCCGGCATTTCTGACAG<br>CTTTGTGAACTGGGTGGCCGAGAAGGAATGGGAGTTGCCGCCAGATTCTGACATGGATCT<br>GAATCTGATTGAGCAGGCACCCCTGACCGTGGCCGAGAAGCTGCAGCGCGACTTTCTGAC<br>GGAATGGCGCCGTGTGAGTAAGGCCCCGGAGGCTCTTTTCTTTGTGCAATTTGAGAAGGG<br>AGAGAGCTACTTCCACATGCACGTGCTCGTGGAAACCACCGGGGTGAAATCCATGGTTTT<br>GGGACGTTTCCTGAGTCAGATTCGCGAAAAACTGATTCAGAGAATTTACCGCGGGATCGA<br>GCCGACTTTGCCAAACTGGTTCGCGGTCACAAAGACCAGAAATGGCGCCGGAGGCGGGA<br>ACAAGGTGGTGGATGAGTGCTACATCCCCAATTACTTGCTCCCCAAAACCCAGCCTGAGC<br>TCCAGTGGGCGTGGACTAATATGGAACAGTATTTAAGCGCCTGTTTGAATCTCACGGAGC<br>GTAAACGGTTGGTGGCGCAGCATCTGACGCACGTGTCGCAGACGCAGGAGCAGAACAAA<br>GAGAATCAGAATCCCAATTCTGATGCGCCGGTGATCAGATCAAAAACTTCAGCCAGGTAC<br>ATGGAGCTGGTCGGGTGGCTCGTGGACAAGGGGATTACCTCGGAGAAGCAGTGGATCCA<br>GGAGGACCAGGCCTCATACATCTCCTTCAATGCGGCCTCCAACTCGCGGTCCCAAATCAA<br>GGCTGCCTTGGACAATGCGGGAAAGATTATGAGCCTGACTAAAACCGCCCCCGACTACCT<br>GGTGGGCCAGCAGCCCGTGGAGGACATTTCCAGCAATCGGATTTATAAAATTTTGGAACT<br>AAACGGGTACGATCCCCAATATGCGGCTTCCGTCTTTCTGGGATGGGCCACGAAAAAGTT<br>CGGCAAGAGGAACACCATCTGGCTGTTTGGGCCTGCAACTACCGGGAAGACCAACATCG<br>CGGAGGCCATAGCCCACACTGTGCCCTTCTACGGGTGCGTAAACTGGACCAATGAGAACT<br>TTCCCTTCAACGACTGTGTCGACAAGATGGTGATCTGGTGGGAGGAGGGGAAGATGACC<br>GCCAAGGTCGTGGAGTCGGCCAAAGCCATTCTCGGAGGAAGCAAGGTGCGCGTGGACCA<br>GAAATGCAAGTCCTCGGCCCAGATAGACCCGACTCCCGTGATCGTCACCTCCAACACCAA<br>CATGTGCGCCGTGATTGACGGGAACTCAACGACCTTCGAACACCAGCAGCCGTTGCAAGA<br>CCGGATGTTCAAATTTGAACTCACCCGCCGTCTGGATCATGACTTTGGGAAGGTCACCAA<br>GCAGGAAGTCAAAGACTTTTTCCGGTGGGCAAAGGATCACGTGGTTGAGGTGGAGCATG<br>AATTCTACGTCAAAAAGGGTGGAGCCAAGAAAAGACCCGCCCCCAGTGACGCAGATATA<br>AGTGAGCCCAAACGGGTGCGCGAGTCAGTTGCGCAGCCATCGACGTCAGACGCGGAAGC<br>TTCGATCAACTACGCAGACAGGTACCAAAACAAATGTTCTCGTCACGTGGGCATGAATCT<br>GATGCTGTTTCCCTGCAGACAATGCGAGAGAATGAATCAGAATTCAAATATCTGCTTCAC<br>TCACGGACAGAAAGACTGTTTAGAGTGCTTTCCCGTGTCAGAATCTCAACCCGTTTCTGTC<br>GTCAAAAAGGCGTATCAGAAACTGTGCTACATTCATCATATCATGGGAAAGGTGCCAGAC<br>GCTTGCACTGCCTGCGATCTGGTCAATGTGGATTTGGATGACTGCATCTTTGAACAATAA<br>ATGATTTAAATCAGGTATGGCTGCCGATGGTTATCTTCCAGATTGGCTCGAGGACACTCTC<br>TCTGAAGGAATAAGACAGTGGTGGAAGCTCAAACCTGGCCCACCACCACCAAAGCCCGC<br>AGAGCGGCATAAGGACGACAGCAGGGGTCTTGTGCTTCCTGGGTACAAGTACCTCGGAC<br>CCTTCAACGGACTCGACAAGGGAGAGCCGGTCAACGAGGCAGACGCCGCGGCCCTCGAG<br>CACGACAAAGCCTACGACCGGCAGCTCGACAGCGGAGACAACCCGTACCTCAAGTACAA<br>CCACGCCGACGCGGAGTTTCAGGAGCGCCTTAAAGAAGATACGTCTTTTGGGGGCAACCT<br>CGGACGAGCAGTCTTCCAGGCGAAAAAGAGGGTTCTTGAACCTCTGGGCCTGGTCCACCA<br>TACCTTCGATTATCCGATTTGCTTGTTAATCAATAAACCGTTTAATTCGTTTCAGTTGAACT<br>TTGGTCTCTGCGTATTTCTTTCTTATCTAGTTTCCATGCTCTAGAGCGGCCGCCACCGCGGT<br>GGAGCTCCAGCTTTTGT |
| CMV9-BSTEII SEQ ID NO: 5 | TTGGCCACTCCCTCTCTGCGCGCTCGCTCGCTCACTGAGGCCGGGCGACCAAAGGTCGCC<br>CGACGCCCGGGCTTTGCCCGGGCGGCCTCAGTGAGCGAGCGAGCGCGCAGAGAGGGAGT<br>GGCCAACTCCATCACTAGGGGTTCCTGGAGGGGTGGAGTCGTGACGATATCGTTTAAACC<br>GCGTCGTTACATAACTTACGGTAAATGGCCCGCCTGGCTGACCGCCCAACGACCCCCGCC<br>CATTGACGTCAATAATGACGTATGTTCCCATAGTAACGCCAATAGGGACTTTCCATTGAC<br>GTCAATGGGTGGAGTATTTACGGTAAACTGCCCACTTGGCAGTACATCAAGTGTATCATA<br>TGCCAAGTACGCCCCCTATTGACGTCAATGACGGTAAATGGCCCGCCTGGCATTATGCCC<br>AGTACATGACCTTATGGGACTTTCCTACTTGGCAGTACATCTACGTATTAGTCATCGCTAT<br>TACCATGGTGATGCGGTTTTGGCAGTACATCAATGGGCGTGGATAGCGGTTTGACTCACG<br>GGGATTTCCAAGTCTCCACCCCATTGACGTCAATGGGAGTTTGTTTTGGCACCAAAATCA<br>ACGGGACTTTCCAAAATGTCGTAACAACTCCGCCCCATTGACGCAAATGGGCGGTAGGCG<br>TGTACGGTGGGAGGTCTATATAAGCAGAGCTCGGGAGCGGTCACCAAGCAGGAAGTCAA<br>AGACTTTTTCCGGTGGGCAAAGGATCACGTGGTTGAGGTGGAGCATGAATTCTACGTCAA<br>AAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTAC<br>GCGGACAGGTACCAAAACAAATGTTCTCGTCACGTGGGCATGAATCTGATGCTGTTTCCC<br>TGCAGACAATGCGAGAGACTGAATCAGAATTCAAATATCTGCTTCACTCACGGTGTCAAA<br>GACTGTTTAGAGTGCTTTCCCGTGTCAGAATCTCAACCCGTTTCTGTCGTCAAAAAGGCGT<br>ATCAGAAACTGTGCTACATTCATCACATCATGGGAAAGGTGCCAGACGCTTGCACTGCTT<br>GCGACCTGGTCAATGTGGACTTGGATGACTGTGTTTCTGAACAATAAATGACTTAAACCA<br>GGTATGGCTGCCGATGGTTATCTTCCAGATTGGCTCGAGGACAACCTTAGTGAAGGAATT<br>CGCGAGTGGTGGGCTTTGAAACCTGGAGCCCCTCAACCCAAGGCAAATCAACAACATCA<br>AGACAACGCTCGAGGTCTTGTGCTTCCGGGTTACAAATACCTTGGACCCGGCAACGGACT<br>CGACAAGGGGGAGCCGGTCAACGCAGCAGACGCGGCGGCCCTCGAGCACGACAAGGCCT<br>ACGACCAGCAGCTCAAGGCCGGAGACAACCCGTACCTCAAGTACAACCACGCCGACGCC<br>GAGTTCCAGGAGCGGCTCAAAGAAGATACGTCTTTTGGGGGCAACCTCGGGCGAGCAGT<br>CTTCCAGGCCAAAAAGAGGCTTCTTGAACCTCTTGGTCTGGTTGAGGAAGCGGCTAAGAC<br>GGCTCCTGGAAAGAAGAGGCCTGTAGAGCAGTCTCCTCAGGAACCGGACTCCTCCGCGG<br>GTATTGGCAAATCGGGTGCACAGCCCGCTAAAAAGAGACTCAATTTCGGTCAGACTGGCG<br>ACACAGAGTCAGTCCCAGACCCTCAACCAATCGGAGAACCTCCCGCAGCCCCCTCAGGTG<br>TGGGATCTCTTACAATGGCTTCAGGTGGTGGCGCACCAGTGGCAGACAATAACGAAGGTG<br>CCGATGGAGTGGGTAGTTCCTCGGGAAATTGGCATTGCGATTCCCAATGGCTGGGGGACA |

TABLE 12-continued

Sequences

| DESCRIPTION SEQ ID NO: | NUCLEIC ACID SEQUENCE |
|---|---|
| | GAGTCATCACCACCAGCACCCGAACCTGGGCCCTGCCCACCTACAACAATCACCTCTACA |
| | AGCAAATCTCCAACAGCACATCTGGAGGATCTTCAAATGACAACGCCTACTTCGGCTACA |
| | GCACCCCCTGGGGGTATTTTGACTTCAACAGATTCCACTGCCACTTCTCACCACGTGACTG |
| | GCAGCGACTCATCAACAACAACTGGGGATTCCGGCCTAAGCGACTCAACTTCAAGCTCTT |
| | CAACATTCAGGTCAAAGAGGTTACGGACAACAATGGAGTCAAGACCATCGCCAATAACC |
| | TTACCAGCACGGTCCAGGTCTTCACGGACTCAGACTATCAGCTCCCGTACGTGCTCGGGT |
| | CGGCTCACGAGGGCTGCCTCCCGCCGTTCCCAGCGGACGTTTTCATGATTCCTCAGTACG |
| | GGTATCTGACGCTTAATGATGGAAGCCAGGCCGTGGGTCGTTCGTCCTTTTACTGCCTGG |
| | AATATTTCCCGTCGCAAATGCTAAGAACGGGTAACAACTTCCAGTTCAGCTACGAGTTTG |
| | AGAACGTACCTTTCCATAGCAGCTACGCTCACAGCCAAAGCCTGGACCGACTAATGAATC |
| | CACTCATCGACCAATACTTGTACTATCTCTCAAAGACTATTAACGGTTCTGGACAGAATC |
| | AACAAACGCTAAAATTCAGTGTGGCCGGACCCAGCAACATGGCTGTCCAGGGAAGAAAC |
| | TACATACCTGGACCCAGCTACCGACAACAACGTGTCTCAACCACTGTGACTCAAAACAAC |
| | AACAGCGAATTTGCTTGGCCTGGAGCTTCTTCTTGGGCTCTCAATGGACGTAATAGCTTGA |
| | TGAATCCTGGACCTGCTATGGCCAGCCACAAAGAAGGAGAGGACCGTTTCTTTCCTTTGT |
| | CTGGATCTTTAATTTTTGGCAAACAAGGAACTGGAAGAGACAACGTGGATGCGGACAAA |
| | GTCATGATAACCAACGAAGAAGAAATTAAAACTACTAACCCGGTAGCAACGGAGTCCTA |
| | TGGACAAGTGGCCACAAACCACCAGAGTGCCCAAGCACAGGCGCAGACCGGCTGGGTTC |
| | AAAACCAAGGAATACTTCCGGGTATGGTTTGGCAGGACAGAGATGTGTACCTGCAAGGA |
| | CCCATTTGGGCCAAAATTCCTCACACGGACGGCAACTTTCACCCTTCTCCGCTGATGGGA |
| | GGGTTTGGAATGAAGCACCCGCCTCCTCAGATCCTCATCAAAAACACACCTGTACCTGCG |
| | GATCCTCCAACGGCCTTCAACAAGGACAAGCTGAACTCTTTCATCACCCAGTATTCTACT |
| | GGCCAAGTCAGCGTGGAGATCGAGTGGGAGCTGCAGAAGGAAAACAGCAAGCGCTGGA |
| | ACCCGGAGATCCAGTACACTTCCAACTATTACAAGTCTAATAATGTTGAATTTGCTGTTAA |
| | TACTGAAGGTGTATATAGTGAACCCCGCCCCATTGGCACCAGATACCTGACTCGTAATCT |
| | GTAATCGATTGTTAATCAATAAACCGTTTAATTCGTTTCAGTTGAACTTTGGTCTCTGCGT |
| | ATTTCTTTCTTATCTAGTTTCCATGGCTACGTAGATAAGTAGCATGGCGGGTTAATCATTA |
| | ACTACAAGGAACCCCTAGTGATGGAGTTGGCCACTCCCTCTCTGCGCGCTCGCTCGCTCA |
| | CTGAGGCCGGGCGACCAAAGGTCGCCCGACGCCCGGGCTTTGCCCGGGCGGCCTCAGTG |
| | AGCGAGCGAGCGCGCAGAGAGGGAGTGGCCAA |
| PREP-AAP | GTCGACGGTATCGGGGGAGCTCGCAGGGTCTCCATTTTGAAGCGGGAGGTTTGAACGCGCAGC |
| SEQ ID NO: 6 | CGCCATGCCGGGGTTTTACGAGATTGTGATTAAGGTCCCCAGCGACCTTGACGAGCATCTGCCC |
| | GGCATTTCTGACAGCTTTGTGAACTGGGTGGCCGAGAAGGAATGGGAGTTGCCGCCAGATTCT |
| | GACATGGATCTGAATCTGATTGAGCAGGCACCCCTGACCGTGGCCGAGAAGCTGCAGCGCGAC |
| | TTTCTGACGGAATGGCGCCGTGTGAGTAAGGCCCCGGAGGCTCTTTTCTTTGTGCAATTTGAGA |
| | AGGGAGAGAGCTACTTCCACATGCACGTGCTCGTGGAAACCACCGGGGTGAAATCCATGGTTT |
| | TGGGACGTTTCCTGAGTCAGATTCGCGAAAAACTGATTCAGAGAATTTACCGCGGGATCGAGC |
| | CGACTTTGCCAAACTGGTTCGCGGTCACAAAGACCAGAAATGGCGCCGGAGGCGGGAACAAG |
| | GTGGTGGATGAGTGCTACATCCCCAATTACTTGCTCCCCAAAACCCAGCCTGAGCTCCAGTGGG |
| | CGTGGACTAATATGGAACAGTATTTAAGCGCCTGTTTGAATCTCACGGAGCGTAAACGGTTGGT |
| | GGCGCAGCATCTGACGCACGTGTCGCAGACGCAGGAGCAGAACAAAGAGAATCAGAATCCCA |
| | ATTCTGATGCGCCGGTGATCAGATCAAAAACTTCAGCCAGGTACATGGAGCTGGTCGGGTGGC |
| | TCGTGGACAAGGGGATTACCTCGGAGAAGCAGTGGATCCAGGAGGACCAGGCCTCATACATCT |
| | CCTTCAATGCGGCCTCCAACTCGCGGTCCCAAATCAAGGCTGCCTTGGACAATGCGGGAAAGA |
| | TTATGAGCCTGACTAAAACCGCCCCCGACTACCTGGTGGGCCAGCAGCCCGTGGAGGACATTT |
| | CCAGCAATCGGATTTATAAAATTTTGGAACTAAACGGGTACGATCCCCAATATGCGGCTTCCGT |
| | CTTTCTGGGATGGGCCACGAAAAAGTTCGGCAAGAGGAACACCATCTGGCTGTTTGGGCCTGC |
| | AACTACCGGGAAGACCAACATCGCGGAGGCCATAGCCCACACTGTGCCCTTCTACGGGTGCGT |
| | AAACTGGACCAATGAGAACTTTCCCTTCAACGACTGTGTCGACAAGATGGTGATCTGGTGGGA |
| | GGAGGGGAAGATGACCGCCAAGGTCGTGGAGTCGGCCAAAGCCATTCTCGGAGGAAGCAAGG |
| | TGCGCGTGGACCAGAAATGCAAGTCCTCGGCCCAGATAGACCCGACTCCCGTGATCGTCACCT |
| | CCAACACCAACATGTGCGCCGTGATTGACGGGAACTCAACGACCTTCGAACACCAGCAGCCGT |
| | TGCAAGACCGGATGTTCAAATTTGAACTCACCCGCCGTCTGGATCATGACTTTGGGAAGGTCAC |
| | CAAGCAGGAAGTCAAAGACTTTTTCCGGTGGGCAAAGGATCACGTGGTTGAGGTGGAGCATGA |
| | ATTCTACGTCAAAAAGGGTGGAGCCAAGAAAAGACCCGCCCCCAGTGACGCAGATATAAGTGA |
| | GCCCAAACGGGTGCGCGAGTCAGTTGCGCAGCCATCGACGTCAGACGCGGAAGCTTCGATCAA |
| | CTACGCGGACAGGTACCAAAACAAATGTTCTCGTCACGTGGGCATGAATCTGATGCTGTTTCCC |
| | TGCAGACAATGCGAGAGACTGAATCAGAATTCAAATATCTGCTTCACTCACGGTGTCAAAGAC |
| | TGTTTAGAGTGCTTTCCCGTGTCAGAATCTCAACCCGTTTCTGTCGTCAAAAAGGCGTATCAGA |
| | AACTGTGCTACATTCATCACATCATGGGAAAGGTGCCAGACGCTTGCACTGCTTGCGACCTGGT |
| | CAATGTGGACTTGGATGACTGTGTTTCTGAACAATAAATGACTTAAACCAGGTATGGCTGCCGA |
| | TGGTTATCTTCCAGATTGGCTCGAGGACAACCTTAGTGAAGGAATTCGCGAGTGGTGGGCTTTG |
| | AAACCTGGAGCCCCTCAACCCAAGGCAAATCAACAACATCAAGACAACGCTCGAGGTCTTGTG |
| | CTTCCGGGTTACAAATACCTTGGACCCGGCAACGGACTCGACAAGGGGGAGCCGGTCAACGCA |
| | GCAGACGCGGCGGCCCTCGAGCACGACAAGGCCTACGACCAGCAGCTCAAGGCCGGAGACAA |
| | CCCGTACCTCAAGTACAACCACGCCGACGCCGAGTTCCAGGAGCGGCTCAAAGAAGATACGTC |
| | TTTTGGGGGCAACCTCGGGCGAGCAGTCTTCCAGGCCAAAAAGAGGCTTCTTGAACCTCTTGGT |
| | CTGGTTGAGGAAGCGGCTAAGACGGCTCCTGGAAAGAAGAGGCCTGTAGAGCAGTCTCCTCAG |
| | GAACCGGACTCCTCCGCGGGTATTGGCAAATCGGGTGCACAGCCCGCTAAAAAGAGACTCAAT |
| | TTCGGTCAGACTGGCGACACAGAGTCAGTCCCAGACCCTCAACCAATCGGAGAACCTCCCGCA |
| | GCCCCCTCAGGTGTGGGATCTCTTACAATGGCTTCAGGTGGTGGCGCACCAGTGGCAGACAAT |
| | AACGAAGGTGCCGATGGAGTGGGTAGTTCCTCGGGAAATTGGCATTGCGATTCCCAATGGCTG |
| | GGGGACAGAGTCATCACCACCAGCACCCGAACCTGGGCCCTGCCCACCTACAACAATCACCTC |
| | TACAAGCAAATCTCCAACAGCACATCTGGAGGATCTTCAAATGACAACGCCTACTTCGGCTAC |

TABLE 12-continued

Sequences

| DESCRIPTION SEQ ID NO: | NUCLEIC ACID SEQUENCE |
|---|---|
| | AGCACCCCCTGGGGGTATTTTGACTTCAACAGATTCCACTGCCACTTCTCACCACGTGACTGGC |
| | AGCGACTCATCAACAACAACTGGGGATTCCGGCCTAAGCGACTCAACTTCAAGCTCTTCAACAT |
| | TCAGGTCAAAGAGGTTACGGACAACAATGGAGTCAAGACCATCGCCAATAACCTTACCAGCAC |
| | GGTCCAGGTCTTCACGGACTCAGACTATCAGCTCCCGTACGTGCTCGGGTCGGCTCACGAGGGC |
| | TGCCTCCCGCCGTTCCCAGCGGACGTTTTCATGATTCCTCAGTACGGGTATCTGACGCTTAATG |
| | ATGGAAGCCAGGCCGTGGGTCGTTCGTCCTTTTACTGCCTGGAATATTTCCCGTCGCAAATGCT |
| | AAGAACGGGTAACAACTTCCAGTTCAGCTACGAGTTTGAGAACGTACCTTTCCATAGCAGCTAC |
| | GCTCACAGCCAAAGCCTGGACCGACTAATGAATCCACTCATCGACCAATACTTGTACTATCTCT |
| | CAAAGACTATTAACGGTTCTGGACAGAATCAACAAACGCTAAAATTCAGTGTGGCCGGACCCA |
| | GCAACATGGCTGTCCAGGGAAGAAACTACATACCTGGACCCAGCTACCGACAACAACGTGTCT |
| | CAACCACTGTGACTCAAAACAACAACAGCGAATTTGCTTGGCCTGGAGCTTCTTCTTGGGCTCT |
| | CAATGGACGTAATAGCTTGATGAATCCTGGACCTGCTATGGCCAAGTCAGCGTGGAGATCGAG |
| | TGGGAGCTGCAGAAGGAAAACAGCAAGCGCTGGAACCCGGAGATCCAGTACACTTCCAACTAT |
| | TACAAGTCTAATAATGTTGAATTTGCTGTTAATACTGAAGGTGTATATAGTGAACCCCGCCCCA |
| | TTGGCACCAGATACCTGACTCGTAATCTGTAATTGCTTGTTAATCAATAAACCGTTTAATTCGTT |
| | TCAGTTGAACTTTGGTCTC |
| PREP3 STOP | GTCGACGGTATCGGGGGAGCTCGCAGGGTCTCCATTTTGAAGCGGGAGGTTTGAACGCGCAGC |
| SEQ ID NO: 7 | CGCCATGCCGGGGTTTTACGAGATTGTGATTAAGGTCCCCAGCGACCTTGACGAGCATCTGCCC |
| | GGCATTTCTGACAGCTTTGTGAACTGGGTGGCCGAGAAGGAATGGGAGTTGCCGCCAGATTCT |
| | GACATGGATCTGAATCTGATTGAGCAGGCACCCCTGACCGTGGCCGAGAAGCTGCAGCGCGAC |
| | TTTCTGACGGAATGGCGCCGTGTGAGTAAGGCCCCGGAGGCTCTTTTCTTTGTGCAATTTGAGA |
| | AGGGAGAGAGCTACTTCCACATGCACGTGCTCGTGGAAACCACCGGGGTGAAATCCATGGTTT |
| | TGGGACGTTTCCTGAGTCAGATTCGCGAAAAACTGATTCAGAGAATTTACCGCGGGATCGAGC |
| | CGACTTTGCCAAACTGGTTCGCGGTCACAAAGACCAGAAATGGCGCCGGAGGCGGGAACAAG |
| | GTGGTGGATGAGTGCTACATCCCCAATTACTTGCTCCCCAAAACCCAGCCTGAGCTCCAGTGGG |
| | CGTGGACTAATATGGAACAGTATTTAAGCGCCTGTTTGAATCTCACGGAGCGTAAACGGTTGGT |
| | GGCGCAGCATCTGACGCACGTGTCGCAGACGCAGGAGCAGAACAAAGAGAATCAGAATCCCA |
| | ATTCTGATGCGCCGGTGATCAGATCAAAAACTTCAGCCAGGTACATGGAGCTGGTCGGGTGGC |
| | TCGTGGACAAGGGGATTACCTCGGAGAAGCAGTGGATCCAGGAGGACCAGGCCTCATACATCT |
| | CCTTCAATGCGGCCTCCAACTCGCGGTCCCAAATCAAGGCTGCCTTGGACAATGCGGGAAAGA |
| | TTATGAGCCTGACTAAAACCGCCCCCGACTACCTGGTGGGCCAGCAGCCCGTGGAGGACATTT |
| | CCAGCAATCGGATTTATAAAATTTTGGAACTAAACGGGTACGATCCCCAATATGCGGCTTCCGT |
| | CTTTCTGGGATGGGCCACGAAAAAGTTCGGCAAGAGGAACACCATCTGGCTGTTTGGGCCTGC |
| | AACTACCGGGAAGACCAACATCGCGGAGGCCATAGCCCACACTGTGCCCTTCTACGGGTGCGT |
| | AAACTGGACCAATGAGAACTTTCCCTTCAACGACTGTGTCGACAAGATGGTGATCTGGTGGGA |
| | GGAGGGGAAGATGACCGCCAAGGTCGTGGAGTCGGCCAAAGCCATTCTCGGAGGAAGCAAGG |
| | TGCGCGTGGACCAGAAATGCAAGTCCTCGGCCCAGATAGACCCGACTCCCGTGATCGTCACCT |
| | CCAACACCAACATGTGCGCCGTGATTGACGGGAACTCAACGACCTTCGAACACCAGCAGCCGT |
| | TGCAAGACCGGATGTTCAAATTTGAACTCACCCGCCGTCTGGATCATGACTTTGGGAAGGTCAC |
| | CAAGCAGGAAGTCAAAGACTTTTTCCGGTGGGCAAAGGATCACGTGGTTGAGGTGGAGCATGA |
| | ATTCTACGTCAAAAAGGGTGGAGCCAAGAAAAGACCCGCCCCCAGTGACGCAGATATAAGTGA |
| | GCCCAAACGGGTGCGCGAGTCAGTTGCGCAGCCATCGACGTCAGACGCGGAAGCTTCGATCAA |
| | CTACGCGGACAGGTACCAAAACAAATGTTCTCGTCACGTGGGCATGAATCTGATGCTGTTTCCC |
| | TGCAGACAATGCGAGAGACTGAATCAGAATTCAAATATCTGCTTCACTCACGGTGTCAAAGAC |
| | TGTTTAGAGTGCTTTCCCGTGTCAGAATCTCAACCCGTTTCTGTCGTCAAAAAGGCGTATCAGA |
| | AACTGTGCTACATTCATCACATCATGGGAAAGGTGCCAGACGCTTGCACTGCTTGCGACCTGGT |
| | CAATGTGGACTTGGATGACTGTGTTTCTGAACAATAAATGACTTAAACCAGGTATGGCTGCCGA |
| | TGGTTAGCTTCCAGATTGGCTCGAGGACAACCTTAGTGAAGGAATTCGCGAGTGGTGGGCTTTG |
| | AAACCTGGAGCCCCTCAACCCAAGGCAAATCAACAACATCAAGACAACGCTCGAGGTCTTGTG |
| | CTTCCGGGTTACAAATACCTTGGACCCGGCAACGGACTCGACAAGGGGGAGCCGGTCAACGCA |
| | GCAGACGCGGCGGCCCTCGAGCACGACAAGGCCTACGACCAGCAGCTCAAGGCCGGAGACAA |
| | CCCGTACCTCAAGTACAACCACGCCGACGCCGAGTTCCAGGAGCGGCTCAAAGAAGATACGTC |
| | TTTTGGGGGCAACCTCGGGCGAGCAGTCTTCCAGGCCAAAAAGAGGCTTCTTGAACCTCTTGGT |
| | CTGGTTGAGGAAGCGGCTAAGACGGCTCCTGGAAAGTAGAGGCCTGTAGAGCAGTCTCCTCAG |
| | GAACCGGACTCCTCCGCGGGTATTGGCAAATCGGGTGCACAGCCCGCTAAAAAGAGACTCAAT |
| | TTCGGTCAGACTGGCGACACAGAGTCAGTCCCAGACCCTCAACCAATCGGAGAACCTCCCGCA |
| | GCCCCCTCAGGTGTGGGATCTCTTACAATGGCTTCAGGTGGTGGCGCACCAGTGGCAGACAAT |
| | AACTAAGGTGCCGATGGAGTGGGTAGTTCCTCGGGAAATTGGCATTGCGATTCCCAATGGCTG |
| | GGGGACAGAGTCATCACCACCAGCACCCGAACCTGGGCCCTGCCCACCTACAACAATCACCTC |
| | TACAAGCAAATCTCCAACAGCACATCTGGAGGATCTTCAAATGACAACGCCTACTTCGGCTAC |
| | AGCACCCCCTGGGGGTATTTTGACTTCAACAGATTCCACTGCCACTTCTCACCACGTGACTGGC |
| | AGCGACTCATCAACAACAACTGGGGATTCCGGCCTAAGCGACTCAACTTCAAGCTCTTCAACAT |
| | TCAGGTCAAAGAGGTTACGGACAACAATGGAGTCAAGACCATCGCCAATAACCTTACCAGCAC |
| | GGTCCAGGTCTTCACGGACTCAGACTATCAGCTCCCGTACGTGCTCGGGTCGGCTCACGAGGGC |
| | TGCCTCCCGCCGTTCCCAGCGGACGTTTTCATGATTCCTCAGTACGGGTATCTGACGCTTAATG |
| | ATGGAAGCCAGGCCGTGGGTCGTTCGTCCTTTTACTGCCTGGAATATTTCCCGTCGCAAATGCT |
| | AAGAACGGGTAACAACTTCCAGTTCAGCTACGAGTTTGAGAACGTACCTTTCCATAGCAGCTAC |
| | GCTCACAGCCAAAGCCTGGACCGACTAATGAATCCACTCATCGACCAATACTTGTACTATCTCT |
| | CAAAGACTATTAACGGTTCTGGACAGAATCAACAAACGCTAAAATTCAGTGTGGCCGGACCCA |
| | GCAACATGGCTGTCCAGGGAAGAAACTACATACCTGGACCCAGCTACCGACAACAACGTGTCT |
| | CAACCACTGTGACTCAAAACAACAACAGCGAATTTGCTTGGCCTGGAGCTTCTTCTTGGGCTCT |

TABLE 12-continued

| Sequences | |
|---|---|
| DESCRIPTION<br>SEQ ID NO: | NUCLEIC ACID SEQUENCE |
| | CAATGGACGTAATAGCTTGATGAATCCTGGACCTGCTATGGCCAAGTCAGCGTGGAGATCGAG<br>TGGGAGCTGCAGAAGGAAAACAGCAAGCGCTGGAACCCGGAGATCCAGTACACTTCCAACTAT<br>TACAAGTCTAATAATGTTGAATTTGCTGTTAATACTGAAGGTGTATATAGTGAACCCCGCCCCA<br>TTGGCACCAGATACCTGACTCGTAATCTGTAATTGCTTGTTAATCAATAAACCGTTTAATTCGTT<br>TCAGTTGAACTTTGGTCTC |
| SYN-CAP9<br>SEQ ID NO: 8 | TTGGCCACTCCCTCTCTGCGCGCTCGCTCGCTCACTGAGGCCGGGCGACCAAAGGTCGCCCGAC<br>GCCCGGGCTTTGCCCGGGCGGCCTCAGTGAGCGAGCGAGCGCGCAGAGAGGGAGTGGCCAACT<br>CCATCACTAGGGGTTCCTGGAGGGGTGGAGTCGTGACGATATCTAGTATCTGCAGAGGGCCCT<br>GCGTATGAGTGCAAGTGGGTTTTAGGACCAGGATGAGGCGGGGTGGGGGTGCCTACCTGACGA<br>CCGACCCCGACCCACTGGACAAGCACCCAACCCCCATTCCCCAAATTGCGCATCCCCTATCAGA<br>GAGGGGGAGGGGAAACAGGATGCGGCGAGGCGCGTGCGCACTGCCAGCTTCAGCACCGCGGA<br>CAGTGCCTTCGCCCCCGCCTGGCGGCGCGCGCCACCGCCGCCTCAGCACTGAAGGCGCGCTGA<br>CGTCACTCGCCGGTCCCCCGCAAACTCCCCTTCCCGGCCACCTTGGTCGCGTCCGCGCCGCCGC<br>CGGCCCAGCCGGACCGCACCACGCGAGGCGCGAGATAGGGGGGCACGGGCGCGACCATCTGC<br>GCTGCGGCGCCGGCGACTCAGCGCTGCCTCAGTCTGCGGTGGGCAGCGGAGGAGTCGTGTCGT<br>GCCTGAGAGCGCAGCTGTGCTCCTGGGCACCGCGCAGTCCGCCCCCGCGGCTCCTGGCCAGAC<br>CACCCCTAGGACCCCCTGCCCCAAGTCGCAGCCGGTCACCAAGCAGGAAGTCAAAGACTTTTT<br>CCGGTGGGCAAAGGATCACGTGGTTGAGGTGGAGCATGAATTCTACGTCAAAAAGGGTGGAGC<br>CAAGAAAAGACCCGCCCCCAGTGACGCAGATATAAGTGAGCCCAAACGGGTGCGCGAGTCAG<br>TTGCGCAGCCATCGACGTCAGACGCGGAAGCTTCGATCAACTACGCGGACAGGTACCAAAACA<br>AATGTTCTCGTCACGTGGGCATGAATCTGATGCTGTTTCCCTGCAGACAATGCGAGAGACTGAA<br>TCAGAATTCAAATATCTGCTTCACTCACGGTGTCAAAGACTGTTTAGAGTGCTTTCCCGTGTCA<br>GAATCTCAACCCGTTTCTGTCGTCAAAAAGGCGTATCAGAAACTGTGCTACATTCATCACATCA<br>TGGGAAAGGTGCCAGACGCTTGCACTGCTTGCGACCTGGTCAATGTGGACTTGGATGACTGTGT<br>TTCTGAACAATAAATGACTTAAACCAGGTATGGCTGCCGATGGTTATCTTCCAGATTGGCTCGA<br>GGACAACCTTAGTGAAGGAATTCGCGAGTGGTGGGCTTTGAAACCTGGAGCCCCTCAACCCAA<br>GGCAAATCAACAACATCAAGACAACGCTCGAGGTCTTGTGCTTCCGGGTTACAAATACCTTGG<br>ACCCGGCAACGGACTCGACAAGGGGGAGCCGGTCAACGCAGCAGACGCGGCGGCCCTCGAGC<br>ACGACAAGGCCTACGACCAGCAGCTCAAGGCCGGAGACAACCCGTACCTCAAGTACAACCACG<br>CCGACGCCGAGTTCCAGGAGCGGCTCAAAGAAGATACGTCTTTTGGGGGCAACCTCGGGCGAG<br>CAGTCTTCCAGGCCAAAAAGAGGCTTCTTGAACCTCTTGGTCTGGTTGAGGAAGCGGCTAAGA<br>CGGCTCCTGGAAAGAAGAGGCCTGTAGAGCAGTCTCCTCAGGAACCGGACTCCTCCGCGGGTA<br>TTGGCAAATCGGGTGCACAGCCCGCTAAAAAGAGACTCAATTTCGGTCAGACTGGCGACACAG<br>AGTCAGTCCCAGACCCTCAACCAATCGGAGAACCTCCCGCAGCCCCCTCAGGTGTGGGATCTCT<br>TACAATGGCTTCAGGTGGTGGCGCACCAGTGGCAGACAATAACGAAGGTGCCGATGGAGTGGG<br>TAGTTCCTCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCAACAGCAC<br>ATCTGGAGGATCTTCAAATGACAACGCCTACTTCGGCTACAGCACCCCCTGGGGGTATTTTGAC<br>TTCAACAGATTCCACTGCCACTTCTCACCACGTGACTGGCAGCGACTCATCAACAACAACTGGG<br>GATTCCGGCCTAAGCGACTCAACTTCAAGCTCTTCAACATTCAGGTCAAAGAGGTTACGGACA<br>ACAATGGAGTCAAGACCATCGCCAATAACCTTACCAGCACGGTCCAGGTCTTCACGGACTCAG<br>ACTATCAGCTCCCGTACGTGCTCGGGTCGGCTCACGAGGGCTGCCTCCCGCCGTTCCCAGCGGA<br>CGTTTTCATGATTCCTCAGTACGGGTATCTGACGCTTAATGATGGAAGCCAGGCCGTGGGTCGT<br>TCGTCCTTTTACTGCCTGGAATATTTCCCGTCGCAAATGCTAAGAACGGGTAACAACTTCCAGT<br>TCAGCTACGAGTTTGAGAACGTACCTTTCCATAGCAGCTACGCTCACAGCCAAAGCCTGGACCG<br>ACTAATGAATCCACTCATCGACCAATACTTGTACTATCTCTCAAAGACTATTAACGGTTCTGGA<br>CAGAATCAACAAACGCTAAAATTCAGTGTGGCCGGACCCAGCAACATGGCTGTCCAGGGAAGA<br>AACTACATACCTGGACCCAGCTACCGACAACAACGTGTCTCAACCACTGTGACTCAAAACAAC<br>AACAGCGAATTTGCTTGGCCTGGAGCTTCTTCTTGGGCTCTCAATGGACGTAATAGCTTGATGA<br>ATCCTGGACCTGCTATGGCCAGCCACAAAGAAGGAGAGGACCGTTTCTTTCCTTTGTCTGGATC<br>TTTAATTTTTGGCAAACAAGGAACTGGAAGAGACAACGTGGATGCGGACAAAGTCATGATAAC<br>CAACGAAGAAGAAATTAAAACTACTAACCCGGTAGCAACGGAGTCCTATGGACAAGTGGCCAC<br>AAACCACCAGAGTGCCCAAGCACAGGCGCAGACCGGCTGGGTTCAAAACCAAGGAATACTTCC<br>GGGTATGGTTTGGCAGGACAGAGATGTGTACCTGCAAGGACCCATTTGGGCCAAAATTCCTCA<br>CACGGACGGCAACTTTCACCCTTCTCCGCTGATGGGAGGGTTTGGAATGAAGCACCCGCCTCCT<br>CAGATCCTCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTGGGAGCTGC<br>AGAAGGAAAACAGCAAGCGCTGGAACCCGGAGATCCAGTACACTTCCAACTATTACAAGTCTA<br>ATAATGTTGAATTTGCTGTTAATACTGAAGGTGTATATAGTGAACCCCGCCCCATTGGCACCAG<br>ATACCTGACTCGTAATCTGTAATCGATTGTTAATCAATAAACCGTTTAATTCGTTTCAGTTGAAC<br>TTTGGTCTCTGCGTATTTCTTTCTTATCTAGTTTCCATGGCTACGTAGATAAGTAGCATGGCGGG<br>TTAATCATTAACTACAAGGAACCCCTAGTGATGGAGTTGGCCACTCCCTCTCTGCGCGCTCGCT<br>CGCTCACTGAGGCCGGGCGACCAAAGGTCGCCCGACGCCCGGGCTTTGCCCGGGCGGCCTCAG<br>TGAGCGAGCGAGCGCGCAGAGAGGGAGTGGCCAA |
| GFAP-CAP9<br>SEQ ID NO: 9 | TTGGCCACTCCCTCTCTGCGCGCTCGCTCGCTCACTGAGGCCGGGCGACCAAAGGTCGCCCGAC<br>GCCCGGGCTTTGCCCGGGCGGCCTCAGTGAGCGAGCGAGCGCGCAGAGAGGGAGTGGCCAACT<br>CCATCACTAGGGGTTCCTGGAGGGGTGGAGTCGTGACGATATCGATCTAACATATCCTGGTGTG<br>GAGTAGCGGACGCTGCTATGACAGAGGCTCGGGGGCCTGAGCTGGCTCTGTGAGCTGGGGAGG<br>AGGCAGACAGCCAGGCCTTGTCTGCAAGCAGACCTGGCAGCATTGGGCTGGCCGCCCCCCAGG<br>GCCTCCTCTTCATGCCCAGTGAATGACTCACCTTGGCACAGACACAATGTTCGGGGTGGGCACA<br>GTGCCTGCTTCCCGCCGCACCCCAGCCCCCCTCAAATGCCTTCCGAGAAGCCCATTGAGCAGGG<br>GGCTTGCATTGCACCCCAGCCTGACAGCCTGGCATCTTGGGATAAAAGCAGCACAGCCCCCTA<br>GGGGCTGCCCTTGCTGTGTGGCGCCACCGGCGGTGGAGAACAAGGCTCTATTCAGCCTGTGCCC |

TABLE 12-continued

| Sequences | |
|---|---|
| DESCRIPTION<br>SEQ ID NO: | NUCLEIC ACID SEQUENCE |
| | AGGAAAGGGGATCAGGGGATGCCCAGGCATGGACAGTGGGTGGCAGGGGGGGAGAGGAGGG<br>CTGTCTGCTTCCCAGAAGTCCAAGGACACAAATGGGTGAGGGGAGAGCTCTCCCCATAGCTGG<br>GCTGCGGCCCAACCCCACCCCCTCAGGCTATGCCAGGGGGTGTTGCCAGGGGCACCCGGGCAT<br>CGCCAGTCTAGCCCACTCCTTCATAAAGCCCTCGCATCCCAGGAGCGAGCAGAGCCAGAGCAG<br>GTTGGAGAGGAGACGCATCACCTCCGCTGCTCGCGGGGATCCTCTAGGGTCACCAAGCAGGAA<br>GTCAAAGACTTTTTCCGGTGGGCAAAGGATCACGTGGTTGAGGTGGAGCATGAATTCTACGTC<br>AAAAAGGGTGGAGCCAAGAAAAGACCCGCCCCCAGTGACGCAGATATAAGTGAGCCCAAACG<br>GGTGCGCGAGTCAGTTGCGCAGCCATCGACGTCAGACGCGGAAGCTTCGATCAACTACGCGGA<br>CAGGTACCAAAACAAATGTTCTCGTCACGTGGGCATGAATCTGATGCTGTTTCCCTGCAGACAA<br>TGCGAGAGACTGAATCAGAATTCAAATATCTGCTTCACTCACGGTGTCAAAGACTGTTTAGAGT<br>GCTTTCCCGTGTCAGAATCTCAACCCGTTTCTGTCGTCAAAAAGGCGTATCAGAAACTGTGCTA<br>CATTCATCACATCATGGGAAAGGTGCCAGACGCTTGCACTGCTTGCGACCTGGTCAATGTGGAC<br>TTGGATGACTGTGTTTCTGAACAATAAATGACTTAAACCAGGTATGGCTGCCGATGGTTATCTT<br>CCAGATTGGCTCGAGGACAACCTTAGTGAAGGAATTCGCGAGTGGTGGGCTTTGAAACCTGGA<br>GCCCCTCAACCCAAGGCAAATCAACAACATCAAGACAACGCTCGAGGTCTTGTGCTTCCGGGT<br>TACAAATACCTTGGACCCGGCAACGGACTCGACAAGGGGGAGCCGGTCAACGCAGCAGACGC<br>GGCGGCCCTCGAGCACGACAAGGCCTACGACCAGCAGCTCAAGGCCGGAGACAACCCGTACCT<br>CAAGTACAACCACGCCGACGCCGAGTTCCAGGAGCGGCTCAAAGAAGATACGTCTTTTGGGGG<br>CAACCTCGGGCGAGCAGTCTTCCAGGCCAAAAAGAGGCTTCTTGAACCTCTTGGTCTGGTTGAG<br>GAAGCGGCTAAGACGGCTCCTGGAAAGAAGAGGCCTGTAGAGCAGTCTCCTCAGGAACCGGA<br>CTCCTCCGCGGGTATTGGCAAATCGGGTGCACAGCCCGCTAAAAAGAGACTCAATTTCGGTCA<br>GACTGGCGACACAGAGTCAGTCCCAGACCCTCAACCAATCGGAGAACCTCCCGCAGCCCCCTC<br>AGGTGTGGGATCTCTTACAATGGCTTCAGGTGGTGGCGCACCAGTGGCAGACAATAACGAAGG<br>TGCCGATGGAGTGGGTAGTTCCTCGGGAAATTGGCATTGCGATTCCCAATGGCTGGGGGACAG<br>AGTCATCACCACCAGCACCCGAACCTGGGCCCTGCCCACCTACAACAATCACCTCTACAAGCA<br>AATCTCCAACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCAGCGACTCA<br>TCAACAACAACTGGGGATTCCGGCCTAAGCGACTCAACTTCAAGCTCTTCAACATTCAGGTCAA<br>AGAGGTTACGGACAACAATGGAGTCAAGACCATCGCCAATAACCTTACCAGCACGGTCCAGGT<br>CTTCACGGACTCAGACTATCAGCTCCCGTACGTGCTCGGGTCGGCTCACGAGGGCTGCCTCCCG<br>CCGTTCCCAGCGGACGTTTTCATGATTCCTCAGTACGGGTATCTGACGCTTAATGATGGAAGCC<br>AGGCCGTGGGTCGTTCGTCCTTTTACTGCCTGGAATATTTCCCGTCGCAAATGCTAAGAACGGG<br>TAACAACTTCCAGTTCAGCTACGAGTTTGAGAACGTACCTTTCCATAGCAGCTACGCTCACAGC<br>CAAAGCCTGGACCGACTAATGAATCCACTCATCGACCAATACTTGTACTATCTCTCAAAGACTA<br>TTAACGGTTCTGGACAGAATCAACAAACGCTAAAATTCAGTGTGGCCGGACCCAGCAACATGG<br>CTGTCCAGGGAAGAAACTACATACCTGGACCCAGCTACCGACAACAACGTGTCTCAACCACTG<br>TGACTCAAAACAACAACAGCGAATTTGCTTGGCCTGGAGCTTCTTCTTGGGCTCTCAATGGACG<br>TAATAGCTTGATGAATCCTGGACCTGCTATGGCCAGCCACAAAGAAGGAGAGGACCGTTTCTTT<br>CCTTTGTCTGGATCTTTAATTTTTGGCAAACAAGGAACTGGAAGAGACAACGTGGATGCGGAC<br>AAAGTCATGATAACCAACGAAGAAGAAATTAAAACTACTAACCCGGTAGCAACGGAGTCCTAT<br>GGACAAGTGGCCACAAACCACCAGAGTGCCCAAGCACAGGCGCAGACCGGCTGGGTTCAAAA<br>CCAAGGAATACTTCCGGGTATGGTTTGGCAGGACAGAGATGTGTACCTGCAAGGACCCATTTG<br>GGCCAAAATTCCTCACACGGACGGCAACTTTCACCCTTCTCCGCTGATGGGAGGGTTTGGAATG<br>AAGCACCCGCCTCCTCAGATCCTCATCAAAAACACACCTGTACCTGCGGATCCTCCAACGGCCT<br>TCAACAAGGACAAGCTGAACTCTTTCATCACCCAGTATTCTACTGGCCAAGTCAGCGTGGAGAT<br>CGAGTGGGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGTGAACCCCG<br>CCCCATTGGCACCAGATACCTGACTCGTAATCTGTAATCGATTGTTAATCAATAAACCGTTTAA<br>TTCGTTTCAGTTGAACTTTGGTCTCTGCGTATTTCTTTCTTATCTAGTTTCCATGGCTACGTAGAT<br>AAGTAGCATGGCGGGTTAATCATTAACTACAAGGAACCCCTAGTGATGGAGTTGGCCACTCCC<br>TCTCTGCGCGCTCGCTCGCTCACTGAGGCCGGGCGACCAAAGGTCGCCCGACGCCCGGGCTTTG<br>CCCGGGCGGCCTCAGTGAGCGAGCGAGCGCGCAGAGAGGGAGTGGCCAA |
| CAG-CAP9<br>SEQ ID NO: 10 | TTGGCCACTCCCTCTCTGCGCGCTCGCTCGCTCACTGAGGCCGGGCGACCAAAGGTCGCC<br>CGACGCCCGGGCTTTGCCCGGGCGGCCTCAGTGAGCGAGCGAGCGCGCAGAGAGGGAGT<br>GGCCAACTCCATCACTAGGGGTTCCTGGAGGGGTGGAGTCGTGACGATATCCATGCGTCG<br>ACATAACGCGTCGACATTGATTATTGACTAGTTATTAATAGTAATCAATTACGGGGTCATT<br>AGTTCATAGCCCATATATGGAGTTCCGCGTTACATAACTTACGGTAAATGGCCCGCCTGG<br>CTGACCGCCCAACGACCCCCGCCCATTGACGTCAATAATGACGTATGTTCCCATAGTAAC<br>GCCAATAGGGACTTTCCATTGACGTCAATGGGTGGAGTATTTACGGTAAACTGCCCACTT<br>GGCAGTACATCAAGTGTATCATATGCCAAGTACGCCCCCTATTGACGTCAATGACGGTAA<br>ATGGCCCGCCTGGCATTATGCCCAGTACATGACCTTATGGGACTTTCCTACTTGGCAGTAC<br>ATCTACGTATTAGTCATCGCTATTACCATGTCGAGGCCACGTTCTGCTTCACTCTCCCCAT<br>CTCCCCCCCCTCCCCACCCCCAATTTTGTATTTATTTATTTTTTAATTATTTTGTGCAGCGA<br>TGGGGGCGGGGGGGGGGGGCGCGCGCCAGGCGGGGCGGGGCGGGGCGAGGGGCGGGGC<br>GGGGCGAGGCGGAGAGGTGCGGCGGCAGCCAATCAGAGCGGCGCGCTCCGAAAGTTTCC<br>TTTTATGGCGAGGCGGCGGCGGCGGCGGCCCTATAAAAAGCGAAGCGCGCGGCGGGCGG<br>GAGCAAGCTTCGTTTAGTGAACCGTCAGATCGCCTGGAGACGCCATCCACGCTGTTTTGA<br>CCTCCATAGAAGACACCGGGACCGATCCAGCCTCCGCGGATTCGAATCCCGGCCGGGAA<br>CGGTGCATTGGAACGCGGATTCCCCGTGCCAAGAGTGACGTAAGTACCGCCTATAGAGTC<br>TATAGGCCCACAAAAAATGCTTTCTTCTTTTAATATACTTTTTTGTTTATCTTATTTCTAAT<br>ACTTTCCCTAATCTCTTTCTTTCAGGGCAATAATGATACAATGTATCATGCCTCTTTGCAC<br>CATTCTAAAGAATAACAGTGATAATTTCTGGGTTAAGGCAATAGCAATATTTCTGCATAT<br>AAATATTTCTGCATATAAATTGTAACTGATGTAAGAGGTTTCATATTGCTAATAGCAGCTA<br>CAATCCAGCTACCATTCTGCTTTTATTTTATGGTTGGGATAAGGCTGGATTATTCTGAGTC |

TABLE 12-continued

| Sequences | |
|---|---|
| DESCRIPTION<br>SEQ ID NO: | NUCLEIC ACID SEQUENCE |
| | CAAGCTAGGCCCTTTTGCTAATCATGTTCATACCTCTTATCTTCCTCCCACAGCTCCTGGG |
| | CAACGTGCTGGTCTGTGTGCTGGCCCATCACTTTGGCAAAGAATTGGGATTCGAACCGGT |
| | CACCAAGCAGGAAGTCAAAGACTTTTTCCGGTGGGCAAAGGATCACGTGGTTGAGGTGG |
| | AGCATGAATTCTACGTCAAAAAGGGTGGAGCCAAGAAAAGACCCGCCCCCAGTGACGCA |
| | GATATAAGTGAGCCCAAACGGGTGCGCGAGTCAGTTGCGCAGCCATCGACGTCAGACGC |
| | GGAAGCTTCGATCAACTACGCGGACAGGTACCAAAACAAATGTTCTCGTCACGTGGGCAT |
| | GAATCTGATGCTGTTTCCCTGCAGACAATGCGAGAGACTGAATCAGAATTCAAATATCTG |
| | CTTCACTCACGGTGTCAAAGACTGTTTAGAGTGCTTTCCCGTGTCAGAATCTCAACCCGTT |
| | TCTGTCGTCAAAAAGGCGTATCAGAAACTGTGCTACATTCATCACATCATGGGAAAGGTG |
| | CCAGACGCTTGCACTGCTTGCGACCTGGTCAATGTGGACTTGGATGACTGTGTTTCTGAAC |
| | AATAAATGACTTAAACCAGGTATGGCTGCCGATGGTTATCTTCCAGATTGGCTCGAGGAC |
| | AACCTTAGTGAAGGAATTCGCGAGTGGTGGGCTTTGAAACCTGGAGCCCCTCAACCCAAG |
| | GCAAATCAACAACATCAAGACAACGCTCGAGGTCTTGTGCTTCCGGGTTACAAATACCTT |
| | GGACCCGGCAACGGACTCGACAAGGGGGAGCCGGTCAACGCAGCAGACGCGGCGGCCCT |
| | CGAGCACGACAAGGCCTACGACCAGCAGCTCAAGGCCGGAGACAACCCGTACCTCAAGT |
| | ACAACCACGCCGACGCCGAGTTCCAGGAGCGGCTCAAAGAAGATACGTCTTTTGGGGGC |
| | AACCTCGGGCGAGCAGTCTTCCAGGCCAAAAAGAGGCTTCTTGAACCTCTTGGTCTGGTT |
| | GAGGAAGCGGCTAAGACGGCTCCTGGAAAGAAGAGGCCTGTAGAGCAGTCTCCTCAGGA |
| | ACCGGACTCCTCCGCGGGTATTGGCAAATCGGGTGCACAGCCCGCTAAAAAGAGACTCA |
| | ATTTCGGTCAGACTGGCGACACAGAGTCAGTCCCAGACCCTCAACCAATCGGAGAACCTC |
| | CCGCAGCCCCCTCAGGTGTGGGATCTCTTACAATGGCTTCAGGTGGTGGCGCACCAGTGG |
| | CAGACAATAACGAAGGTGCCGATGGAGTGGGTAGTTCCTCGGGAAATTGGCATTGCGATT |
| | CCCAATGGCTGGGGGACAGAGTCATCACCACCAGCACCCGAACCTGGGCCCTGCCCACCT |
| | ACAACAATCACCTCTACAAGCAAATCTCCAACAGCACATCTGGAGGATCTTCAAATGACA |
| | ACGCCTACTTCGGCTACAGCACCCCCTGGGGGTATTTTGACTTCAACAGATTCCACTGCCA |
| | CTTCTCACCACGTGACTGGCAGCGACTCATCAACAACAACTGGGGATTCCGGCCTAAGCG |
| | ACTCAACTTCAAGCTCTTCAACATTCAGGTCAAAGAGGTTACGGACAACAATGGAGTCAA |
| | GACCATCGCCAATAACCTTACCAGCACGGTCCAGGTCTTCACGGACTCAGACTATCAGCT |
| | CCCGTACGTGCTCGGGTCGGCTCACGAGGGCTGCCTCCCGCCGTTCCCAGCGGACGTTTT |
| | CATGATTCCTCAGTACGGGTATCTGACGCTTAATGATGGAAGCCAGGCCGTGGGTCGTTC |
| | GTCCTTTTACTGCCTGGAATATTTCCCGTCGCAAATGCTAAGAACGGGTAACAACTTCCA |
| | GTTCAGCTACGAGTTTGAGAACGTACCTTTCCATAGCAGCTACGCTCACAGCCAAAGCCT |
| | GGACCGACTAATGAATCCACTCATCGACCAATACTTGTACTATCTCTCAAAGACTATTAA |
| | CGGTTCTGGACAGAATCAACAAACGCTAAAATTCAGTGTGGCCGGACCCAGCAACATGG |
| | CTGTCCAGGGAAGAAACTACATACCTGGACCCAGCTACCGACAACAACGTGTCTCAACCA |
| | CTGTGACTCAAAACAACAACAGCGAATTTGCTTGGCCTGGAGCTTCTTCTTGGGCTCTCA |
| | ATGGACGTAATAGCTTGATGAATCCTGGACCTGCTATGGCCAGCCACAAAGAAGGAGAG |
| | GACCGTTTCTTTCCTTTGTCTGGATCTTTAATTTTGGCAAACAAGGAACTGGAAGAGACA |
| | ACGTGGATGCGGACAAAGTCATGATAACCAACGAAGAAGAAATTAAAACTACTAACCCG |
| | GTAGCAACGGAGTCCTATGGACAAGTGGCCACAAACCACCAGAGTGCCCAAGCACAGGC |
| | GCAGACCGGCTGGGTTCAAAACCAAGGAATACTTCCGGGTATGGTTTGGCAGGACAGAG |
| | ATGTGTACCTGCAAGGACCCATTTGGGCCAAAATTCCTCACACGGACGGCAACTTTCACC |
| | CTTCTCCGCTGATGGGAGGGTTTGGAATGAAGCACCCGCCTCCTCAGATCCTCATCAAAA |
| | ACACACCTGTACCTGCGGATCCTCCAACGGCCTTCAACAAGGACAAGCTGAACTCTTTCA |
| | TCACCCAGTATTCTACTGGCCAAGTCAGCGTGGAGATCGAGTGGGAGCTGCAGAAGGAA |
| | AACAGCAAGCGCTGGAACCCGGAGATCCAGTACACTTCCAACTATTACAAGTCTAATAAT |
| | GTTGAATTTGCTGTTAATACTGAAGGTGTATATAGTGAACCCCGCCCCATTGGCACCAGA |
| | TACCTGACTCGTAATCTGTAATCGATTGTTAATCAATAAACCGTTTAATTCGTTTCAGTTG |
| | AACTTTGGTCTCTGCGTATTTCTTTCTTATCTAGTTTCCATGGCTACGTAGATAAGTAGCAT |
| | GGCGGGTTAATCATTAACTACAAGGAACCCCTAGTGATGGAGTTGGCCACTCCCTCTCTG |
| | CGCGCTCGCTCGCTCACTGAGGCCGGGCGACCAAAGGTCGCCCGACGCCCGGGCTTTGCC |
| | CGGGCGGCCTCAGTGAGCGAGCGAGCGCGCAGAGAGGGAGTGGCCAA |
| SYNG-CAP9 | TTGGCCACTCCCTCTCTGCGCGCTCGCTCGCTCACTGAGGCCGGGCGACCAAAGGTCGCC |
| SEQ ID NO: 11 | CGACGCCCGGGCTTTGCCCGGGCGGCCTCAGTGAGCGAGCGAGCGCGCAGAGAGGGAGT |
| | GGCCAACTCCATCACTAGGGGTTCCTGGAGGGGTGGAGTCGTGACGATATCCATGCGTCG |
| | ACATAACGCGTGATCTAACATATCCTGGTGTGGAGTAGCGGACGCTGCTATGACAGAGGC |
| | TCGGGGGCCTGAGCTGGCTCTGTGAGCTGGGGAGGAGGCAGACAGCCAGGCCTTGTCTG |
| | CAAGCAGACCTGGCAGCATTGGGCTGGCCGCCCCCCAGGGCCTCCTCTTCATGCCCAGTG |
| | AATGACTCACCTTGGCACAGACACAATGTTCGGGGTGGGCACAGTGCCTGCTTCCCGCCG |
| | CACCCCAGCCCCCCTCAAATGCCTTCCGAGAAGCCCATTGAGCAGGGGGCTTGCATTGCA |
| | CCCCAGCCTGACAGCCTGGCATCTTGGGATAAAAGCAGCACAGCCCCCTAGGGGCTGCCC |
| | TTGCTGTGTGGCGCCACCGGCGGTGGAGAACAAGGCTCTATTCAGCCTGTGCCCAGGAAA |
| | GGGGATCAGGGGATGCCCAGGCATGGACAGTGGGTGGCAGGGGGGGAGAGGAGGGCTG |
| | TCTGCTTCCCAGAAGTCCAAGGACACAAATGGGTGAGGGGAGAGCTCTCCCCATAGCTGG |
| | GCTGCGGCCCAACCCCACCCCCTCAGGCTATGCCAGGGGGTGTTGCCAGGGGCACCCGGG |
| | CATCGCCAGTCTAGCCCACTCCTTCATAAAGCCCTCGCATCCCAGGAGCGAGCAGAGCCA |
| | GAGCAGGTTGGAGAGGAGACGCATCACCTCCGCTGCTCGCGGGGATCCTCTAGAAGCTTC |
| | GTTTAGTGAACCGTCAGATCGCCTGGAGACGCCATCCACGCTGTTTTGACCTCCATAGAA |
| | GACACCGGGACCGATCCAGCCTCCGCGGATTCGAATCCCGGCCGGGAACGGTGCATTGG |
| | AACGCGGATTCCCCGTGCCAAGAGTGACGTAAGTACCGCCTATAGAGTCTATAGGCCCAC |
| | AAAAAATGCTTTCTTCTTTTAATATACTTTTTTGTTTATCTTATTTCTAATACTTTCCCTAAT |
| | CTCTTTCTTTCAGGGCAATAATGATACAATGTATCATGCCTCTTTGCACCATTCTAAAGAA |
| | TAACAGTGATAATTTCTGGGTTAAGGCAATAGCAATATTTCTGCATATAAATATTTCTGCA |
| | TATAAATTGTAACTGATGTAAGAGGTTTCATATTGCTAATAGCAGCTACAATCCAGCTAC |

TABLE 12-continued

| Sequences | |
|---|---|
| DESCRIPTION<br>SEQ ID NO: | NUCLEIC ACID SEQUENCE |
| | CATTCTGCTTTTATTTTATGGTTGGGATAAGGCTGGATTATTCTGAGTCCAAGCTAGGCCC<br>TTTTGCTAATCATGTTCATACCTCTTATCTTCCTCCCACAGCTCCTGGGCAACGTGCTGGTC<br>TGTGTGCTGGCCCATCACTTTGGCAAAGAATTGGGATTCGAACCGGTCGCCACCGGTCAC<br>CAAGCAGGAAGTCAAAGACTTTTTCCGGTGGGCAAAGGATCACGTGGTTGAGGTGGAGC<br>ATGAATTCTACGTCAAAAAGGGTGGAGCCAAGAAAAGACCCGCCCCCAGTGACGCAGAT<br>ATAAGTGAGCCCAAACGGGTGCGCGAGTCAGTTGCGCAGCCATCGACGTCAGACGCGGA<br>AGCTTCGATCAACTACGCGGACAGGTACCAAAACAAATGTTCTCGTCACGTGGGCATGAA<br>TCTGATGCTGTTTCCCTGCAGACAATGCGAGAGACTGAATCAGAATTCAAATATCTGCTT<br>CACTCACGGTGTCAAAGACTGTTTAGAGTGCTTTCCCGTGTCAGAATCTCAACCCGTTTCT<br>GTCGTCAAAAAGGCGTATCAGAAACTGTGCTACATTCATCACATCATGGGAAAGGTGCCA<br>GACGCTTGCACTGCTTGCGACCTGGTCAATGTGGACTTGGATGACTGTGTTTCTGAACAAT<br>AAATGACTTAAACCAGGTATGGCTGCCGATGGTTATCTTCCAGATTGGCTCGAGGACAAC<br>CTTAGTGAAGGAATTCGCGAGTGGTGGGCTTTGAAACCTGGAGCCCCTCAACCCAAGGCA<br>AATCAACAACATCAAGACAACGCTCGAGGTCTTGTGCTTCCGGGTTACAAATACCTTGGA<br>CCCGGCAACGGACTCGACAAGGGGGAGCCGGTCAACGCAGCAGACGCGGCGGCCCTCGA<br>GCACGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGCAAC<br>CTCGGGCGAGCAGTCTTCCAGGCCAAAAAGAGGCTTCTTGAACCTCTTGGTCTGGTTGAG<br>GAAGCGGCTAAGACGGCTCCTGGAAAGAAGAGGCCTGTAGAGCAGTCTCCTCAGGAACC<br>GGACTCCTCCGCGGGTATTGGCAAATCGGGTGCACAGCCCGCTAAAAAGAGACTCAATTT<br>CGGTCAGACTGGCGACACAGAGTCAGTCCCAGACCCTCAACCAATCGGAGAACCTCCCG<br>CAGCCCCCTCAGGTGTGGGATCTCTTACAATGGCTTCAGGTGGTGGCGCACCAGTGGCAG<br>ACAATAACGAAGGTGCCGATGGAGTGGGTAGTTCCTCGGGAAATTGGCATTGCGATTCCC<br>AATGGCTGGGGGACAGAGTCATCACCACCAGCACCCGAACCTGGGCCCTGCCCACCTAC<br>AACAATCACCTCTACAAGCAAATCTCCAACAGCACATCTGGAGGATCTTCAAATGACAAC<br>GCCTACTTCGGCTACAGCACCCCCTGGGGGTATTTTGACTTCAACAGATTCCACTGCCACT<br>TCTCACCACGTGACTGGCAGCGACTCATCAACAACAACTGGGGATTCCGGCCTAAGCGAC<br>TCAACTTCAAGCTCTTCAACATTCAGGTCAAAGAGGTTACGGACAACAATGGAGTCAAGA<br>CCATCGCCAATAACCTTACCAGCACGGTCCAGGTCTTCACGGACTCAGACTATCAGCTCC<br>CGTACGTGCTCGGGTCGGCTCACGAGGGCTGCCTCCCGCCGTTCCCAGCGGACGTTTTCA<br>TGATTCCTCAGTACGGGTATCTGACGCTTAATGATGGAAGCCAGGCCGTGGGTCGTTCGT<br>CCTTTTACTGCCTGGAATATTTCCCGTCGCAAATGCTAAGAACGGGTAACAACTTCCAGTT<br>CAGCTACGAGTTTGAGAACGTACCTTTCCATAGCAGCTACGCTCACAGCCAAAGCCTGGA<br>CCGACTAATGAATCCACTCATCGACCAATACTTGTACTATCTCTCAAAGACTATTAACGGT<br>TCTGGACAGAATCAACAAACGCTAAAATTCAGTGTGGCCGGACCCAGCAACATGGCTGTC<br>CAGGGAAGAAACTACATACCTGGACCCAGCTACCGACAACAACGTGTCTCAACCACTGT<br>GACTCAAAACAACAACAGCGAATTTGCTTGGCCTGGAGCTTCTTCTTGGGCTCTCAATGG<br>ACGTAATAGCTTGATGAATCCTGGACCTGCTATGGCCAGCCACAAAGAAGGAGAGGACC<br>GTTTCTTTCCTTTGTCTGGATCTTTAATTTTTGGCAAACAAGGAACTGGAAGAGACAACGT<br>GGATGCGGACAAAGTCATGATAACCAACGAAGAAGAAATTAAAACTACTAACCCGGTAG<br>CAACGGAGTCCTATGGACAAGTGGCCACAAACCACCAGAGTGCCCAAGCACAGGCGCAG<br>ACCGGCTGGGTTCAAAACCAAGGAATACTTCCGGGTATGGTTTGGCAGGACAGAGATGT<br>GTACCTGCAAGGACCCATTTGGGCCAAAATTCCTCACACGGACGGCAACTTTCACCCTTC<br>TCCGCTGATGGGAGGGTTTGGAATGAAGCACCCGCCTCCTCAGATCCTCATCAAAAACAC<br>ACCTGTACCTGCGGATCCTCCAACGGCCTTCAACAAGGACAAGCTGAACTCTTTCATCAC<br>CCAGTATTCTACTGGCCAAGTCAGCGTGGAGATCGAGTGGGAGCTGCAGAAGGAAAACA<br>GCAAGCGCTGGAACCCGGAGATCCAGTACACTTCCAACTATTACAAGTCTAATAATGTTG<br>AATTTGCTGTTAATACTGAAGGTGTATATAGTGAACCCCGCCCCATTGGCACCAGATACC<br>TGACTCGTAATCTGTAATCGATTGTTAATCAATAAACCGTTTAATTCGTTTCAGTTGAACT<br>TTGGTCTCTGCGTATTTCTTTCTTATCTAGTTTCCATGGCTACGTAGATAAGTAGCATGGC<br>GGGTTAATCATTAACTACAAGGAACCCCTAGTGATGGAGTTGGCCACTCCCTCTCTGCGC<br>GCTCGCTCGCTCACTGAGGCCGGGCGACCAAAGGTCGCCCGACGCCCGGGCTTTGCCCGG<br>GCGGCCTCAGTGAGCGAGCGAGCGCGCAGAGAGGGAGTGGCCAA |
| GFAPG-CAP9<br>SEQ ID NO: 12 | TTGGCCACTCCCTCTCTGCGCGCTCGCTCGCTCACTGAGGCCGGGCGACCAAAGGTCGCC<br>CGACGCCCGGGCTTTGCCCGGGCGGCCTCAGTGAGCGAGCGAGCGCGCAGAGAGGGAGT<br>GGCCAACTCCATCACTAGGGGTTCCTGGAGGGGTGGAGTCGTGACGATATCCATGCGTCG<br>ACATAACGCGTTAGTATCTGCAGAGGGCCCTGCGTATGAGTGCAAGTGGGTTTTAGGACC<br>AGGATGAGGCGGGGTGGGGGTGCCTACCTGACGACCGACCCCGACCCACTGGACAAGCA<br>CCCAACCCCCATTCCCCAAATTGCGCATCCCCTATCAGAGAGGGGGAGGGGAAACAGGA<br>TGCGGCGAGGCGCGTGCGCACTGCCAGCTTCAGCACCGCGGACAGTGCCTTCGCCCCCGC<br>CTGGCGGCGCGCGCCACCGCCGCCTCAGCACTGAAGGCGCGCTGACGTCACTCGCCGGTC<br>CCCCGCAAACTCCCCTTCCCGGCCACCTTGGTCGCGTCCGCGCCGCCGCCGGCCCAGCCG<br>GACCGCACCACGCGAGGCGCGAGATAGGGGGGCACGGGCGCGACCATCTGCGCTGCGGC<br>GCCGGCGACTCAGCGCTGCCTCAGTCTGCGGTGGGCAGCGGAGGAGTCGTGTCGTGCCTG<br>AGAGCGCAGCTGTGCTCCTGGGCACCGCGCAGTCCGCCCCCGCGGCTCCTGGCCAGACCA<br>CCCCTAGGACCCCCTGCCCCAAGTCGCAGCCAAGCTTCGTTTAGTGAACCGTCAGATCGC<br>CTGGAGACGCCATCCACGCTGTTTTGACCTCCATAGAAGACACCGGGACCGATCCAGCCT<br>CCGCGGATTCGAATCCCGGCCGGGAACGGTGCATTGGAACGCGGATTCCCCGTGCCAAG<br>AGTGACGTAAGTACCGCCTATAGAGTCTATAGGCCCACAAAAAATGCTTTCTTCTTTTAAT<br>ATACTTTTTTGTTTATCTTATTTCTAATACTTTCCCTAATCTCTTTCTTTCAGGGCAATAATG<br>ATACAATGTATCATGCCTCTTTGCACCATTCTAAAGAATAACAGTGATAATTTCTGGGTTA<br>AGGCAATAGCAATATTTCTGCATATAAATATTTCTGCATATAAATTGTAACTGATGTAAG<br>AGGTTTCATATTGCTAATAGCAGCTACAATCCAGCTACCATTCTGCTTTTATTTTATGGTT<br>GGGATAAGGCTGGATTATTCTGAGTCCAAGCTAGGCCCTTTTGCTAATCATGTTCATACCT |

TABLE 12-continued

Sequences

| DESCRIPTION<br>SEQ ID NO: | NUCLEIC ACID SEQUENCE |
|---|---|
| | CTTATCTTCCTCCCACAGCTCCTGGGCAACGTGCTGGTCTGTGTGCTGGCCCATCACTTTG<br>GCAAAGAATTGGGATTCGAACCGGTCGCCACCGGTCACCAAGCAGGAAGTCAAAGACTT<br>TTTCCGGTGGGCAAAGGATCACGTGGTTGAGGTGGAGCATGAATTCTACGTCAAAAAGG<br>GTGGAGCCAAGAAAAGACCCGCCCCCAGTGACGCAGATATAAGTGAGCCCAAACGGGTG<br>CGCGAGTCAGTTGCGCAGCCATCGACGTCAGACGCGGAAGCTTCGATCAACTACGCGGA<br>CAGGTACCAAAACAAATGTTCTCGTCACGTGGGCATGAATCTGATGCTGTTTCCCTGCAG<br>ACAATGCGAGAGACTGAATCAGAATTCAAATATCTGCTTCACTCACGGTGTCAAAGACTG<br>TTTAGAGTGCTTTCCCGTGTCAGAATCTCAACCCGTTTCTGTCGTCAAAAAGGCGTATCAG<br>AAACTGTGCTACATTCATCACATCATGGGAAAGGTGCCAGACGCTTGCACTGCTTGCGAC<br>CTGGTCAATGTGGACTTGGATGACTGTGTTTCTGAACAATAAATGACTTAAACCAGGTAT<br>GGCTGCCGATGGTTATCTTCCAGATTGGCTCGAGGACAACCTTAGTGAAGGAATTCGCGA<br>GTGGTGGGCTTTGAAACCTGGAGCCCCTCAACCCAAGGCAAATCAACAACATCAAGACA<br>ACGCTCGAGGTCTTGTGCTTCCGGGTTACAAATACCTTGGACCCGGCAACGGACTCGACA<br>AGGGGGAGCCGGTCAACGCAGCAGACGCGGCGGCCCTCGAGCACGACAAGGCCTACGAC<br>CAGCAGCTCAAGGCCGGAGACAACCCGTACCTCAAGTACAACCACGCCGACGCCGAGTT<br>CCAGGAGCGGCTCAAAGAAGATACGTCTTTTGGGGGCAACCTCGGGCGAGCAGTCTTCCA<br>GGCCAAAAAGAGGCTTCTTGAACCTCTTGGTCTGGTTGAGGAAGCGGCTAAGACGGCTCC<br>TGGAAAGAAGAGGCCTGTAGAGCAGTCTCCTCAGGAACCGGACTCCTCCGCGGGTATTG<br>GCAAATCGGGTGCACAGCCCGCTAAAAAGAGACTCAATTTCGGTCAGACTGGCGACACA<br>GAGTCAGTCCCAGACCCTCAACCAATCGGAGAACCTCCCGCAGCCCCCTCAGGTGTGGGA<br>TCTCTTACAATGGCTTCAGGTGGTGGCGCACCAGTGGCAGACAATAACGAAGGTGCCGAT<br>GGAGTGGGTAGTTCCTCGGGAAATTGGCATTGCGATTCCCAATGGCTGGGGGACAGAGTC<br>ATCACCACCAGCACCCGAACCTGGGCCCTGCCCACCTACAACAATCACCTCTACAAGCAA<br>ATCTCCAACAGCACATCTGGAGGATCTTCAAATGACAACGCCTACTTCGGCTACAGCACC<br>CCCTGGGGGTATTTTGACTTCAACAGATTCCACTGCCACTTCTCACCACGTGACTGGCAGC<br>GACTCATCAACAACAACTGGGGATTCCGGCCTAAGCGACTCAACTTCAAGCTCTTCAACA<br>TTCAGGTCAAAGAGGTTACGGACAACAATGGAGTCAAGACCATCGCCAATAACCTTACC<br>AGCACGGTCCAGGTCTTCACGGACTCAGACTATCAGCTCCCGTACGTGCTCGGGTCGGCT<br>CACGAGGGCTGCCTCCCGCCGTTCCCAGCGGACGTTTTCATGATTCCTCAGTACGGGTATC<br>TGACGCTTAATGATGGAAGCCAGGCCGTGGGTCGTTCGTCCTTTTACTGCCTGGAATATTT<br>CCCGTCGCAAATGCTAAGAACGGGTAACAACTTCCAGTTCAGCTACGAGTTTGAGAACGT<br>ACCTTTCCATAGCAGCTACGCTCACAGCCAAAGCCTGGACCGACTAATGAATCCACTCAT<br>CGACCAATACTTGTACTATCTCTCAAAGACTATTAACGGTTCTGGACAGAATCAACAAAC<br>GCTAAAATTCAGTGTGGCCGGACCCAGCAACATGGCTGTCCAGGGAAGAAACTACATAC<br>CTGGACCCAGCTACCGACAACAACGTGTCTCAACCACTGTGACTCAAAACAACAACAGC<br>GAATTTGCTTGGCCTGGAGCTTCTTCTTGGGCTCTCAATGGACGTAATAGCTTGATGAATC<br>CTGGACCTGCTATGGCCAGCCACAAAGAAGGAGAGGACCGTTTCTTTCCTTTGTCTGGAT<br>CTTTAATTTTTGGCAAACAAGGAACTGGAAGAGACAACGTGGATGCGGACAAAGTCATG<br>ATAACCAACGAAGAAGAAATTAAAACTACTAACCCGGTAGCAACGGAGTCCTATGGACA<br>AGTGGCCACAAACCACCAGAGTGCCCAAGCACAGGCGCAGACCGGCTGGGTTCAAAACC<br>AAGGAATACTTCCGGGTATGGTTTGGCAGGACAGAGATGTGTACCTGCAAGGACCCATTT<br>GGGCCAAAATTCCTCACACGGACGGCAACTTTCACCCTTCTCCGCTGATGGGAGGGTTTG<br>GAATGAAGCACCCGCCTCCTCAGATCCTCATCAAAAACACACCTGTACCTGCGGATCCTC<br>CAACGGCCTTCAACAAGGACAAGCTGAACTCTTTCATCACCCAGTATTCTACTGGCCAAG<br>TCAGCGTGGAGATCGAGTGGGAGCTGCAGAAGGAAAACAGCAAGCGCTGGAACCCGGA<br>GATCCAGTACACTTCCAACTATTACAAGTCTAATAATGTTGAATTTGCTGTTAATACTGAA<br>GGTGTATATAGTGAACCCCGCCCCATTGGCACCAGATACCTGACTCGTAATCTGTAATCG<br>ATTGTTAATCAATAAACCGTTTAATTCGTTTCAGTTGAACTTTGGTCTCTGCGTATTTCTTT<br>CTTATCTAGTTTCCATGGCTACGTAGATAAGTAGCATGGCGGGTTAATCATTAACTACAA<br>GGAACCCCTAGTGATGGAGTTGGCCACTCCCTCTCTGCGCGCTCGCTCGCTCACTGAGGC<br>CGGGCGACCAAAGGTCGCCCGACGCCCGGGCTTTGCCCGGGCGGCCTCAGTGAGCGAGC<br>GAGCGCGCAGAGAGGGAGTGGCCAA |
| GLOSPLICEF6<br>SEQ ID NO: 13 | GTGCCAAGAGTGACCTCCTG |
| CAP5L8<br>GBLOCKSEQ<br>ID NO: 14 | ACTGCCCCCGCGACCGGCACGTACAACCTCCAGGAAATCGTGCCCGGCAGCGTGTGGATG<br>GAGAGGGACGTGTACCTCCAAGGACCCATCTGGGCCAAGATCCCAGAGACGGGGGCGCA<br>CTTTCACCCCTCTCCGGCTATGGGCGGATTCGGACTCAAACACCCACCGCCCATGATGCTC<br>ATCAAGAACACGCCTGTGCCCGGAAATATCACCAGCTTCTCGGACGTGCCCGTCAGCAGC<br>TTCATCACCCAGTACAGCACCGGGCAGGTCACCGTGGAGATGGAGTGGGAGCTCAAGAA<br>GGAAAACTCCAAGAGGTGGAACCCAGAGATCCAGTACACAAACAACTACAACGACCCCC<br>AGTTTGTGGACTTTGCCCCGGACAGCACCGGGGAATACAGAACCACCAGACCTATCGGA<br>ACCCGATACCTTACCCGACCCCTTTAA |
| CAP6L8<br>GBLOCKSEQ<br>ID NO: 15 | ACCGGAGATGTGCATGTTATGGGAGCCTTACCTGGAATGGTGTGGCAAGACAGGGACGT<br>CTACCTGCAGGGTCCTATTTGGGCCAAAATTCCTCACACGGATGGACACTTTCACCCATCT<br>CCTCTCATGGGCGGCTTTGGACTTAAGCACCCGCCTCCTCAGATCCTCATCAAAAACACG<br>CCTGTTCCTGCGAATCCTCCGGCAGAGTTTTCGGCTACAAAGTTTGCTTCATTCATCACCC<br>AGTATTCCACAGGACAAGTGAGCGTGGAGATTGAATGGGAGCTGCAGAAAGAAAACAGC<br>AAACGCTGGAATCCCGAAGTGCAATATACATCTAACTATGCAAAATCTGCCAACGTTGAT<br>TTCACTGTGGACAACAATGGACTTTATACTGAGCCTCGCCCCATTGGCACCCGTTACCTCA<br>CCCGTCCCCTGTAATCGAT |

TABLE 12-continued

| Sequences | |
|---|---|
| DESCRIPTION SEQ ID NO: | NUCLEIC ACID SEQUENCE |
| CAPDJ8L8 GBLOCKSEQ ID NO: 16 | ACACAAGCAGCTACCGCAGATGTCAACACACAAGGCGTTCTTCCAGGCATGGTCTGGCAG<br>GACAGAGATGTGTACCTTCAGGGGCCCATCTGGGCAAAGATTCCACACACGGACGGACA<br>TTTTCACCCCTCTCCCCTCATGGGTGGATTCGGACTTAAACACCCTCCGCCTCAGATCCTG<br>ATCAAGAACACGCCTGTACCTGCGGACCCTCCGACCACCTTCAACCAGTCAAAGCTGAAC<br>TCTTTCATCACCCAGTATTCTACTGGCCAAGTCAGCGTGGAGATCGAGTGGGAGCTGCAG<br>AAGGAAAACAGCAAGCGCTGGAACCCCGAGATCCAGTACACCTCCAACTACTACAAATC<br>TACAAGTGTGGACTTTGCTGTTAATACAGAAGGCGTGTACTCTGAACCCCGCCCCATTGG<br>CACCCGTTACCTCACCCGTAATCTGTAA |
| CAP9L8M GBLOCKSEQ ID NO: 17 | GCACAGGCGCAGACCGGCTGGGTTCAAAACCAAGGAATACTTCCGGGTATGGTTTGGCA<br>GGACAGAGATGTGTACCTGCAAGGACCCATTTGGGCCAAAATTCCTCACACGGACGGCA<br>ACTTTCACCCTTCTCCGCTGATGGGAGGGTTTGGAATGAAGCACCCGCCTCCTCAGATCCT<br>CATCAAAAACACACCTGTACCTGCCGATCCTCCAACGGCCTTCAACAAGGACAAGCTGAA<br>CTCTTTCATCACCCAGTATTCTACTGGCCAAGTCAGCGTGGAGATCGAGTGGGAGCTGCA<br>GAAGGAAAACAGCAAGCGGTGGAACCCGGAGATCCAGTACACTTCCAACTATTACAAGT<br>CTAATAATGTTGAATTTGCTGTTAATACTGAAGGTGTATATAGTGAACCCCGCCCCATTGG<br>CACCAGATACCTGACTCGTAATCTGTAA |
| TELN-SYNG9-BSRGI SEQ ID NO: 18 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTTAGTATCTGCAGAGGGCCCTG<br>CGTATGAGTGCAAGTGGGTTTTAGGACCAGGATGAGGCGGGGTGGGGGTGCCTACCTGA<br>CGACCGACCCCGACCCACTGGACAAGCACCCAACCCCCATTCCCCAAATTGCGCATCCCC<br>TATCAGAGAGGGGGAGGGGAAACAGGATGCGGCGAGGCGCGTGCGCACTGCCAGCTTCA<br>GCACCGCGGACAGTGCCTTCGCCCCCGCCTGGCGGCGCGCGCCACCGCCGCCTCAGCACT<br>GAAGGCGCGCTGACGTCACTCGCCGGTCCCCCGCAAACTCCCCTTCCCGGCCACCTTGGT<br>CGCGTCCGCGCCGCCGCCGGCCCAGCCGGACCGCACCACGCGAGGCGCGAGATAGGGGG<br>GCACGGGCGCGACCATCTGCGCTGCGGCGCCGGCGACTCAGCGCTGCCTCAGTCTGCGGT<br>GGGCAGCGGAGGAGTCGTGTCGTGCCTGAGAGCGCAGCTGTGCTCCTGGGCACCGCGCA<br>GTCCGCCCCCGCGGCTCCTGGCCAGACCACCCCTAGGACCCCCTGCCCCAAGTCGCAGCC<br>AAGCTTCGTTTAGTGAACCGTCAGATCGCCTGGAGACGCCATCCACGCTGTTTTGACCTCC<br>ATAGAAGACACCGGGACCGATCCAGCCTCCGCGGATTCGAATCCCGGCCGGGAACGGTG<br>CATTGGAACGCGGATTCCCCGTGCCAAGAGTGACGTAAGTACCGCCTATAGAGTCTATAG<br>GCCCACAAAAAATGCTTTCTTCTTTTAATATACTTTTTTGTTTATCTTATTTCTAATACTTTC<br>CCTAATCTCTTTCTTTCAGGGCAATAATGATACAATGTATCATGCCTCTTTGCACCATTCT<br>AAAGAATAACAGTGATAATTTCTGGGTTAAGGCAATAGCAATATTTCTGCATATAAATAT<br>TTCTGCATATAAATTGTAACTGATGTAAGAGGTTTCATATTGCTAATAGCAGCTACAATCC<br>AGCTACCATTCTGCTTTTATTTTATGGTTGGGATAAGGCTGGATTATTCTGAGTCCAAGCT<br>AGGCCCTTTTGCTAATCATGTTCATACCTCTTATCTTCCTCCCACAGCTCCTGGGCAACGT<br>GCTGGTCTGTGTGCTGGCCCATCACTTTGGCAAAGAATTGGGATTCGAACCGGTCGCCAC<br>CGGTCACCAAGCAGGAAGTCAAAGACTTTTTCCGGTGGGCAAAGGATCACGTGGTTGAG<br>GTGGAGCATGAATTCTACGTCAAAAAGGGTGGAGCCAAGAAAAGACCCGCCCCCAGTGA<br>CGCAGATATAAGTGAGCCCAAACGGGTGCGCGAGTCAGTTGCGCAGCCATCGACGTCAG<br>ACGCGGAAGCTTCGATCAACTACGCGGACAGGTACCAAAACAAATGTTCTCGTCACGTGG<br>GCATGAATCTGATGCTGTTTCCCTGCAGACAATGCGAGAGACTGAATCAGAATTCAAATA<br>TCTGCTTCACTCACGGTGTCAAAGACTGTTTAGAGTGCTTTCCCGTGTCAGAATCTCAACC<br>CGTTTCTGTCGTCAAAAAGGCGTATCAGAAACTGTGCTACATTCATCACATCATGGGAAA<br>GGTGCCAGACGCTTGCACTGCTTGCGACCTGGTCAATGTGGACTTGGATGACTGTGTTTCT<br>GAACAATAAATGACTTAAACCAGGTATGGCTGCCGATGGTTATCTTCCAGATTGGCTCGA<br>GGACAACCTTAGTGAAGGAATTCGCGAGTGGTGGGCTTTGAAACCTGGAGCCCCTCAACC<br>CAAGGCAAATCAACAACATCAAGACAACGCTCGAGGTCTTGTGCTTCCGGGTTACAAATA<br>CCTTGGACCCGGCAACGGACTCGACAAGGGGGAGCCGGTCAACGCAGCAGACGCGGCGG<br>CCCTCGAGCACGACAAGGCCTACGACCAGCAGCTCAAGGCCGGAGACAACCCGTACCTC<br>AAGTACAACCACGCCGACGCCGAGTTCCAGGAGCGGCTCAAAGAAGATACGTCTTTTGG<br>GGGCAACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTCCTC<br>AGGAACCGGACTCCTCCGCGGGTATTGGCAAATCGGGTGCACAGCCCGCTAAAAAGAGA<br>CTCAATTTCGGTCAGACTGGCGACACAGAGTCAGTCCCAGACCCTCAACCAATCGGAGAA<br>CCTCCCGCAGCCCCCTCAGGTGTGGGATCTCTTACAATGGCTTCAGGTGGTGGCGCACCA<br>GTGGCAGACAATAACGAAGGTGCCGATGGAGTGGGTAGTTCCTCGGGAAATTGGCATTG<br>CGATTCCCAATGGCTGGGGGACAGAGTCATCACCACCAGCACCCGAACCTGGGCCCTGCC<br>CACCTACAACAATCACCTCTACAAGCAAATCTCCAACAGCACATCTGGAGGATCTTCAAA<br>TGACAACGCCTACTTCGGCTACAGCACCCCCTGGGGGTATTTTGACTTCAACAGATTCCA<br>CTGCCACTTCTCACCACGTGACTGGCAGCGACTCATCAACAACAACTGGGGATTCCGGCC<br>TAAGCGACTCAACTTCAAGCTCTTCAACATTCAGGTCAAAGAGGTTACGGACAACAATGG<br>AGTCAAGACCATCGCCAATAACCTTACCAGCACGGTCCAGGTCTTCACGGACTCAGACTA<br>TCAGCTCCCGTACGTGCTCGGGTCGGCTCACGAGGGCTGCCTCCCGCCGTTCCCAGCGGA<br>CGTTTTCATGATTCCTCAGTACGGGTATCTGACGCTTAATGATGGAAGCCAGGCCGTGGG<br>TCGTTCGTCCTTTTACTGCCTGGAATATTTCCCGTCGCAAATGCTAAGAACGGGTAACAAC |

TABLE 12-continued

| Sequences | |
|---|---|
| DESCRIPTION<br>SEQ ID NO: | NUCLEIC ACID SEQUENCE |
| | TTCCAGTTCAGCTACGAGTTTGAGAACGTACCTTTCCATAGCAGCTACGCTCACAGCCAA |
| | AGCCTGGACCGACTAATGAATCCACTCATCGACCAATACTTGTACTATCTCTCAAAGACT |
| | ATTAACGGTTCTGGACAGAATCAACAAACGCTAAAATTCAGTGTGGCCGGACCCAGCAA |
| | CATGGCTGTCCAGGGAAGAAACTACATACCTGGACCCAGCTACCGACAACAACGTGTCTC |
| | AACCACTGTGACTCAAAACAACAACAGCGAATTTGCTTGGCCTGGAGCTTCTTCTTGGGC |
| | TCTCAATGGACGTAATAGCTTGATGAATCCTGGACCTGCTATGGCCAGCCACAAAGAAGG |
| | AGAGGACCGTTTCTTTCCTTTGTCTGGATCTTTAATTTTTGGCAAACAAGGAACTGGAAGA |
| | GACAACGTGGATGCGGACAAAGTCATGATAACCAACGAAGAAGAAATTAAAACTACTAA |
| | CCCGGTAGCAACGGAGTCCTATGGACAAGTGGCCACAAACCACCAGAGTGTACATCGAT |
| | TGTTAATCAATAAACCGTTTAATTCGTTTCAGTTGAACTTTGGTCTCTGCGTATTTCTTTCT |
| | TATCTAGTTTCCATGGCTACGTAGATAAGTAGCATGGCGGGTTAATCATTAACTACAAGG |
| | AACCCCTAGTGATGGAGTTGGCCACTCCCTCTCTGCGCGCTCGCTCGCTCACTGAGGCCG |
| | GGCGACCAAAGGTCGCCCGACGCCCGGGCTTTGCCCGGGCGGCCTCAGTGAGCGAGCGA |
| | GCGCGCAGAGAGGGAGTGGCCAAGCATGCAATTAACTGGCCGTCGTTTTACAACGTCGTG |
| | ACTGGGAAAACCCTGGCGTTACCCAACTTAATCGCCTTGCAGCACATCCCCCTTTCGCCA |
| | GCTGTATCAGCACACAATTGCCCATTATACGCGCGTATAATGGACTATTGTGTGCTGATA |
| TELN- | TATCAGCACACAATAGTCCATTATACGCGCGTATAATGGGCAATTGTGTGCTGATACAGC |
| GFAPG9- | TGGCACGACAGGTTTCCCGACTGGAAAGCGGGCAGTGAGCGCAACGCAATTAATGTGAG |
| BSRGI SEQ ID | TTAGCTCACTCATTAGGCACCCCAGGCTTTACACTTTATGCTTCCGGCTCGTATGTTGTGT |
| NO: 19 | GGAATTGTGAGCGGATAACAATTTCACACAGGAAACAGCTATGACCATGATTACGCCAG |
| | ATTTAATTAAGGCCTTAATTAGGCTAGCTTGGCCACTCCCTCTCTGCGCGCTCGCTCGCTC |
| | ACTGAGGCCGGGCGACCAAAGGTCGCCCGACGCCCGGGCTTTGCCCGGGCGGCCTCAGT |
| | GAGCGAGCGAGCGCGCAGAGAGGGAGTGGCCAACTCCATCACTAGGGGTTCCTGGAGGG |
| | GTGGAGTCGTGACGATATCCATGCGTCGACATAACGCGTGATCTAACATATCCTGGTGTG |
| | GAGTAGCGGACGCTGCTATGACAGAGGCTCGGGGGCCTGAGCTGGCTCTGTGAGCTGGG |
| | GAGGAGGCAGACAGCCAGGCCTTGTCTGCAAGCAGACCTGGCAGCATTGGGCTGGCCGC |
| | CCCCCAGGGCCTCCTCTTCATGCCCAGTGAATGACTCACCTTGGCACAGACACAATGTTC |
| | GGGGTGGGCACAGTGCCTGCTTCCCGCCGCACCCCAGCCCCCCTCAAATGCCTTCCGAGA |
| | AGCCCATTGAGCAGGGGGCTTGCATTGCACCCCAGCCTGACAGCCTGGCATCTTGGGATA |
| | AAAGCAGCACAGCCCCCTAGGGGCTGCCCTTGCTGTGTGGCGCCACCGGCGGTGGAGAA |
| | CAAGGCTCTATTCAGCCTGTGCCCAGGAAAGGGGATCAGGGGATGCCCAGGCATGGACA |
| | GTGGGTGGCAGGGGGGGAGAGGAGGGCTGTCTGCTTCCCAGAAGTCCAAGGACACAAAT |
| | GGGTGAGGGGAGAGCTCTCCCCATAGCTGGGCTGCGGCCCAACCCCACCCCCTCAGGCTA |
| | TGCCAGGGGGTGTTGCCAGGGGCACCCGGGCATCGCCAGTCTAGCCCACTCCTTCATAAA |
| | GCCCTCGCATCCCAGGAGCGAGCAGAGCCAGAGCAGGTTGGAGAGGAGACGCATCACCT |
| | CCGCTGCTCGCGGGGATCCTCTAGAAGCTTCGTTTAGTGAACCGTCAGATCGCCTGGAGA |
| | CGCCATCCACGCTGTTTTGACCTCCATAGAAGACACCGGGACCGATCCAGCCTCCGCGGA |
| | TTCGAATCCCGGCCGGGAACGGTGCATTGGAACGCGGATTCCCCGTGCCAAGAGTGACGT |
| | AAGTACCGCCTATAGAGTCTATAGGCCCACAAAAAATGCTTTCTTCTTTTAATATACTTTT |
| | TTGTTTATCTTATTTCTAATACTTTCCCTAATCTCTTTCTTTCAGGGCAATAATGATACAAT |
| | GTATCATGCCTCTTTGCACCATTCTAAAGAATAACAGTGATAATTTCTGGGTTAAGGCAAT |
| | AGCAATATTTCTGCATATAAATATTTCTGCATATAAATTGTAACTGATGTAAGAGGTTTCA |
| | TATTGCTAATAGCAGCTACAATCCAGCTACCATTCTGCTTTTATTTTATGGTTGGGATAAG |
| | GCTGGATTATTCTGAGTCCAAGCTAGGCCCTTTTGCTAATCATGTTCATACCTCTTATCTTC |
| | CTCCCACAGCTCCTGGGCAACGTGCTGGTCTGTGTGCTGGCCCATCACTTTGGCAAAGAA |
| | TTGGGATTCGAACCGGTCGCCACCGGTCACCAAGCAGGAAGTCAAAGACTTTTTCCGGTG |
| | GGCAAAGGATCACGTGGTTGAGGTGGAGCATGAATTCTACGTCAAAAAGGGTGGAGCCA |
| | AGAAAAGACCCGCCCCCAGTGACGCAGATATAAGTGAGCCCAAACGGGTGCGCGAGTCA |
| | GTTGCGCAGCCATCGACGTCAGACGCGGAAGCTTCGATCAACTACGCGGACAGGTACCA |
| | AAACAAATGTTCTCGTCACGTGGGCATGAATCTGATGCTGTTTCCCTGCAGACAATGCGA |
| | GAGACTGAATCAGAATTCAAATATCTGCTTCACTCACGGTGTCAAAGACTGTTTAGAGTG |
| | CTTTCCCGTGTCAGAATCTCAACCCGTTTCTGTCGTCAAAAAGGCGTATCAGAAACTGTGC |
| | TACATTCATCACATCATGGGAAAGGTGCCAGACGCTTGCACTGCTTGCGACCTGGTCAAT |
| | GTGGACTTGGATGACTGTGTTTCTGAACAATAAATGACTTAAACCAGGTATGGCTGCCGA |
| | TGGTTATCTTCCAGATTGGCTCGAGGACAACCTTAGTGAAGGAATTCGCGAGTGGTGGGC |
| | TTTGAAACCTGGAGCCCCTCAACCCAAGGCAAATCAACAACATCAAGACAACGCTCGAG |
| | GTCTTGTGCTTCCGGGTTACAAATACCTTGGACCCGGCAACGGACTCGACAAGGGGGAGC |
| | CGGTCAACGCAGCAGACGCGGCGGCCCTCGAGCACGACAAGGCCTACGACCAGCAGCTC |
| | AAGGCCGGAGACAACCCGTACCTCAAGTACAACCACGCCGACGCCGAGTTCCAGGAGCG |
| | GCTCAAAGAAGATACGTCTTTTGGGGGCAACCTCGGGCGAGCAGTCTTCCAGGCCAAAA |
| | AGAGGCTTCTTGAACCTCTTGGTCTGGTTGAGGAAGCGGCTAAGACGGCTCCTGGAAAGA |
| | AGAGGCCTGTAGAGCAGTCTCCTCAGGAACCGGACTCCTCCGCGGGTATTGGCAAATCGG |
| | GTGCACAGCCCGCTAAAAAGAGACTCAATTTCGGTCAGACTGGCGACACAGAGTCAGTC |
| | CCAGACCCTCAACCAATCGGAGAACCTCCCGCAGCCCCCTCAGGTGTGGGATCTCTTACA |
| | ATGGCTTCAGGTGGTGGCGCACCAGTGGCAGACAATAACGAAGGTGCCGATGGAGTGGG |
| | TAGTTCCTCGGGAAATTGGCATTGCGATTCCCAATGGCTGGGGGACAGAGTCATCACCAC |
| | CAGCACCCGAACCTGGGCCCTGCCCACCTACAACAATCACCTCTACAAGCAAATCTCCAA |
| | CAGCACATCTGGAGGATCTTCAAATGACAACGCCTACTTCGGCTACAGCACCCCCTGGGG |
| | GTATTTTGACTTCAACAGATTCCACTGCCACTTCTCACCACGTGACTGGCAGCGACTCATC |
| | AACAACAACTGGGGATTCCGGCCTAAGCGACTCAACTTCAAGCTCTTCAACATTCAGGTC |
| | AAAGAGGTTACGGACAACAATGGAGTCAAGACCATCGCCAATAACCTTACCAGCACGGT |
| | CCAGGTCTTCACGGACTCAGACTATCAGCTCCCGTACGTGCTCGGGTCGGCTCACGAGGG |
| | CTGCCTCCCGCCGTTCCCAGCGGACGTTTTCATGATTCCTCAGTACGGGTATCTGACGCTT |
| | AATGATGGAAGCCAGGCCGTGGGTCGTTCGTCCTTTTACTGCCTGGAATATTTCCCGTCGC |

TABLE 12-continued

| Sequences | |
|---|---|
| DESCRIPTION SEQ ID NO: | NUCLEIC ACID SEQUENCE |
| | AAATGCTAAGAACGGGTAACAACTTCCAGTTCAGCTACGAGTTTGAGAACGTACCTTTCC<br>ATAGCAGCTACGCTCACAGCCAAAGCCTGGACCGACTAATGAATCCACTCATCGACCAAT<br>ACTTGTACTATCTCTCAAAGACTATTAACGGTTCTGGACAGAATCAACAAACGCTAAAAT<br>TCAGTGTGGCCGGACCCAGCAACATGGCTGTCCAGGGAAGAAACTACATACCTGGACCC<br>AGCTACCGACAACAACGTGTCTCAACCACTGTGACTCAAAACAACAACAGCGAATTTGCT<br>TGGCCTGGAGCTTCTTCTTGGGCTCTCAATGGACGTAATAGCTTGATGAATCCTGGACCTG<br>CTATGGCCAGCCACAAAGAAGGAGAGGACCGTTTCTTTCCTTTGTCTGGATCTTTAATTTT<br>TGGCAAACAAGGAACTGGAAGAGACAACGTGGATGCGGACAAAGTCATGATAACCAACG<br>AAGAAGAAATTAAAACTACTAACCCGGTAGCAACGGAGTCCTATGGACAAGTGGCCACA<br>AACCACCAGAGTGTACATCGATTGTTAATCAATAAACCGTTTAATTCGTTTCAGTTGAACT<br>TTGGTCTCTGCGTATTTCTTTCTTATCTAGTTTCCATGGCTACGTAGATAAGTAGCATGGC<br>GGGTTAATCATTAACTACAAGGAACCCCTAGTGATGGAGTTGGCCACTCCCTCTCTGCGC<br>GCTCGCTCGCTCACTGAGGCCGGGCGACCAAAGGTCGCCCGACGCCCGGGCTTTGCCCGG<br>GCGGCCTCAGTGAGCGAGCGAGCGCGCAGAGAGGGAGTGGCCAAGCATGCAATTAACTG<br>GCCGTCGTTTTACAACGTCGTGACTGGGAAAACCCTGGCGTTACCCAACTTAATCGCCTT<br>GCAGCACATCCCCCTTTCGCCAGCTGTATCAGCACACAATTGCCCATTATACGCGCGTAT<br>AATGGACTATTGTGTGCTGATA |
| TELN-SYNG5-BSRGI SEQ ID NO: 20 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTTAGTATCTGCAGAGGGCCCTG<br>CGTATGAGTGCAAGTGGGTTTTAGGACCAGGATGAGGCGGGGTGGGGGTGCCTACCTGA<br>CGACCGACCCCGACCCACTGGACAAGCACCCAACCCCCATTCCCCAAATTGCGCATCCCC<br>TATCAGAGAGGGGGAGGGGAAACAGGATGCGGCGAGGCGCGTGCGCACTGCCAGCTTCA<br>GCACCGCGGACAGTGCCTTCGCCCCCGCCTGGCGGCGCGCGCCACCGCCGCCTCAGCACT<br>GAAGGCGCGCTGACGTCACTCGCCGGTCCCCCGCAAACTCCCCTTCCCGGCCACCTTGGT<br>CGCGTCCGCGCCGCCGCCGGCCCAGCCGGACCGCACCACGCGAGGCGCGAGATAGGGGG<br>GCACGGGCGCGACCATCTGCGCTGCGGCGCCGGCGACTCAGCGCTGCCTCAGTCTGCGGT<br>GGGCAGCGGAGGAGTCGTGTCGTGCCTGAGAGCGCAGCTGTGCTCCTGGGCACCGCGCA<br>GTCCGCCCCCGCGGCTCCTGGCCAGACCACCCCTAGGACCCCCTGCCCCAAGTCGCAGCC<br>AAGCTTCGTTTAGTGAACCGTCAGATCGCCTGGAGACGCCATCCACGCTGTTTTGACCTCC<br>ATAGAAGACACCGGGACCGATCCAGCCTCCGCGGATTCGAATCCCGGCCGGGAACGGTG<br>CATTGGAACGCGGATTCCCCGTGCCAAGAGTGACGTAAGTACCGCCTATAGAGTCTATAG<br>GCCCACAAAAAATGCTTTCTTCTTTTAATATACTTTTTTGTTTATCTTATTTCTAATACTTTC<br>CCTAATCTCTTTCTTTCAGGGCAATAATGATACAATGTATCATGCCTCTTTGCACCATTCT<br>AAAGAATAACAGTGATAATTTCTGGGTTAAGGCAATAGCAATATTTCTGCATATAAATAT<br>TTCTGCATATAAATTGTAACTGATGTAAGAGGTTTCATATTGCTAATAGCAGCTACAATCC<br>AGCTACCATTCTGCTTTTATTTTATGGTTGGGATAAGGCTGGATTATTCTGAGTCCAAGCT<br>AGGCCCTTTTGCTAATCATGTTCATACCTCTTATCTTCCTCCCACAGCTCCTGGGCAACGT<br>GCTGGTCTGTGTGCTGGCCCATCACTTTGGCAAAGAATTGGGATTCGAACCGGTCGCCAC<br>CGGTCACAAGCAGGAAGTCAAAGACTTTTTCCGGTGGGCAAAGGATCACGTGGTTGAGG<br>TGGAGCATGAATTCTACGTCAAAAAGGGTGGAGCCAAGAAAAGACCCGCCCCCAGTGAC<br>GCAGATATAAGTGAGCCCAAACGGGTGCGCGAGTCAGTTGCGCAGCCATCGACGTCAGA<br>CGCGGAAGCTTCGATCAACTACGCGGACAGGTACCAAAACAAATGTTCTCGTCACGTGGG<br>CATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACC<br>CGTTTCTGTCGTCAAAAAGGCGTATCAGAAACTGTGCTACATTCATCATATCATGGGAAA<br>GGTGCCAGACGCTTGCACTGCCTGCGATCTGGTCAATGTGGATTTGGATGACTGCATCTTT<br>GAACAATAAATGATTTAAATCAGGTATGTCTTTTGTTGATCACCCTCCAGATTGGTTGGAA<br>GAAGTTGGTGAAGGTCTTCGCGAGTTTTTGGGCCTTGAAGCGGGCCCACCGAAACCAAAA<br>CCCAATCAGCAGCATCAAGATCAAGCCCGTGGTCTTGTGCTGCCTGGTTATAACTATCTC<br>GGACCCGGAAACGGTCTCGATCGAGGAGAGCCTGTCAACAGGGCAGACGAGGTCGCGCG<br>AGAGCACGACATCTCGTACAACGAGCAGCTTGAGGCGGGAGACAACCCCTACCTCAAGT<br>ACAACCACGCGGACGCCGAGTTTCAGGAGAAGCTCGCCGACGACACATCCTTCGGGGGA<br>AACCTCGGAAAGGCAGTCTTTCAGGCCAAGAAAAGGGTTCTCGAACCTTTTGGCCTGGTT<br>GAAGAGGGTGCTAAGACGGCCCCTACCGGAAAGCGGATAGACGACCACTTTCCAAAAAG<br>AAAGAAGGCCCGGACCGAAGAGGACTCCAAGCCTTCCACCTCGTCAGACGCCGAAGCTG<br>GACCCAGCGGATCCCAGCAGCTGCAAATCCCAGCCCAACCAGCCTCAAGTTTGGGAGCTG<br>ATACAATGTCTGCGGGAGGTGGCGGCCCATTGGGCGACAATAACCAAGGTGCCGATGGA<br>GTGGGCAATGCCTCGGGAGATTGGCATTGCGATTCCACGTGGATGGGGGACAGAGTCGTC<br>ACCAAGTCCACCCGAACCTGGGTGCTGCCCAGCTACAACAACCACCAGTACCGAGAGAT<br>CAAAAGCGGCTCCGTCGACGGAAGCAACGCCAACGCCTACTTTGGATACAGCACCCCCTG<br>GGGGTACTTTGACTTTAACCGCTTCCACAGCCACTGGAGCCCCCGAGACTGGCAAAGACT<br>CATCAACAACTACTGGGGCTTCAGACCCCGGTCCCTCAGAGTCAAAATCTTCAACATTCA<br>AGTCAAAGAGGTCACGGTGCAGGACTCCACCACCACCATCGCCAACAACCTCACCTCCAC<br>CGTCCAAGTGTTTACGGACGACGACTACCAGCTGCCCTACGTCGTCGGCAACGGGACCGA<br>GGGATGCCTGCCGGCCTTCCCTCCGCAGGTCTTTACGCTGCCGCAGTACGGTTACGCGAC<br>GCTGAACCGCGACAACACAGAAAATCCCACCGAGAGGAGCAGCTTCTTCTGCCTAGAGT<br>ACTTTCCCAGCAAGATGCTGAGAACGGGCAACAACTTTGAGTTTACCTACAACTTTGAGG<br>AGGTGCCCTTCCACTCCAGCTTCGCTCCCAGTCAGAACCTCTTCAAGCTGGCCAACCCGCT |

TABLE 12-continued

| Sequences | |
|---|---|
| DESCRIPTION SEQ ID NO: | NUCLEIC ACID SEQUENCE |
| | GGTGGACCAGTACTTGTACCGCTTCGTGAGCACAAATAACACTGGCGGAGTCCAGTTCAA<br>CAAGAACCTGGCCGGGAGATACGCCAACACCTACAAAAACTGGTTCCCGGGGCCCATGG<br>GCCGAACCCAGGGCTGGAACCTGGGCTCCGGGGTCAACCGCGCCAGTGTCAGCGCCTTCG<br>CCACGACCAATAGGATGGAGCTCGAGGGCGCGAGTTACCAGGTGCCCCCGCAGCCGAAC<br>GGCATGACCAACAACCTCCAGGGCAGCAACACCTATGCCCTGGAGAACACTATGATCTTC<br>AACAGCCAGCCGGCGAACCCGGGCACCACCGCCACGTACCTCGAGGGCAACATGCTCAT<br>CACCAGCGAGAGCGAGACGCAGCCGGTGAACCGCGTGGCGTACAACGTCGGCGGGCAGA<br>TGGCCACCAACAACCAGAGCTCTGTACATCGATTGTTAATCAATAAACCGTTTAATTCGTT<br>TCAGTTGAACTTTGGTCTCTGCGTATTTCTTTCTTATCTAGTTTCCATGGCTACGTAGATAA<br>GTAGCATGGCGGGTTAATCATTAACTACAAGGAACCCCTAGTGATGGAGTTGGCCACTCC<br>CTCTCTGCGCGCTCGCTCGCTCACTGAGGCCGGGCGACCAAAGGTCGCCCGACGCCCGGG<br>CTTTGCCCGGGCGGCCTCAGTGAGCGAGCGAGCGCGCAGAGAGGGAGTGGCCAAGCATG<br>CAATTAACTGGCCGTCGTTTTACAACGTCGTGACTGGGAAAACCCTGGCGTTACCCAACT<br>TAATCGCCTTGCAGCACATCCCCCTTTCGCCAGCTGTATCAGCACACAATTGCCCATTATA<br>CGCGCGTATAATGGACTATTGTGTGCTGATA |
| TELN-GFAPG5-BSRGI SEQ ID NO: 21 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTGATCTAACATATCCTGGTGTG<br>GAGTAGCGGACGCTGCTATGACAGAGGCTCGGGGGCCTGAGCTGGCTCTGTGAGCTGGG<br>GAGGAGGCAGACAGCCAGGCCTTGTCTGCAAGCAGACCTGGCAGCATTGGGCTGGCCGC<br>CCCCCAGGGCCTCCTCTTCATGCCCAGTGAATGACTCACCTTGGCACAGACACAATGTTC<br>GGGGTGGGCACAGTGCCTGCTTCCCGCCGCACCCCAGCCCCCCTCAAATGCCTTCCGAGA<br>AGCCCATTGAGCAGGGGGCTTGCATTGCACCCCAGCCTGACAGCCTGGCATCTTGGGATA<br>AAAGCAGCACAGCCCCCTAGGGGCTGCCCTTGCTGTGTGGCGCCACCGGCGGTGGAGAA<br>CAAGGCTCTATTCAGCCTGTGCCCAGGAAAGGGGATCAGGGGATGCCCAGGCATGGACA<br>GTGGGTGGCAGGGGGGGAGAGGAGGGCTGTCTGCTTCCCAGAAGTCCAAGGACACAAAT<br>GGGTGAGGGGAGAGCTCTCCCCATAGCTGGGCTGCGGCCCAACCCCACCCCCTCAGGCTA<br>TGCCAGGGGGTGTTGCCAGGGGCACCCGGGCATCGCCAGTCTAGCCCACTCCTTCATAAA<br>GCCCTCGCATCCCAGGAGCGAGCAGAGCCAGAGCAGGTTGGAGAGGAGACGCATCACCT<br>CCGCTGCTCGCGGGGATCCTCTAGAAGCTTCGTTTAGTGAACCGTCAGATCGCCTGGAGA<br>CGCCATCCACGCTGTTTTGACCTCCATAGAAGACACCGGGACCGATCCAGCCTCCGCGGA<br>TTCGAATCCCGGCCGGGAACGGTGCATTGGAACGCGGATTCCCCGTGCCAAGAGTGACGT<br>AAGTACCGCCTATAGAGTCTATAGGCCCACAAAAAATGCTTTCTTCTTTTAATATACTTTT<br>TTGTTTATCTTATTTCTAATACTTTCCCTAATCTCTTTCTTTCAGGGCAATAATGATACAAT<br>GTATCATGCCTCTTTGCACCATTCTAAAGAATAACAGTGATAATTTCTGGGTTAAGGCAAT<br>AGCAATATTTCTGCATATAAATATTTCTGCATATAAATTGTAACTGATGTAAGAGGTTTCA<br>TATTGCTAATAGCAGCTACAATCCAGCTACCATTCTGCTTTTATTTTATGGTTGGGATAAG<br>GCTGGATTATTCTGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTTTGGCAAAGAA<br>TTGGGATTCGAACCGGTCGCCACCGGTCACCAAGCAGGAAGTCAAAGACTTTTTCCGGTG<br>GGCAAAGGATCACGTGGTTGAGGTGGAGCATGAATTCTACGTCAAAAAGGGTGGAGCCA<br>AGAAAAGACCCGCCCCCAGTGACGCAGATATAAGTGAGCCCAAACGGGTGCGCGAGTCA<br>GTTGCGCAGCCATCGACGTCAGACGCGGAAGCTTCGATCAACTACGCGGACAGGTACCA<br>AAACAAATGTTCTCGTCACGTGGGCATGAATCTGATGCTGTTTCCCTGCAGACAATGCGA<br>GAGAATGAATCAGAATTCAAATATCTGCTTCACTCACGGACAGAAAGACTGTTTAGAGTG<br>CTTTCCCGTGTCAGAATCTCAACCCGTTTCTGTCGTCAAAAAGGCGTATCAGAAACTGTGC<br>TACATTCATCATATCATGGGAAAGGTGCCAGACGCTTGCACTGCCTGCGATCTGGTCAAT<br>GTGGATTTGGATGACTGCATCTTTGAACAATAAATGATTTAAATCAGGTATGTCTTTTGTT<br>GATCACCCTCCAGATTGGTTGGAAGAAGTTGGTGAAGGTCTTCGCGAGTTTTTGGGCCTT<br>GAAGCGGGCCCACCGAAACCAAAACCCAATCAGCAGCATCAAGATCAAGCCCGTGGTCT<br>TGTGCTGCCTGGTTATAACTATCTCGGACCCGGAAACGGTCTCGATCGAGGAGAGCCTGT<br>CAACAGGGCAGACGAGGTCGCGCGAGAGCACGACATCTCGTACAACGAGCAGCTTGAGG<br>CGGGAGACAACCCCTACCTCAAGTACAACCACGCGGACGCCGAGTTTCAGGAGAAGCTC<br>GCCGACGACACATCCTTCGGGGGAAACCTCGGAAAGGCAGTCTTTCAGGCCAAGAAAAG<br>GGTTCTCGAACCTTTTGGCCTGGTTGAAGAGGGTGCTAAGACGGCCCCTACCGGAAAGCG<br>GATAGACGACCACTTTCCAAAAAGAAAGAAGGCCCGGACCGAAGAGGACTCCAAGCCTT<br>CCACCTCGTCAGACGCCGAAGCTGGACCCAGCGGATCCCAGCAGCTGCAAATCCCAGCCC<br>AACCAGCCTCAAGTTTGGGAGCTGATACAATGTCTGCGGGAGGTGGCGGCCCATTGGGCG<br>ACAATAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCAGCTA<br>CAACAACCACCAGTACCGAGAGATCAAAAGCGGCTCCGTCGACGGAAGCAACGCCAACG<br>CCTACTTTGGATACAGCACCCCCTGGGGGTACTTTGACTTTAACCGCTTCCACAGCCACTG<br>GAGCCCCCGAGACTGGCAAAGACTCATCAACAACTACTGGGGCTTCAGACCCCGGTCCCT<br>CAGAGTCAAAATCTTCAACATTCAAGTCAAAGAGGTCACGGTGCAGGACTCCACCACCAC<br>CATCGCCAACAACCTCACCTCCACCGTCCAAGTGTTTACGGACGACGACTACCAGCTGCC<br>CTACGTCGTCGGCAACGGGACCGAGGGATGCCTGCCGGCCTTCCCTCCGCAGGTCTTTAC<br>GCTGCCGCAGTACGGTTACGCGACGCTGAACCGCGACAACACAGAAAATCCCACCGAGA<br>GGAGCAGCTTCTTCTGCCTAGAGTACTTTCCCAGCAAGATGCTGAGAACGGGCAACAACT<br>TTGAGTTTACCTACAACTTTGAGGAGGTGCCCTTCCACTCCAGCTTCGCTCCCAGTCAGAA |

TABLE 12-continued

Sequences

| DESCRIPTION SEQ ID NO: | NUCLEIC ACID SEQUENCE |
|---|---|
| | CCTCTTCAAGCTGGCCAACCCGCTGGTGGACCAGTACTTGTACCGCTTCGTGAGCACAAA<br>TAACACTGGCGGAGTCCAGTTCAACAAGAACCTGGCCGGGAGATACGCCAACACCTACA<br>AAAACTGGTTCCCGGGGCCCATGGGCCGAACCCAGGGCTGGAACCTGGGCTCCGGGGTC<br>AACCGCGCCAGTGTCAGCGCCTTCGCCACGACCAATAGGATGGAGCTCGAGGGCGCGAG<br>TTACCAGGTGCCCCCGCAGCCGAACGGCATGACCAACAACCTCCAGGGCAGCAACACCT<br>ATGCCCTGGAGAACACTATGATCTTCAACAGCCAGCCGGCGAACCCGGGCACCACCGCC<br>ACGTACCTCGAGGGCAACATGCTCATCACCAGCGAGAGCGAGACGCAGCCGGTGAACCG<br>CGTGGCGTACAACGTCGGCGGGCAGATGGCCACCAACAACCAGAGCTCTGTACATCGATT<br>GTTAATCAATAAACCGTTTAATTCGTTTCAGTTGAACTTTGGTCTCTGCGTATTTCTTTCTT<br>ATCTAGTTTCCATGGCTACGTAGATAAGTAGCATGGCGGGTTAATCATTAACTACAAGGA<br>ACCCCTAGTGATGGAGTTGGCCACTCCCTCTCTGCGCGCTCGCTCGCTCACTGAGGCCGG<br>GCGACCAAAGGTCGCCCGACGCCCGGGCTTTGCCCGGGCGGCCTCAGTGAGCGAGCGAG<br>CGCGCAGAGAGGGAGTGGCCAAGCATGCAATTAACTGGCCGTCGTTTTACAACGTCGTGA<br>CTGGGAAAACCCTGGCGTTACCCAACTTAATCGCCTTGCAGCACATCCCCCTTTCGCCAG<br>CTGTATCAGCACACAATTGCCCATTATACGCGCGTATAATGGACTATTGTGTGCTGATA |
| TELN-SYNG6-BSRGI SEQ ID NO: 22 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTTAGTATCTGCAGAGGGCCCTG<br>CGTATGAGTGCAAGTGGGTTTTAGGACCAGGATGAGGCGGGGTGGGGGTGCCTACCTGA<br>CGACCGACCCCGACCCACTGGACAAGCACCCAACCCCCATTCCCCAAATTGCGCATCCCC<br>TATCAGAGAGGGGGAGGGGAAACAGGATGCGGCGAGGCGCGTGCGCACTGCCAGCTTCA<br>GCACCGCGGACAGTGCCTTCGCCCCCGCCTGGCGGCGCGCGCCACCGCCGCCTCAGCACT<br>GAAGGCGCGCTGACGTCACTCGCCGGTCCCCCGCAAACTCCCCTTCCCGGCCACCTTGGT<br>CGCGTCCGCGCCGCCGCCGGCCCAGCCGGACCGCACCACGCGAGGCGCGAGATAGGGGG<br>GCACGGGCGCGACCATCTGCGCTGCGGCGCCGGCGACTCAGCGCTGCCTCAGTCTGCGGT<br>GGGCAGCGGAGGAGTCGTGTCGTGCCTGAGAGCGCAGCTGTGCTCCTGGGCACCGCGCA<br>GTCCGCCCCCGCGGCTCCTGGCCAGACCACCCCTAGGACCCCCTGCCCCAAGTCGCAGCC<br>AAGCTTCGTTTAGTGAACCGTCAGATCGCCTGGAGACGCCATCCACGCTGTTTTGACCTCC<br>ATAGAAGACACCGGGACCGATCCAGCCTCCGCGGATTCGAATCCCGGCCGGGAACGGTG<br>CATTGGAACGCGGATTCCCCGTGCCAAGAGTGACGTAAGTACCGCCTATAGAGTCTATAG<br>GCCCACAAAAAATGCTTTCTTCTTTTAATATACTTTTTTGTTTATCTTATTTCTAATACTTTC<br>CCTAATCTCTTTCTTTCAGGGCAATAATGATACAATGTATCATGCCTCTTTGCACCATTCT<br>AAAGAATAACAGTGATAATTTCTGGGTTAAGGCAATAGCAATATTTCTGCATATAAATAT<br>TTCTGCATATAAATTGTAACTGATGTAAGAGGTTTCATATTGCTAATAGCAGCTACAATCC<br>AGCTACCATTCTGCTTTTATTTTATGGTTGGGATAAGGCTGGATTATTCTGAGTCCAAGCT<br>AGGCCCTTTTGCTAATCATGTTCATACCTCTTATCTTCCTCCCACAGCTCCTGGGCAACGT<br>GCTGGTCTGTGTGCTGGCCCATCACTTTGGCAAAGAATTGGGATTCGAACCGGTCGCCAC<br>CGGTCACAAGCAGGAAGTCAAAGACTTTTTCCGGTGGGCAAAGGATCACGTGGTTGAGG<br>TGGAGCATGAATTCTACGTCAAAAAGGGTGGAGCCAAGAAAAGACCCGCCCCCAGTGAC<br>GCAGATATAAGTGAGCCCAAACGGGTGCGCGAGTCAGTTGCGCAGCCATCGACGTCAGA<br>CGCGGAAGCTTCGATCAACTACGCGGACAGGTACCAAAACAAATGTTCTCGTCACGTGGG<br>CATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACC<br>CGTTTCTGTCGTCAAAAAGGCGTATCAGAAACTGTGCTACATTCATCATATCATGGGAAA<br>GGTGCCAGACGCTTGCACTGCCTGCGATCTGGTCAATGTGGATTTGGATGACTGCATCTTT<br>GAACAATAAATGATTTAAATCAGGTATGGCTGCCGATGGTTATCTTCCAGATTGGCTCGA<br>GGACAACCTCTCTGAGGGCATTCGCGAGTGGTGGGACTTGAAACCTGGAGCCCCGAAAC<br>CCAAAGCCAACCAGCAAAAGCAGGACGACGGCCGGGGTCTGGTGCTTCCTGGCTACAAG<br>TACCTCGGACCCTTCAACGGACTCGACAAGGGGGAGCCCGTCAACGCGGCGGATGCAGC<br>GGCCCTCGAGCACGACAAGGCCTACGACCAGCAGCTCAAAGCGGGTGACAATCCGTACC<br>TGCGGTATAACCACGCCGACGCCGAGTTTCAGGAGCGTCTGCAAGAAGATACGTCTTTTG<br>GGGGCAACCTCGGGCGAGCAGTCTTCCAGGCCAAGAAGAGGGTTCTCGAACCTTTTGGTC<br>TGGTTGAGGAAGGTGCTAAGACGGCTCCTGGAAAGAAACGTCCGGTAGAGCAGTCGCCA<br>CAAGAGCCAGACTCCTCCTCGGGCATTGGCAAGACAGGCCAGCAGCCCGCTAAAAAGAG<br>ACTCAATTTTGGTCAGACTGGCGACTCAGAGTCAGTCCCCGACCCACAACCTCTCGGAGA<br>ACCTCCAGCAACCCCCGCTGCTGTGGGACCTACTACAATGGCTTCAGGCGGTGGCGCACC<br>AATGGCAGACAATAACGAAGGCGCCGACGGAGTGGGTAATGCCTCAGGAAATTGGCATT<br>GCGATTCCACATGGCTGGGCGACAGAGTCATCACCACCAGCACCCGAACATGGGCCTTGC<br>CCACCTATAACAACCACCTCTACAAGCAAATCTCCAGTGCTTCAACGGGGGCCAGCAACG<br>ACAACCACTACTTCGGCTACAGCACCCCCTGGGGGTATTTTGATTTCAACAGATTCCACTG<br>CCATTTCTCACCACGTGACTGGCAGCGACTCATCAACAACAATTGGGGATTCCGGCCCAA<br>GAGACTCAACTTCAAGCTCTTCAACATCCAAGTCAAGGAGGTCACGACGAATGATGGCGT<br>CACGACCATCGCTAATAACCTTACCAGCACGGTTCAAGTCTTCTCGGACTCGGAGTACCA<br>GTTGCCGTACGTCCTCGGCTCTGCGCACCAGGGCTGCCTCCCTCCGTTCCCGGCGGACGTG<br>TTCATGATTCCGCAGTACGGCTACCTAACGCTCAACAATGGCAGCCAGGCAGTGGGACGG<br>TCATCCTTTTACTGCCTGGAATATTTCCCATCGCAGATGCTGAGAACGGGCAATAACTTTA<br>CCTTCAGCTACACCTTCGAGGACGTGCCTTTCCACAGCAGCTACGCGCACAGCCAGAGCC<br>TGGACCGGCTGATGAATCCTCTCATCGACCAGTACCTGTATTACCTGAACAGAACTCAGA<br>ATCAGTCCGGAAGTGCCCAAAACAAGGACTTGCTGTTTAGCCGGGGGTCTCCAGCTGGCA |

TABLE 12-continued

Sequences

| DESCRIPTION SEQ ID NO: | NUCLEIC ACID SEQUENCE |
|---|---|
| | TGTCTGTTCAGCCCAAAAACTGGCTACCTGGACCCTGTTACCGGCAGCAGCGCGTTTCTA<br>AAACAAAAACAGACAACAACAACAGCAACTTTACCTGGACTGGTGCTTCAAAATATAAC<br>CTTAATGGGCGTGAATCTATAATCAACCCTGGCACTGCTATGGCCTCACACAAAGACGAC<br>AAAGACAAGTTCTTTCCCATGAGCGGTGTCATGATTTTTGGAAAGGAGAGCGCCGGAGCT<br>TCAAACACTGCATTGGACAATGTCATGATCACAGACGAAGAGGAAATCAAAGCCACTAA<br>CCCCGTGGCCACCGAAAGATTTGGGACTGTGGCAGTCAATCTCCAGAGTGTACATCGATT<br>GTTAATCAATAAACCGTTTAATTCGTTTCAGTTGAACTTTGGTCTCTGCGTATTTCTTTCTT<br>ATCTAGTTTCCATGGCTACGTAGATAAGTAGCATGGCGGGTTAATCATTAACTACAAGGA<br>ACCCCTAGTGATGGAGTTGGCCACTCCCTCTCTGCGCGCTCGCTCGCTCACTGAGGCCGG<br>GCGACCAAAGGTCGCCCGACGCCCGGGCTTTGCCCGGGCGGCCTCAGTGAGCGAGCGAG<br>CGCGCAGAGAGGGAGTGGCCAAGCATGCAATTAACTGGCCGTCGTTTTACAACGTCGTGA<br>CTGGGAAAACCCTGGCGTTACCCAACTTAATCGCCTTGCAGCACATCCCCCTTTCGCCAG<br>CTGTATCAGCACACAATTGCCCATTATACGCGCGTATAATGGACTATTGTGTGCTGATA |
| TELN-GFAPG6-BSRGI SEQ ID NO: 23 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTGATCTAACATATCCTGGTGTG<br>GAGTAGCGGACGCTGCTATGACAGAGGCTCGGGGGCCTGAGCTGGCTCTGTGAGCTGGG<br>GAGGAGGCAGACAGCCAGGCCTTGTCTGCAAGCAGACCTGGCAGCATTGGGCTGGCCGC<br>CCCCCAGGGCCTCCTCTTCATGCCCAGTGAATGACTCACCTTGGCACAGACACAATGTTC<br>GGGGTGGGCACAGTGCCTGCTTCCCGCCGCACCCCAGCCCCCCTCAAATGCCTTCCGAGA<br>AGCCCATTGAGCAGGGGGCTTGCATTGCACCCCAGCCTGACAGCCTGGCATCTTGGGATA<br>AAAGCAGCACAGCCCCCTAGGGGCTGCCCTTGCTGTGTGGCGCCACCGGCGGTGGAGAA<br>CAAGGCTCTATTCAGCCTGTGCCCAGGAAAGGGGATCAGGGGATGCCCAGGCATGGACA<br>GTGGGTGGCAGGGGGGGAGAGGAGGGCTGTCTGCTTCCCAGAAGTCCAAGGACACAAAT<br>GGGTGAGGGGAGAGCTCTCCCCATAGCTGGGCTGCGGCCCAACCCCACCCCCTCAGGCTA<br>TGCCAGGGGGTGTTGCCAGGGGCACCCGGGCATCGCCAGTCTAGCCCACTCCTTCATAAA<br>GCCCTCGCATCCCAGGAGCGAGCAGAGCCAGAGCAGGTTGGAGAGGAGACGCATCACCT<br>CCGCTGCTCGCGGGGATCCTCTAGAAGCTTCGTTTAGTGAACCGTCAGATCGCCTGGAGA<br>CGCCATCCACGCTGTTTTGACCTCCATAGAAGACACCGGGACCGATCCAGCCTCCGCGGA<br>TTCGAATCCCGGCCGGGAACGGTGCATTGGAACGCGGATTCCCCGTGCCAAGAGTGACGT<br>AAGTACCGCCTATAGAGTCTATAGGCCCACAAAAAATGCTTTCTTCTTTTAATATACTTTT<br>TTGTTTATCTTATTTCTAATACTTTCCCTAATCTCTTTCTTTCAGGGCAATAATGATACAAT<br>GTATCATGCCTCTTTGCACCATTCTAAAGAATAACAGTGATAATTTCTGGGTTAAGGCAAT<br>AGCAATATTTCTGCATATAAATATTTCTGCATATAAATTGTAACTGATGTAAGAGGTTTCA<br>TATTGCTAATAGCAGCTACAATCCAGCTACCATTCTGCTTTTATTTTATGGTTGGGATAAG<br>GCTGGATTATTCTGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTTTGGCAAAGAA<br>TTGGGATTCGAACCGGTCGCCACCGGTCACCAAGCAGGAAGTCAAAGACTTTTTCCGGTG<br>GGCAAAGGATCACGTGGTTGAGGTGGAGCATGAATTCTACGTCAAAAAGGGTGGAGCCA<br>AGAAAAGACCCGCCCCCAGTGACGCAGATATAAGTGAGCCCAAACGGGTGCGCGAGTCA<br>GTTGCGCAGCCATCGACGTCAGACGCGGAAGCTTCGATCAACTACGCGGACAGGTACCA<br>AAACAAATGTTCTCGTCACGTGGGCATGAATCTGATGCTGTTTCCCTGCAGACAATGCGA<br>GAGAATGAATCAGAATTCAAATATCTGCTTCACTCACGGACAGAAAGACTGTTTAGAGTG<br>CTTTCCCGTGTCAGAATCTCAACCCGTTTCTGTCGTCAAAAAGGCGTATCAGAAACTGTGC<br>TACATTCATCATATCATGGGAAAGGTGCCAGACGCTTGCACTGCCTGCGATCTGGTCAAT<br>GTGGATTTGGATGACTGCATCTTTGAACAATAAATGATTTAAATCAGGTATGGCTGCCGA<br>TGGTTATCTTCCAGATTGGCTCGAGGACAACCTCTCTGAGGGCATTCGCGAGTGGTGGGA<br>CTTGAAACCTGGAGCCCCGAAACCCAAAGCCAACCAGCAAAAGCAGGACGACGGCCGGG<br>GTCTGGTGCTTCCTGGCTACAAGTACCTCGGACCCTTCAACGGACTCGACAAGGGGGAGC<br>CCGTCAACGCGGCGGATGCAGCGGCCCTCGAGCACGACAAGGCCTACGACCAGCAGCTC<br>AAAGCGGGTGACAATCCGTACCTGCGGTATAACCACGCCGACGCCGAGTTTCAGGAGCG<br>TCTGCAAGAAGATACGTCTTTTGGGGGCAACCTCGGGCGAGCAGTCTTCCAGGCCAAGAA<br>GAGGGTTCTCGAACCTTTTGGTCTGGTTGAGGAAGGTGCTAAGACGGCTCCTGGAAAGAA<br>ACGTCCGGTAGAGCAGTCGCCACAAGAGCCAGACTCCTCCTCGGGCATTGGCAAGACAG<br>GCCAGCAGCCCGCTAAAAAGAGACTCAATTTTGGTCAGACTGGCGACTCAGAGTCAGTCC<br>CCGACCCACAACCTCTCGGAGAACCTCCAGCAACCCCCGCTGCTGTGGGACCTACTACAA<br>TGGCTTCAGGCGGTGGCGCACCAATGGCAGACAATAACGAAGGCGCCGACGGAGTGGGT<br>AATGCCTCAGGAAATTGGCATTGCGATTCCACATGGCTGGGCGACAGAGTCATCACCACC<br>AGCACCCGAACATGGGCCTTGCCCACCTATAACAACCACCTCTACAAGCAAATCTCCAGT<br>GCTTCAACGGGGGCCAGCAACGACAACCACTACTTCGGCTACAGCACCCCCTGGGGGTAT<br>TTTGATTTCAACAGATTCCACTGCCATTTCTCACCACGTGACTGGCAGCGACTCATCAACA<br>ACAATTGGGGATTCCGGCCCAAGAGACTCAACTTCAAGCTCTTCAACATCCAAGTCAAGG<br>AGGTCACGACGAATGATGGCGTCACGACCATCGCTAATAACCTTACCAGCACGGTTCAAG<br>TCTTCTCGGACTCGGAGTACCAGTTGCCGTACGTCCTCGGCTCTGCGCACCAGGGCTGCCT<br>CCCTCCGTTCCCGGCGGACGTGTTCATGATTCCGCAGTACGGCTACCTAACGCTCAACAA<br>TGGCAGCCAGGCAGTGGGACGGTCATCCTTTTACTGCCTGGAATATTTCCCATCGCAGAT<br>GCTGAGAACGGGCAATAACTTTACCTTCAGCTACACCTTCGAGGACGTGCCTTTCCACAG<br>CAGCTACGCGCACAGCCAGAGCCTGGACCGGCTGATGAATCCTCTCATCGACCAGTACCT<br>GTATTACCTGAACAGAACTCAGAATCAGTCCGGAAGTGCCCAAAACAAGGACTTGCTGTT |

TABLE 12-continued

Sequences

| DESCRIPTION SEQ ID NO: | NUCLEIC ACID SEQUENCE |
|---|---|
| | TAGCCGGGGGTCTCCAGCTGGCATGTCTGTTCAGCCCAAAAACTGGCTACCTGGACCCTG<br>TTACCGGCAGCAGCGCGTTTCTAAAACAAAAACAGACAACAACAACAGCAACTTTACCT<br>GGACTGGTGCTTCAAAATATAACCTTAATGGGCGTGAATCTATAATCAACCCTGGCACTG<br>CTATGGCCTCACACAAAGACGACAAAGACAAGTTCTTTCCCATGAGCGGTGTCATGATTT<br>TTGGAAAGGAGAGCGCCGGAGCTTCAAACACTGCATTGGACAATGTCATGATCACAGAC<br>GAAGAGGAAATCAAAGCCACTAACCCCGTGGCCACCGAAAGATTTGGGACTGTGGCAGT<br>CAATCTCCAGAGTGTACATCGATTGTTAATCAATAAACCGTTTAATTCGTTTCAGTTGAAC<br>TTTGGTCTCTGCGTATTTCTTTCTTATCTAGTTTCCATGGCTACGTAGATAAGTAGCATGGC<br>GGGTTAATCATTAACTACAAGGAACCCCTAGTGATGGAGTTGGCCACTCCCTCTCTGCGC<br>GCTCGCTCGCTCACTGAGGCCGGGCGACCAAAGGTCGCCCGACGCCCGGGCTTTGCCCGG<br>GCGGCCTCAGTGAGCGAGCGAGCGCGCAGAGAGGGAGTGGCCAAGCATGCAATTAACTG<br>GCCGTCGTTTTACAACGTCGTGACTGGGAAAACCCTGGCGTTACCCAACTTAATCGCCTT<br>GCAGCACATCCCCCTTTCGCCAGCTGTATCAGCACACAATTGCCCATTATACGCGCGTAT<br>AATGGACTATTGTGTGCTGATA |
| TELN-SYNGDJ8-BSRGI SEQ ID NO: 24 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTTAGTATCTGCAGAGGGCCCTG<br>CGTATGAGTGCAAGTGGGTTTTAGGACCAGGATGAGGCGGGGTGGGGGTGCCTACCTGA<br>CGACCGACCCCGACCCACTGGACAAGCACCCAACCCCCATTCCCCAAATTGCGCATCCCC<br>TATCAGAGAGGGGGAGGGGAAACAGGATGCGGCGAGGCGCGTGCGCACTGCCAGCTTCA<br>GCACCGCGGACAGTGCCTTCGCCCCCGCCTGGCGGCGCGCGCCACCGCCGCCTCAGCACT<br>GAAGGCGCGCTGACGTCACTCGCCGGTCCCCCGCAAACTCCCCTTCCCGGCCACCTTGGT<br>CGCGTCCGCGCCGCCGCCGGCCCAGCCGGACCGCACCACGCGAGGCGCGAGATAGGGGG<br>GCACGGGCGCGACCATCTGCGCTGCGGCGCCGGCGACTCAGCGCTGCCTCAGTCTGCGGT<br>GGGCAGCGGAGGAGTCGTGTCGTGCCTGAGAGCGCAGCTGTGCTCCTGGGCACCGCGCA<br>GTCCGCCCCCGCGGCTCCTGGCCAGACCACCCCTAGGACCCCCTGCCCCAAGTCGCAGCC<br>AAGCTTCGTTTAGTGAACCGTCAGATCGCCTGGAGACGCCATCCACGCTGTTTTGACCTCC<br>ATAGAAGACACCGGGACCGATCCAGCCTCCGCGGATTCGAATCCCGGCCGGGAACGGTG<br>CATTGGAACGCGGATTCCCCGTGCCAAGAGTGACGTAAGTACCGCCTATAGAGTCTATAG<br>GCCCACAAAAAATGCTTTCTTCTTTTAATATACTTTTTTGTTTATCTTATTTCTAATACTTTC<br>CCTAATCTCTTTCTTTCAGGGCAATAATGATACAATGTATCATGCCTCTTTGCACCATTCT<br>AAAGAATAACAGTGATAATTTCTGGGTTAAGGCAATAGCAATATTTCTGCATATAAATAT<br>TTCTGCATATAAATTGTAACTGATGTAAGAGGTTTCATATTGCTAATAGCAGCTACAATCC<br>AGCTACCATTCTGCTTTTATTTTATGGTTGGGATAAGGCTGGATTATTCTGAGTCCAAGCT<br>AGGCCCTTTTGCTAATCATGTTCATACCTCTTATCTTCCTCCCACAGCTCCTGGGCAACGT<br>GCTGGTCTGTGTGCTGGCCCATCACTTTGGCAAAGAATTGGGATTCGAACCGGTCGCCAC<br>CGGTCACAAGCAGGAAGTCAAAGACTTTTTCCGGTGGGCAAAGGATCACGTGGTTGAGG<br>TGGAGCATGAATTCTACGTCAAAAAGGGTGGAGCCAAGAAAAGACCCGCCCCCAGTGAC<br>GCAGATATAAGTGAGCCCAAACGGGTGCGCGAGTCAGTTGCGCAGCCATCGACGTCAGA<br>CGCGGAAGCTTCGATCAACTACGCGGACAGGTACCAAAACAAATGTTCTCGTCACGTGGG<br>CATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACC<br>CGTTTCTGTCGTCAAAAAGGCGTATCAGAAACTGTGCTACATTCATCATATCATGGGAAA<br>GGTGCCAGACGCTTGCACTGCCTGCGATCTGGTCAATGTGGATTTGGATGACTGCATCTTT<br>GAACAATAAATGATTTAAATCAGGTATGGCTGCCGATGGTTATCTTCCAGATTGGCTCGA<br>GGACACTCTCTCTGAAGGAATAAGACAGTGGTGGAAGCTCAAACCTGGCCCACCACCAC<br>CAAAGCCCGCAGAGCGGCATAAGGACGACAGCAGGGGTCTTGTGCTTCCTGGGTACAAG<br>TACCTCGGACCCTTCAACGGACTCGACAAGGGAGAGCCGGTCAACGAGGCAGACGCCGC<br>GGCCCTCGAGCACGACAAAGCCTACGACCGGCAGCTCGACAGCGGAGACAACCCGTACC<br>TCAAGTACAACCACGCCGACGCCGAGTTCCAGGAGCGGCTCAAAGAAGATACGTCTTTTG<br>GGGGCAACCTCGGGCGAGCAGTCTTCCAGGCCAAAAAGAGGCTTCTTGAACCTCTTGGTC<br>TGGTTGAGGAAGCGGCTAAGACGGCTCCTGGAAAGAAGAGGCCTGTAGAGCACTCTCCT<br>GTGGAGCCAGACTCCTCCTCGGGAACCGGAAAGGCGGGCCAGCAGCCTGCAAGAAAAAG<br>ATTGAATTTTGGTCAGACTGGAGACGCAGACTCAGTCCCAGACCCTCAACCAATCGGAGA<br>ACCTCCCGCAGCCCCCTCAGGTGTGGGATCTCTTACAATGGCTGCAGGCGGTGGCGCACC<br>AATGGCAGACAATAACGAGGGCGCCGACGGAGTGGGTAATTCCTCGGGAAATTGGCATT<br>GCGATTCCACATGGATGGGCGACAGAGTCATCACCACCAGCACCCGAACCTGGGCCCTGC<br>CCACCTACAACAACCACCTCTACAAGCAAATCTCCAACAGCACATCTGGAGGATCTTCAA<br>ATGACAACGCCTACTTCGGCTACAGCACCCCCTGGGGGTATTTTGACTTTAACAGATTCC<br>ACTGCCACTTTTCACCACGTGACTGGCAGCGACTCATCAACAACAACTGGGGATTCCGGC<br>CCAAGAGACTCAGCTTCAAGCTCTTCAACATCCAGGTCAAGGAGGTCACGCAGAATGAA<br>GGCACCAAGACCATCGCCAATAACCTCACCAGCACCATCCAGGTGTTTACGGACTCGGAG<br>TACCAGCTGCCGTACGTTCTCGGCTCTGCCCACCAGGGCTGCCTGCCTCCGTTCCCGGCGG<br>ACGTGTTCATGATTCCCCAGTACGGCTACCTAACACTCAACAACGGTAGTCAGGCCGTGG<br>GACGCTCCTCCTTCTACTGCCTGGAATACTTTCCTTCGCAGATGCTGAGAACCGGCAACA<br>ACTTCCAGTTTACTTACACCTTCGAGGACGTGCCTTTCCACAGCAGCTACGCCCACAGCCA<br>GAGCTTGGACCGGCTGATGAATCCTCTGATTGACCAGTACCTGTACTACTTGTCTCGGACT<br>CAAACAACAGGAGGCACGACAAATACGCAGACTCTGGGCTTCAGCCAAGGTGGGCCTAA<br>TACAATGGCCAATCAGGCAAAGAACTGGCTGCCAGGACCCTGTTACCGCCAGCAGCGAG |

TABLE 12-continued

| Sequences | |
|---|---|
| DESCRIPTION<br>SEQ ID NO: | NUCLEIC ACID SEQUENCE |
| | TATCAAAGACATCTGCGGATAACAACAACAGTGAATACTCGTGGACTGGAGCTACCAAG<br>TACCACCTCAATGGCAGAGACTCTCTGGTGAATCCGGGCCCGGCCATGGCAAGCCACAAG<br>GACGATGAAGAAAAGTTTTTTCCTCAGAGCGGGGTTCTCATCTTTGGGAAGCAAGGCTCA<br>GAGAAAACAAATGTGGACATTGAAAAGGTCATGATTACAGACGAAGAGGAAATCAGGAC<br>AACCAATCCCGTGGCTACGGAGCAGTATGGTTCTGTATCTACCAACCTCCAGCAAGGTGT<br>ACATCGATTGTTAATCAATAAACCGTTTAATTCGTTTCAGTTGAACTTTGGTCTCTGCGTA<br>TTTCTTTCTTATCTAGTTTCCATGGCTACGTAGATAAGTAGCATGGCGGGTTAATCATTAA<br>CTACAAGGAACCCCTAGTGATGGAGTTGGCCACTCCCTCTCTGCGCGCTCGCTCGCTCACT<br>GAGGCCGGGCGACCAAAGGTCGCCCGACGCCCGGGCTTTGCCCGGGCGGCCTCAGTGAG<br>CGAGCGAGCGCGCAGAGAGGGAGTGGCCAAGCATGCAATTAACTGGCCGTCGTTTTACA<br>ACGTCGTGACTGGGAAAACCCTGGCGTTACCCAACTTAATCGCCTTGCAGCACATCCCCC<br>TTTCGCCAGCTGTATCAGCACACAATTGCCCATTATACGCGCGTATAATGGACTATTGTGT<br>GCTGATA |
| TELN-GFAPG-<br>DJ8-BSRGI<br>SEQ ID NO: 25 | TATCAGCACACAATAGTCCATTATACGCGCGTATAATGGGCAATTGTGTGCTGATACAGC<br>TGGCACGACAGGTTTCCCGACTGGAAAGCGGGCAGTGAGCGCAACGCAATTAATGTGAG<br>TTAGCTCACTCATTAGGCACCCCAGGCTTTACACTTTATGCTTCCGGCTCGTATGTTGTGT<br>GGAATTGTGAGCGGATAACAATTTCACACAGGAAACAGCTATGACCATGATTACGCCAG<br>ATTTAATTAAGGCCTTAATTAGGCTAGCTTGGCCACTCCCTCTCTGCGCGCTCGCTCGCTC<br>ACTGAGGCCGGGCGACCAAAGGTCGCCCGACGCCCGGGCTTTGCCCGGGCGGCCTCAGT<br>GAGCGAGCGAGCGCGCAGAGAGGGAGTGGCCAACTCCATCACTAGGGGTTCCTGGAGGG<br>GTGGAGTCGTGACGATATCCATGCGTCGACATAACGCGTGATCTAACATATCCTGGTGTG<br>GAGTAGCGGACGCTGCTATGACAGAGGCTCGGGGGCCTGAGCTGGCTCTGTGAGCTGGG<br>GAGGAGGCAGACAGCCAGGCCTTGTCTGCAAGCAGACCTGGCAGCATTGGGCTGGCCGC<br>CCCCCAGGGCCTCCTCTTCATGCCCAGTGAATGACTCACCTTGGCACAGACACAATGTTC<br>GGGGTGGGCACAGTGCCTGCTTCCCGCCGCACCCCAGCCCCCCTCAAATGCCTTCCGAGA<br>AGCCCATTGAGCAGGGGGCTTGCATTGCACCCCAGCCTGACAGCCTGGCATCTTGGGATA<br>AAAGCAGCACAGCCCCCTAGGGGCTGCCCTTGCTGTGTGGCGCCACCGGCGGTGGAGAA<br>CAAGGCTCTATTCAGCCTGTGCCCAGGAAAGGGGATCAGGGGATGCCCAGGCATGGACA<br>GTGGGTGGCAGGGGGGGAGAGGAGGGCTGTCTGCTTCCCAGAAGTCCAAGGACACAAAT<br>GGGTGAGGGGAGAGCTCTCCCCATAGCTGGGCTGCGGCCCAACCCCACCCCCTCAGGCTA<br>TGCCAGGGGGTGTTGCCAGGGGCACCCGGGCATCGCCAGTCTAGCCCACTCCTTCATAAA<br>GCCCTCGCATCCCAGGAGCGAGCAGAGCCAGAGCAGGTTGGAGAGGAGACGCATCACCT<br>CCGCTGCTCGCGGGGATCCTCTAGAAGCTTCGTTTAGTGAACCGTCAGATCGCCTGGAGA<br>CGCCATCCACGCTGTTTTGACCTCCATAGAAGACACCGGGACCGATCCAGCCTCCGCGGA<br>TTCGAATCCCGGCCGGGAACGGTGCATTGGAACGCGGATTCCCCGTGCCAAGAGTGACGT<br>AAGTACCGCCTATAGAGTCTATAGGCCCACAAAAAATGCTTTCTTCTTTTAATATACTTTT<br>TTGTTTATCTTATTTCTAATACTTTCCCTAATCTCTTTCTTTCAGGGCAATAATGATACAAT<br>GTATCATGCCTCTTTGCACCATTCTAAAGAATAACAGTGATAATTTCTGGGTTAAGGCAAT<br>AGCAATATTTCTGCATATAAATATTTCTGCATATAAATTGTAACTGATGTAAGAGGTTTCA<br>TATTGCTAATAGCAGCTACAATCCAGCTACCATTCTGCTTTTATTTTATGGTTGGGATAAG<br>GCTGGATTATTCTGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTTTGGCAAAGAA<br>TTGGGATTCGAACCGGTCGCCACCGGTCACCAAGCAGGAAGTCAAAGACTTTTTCCGGTG<br>GGCAAAGGATCACGTGGTTGAGGTGGAGCATGAATTCTACGTCAAAAAGGGTGGAGCCA<br>AGAAAAGACCCGCCCCCAGTGACGCAGATATAAGTGAGCCCAAACGGGTGCGCGAGTCA<br>GTTGCGCAGCCATCGACGTCAGACGCGGAAGCTTCGATCAACTACGCGGACAGGTACCA<br>AAACAAATGTTCTCGTCACGTGGGCATGAATCTGATGCTGTTTCCCTGCAGACAATGCGA<br>GAGAATGAATCAGAATTCAAATATCTGCTTCACTCACGGACAGAAAGACTGTTTAGAGTG<br>CTTTCCCGTGTCAGAATCTCAACCCGTTTCTGTCGTCAAAAAGGCGTATCAGAAACTGTGC<br>TACATTCATCATATCATGGGAAAGGTGCCAGACGCTTGCACTGCCTGCGATCTGGTCAAT<br>GTGGATTTGGATGACTGCATCTTTGAACAATAAATGATTTAAATCAGGTATGGCTGCCGA<br>TGGTTATCTTCCAGATTGGCTCGAGGACACTCTCTCTGAAGGAATAAGACAGTGGTGGAA<br>GCTCAAACCTGGCCCACCACCACCAAAGCCCGCAGAGCGGCATAAGGACGACAGCAGGG<br>GTCTTGTGCTTCCTGGGTACAAGTACCTCGGACCCTTCAACGGACTCGACAAGGGAGAGC<br>CGGTCAACGAGGCAGACGCCGCGGCCCTCGAGCACGACAAAGCCTACGACCGGCAGCTC<br>GACAGCGGAGACAACCCGTACCTCAAGTACAACCACGCCGACGCCGAGTTCCAGGAGCG<br>GCTCAAAGAAGATACGTCTTTTGGGGGCAACCTCGGGCGAGCAGTCTTCCAGGCCAAAA<br>AGAGGCTTCTTGAACCTCTTGGTCTGGTTGAGGAAGCGGCTAAGACGGCTCCTGGAAAGA<br>AGAGGCCTGTAGAGCACTCTCCTGTGGAGCCAGACTCCTCCTCGGGAACCGGAAAGGCG<br>GGCCAGCAGCCTGCAAGAAAAAGATTGAATTTTGGTCAGACTGGAGACGCAGACTCAGT<br>CCCAGACCCTCAACCAATCGGAGAACCTCCCGCAGCCCCCTCAGGTGTGGGATCTCTTAC<br>AATGGCTGCAGGCGGTGGCGCACCAATGGCAGACAATAACGAGGGCGCCGACGGAGTGG<br>GTAATTCCTCGGGAAATTGGCATTGCGATTCCACATGGATGGGCGACAGAGTCATCACCA<br>CCAGCACCCGAACCTGGGCCCTGCCCACCTACAACAACCACCTCTACAAGCAAATCTCCA<br>ACAGCACATCTGGAGGATCTTCAAATGACAACGCCTACTTCGGCTACAGCACCCCCTGGG<br>GGTATTTTGACTTTAACAGATTCCACTGCCACTTTTCACCACGTGACTGGCAGCGACTCAT<br>CAACAACAACTGGGGATTCCGGCCCAAGAGACTCAGCTTCAAGCTCTTCAACATCCAGGT<br>CAAGGAGGTCACGCAGAATGAAGGCACCAAGACCATCGCCAATAACCTCACCAGCACCA<br>TCCAGGTGTTTACGGACTCGGAGTACCAGCTGCCGTACGTTCTCGGCTCTGCCCACCAGG<br>GCTGCCTGCCTCCGTTCCCGGCGGACGTGTTCATGATTCCCCAGTACGGCTACCTAACACT<br>CAACAACGGTAGTCAGGCCGTGGGACGCTCCTCCTTCTACTGCCTGGAATACTTTCCTTCG<br>CAGATGCTGAGAACCGGCAACAACTTCCAGTTTACTTACACCTTCGAGGACGTGCCTTTC<br>CACAGCAGCTACGCCCACAGCCAGAGCTTGGACCGGCTGATGAATCCTCTGATTGACCAG<br>TACCTGTACTACTTGTCTCGGACTCAAACAACAGGAGGCACGACAAATACGCAGACTCTG |

TABLE 12-continued

| Sequences | |
|---|---|
| DESCRIPTION<br>SEQ ID NO: | NUCLEIC ACID SEQUENCE |
| | GGCTTCAGCCAAGGTGGGCCTAATACAATGGCCAATCAGGCAAAGAACTGGCTGCCAGG<br>ACCCTGTTACCGCCAGCAGCGAGTATCAAAGACATCTGCGGATAACAACAACAGTGAAT<br>ACTCGTGGACTGGAGCTACCAAGTACCACCTCAATGGCAGAGACTCTCTGGTGAATCCGG<br>GCCCGGCCATGGCAAGCCACAAGGACGATGAAGAAAAGTTTTTTCCTCAGAGCGGGGTT<br>CTCATCTTTGGGAAGCAAGGCTCAGAGAAAACAAATGTGGACATTGAAAAGGTCATGAT<br>TACAGACGAAGAGGAAATCAGGACAACCAATCCCGTGGCTACGGAGCAGTATGGTTCTG<br>TATCTACCAACCTCCAGCAAGGTGTACATCGATTGTTAATCAATAAACCGTTTAATTCGTT<br>TCAGTTGAACTTTGGTCTCTGCGTATTTCTTTCTTATCTAGTTTCCATGGCTACGTAGATAA<br>GTAGCATGGCGGGTTAATCATTAACTACAAGGAACCCCTAGTGATGGAGTTGGCCACTCC<br>CTCTCTGCGCGCTCGCTCGCTCACTGAGGCCGGGCGACCAAAGGTCGCCCGACGCCCGGG<br>CTTTGCCCGGGCGGCCTCAGTGAGCGAGCGAGCGCGCAGAGAGGGAGTGGCCAAGCATG<br>CAATTAACTGGCCGTCGTTTTACAACGTCGTGACTGGGAAAACCCTGGCGTTACCCAACT<br>TAATCGCCTTGCAGCACATCCCCCTTTCGCCAGCTGTATCAGCACACAATTGCCCATTATA<br>CGCGCGTATAATGGACTATTGTGTGCTGATA |

LITERATURE CITED

Berns K I, Giraud C. Biology of adeno-associated virus. Curr Top Microbiol Immunol. 1996; 218:1-23.

Chan K Y, Jang M J, Yoo B B, Greenbaum A, Ravi N, Wu W L, Sánchez-Guardado L, Lois C, Mazmanian S K, Deverman B E, Gradinaru V. Engineered AAVs for efficient noninvasive gene delivery to the central and peripheral nervous systems. Nat Neurosci. 2017 August; 20(8): 1172-1179.

Heinrich J, Schultz J, Bosse M, Ziegelin G, Lanka E, Moelling K. Linear closed mini DNA generated by the prokaryotic cleaving-joining enzyme TelN is functional in mammalian cells. J Mol Med (Berl). 2002 October; 80(10):648-54.

Hordeaux J, Wang Q, Katz N, Buza E L, Bell P, Wilson J M. The Neurotropic Properties of AAV-PHP.B Are Limited to C57BL/6J Mice. Mol Ther. 2018 Mar. 7; 26(3):664-668.

Huovinen T, Brockmann E C, Akter S, Perez-Gamarra S, Ylä-Pelto J, Liu Y, Lamminmäki U. Primer extension mutagenesis powered by selective rolling circle amplification. PLoS One. 2012; 7(2):e31817.

Huovinen T, Julin M, Sanmark H, Lamminmäki U. Enhanced error-prone RCA mutagenesis by concatemer resolution. Plasmid. 2011 October; 66(1):47-51.

Hutchison C A 3rd, Smith H O, Pfannkoch C, Venter J C. Cell-free cloning using phi29 DNA polymerase. Proc Natl Acad Sci USA. 2005 Nov. 29; 102(48):17332-6.

Miyazaki J, Takaki S, Araki K, Tashiro F, Tominaga A, Takatsu K, Yamamura K. Expression vector system based on the chicken beta-actin promoter directs efficient production of interleukin-5. Gene. 1989 Jul. 15; 79(2):269-77.

Mouw M B, Pintel D J. Adeno-associated virus RNAs appear in a temporal order and their splicing is stimulated during coinfection with adenovirus. J Virol. 2000 November; 74(21):9878-88.

Niwa H, Yamamura K, Miyazaki J. Efficient selection for high-expression transfectants with a novel eukaryotic vector. Gene. 1991 Dec. 15; 108(2):193-9.

Nonnenmacher M, van Bakel H, Hajjar R J, Weber T. High capsid-genome correlation facilitates creation of AAV libraries for directed evolution. Mol Ther. 2015 April; 23(4):675-82.

Picher ÁJ, Budeus B, Wafzig O, Krüger C, García-Gómez S, Martínez-Jiménez M I, Díaz-Talavera A, Weber D, Blanco L, Schneider A. TruePrime is a novel method for whole-genome amplification from single cells based on TthPrimPol. Nat Commun. 2016 Nov. 29; 7:13296.

Powell S K, Rivera-Soto R, Gray S J. Viral expression cassette elements to enhance transgene target specificity and expression in gene therapy. Discov Med. 2015 January; 19(102):49-57.

Rybchin V N, Svarchevsky A N. The plasmid prophage N15: a linear DNA with covalently closed ends. Mol Microbiol. 1999 September; 33(5):895-903.

Zolotukhin S, Byrne B J, Mason E, Zolotukhin I, Potter M, Chesnut K, Summerford C, Samulski R J, Muzyczka N. Recombinant adeno-associated virus purification using novel methods improves infectious titer and yield. Gene Ther. 1999 June; 6(6):973-85.

The invention claimed is:

1. A method for generating an adeno-associated virus (AAV) vector library encoding variant AAV capsid polypeptides, the method comprising:

(a) providing first nucleic acids comprising a P40 promoter and a cell-type specific promoter, wherein the cell-type specific promoter drives capsid mRNA expression in the absence of helper virus co-infection; and second nucleic acids encoding the variant AAV capsid polypeptides having a region of randomized sequence of 2, 3, 4, 5, 6, 7, 8, or 9 consecutive amino acids; and (b) cloning the first nucleic acids and the second nucleic acids under conditions suitable to generate the AAV vector library.

2. The method of claim 1, wherein the cell-type specific promoter is a blood cell specific promoter, an eye specific promoter, a heart specific promoter, a muscle specific promoter, a kidney specific promoter, a lung specific promoter, a pancreas specific promoter, a vasculature specific promoter, a neuron specific promoter or an astrocyte-specific promoter.

3. The method of claim 1, wherein the cell-type specific promoter is a synapsin promoter.

4. The method of claim 1, wherein the cell-type specific promoter is a GFAP promoter.

5. The method of claim 1, wherein:

(i) the P40 promoter and the cell-type specific promoter are located upstream of a transgene encoding the variant AAV capsid polypeptide; or (ii) the P40 promoter is located upstream of a transgene encoding the variant AAV capsid polypeptide and the cell-type specific promoter is located downstream of a transgene encoding the variant AAV capsid polypeptide.

6. The method of claim 1, wherein the region of randomized sequence comprises a peptide insert of 4, 5, 6, 7, 8, or 9 consecutive amino acids.

7. The method of claim 1, wherein the region of randomized sequence of 2, 3, 4, 5, 6, 7, 8, or 9 consecutive amino acids is present in a hypervariable region of the AAV capsid polypeptide.

8. The method of claim 1, wherein the parental AAV capsid polypeptide comprises an AAV9 capsid polypeptide or an AAV5 capsid polypeptide.

9. The method of claim 1, further comprising (c) generating a plurality of AAV particles comprising the AAV vector library.

10. The method of claim 9, further comprising (d) administering the AAV particles to an animal.

11. The method of claim 10, further comprising (e) collection and/or isolation of a target cell or tissue from the animal.

12. The method of claim 11, further comprising (f) recovery of RNA and/or antisense RNA encoding the variant AAV capsid polypeptides from the target cell or tissue.

13. The method of claim 12, further comprising (g) determination of the sequence of the variant AAV capsid polypeptides.

14. The method of claim 13, further comprising (h) measuring the amount of DNA encoding the variant AAV capsid polypeptides or the amount of RNA encoding the variant AAV capsid polypeptides in a target cell or tissue.

15. The method of claim 14, wherein the method further comprises repeating steps (a)-(h).

16. The method of claim 1, wherein the encoded variant AAV capsid polypeptides demonstrate one, two, three, four, or all of the following properties:

(i) increased target cell transduction or target cell specificity to a cell of the central nervous system (CNS), as compared to a parental capsid polypeptide;

(ii) increased transduction of the brain as compared to a parental capsid polypeptide, optionally wherein the level of transduction is at least 10, 30, 50, 70, 90, 100, 170, or 380-fold greater than the parental capsid polypeptide;

(iii) increased transduction of the spinal cord as compared to a parental capsid polypeptide, optionally wherein the level of transduction is at least 10, 30, 50, 70, 110, 120, 140, 220, 230, or 1,000-fold greater than the parental capsid polypeptide;

(iv) delivery of an increased level of viral genomes to the brain as compared to a parental capsid polypeptide; and/or (v) delivery of an increased level of viral genomes to the spinal cord as compared to a parental capsid polypeptide.

17. The method of claim 11, wherein:

(i) the target cell is a neuronal cell, a neural stem cell, an astrocyte, an oligodendrocyte, a microglia cell, a retinal cell, a tumor cell, a hematopoietic stem cell, an insulin producing beta cell, a lung epithelium cell, an endothelial cell, a liver cell, a skeletal muscle cell, a muscle stem cell, a muscle satellite cell, or a cardiac muscle cell; and/or (ii) the target tissue is a central nervous system (CNS) tissue, a peripheral nervous system tissue (PNS) tissue, and/or a peripheral tissue.

18. The method of claim 1, wherein the vectors of the AAV vector library comprise in order:

(i) a first inverted terminal repeat (ITR);

(ii) the cell-type specific promoter;

(iii) the P40 promoter;

(iv) a transgene encoding the variant AAV capsid polypeptide comprising the region of randomized sequence of 2, 3, 4, 5, 6, 7, 8, or 9 consecutive amino acids;

(v) a polyadenylation (polyA) sequence; and (vi) a second ITR.

19. The method of claim 10, wherein:

(i) the animal is a mouse or a non-human primate (NHP); and/or (ii) the particles are administered intravenously.

20. The method of claim 11, wherein the target cell or tissue is collected four weeks post-administration of the AAV particles.

21. The method of claim 12, wherein:

(a) wherein the RNA encoding the variant AAV capsid polypeptides is enriched and/or reverse transcribed to cDNA; and/or (b) the cDNA is amplified.

22. The method of claim 17, wherein:

(i) the CNS tissue is a brain tissue, a spinal cord tissue, and/or a dorsal root ganglion tissue; and/or (ii) the peripheral tissue is a muscle tissue, a liver tissue, a heart tissue, a gastrocnemius muscle tissue, a soleus muscle tissue, a pancreas tissue, a kidney tissue, a spleen tissue, a lung tissue, an adrenal glands tissue, a stomach tissue, a sciatic nerve tissue, a saphenous nerve tissue, a thyroid gland tissue, an eye tissue, a pituitary gland tissue, a skeletal muscle tissue, a colon tissue, a duodenum tissue, an ileum tissue, a jejunum tissue, a skin tissue of the leg, a superior cervical ganglia tissue, a urinary bladder tissue, an ovary tissue, a uterus tissue, a prostate gland tissue, and/or a testes tissue.

23. The method of claim 22, wherein the brain tissue is a cortex tissue, a frontal cortex tissue, a parietal cortex tissue, a occipital cortex tissue, a temporal cortex tissue, a thalamus tissue, a hypothalamus tissue, a striatum tissue, a putamen tissue, a caudate nucleus tissue, a hippocampus tissue, a entorhinal cortex tissue, a basal ganglia tissue, and/or a deep cerebellar nuclei tissue.

24. The method of claim 1, wherein the region of randomized sequence of 2, 3, 4, 5, 6, 7, 8, or 9 consecutive amino acids is present in loop IV, loop VIII, or both loop IV and loop VIII of the parental AAV capsid polypeptide.

25. The method of claim 1, wherein the region of randomized sequence of 2, 3, 4, 5, 6, 7, 8, or 9 consecutive amino acids is present immediately subsequent to a position selected from 452-458 of the parental sequence.

26. The method of claim 1, wherein the region of randomized sequence of 2, 3, 4, 5, 6, 7, 8, or 9 consecutive amino acids is present immediately subsequent to a position selected from 586-592 of the parental sequence.

27. A method for generating an adeno-associated virus (AAV) vector library encoding variant AAV capsid polypeptides, the method comprising:

(a) providing first nucleic acids comprising a first promoter and a second promoter, wherein the second promoter is a cell-type specific promoter which drives capsid mRNA expression in the absence of helper virus co-infection; and second nucleic acids encoding the variant AAV capsid polypeptides having a region of randomized sequence of 2, 3, 4, 5, 6, 7, 8, or 9 consecutive amino acids; and (b) cloning the first nucleic acids and the second nucleic acids under conditions suitable to generate the AAV vector library;

wherein the cell-type specific promoter is a neuron specific promoter, an astrocyte-specific promoter, a blood cell specific promoter, an eye specific promoter, a heart specific promoter, a muscle specific promoter, a kidney specific promoter, a lung specific promoter, a pancreas specific promoter, or a vasculature specific promoter.

28. A method for generating a plurality of variant adeno-associated virus (AAV) capsid polypeptides, the method comprising:

(a) providing a plurality of AAV particles comprising an AAV vector library, wherein the AAV vector library comprises nucleic acids comprising a P40 promoter and a cell-type specific promoter which drives capsid mRNA expression in the absence of helper virus co-infection; and wherein the nucleic acids encode a plurality of the variant AAV capsid polypeptides having a region of randomized sequence of 2, 3, 4, 5, 6, 7, 8, or 9 consecutive amino acids;

(b) administering the AAV particles to an animal, wherein the particles are administered intravenously;

(c) recovery of RNA and/or antisense RNA encoding the variant AAV capsid polypeptides from a target cell or tissue, (d) determination of the sequence of the variant AAV capsid polypeptides; and (e) measuring the amount of DNA encoding the variant AAV capsid polypeptides or the amount of RNA encoding the variant AAV capsid polypeptides, in a target cell or tissue; and wherein the method occurs in the absence of a helper virus;

thereby generating the plurality of variant AAV capsid polypeptides.

29. The method of claim 28, wherein the cell-type specific promoter is a synapsin promoter or a GFAP promoter.

* * * * *

SEQUENCE LISTING

```
<160> NUMBER OF SEQ ID NOS: 1185

<210> SEQ ID NO 1
<211> LENGTH: 2211
<212> TYPE: DNA
<213> ORGANISM: Unknown
<220> FEATURE:
<223> OTHER INFORMATION: Description of Unknown:
      adeno-associated virus, human clone 9

<400> SEQUENCE: 1

atggctgccg atggttatct tccagattgg ctcgaggaca accttagtga aggaattcgc      60

gagtggtggg ctttgaaacc tggagcccct caacccaagg caaatcaaca acatcaagac     120
```

```
aacgctcgag gtcttgtgct tccgggttac aaataccttg gacccggcaa cggactcgac    180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctgggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

<210> SEQ ID NO 2
<211> LENGTH: 736
<212> TYPE: PRT
<213> ORGANISM: Unknown
<220> FEATURE:
<223> OTHER INFORMATION: Description of Unknown:
      capsid of hu.14/AAV9

<400> SEQUENCE: 2

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

Gln Val Lys Glu Val Thr Asp Asn Asn Gly Val Lys Thr Ile Ala Asn
325 330 335

Asn Leu Thr Ser Thr Val Gln Val Phe Thr Asp Ser Asp Tyr Gln Leu
340 345 350

Pro Tyr Val Leu Gly Ser Ala His Glu Gly Cys Leu Pro Pro Phe Pro
355 360 365

Ala Asp Val Phe Met Ile Pro Gln Tyr Gly Tyr Leu Thr Leu Asn Asp
370 375 380

Gly Ser Gln Ala Val Gly Arg Ser Ser Phe Tyr Cys Leu Glu Tyr Phe
385 390 395 400

Pro Ser Gln Met Leu Arg Thr Gly Asn Asn Phe Gln Phe Ser Tyr Glu

```
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 3
<211> LENGTH: 736
<212> TYPE: PRT
<213> ORGANISM: Artificial Sequence
<220> FEATURE:
<223> OTHER INFORMATION: Description of Artificial Sequence: Synthetic
      AAV9 Capsid Sequence

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30
```

-continued

```
Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Ile Asn Gly Ser Gly Gln Asn Gln Gln Thr Leu Lys Phe Ser
```

```
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 4
<211> LENGTH: 2470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
cgcagggtct ccattttgaa gcgggaggtt tgaacgcgca gccgccatgc cggggtttta      60

cgagattgtg attaaggtcc ccagcgacct tgacgagcat ctgcccggca tttctgacag     120

ctttgtgaac tgggtggccg agaaggaatg ggagttgccg ccagattctg acatggatct     180

gaatctgatt gagcaggcac ccctgaccgt ggccgagaag ctgcagcgcg actttctgac     240

ggaatggcgc cgtgtgagta aggccccgga ggctcttttc tttgtgcaat ttgagaaggg     300

agagagctac ttccacatgc acgtgctcgt ggaaaccacc ggggtgaaat ccatggtttt     360

gggacgtttc ctgagtcaga ttcgcgaaaa actgattcag agaatttacc gcgggatcga     420

gccgactttg ccaaactggt tcgcggtcac aaagaccaga aatggcgccg gaggcgggaa     480
```

```
caaggtggtg gatgagtgct acatccccaa ttacttgctc cccaaaaccc agcctgagct    540
ccagtgggcg tggactaata tggaacagta tttaagcgcc tgtttgaatc tcacggagcg    600
taaacggttg gtggcgcagc atctgacgca cgtgtcgcag acgcaggagc agaacaaaga    660
gaatcagaat cccaattctg atgcgccggt gatcagatca aaaacttcag ccaggtacat    720
ggagctggtc gggtggctcg tggacaaggg gattacctcg gagaagcagt ggatccagga    780
ggaccaggcc tcatacatct ccttcaatgc ggcctccaac tcgcggtccc aaatcaaggc    840
tgccttggac aatgcgggaa agattatgag cctgactaaa accgcccccg actacctggt    900
gggccagcag cccgtggagg acatttccag caatcggatt tataaaattt tggaactaaa    960
cgggtacgat ccccaatatg cggcttccgt ctttctggga tgggccacga aaaagttcgg   1020
caagaggaac accatctggc tgtttgggcc tgcaactacc gggaagacca acatcgcgga   1080
ggccatagcc cacactgtgc ccttctacgg gtgcgtaaac tggaccaatg agaactttcc   1140
cttcaacgac tgtgtcgaca agatggtgat ctggtgggag gaggggaaga tgaccgccaa   1200
ggtcgtggag tcggccaaag ccattctcgg aggaagcaag gtgcgcgtgg accagaaatg   1260
caagtcctcg gcccagatag acccgactcc cgtgatcgtc acctccaaca ccaacatgtg   1320
cgccgtgatt gacgggaact caacgacctt cgaacaccag cagccgttgc aagaccggat   1380
gttcaaattt gaactcaccc gccgtctgga tcatgacttt gggaaggtca ccaagcagga   1440
agtcaaagac tttttccggt gggcaaagga tcacgtggtt gaggtggagc atgaattcta   1500
cgtcaaaaag ggtggagcca agaaaagacc cgcccccagt gacgcagata taagtgagcc   1560
caaacgggtg cgcgagtcag ttgcgcagcc atcgacgtca gacgcggaag cttcgatcaa   1620
ctacgcagac aggtaccaaa acaaatgttc tcgtcacgtg ggcatgaatc tgatgctgtt   1680
tccctgcaga caatgcgaga gaatgaatca gaattcaaat atctgcttca ctcacggaca   1740
gaaagactgt ttagagtgct ttcccgtgtc agaatctcaa cccgtttctg tcgtcaaaaa   1800
ggcgtatcag aaactgtgct acattcatca tatcatggga aaggtgccag acgcttgcac   1860
tgcctgcgat ctggtcaatg tggatttgga tgactgcatc tttgaacaat aaatgattta   1920
aatcaggtat ggctgccgat ggttatcttc cagattggct cgaggacact ctctctgaag   1980
gaataagaca gtggtggaag ctcaaacctg gcccaccacc accaaagccc gcagagcggc   2040
ataaggacga cagcaggggt cttgtgcttc ctgggtacaa gtacctcgga cccttcaacg   2100
gactcgacaa gggagagccg gtcaacgagg cagacgccgc ggccctcgag cacgacaaag   2160
cctacgaccg gcagctcgac agcggagaca acccgtacct caagtacaac cacgccgacg   2220
cggagtttca ggagcgcctt aaagaagata cgtcttttgg gggcaacctc ggacgagcag   2280
tcttccaggc gaaaaagagg gttcttgaac ctctgggcct ggtccaccat accttcgatt   2340
atccgatttg cttgttaatc aataaaccgt ttaattcgtt tcagttgaac tttggtctct   2400
gcgtatttct ttcttatcta gtttccatgc tctagagcgg ccgccaccgc ggtggagctc   2460
cagcttttgt                                                          2470
```

<210> SEQ ID NO 5
<211> LENGTH: 3681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

-continued

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgatatc gtttaaaccg    180
cgtcgttaca taacttacgg taaatggccc gcctggctga ccgcccaacg acccccgccc    240
attgacgtca ataatgacgt atgttcccat agtaacgcca atagggactt tccattgacg    300
tcaatgggtg gagtatttac ggtaaactgc ccacttggca gtacatcaag tgtatcatat    360
gccaagtacg ccccctattg acgtcaatga cggtaaatgg cccgcctggc attatgccca    420
gtacatgacc ttatgggact ttcctacttg gcagtacatc tacgtattag tcatcgctat    480
taccatggtg atgcggtttt ggcagtacat caatgggcgt ggatagcggt ttgactcacg    540
gggatttcca agtctccacc ccattgacgt caatgggagt ttgttttggc accaaaatca    600
acgggacttt ccaaaatgtc gtaacaactc cgccccattg acgcaaatgg gcggtaggcg    660
tgtacggtgg gaggtctata taagcagagc tcgggagcgg tcaccaagca ggaagtcaaa    720
gactttttcc ggtgggcaaa ggatcacgtg gttgaggtgg agcatgaatt ctacgtcaaa    780
aagggtggag ccaagaaaag acccgccccc agtgacgcag atataagtga gcccaaacgg    840
gtgcgcgagt cagttgcgca gccatcgacg tcagacgcgg aagcttcgat caactacgcg    900
gacaggtacc aaaacaaatg ttctcgtcac gtgggcatga atctgatgct gtttccctgc    960
agacaatgcg agagactgaa tcagaattca aatatctgct tcactcacgg tgtcaaagac   1020
tgtttagagt gctttcccgt gtcagaatct caacccgttt ctgtcgtcaa aaaggcgtat   1080
cagaaactgt gctacattca tcacatcatg ggaaaggtgc cagacgcttg cactgcttgc   1140
gacctggtca atgtggactt ggatgactgt gtttctgaac aataaatgac ttaaaccagg   1200
tatggctgcc gatggttatc ttccagattg gctcgaggac aaccttagtg aaggaattcg   1260
cgagtggtgg gctttgaaac ctggagcccc tcaacccaag gcaaatcaac aacatcaaga   1320
caacgctcga ggtcttgtgc ttccgggtta caaatacctt ggacccggca acggactcga   1380
caagggggag ccggtcaacg cagcagacgc ggcggccctc gagcacgaca aggcctacga   1440
ccagcagctc aaggccggag acaacccgta cctcaagtac aaccacgccg acgccgagtt   1500
ccaggagcgg ctcaaagaag atacgtcttt tgggggcaac ctcgggcgag cagtcttcca   1560
ggccaaaaag aggcttcttg aacctcttgg tctggttgag gaagcggcta agacggctcc   1620
tggaaagaag aggcctgtag agcagtctcc tcaggaaccg gactcctccg cgggtattgg   1680
caaatcgggt gcacagcccg ctaaaaagag actcaatttc ggtcagactg gcgacacaga   1740
gtcagtccca gaccctcaac caatcggaga acctcccgca gccccctcag gtgtgggatc   1800
tcttacaatg gcttcaggtg gtggcgcacc agtggcagac aataacgaag gtgccgatgg   1860
agtgggtagt tcctcgggaa attggcattg cgattcccaa tggctggggg acagagtcat   1920
caccaccagc acccgaacct gggccctgcc cacctacaac aatcacctct acaagcaaat   1980
ctccaacagc acatctggag gatcttcaaa tgacaacgcc tacttcggct acagcacccc   2040
ctgggggtat tttgacttca acagattcca ctgccacttc tcaccacgtg actggcagcg   2100
actcatcaac aacaactggg gattccggcc taagcgactc aacttcaagc tcttcaacat   2160
tcaggtcaaa gaggttacgg acaacaatgg agtcaagacc atcgccaata accttaccag   2220
cacggtccag gtcttcacgg actcagacta tcagctcccg tacgtgctcg ggtcggctca   2280
cgagggctgc ctcccgccgt tcccagcgga cgttttcatg attcctcagt acgggtatct   2340
```

```
gacgcttaat gatggaagcc aggccgtggg tcgttcgtcc ttttactgcc tggaatattt   2400

cccgtcgcaa atgctaagaa cgggtaacaa cttccagttc agctacgagt ttgagaacgt   2460

acctttccat agcagctacg ctcacagcca aagcctggac cgactaatga atccactcat   2520

cgaccaatac ttgtactatc tctcaaagac tattaacggt tctggacaga atcaacaaac   2580

gctaaaattc agtgtggccg gacccagcaa catggctgtc cagggaagaa actacatacc   2640

tggacccagc taccgacaac aacgtgtctc aaccactgtg actcaaaaca acaacagcga   2700

atttgcttgg cctggagctt cttcttgggc tctcaatgga cgtaatagct tgatgaatcc   2760

tggacctgct atggccagcc acaaagaagg agaggaccgt ttctttcctt tgtctggatc   2820

tttaattttt ggcaaacaag gaactggaag agacaacgtg gatgcggaca aagtcatgat   2880

aaccaacgaa gaagaaatta aaactactaa cccggtagca acggagtcct atggacaagt   2940

ggccacaaac caccagagtg cccaagcaca ggcgcagacc ggctgggttc aaaaccaagg   3000

aatacttccg ggtatggttt ggcaggacag agatgtgtac ctgcaaggac ccatttgggc   3060

caaaattcct cacacggacg gcaactttca cccttctccg ctgatgggag ggtttggaat   3120

gaagcacccg cctcctcaga tcctcatcaa aaacacacct gtacctgcgg atcctccaac   3180

ggccttcaac aaggacaagc tgaactcttt catcacccag tattctactg gccaagtcag   3240

cgtggagatc gagtgggagc tgcagaagga aaacagcaag cgctggaacc cggagatcca   3300

gtacacttcc aactattaca agtctaataa tgttgaattt gctgttaata ctgaaggtgt   3360

atatagtgaa ccccgcccca ttggcaccag atacctgact cgtaatctgt aatcgattgt   3420

taatcaataa accgtttaat tcgtttcagt tgaactttgg tctctgcgta tttctttctt   3480

atctagtttc catggctacg tagataagta gcatggcggg ttaatcatta actacaagga   3540

acccctagtg atggagttgg ccactccctc tctgcgcgct cgctcgctca ctgaggccgg   3600

gcgaccaaag gtcgcccgac gcccgggctt tgcccgggcg gcctcagtga gcgagcgagc   3660

gcgcagagag ggagtggcca a                                             3681
```

<210> SEQ ID NO 6
<211> LENGTH: 3755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gtcgacggta tcgggggagc tcgcagggtc tccattttga agcgggaggt ttgaacgcgc     60

agccgccatg ccggggtttt acgagattgt gattaaggtc cccagcgacc ttgacgagca    120

tctgcccggc atttctgaca gctttgtgaa ctgggtggcc gagaaggaat gggagttgcc    180

gccagattct gacatggatc tgaatctgat tgagcaggca cccctgaccg tggccgagaa    240

gctgcagcgc gactttctga cggaatggcg ccgtgtgagt aaggccccgg aggctctttt    300

ctttgtgcaa tttgagaagg gagagagcta cttccacatg cacgtgctcg tggaaaccac    360

cggggtgaaa tccatggttt tgggacgttt cctgagtcag attcgcgaaa aactgattca    420

gagaatttac cgcgggatcg agccgacttt gccaaactgg ttcgcggtca caaagaccag    480

aaatggcgcc ggaggcggga acaaggtggt ggatgagtgc tacatcccca attacttgct    540

ccccaaaacc cagcctgagc tccagtgggc gtggactaat atggaacagt atttaagcgc    600

ctgtttgaat ctcacggagc gtaaacggtt ggtggcgcag catctgacgc acgtgtcgca    660
```

-continued

```
gacgcaggag cagaacaaag agaatcagaa tcccaattct gatgcgccgg tgatcagatc    720
aaaaacttca gccaggtaca tggagctggt cgggtggctc gtggacaagg ggattacctc    780
ggagaagcag tggatccagg aggaccaggc ctcatacatc tccttcaatg cggcctccaa    840
ctcgcggtcc caaatcaagg ctgccttgga caatgcggga aagattatga gcctgactaa    900
aaccgccccc gactacctgg tgggccagca gcccgtggag gacatttcca gcaatcggat    960
ttataaaatt ttggaactaa acgggtacga tccccaatat gcggcttccg tctttctggg   1020
atgggccacg aaaaagttcg gcaagaggaa caccatctgg ctgtttgggc ctgcaactac   1080
cgggaagacc aacatcgcgg aggccatagc ccacactgtg cccttctacg ggtgcgtaaa   1140
ctggaccaat gagaactttc ccttcaacga ctgtgtcgac aagatggtga tctggtggga   1200
ggaggggaag atgaccgcca aggtcgtgga gtcggccaaa gccattctcg gaggaagcaa   1260
ggtgcgcgtg gaccagaaat gcaagtcctc ggcccagata gacccgactc ccgtgatcgt   1320
cacctccaac accaacatgt gcgccgtgat tgacgggaac tcaacgacct tcgaacacca   1380
gcagccgttg caagaccgga tgttcaaatt tgaactcacc cgccgtctgg atcatgactt   1440
tgggaaggtc accaagcagg aagtcaaaga ctttttccgg tgggcaaagg atcacgtggt   1500
tgaggtggag catgaattct acgtcaaaaa gggtggagcc aagaaaagac ccgcccccag   1560
tgacgcagat ataagtgagc ccaaacgggt gcgcgagtca gttgcgcagc catcgacgtc   1620
agacgcggaa gcttcgatca actacgcgga caggtaccaa aacaaatgtt ctcgtcacgt   1680
gggcatgaat ctgatgctgt ttccctgcag acaatgcgag agactgaatc agaattcaaa   1740
tatctgcttc actcacggtg tcaaagactg tttagagtgc tttcccgtgt cagaatctca   1800
acccgtttct gtcgtcaaaa aggcgtatca gaaactgtgc tacattcatc acatcatggg   1860
aaaggtgcca gacgcttgca ctgcttgcga cctggtcaat gtggacttgg atgactgtgt   1920
ttctgaacaa taaatgactt aaaccaggta tggctgccga tggttatctt ccagattggc   1980
tcgaggacaa ccttagtgaa ggaattcgcg agtggtgggc tttgaaacct ggagcccctc   2040
aacccaaggc aaatcaacaa catcaagaca acgctcgagg tcttgtgctt ccgggttaca   2100
aataccttgg acccggcaac ggactcgaca agggggagcc ggtcaacgca gcagacgcgg   2160
cggccctcga gcacgacaag gcctacgacc agcagctcaa ggccggagac aacccgtacc   2220
tcaagtacaa ccacgccgac gccgagttcc aggagcggct caaagaagat acgtcttttg   2280
ggggcaacct cgggcgagca gtcttccagg ccaaaaagag gcttcttgaa cctcttggtc   2340
tggttgagga agcggctaag acggctcctg gaaagaagag gcctgtagag cagtctcctc   2400
aggaaccgga ctcctccgcg ggtattggca aatcgggtgc acagcccgct aaaaagagac   2460
tcaatttcgg tcagactggc gacacagagt cagtcccaga ccctcaacca atcggagaac   2520
ctcccgcagc cccctcaggt gtgggatctc ttacaatggc ttcaggtggt ggcgcaccag   2580
tggcagacaa taacgaaggt gccgatggag tgggtagttc ctcgggaaat tggcattgcg   2640
attcccaatg gctgggggac agagtcatca ccaccagcac ccgaacctgg gccctgccca   2700
cctacaacaa tcacctctac aagcaaatct ccaacagcac atctggagga tcttcaaatg   2760
acaacgccta cttcggctac agcaccccct gggggtattt tgacttcaac agattccact   2820
gccacttctc accacgtgac tggcagcgac tcatcaacaa caactgggga ttccggccta   2880
agcgactcaa cttcaagctc ttcaacattc aggtcaaaga ggttacggac aacaatggag   2940
tcaagaccat cgccaataac cttaccagca cggtccaggt cttcacggac tcagactatc   3000
agctcccgta cgtgctcggg tcggctcacg agggctgcct cccgccgttc ccagcggacg   3060
```

ttttcatgat tcctcagtac gggtatctga cgcttaatga tggaagccag gccgtgggtc 3120
gttcgtcctt ttactgcctg gaatatttcc cgtcgcaaat gctaagaacg ggtaacaact 3180
tccagttcag ctacgagttt gagaacgtac ctttccatag cagctacgct cacagccaaa 3240
gcctggaccg actaatgaat ccactcatcg accaatactt gtactatctc tcaaagacta 3300
ttaacggttc tggacagaat caacaaacgc taaaattcag tgtggccgga cccagcaaca 3360
tggctgtcca gggaagaaac tacatacctg gacccagcta ccgacaacaa cgtgtctcaa 3420
ccactgtgac tcaaaacaac aacagcgaat ttgcttggcc tggagcttct tcttgggctc 3480
tcaatggacg taatagcttg atgaatcctg gacctgctat ggccaagtca gcgtggagat 3540
cgagtgggag ctgcagaagg aaaacagcaa gcgctggaac ccggagatcc agtacacttc 3600
caactattac aagtctaata atgttgaatt tgctgttaat actgaaggtg tatatagtga 3660
accccgcccc attggcacca gatacctgac tcgtaatctg taattgcttg ttaatcaata 3720
aaccgtttaa ttcgtttcag ttgaactttg gtctc 3755

<210> SEQ ID NO 7
<211> LENGTH: 3755
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
gtcgacggta tcgggggagc tcgcagggtc tccattttga agcgggaggt ttgaacgcgc 60
agccgccatg ccggggtttt acgagattgt gattaaggtc cccagcgacc ttgacgagca 120
tctgcccggc atttctgaca gctttgtgaa ctgggtggcc gagaaggaat gggagttgcc 180
gccagattct gacatggatc tgaatctgat tgagcaggca cccctgaccg tggccgagaa 240
gctgcagcgc gactttctga cggaatggcg ccgtgtgagt aaggccccgg aggctctttt 300
ctttgtgcaa tttgagaagg gagagagcta cttccacatg cacgtgctcg tggaaaccac 360
cggggtgaaa tccatggttt tgggacgttt cctgagtcag attcgcgaaa aactgattca 420
gagaatttac cgcgggatcg agccgacttt gccaaactgg ttcgcggtca caaagaccag 480
aaatggcgcc ggaggcggga acaaggtggt ggatgagtgc tacatcccca attacttgct 540
ccccaaaacc cagcctgagc tccagtgggc gtggactaat atggaacagt atttaagcgc 600
ctgtttgaat ctcacggagc gtaaacggtt ggtggcgcag catctgacgc acgtgtcgca 660
gacgcaggag cagaacaaag agaatcagaa tcccaattct gatgcgccgg tgatcagatc 720
aaaaacttca gccaggtaca tggagctggt cgggtggctc gtggacaagg ggattacctc 780
ggagaagcag tggatccagg aggaccaggc ctcatacatc tccttcaatg cggcctccaa 840
ctcgcggtcc caaatcaagg ctgccttgga caatgcggga aagattatga gcctgactaa 900
aaccgccccc gactacctgg tgggccagca gcccgtggag gacatttcca gcaatcggat 960
ttataaaatt ttggaactaa acgggtacga tccccaatat gcggcttccg tctttctggg 1020
atgggccacg aaaaagttcg gcaagaggaa caccatctgg ctgtttgggc ctgcaactac 1080
cgggaagacc aacatcgcgg aggccatagc ccacactgtg cccttctacg ggtgcgtaaa 1140
ctggaccaat gagaactttc ccttcaacga ctgtgtcgac aagatggtga tctggtggga 1200
ggaggggaag atgaccgcca aggtcgtgga gtcggccaaa gccattctcg gaggaagcaa 1260
ggtgcgcgtg gaccagaaat gcaagtcctc ggcccagata gacccgactc ccgtgatcgt 1320

```
cacctccaac accaacatgt gcgccgtgat tgacgggaac tcaacgacct tcgaacacca   1380

gcagccgttg caagaccgga tgttcaaatt tgaactcacc cgccgtctgg atcatgactt   1440

tgggaaggtc accaagcagg aagtcaaaga ctttttccgg tgggcaaagg atcacgtggt   1500

tgaggtggag catgaattct acgtcaaaaa gggtggagcc aagaaaagac ccgcccccag   1560

tgacgcagat ataagtgagc ccaaacgggt gcgcgagtca gttgcgcagc catcgacgtc   1620

agacgcggaa gcttcgatca actacgcgga caggtaccaa aacaaatgtt ctcgtcacgt   1680

gggcatgaat ctgatgctgt ttccctgcag acaatgcgag agactgaatc agaattcaaa   1740

tatctgcttc actcacggtg tcaaagactg tttagagtgc tttcccgtgt cagaatctca   1800

acccgtttct gtcgtcaaaa aggcgtatca gaaactgtgc tacattcatc acatcatggg   1860

aaaggtgcca gacgcttgca ctgcttgcga cctggtcaat gtggacttgg atgactgtgt   1920

ttctgaacaa taaatgactt aaaccaggta tggctgccga tggttagctt ccagattggc   1980

tcgaggacaa ccttagtgaa ggaattcgcg agtggtgggc tttgaaacct ggagcccctc   2040

aacccaaggc aaatcaacaa catcaagaca acgctcgagg tcttgtgctt ccgggttaca   2100

aataccttgg acccggcaac ggactcgaca agggggagcc ggtcaacgca gcagacgcgg   2160

cggccctcga gcacgacaag gcctacgacc agcagctcaa ggccggagac aacccgtacc   2220

tcaagtacaa ccacgccgac gccgagttcc aggagcggct caaagaagat acgtcttttg   2280

ggggcaacct cgggcgagca gtcttccagg ccaaaaagag gcttcttgaa cctcttggtc   2340

tggttgagga agcggctaag acggctcctg gaaagtagag gcctgtagag cagtctcctc   2400

aggaaccgga ctcctccgcg ggtattggca aatcgggtgc acagcccgct aaaaagagac   2460

tcaatttcgg tcagactggc gacacagagt cagtcccaga ccctcaacca atcggagaac   2520

ctcccgcagc cccctcaggt gtgggatctc ttacaatggc ttcaggtggt ggcgcaccag   2580

tggcagacaa taactaaggt gccgatggag tgggtagttc ctcgggaaat tggcattgcg   2640

attcccaatg gctgggggac agagtcatca ccaccagcac ccgaacctgg gccctgccca   2700

cctacaacaa tcacctctac aagcaaatct ccaacagcac atctggagga tcttcaaatg   2760

acaacgccta cttcggctac agcaccccct gggggtattt tgacttcaac agattccact   2820

gccacttctc accacgtgac tggcagcgac tcatcaacaa caactgggga ttccggccta   2880

agcgactcaa cttcaagctc ttcaacattc aggtcaaaga ggttacggac aacaatggag   2940

tcaagaccat cgccaataac cttaccagca cggtccaggt cttcacggac tcagactatc   3000

agctcccgta cgtgctcggg tcggctcacg agggctgcct cccgccgttc ccagcggacg   3060

ttttcatgat tcctcagtac gggtatctga cgcttaatga tggaagccag gccgtgggtc   3120

gttcgtcctt ttactgcctg gaatatttcc cgtcgcaaat gctaagaacg ggtaacaact   3180

tccagttcag ctacgagttt gagaacgtac ctttccatag cagctacgct cacagccaaa   3240

gcctggaccg actaatgaat ccactcatcg accaatactt gtactatctc tcaaagacta   3300

ttaacggttc tggacagaat caacaaacgc taaaattcag tgtggccgga cccagcaaca   3360

tggctgtcca gggaagaaac tacatacctg gacccagcta ccgacaacaa cgtgtctcaa   3420

ccactgtgac tcaaaacaac aacagcgaat ttgcttggcc tggagcttct tcttgggctc   3480

tcaatggacg taatagcttg atgaatcctg gacctgctat ggccaagtca gcgtggagat   3540

cgagtgggag ctgcagaagg aaaacagcaa gcgctggaac ccggagatcc agtacacttc   3600

caactattac aagtctaata atgttgaatt tgctgttaat actgaaggtg tatatagtga   3660
```

accccgcccc attggcacca gatacctgac tcgtaatctg taattgcttg ttaatcaata 3720
aaccgtttaa ttcgtttcag ttgaactttg gtctc 3755

<210> SEQ ID NO 8
<211> LENGTH: 3710
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgatatc tagtatctgc 180
agagggccct gcgtatgagt gcaagtgggt tttaggacca ggatgaggcg gggtgggggt 240
gcctacctga cgaccgaccc cgacccactg gacaagcacc caacccccat tccccaaatt 300
gcgcatcccc tatcagagag ggggagggga aacaggatgc ggcgaggcgc gtgcgcactg 360
ccagcttcag caccgcggac agtgccttcg cccccgcctg gcggcgcgcg ccaccgccgc 420
ctcagcactg aaggcgcgct gacgtcactc gccggtcccc cgcaaactcc ccttcccggc 480
caccttggtc gcgtccgcgc cgccgccggc ccagccggac cgcaccacgc gaggcgcgag 540
ataggggggc acgggcgcga ccatctgcgc tgcggcgccg gcgactcagc gctgcctcag 600
tctgcggtgg gcagcggagg agtcgtgtcg tgcctgagag cgcagctgtg ctcctgggca 660
ccgcgcagtc cgcccccgcg gctcctggcc agaccacccc taggaccccc tgccccaagt 720
cgcagccggt caccaagcag gaagtcaaag actttttccg gtgggcaaag gatcacgtgg 780
ttgaggtgga gcatgaattc tacgtcaaaa agggtggagc caagaaaaga cccgccccca 840
gtgacgcaga tataagtgag cccaaacggg tgcgcgagtc agttgcgcag ccatcgacgt 900
cagacgcgga agcttcgatc aactacgcgg acaggtacca aaacaaatgt tctcgtcacg 960
tgggcatgaa tctgatgctg tttccctgca gacaatgcga gagactgaat cagaattcaa 1020
atatctgctt cactcacggt gtcaaagact gtttagagtg ctttcccgtg tcagaatctc 1080
aacccgtttc tgtcgtcaaa aaggcgtatc agaaactgtg ctacattcat cacatcatgg 1140
gaaaggtgcc agacgcttgc actgcttgcg acctggtcaa tgtggacttg gatgactgtg 1200
tttctgaaca ataaatgact taaaccaggt atggctgccg atggttatct tccagattgg 1260
ctcgaggaca accttagtga aggaattcgc gagtggtggg ctttgaaacc tggagcccct 1320
caacccaagg caaatcaaca acatcaagac aacgctcgag gtcttgtgct tccgggttac 1380
aaataccttg gacccggcaa cggactcgac aaggggggagc cggtcaacgc agcagacgcg 1440
gcggccctcg agcacgacaa ggcctacgac cagcagctca aggccggaga caacccgtac 1500
ctcaagtaca accacgccga cgccgagttc caggagcggc tcaaagaaga tacgtctttt 1560
gggggcaacc tcgggcgagc agtcttccag gccaaaaaga ggcttcttga acctcttggt 1620
ctggttgagg aagcggctaa gacggctcct ggaaagaaga ggcctgtaga gcagtctcct 1680
caggaaccgg actcctccgc gggtattggc aaatcgggtg cacagcccgc taaaaagaga 1740
ctcaatttcg gtcagactgg cgacacagag tcagtcccag accctcaacc aatcggagaa 1800
cctcccgcag ccccctcagg tgtgggatct cttacaatgg cttcaggtgg tggcgcacca 1860
gtggcagaca ataacgaagg tgccgatgga gtgggtagtt cctcgggaaa ttggcattgc 1920

```
gattcccaat ggctggggga cagagtcatc accaccagca cccgaacctg ggccctgccc   1980

acctacaaca atcacctcta caagcaaatc tccaacagca catctggagg atcttcaaat   2040

gacaacgcct acttcggcta cagcaccccc tgggggtatt ttgacttcaa cagattccac   2100

tgccacttct caccacgtga ctggcagcga ctcatcaaca acaactgggg attccggcct   2160

aagcgactca acttcaagct cttcaacatt caggtcaaag aggttacgga caacaatgga   2220

gtcaagacca tcgccaataa ccttaccagc acggtccagg tcttcacgga ctcagactat   2280

cagctcccgt acgtgctcgg gtcggctcac gagggctgcc tcccgccgtt cccagcggac   2340

gttttcatga ttcctcagta cgggtatctg acgcttaatg atggaagcca ggccgtgggt   2400

cgttcgtcct tttactgcct ggaatatttc ccgtcgcaaa tgctaagaac gggtaacaac   2460

ttccagttca gctacgagtt tgagaacgta cctttccata gcagctacgc tcacagccaa   2520

agcctggacc gactaatgaa tccactcatc gaccaatact tgtactatct ctcaaagact   2580

attaacggtt ctggacagaa tcaacaaacg ctaaaattca gtgtggccgg acccagcaac   2640

atggctgtcc agggaagaaa ctacatacct ggacccagct accgacaaca acgtgtctca   2700

accactgtga ctcaaaacaa caacagcgaa tttgcttggc ctggagcttc ttcttgggct   2760

ctcaatggac gtaatagctt gatgaatcct ggacctgcta tggccagcca caaagaagga   2820

gaggaccgtt tctttccttt gtctggatct ttaatttttg gcaaacaagg aactggaaga   2880

gacaacgtgg atgcggacaa agtcatgata accaacgaag aagaaattaa aactactaac   2940

ccggtagcaa cggagtccta tggacaagtg gccacaaacc accagagtgc ccaagcacag   3000

gcgcagaccg gctgggttca aaaccaagga atacttccgg gtatggtttg gcaggacaga   3060

gatgtgtacc tgcaaggacc catttgggcc aaaattcctc acacggacgg caactttcac   3120

ccttctccgc tgatgggagg gtttggaatg aagcacccgc ctcctcagat cctcatcaaa   3180

aacacacctg tacctgcgga tcctccaacg gccttcaaca aggacaagct gaactctttc   3240

atcacccagt attctactgg ccaagtcagc gtggagatcg agtgggagct gcagaaggaa   3300

aacagcaagc gctggaaccc ggagatccag tacacttcca actattacaa gtctaataat   3360

gttgaatttg ctgttaatac tgaaggtgta tatagtgaac cccgccccat tggcaccaga   3420

tacctgactc gtaatctgta atcgattgtt aatcaataaa ccgtttaatt cgtttcagtt   3480

gaactttggt ctctgcgtat ttctttctta tctagtttcc atggctacgt agataagtag   3540

catggcgggt taatcattaa ctacaaggaa cccctagtga tggagttggc cactccctct   3600

ctgcgcgctc gctcgctcac tgaggccggg cgaccaaagg tcgcccgacg cccgggcttt   3660

gcccgggcgg cctcagtgag cgagcgagcg cgcagagagg gagtggccaa              3710
```

<210> SEQ ID NO 9
<211> LENGTH: 3852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgatatc gatctaacat    180

atcctggtgt ggagtagcgg acgctgctat gacagaggct cgggggcctg agctggctct    240
```

-continued

```
gtgagctggg gaggaggcag acagccaggc cttgtctgca agcagacctg gcagcattgg    300
gctggccgcc ccccagggcc tcctcttcat gcccagtgaa tgactcacct tggcacagac    360
acaatgttcg gggtgggcac agtgcctgct tcccgccgca ccccagcccc cctcaaatgc    420
cttccgagaa gcccattgag caggggggctt gcattgcacc ccagcctgac agcctggcat    480
cttgggataa aagcagcaca gcccccctagg ggctgccctt gctgtgtggc gccaccggcg    540
gtggagaaca aggctctatt cagcctgtgc ccaggaaagg ggatcagggg atgcccaggc    600
atggacagtg ggtggcaggg ggggagagga gggctgtctg cttcccagaa gtccaaggac    660
acaaatgggt gaggggagag ctctccccat agctgggctg cggcccaacc ccaccccctc    720
aggctatgcc agggggtgtt gccaggggca cccgggcatc gccagtctag cccactcctt    780
cataaagccc tcgcatccca ggagcgagca gagccagagc aggttggaga ggagacgcat    840
cacctccgct gctcgcgggg atcctctagg gtcaccaagc aggaagtcaa agactttttc    900
cggtgggcaa aggatcacgt ggttgaggtg gagcatgaat tctacgtcaa aaagggtgga    960
gccaagaaaa gacccgcccc cagtgacgca gatataagtg agcccaaacg ggtgcgcgag   1020
tcagttgcgc agccatcgac gtcagacgcg gaagcttcga tcaactacgc ggacaggtac   1080
caaaacaaat gttctcgtca cgtgggcatg aatctgatgc tgtttccctg cagacaatgc   1140
gagagactga atcagaattc aaatatctgc ttcactcacg gtgtcaaaga ctgtttagag   1200
tgctttcccg tgtcagaatc tcaacccgtt tctgtcgtca aaaaggcgta tcagaaactg   1260
tgctacattc atcacatcat gggaaaggtg ccagacgctt gcactgcttg cgacctggtc   1320
aatgtggact tggatgactg tgtttctgaa caataaatga cttaaaccag gtatggctgc   1380
cgatggttat cttccagatt ggctcgagga caaccttagt gaaggaattc gcgagtggtg   1440
ggctttgaaa cctggagccc ctcaacccaa ggcaaatcaa caacatcaag acaacgctcg   1500
aggtcttgtg cttccgggtt acaaatacct tggacccggc aacggactcg acaaggggga   1560
gccggtcaac gcagcagacg cggcggccct cgagcacgac aaggcctacg accagcagct   1620
caaggccgga gacaacccgt acctcaagta caaccacgcc gacgccgagt tccaggagcg   1680
gctcaaagaa gatacgtctt ttgggggcaa cctcgggcga gcagtcttcc aggccaaaaa   1740
gaggcttctt gaacctcttg gtctggttga ggaagcggct aagacggctc ctggaaagaa   1800
gaggcctgta gagcagtctc ctcaggaacc ggactcctcc gcgggtattg gcaaatcggg   1860
tgcacagccc gctaaaaaga gactcaattt cggtcagact ggcgacacag agtcagtccc   1920
agaccctcaa ccaatcggag aacctcccgc agccccctca ggtgtgggat ctcttacaat   1980
ggcttcaggt ggtggcgcac cagtggcaga caataacgaa ggtgccgatg gagtgggtag   2040
ttcctcggga aattggcatt gcgattccca atggctgggg gacagagtca tcaccaccag   2100
cacccgaacc tgggccctgc ccacctacaa caatcacctc tacaagcaaa tctccaacag   2160
cacatctgga ggatcttcaa atgacaacgc ctacttcggc tacagcaccc cctgggggta   2220
ttttgacttc aacagattcc actgccactt ctcaccacgt gactggcagc gactcatcaa   2280
caacaactgg ggattccggc ctaagcgact caacttcaag ctcttcaaca ttcaggtcaa   2340
agaggttacg gacaacaatg gagtcaagac catcgccaat aaccttacca gcacggtcca   2400
ggtcttcacg gactcagact atcagctccc gtacgtgctc gggtcggctc acgagggctg   2460
cctcccgccg ttcccagcgg acgttttcat gattcctcag tacgggtatc tgacgcttaa   2520
tgatggaagc caggccgtgg gtcgttcgtc cttttactgc ctggaatatt tcccgtcgca   2580
aatgctaaga acgggtaaca acttccagtt cagctacgag tttgagaacg tacctttcca   2640
```

```
tagcagctac gctcacagcc aaagcctgga ccgactaatg aatccactca tcgaccaata   2700

cttgtactat ctctcaaaga ctattaacgg ttctggacag aatcaacaaa cgctaaaatt   2760

cagtgtggcc ggacccagca acatggctgt ccagggaaga aactacatac ctggacccag   2820

ctaccgacaa caacgtgtct caaccactgt gactcaaaac aacaacagcg aatttgcttg   2880

gcctggagct tcttcttggg ctctcaatgg acgtaatagc ttgatgaatc ctggacctgc   2940

tatggccagc cacaaagaag gagaggaccg tttctttcct ttgtctggat ctttaatttt   3000

tggcaaacaa ggaactggaa gagacaacgt ggatgcggac aaagtcatga taaccaacga   3060

agaagaaatt aaaactacta acccggtagc aacggagtcc tatggacaag tggccacaaa   3120

ccaccagagt gcccaagcac aggcgcagac cggctgggtt caaaaccaag gaatacttcc   3180

gggtatggtt tggcaggaca gagatgtgta cctgcaagga cccatttggg ccaaaattcc   3240

tcacacggac ggcaactttc acccttctcc gctgatggga gggtttggaa tgaagcaccc   3300

gcctcctcag atcctcatca aaaacacacc tgtacctgcg gatcctccaa cggccttcaa   3360

caaggacaag ctgaactctt tcatcaccca gtattctact ggccaagtca gcgtggagat   3420

cgagtgggag ctgcagaagg aaaacagcaa gcgctggaac ccggagatcc agtacacttc   3480

caactattac aagtctaata atgttgaatt tgctgttaat actgaaggtg tatatagtga   3540

accccgcccc attggcacca gatacctgac tcgtaatctg taatcgattg ttaatcaata   3600

aaccgtttaa ttcgtttcag ttgaactttg gtctctgcgt atttctttct tatctagttt   3660

ccatggctac gtagataagt agcatggcgg gttaatcatt aactacaagg aacccctagt   3720

gatggagttg gccactccct ctctgcgcgc tcgctcgctc actgaggccg ggcgaccaaa   3780

ggtcgcccga cgcccgggct ttgcccgggc ggcctcagtg agcgagcgag cgcgcagaga   3840

gggagtggcc aa                                                        3852
```

```
<210> SEQ ID NO 10
<211> LENGTH: 4425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgatatc catgcgtcga    180

cataacgcgt cgacattgat tattgactag ttattaatag taatcaatta cggggtcatt    240

agttcatagc ccatatatgg agttccgcgt tacataactt acggtaaatg gcccgcctgg    300

ctgaccgccc aacgaccccc gcccattgac gtcaataatg acgtatgttc ccatagtaac    360

gccaataggg actttccatt gacgtcaatg ggtggagtat ttacggtaaa ctgcccactt    420

ggcagtacat caagtgtatc atatgccaag tacgccccct attgacgtca atgacggtaa    480

atggcccgcc tggcattatg cccagtacat gaccttatgg gactttccta cttggcagta    540

catctacgta ttagtcatcg ctattaccat gtcgaggcca cgttctgctt cactctcccc    600

atctcccccc cctccccacc cccaattttg tatttattta tttttaatt attttgtgca     660

gcgatggggg cggggggggg gggcgcgcgc caggcggggc ggggcggggc gaggggcggg    720

gcggggcgag gcggagaggt gcggcggcag ccaatcagag cggcgcgctc cgaaagtttc    780
```

```
cttttatggc gaggcggcgg cggcggcggc cctataaaaa gcgaagcgcg cggcgggcgg    840
gagcaagctt cgtttagtga accgtcagat cgcctggaga cgccatccac gctgttttga    900
cctccataga agacaccggg accgatccag cctccgcgga ttcgaatccc ggccgggaac    960
ggtgcattgg aacgcggatt ccccgtgcca agagtgacgt aagtaccgcc tatagagtct   1020
ataggcccac aaaaaatgct ttcttctttt aatatacttt tttgtttatc ttatttctaa   1080
tactttccct aatctctttc tttcagggca ataatgatac aatgtatcat gcctctttgc   1140
accattctaa agaataacag tgataatttc tgggttaagg caatagcaat atttctgcat   1200
ataaatattt ctgcatataa attgtaactg atgtaagagg tttcatattg ctaatagcag   1260
ctacaatcca gctaccattc tgcttttatt ttatggttgg gataaggctg gattattctg   1320
agtccaagct aggccctttt gctaatcatg ttcatacctc ttatcttcct cccacagctc   1380
ctgggcaacg tgctggtctg tgtgctggcc catcactttg gcaaagaatt gggattcgaa   1440
ccggtcacca agcaggaagt caaagacttt ttccggtggg caaaggatca cgtggttgag   1500
gtggagcatg aattctacgt caaaaagggt ggagccaaga aaagacccgc ccccagtgac   1560
gcagatataa gtgagcccaa acgggtgcgc gagtcagttg cgcagccatc gacgtcagac   1620
gcggaagctt cgatcaacta cgcggacagg taccaaaaca aatgttctcg tcacgtgggc   1680
atgaatctga tgctgtttcc ctgcagacaa tgcgagagac tgaatcagaa ttcaaatatc   1740
tgcttcactc acggtgtcaa agactgttta gagtgctttc ccgtgtcaga atctcaaccc   1800
gtttctgtcg tcaaaaaggc gtatcagaaa ctgtgctaca ttcatcacat catgggaaag   1860
gtgccagacg cttgcactgc ttgcgacctg gtcaatgtgg acttggatga ctgtgtttct   1920
gaacaataaa tgacttaaac caggtatggc tgccgatggt tatcttccag attggctcga   1980
ggacaacctt agtgaaggaa ttcgcgagtg gtgggctttg aaacctggag cccctcaacc   2040
caaggcaaat caacaacatc aagacaacgc tcgaggtctt gtgcttccgg gttacaaata   2100
ccttggaccc ggcaacggac tcgacaaggg ggagccggtc aacgcagcag acgcggcggc   2160
cctcgagcac gacaaggcct acgaccagca gctcaaggcc ggagacaacc cgtacctcaa   2220
gtacaaccac gccgacgccg agttccagga gcggctcaaa gaagatacgt cttttggggg   2280
caacctcggg cgagcagtct tccaggccaa aaagaggctt cttgaacctc ttggtctggt   2340
tgaggaagcg gctaagacgg ctcctggaaa gaagaggcct gtagagcagt ctcctcagga   2400
accggactcc tccgcgggta ttggcaaatc gggtgcacag cccgctaaaa agagactcaa   2460
tttcggtcag actggcgaca cagagtcagt cccagaccct caaccaatcg gagaacctcc   2520
cgcagccccc tcaggtgtgg gatctcttac aatggcttca ggtggtggcg caccagtggc   2580
agacaataac gaaggtgccg atggagtggg tagttcctcg ggaaattggc attgcgattc   2640
ccaatggctg gggggacagag tcatcaccac cagcacccga acctgggccc tgcccaccta   2700
caacaatcac ctctacaagc aaatctccaa cagcacatct ggaggatctt caaatgacaa   2760
cgcctacttc ggctacagca ccccctgggg gtattttgac ttcaacagat tccactgcca   2820
cttctcacca cgtgactggc agcgactcat caacaacaac tggggattcc ggcctaagcg   2880
actcaacttc aagctcttca acattcaggt caaagaggtt acggacaaca atggagtcaa   2940
gaccatcgcc aataacctta ccagcacggt ccaggtcttc acggactcag actatcagct   3000
cccgtacgtg ctcgggtcgg ctcacgaggg ctgcctcccg ccgttcccag cggacgtttt   3060
catgattcct cagtacgggt atctgacgct taatgatgga agccaggccg tgggtcgttc   3120
```

```
gtccttttac tgcctggaat atttcccgtc gcaaatgcta agaacgggta acaacttcca   3180

gttcagctac gagtttgaga acgtaccttt ccatagcagc tacgctcaca gccaaagcct   3240

ggaccgacta atgaatccac tcatcgacca atacttgtac tatctctcaa agactattaa   3300

cggttctgga cagaatcaac aaacgctaaa attcagtgtg gccggaccca gcaacatggc   3360

tgtccaggga agaaactaca tacctggacc cagctaccga caacaacgtg tctcaaccac   3420

tgtgactcaa aacaacaaca gcgaatttgc ttggcctgga gcttcttctt gggctctcaa   3480

tggacgtaat agcttgatga atcctggacc tgctatggcc agccacaaag aaggagagga   3540

ccgtttcttt cctttgtctg gatctttaat ttttggcaaa caaggaactg gaagagacaa   3600

cgtggatgcg gacaaagtca tgataaccaa cgaagaagaa attaaaacta ctaacccggt   3660

agcaacggag tcctatggac aagtggccac aaaccaccag agtgcccaag cacaggcgca   3720

gaccggctgg gttcaaaacc aaggaatact tccgggtatg gtttggcagg acagagatgt   3780

gtacctgcaa ggacccattt gggccaaaat tcctcacacg gacggcaact ttcacccttc   3840

tccgctgatg ggagggtttg gaatgaagca cccgcctcct cagatcctca tcaaaaacac   3900

acctgtacct gcggatcctc caacggcctt caacaaggac aagctgaact ctttcatcac   3960

ccagtattct actggccaag tcagcgtgga gatcgagtgg gagctgcaga aggaaaacag   4020

caagcgctgg aacccggaga tccagtacac ttccaactat tacaagtcta ataatgttga   4080

atttgctgtt aatactgaag gtgtatatag tgaaccccgc cccattggca ccagatacct   4140

gactcgtaat ctgtaatcga ttgttaatca ataaaccgtt taattcgttt cagttgaact   4200

ttggtctctg cgtatttctt tcttatctag tttccatggc tacgtagata agtagcatgg   4260

cgggttaatc attaactaca aggaacccct agtgatggag ttggccactc cctctctgcg   4320

cgctcgctcg ctcactgagg ccgggcgacc aaaggtcgcc cgacgcccgg gctttgcccg   4380

ggcggcctca gtgagcgagc gagcgcgcag agagggagtg gccaa                   4425
```

<210> SEQ ID NO 11
<211> LENGTH: 4480
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgatatc catgcgtcga    180

cataacgcgt gatctaacat atcctggtgt ggagtagcgg acgctgctat gacagaggct    240

cgggggcctg agctggctct gtgagctggg gaggaggcag acagccaggc cttgtctgca    300

agcagacctg gcagcattgg gctggccgcc ccccagggcc tcctcttcat gcccagtgaa    360

tgactcacct tggcacagac acaatgttcg ggtgggcac agtgcctgct tcccgccgca    420

ccccagcccc cctcaaatgc cttccgagaa gcccattgag caggggggctt gcattgcacc   480

ccagcctgac agcctggcat cttgggataa aagcagcaca gccccctagg ggctgccctt    540

gctgtgtggc gccaccggcg gtggagaaca aggctctatt cagcctgtgc ccaggaaagg    600

ggatcagggg atgcccaggc atggacagtg ggtggcaggg ggggagagga gggctgtctg    660

cttcccagaa gtccaaggac acaaatgggt gaggggagag ctctccccat agctgggctg    720
```

-continued

```
cggcccaacc ccaccccctc aggctatgcc agggggtgtt gccaggggca cccgggcatc    780
gccagtctag cccactcctt cataaagccc tcgcatccca ggagcgagca gagccagagc    840
aggttggaga ggagacgcat cacctccgct gctcgcgggg atcctctaga agcttcgttt    900
agtgaaccgt cagatcgcct ggagacgcca tccacgctgt tttgacctcc atagaagaca    960
ccgggaccga tccagcctcc gcggattcga atcccggccg ggaacggtgc attggaacgc   1020
ggattccccg tgccaagagt gacgtaagta ccgcctatag agtctatagg cccacaaaaa   1080
atgctttctt cttttaatat actttttttgt ttatcttatt tctaatactt tccctaatct   1140
ctttctttca gggcaataat gatacaatgt atcatgcctc tttgcaccat tctaaagaat   1200
aacagtgata atttctgggt taaggcaata gcaatatttc tgcatataaa tatttctgca   1260
tataaattgt aactgatgta agaggtttca tattgctaat agcagctaca atccagctac   1320
cattctgctt ttattttatg gttgggataa ggctggatta ttctgagtcc aagctaggcc   1380
cttttgctaa tcatgttcat acctcttatc ttcctcccac agctcctggg caacgtgctg   1440
gtctgtgtgc tggcccatca ctttggcaaa gaattgggat tcgaaccggt cgccaccggt   1500
caccaagcag gaagtcaaag actttttccg gtgggcaaag gatcacgtgg ttgaggtgga   1560
gcatgaattc tacgtcaaaa agggtggagc caagaaaaga cccgccccca gtgacgcaga   1620
tataagtgag cccaaacggg tgcgcgagtc agttgcgcag ccatcgacgt cagacgcgga   1680
agcttcgatc aactacgcgg acaggtacca aaacaaatgt tctcgtcacg tgggcatgaa   1740
tctgatgctg tttccctgca gacaatgcga gagactgaat cagaattcaa atatctgctt   1800
cactcacggt gtcaaagact gtttagagtg ctttcccgtg tcagaatctc aacccgtttc   1860
tgtcgtcaaa aaggcgtatc agaaactgtg ctacattcat cacatcatgg gaaaggtgcc   1920
agacgcttgc actgcttgcg acctggtcaa tgtggacttg gatgactgtg tttctgaaca   1980
ataaatgact taaaccaggt atggctgccg atggttatct tccagattgg ctcgaggaca   2040
accttagtga aggaattcgc gagtggtggg ctttgaaacc tggagcccct caacccaagg   2100
caaatcaaca acatcaagac aacgctcgag gtcttgtgct tccgggttac aaataccttg   2160
gacccggcaa cggactcgac aagggggagc cggtcaacgc agcagacgcg gcggccctcg   2220
agcacgacaa ggcctacgac cagcagctca aggccggaga caacccgtac ctcaagtaca   2280
accacgccga cgccgagttc caggagcggc tcaaagaaga tacgtctttt gggggcaacc   2340
tcgggcgagc agtcttccag gccaaaaaga ggcttcttga acctcttggt ctggttgagg   2400
aagcggctaa gacggctcct ggaaagaaga ggcctgtaga gcagtctcct caggaaccgg   2460
actcctccgc gggtattggc aaatcgggtg cacagcccgc taaaaagaga ctcaatttcg   2520
gtcagactgg cgacacagag tcagtcccag accctcaacc aatcggagaa cctcccgcag   2580
ccccctcagg tgtgggatct cttacaatgg cttcaggtgg tggcgcacca gtggcagaca   2640
ataacgaagg tgccgatgga gtgggtagtt cctcgggaaa ttggcattgc gattcccaat   2700
ggctggggga cagagtcatc accaccagca cccgaacctg ggccctgccc acctacaaca   2760
atcacctcta caagcaaatc tccaacagca catctggagg atcttcaaat gacaacgcct   2820
acttcggcta cagcaccccc tgggggtatt ttgacttcaa cagattccac tgccacttct   2880
caccacgtga ctggcagcga ctcatcaaca acaactgggg attccggcct aagcgactca   2940
acttcaagct cttcaacatt caggtcaaag aggttacgga caacaatgga gtcaagacca   3000
tcgccaataa ccttaccagc acggtccagg tcttcacgga ctcagactat cagctcccgt   3060
acgtgctcgg gtcggctcac gagggctgcc tcccgccgtt cccagcggac gttttcatga   3120
```

ttcctcagta cgggtatctg acgcttaatg atggaagcca ggccgtgggt cgttcgtcct 3180
tttactgcct ggaatatttc ccgtcgcaaa tgctaagaac gggtaacaac ttccagttca 3240
gctacgagtt tgagaacgta cctttccata gcagctacgc tcacagccaa agcctggacc 3300
gactaatgaa tccactcatc gaccaatact tgtactatct ctcaaagact attaacggtt 3360
ctggacagaa tcaacaaacg ctaaaattca gtgtggccgg acccagcaac atggctgtcc 3420
agggaagaaa ctacatacct ggacccagct accgacaaca acgtgtctca accactgtga 3480
ctcaaaacaa caacagcgaa tttgcttggc ctggagcttc ttcttgggct ctcaatggac 3540
gtaatagctt gatgaatcct ggacctgcta tggccagcca caaagaagga gaggaccgtt 3600
tctttccttt gtctggatct ttaatttttg gcaaacaagg aactggaaga gacaacgtgg 3660
atgcggacaa agtcatgata accaacgaag aagaaattaa aactactaac ccggtagcaa 3720
cggagtccta tggacaagtg gccacaaacc accagagtgc ccaagcacag gcgcagaccg 3780
gctgggttca aaaccaagga atacttccgg gtatggtttg gcaggacaga gatgtgtacc 3840
tgcaaggacc catttgggcc aaaattcctc acacggacgg caactttcac ccttctccgc 3900
tgatgggagg gtttggaatg aagcacccgc ctcctcagat cctcatcaaa aacacacctg 3960
tacctgcgga tcctccaacg gccttcaaca aggacaagct gaactctttc atcacccagt 4020
attctactgg ccaagtcagc gtggagatcg agtgggagct gcagaaggaa aacagcaagc 4080
gctggaaccc ggagatccag tacacttcca actattacaa gtctaataat gttgaatttg 4140
ctgttaatac tgaaggtgta tatagtgaac cccgccccat tggcaccaga tacctgactc 4200
gtaatctgta atcgattgtt aatcaataaa ccgtttaatt cgtttcagtt gaactttggt 4260
ctctgcgtat ttctttctta tctagtttcc atggctacgt agataagtag catggcgggt 4320
taatcattaa ctacaaggaa cccctagtga tggagttggc cactccctct ctgcgcgctc 4380
gctcgctcac tgaggccggg cgaccaaagg tcgcccgacg cccgggcttt gcccgggcgg 4440
cctcagtgag cgagcgagcg cgcagagagg gagtggccaa 4480

<210> SEQ ID NO 12
<211> LENGTH: 4338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgatatc catgcgtcga 180
cataacgcgt tagtatctgc agagggccct gcgtatgagt gcaagtgggt tttaggacca 240
ggatgaggcg gggtgggggt gcctacctga cgaccgaccc cgacccactg gacaagcacc 300
caacccccat tccccaaatt gcgcatcccc tatcagagag ggggagggga aacaggatgc 360
ggcgaggcgc gtgcgcactg ccagcttcag caccgcggac agtgccttcg cccccgcctg 420
gcggcgcgcg ccaccgccgc ctcagcactg aaggcgcgct gacgtcactc gccggtcccc 480
cgcaaactcc ccttcccggc caccttggtc gcgtccgcgc cgccgccggc ccagccggac 540
cgcaccacgc gaggcgcgag ataggggggc acgggcgcga ccatctgcgc tgcggcgccg 600
gcgactcagc gctgcctcag tctgcggtgg gcagcggagg agtcgtgtcg tgcctgagag 660

```
cgcagctgtg ctcctgggca ccgcgcagtc cgcccccgcg gctcctggcc agaccacccc    720
taggaccccc tgccccaagt cgcagccaag cttcgtttag tgaaccgtca gatcgcctgg    780
agacgccatc cacgctgttt tgacctccat agaagacacc gggaccgatc cagcctccgc    840
ggattcgaat cccggccggg aacggtgcat tggaacgcgg attccccgtg ccaagagtga    900
cgtaagtacc gcctatagag tctataggcc cacaaaaaat gctttcttct tttaatatac    960
tttttgttt atcttatttc taatactttc cctaatctct ttctttcagg gcaataatga   1020
tacaatgtat catgcctctt tgcaccattc taaagaataa cagtgataat ttctgggtta   1080
aggcaatagc aatatttctg catataaata tttctgcata taaattgtaa ctgatgtaag   1140
aggtttcata ttgctaatag cagctacaat ccagctacca ttctgctttt attttatggt   1200
tgggataagg ctggattatt ctgagtccaa gctaggccct tttgctaatc atgttcatac   1260
ctcttatctt cctcccacag ctcctgggca acgtgctggt ctgtgtgctg gcccatcact   1320
ttggcaaaga attgggattc gaaccggtcg ccaccggtca ccaagcagga agtcaaagac   1380
tttttccggt gggcaaagga tcacgtggtt gaggtggagc atgaattcta cgtcaaaaag   1440
ggtggagcca agaaaagacc cgcccccagt gacgcagata taagtgagcc caaacgggtg   1500
cgcgagtcag ttgcgcagcc atcgacgtca gacgcggaag cttcgatcaa ctacgcggac   1560
aggtaccaaa acaaatgttc tcgtcacgtg ggcatgaatc tgatgctgtt tccctgcaga   1620
caatgcgaga gactgaatca gaattcaaat atctgcttca ctcacggtgt caaagactgt   1680
ttagagtgct ttcccgtgtc agaatctcaa cccgtttctg tcgtcaaaaa ggcgtatcag   1740
aaactgtgct acattcatca catcatggga aaggtgccag acgcttgcac tgcttgcgac   1800
ctggtcaatg tggacttgga tgactgtgtt tctgaacaat aaatgactta aaccaggtat   1860
ggctgccgat ggttatcttc cagattggct cgaggacaac cttagtgaag gaattcgcga   1920
gtggtgggct ttgaaacctg gagcccctca acccaaggca aatcaacaac atcaagacaa   1980
cgctcgaggt cttgtgcttc cgggttacaa ataccttgga cccggcaacg gactcgacaa   2040
gggggagccg gtcaacgcag cagacgcggc ggccctcgag cacgacaagg cctacgacca   2100
gcagctcaag gccggagaca acccgtacct caagtacaac cacgccgacg ccgagttcca   2160
ggagcggctc aaagaagata cgtcttttgg gggcaacctc gggcgagcag tcttccaggc   2220
caaaaagagg cttcttgaac ctcttggtct ggttgaggaa gcggctaaga cggctcctgg   2280
aaagaagagg cctgtagagc agtctcctca ggaaccggac tcctccgcgg gtattggcaa   2340
atcgggtgca cagcccgcta aaaagagact caatttcggt cagactggcg acacagagtc   2400
agtcccagac cctcaaccaa tcggagaacc tcccgcagcc ccctcaggtg tgggatctct   2460
tacaatggct tcaggtggtg gcgcaccagt ggcagacaat aacgaaggtg ccgatggagt   2520
gggtagttcc tcgggaaatt ggcattgcga ttcccaatgg ctgggggaca gagtcatcac   2580
caccagcacc cgaacctggg ccctgcccac ctacaacaat cacctctaca agcaaatctc   2640
caacagcaca tctggaggat cttcaaatga caacgcctac ttcggctaca gcaccccctg   2700
gggtatttt gacttcaaca gattccactg ccacttctca ccacgtgact ggcagcgact   2760
catcaacaac aactggggat tccggcctaa gcgactcaac ttcaagctct tcaacattca   2820
ggtcaaagag gttacggaca acaatggagt caagaccatc gccaataacc ttaccagcac   2880
ggtccaggtc ttcacggact cagactatca gctcccgtac gtgctcgggt cggctcacga   2940
gggctgcctc ccgccgttcc cagcggacgt tttcatgatt cctcagtacg ggtatctgac   3000
```

gcttaatgat ggaagccagg ccgtgggtcg ttcgtccttt tactgcctgg aatatttccc 3060
gtcgcaaatg ctaagaacgg gtaacaactt ccagttcagc tacgagtttg agaacgtacc 3120
tttccatagc agctacgctc acagccaaag cctggaccga ctaatgaatc cactcatcga 3180
ccaatacttg tactatctct caaagactat taacggttct ggacagaatc aacaaacgct 3240
aaaattcagt gtggccggac ccagcaacat ggctgtccag ggaagaaact acatacctgg 3300
acccagctac cgacaacaac gtgtctcaac cactgtgact caaaacaaca acagcgaatt 3360
tgcttggcct ggagcttctt cttgggctct caatggacgt aatagcttga tgaatcctgg 3420
acctgctatg gccagccaca aagaaggaga ggaccgtttc tttcctttgt ctggatcttt 3480
aatttttggc aaacaaggaa ctggaagaga caacgtggat gcggacaaag tcatgataac 3540
caacgaagaa gaaattaaaa ctactaaccc ggtagcaacg gagtcctatg gacaagtggc 3600
cacaaaccac cagagtgccc aagcacaggc gcagaccggc tgggttcaaa accaaggaat 3660
acttccgggt atggtttggc aggacagaga tgtgtacctg caaggaccca tttgggccaa 3720
aattcctcac acggacggca actttcaccc ttctccgctg atgggagggt ttggaatgaa 3780
gcacccgcct cctcagatcc tcatcaaaaa cacacctgta cctgcggatc ctccaacggc 3840
cttcaacaag gacaagctga actctttcat cacccagtat tctactggcc aagtcagcgt 3900
ggagatcgag tgggagctgc agaaggaaaa cagcaagcgc tggaacccgg agatccagta 3960
cacttccaac tattacaagt ctaataatgt tgaatttgct gttaatactg aaggtgtata 4020
tagtgaaccc cgccccattg gcaccagata cctgactcgt aatctgtaat cgattgttaa 4080
tcaataaacc gtttaattcg tttcagttga actttggtct ctgcgtattt ctttcttatc 4140
tagtttccat ggctacgtag ataagtagca tggcgggtta atcattaact acaaggaacc 4200
cctagtgatg gagttggcca ctccctctct gcgcgctcgc tcgctcactg aggccgggcg 4260
accaaaggtc gcccgacgcc cgggctttgc ccgggcggcc tcagtgagcg agcgagcgcg 4320
cagagaggga gtggccaa 4338

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
gtgccaagag tgacctcctg 20

<210> SEQ ID NO 14
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14 actgccccg cgaccggcac gtacaacctc caggaaatcg tgcccggcag cgtgtggatg 60
gagagggacg tgtacctcca aggacccatc tgggccaaga tcccagagac gggggcgcac 120
tttcacccct ctccggctat gggcggattc ggactcaaac acccaccgcc catgatgctc 180
atcaagaaca cgcctgtgcc cggaaatatc accagcttct cggacgtgcc cgtcagcagc 240
ttcatcaccc agtacagcac cgggcaggtc accgtggaga tggagtggga gctcaagaag 300
gaaaactcca agaggtggaa cccagagatc cagtacacaa acaactacaa cgacccccag 360
tttgtggact ttgccccgga cagcaccggg gaatacagaa ccaccagacc tatcggaacc 420 cgataccttta cccgacccct ttaa 444

<210> SEQ ID NO 15
<211> LENGTH: 440
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
accggagatg tgcatgttat gggagcctta cctggaatgg tgtggcaaga cagggacgtc 60
tacctgcagg gtcctatttg ggccaaaatt cctcacacgg atggacactt tcacccatct 120
cctctcatgg gcggctttgg acttaagcac ccgcctcctc agatcctcat caaaaacacg 180
cctgttcctg cgaatcctcc ggcagagttt tcggctacaa agtttgcttc attcatcacc 240
cagtattcca caggacaagt gagcgtggag attgaatggg agctgcagaa agaaaacagc 300
aaacgctgga atcccgaagt gcaatataca tctaactatg caaaatctgc caacgttgat 360
ttcactgtgg acaacaatgg actttatact gagcctcgcc ccattggcac ccgttacctc 420
acccgtcccc tgtaatcgat 440

<210> SEQ ID NO 16
<211> LENGTH: 447
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
acacaagcag ctaccgcaga tgtcaacaca caaggcgttc ttccaggcat ggtctggcag 60
gacagagatg tgtaccttca ggggcccatc tgggcaaaga ttccacacac ggacggacat 120
tttcacccct ctcccctcat gggtggattc ggacttaaac accctccgcc tcagatcctg 180
atcaagaaca cgcctgtacc tgcggaccct ccgaccacct tcaaccagtc aaagctgaac 240
tctttcatca cccagtattc tactggccaa gtcagcgtgg agatcgagtg ggagctgcag 300
aaggaaaaca gcaagcgctg gaaccccgag atccagtaca cctccaacta ctacaaatct 360
acaagtgtgg actttgctgt taatacagaa ggcgtgtact ctgaaccccg ccccattggc 420
acccgttacc tcacccgtaa tctgtaa 447

<210> SEQ ID NO 17
<211> LENGTH: 447
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
gcacaggcgc agaccggctg ggttcaaaac caaggaatac ttccgggtat ggtttggcag 60
gacagagatg tgtacctgca aggacccatt tgggccaaaa ttcctcacac ggacggcaac 120
tttcaccctt ctccgctgat gggagggttt ggaatgaagc acccgcctcc tcagatcctc 180
atcaaaaaca cacctgtacc tgccgatcct ccaacggcct tcaacaagga caagctgaac 240

```
tctttcatca cccagtattc tactggccaa gtcagcgtgg agatcgagtg ggagctgcag    300

aaggaaaaca gcaagcggtg gaacccggag atccagtaca cttccaacta ttacaagtct    360

aataatgttg aatttgctgt taatactgaa ggtgtatata gtgaaccccg ccccattggc    420

accagatacc tgactcgtaa tctgtaa                                        447
```

<210> SEQ ID NO 18
<211> LENGTH: 4314
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tatcagcaca caatagtcca ttatacgcgc gtataatggg caattgtgtg ctgatacagc     60

tggcacgaca ggtttcccga ctggaaagcg ggcagtgagc gcaacgcaat taatgtgagt    120

tagctcactc attaggcacc ccaggcttta cactttatgc ttccggctcg tatgttgtgt    180

ggaattgtga gcggataaca atttcacaca ggaaacagct atgaccatga ttacgccaga    240

tttaattaag gccttaatta ggctagcttg gccactccct ctctgcgcgc tcgctcgctc    300

actgaggccg ggcgaccaaa ggtcgcccga cgcccgggct ttgcccgggc ggcctcagtg    360

agcgagcgag cgcgcagaga gggagtggcc aactccatca ctaggggttc ctggaggggt    420

ggagtcgtga cgatatccat gcgtcgacat aacgcgttag tatctgcaga gggccctgcg    480

tatgagtgca agtgggtttt aggaccagga tgaggcgggg tgggggtgcc tacctgacga    540

ccgaccccga cccactggac aagcacccaa cccccattcc ccaaattgcg catcccctat    600

cagagagggg gaggggaaac aggatgcggc gaggcgcgtg cgcactgcca gcttcagcac    660

cgcggacagt gccttcgccc ccgcctggcg gcgcgcgcca ccgccgcctc agcactgaag    720

gcgcgctgac gtcactcgcc ggtcccccgc aaactcccct tcccggccac cttggtcgcg    780

tccgcgccgc cgccggccca gccggaccgc accacgcgag gcgcgagata ggggggcacg    840

ggcgcgacca tctgcgctgc ggcgccggcg actcagcgct gcctcagtct gcggtgggca    900

gcggaggagt cgtgtcgtgc ctgagagcgc agctgtgctc ctgggcaccg cgcagtccgc    960

ccccgcggct cctggccaga ccacccctag gacccccctgc cccaagtcgc agccaagctt   1020

cgtttagtga accgtcagat cgcctggaga cgccatccac gctgttttga cctccataga   1080

agacaccggg accgatccag cctccgcgga ttcgaatccc ggccgggaac ggtgcattgg   1140

aacgcggatt ccccgtgcca agagtgacgt aagtaccgcc tatagagtct ataggcccac   1200

aaaaaatgct ttcttctttt aatatacttt tttgtttatc ttatttctaa tactttccct   1260

aatctctttc tttcagggca ataatgatac aatgtatcat gcctctttgc accattctaa   1320

agaataacag tgataatttc tgggttaagg caatagcaat atttctgcat ataaatattt   1380

ctgcatataa attgtaactg atgtaagagg tttcatattg ctaatagcag ctacaatcca   1440

gctaccattc tgcttttatt ttatggttgg gataaggctg gattattctg agtccaagct   1500

aggccctttt gctaatcatg ttcatacctc ttatcttcct cccacagctc ctgggcaacg   1560

tgctggtctg tgtgctggcc catcactttg gcaaagaatt gggattcgaa ccggtcgcca   1620

ccggtcacca agcaggaagt caaagacttt ttccggtggg caaaggatca cgtggttgag   1680

gtggagcatg aattctacgt caaaaagggt ggagccaaga aaagacccgc ccccagtgac   1740

gcagatataa gtgagcccaa acgggtgcgc gagtcagttg cgcagccatc gacgtcagac   1800
```

```
gcggaagctt cgatcaacta cgcggacagg taccaaaaca aatgttctcg tcacgtgggc   1860
atgaatctga tgctgtttcc ctgcagacaa tgcgagagac tgaatcagaa ttcaaatatc   1920
tgcttcactc acggtgtcaa agactgttta gagtgctttc ccgtgtcaga atctcaaccc   1980
gtttctgtcg tcaaaaaggc gtatcagaaa ctgtgctaca ttcatcacat catgggaaag   2040
gtgccagacg cttgcactgc ttgcgacctg gtcaatgtgg acttggatga ctgtgtttct   2100
gaacaataaa tgacttaaac caggtatggc tgccgatggt tatcttccag attggctcga   2160
ggacaacctt agtgaaggaa ttcgcgagtg gtgggctttg aaacctggag cccctcaacc   2220
caaggcaaat caacaacatc aagacaacgc tcgaggtctt gtgcttccgg gttacaaata   2280
ccttggaccc ggcaacggac tcgacaaggg ggagccggtc aacgcagcag acgcggcggc   2340
cctcgagcac gacaaggcct acgaccagca gctcaaggcc ggagacaacc cgtacctcaa   2400
gtacaaccac gccgacgccg agttccagga gcggctcaaa gaagatacgt cttttggggg   2460
caacctcggg cgagcagtct tccaggccaa aaagaggctt cttgaacctc ttggtctggt   2520
tgaggaagcg gctaagacgg ctcctggaaa gaagaggcct gtagagcagt ctcctcagga   2580
accggactcc tccgcgggta ttggcaaatc gggtgcacag cccgctaaaa agagactcaa   2640
tttcggtcag actggcgaca cagagtcagt cccagaccct caaccaatcg gagaacctcc   2700
cgcagccccc tcaggtgtgg gatctcttac aatggcttca ggtggtggcg caccagtggc   2760
agacaataac gaaggtgccg atggagtggg tagttcctcg ggaaattggc attgcgattc   2820
ccaatggctg ggggacagag tcatcaccac cagcacccga acctgggccc tgcccaccta   2880
caacaatcac ctctacaagc aaatctccaa cagcacatct ggaggatctt caaatgacaa   2940
cgcctacttc ggctacagca ccccctgggg gtattttgac ttcaacagat tccactgcca   3000
cttctcacca cgtgactggc agcgactcat caacaacaac tggggattcc ggcctaagcg   3060
actcaacttc aagctcttca acattcaggt caaagaggtt acggacaaca atggagtcaa   3120
gaccatcgcc aataacctta ccagcacggt ccaggtcttc acggactcag actatcagct   3180
cccgtacgtg ctcgggtcgg ctcacgaggg ctgcctcccg ccgttcccag cggacgtttt   3240
catgattcct cagtacgggt atctgacgct taatgatgga agccaggccg tgggtcgttc   3300
gtccttttac tgcctggaat atttcccgtc gcaaatgcta agaacgggta acaacttcca   3360
gttcagctac gagtttgaga acgtaccttt ccatagcagc tacgctcaca gccaaagcct   3420
ggaccgacta atgaatccac tcatcgacca atacttgtac tatctctcaa agactattaa   3480
cggttctgga cagaatcaac aaacgctaaa attcagtgtg gccggaccca gcaacatggc   3540
tgtccaggga agaaactaca tacctggacc cagctaccga caacaacgtg tctcaaccac   3600
tgtgactcaa aacaacaaca gcgaatttgc ttggcctgga gcttcttctt gggctctcaa   3660
tggacgtaat agcttgatga atcctggacc tgctatggcc agccacaaag aaggagagga   3720
ccgtttcttt cctttgtctg gatctttaat tttggcaaa caaggaactg gaagagacaa   3780
cgtggatgcg gacaaagtca tgataaccaa cgaagaagaa attaaaacta ctaacccggt   3840
agcaacggag tcctatggac aagtggccac aaaccaccag agtgtacatc gattgttaat   3900
caataaaccg tttaattcgt ttcagttgaa ctttggtctc tgcgtatttc tttcttatct   3960
agtttccatg gctacgtaga taagtagcat ggcgggttaa tcattaacta caaggaaccc   4020
ctagtgatgg agttggccac tccctctctg cgcgctcgct cgctcactga ggccgggcga   4080
ccaaaggtcg cccgacgccc gggctttgcc cgggcggcct cagtgagcga gcgagcgcgc   4140
```

agagagggag tggccaagca tgcaattaac tggccgtcgt tttacaacgt cgtgactggg 4200
aaaaccctgg cgttacccaa cttaatcgcc ttgcagcaca tccccctttc gccagctgta 4260
tcagcacaca attgcccatt atacgcgcgt ataatggact attgtgtgct gata 4314

<210> SEQ ID NO 19
<211> LENGTH: 4456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
tatcagcaca caatagtcca ttatacgcgc gtataatggg caattgtgtg ctgatacagc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgaccatga ttacgccaga 240
tttaattaag gccttaatta ggctagcttg gccactccct ctctgcgcgc tcgctcgctc 300
actgaggccg ggcgaccaaa ggtcgcccga cgcccgggct ttgcccgggc ggcctcagtg 360
agcgagcgag cgcgcagaga gggagtggcc aactccatca ctaggggttc ctggaggggt 420
ggagtcgtga cgatatccat gcgtcgacat aacgcgtgat ctaacatatc ctggtgtgga 480
gtagcggacg ctgctatgac agaggctcgg gggcctgagc tggctctgtg agctggggag 540
gaggcagaca gccaggcctt gtctgcaagc agacctggca gcattgggct ggccgccccc 600
cagggcctcc tcttcatgcc cagtgaatga ctcaccttgg cacagacaca atgttcgggg 660
tgggcacagt gcctgcttcc cgccgcaccc cagcccccct caaatgcctt ccgagaagcc 720
cattgagcag gggcttgca ttgcacccca gcctgacagc ctggcatctt gggataaaag 780
cagcacagcc ccctaggggc tgcccttgct gtgtggcgcc accggcggtg gagaacaagg 840
ctctattcag cctgtgccca ggaaagggga tcaggggatg cccaggcatg gacagtgggt 900
ggcagggggg gagaggaggg ctgtctgctt cccagaagtc caaggacaca aatgggtgag 960
gggagagctc tccccatagc tgggctgcgg cccaacccca ccccctcagg ctatgccagg 1020
gggtgttgcc aggggcaccc gggcatcgcc agtctagccc actccttcat aaagccctcg 1080
catcccagga gcgagcagag ccagagcagg ttggagagga gacgcatcac ctccgctgct 1140
cgcggggatc ctctagaagc ttcgtttagt gaaccgtcag atcgcctgga gacgccatcc 1200
acgctgtttt gacctccata gaagacaccg ggaccgatcc agcctccgcg gattcgaatc 1260
ccggccggga acggtgcatt ggaacgcgga ttccccgtgc caagagtgac gtaagtaccg 1320
cctatagagt ctataggccc acaaaaaatg ctttcttctt ttaatatact tttttgttta 1380
tcttatttct aatactttcc ctaatctctt tctttcaggg caataatgat acaatgtatc 1440
atgcctcttt gcaccattct aaagaataac agtgataatt tctgggttaa ggcaatagca 1500
atatttctgc atataaatat ttctgcatat aaattgtaac tgatgtaaga ggtttcatat 1560
tgctaatagc agctacaatc cagctaccat tctgctttta ttttatggtt gggataaggc 1620
tggattattc tgagtccaag ctaggccctt ttgctaatca tgttcatacc tcttatcttc 1680
ctcccacagc tcctgggcaa cgtgctggtc tgtgtgctgg cccatcactt tggcaaagaa 1740
ttgggattcg aaccggtcgc caccggtcac caagcaggaa gtcaaagact tttccggtg 1800 ggcaaaggat cacgtggttg aggtggagca tgaattctac gtcaaaaagg gtggagccaa 1860
gaaaagaccc gcccccagtg acgcagatat aagtgagccc aaacgggtgc gcgagtcagt 1920
tgcgcagcca tcgacgtcag acgcggaagc ttcgatcaac tacgcggaca ggtaccaaaa 1980
caaatgttct cgtcacgtgg gcatgaatct gatgctgttt ccctgcagac aatgcgagag 2040
actgaatcag aattcaaata tctgcttcac tcacggtgtc aaagactgtt tagagtgctt 2100
tcccgtgtca gaatctcaac ccgtttctgt cgtcaaaaag gcgtatcaga aactgtgcta 2160
cattcatcac atcatgggaa aggtgccaga cgcttgcact gcttgcgacc tggtcaatgt 2220
ggacttggat gactgtgttt ctgaacaata aatgacttaa accaggtatg gctgccgatg 2280
gttatcttcc agattggctc gaggacaacc ttagtgaagg aattcgcgag tggtgggctt 2340
tgaaacctgg agcccctcaa cccaaggcaa atcaacaaca tcaagacaac gctcgaggtc 2400
ttgtgcttcc gggttacaaa taccttggac ccggcaacgg actcgacaag gggagccgg 2460
tcaacgcagc agacgcggcg gccctcgagc acgacaaggc ctacgaccag cagctcaagg 2520
ccggagacaa cccgtacctc aagtacaacc acgccgacgc cgagttccag gagcggctca 2580
aagaagatac gtcttttggg ggcaacctcg ggcgagcagt cttccaggcc aaaaagaggc 2640
ttcttgaacc tcttggtctg gttgaggaag cggctaagac ggctcctgga aagaagaggc 2700
ctgtagagca gtctcctcag gaaccggact cctccgcggg tattggcaaa tcgggtgcac 2760
agcccgctaa aaagagactc aatttcggtc agactggcga cacagagtca gtcccagacc 2820
ctcaaccaat cggagaacct cccgcagccc cctcaggtgt gggatctctt acaatggctt 2880
caggtggtgg cgcaccagtg gcagacaata acgaaggtgc cgatggagtg ggtagttcct 2940
cgggaaattg gcattgcgat tcccaatggc tgggggacag agtcatcacc accagcaccc 3000
gaacctgggc cctgcccacc tacaacaatc acctctacaa gcaaatctcc aacagcacat 3060
ctggaggatc ttcaaatgac aacgcctact tcggctacag caccccctgg gggtattttg 3120
acttcaacag attccactgc cacttctcac cacgtgactg gcagcgactc atcaacaaca 3180
actggggatt ccggcctaag cgactcaact tcaagctctt caacattcag gtcaaagagg 3240
ttacggacaa caatggagtc aagaccatcg ccaataacct taccagcacg gtccaggtct 3300
tcacggactc agactatcag ctcccgtacg tgctcgggtc ggctcacgag ggctgcctcc 3360
cgccgttccc agcggacgtt ttcatgattc ctcagtacgg gtatctgacg cttaatgatg 3420
gaagccaggc cgtgggtcgt tcgtcctttt actgcctgga atatttcccg tcgcaaatgc 3480
taagaacggg taacaacttc cagttcagct acgagtttga gaacgtacct ttccatagca 3540
gctacgctca cagccaaagc ctggaccgac taatgaatcc actcatcgac caatacttgt 3600
actatctctc aaagactatt aacggttctg gacagaatca acaaacgcta aaattcagtg 3660
tggccggacc cagcaacatg gctgtccagg gaagaaacta catacctgga cccagctacc 3720
gacaacaacg tgtctcaacc actgtgactc aaaacaacaa cagcgaattt gcttggcctg 3780
gagcttcttc ttgggctctc aatggacgta atagcttgat gaatcctgga cctgctatgg 3840
ccagccacaa agaaggagag gaccgtttct ttcctttgtc tggatcttta atttttggca 3900
aacaaggaac tggaagagac aacgtggatg cggacaaagt catgataacc aacgaagaag 3960
aaattaaaac tactaacccg gtagcaacgg agtcctatgg acaagtggcc acaaaccacc 4020
agagtgtaca tcgattgtta atcaataaac cgtttaattc gtttcagttg aactttggtc 4080
tctgcgtatt tctttcttat ctagtttcca tggctacgta gataagtagc atggcgggtt 4140
aatcattaac tacaaggaac ccctagtgat ggagttggcc actccctctc tgcgcgctcg 4200
ctcgctcact gaggccgggc gaccaaaggt cgcccgacgc ccgggctttg cccgggcggc 4260
ctcagtgagc gagcgagcgc gcagagaggg agtggccaag catgcaatta actggccgtc 4320
gttttacaac gtcgtgactg ggaaaaccct ggcgttaccc aacttaatcg ccttgcagca 4380
catccccctt tcgccagctg tatcagcaca caattgccca ttatacgcgc gtataatgga 4440
ctattgtgtg ctgata 4456

<210> SEQ ID NO 20
<211> LENGTH: 4283
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
tatcagcaca caatagtcca ttatacgcgc gtataatggg caattgtgtg ctgatacagc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgaccatga ttacgccaga 240
tttaattaag gccttaatta ggctagcttg gccactccct ctctgcgcgc tcgctcgctc 300
actgaggccg ggcgaccaaa ggtcgcccga cgcccgggct ttgcccgggc ggcctcagtg 360
agcgagcgag cgcgcagaga gggagtggcc aactccatca ctaggggttc ctggaggggt 420
ggagtcgtga cgatatccat gcgtcgacat aacgcgttag tatctgcaga gggccctgcg 480
tatgagtgca agtgggtttt aggaccagga tgaggcgggg tgggggtgcc tacctgacga 540
ccgaccccga cccactggac aagcacccaa cccccattcc ccaaattgcg catcccctat 600
cagagagggg gaggggaaac aggatgcggc gaggcgcgtg cgcactgcca gcttcagcac 660
cgcggacagt gccttcgccc ccgcctggcg gcgcgcgcca ccgccgcctc agcactgaag 720
gcgcgctgac gtcactcgcc ggtcccccgc aaactcccct tcccggccac cttggtcgcg 780
tccgcgccgc cgccggccca gccggaccgc accacgcgag gcgcgagata ggggggcacg 840
ggcgcgacca tctgcgctgc ggcgccggcg actcagcgct gcctcagtct gcggtgggca 900
gcggaggagt cgtgtcgtgc ctgagagcgc agctgtgctc ctgggcaccg cgcagtccgc 960
ccccgcggct cctggccaga ccacccctag gacccccctgc cccaagtcgc agccaagctt 1020
cgtttagtga accgtcagat cgcctggaga cgccatccac gctgttttga cctccataga 1080
agacaccggg accgatccag cctccgcgga ttcgaatccc ggccgggaac ggtgcattgg 1140
aacgcggatt ccccgtgcca agagtgacgt aagtaccgcc tatagagtct ataggcccac 1200
aaaaaatgct ttcttctttt aatatacttt tttgtttatc ttatttctaa tactttccct 1260
aatctctttc tttcagggca ataatgatac aatgtatcat gcctctttgc accattctaa 1320
agaataacag tgataatttc tgggttaagg caatagcaat atttctgcat ataaatattt 1380
ctgcatataa attgtaactg atgtaagagg tttcatattg ctaatagcag ctacaatcca 1440
gctaccattc tgcttttatt ttatggttgg gataaggctg gattattctg agtccaagct 1500
aggccctttt gctaatcatg ttcatacctc ttatcttcct cccacagctc ctgggcaacg 1560
tgctggtctg tgtgctggcc catcactttg gcaaagaatt gggattcgaa ccggtcgcca 1620
ccggtcacaa gcaggaagtc aaagactttt tccggtgggc aaaggatcac gtggttgagg 1680
tggagcatga attctacgtc aaaaagggtg gagccaagaa aagacccgcc cccagtgacg 1740
cagatataag tgagcccaaa cgggtgcgcg agtcagttgc gcagccatcg acgtcagacg 1800

```
cggaagcttc gatcaactac gcggacaggt accaaaacaa atgttctcgt cacgtgggca   1860
tgaatctgat gctgtttccc tgcagacaat gcgagagaat gaatcagaat tcaaatatct   1920
gcttcactca cggacagaaa gactgtttag agtgctttcc cgtgtcagaa tctcaacccg   1980
tttctgtcgt caaaaaggcg tatcagaaac tgtgctacat tcatcatatc atgggaaagg   2040
tgccagacgc ttgcactgcc tgcgatctgg tcaatgtgga tttggatgac tgcatctttg   2100
aacaataaat gatttaaatc aggtatgtct tttgttgatc accctccaga ttggttggaa   2160
gaagttggtg aaggtcttcg cgagtttttg ggccttgaag cgggcccacc gaaaccaaaa   2220
cccaatcagc agcatcaaga tcaagcccgt ggtcttgtgc tgcctggtta taactatctc   2280
ggacccggaa acggtctcga tcgaggagag cctgtcaaca gggcagacga ggtcgcgcga   2340
gagcacgaca tctcgtacaa cgagcagctt gaggcgggag acaaccccta cctcaagtac   2400
aaccacgcgg acgccgagtt tcaggagaag ctcgccgacg acacatcctt cgggggaaac   2460
ctcggaaagg cagtctttca ggccaagaaa agggttctcg aaccttttgg cctggttgaa   2520
gagggtgcta agacggcccc taccggaaag cggatagacg accactttcc aaaaagaaag   2580
aaggcccgga ccgaagagga ctccaagcct tccacctcgt cagacgccga agctggaccc   2640
agcggatccc agcagctgca aatcccagcc caaccagcct caagtttggg agctgataca   2700
atgtctgcgg gaggtggcgg cccattgggc gacaataacc aaggtgccga tggagtgggc   2760
aatgcctcgg gagattggca ttgcgattcc acgtggatgg gggacagagt cgtcaccaag   2820
tccacccgaa cctgggtgct gcccagctac aacaaccacc agtaccgaga gatcaaaagc   2880
ggctccgtcg acggaagcaa cgccaacgcc tactttggat acagcacccc ctgggggtac   2940
tttgacttta accgcttcca cagccactgg agcccccgag actggcaaag actcatcaac   3000
aactactggg gcttcagacc ccggtccctc agagtcaaaa tcttcaacat tcaagtcaaa   3060
gaggtcacgg tgcaggactc caccaccacc atcgccaaca acctcacctc caccgtccaa   3120
gtgtttacgg acgacgacta ccagctgccc tacgtcgtcg gcaacgggac cgagggatgc   3180
ctgccggcct tccctccgca ggtctttacg ctgccgcagt acggttacgc gacgctgaac   3240
cgcgacaaca cagaaaatcc caccgagagg agcagcttct tctgcctaga gtactttccc   3300
agcaagatgc tgagaacggg caacaacttt gagtttacct acaactttga ggaggtgccc   3360
ttccactcca gcttcgctcc cagtcagaac ctcttcaagc tggccaaccc gctggtggac   3420
cagtacttgt accgcttcgt gagcacaaat aacactggcg gagtccagtt caacaagaac   3480
ctggccggga gatacgccaa cacctacaaa aactggttcc cggggcccat gggccgaacc   3540
cagggctgga acctgggctc cggggtcaac cgcgccagtg tcagcgcctt cgccacgacc   3600
aataggatgg agctcgaggg cgcgagttac caggtgcccc cgcagccgaa cggcatgacc   3660
aacaacctcc agggcagcaa cacctatgcc ctggagaaca ctatgatctt caacagccag   3720
ccggcgaacc cgggcaccac cgccacgtac ctcgagggca acatgctcat caccagcgag   3780
agcgagacgc agccggtgaa ccgcgtggcg tacaacgtcg gcgggcagat ggccaccaac   3840
aaccagagct ctgtacatcg attgttaatc aataaaccgt ttaattcgtt tcagttgaac   3900
tttggtctct gcgtatttct ttcttatcta gtttccatgg ctacgtagat aagtagcatg   3960
gcgggttaat cattaactac aaggaacccc tagtgatgga gttggccact ccctctctgc   4020
gcgctcgctc gctcactgag gccgggcgac caaaggtcgc ccgacgcccg ggctttgccc   4080
gggcggcctc agtgagcgag cgagcgcgca gagagggagt ggccaagcat gcaattaact   4140
```

ggccgtcgtt ttacaacgtc gtgactggga aaaccctggc gttacccaac ttaatcgcct 4200
tgcagcacat ccccctttcg ccagctgtat cagcacacaa ttgcccatta tacgcgcgta 4260
taatggacta ttgtgtgctg ata 4283

<210> SEQ ID NO 21
<211> LENGTH: 4426
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
tatcagcaca caatagtcca ttatacgcgc gtataatggg caattgtgtg ctgatacagc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgaccatga ttacgccaga 240
tttaattaag gccttaatta ggctagcttg gccactccct ctctgcgcgc tcgctcgctc 300
actgaggccg ggcgaccaaa ggtcgcccga cgcccgggct ttgcccgggc ggcctcagtg 360
agcgagcgag cgcgcagaga gggagtggcc aactccatca ctaggggttc ctggaggggt 420
ggagtcgtga cgatatccat gcgtcgacat aacgcgtgat ctaacatatc ctggtgtgga 480
gtagcggacg ctgctatgac agaggctcgg gggcctgagc tggctctgtg agctggggag 540
gaggcagaca gccaggcctt gtctgcaagc agacctggca gcattgggct ggccgccccc 600
cagggcctcc tcttcatgcc cagtgaatga ctcaccttgg cacagacaca atgttcgggg 660
tgggcacagt gcctgcttcc cgccgcaccc cagccccccct caaatgcctt ccgagaagcc 720
cattgagcag gggcttgca ttgcacccca gcctgacagc ctggcatctt gggataaaag 780
cagcacagcc ccctaggggc tgcccttgct gtgtggcgcc accggcggtg gagaacaagg 840
ctctattcag cctgtgccca ggaaagggga tcaggggatg cccaggcatg gacagtgggt 900
ggcagggggg gagaggaggg ctgtctgctt cccagaagtc caaggacaca aatgggtgag 960
gggagagctc tccccatagc tgggctgcgg cccaacccca ccccctcagg ctatgccagg 1020
gggtgttgcc aggggcaccc gggcatcgcc agtctagccc actccttcat aaagccctcg 1080
catcccagga gcgagcagag ccagagcagg ttggagagga gacgcatcac ctccgctgct 1140
cgcggggatc ctctagaagc ttcgtttagt gaaccgtcag atcgcctgga gacgccatcc 1200
acgctgtttt gacctccata gaagacaccg ggaccgatcc agcctccgcg gattcgaatc 1260
ccggccggga acggtgcatt ggaacgcgga ttccccgtgc caagagtgac gtaagtaccg 1320
cctatagagt ctataggccc acaaaaaatg ctttcttctt ttaatatact tttttgttta 1380
tcttatttct aatactttcc ctaatctctt tctttcaggg caataatgat acaatgtatc 1440
atgcctcttt gcaccattct aaagaataac agtgataatt tctgggttaa ggcaatagca 1500
atatttctgc atataaatat ttctgcatat aaattgtaac tgatgtaaga ggtttcatat 1560
tgctaatagc agctacaatc cagctaccat tctgctttta ttttatggtt gggataaggc 1620
tggattattc tgagtccaag ctaggccctt ttgctaatca tgttcatacc tcttatcttc 1680
ctcccacagc tcctgggcaa cgtgctggtc tgtgtgctgg cccatcactt tggcaaagaa 1740
ttgggattcg aaccggtcgc caccggtcac caagcaggaa gtcaaagact tttccggtg 1800 ggcaaaggat cacgtggttg aggtggagca tgaattctac gtcaaaaagg gtggagccaa 1860

```
gaaaagaccc gcccccagtg acgcagatat aagtgagccc aaacgggtgc gcgagtcagt   1920
tgcgcagcca tcgacgtcag acgcggaagc ttcgatcaac tacgcggaca ggtaccaaaa   1980
caaatgttct cgtcacgtgg gcatgaatct gatgctgttt ccctgcagac aatgcgagag   2040
aatgaatcag aattcaaata tctgcttcac tcacggacag aaagactgtt tagagtgctt   2100
tcccgtgtca gaatctcaac ccgtttctgt cgtcaaaaag gcgtatcaga aactgtgcta   2160
cattcatcat atcatgggaa aggtgccaga cgcttgcact gcctgcgatc tggtcaatgt   2220
ggatttggat gactgcatct ttgaacaata aatgatttaa atcaggtatg tcttttgttg   2280
atcaccctcc agattggttg gaagaagttg gtgaaggtct tcgcgagttt ttgggccttg   2340
aagcgggccc accgaaacca aaacccaatc agcagcatca agatcaagcc cgtggtcttg   2400
tgctgcctgg ttataactat ctcggacccg gaaacggtct cgatcgagga gagcctgtca   2460
acagggcaga cgaggtcgcg cgagagcacg acatctcgta caacgagcag cttgaggcgg   2520
gagacaaccc ctacctcaag tacaaccacg cggacgccga gtttcaggag aagctcgccg   2580
acgacacatc cttcgggggga aacctcggaa aggcagtctt tcaggccaag aaaagggttc   2640
tcgaaccttt tggcctggtt gaagagggtg ctaagacggc ccctaccgga aagcggatag   2700
acgaccactt tccaaaaaga aagaaggccc ggaccgaaga ggactccaag ccttccacct   2760
cgtcagacgc cgaagctgga cccagcggat cccagcagct gcaaatccca gcccaaccag   2820
cctcaagttt gggagctgat acaatgtctg cgggaggtgg cggcccattg ggcgacaata   2880
accaaggtgc cgatggagtg ggcaatgcct cgggagattg gcattgcgat tccacgtgga   2940
tgggggacag agtcgtcacc aagtccaccc gaacctgggt gctgcccagc tacaacaacc   3000
accagtaccg agagatcaaa agcggctccg tcgacggaag caacgccaac gcctactttg   3060
gatacagcac cccctggggg tactttgact ttaaccgctt ccacagccac tggagccccc   3120
gagactggca aagactcatc aacaactact ggggcttcag accccggtcc ctcagagtca   3180
aaatcttcaa cattcaagtc aaagaggtca cggtgcagga ctccaccacc accatcgcca   3240
acaacctcac ctccaccgtc caagtgttta cggacgacga ctaccagctg ccctacgtcg   3300
tcggcaacgg gaccgaggga tgcctgccgg ccttccctcc gcaggtcttt acgctgccgc   3360
agtacggtta cgcgacgctg aaccgcgaca acacagaaaa tcccaccgag aggagcagct   3420
tcttctgcct agagtacttt cccagcaaga tgctgagaac gggcaacaac tttgagttta   3480
cctacaactt tgaggaggtg cccttccact ccagcttcgc tcccagtcag aacctcttca   3540
agctggccaa cccgctggtg gaccagtact tgtaccgctt cgtgagcaca aataacactg   3600
gcggagtcca gttcaacaag aacctggccg ggagatacgc caacacctac aaaaactggt   3660
tcccggggcc catgggccga acccagggct ggaacctggg ctccggggtc aaccgcgcca   3720
gtgtcagcgc cttcgccacg accaatagga tggagctcga gggcgcgagt taccaggtgc   3780
cccgcagcc  gaacggcatg accaacaacc tccagggcag caacacctat gccctggaga   3840
acactatgat cttcaacagc cagccggcga acccgggcac caccgccacg tacctcgagg   3900
gcaacatgct catcaccagc gagagcgaga cgcagccggt gaaccgcgtg gcgtacaacg   3960
tcggcgggca gatggccacc aacaaccaga gctctgtaca tcgattgtta atcaataaac   4020
cgtttaattc gtttcagttg aactttggtc tctgcgtatt tctttcttat ctagtttcca   4080
tggctacgta gataagtagc atggcgggtt aatcattaac tacaaggaac ccctagtgat   4140
ggagttggcc actccctctc tgcgcgctcg ctcgctcact gaggccgggc gaccaaaggt   4200
cgcccgacgc ccgggctttg cccgggcggc ctcagtgagc gagcgagcgc gcagagaggg   4260
```

agtggccaag catgcaatta actggccgtc gttttacaac gtcgtgactg ggaaaaccct 4320
ggcgttaccc aacttaatcg ccttgcagca catccccctt tcgccagctg tatcagcaca 4380
caattgccca ttatacgcgc gtataatgga ctattgtgtg ctgata 4426

<210> SEQ ID NO 22
<211> LENGTH: 4313
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
tatcagcaca caatagtcca ttatacgcgc gtataatggg caattgtgtg ctgatacagc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgaccatga ttacgccaga 240
tttaattaag gccttaatta ggctagcttg gccactccct ctctgcgcgc tcgctcgctc 300
actgaggccg ggcgaccaaa ggtcgcccga cgcccgggct ttgcccgggc ggcctcagtg 360
agcgagcgag cgcgcagaga gggagtggcc aactccatca ctaggggttc ctggaggggt 420
ggagtcgtga cgatatccat gcgtcgacat aacgcgttag tatctgcaga gggccctgcg 480
tatgagtgca agtgggtttt aggaccagga tgaggcgggg tgggggtgcc tacctgacga 540
ccgaccccga cccactggac aagcacccaa cccccattcc ccaaattgcg catcccctat 600
cagagagggg gaggggaaac aggatgcggc gaggcgcgtg cgcactgcca gcttcagcac 660
cgcggacagt gccttcgccc ccgcctggcg gcgcgcgcca ccgccgcctc agcactgaag 720
gcgcgctgac gtcactcgcc ggtcccccgc aaactcccct tcccggccac cttggtcgcg 780
tccgcgccgc cgccggccca gccggaccgc accacgcgag gcgcgagata ggggggcacg 840
ggcgcgacca tctgcgctgc ggcgccggcg actcagcgct gcctcagtct gcggtgggca 900
gcggaggagt cgtgtcgtgc ctgagagcgc agctgtgctc ctgggcaccg cgcagtccgc 960
ccccgcggct cctggccaga ccacccctag gaccccctgc cccaagtcgc agccaagctt 1020
cgtttagtga accgtcagat cgcctggaga cgccatccac gctgttttga cctccataga 1080
agacaccggg accgatccag cctccgcgga ttcgaatccc ggccgggaac ggtgcattgg 1140
aacgcggatt ccccgtgcca agagtgacgt aagtaccgcc tatagagtct ataggcccac 1200
aaaaaatgct ttcttctttt aatatacttt tttgtttatc ttatttctaa tactttccct 1260
aatctctttc tttcagggca ataatgatac aatgtatcat gcctctttgc accattctaa 1320
agaataacag tgataatttc tgggttaagg caatagcaat atttctgcat ataaatattt 1380
ctgcatataa attgtaactg atgtaagagg tttcatattg ctaatagcag ctacaatcca 1440
gctaccattc tgcttttatt ttatggttgg gataaggctg gattattctg agtccaagct 1500
aggccctttt gctaatcatg ttcatacctc ttatcttcct cccacagctc ctgggcaacg 1560
tgctggtctg tgtgctggcc catcactttg gcaaagaatt gggattcgaa ccggtcgcca 1620
ccggtcacaa gcaggaagtc aaagactttt tccggtgggc aaaggatcac gtggttgagg 1680
tggagcatga attctacgtc aaaaagggtg gagccaagaa aagacccgcc cccagtgacg 1740
cagatataag tgagcccaaa cgggtgcgcg agtcagttgc gcagccatcg acgtcagacg 1800
cggaagcttc gatcaactac gcggacaggt accaaaacaa atgttctcgt cacgtgggca 1860

```
tgaatctgat gctgtttccc tgcagacaat gcgagagaat gaatcagaat tcaaatatct   1920
gcttcactca cggacagaaa gactgtttag agtgctttcc cgtgtcagaa tctcaacccg   1980
tttctgtcgt caaaaaggcg tatcagaaac tgtgctacat tcatcatatc atgggaaagg   2040
tgccagacgc ttgcactgcc tgcgatctgg tcaatgtgga tttggatgac tgcatctttg   2100
aacaataaat gatttaaatc aggtatggct gccgatggtt atcttccaga ttggctcgag   2160
gacaacctct ctgagggcat tcgcgagtgg tgggacttga aacctggagc cccgaaaccc   2220
aaagccaacc agcaaaagca ggacgacggc cggggtctgg tgcttcctgg ctacaagtac   2280
ctcggaccct tcaacggact cgacaagggg gagcccgtca acgcggcgga tgcagcggcc   2340
ctcgagcacg acaaggccta cgaccagcag ctcaaagcgg gtgacaatcc gtacctgcgg   2400
tataaccacg ccgacgccga gtttcaggag cgtctgcaag aagatacgtc ttttgggggc   2460
aacctcgggc gagcagtctt ccaggccaag aagagggttc tcgaaccttt tggtctggtt   2520
gaggaaggtg ctaagacggc tcctggaaag aaacgtccgg tagagcagtc gccacaagag   2580
ccagactcct cctcgggcat tggcaagaca ggccagcagc ccgctaaaaa gagactcaat   2640
tttggtcaga ctggcgactc agagtcagtc cccgacccac aacctctcgg agaacctcca   2700
gcaacccccg ctgctgtggg acctactaca atggcttcag gcggtggcgc accaatggca   2760
gacaataacg aaggcgccga cggagtgggt aatgcctcag gaaattggca ttgcgattcc   2820
acatggctgg gcgacagagt catcaccacc agcacccgaa catgggcctt gcccacctat   2880
aacaaccacc tctacaagca aatctccagt gcttcaacgg gggccagcaa cgacaaccac   2940
tacttcggct acagcacccc ctgggggtat tttgatttca acagattcca ctgccatttc   3000
tcaccacgtg actggcagcg actcatcaac aacaattggg gattccggcc caagagactc   3060
aacttcaagc tcttcaacat ccaagtcaag gaggtcacga cgaatgatgg cgtcacgacc   3120
atcgctaata accttaccag cacggttcaa gtcttctcgg actcggagta ccagttgccg   3180
tacgtcctcg gctctgcgca ccagggctgc ctccctccgt tcccggcgga cgtgttcatg   3240
attccgcagt acggctacct aacgctcaac aatggcagcc aggcagtggg acggtcatcc   3300
ttttactgcc tggaatattt cccatcgcag atgctgagaa cgggcaataa ctttaccttc   3360
agctacacct tcgaggacgt gcctttccac agcagctacg cgcacagcca gagcctggac   3420
cggctgatga atcctctcat cgaccagtac ctgtattacc tgaacagaac tcagaatcag   3480
tccggaagtg cccaaaacaa ggacttgctg tttagccggg ggtctccagc tggcatgtct   3540
gttcagccca aaaactggct acctggaccc tgttaccggc agcagcgcgt ttctaaaaca   3600
aaaacagaca acaacaacag caactttacc tggactggtg cttcaaaata taaccttaat   3660
gggcgtgaat ctataatcaa ccctggcact gctatggcct cacacaaaga cgacaaagac   3720
aagttctttc ccatgagcgg tgtcatgatt tttggaaagg agagcgccgg agcttcaaac   3780
actgcattgg acaatgtcat gatcacagac gaagaggaaa tcaaagccac taaccccgtg   3840
gccaccgaaa gatttgggac tgtggcagtc aatctccaga gtgtacatcg attgttaatc   3900
aataaaccgt ttaattcgtt tcagttgaac tttggtctct gcgtatttct ttcttatcta   3960
gtttccatgg ctacgtagat aagtagcatg gcgggttaat cattaactac aaggaacccc   4020
tagtgatgga gttggccact ccctctctgc gcgctcgctc gctcactgag gccgggcgac   4080
caaaggtcgc ccgacgcccg ggctttgccc gggcggcctc agtgagcgag cgagcgcgca   4140
gagagggagt ggccaagcat gcaattaact ggccgtcgtt ttacaacgtc gtgactggga   4200
```

```
aaaccctggc gttacccaac ttaatcgcct tgcagcacat ccccctttcg ccagctgtat   4260

cagcacacaa ttgcccatta tacgcgcgta taatggacta ttgtgtgctg ata          4313
```

<210> SEQ ID NO 23
<211> LENGTH: 4456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
tatcagcaca caatagtcca ttatacgcgc gtataatggg caattgtgtg ctgatacagc     60

tggcacgaca ggtttcccga ctggaaagcg ggcagtgagc gcaacgcaat taatgtgagt    120

tagctcactc attaggcacc ccaggcttta cactttatgc ttccggctcg tatgttgtgt    180

ggaattgtga gcggataaca atttcacaca ggaaacagct atgaccatga ttacgccaga    240

tttaattaag gccttaatta ggctagcttg gccactccct ctctgcgcgc tcgctcgctc    300

actgaggccg ggcgaccaaa ggtcgcccga cgcccgggct ttgcccgggc ggcctcagtg    360

agcgagcgag cgcgcagaga gggagtggcc aactccatca ctaggggttc ctggaggggt    420

ggagtcgtga cgatatccat gcgtcgacat aacgcgtgat ctaacatatc ctggtgtgga    480

gtagcggacg ctgctatgac agaggctcgg gggcctgagc tggctctgtg agctggggag    540

gaggcagaca gccaggcctt gtctgcaagc agacctggca gcattgggct ggccgccccc    600

cagggcctcc tcttcatgcc cagtgaatga ctcaccttgg cacagacaca atgttcgggg    660

tgggcacagt gcctgcttcc cgccgcaccc cagcccccct caaatgcctt ccgagaagcc    720

cattgagcag gggcttgca ttgcacccca gcctgacagc ctggcatctt gggataaaag    780

cagcacagcc ccctaggggc tgcccttgct gtgtggcgcc accggcggtg gagaacaagg    840

ctctattcag cctgtgccca ggaaagggga tcaggggatg cccaggcatg gacagtgggt    900

ggcagggggg gagaggaggg ctgtctgctt cccagaagtc caaggacaca aatgggtgag    960

gggagagctc tccccatagc tgggctgcgg cccaacccca ccccctcagg ctatgccagg   1020

gggtgttgcc aggggcaccc gggcatcgcc agtctagccc actccttcat aaagccctcg   1080

catcccagga gcgagcagag ccagagcagg ttggagagga gacgcatcac ctccgctgct   1140

cgcggggatc ctctagaagc ttcgtttagt gaaccgtcag atcgcctgga gacgccatcc   1200

acgctgtttt gacctccata gaagacaccg ggaccgatcc agcctccgcg gattcgaatc   1260

ccggccggga acggtgcatt ggaacgcgga ttccccgtgc caagagtgac gtaagtaccg   1320

cctatagagt ctataggccc acaaaaaatg ctttcttctt ttaatatact tttttgttta   1380

tcttatttct aatactttcc ctaatctctt tctttcaggg caataatgat acaatgtatc   1440

atgcctcttt gcaccattct aaagaataac agtgataatt tctgggttaa ggcaatagca   1500

atatttctgc atataaatat ttctgcatat aaattgtaac tgatgtaaga ggtttcatat   1560

tgctaatagc agctacaatc cagctaccat tctgctttta ttttatggtt gggataaggc   1620

tggattattc tgagtccaag ctaggccctt ttgctaatca tgttcatacc tcttatcttc   1680

ctcccacagc tcctgggcaa cgtgctggtc tgtgtgctgg cccatcactt tggcaaagaa   1740

ttgggattcg aaccggtcgc caccggtcac caagcaggaa gtcaaagact ttttccggtg   1800

ggcaaaggat cacgtggttg aggtggagca tgaattctac gtcaaaaagg gtggagccaa   1860

gaaaagaccc gcccccagtg acgcagatat aagtgagccc aaacgggtgc gcgagtcagt   1920
```

-continued

```
tgcgcagcca tcgacgtcag acgcggaagc ttcgatcaac tacgcggaca ggtaccaaaa   1980
caaatgttct cgtcacgtgg gcatgaatct gatgctgttt ccctgcagac aatgcgagag   2040
aatgaatcag aattcaaata tctgcttcac tcacggacag aaagactgtt tagagtgctt   2100
tcccgtgtca gaatctcaac ccgtttctgt cgtcaaaaag gcgtatcaga aactgtgcta   2160
cattcatcat atcatgggaa aggtgccaga cgcttgcact gcctgcgatc tggtcaatgt   2220
ggatttggat gactgcatct ttgaacaata aatgatttaa atcaggtatg gctgccgatg   2280
gttatcttcc agattggctc gaggacaacc tctctgaggg cattcgcgag tggtgggact   2340
tgaaacctgg agccccgaaa cccaaagcca accagcaaaa gcaggacgac ggccggggtc   2400
tggtgcttcc tggctacaag tacctcggac ccttcaacgg actcgacaag ggggagcccg   2460
tcaacgcggc ggatgcagcg gccctcgagc acgacaaggc ctacgaccag cagctcaaag   2520
cgggtgacaa tccgtacctg cggtataacc acgccgacgc cgagtttcag gagcgtctgc   2580
aagaagatac gtcttttggg ggcaacctcg ggcgagcagt cttccaggcc aagaagaggg   2640
ttctcgaacc ttttggtctg gttgaggaag gtgctaagac ggctcctgga aagaaacgtc   2700
cggtagagca gtcgccacaa gagccagact cctcctcggg cattggcaag acaggccagc   2760
agcccgctaa aaagagactc aattttggtc agactggcga ctcagagtca gtccccgacc   2820
cacaacctct cggagaacct ccagcaaccc ccgctgctgt gggacctact acaatggctt   2880
caggcggtgg cgcaccaatg gcagacaata acgaaggcgc cgacggagtg ggtaatgcct   2940
caggaaattg gcattgcgat tccacatggc tgggcgacag agtcatcacc accagcaccc   3000
gaacatgggc cttgcccacc tataacaacc acctctacaa gcaaatctcc agtgcttcaa   3060
cgggggccag caacgacaac cactacttcg gctacagcac cccctggggg tattttgatt   3120
tcaacagatt ccactgccat ttctcaccac gtgactggca gcgactcatc aacaacaatt   3180
ggggattccg gcccaagaga ctcaacttca agctcttcaa catccaagtc aaggaggtca   3240
cgacgaatga tggcgtcacg accatcgcta ataaccttac cagcacggtt caagtcttct   3300
cggactcgga gtaccagttg ccgtacgtcc tcggctctgc gcaccagggc tgcctccctc   3360
cgttcccggc ggacgtgttc atgattccgc agtacggcta cctaacgctc aacaatggca   3420
gccaggcagt gggacggtca tccttttact gcctggaata tttcccatcg cagatgctga   3480
gaacgggcaa taactttacc ttcagctaca ccttcgagga cgtgcctttc cacagcagct   3540
acgcgcacag ccagagcctg gaccggctga tgaatcctct catcgaccag tacctgtatt   3600
acctgaacag aactcagaat cagtccggaa gtgcccaaaa caaggacttg ctgtttagcc   3660
gggggtctcc agctggcatg tctgttcagc ccaaaaactg gctacctgga ccctgttacc   3720
ggcagcagcg cgtttctaaa acaaaaacag acaacaacaa cagcaacttt acctggactg   3780
gtgcttcaaa atataacctt aatgggcgtg aatctataat caaccctggc actgctatgg   3840
cctcacacaa agacgacaaa gacaagttct ttcccatgag cggtgtcatg atttttggaa   3900
aggagagcgc cggagcttca aacactgcat tggacaatgt catgatcaca gacgaagagg   3960
aaatcaaagc cactaacccc gtggccaccg aaagatttgg gactgtggca gtcaatctcc   4020
agagtgtaca tcgattgtta atcaataaac cgtttaattc gtttcagttg aactttggtc   4080
tctgcgtatt tctttcttat ctagtttcca tggctacgta gataagtagc atggcgggtt   4140
aatcattaac tacaaggaac ccctagtgat ggagttggcc actccctctc tgcgcgctcg   4200
ctcgctcact gaggccgggc gaccaaaggt cgcccgacgc ccgggctttg cccgggcggc   4260
ctcagtgagc gagcgagcgc gcagagaggg agtggccaag catgcaatta actggccgtc   4320
```

```
gttttacaac gtcgtgactg ggaaaaccct ggcgttaccc aacttaatcg ccttgcagca   4380

catccccctt tcgccagctg tatcagcaca caattgccca ttatacgcgc gtataatgga   4440

ctattgtgtg ctgata                                                   4456


<210> SEQ ID NO 24
<211> LENGTH: 4319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

tatcagcaca caatagtcca ttatacgcgc gtataatggg caattgtgtg ctgatacagc     60

tggcacgaca ggtttcccga ctggaaagcg ggcagtgagc gcaacgcaat taatgtgagt    120

tagctcactc attaggcacc ccaggcttta cactttatgc ttccggctcg tatgttgtgt    180

ggaattgtga gcggataaca atttcacaca ggaaacagct atgaccatga ttacgccaga    240

tttaattaag gccttaatta ggctagcttg gccactccct ctctgcgcgc tcgctcgctc    300

actgaggccg ggcgaccaaa ggtcgcccga cgcccgggct ttgcccgggc ggcctcagtg    360

agcgagcgag cgcgcagaga gggagtggcc aactccatca ctaggggttc ctggaggggt    420

ggagtcgtga cgatatccat gcgtcgacat aacgcgttag tatctgcaga gggccctgcg    480

tatgagtgca agtgggtttt aggaccagga tgaggcgggg tgggggtgcc tacctgacga    540

ccgaccccga cccactggac aagcacccaa cccccattcc ccaaattgcg catcccctat    600

cagagagggg gaggggaaac aggatgcggc gaggcgcgtg cgcactgcca gcttcagcac    660

cgcggacagt gccttcgccc ccgcctggcg gcgcgcgcca ccgccgcctc agcactgaag    720

gcgcgctgac gtcactcgcc ggtcccccgc aaactcccct tcccggccac cttggtcgcg    780

tccgcgccgc cgccggccca gccggaccgc accacgcgag gcgcgagata ggggggcacg    840

ggcgcgacca tctgcgctgc ggcgccggcg actcagcgct gcctcagtct gcggtgggca    900

gcggaggagt cgtgtcgtgc ctgagagcgc agctgtgctc ctgggcaccg cgcagtccgc    960

ccccgcggct cctggccaga ccacccctag gacccccctgc cccaagtcgc agccaagctt   1020

cgtttagtga accgtcagat cgcctggaga cgccatccac gctgttttga cctccataga   1080

agacaccggg accgatccag cctccgcgga ttcgaatccc ggccgggaac ggtgcattgg   1140

aacgcggatt ccccgtgcca agagtgacgt aagtaccgcc tatagagtct ataggcccac   1200

aaaaaatgct ttcttctttt aatatacttt tttgtttatc ttatttctaa tactttccct   1260

aatctctttc tttcagggca ataatgatac aatgtatcat gcctctttgc accattctaa   1320

agaataacag tgataatttc tgggttaagg caatagcaat atttctgcat ataaatattt   1380

ctgcatataa attgtaactg atgtaagagg tttcatattg ctaatagcag ctacaatcca   1440

gctaccattc tgcttttatt ttatggttgg gataaggctg gattattctg agtccaagct   1500

aggccctttt gctaatcatg ttcatacctc ttatcttcct cccacagctc ctgggcaacg   1560

tgctggtctg tgtgctggcc catcactttg gcaaagaatt gggattcgaa ccggtcgcca   1620

ccggtcacaa gcaggaagtc aaagactttt tccggtgggc aaaggatcac gtggttgagg   1680

tggagcatga attctacgtc aaaaagggtg gagccaagaa aagacccgcc cccagtgacg   1740

cagatataag tgagcccaaa cgggtgcgcg agtcagttgc gcagccatcg acgtcagacg   1800

cggaagcttc gatcaactac gcggacaggt accaaaacaa atgttctcgt cacgtgggca   1860
```

```
tgaatctgat gctgtttccc tgcagacaat gcgagagaat gaatcagaat tcaaatatct   1920
gcttcactca cggacagaaa gactgtttag agtgctttcc cgtgtcagaa tctcaacccg   1980
tttctgtcgt caaaaaggcg tatcagaaac tgtgctacat tcatcatatc atgggaaagg   2040
tgccagacgc ttgcactgcc tgcgatctgg tcaatgtgga tttggatgac tgcatctttg   2100
aacaataaat gatttaaatc aggtatggct gccgatggtt atcttccaga ttggctcgag   2160
gacactctct ctgaaggaat aagacagtgg tggaagctca aacctggccc accaccacca   2220
aagcccgcag agcggcataa ggacgacagc aggggtcttg tgcttcctgg gtacaagtac   2280
ctcggaccct tcaacggact cgacaaggga gagccggtca acgaggcaga cgccgcggcc   2340
ctcgagcacg acaaagccta cgaccggcag ctcgacagcg gagacaaccc gtacctcaag   2400
tacaaccacg ccgacgccga gttccaggag cggctcaaag aagatacgtc ttttgggggc   2460
aacctcgggc gagcagtctt ccaggccaaa aagaggcttc ttgaacctct tggtctggtt   2520
gaggaagcgg ctaagacggc tcctggaaag aagaggcctg tagagcactc tcctgtggag   2580
ccagactcct cctcgggaac cggaaaggcg ggccagcagc ctgcaagaaa aagattgaat   2640
tttggtcaga ctggagacgc agactcagtc ccagaccctc aaccaatcgg agaacctccc   2700
gcagcccccct caggtgtggg atctcttaca atggctgcag gcggtggcgc accaatggca   2760
gacaataacg agggcgccga cggagtgggt aattcctcgg gaaattggca ttgcgattcc   2820
acatggatgg gcgacagagt catcaccacc agcacccgaa cctgggccct gcccacctac   2880
aacaaccacc tctacaagca aatctccaac agcacatctg gaggatcttc aaatgacaac   2940
gcctacttcg gctacagcac cccctggggg tattttgact ttaacagatt ccactgccac   3000
ttttcaccac gtgactggca gcgactcatc aacaacaact ggggattccg gcccaagaga   3060
ctcagcttca agctcttcaa catccaggtc aaggaggtca cgcagaatga aggcaccaag   3120
accatcgcca ataacctcac cagcaccatc caggtgttta cggactcgga gtaccagctg   3180
ccgtacgttc tcggctctgc ccaccagggc tgcctgcctc cgttcccggc ggacgtgttc   3240
atgattcccc agtacggcta cctaacactc aacaacggta gtcaggccgt gggacgctcc   3300
tccttctact gcctggaata ctttccttcg cagatgctga gaaccggcaa caacttccag   3360
tttacttaca ccttcgagga cgtgcctttc cacagcagct acgcccacag ccagagcttg   3420
gaccggctga tgaatcctct gattgaccag tacctgtact acttgtctcg gactcaaaca   3480
acaggaggca cgacaaatac gcagactctg ggcttcagcc aaggtgggcc taatacaatg   3540
gccaatcagg caaagaactg gctgccagga ccctgttacc gccagcagcg agtatcaaag   3600
acatctgcgg ataacaacaa cagtgaatac tcgtggactg gagctaccaa gtaccacctc   3660
aatggcagag actctctggt gaatccgggc ccggccatgg caagccacaa ggacgatgaa   3720
gaaaagtttt ttcctcagag cggggttctc atctttggga agcaaggctc agagaaaaca   3780
aatgtggaca ttgaaaaggt catgattaca gacgaagagg aaatcaggac aaccaatccc   3840
gtggctacgg agcagtatgg ttctgtatct accaacctcc agcaaggtgt acatcgattg   3900
ttaatcaata aaccgtttaa ttcgtttcag ttgaactttg gtctctgcgt atttctttct   3960
tatctagttt ccatggctac gtagataagt agcatggcgg gttaatcatt aactacaagg   4020
aacccctagt gatggagttg gccactccct ctctgcgcgc tcgctcgctc actgaggccg   4080
ggcgaccaaa ggtcgcccga cgcccgggct ttgcccgggc ggcctcagtg agcgagcgag   4140
cgcgcagaga gggagtggcc aagcatgcaa ttaactggcc gtcgttttac aacgtcgtga   4200
```

ctgggaaaac cctggcgtta cccaacttaa tcgccttgca gcacatcccc ctttcgccag 4260
ctgtatcagc acacaattgc ccattatacg cgcgtataat ggactattgt gtgctgata 4319

<210> SEQ ID NO 25
<211> LENGTH: 4462
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25
tatcagcaca caatagtcca ttatacgcgc gtataatggg caattgtgtg ctgatacagc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgaccatga ttacgccaga 240
tttaattaag gccttaatta ggctagcttg gccactccct ctctgcgcgc tcgctcgctc 300
actgaggccg ggcgaccaaa ggtcgcccga cgcccgggct ttgcccgggc ggcctcagtg 360
agcgagcgag cgcgcagaga gggagtggcc aactccatca ctaggggttc ctggaggggt 420
ggagtcgtga cgatatccat gcgtcgacat aacgcgtgat ctaacatatc ctggtgtgga 480
gtagcggacg ctgctatgac agaggctcgg gggcctgagc tggctctgtg agctggggag 540
gaggcagaca gccaggcctt gtctgcaagc agacctggca gcattgggct ggccgccccc 600
cagggcctcc tcttcatgcc cagtgaatga ctcaccttgg cacagacaca atgttcgggg 660
tgggcacagt gcctgcttcc cgccgcaccc cagcccccct caaatgcctt ccgagaagcc 720
cattgagcag gggggcttgca ttgcacccca gcctgacagc ctggcatctt gggataaaag 780
cagcacagcc ccctaggggc tgcccttgct gtgtggcgcc accggcggtg gagaacaagg 840
ctctattcag cctgtgccca ggaaagggga tcaggggatg cccaggcatg gacagtgggt 900
ggcagggggg gagaggaggg ctgtctgctt cccagaagtc caaggacaca aatgggtgag 960
gggagagctc tccccatagc tgggctgcgg cccaacccca ccccctcagg ctatgccagg 1020
gggtgttgcc aggggcaccc gggcatcgcc agtctagccc actccttcat aaagccctcg 1080
catcccagga gcgagcagag ccagagcagg ttggagagga gacgcatcac ctccgctgct 1140
cgcggggatc ctctagaagc ttcgtttagt gaaccgtcag atcgcctgga gacgccatcc 1200
acgctgtttt gacctccata gaagacaccg ggaccgatcc agcctccgcg gattcgaatc 1260
ccggccggga acggtgcatt ggaacgcgga ttccccgtgc caagagtgac gtaagtaccg 1320
cctatagagt ctataggccc acaaaaaatg ctttcttctt ttaatatact tttttgttta 1380
tcttatttct aatactttcc ctaatctctt tctttcaggg caataatgat acaatgtatc 1440
atgcctcttt gcaccattct aaagaataac agtgataatt tctgggttaa ggcaatagca 1500
atatttctgc atataaatat ttctgcatat aaattgtaac tgatgtaaga ggtttcatat 1560
tgctaatagc agctacaatc cagctaccat tctgctttta ttttatggtt gggataaggc 1620
tggattattc tgagtccaag ctaggccctt ttgctaatca tgttcatacc tcttatcttc 1680
ctcccacagc tcctgggcaa cgtgctggtc tgtgtgctgg cccatcactt tggcaaagaa 1740
ttgggattcg aaccggtcgc caccggtcac caagcaggaa gtcaaagact tttccggtg 1800 ggcaaaggat cacgtggttg aggtggagca tgaattctac gtcaaaaagg gtggagccaa 1860
gaaaagaccc gcccccagtg acgcagatat aagtgagccc aaacgggtgc gcgagtcagt 1920

-continued

```
tgcgcagcca tcgacgtcag acgcggaagc ttcgatcaac tacgcggaca ggtaccaaaa   1980
caaatgttct cgtcacgtgg gcatgaatct gatgctgttt ccctgcagac aatgcgagag   2040
aatgaatcag aattcaaata tctgcttcac tcacggacag aaagactgtt tagagtgctt   2100
tcccgtgtca gaatctcaac ccgtttctgt cgtcaaaaag gcgtatcaga aactgtgcta   2160
cattcatcat atcatgggaa aggtgccaga cgcttgcact gcctgcgatc tggtcaatgt   2220
ggatttggat gactgcatct ttgaacaata aatgatttaa atcaggtatg gctgccgatg   2280
gttatcttcc agattggctc gaggacactc tctctgaagg aataagacag tggtggaagc   2340
tcaaacctgg cccaccacca ccaaagcccg cagagcggca taaggacgac agcaggggtc   2400
ttgtgcttcc tgggtacaag tacctcggac ccttcaacgg actcgacaag ggagagccgg   2460
tcaacgaggc agacgccgcg gccctcgagc acgacaaagc ctacgaccgg cagctcgaca   2520
gcggagacaa cccgtacctc aagtacaacc acgccgacgc cgagttccag gagcggctca   2580
aagaagatac gtcttttggg ggcaacctcg ggcgagcagt cttccaggcc aaaaagaggc   2640
ttcttgaacc tcttggtctg gttgaggaag cggctaagac ggctcctgga aagaagaggc   2700
ctgtagagca ctctcctgtg gagccagact cctcctcggg aaccggaaag gcgggccagc   2760
agcctgcaag aaaaagattg aattttggtc agactggaga cgcagactca gtcccagacc   2820
ctcaaccaat cggagaacct cccgcagccc cctcaggtgt gggatctctt acaatggctg   2880
caggcggtgg cgcaccaatg gcagacaata acgagggcgc cgacggagtg ggtaattcct   2940
cgggaaattg gcattgcgat tccacatgga tgggcgacag agtcatcacc accagcaccc   3000
gaacctgggc cctgcccacc tacaacaacc acctctacaa gcaaatctcc aacagcacat   3060
ctggaggatc ttcaaatgac aacgcctact tcggctacag caccccctgg gggtattttg   3120
actttaacag attccactgc cacttttcac cacgtgactg gcagcgactc atcaacaaca   3180
actggggatt ccggcccaag agactcagct tcaagctctt caacatccag gtcaaggagg   3240
tcacgcagaa tgaaggcacc aagaccatcg ccaataacct caccagcacc atccaggtgt   3300
ttacggactc ggagtaccag ctgccgtacg ttctcggctc tgcccaccag ggctgcctgc   3360
ctccgttccc ggcggacgtg ttcatgattc cccagtacgg ctacctaaca ctcaacaacg   3420
gtagtcaggc cgtgggacgc tcctccttct actgcctgga atactttcct tcgcagatgc   3480
tgagaaccgg caacaacttc cagtttactt acaccttcga ggacgtgcct ttccacagca   3540
gctacgccca cagccagagc ttggaccggc tgatgaatcc tctgattgac cagtacctgt   3600
actacttgtc tcggactcaa acaacaggag gcacgacaaa tacgcagact ctgggcttca   3660
gccaaggtgg gcctaataca atggccaatc aggcaaagaa ctggctgcca ggaccctgtt   3720
accgccagca gcgagtatca aagacatctg cggataacaa caacagtgaa tactcgtgga   3780
ctggagctac caagtaccac ctcaatggca gagactctct ggtgaatccg ggcccggcca   3840
tggcaagcca caaggacgat gaagaaaagt tttttcctca gagcggggtt ctcatctttg   3900
ggaagcaagg ctcagagaaa acaaatgtgg acattgaaaa ggtcatgatt acagacgaag   3960
aggaaatcag gacaaccaat cccgtggcta cggagcagta tggttctgta tctaccaacc   4020
tccagcaagg tgtacatcga ttgttaatca ataaaccgtt taattcgttt cagttgaact   4080
ttggtctctg cgtatttctt tcttatctag tttccatggc tacgtagata agtagcatgg   4140
cgggttaatc attaactaca aggaacccct agtgatggag ttggccactc cctctctgcg   4200
cgctcgctcg ctcactgagg ccgggcgacc aaaggtcgcc cgacgcccgg gctttgcccg   4260
ggcggcctca gtgagcgagc gagcgcgcag agagggagtg gccaagcatg caattaactg   4320
```

gccgtcgttt tacaacgtcg tgactgggaa aaccctggcg ttacccaact taatcgcctt 4380
gcagcacatc ccccttcgc cagctgtatc agcacacaat tgcccattat acgcgcgtat 4440
aatggactat tgtgtgctga ta 4462

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ccgtgccaag agtgacctcc 20

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(51)
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 27

```
ctc cag agt agc agc nnk nnk nnk nnk nnk nnk nnk aca gac cct gcg       48
Leu Gln Ser Ser Ser Xaa Xaa Xaa Xaa Xaa Xaa Xaa Thr Asp Pro Ala
1               5                   10                  15

acc                                                                   51
Thr
```

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (6)..(12)
<223> OTHER INFORMATION: Any naturally occurring amino acid

<400> SEQUENCE: 28

```
Leu Gln Ser Ser Ser Xaa Xaa Xaa Xaa Xaa Xaa Xaa Thr Asp Pro Ala
1               5                   10                  15

Thr
```

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(51)
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 29

```
aac cag agc tct acc nnk nnk nnk nnk nnk nnk nnk act gcc ccc gcg       48
Asn Gln Ser Ser Thr Xaa Xaa Xaa Xaa Xaa Xaa Xaa Thr Ala Pro Ala
1               5                   10                  15

acc                                                                   51
Thr
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (6)..(12)
<223> OTHER INFORMATION: Any naturally occurring amino acid

<400> SEQUENCE: 30

```
Asn Gln Ser Ser Thr Xaa Xaa Xaa Xaa Xaa Xaa Xaa Thr Ala Pro Ala
1               5                   10                  15

Thr
```

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 31

```
ctc cag caa ggt aac nnk nnk nnk nnk nnk nnk nnk aca caa gca gct       48
Leu Gln Gln Gly Asn Xaa Xaa Xaa Xaa Xaa Xaa Xaa Thr Gln Ala Ala
1               5                   10                  15

acc                                                                   51
Thr
```

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(12)
<223> OTHER INFORMATION: Any naturally occurring amino acid

<400> SEQUENCE: 32

```
Leu Gln Gln Gly Asn Xaa Xaa Xaa Xaa Xaa Xaa Xaa Thr Gln Ala Ala
1               5                   10                  15

Thr
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS

<222> LOCATION: (1)..(30)

<400> SEQUENCE: 33

```
cac cag agt gcc caa gca cag gcg cag acc                              30
His Gln Ser Ala Gln Ala Gln Ala Gln Thr
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
His Gln Ser Ala Gln Ala Gln Ala Gln Thr
1               5                   10
```

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 35

```
cac cag agt gat ggg act ttg gcg gtg cct ttt aag gca cag gcg cag      48
His Gln Ser Asp Gly Thr Leu Ala Val Pro Phe Lys Ala Gln Ala Gln
1               5                   10                  15

acc                                                                  51
Thr
```

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
His Gln Ser Asp Gly Thr Leu Ala Val Pro Phe Lys Ala Gln Ala Gln
1               5                   10                  15

Thr
```

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:

<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 37

```
cac cag agt gcc caa nnk nnk nnk nnk nnk nnk nnk gca cag gcg cag       48
His Gln Ser Ala Gln Xaa Xaa Xaa Xaa Xaa Xaa Xaa Ala Gln Ala Gln
1               5                   10                  15

acc                                                                   51
Thr
```

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (6)..(12)
<223> OTHER INFORMATION: Any naturally occurring amino acid

<400> SEQUENCE: 38

```
His Gln Ser Ala Gln Xaa Xaa Xaa Xaa Xaa Xaa Xaa Ala Gln Ala Gln
1               5                   10                  15

Thr
```

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(51)
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)

```
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 39

cac cag agt gat ggg nnk nnk nnk nnk nnk nnk nnk gca cag gcg cag       48
His Gln Ser Asp Gly Xaa Xaa Xaa Xaa Xaa Xaa Xaa Ala Gln Ala Gln
1               5                   10                  15

acc                                                                   51
Thr


<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(12)
<223> OTHER INFORMATION: Any naturally occurring amino acid

<400> SEQUENCE: 40

His Gln Ser Asp Gly Xaa Xaa Xaa Xaa Xaa Xaa Xaa Ala Gln Ala Gln
1               5                   10                  15

Thr


<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 41

cac cag agt gat ggc acc nnk nnk nnk nnk nnk nnk gca cag gcg cag       48
His Gln Ser Asp Gly Thr Xaa Xaa Xaa Xaa Xaa Xaa Ala Gln Ala Gln
```

1 5 10 15 acc 51
Thr

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(12)
<223> OTHER INFORMATION: Any naturally occurring amino acid

<400> SEQUENCE: 42

His Gln Ser Asp Gly Thr Xaa Xaa Xaa Xaa Xaa Xaa Ala Gln Ala Gln
1 5 10 15

Thr

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
gccaccaaca accagagctc tgtacatcga ttgttaatca ataaa 45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
gtggcagtca atctccagag tgtacatcga ttgttaatca ataaa 45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tctaccaacc tccagcaagg tgtacatcga ttgttaatca ataaa 45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
gtggccacaa accaccagag tgtacatcga ttgttaatca ataaa 45

<210> SEQ ID NO 47

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other

<400> SEQUENCE: 47
nnknnknnkn nknnknnknn k 21

<210> SEQ ID NO 48
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(69)
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other

<400> SEQUENCE: 48 caa gtg gcc aca aac cac cag agt gcc caa nnk nnk nnk nnk nnk nnk 48
Gln Val Ala Thr Asn His Gln Ser Ala Gln Xaa Xaa Xaa Xaa Xaa Xaa
1 5 10 15 nnk gca cag gcg cag acc ggc tg 71
Xaa Ala Gln Ala Gln Thr Gly
20

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (11)..(17)
<223> OTHER INFORMATION: Any naturally occurring amino acid

<400> SEQUENCE: 49

Gln Val Ala Thr Asn His Gln Ser Ala Gln Xaa Xaa Xaa Xaa Xaa Xaa
1 5 10 15

Xaa Ala Gln Ala Gln Thr Gly
20

<210> SEQ ID NO 50
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(69)
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other

<400> SEQUENCE: 50 cag gtc gct acc aat cat caa tcc gca cag nnk nnk nnk nnk nnk nnk 48
Gln Val Ala Thr Asn His Gln Ser Ala Gln Xaa Xaa Xaa Xaa Xaa Xaa
1 5 10 15 nnk gct caa gca caa aca gga 69
Xaa Ala Gln Ala Gln Thr Gly

20

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
caagtggcca caaaccacca gagt 24

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
caggtcgcta ccaatcatca a 21

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
agtgcccaag cacaggcgca gacc 24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
agtgctcagg cacaggcgca gacc 24

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
gacggaacac tcgcagtccc attcaaa 27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
gatgggactt tggcggtgcc ttttaag 27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gcacaaacac tcgcagtccc attcaaa 27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
gcccaaactt tggcggtgcc ttttaag 27

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Asp Gly Thr Ser Ser Tyr Tyr Asp Ser
1 5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ala Gln Pro Glu Gly Ser Ala Arg Trp
1 5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Asp Gly Thr Ala Ser Tyr Tyr Asp Ser
1 5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Ala Gln Trp Pro Thr Ser Tyr Asp Ala
1 5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Asp Gly Thr Ala Asp Lys Pro Phe Arg
1 5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Asp Gly Ser Ser Ser Tyr Tyr Asp Ala
1 5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Asp Gly Thr Leu Ser Gln Pro Phe Arg
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Ala Gln Phe Pro Thr Asn Tyr Asp Ser
1 5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Asp Gly Thr Ala Ile His Leu Ser Ser
1 5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Asp Gly Thr Gly Gln Val Thr Gly Trp
1 5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Asp Gly Thr Gly Asn Val Thr Gly Trp
1 5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Asp Gly Thr Met Asp Lys Pro Phe Arg
1 5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Asp Gly Thr Leu Ala Val Pro Phe Lys
1 5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Asp Gly Thr Gly Asn Thr His Gly Trp
1 5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Asp Gly Thr Val Ile His Leu Ser Ser
1 5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Asp Gly Thr Gly Thr Thr Val Gly Trp
1 5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Asp Gly Thr Thr Tyr Val Pro Pro Arg
1 5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Asp Gly Thr Asn Gly Leu Lys Gly Trp
1 5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Asp Gly Thr Thr Thr Tyr Gly Ala Arg
1 5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Asp Gly Thr Ser Tyr Val Pro Pro Arg
1 5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Asp Gly Thr Thr Phe Thr Pro Pro Arg
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Ala Gln Gly Ser Trp Asn Pro Pro Ala
1 5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Asp Gly Thr Ser Phe Thr Pro Pro Lys
1 5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Ala Gln Gly Thr Trp Asn Pro Pro Ala
1 5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Ala Gln Thr Thr Glu Lys Pro Trp Leu
1 5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Ala Gln Asn Gly Asn Pro Gly Arg Trp
1 5

<210> SEQ ID NO 85
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 85

Ala Gln Thr Thr Asp Arg Pro Phe Leu
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Gly Thr Ser Phe Pro Tyr Ala Arg
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Gly Thr Ile Glu Arg Pro Phe Arg
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Gly Thr Ser Phe Thr Pro Pro Arg
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Gly Thr Leu Gln Gln Pro Phe Arg
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Gly Thr His Thr Arg Thr Gly Trp
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Ala Gln Gly Gly Asn Pro Gly Arg Trp
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Asp Gly Lys Gln Tyr Gln Leu Ser Ser
1 5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ala Gln Thr Arg Glu Tyr Leu Leu Gly
1 5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Asp Gly Thr Gly Asn Thr Arg Gly Trp
1 5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Ala Gln Phe Val Val Gly Gln Gln Tyr
1 5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Ala Gln Gly Glu Asn Pro Gly Arg Trp
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Gly Thr Ser Tyr Val Pro Pro Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Gln Thr Leu Ala Arg Pro Phe Val
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Gly Ser Thr Glu Arg Pro Phe Arg
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Gln Thr Ser Ala Arg Pro Phe Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Gly Thr Ser Gly Leu Lys Gly Trp
1               5

<210> SEQ ID NO 102
<211> LENGTH: 9

<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Asp Gly Thr Met Asp Arg Pro Phe Lys
1 5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Ala Gln Gly Ser Asn Pro Gly Arg Trp
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Asp Gly Val His Pro Gly Leu Ser Ser
1 5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Asp Gly Thr Ile Ser Gln Pro Phe Lys
1 5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Asp Gly Thr Arg Thr Thr Thr Gly Trp
1 5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Asp Gly Thr Gly Gly Thr Lys Gly Trp 1 5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Asp Gly Thr Gln Phe Ser Pro Pro Arg
1 5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Asp Gly Thr Leu Asn Asn Pro Phe Arg
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Asp Gly Gln His Phe Ala Pro Pro Arg
1 5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Asp Gly Thr Lys Ile Arg Leu Ser Ser
1 5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Asp Gly Thr His Phe Ala Pro Pro Arg
1 5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Asp Gly Thr Asn Thr Thr His Gly Trp
1 5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Asp Gly Ser Gly Thr Thr Arg Gly Trp
1 5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Ala Gln Leu Lys Tyr Gly Leu Ala Gln
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Asp Gly Thr Thr Leu Val Pro Pro Arg
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Asp Gly Thr Gly Arg Thr Val Gly Trp
1 5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Asp Gly Thr Lys Leu Arg Leu Ser Ser
1 5

<210> SEQ ID NO 119

<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Asp Gly Thr Gly Ser Thr His Gly Trp
1 5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Asp Gly Thr Leu Ala Ala Pro Phe Lys
1 5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Asp Gly Thr Leu Leu Arg Leu Ser Ser
1 5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Asp Gly Thr Lys Val Leu Val Gln Leu
1 5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Ala Gln Leu Arg Val Gly Phe Ala Gln
1 5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Asp Gly Thr Asn Thr Ile Asn Gly Trp
1 5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Ala Gln Gly Pro Thr Arg Pro Phe Leu
1 5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Ala Gln Thr Arg Ala Gly Tyr Ala Gln
1 5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Asp Gly Ser Ser Phe Tyr Pro Pro Lys
1 5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Ala Gln Gly Ser Asp Val Gly Arg Trp
1 5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Asp Gly Thr Gln Phe Arg Leu Ser Ser
1 5

<210> SEQ ID NO 130
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 130

Asp Gly Thr Gly Thr Thr Thr Gly Trp
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Gly Thr Gly Gly Ile Lys Gly Trp
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Gly Thr Ala Ala Arg Leu Ser Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Gly Thr Gly Asn Leu Arg Gly Trp
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Gly Thr Gly Ser Thr Thr Gly Trp
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Gly Thr Arg Asn Met Tyr Glu Gly
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Asp Gly Ser Gln Ser Thr Thr Gly Trp
1 5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Asp Gly Thr Gly Asn Thr Ser Gly Trp
1 5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Ala Gln Arg Tyr Thr Gly Asp Ser Ser
1 5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Asp Gly Thr Thr Trp Thr Pro Pro Arg
1 5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Asp Gly Thr Ala Glu Arg Pro Phe Arg
1 5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Ala Gln Thr Arg Ala Gly Tyr Ser Gln
1 5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Asp Gly Thr Lys Met Val Leu Gln Leu
1 5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Asp Gly Thr Asn Ser Thr Thr Gly Trp
1 5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Ala Gln Glu Leu Thr Arg Pro Phe Leu
1 5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Asp Gly Thr His Ser Thr Thr Gly Trp
1 5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Asp Gly Thr Lys Ile Gln Leu Ser Ser
1 5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Asp Gly Ser Gly Arg Thr Thr Gly Trp
1 5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Asp Gly Thr Met Leu Arg Leu Ser Ser
1 5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Ala Gln Gly Ala Ser Pro Gly Arg Trp
1 5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Asp Gly Thr Val Leu Val Pro Phe Arg
1 5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Asp Gly Ala Gly Gly Thr Ser Gly Trp
1 5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Ala Gln Tyr Leu Lys Gly Tyr Ser Val
1 5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Asp Gly Thr His Ala Tyr Met Ala Ser
1 5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Asp Gly Thr Gly Gly Leu Arg Gly Trp
1 5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Asp Gly Thr Ala Asp Arg Pro Phe Arg
1 5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Asp Gly Thr Leu Glu Arg Pro Phe Arg
1 5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Asp Gly Thr Lys Leu Met Leu Ser Ser
1 5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Asp Gly Thr Gln Gly Leu Lys Gly Trp
1 5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Asp Gly Thr Gly Arg Leu Thr Gly Trp
1 5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Asp Gly Ser Pro Glu Lys Pro Phe Arg
1 5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Ala Gln Thr Gly Phe Ala Pro Pro Arg
1 5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Asp Gly Thr His Ile His Leu Ser Ser
1 5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Ala Gln Thr Ser Ala Lys Pro Phe Leu
1 5

<210> SEQ ID NO 164
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 164

Asp Gly Thr Val Arg Val Pro Phe Arg
1 5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Ala Gln Val His Val Gly Ser Val Tyr
1 5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Asp Gly Thr Ser Leu Arg Leu Ser Ser
1 5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Asp Gly Asn Gly Gly Leu Lys Gly Trp
1 5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Ala Gln Thr Leu Ala Val Pro Phe Lys
1 5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Ala Gln Ser Leu Ala Thr Pro Phe Arg
1 5

<210> SEQ ID NO 170
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (15)..(16)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other

<400> SEQUENCE: 170
nnnnnnnnnn tactnnccgg tagnncngag tcctatggac aagtggccac aaaccaccag 60
agtgcccaat gggggggggg gggggggggg gcacaggcgc agaccggctg ggttcaaaac 120
caaggaatac ttccg 135

<210> SEQ ID NO 171
<211> LENGTH: 138
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (82)..(83)
<223> OTHER INFORMATION: a, c, t, g, unknown or other
<220> FEATURE:
<221> NAME/KEY: modified_base
<222> LOCATION: (85)..(86)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other

<400> SEQUENCE: 171
nnnnnnnnnn nntactaacc cggtancncg gagtcctatg gacaagtggc cacaaaccac 60
cagagtgccc aaagccnctt cnncnncaac nacgcacagg cgcagaccgg ctgggttcaa 120
aaccaaggaa tacttccg 138

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 172
tggccacaaa ccaccagagt 20

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
cagccggtct gcgcctgt 18

<210> SEQ ID NO 174
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 174
ctatggacaa gtggccacaa accaccagag tgcccaa 37

<210> SEQ ID NO 175
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
gcacaggcgc ag 12

<210> SEQ ID NO 176
<211> LENGTH: 56
<212> TYPE: DNA
<213> ORGANISM: Unknown
<220> FEATURE:
<223> OTHER INFORMATION: Description of Unknown:
protelomerase recognition sequence

<400> SEQUENCE: 176
tatcagcaca caattgccca ttatacgcgc gtataatgga ctattgtgtg ctgata 56

<210> SEQ ID NO 177
<211> LENGTH: 56
<212> TYPE: DNA
<213> ORGANISM: Unknown
<220> FEATURE:
<223> OTHER INFORMATION: Description of Unknown:
protelomerase sequence

<400> SEQUENCE: 177
tatcagcaca caattgccca ttatacgcgc gtataatggg caattgtgtg ctgata 56

<210> SEQ ID NO 178
<211> LENGTH: 56
<212> TYPE: DNA
<213> ORGANISM: Unknown
<220> FEATURE:
<223> OTHER INFORMATION: Description of Unknown:
protelomerase sequence

<400> SEQUENCE: 178
tatcagcaca caatagtcca ttatacgcgc gtataatgga ctattgtgtg ctgata 56

<210> SEQ ID NO 179
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Thr Asn His Gln Ser Asp Gly Thr Leu Ser Gln Pro Phe Arg Ala Gln
1 5 10 15

Ala Gln Thr Gly
20

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Thr Asn His Gln Ser Asp Gly Thr Thr Tyr Val Pro Pro Arg Ala Gln
1 5 10 15

Ala Gln Thr Gly
20

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Thr Asn His Gln Ser Asp Gly Thr Ala Asp Lys Pro Phe Arg Ala Gln
1 5 10 15

Ala Gln Thr Gly
20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Thr Asn His Gln Ser Asp Gly Thr Asn Gly Leu Lys Gly Trp Ala Gln
1 5 10 15

Ala Gln Thr Gly
20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 183

Thr Asn His Gln Ser Ala Gln Pro Glu Gly Ser Ala Arg Trp Ala Gln
1               5                   10                  15

Ala Gln Thr Gly
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Thr Asn His Gln Ser Ala Gln Trp Pro Thr Ser Tyr Asp Ala Ala Gln
1               5                   10                  15

Ala Gln Thr Gly
            20

<210> SEQ ID NO 185
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Thr Asn His Gln Ser Asp Gly Thr Ser Ser Tyr Tyr Asp Ser Ala Gln
1               5                   10                  15

Ala Gln Thr Gly
            20

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Thr Asn His Gln Ser Asp Gly Thr Leu Ala Val Pro Phe Lys Ala Gln
1               5                   10                  15

Ala Gln Thr Gly
            20

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Thr Asn His Gln Ser Ala Gln Thr Leu Ala Val Pro Phe Lys Ala Gln
1 5 10 15

Ala Gln Thr Gly
20

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Thr Asn His Gln Ser Ala Gln Ala Gln Ala Gln Thr Gly
1 5 10

<210> SEQ ID NO 189
<211> LENGTH: 133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189
gatcaactac gcggacaggt accaaaacaa atgttctcgt cacgtgggca tgaatctgat 60
gctgtttccc tgcagacaat gcgagagact gaatcagaat tcaaatatct gcttcactca 120
cggtgtcaaa gac 133

<210> SEQ ID NO 190
<211> LENGTH: 107
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:

<221> NAME/KEY: modified_base
<222> LOCATION: (72)..(72)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other

<400> SEQUENCE: 190
gatcaactac gcggacaggt accaaaansw nswnswnswn swaggtcatt ccatcgagat 60
ctnswnswns wnswnswgtt taaaccttca ctcacggtgt caaagac 107

<210> SEQ ID NO 191
<211> LENGTH: 115
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (71)..(71)
<223> OTHER INFORMATION: a, c, t, g, unknown or other
<220> FEATURE:
<221> NAME/KEY: modified_base
<222> LOCATION: (74)..(74)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other

<400> SEQUENCE: 191
gatcaactac gcggacaggt accaaaacaa atgttnswns wnswnswnsw aggtcattcc 60
atcgagatct nswnswnswn swnswgttta aaccttcact cacggtgtca aagac 115

<210> SEQ ID NO 192
<211> LENGTH: 124
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other
<220> FEATURE:
<221> NAME/KEY: modified_base
<222> LOCATION: (86)..(86)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (92)..(92)
<223> OTHER INFORMATION: a, c, t, g, unknown or other

<400> SEQUENCE: 192
gatcaactac gcggacaggt accaaaacaa atgttctcgt cacgnswnsw nswnswnswa 60
ggtcattcca tcgagatctn swnswnswns wnswgtttaa accttcactc acggtgtcaa 120
agac 124

<210> SEQ ID NO 193
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (60)..(60)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (92)..(92)
<223> OTHER INFORMATION: a, c, t, g, unknown or other
<220> FEATURE:
<221> NAME/KEY: modified_base
<222> LOCATION: (95)..(95)
<223> OTHER INFORMATION: a, c, t, g, unknown or other
<220> FEATURE:
<221> NAME/KEY: modified_base
<222> LOCATION: (98)..(98)
<223> OTHER INFORMATION: a, c, t, g, unknown or other
<220> FEATURE:
<221> NAME/KEY: modified_base
<222> LOCATION: (101)..(101)
<223> OTHER INFORMATION: a, c, t, g, unknown or other

<400> SEQUENCE: 193
gatcaactac gcggacaggt accaaaacaa atgttctcgt cacgtgggca tganswnswn 60
swnswnswag gtcattccat cgagatctns wnswnswnsw nswgtttaaa ccttcactca 120
cggtgtcaaa gac 133

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Ala Gln Ala Gly Ala Gly Ser Glu Arg
1 5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 195

Ala Gln Asp Gln Asn Pro Gly Arg Trp
1 5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 196

Ala Gln Glu Val Pro Gly Tyr Arg Trp
1 5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 197

Ala Gln Gly Gly Ser Thr Gly Ser Asn 1 5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ala Gln Gly Arg Asp Gly Trp Ala Ala
1 5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ala Gln Gly Arg Met Thr Asp Ser Gln
1 5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Ala Gln Gly Ser Asn Ser Pro Gln Val
1 5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Ala Gln Gly Val Phe Ile Pro Pro Lys
1 5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Ala Gln His Val Asn Ala Ser Gln Ser
1 5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Ala Gln Ile Lys Ala Gly Trp Ala Gln
1 5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Ala Gln Ile Met Ser Gly Tyr Ala Gln
1 5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Ala Gln Lys Ser Val Gly Ser Val Tyr
1 5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Ala Gln Leu Glu His Gly Phe Ala Gln
1 5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Ala Gln Leu Gly Gly Val Leu Ser Ala
1 5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Ala Gln Leu Gly Leu Ser Gln Gly Arg
1 5

<210> SEQ ID NO 209

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Gln Leu Gly Tyr Gly Phe Ala Gln
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Gln Leu Arg Ile Gly Phe Ala Gln
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Gln Leu Arg Met Gly Tyr Ser Gln
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Gln Leu Arg Gln Gly Tyr Ala Gln
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Gln Leu Ser Cys Arg Ser Gln Met
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Gln Leu Thr Tyr Ser Gln Ser Leu
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Gln Leu Tyr Lys Gly Tyr Ser Gln
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Gln Met Pro Gln Arg Pro Phe Leu
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Gln Pro Leu Ala Val Tyr Gly Ala
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Gln Pro Gln Ser Ser Ser Met Ser
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Gln Pro Ser Val Gly Gly Tyr Trp
1               5

<210> SEQ ID NO 220
<211> LENGTH: 9
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 220

Ala Gln Gln Ala Val Gly Gln Ser Trp
1 5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Ala Gln Gln Arg Ser Leu Ala Ser Gly
1 5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Ala Gln Gln Val Met Asn Ser Gln Gly
1 5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Ala Gln Arg Gly Val Gly Leu Ser Gln
1 5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Ala Gln Arg His Asp Ala Glu Gly Ser
1 5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Ala Gln Arg Lys Gly Glu Pro His Tyr
1 5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Ala Gln Ser Ala Met Ala Ala Lys Gly
1 5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Ala Gln Ser Gly Gly Leu Thr Gly Ser
1 5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Ala Gln Ser Gly Gly Val Gly Gln Val
1 5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Ala Gln Ser Met Ser Arg Pro Phe Leu
1 5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Ala Gln Ser Gln Leu Arg Pro Phe Leu
1 5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Ala Gln Ser Val Ala Lys Pro Phe Leu
1 5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Ala Gln Ser Val Ser Gln Pro Phe Arg
1 5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Ala Gln Ser Val Val Arg Pro Phe Leu
1 5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Ala Gln Thr Ala Leu Ser Ser Ser Thr
1 5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Ala Gln Thr Glu Met Gly Gly Arg Cys
1 5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Ala Gln Thr Ile Arg Gly Tyr Ser Ser
1 5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Ala Gln Thr Ile Ser Asn Tyr His Thr
1 5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Ala Gln Thr Pro Asp Arg Pro Trp Leu
1 5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Ala Gln Thr Val Ala Arg Pro Phe Tyr
1 5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Ala Gln Thr Val Ala Thr Pro Phe Arg
1 5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Ala Gln Thr Val Thr Gln Leu Phe Lys
1 5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Ala Gln Val Leu Ala Gly Tyr Asn Met
1 5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Ala Gln Val Ser Glu Ala Arg Val Arg
1 5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Ala Gln Val Val Val Gly Tyr Ser Gln
1 5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Ala Gln Trp Ala Ala Gly Tyr Asn Val
1 5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Ala Gln Trp Glu Leu Ser Asn Gly Tyr
1 5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Ala Gln Trp Glu Val Lys Gly Gly Tyr
1 5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Ala Gln Trp Glu Val Lys Arg Gly Tyr
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Ala Gln Trp Glu Val Gln Ser Gly Phe
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Ala Gln Trp Glu Val Arg Gly Gly Tyr
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Ala Gln Trp Glu Val Thr Ser Gly Trp
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 252

Ala Gln Trp Gly Ala Pro Ser His Gly
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Ala Gln Trp Met Glu Leu Gly Ser Ser
1               5

<210> SEQ ID NO 254
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 254

Ala Gln Trp Met Phe Gly Gly Ser Gly
1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Gln Trp Met Leu Gly Gly Ala Gln
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Gln Trp Pro Thr Ala Tyr Asp Ala
1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Gln Trp Gln Val Gln Thr Gly Phe
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Gln Trp Ser Thr Glu Gly Gly Tyr
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Gln Trp Thr Ala Ala Gly Gly Tyr
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 260

Ala Gln Trp Thr Thr Glu Ser Gly Tyr
1 5

<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

Ala Gln Trp Val Tyr Gly Ser Ser His
1 5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Ala Gln Tyr Leu Ala Gly Tyr Thr Val
1 5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Ala Gln Tyr Leu Ser Gly Tyr Asn Thr
1 5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 264

Asp Gly Ala Ala Ala Thr Thr Gly Trp
1 5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 265

Asp Gly Ala Gly Thr Thr Ser Gly Trp
1 5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Asp Gly Ala His Gly Leu Ser Gly Trp
1 5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Asp Gly Ala His Val Gly Leu Ser Ser
1 5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Asp Gly Ala Arg Thr Val Leu Gln Leu
1 5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Asp Gly Glu Tyr Gln Lys Pro Phe Arg
1 5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Asp Gly Gly Gly Thr Thr Thr Gly Trp
1 5

<210> SEQ ID NO 271
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Asp Gly His Ala Thr Ser Met Gly Trp
1 5

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 272

Asp Gly Lys Gly Ser Thr Gln Gly Trp
1 5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

Asp Gly Gln Gly Gly Leu Ser Gly Trp
1 5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 274

Asp Gly Arg Ala Thr Lys Thr Leu Tyr
1 5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 275

Asp Gly Arg Asn Ala Leu Thr Gly Trp
1 5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 276

Asp Gly Arg Arg Gln Val Ile Gln Leu 1 5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Asp Gly Arg Val Tyr Gly Leu Ser Ser
1 5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Asp Gly Ser Gly Thr Val Ser Gly Trp
1 5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Asp Gly Thr Ala Ile Tyr Leu Ser Ser
1 5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Asp Gly Thr Ala Leu Met Leu Ser Ser
1 5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Asp Gly Thr Ala Ser Ile Ser Gly Trp
1 5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 282

Asp Gly Thr Ala Ser Thr Ser Gly Trp
1 5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

Asp Gly Thr Ala Ser Val Thr Gly Trp
1 5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

Asp Gly Thr Ala Thr Thr Met Gly Trp
1 5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Asp Gly Thr Ala Thr Thr Thr Gly Trp
1 5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Asp Gly Thr Ala Tyr Arg Leu Ser Ser
1 5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Asp Gly Thr Asp Lys Met Trp Ser Ile
1 5

<210> SEQ ID NO 288

<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Asp Gly Thr Gly Gly Ile Met Gly Trp
1 5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 289

Asp Gly Thr Gly Gly Ile Ser Gly Trp
1 5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 290

Asp Gly Thr Gly Gly Leu Ala Gly Trp
1 5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Asp Gly Thr Gly Gly Leu His Gly Trp
1 5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Asp Gly Thr Gly Gly Leu Gln Gly Trp
1 5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Asp Gly Thr Gly Gly Leu Ser Gly Trp
1 5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Asp Gly Thr Gly Gly Leu Thr Gly Trp
1 5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Asp Gly Thr Gly Gly Thr Ser Gly Trp
1 5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Asp Gly Thr Gly Gly Val His Gly Trp
1 5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Asp Gly Thr Gly Gly Val Met Gly Trp
1 5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Asp Gly Thr Gly Gly Val Ser Gly Trp
1 5

<210> SEQ ID NO 299
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 299

Asp Gly Thr Gly Gly Val Thr Gly Trp
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp Gly Thr Gly Gly Val Tyr Gly Trp
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Gly Thr Gly Asn Leu Gln Gly Trp
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Gly Thr Gly Asn Leu Ser Gly Trp
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asp Gly Thr Gly Asn Val Ser Gly Trp
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asp Gly Thr Gly Gln Leu Val Gly Trp
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 305

Asp Gly Thr Gly Gln Thr Ile Gly Trp
1 5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 306

Asp Gly Thr Gly Ser Gly Met Met Thr
1 5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 307

Asp Gly Thr Gly Ser Ile Ser Gly Trp
1 5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 308

Asp Gly Thr Gly Ser Leu Ala Gly Trp
1 5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 309

Asp Gly Thr Gly Ser Leu Asn Gly Trp
1 5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 310

Asp Gly Thr Gly Ser Leu Gln Gly Trp
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Asp Gly Thr Gly Ser Leu Ser Gly Trp
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Asp Gly Thr Gly Ser Leu Val Gly Trp
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp Gly Thr Gly Ser Thr Lys Gly Trp
1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asp Gly Thr Gly Ser Thr Met Gly Trp
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asp Gly Thr Gly Ser Thr Gln Gly Trp
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Asp Gly Thr Gly Ser Thr Ser Gly Trp
1 5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

Asp Gly Thr Gly Ser Val Met Gly Trp
1 5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Asp Gly Thr Gly Ser Val Thr Gly Trp
1 5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Asp Gly Thr Gly Thr Leu Ala Gly Trp
1 5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Asp Gly Thr Gly Thr Leu His Gly Trp
1 5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Asp Gly Thr Gly Thr Leu Lys Gly Trp
1 5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Asp Gly Thr Gly Thr Leu Ser Gly Trp
1 5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Asp Gly Thr Gly Thr Thr Leu Gly Trp
1 5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Asp Gly Thr Gly Thr Thr Met Gly Trp
1 5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Asp Gly Thr Gly Thr Thr Tyr Gly Trp
1 5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Asp Gly Thr Gly Thr Val His Gly Trp
1 5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Asp Gly Thr Gly Thr Val Gln Gly Trp
1 5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Asp Gly Thr Gly Thr Val Ser Gly Trp
1 5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Asp Gly Thr Gly Thr Val Thr Gly Trp
1 5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Asp Gly Thr His Ala Arg Leu Ser Ser
1 5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Asp Gly Thr His Ile Arg Ala Leu Ser
1 5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Asp Gly Thr His Ile Arg Leu Ala Ser
1 5

<210> SEQ ID NO 333
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 333

Asp Gly Thr His Leu Gln Pro Phe Arg
1 5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Asp Gly Thr His Ser Phe Tyr Asp Ala
1 5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Asp Gly Thr His Val Arg Ala Leu Ser
1 5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Asp Gly Thr His Val Tyr Met Ala Ser
1 5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Asp Gly Thr His Val Tyr Met Ser Ser
1 5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Asp Gly Thr Ile Ala Leu Pro Phe Lys
1 5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Asp Gly Thr Ile Ala Leu Pro Phe Arg
1 5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Asp Gly Thr Ile Ala Thr Arg Tyr Val
1 5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 341

Asp Gly Thr Ile Gly Tyr Ala Tyr Val
1 5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

Asp Gly Thr Ile Gln Ala Pro Phe Lys
1 5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

Asp Gly Thr Ile Arg Leu Pro Phe Lys
1 5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Asp Gly Thr Ile Ser Lys Glu Val Gly
1 5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Asp Gly Thr Lys Ser Leu Val Gln Leu
1 5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Asp Gly Thr Leu Ala Val Asn Phe Lys
1 5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Asp Gly Thr Leu Ala Tyr Pro Phe Lys
1 5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Asp Gly Thr Leu Glu Val His Phe Lys
1 5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

Asp Gly Thr Leu Ser Arg Thr Leu Trp
1 5

<210> SEQ ID NO 350
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

Asp Gly Thr Leu Ser Ser Pro Phe Arg
1 5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 351

Asp Gly Thr Leu Thr Val Pro Phe Arg
1 5

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 352

Asp Gly Thr Leu Val Ala Pro Phe Arg
1 5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 353

Asp Gly Thr Met Gln Leu Thr Gly Trp
1 5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 354

Asp Gly Thr Asn Ser Ile Ser Gly Trp
1 5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 355

Asp Gly Thr Asn Ser Leu Ser Gly Trp 1 5

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Asp Gly Thr Asn Ser Val Thr Gly Trp
1 5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Asp Gly Thr Asn Thr Leu Gly Gly Trp
1 5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

Asp Gly Thr Asn Tyr Arg Leu Ser Ser
1 5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Asp Gly Thr Gln Ala Leu Ser Gly Trp
1 5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Asp Gly Thr Gln Thr Thr Ser Gly Trp
1 5

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Asp Gly Thr Arg Ala Leu Thr Gly Trp
1 5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Asp Gly Thr Arg Phe Ser Leu Ser Ser
1 5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Asp Gly Thr Arg Gly Leu Ser Gly Trp
1 5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Asp Gly Thr Arg Ile Gly Leu Ser Ser
1 5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 365

Asp Gly Thr Arg Leu His Leu Ala Ser
1 5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Asp Gly Thr Arg Leu His Leu Ser Ser
1 5

<210> SEQ ID NO 367

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asp Gly Thr Arg Leu Leu Leu Ser Ser
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asp Gly Thr Arg Leu Met Leu Ser Ser
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Asp Gly Thr Arg Leu Asn Leu Ser Ser
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Asp Gly Thr Arg Met Val Val Gln Leu
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Asp Gly Thr Arg Ser Ile Thr Gly Trp
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asp Gly Thr Arg Ser Leu His Gly Trp
1 5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 373

Asp Gly Thr Arg Ser Thr Thr Gly Trp
1 5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Asp Gly Thr Arg Thr Val Thr Gly Trp
1 5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Asp Gly Thr Arg Thr Val Val Gln Leu
1 5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Asp Gly Thr Arg Val His Leu Ser Ser
1 5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 377

Asp Gly Thr Ser Gly Leu His Gly Trp
1 5

<210> SEQ ID NO 378
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 378

Asp Gly Thr Ser Ile His Leu Ser Ser
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Asp Gly Thr Ser Ile Met Leu Ser Ser
1               5

<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Asp Gly Thr Ser Asn Tyr Gly Ala Arg
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Asp Gly Thr Ser Ser Tyr Tyr Asp Ala
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Asp Gly Thr Ser Thr Ile Ser Gly Trp
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Asp Gly Thr Ser Thr Ile Thr Gly Trp
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 384

Asp Gly Thr Ser Thr Leu His Gly Trp
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 385

Asp Gly Thr Ser Thr Leu Arg Gly Trp
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 386

Asp Gly Thr Ser Thr Leu Ser Gly Trp
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 387

Asp Gly Thr Thr Ala Thr Tyr Tyr Lys
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Asp Gly Thr Thr Leu Ala Pro Phe Arg
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Asp Gly Thr Thr Ser Lys Thr Leu Trp
1 5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Asp Gly Thr Thr Ser Arg Thr Leu Trp
1 5

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Asp Gly Thr Thr Thr Arg Ser Leu Tyr
1 5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Asp Gly Thr Thr Thr Thr Thr Gly Trp
1 5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

Asp Gly Thr Thr Tyr Met Leu Ser Ser
1 5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 394

Asp Gly Thr Val Ala Asn Pro Phe Arg
1 5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Asp Gly Thr Val Asp Arg Pro Phe Lys
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Asp Gly Thr Val Ile Leu Leu Ser Ser
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Asp Gly Thr Val Ile Met Leu Ser Ser
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asp Gly Thr Val Leu His Leu Ser Ser
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Asp Gly Thr Val Leu Met Leu Ser Ser
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Asp Gly Thr Val Pro Tyr Leu Ala Ser
1               5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 401

Asp Gly Thr Val Pro Tyr Leu Ser Ser
1 5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 402

Asp Gly Thr Val Ser Met Pro Phe Lys
1 5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 403

Asp Gly Thr Val Ser Asn Pro Phe Arg
1 5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 404

Asp Gly Thr Val Ser Thr Arg Trp Val
1 5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 405

Asp Gly Thr Val Thr Thr Thr Gly Trp
1 5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 406

Asp Gly Thr Val Thr Val Thr Gly Trp
1 5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Asp Gly Thr Val Trp Val Pro Pro Arg
1 5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 408

Asp Gly Thr Val Tyr Arg Leu Ser Ser
1 5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Asp Gly Thr Tyr Ala Arg Leu Ser Ser
1 5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 410

Asp Gly Thr Tyr Gly Asn Lys Leu Trp
1 5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Asp Gly Thr Tyr Ile His Leu Ser Ser
1 5

<210> SEQ ID NO 412
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 412

Asp Gly Thr Tyr Ser Thr Ser Gly Trp
1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asp Gly Val Val Ala Leu Leu Ala Ser
1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Asp Gly Tyr Val Gly Val Gly Ser Leu
1               5

<210> SEQ ID NO 415
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
gaaacgaatt aaacggttta ttgattaaca atcgatta 38

<210> SEQ ID NO 416
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
cggtttattg attaacaatc gattacagat tacgagtcag gtatc 45

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Asp Gly Thr Leu Ala Val His Phe Lys
1               5

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Asp Gly Thr Phe Ala Val Pro Phe Lys
1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Glu Gly Thr Leu Ala Val Pro Phe Lys
1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Asp Gly Thr Met Ala Val Pro Phe Lys
1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Asp Gly Thr Leu Ala Val Thr Phe Lys
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Asp Gly Thr Leu Ala Val Pro Ile Lys
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Asp Gly Thr Leu Glu Val Thr Phe Lys
1 5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Glu Arg Thr Leu Ala Val Pro Phe Lys
1 5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Ser Gly Ser Leu Ala Val Pro Phe Lys
1 5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 426

Gly Gly Thr Arg Asn Thr Ala Pro Met
1 5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 427

Asp Gly Asn Ser Tyr Val Pro Pro Arg
1 5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 428

Ala Gln Ala Gly Val Ser Gly Gln Arg
1 5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 429

Ala Gln Ala Gly Asn Ser Asn Ala Val
1 5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 430

Ala Gln Trp Val Tyr Gly Gln Thr Val
1 5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 431

Asp Gly Thr Ser Phe Ser Pro Pro Lys
1 5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 432

Ala Gln Gly Leu Asp Leu Gly Arg Trp
1 5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 433

Ala Gln Val Met Ser Gly Val Gly Gln
1 5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 434

Asp Gly Thr His Gly Leu Arg Gly Trp
1 5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Ala Gln Arg Trp Ala Ala Asp Ser Ser
1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ala Gln Thr Gly Ala Ser Gly Ala Thr
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Ala Gln Leu Val Ala Gly Tyr Ser Gln
1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ala Gln Ser Leu Ala Arg Leu Phe Pro
1               5

<210> SEQ ID NO 439
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
cagagtgctc aggcacag                                                  18

<210> SEQ ID NO 440
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
cagagtgccc aagcgggtgc ggggtcggag cgggcacag 39

<210> SEQ ID NO 441
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 441
cagagtgccc aagatcagaa tccggggcgt tgggcacag 39

<210> SEQ ID NO 442
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 442
cagagtgccc aagagttgac gcgtccgttt ttggcacag 39

<210> SEQ ID NO 443
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 443
cagagtgccc aagaggtgcc tgggtatagg tgggcacag 39

<210> SEQ ID NO 444
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 444
cagagtgccc aatttcctac gaattatgat tctgcacag 39

<210> SEQ ID NO 445
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 445
cagagtgccc aatttgtggt tggtcagcag tatgcacag 39

<210> SEQ ID NO 446
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 446
cagagtgccc aaggggctag tccggggcgg tgggcacag 39

<210> SEQ ID NO 447
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 447
cagagtgccc aaggggagaa tccgggtagg tgggcacag 39

<210> SEQ ID NO 448
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 448
cagagtgccc aagggggaa tccgggtcgg tgggcacag 39

<210> SEQ ID NO 449
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 449
cagagtgccc aaggtggttc tacggggtcg aatgcacag 39

<210> SEQ ID NO 450
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 450
cagagtgccc aagggccgac taggccgttt ttggcacag 39

<210> SEQ ID NO 451
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 451
cagagtgccc aaggtcggga tggttgggcg gcggcacag 39

<210> SEQ ID NO 452
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 452
cagagtgccc aaggtcgtat gactgattcg caggcacag 39

<210> SEQ ID NO 453
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cagagtgccc aaggtagtga tgtggggcgg tgggcacag 39

<210> SEQ ID NO 454
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
cagagtgccc aaggtagtaa tccggggagg tgggcacag 39

<210> SEQ ID NO 455
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
cagagtgccc aagggtctaa ttcgcctcag gtggcacag 39

<210> SEQ ID NO 456
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
cagagtgccc aaggttcgtg gaatccgccg gcggcacag 39

<210> SEQ ID NO 457
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
cagagtgccc aaggtacttg gaatccgccg gctgcacag 39

<210> SEQ ID NO 458
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
cagagtgccc aaggtgtttt tattccgccg aaggcacag 39

<210> SEQ ID NO 459
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 459
cagagtgccc aacatgtgaa tgcttctcag tctgcacag 39

<210> SEQ ID NO 460
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 460
cagagtgccc aaattaaggc ggggtgggcg caggcacag 39

<210> SEQ ID NO 461
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 461
cagagtgccc aaattatgag tgggtatgct caggcacag 39

<210> SEQ ID NO 462
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 462
cagagtgccc aaaagagtgt gggtagtgtt tatgcacag 39

<210> SEQ ID NO 463
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 463
cagagtgccc aacttgagca tgggtttgct caggcacag 39

<210> SEQ ID NO 464
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 464
cagagtgccc aactgggtgg ggtgttgagt gctgcacag 39

<210> SEQ ID NO 465
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 465
cagagtgccc aactggggct ttcgcagggg cgggcacag 39

<210> SEQ ID NO 466
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 466
cagagtgccc aattggggta tgggtttgct caggcacag 39

<210> SEQ ID NO 467
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 467
cagagtgccc aattgaagta tggtcttgcg caggcacag 39

<210> SEQ ID NO 468
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 468
cagagtgccc aacttcggat tggttttgct caggcacag 39

<210> SEQ ID NO 469
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 469
cagagtgccc aattgcgtat gggttatagt caggcacag 39

<210> SEQ ID NO 470
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 470
cagagtgccc aactgaggca ggggtatgct caggcacag 39

<210> SEQ ID NO 471

<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 471
cagagtgccc aattgcgtgt tggttttgcg caggcacag 39

<210> SEQ ID NO 472
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 472
cagagtgccc aactgtcgtg tcggagtcag atggcacag 39

<210> SEQ ID NO 473
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
cagagtgccc aattgacgta tagtcagtcg ctggcacag 39

<210> SEQ ID NO 474
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 474
cagagtgccc aactgtataa gggttatagt caggcacag 39

<210> SEQ ID NO 475
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 475
cagagtgccc aaatgcctca gcggccgttt ttggcacag 39

<210> SEQ ID NO 476
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476
cagagtgccc aaaatggtaa tccggggcgg tgggcacag 39

<210> SEQ ID NO 477
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
cagagtgccc aacctgaggg tagtgcgagg tgggcacag 39

<210> SEQ ID NO 478
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 478
cagagtgccc aaccgttggc tgtttatggg gcggcacag 39

<210> SEQ ID NO 479
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 479
cagagtgccc aaccgcagtc gtcgtcgatg agtgcacag 39

<210> SEQ ID NO 480
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 480
cagagtgccc aaccgagtgt gggtgggtat tgggcacag 39

<210> SEQ ID NO 481
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 481
cagagtgccc aacaggctgt gggtcagtct tgggcacag 39

<210> SEQ ID NO 482
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 482
cagagtgccc aacagcgttc gctggcttcg ggtgcacag 39

<210> SEQ ID NO 483
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 483
cagagtgccc aacaggtgat gaatagtcag ggggcacag 39

<210> SEQ ID NO 484
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 484
cagagtgccc aacgtggggt tgggttgagt caggcacag 39

<210> SEQ ID NO 485
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 485
cagagtgccc aaaggcatga tgcggagggt agtgcacag 39

<210> SEQ ID NO 486
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 486
cagagtgccc aacgtaaggg ggagcctcat tatgcacag 39

<210> SEQ ID NO 487
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 487
cagagtgccc aaaggtatac gggggattct agtgcacag 39

<210> SEQ ID NO 488
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 488
cagagtgccc aatcggcgat ggctgcgaag ggtgcacag 39

<210> SEQ ID NO 489
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 489
cagagtgccc aatctggggg tcttacgggg agtgcacag 39

<210> SEQ ID NO 490
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 490
cagagtgccc aatcgggtgg ggtggggcag gtggcacag 39

<210> SEQ ID NO 491
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 491
cagagtgccc aatctctggc gacgcctttt cgtgcacag 39

<210> SEQ ID NO 492
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 492
cagagtgccc aaagtatgtc gcgtccgttt ctggcacag 39

<210> SEQ ID NO 493
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 493
cagagtgccc aaagtcagct taggccgttt cttgcacag 39

<210> SEQ ID NO 494
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 494
cagagtgccc aatctgtggc taagcctttt ttggcacag 39

<210> SEQ ID NO 495
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 495
cagagtgccc aatcggtttc gcagccgttt agggcacag 39

<210> SEQ ID NO 496
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
cagagtgccc aatctgtggt gcgtcctttt ctggcacag 39

<210> SEQ ID NO 497
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
cagagtgccc aaactgcgct ttcgtcgtcg acggcacag 39

<210> SEQ ID NO 498
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
cagagtgccc aaacggagat gggtgggagg tgtgcacag 39

<210> SEQ ID NO 499
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
cagagtgccc aaacggggtt tgctccgccg cgtgcacag 39

<210> SEQ ID NO 500
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
cagagtgccc aaacgattcg ggggtattcg tctgcacag 39

<210> SEQ ID NO 501
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 501
cagagtgccc aaactatttc taattatcat acggcacag 39

<210> SEQ ID NO 502
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
cagagtgccc aaactttggc gcgtccgttt gtggcacag 39

<210> SEQ ID NO 503
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
cagagtgccc aaactttggc ggtgcctttt aaggcacag 39

<210> SEQ ID NO 504
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
cagagtgccc aaactcctga tcgtccttgg ttggcacag 39

<210> SEQ ID NO 505
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
cagagtgccc aaactcgggc tgggtatgct caggcacag 39

<210> SEQ ID NO 506
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 506
cagagtgccc aaactagggc ggggtattct caggcacag 39

<210> SEQ ID NO 507
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 507
cagagtgccc aaacgcgtga gtatctgctg ggggcacag 39

<210> SEQ ID NO 508
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
cagagtgccc aaacttctgc gaagccgttt cttgcacag 39

<210> SEQ ID NO 509
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 509
cagagtgccc aaacttctgc taggcctttt ctggcacag 39

<210> SEQ ID NO 510
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
cagagtgccc aaactactga taggcctttt ttggcacag 39

<210> SEQ ID NO 511
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 511
cagagtgccc aaacgactga gaagccgtgg ctggcacag 39

<210> SEQ ID NO 512
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 512
cagagtgccc aaacggttgc gcggcctttt tatgcacag 39

<210> SEQ ID NO 513
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 513
cagagtgccc aaactgttgc tacgccgttt agggcacag 39

<210> SEQ ID NO 514
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 514
cagagtgccc aaacggtgac gcagttgttt aaggcacag 39

<210> SEQ ID NO 515
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 515
cagagtgccc aagttcatgt tgggagtgtt tatgcacag 39

<210> SEQ ID NO 516
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 516
cagagtgccc aagttcttgc tgggtataat atggcacag 39

<210> SEQ ID NO 517
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 517
cagagtgccc aagtttctga ggcgagggtt agggcacag 39

<210> SEQ ID NO 518
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
cagagtgccc aagttgtggt gggttatagt caggcacag 39

<210> SEQ ID NO 519
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 519
cagagtgccc aatgggctgc tgggtataat gtggcacag 39

<210> SEQ ID NO 520
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 520
cagagtgccc aatgggagct gagtaatggg tatgcacag 39

<210> SEQ ID NO 521
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 521
cagagtgccc aatgggaggt gaagggggt tatgcacag 39

<210> SEQ ID NO 522
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 522
cagagtgccc aatgggaggt gaagcggggg tatgcacag 39

<210> SEQ ID NO 523
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 523
cagagtgccc aatgggaggt tcagtctggg tttgcacag 39

<210> SEQ ID NO 524
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 524
cagagtgccc aatgggaggt tcgtggtggt tatgcacag 39

<210> SEQ ID NO 525
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 525
cagagtgccc aatgggaggt gacgagtggt tgggcacag 39

<210> SEQ ID NO 526
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 526
cagagtgccc aatggggggc gccgagtcat ggggcacag 39

<210> SEQ ID NO 527
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 527
cagagtgccc aatggatgga gcttggtagt tcggcacag 39

<210> SEQ ID NO 528
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 528
cagagtgccc aatggatgtt tgggggtagt ggggcacag 39

<210> SEQ ID NO 529
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
cagagtgccc aatggatgct ggggggggcg caggcacag 39

<210> SEQ ID NO 530
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
cagagtgccc aatggccgac tgcttatgat gcggcacag 39

<210> SEQ ID NO 531
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 531
cagagtgccc aatggcctac gagttatgat gctgcacag 39

<210> SEQ ID NO 532
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 532
cagagtgccc aatggcaggt tcagacgggg tttgcacag 39

<210> SEQ ID NO 533
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
cagagtgccc aatggtcgac tgagggtggg tatgcacag 39

<210> SEQ ID NO 534
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
cagagtgccc aatggactgc tgcgggtggt tatgcacag 39

<210> SEQ ID NO 535
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 535
cagagtgccc aatggacgac ggagtcgggt tatgcacag 39

<210> SEQ ID NO 536
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 536
cagagtgccc aatgggttta tgggagttcg catgcacag 39

<210> SEQ ID NO 537
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 537
cagagtgccc aatatttggc ggggtatacg gtggcacag 39

<210> SEQ ID NO 538
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 538
cagagtgccc aatatctgaa ggggtattct gtggcacag 39

<210> SEQ ID NO 539
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 539
cagagtgccc aatatttgtc gggttataat acggcacag 39

<210> SEQ ID NO 540
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 540
cagagtgatg gcgctgcggc gactactggg tgggcacag 39

<210> SEQ ID NO 541
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 541
cagagtgatg gcgcgggtgg gacgagtggt tgggcacag 39

<210> SEQ ID NO 542
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
cagagtgatg gcgcgggtac tacttcgggt tgggcacag 39

<210> SEQ ID NO 543
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 543
cagagtgatg gcgctcatgg gctgtcgggg tgggcacag 39

<210> SEQ ID NO 544
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 544
cagagtgatg gcgctcatgt tgggctgtcg tcggcacag 39

<210> SEQ ID NO 545
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 545
cagagtgatg gcgctcggac ggtgcttcag ttggcacag 39

<210> SEQ ID NO 546
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 546
cagagtgatg gcgagtatca gaagccgttt agggcacag 39

<210> SEQ ID NO 547
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 547
cagagtgatg gcggtgggac tacgacgggg tgggcacag 39

<210> SEQ ID NO 548
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 548
cagagtgatg gccatgcgac gagtatgggt tgggcacag 39

<210> SEQ ID NO 549
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 549
cagagtgatg gcaagggttc gacgcagggg tgggcacag 39

<210> SEQ ID NO 550

<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 550
cagagtgatg gcaagcagta tcagctgtct tcggcacag 39

<210> SEQ ID NO 551
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 551
cagagtgatg gcaatggtgg gttgaagggg tgggcacag 39

<210> SEQ ID NO 552
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 552
cagagtgatg gccagggggg tttgtctggg tgggcacag 39

<210> SEQ ID NO 553
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 553
cagagtgatg gccagcattt tgctccgccg cgggcacag 39

<210> SEQ ID NO 554
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 554
cagagtgatg gccgtgcgac taagacgctt tatgcacag 39

<210> SEQ ID NO 555
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 555
cagagtgatg gccgtaatgc gttgacgggg tgggcacag 39

<210> SEQ ID NO 556
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
cagagtgatg gcaggaggca ggtgattcag ctggcacag 39

<210> SEQ ID NO 557
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 557
cagagtgatg gcagggttta tggtctttcg tcggcacag 39

<210> SEQ ID NO 558
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
cagagtgatg gcagtgggcg tacgacgggt tgggcacag 39

<210> SEQ ID NO 559
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 559
cagagtgatg gctctggtac gacgcggggt tgggcacag 39

<210> SEQ ID NO 560
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 560
cagagtgatg gctcgggtac ggttagtggg tgggcacag 39

<210> SEQ ID NO 561
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 561
cagagtgatg gcagtccgga gaagccgttt cgggcacag 39

<210> SEQ ID NO 562
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 562
cagagtgatg gcagtcagtc tactacgggg tgggcacag 39

<210> SEQ ID NO 563
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 563
cagagtgatg gcagtagttt ttatcctcct aaggcacag 39

<210> SEQ ID NO 564
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 564
cagagtgatg gcagtagttc ttattatgat gcggcacag 39

<210> SEQ ID NO 565
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 565
cagagtgatg gctctacgga gaggccgttt agggcacag 39

<210> SEQ ID NO 566
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 566
cagagtgatg gcaccgcggc tcggctgtcg tcggcacag 39

<210> SEQ ID NO 567
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 567
cagagtgatg gcaccgctga taagccgttt cgggcacag 39

<210> SEQ ID NO 568
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
cagagtgatg gcacggcgga tcgtcctttt cgggcacag 39

<210> SEQ ID NO 569
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
cagagtgatg gcaccgcgga gaggcctttt agggcacag 39

<210> SEQ ID NO 570
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
cagagtgatg gcaccgcgat tcatctttcg tctgcacag 39

<210> SEQ ID NO 571
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
cagagtgatg gcaccgcgat ttatctgtct tctgcacag 39

<210> SEQ ID NO 572
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
cagagtgatg gcaccgctct tatgttgtcg tctgcacag 39

<210> SEQ ID NO 573
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
cagagtgatg gcaccgcgag tattagtggt tgggcacag 39

<210> SEQ ID NO 574
<211> LENGTH: 39
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 574
cagagtgatg gcaccgcgtc gacgagtggg tgggcacag 39

<210> SEQ ID NO 575
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 575
cagagtgatg gcaccgcgtc ggtgacgggg tgggcacag 39

<210> SEQ ID NO 576
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 576
cagagtgatg gcaccgcgag ttattatgat tctgcacag 39

<210> SEQ ID NO 577
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 577
cagagtgatg gcaccgcgac gacgatgggg tgggcacag 39

<210> SEQ ID NO 578
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 578
cagagtgatg gcaccgcgac gacgacgggt tgggcacag 39

<210> SEQ ID NO 579
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 579
cagagtgatg gcaccgcgta tcgtttgtcg tctgcacag 39

<210> SEQ ID NO 580
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 580
cagagtgatg gcaccgataa gatgtggagt attgcacag 39

<210> SEQ ID NO 581
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 581
cagagtgatg gcaccggtgg tattaagggg tgggcacag 39

<210> SEQ ID NO 582
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 582
cagagtgatg gcaccggggg gattatgggt tgggcacag 39

<210> SEQ ID NO 583
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 583
cagagtgatg gcaccggtgg gatttcgggg tgggcacag 39

<210> SEQ ID NO 584
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 584
cagagtgatg gcaccggggg tcttgctggt tgggcacag 39

<210> SEQ ID NO 585
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 585
cagagtgatg gcaccggggg gttgcatggt tgggcacag 39

<210> SEQ ID NO 586
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 586
cagagtgatg gcaccggggg tttgcagggt tgggcacag 39

<210> SEQ ID NO 587
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 587
cagagtgatg gcaccggggg tttgcgtggt tgggcacag 39

<210> SEQ ID NO 588
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 588
cagagtgatg gcaccggtgg gttgtcgggt tgggcacag 39

<210> SEQ ID NO 589
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 589
cagagtgatg gcaccggggg gttgacgggt tgggcacag 39

<210> SEQ ID NO 590
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 590
cagagtgatg gcaccggtgg gactaagggt tgggcacag 39

<210> SEQ ID NO 591
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 591
cagagtgatg gcaccggggg gacgagtggt tgggcacag 39

<210> SEQ ID NO 592
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 592
cagagtgatg gcaccggtgg ggtgcatggt tgggcacag 39

<210> SEQ ID NO 593
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 593
cagagtgatg gcaccggtgg tgttatgggg tgggcacag 39

<210> SEQ ID NO 594
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 594
cagagtgatg gcaccggggg ggtgtctggt tgggcacag 39

<210> SEQ ID NO 595
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 595
cagagtgatg gcaccggtgg tgtgacgggg tgggcacag 39

<210> SEQ ID NO 596
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 596
cagagtgatg gcaccggtgg tgtgtatggg tgggcacag 39

<210> SEQ ID NO 597
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 597
cagagtgatg gcaccggtaa tttgcagggt tgggcacag 39

<210> SEQ ID NO 598
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 598
cagagtgatg gcaccgggaa tcttaggggg tgggcacag 39

<210> SEQ ID NO 599
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 599
cagagtgatg gcaccgggaa tttgagtggg tgggcacag 39

<210> SEQ ID NO 600
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 600
cagagtgatg gcaccgggaa tactcatggg tgggcacag 39

<210> SEQ ID NO 601
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 601
cagagtgatg gcaccgggaa tactcggggg tgggcacag 39

<210> SEQ ID NO 602
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 602
cagagtgatg gcaccggtaa tactagtggt tgggcacag 39

<210> SEQ ID NO 603
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 603
cagagtgatg gcaccgggaa tgtgtcgggg tgggcacag 39

<210> SEQ ID NO 604
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 604
cagagtgatg gcaccggtaa tgtgacgggg tgggcacag 39

<210> SEQ ID NO 605
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 605
cagagtgatg gcaccgggca gcttgtgggt tgggcacag 39

<210> SEQ ID NO 606
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 606
cagagtgatg gcaccggtca gacgattggt tgggcacag 39

<210> SEQ ID NO 607
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 607
cagagtgatg gcaccgggca ggtgactggg tgggcacag 39

<210> SEQ ID NO 608
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 608
cagagtgatg gcaccggtcg gttgacgggt tgggcacag 39

<210> SEQ ID NO 609
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 609
cagagtgatg gcaccggtcg gactgttggg tgggcacag 39

<210> SEQ ID NO 610
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 610
cagagtgatg gcaccggttc gggtatgatg acggcacag 39

<210> SEQ ID NO 611
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 611
cagagtgatg gcaccgggtc gattagtggg tgggcacag 39

<210> SEQ ID NO 612
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 612
cagagtgatg gcaccggttc tttggcgggg tgggcacag 39

<210> SEQ ID NO 613
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 613
cagagtgatg gcaccgggtc tttgaatggg tgggcacag 39

<210> SEQ ID NO 614
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 614
cagagtgatg gcaccgggtc gctgcagggt tgggcacag 39

<210> SEQ ID NO 615
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 615
cagagtgatg gcaccgggag tctgtcgggg tgggcacag 39

<210> SEQ ID NO 616
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 616
cagagtgatg gcaccgggtc gttggtgggt tgggcacag 39

<210> SEQ ID NO 617
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 617
cagagtgatg gcaccgggag tacgcatggg tgggcacag 39

<210> SEQ ID NO 618
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 618
cagagtgatg gcaccgggag tactaagggg tgggcacag 39

<210> SEQ ID NO 619
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 619
cagagtgatg gcaccggttc tactatgggt tgggcacag 39

<210> SEQ ID NO 620
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 620
cagagtgatg gcaccggtag tacgcagggt tgggcacag 39

<210> SEQ ID NO 621
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 621
cagagtgatg gcaccgggag tacttcgggg tgggcacag 39

<210> SEQ ID NO 622
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 622
cagagtgatg gcaccgggag tacgacgggg tgggcacag 39

<210> SEQ ID NO 623
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 623
cagagtgatg gcaccggttc ggttatgggg tgggcacag 39

<210> SEQ ID NO 624
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 624
cagagtgatg gcaccgggtc tgtgactggg tgggcacag 39

<210> SEQ ID NO 625
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 625
cagagtgatg gcaccgggac gcttgcgggg tgggcacag 39

<210> SEQ ID NO 626
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 626
cagagtgatg gcaccggtac tttgcatggt tgggcacag 39

<210> SEQ ID NO 627
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 627
cagagtgatg gcaccggtac tcttaagggt tgggcacag 39

<210> SEQ ID NO 628
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 628
cagagtgatg gcaccgggac tctgtcgggt tgggcacag 39

<210> SEQ ID NO 629

<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 629
cagagtgatg gcaccgggac tacgctgggg tgggcacag 39

<210> SEQ ID NO 630
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 630
cagagtgatg gcaccgggac tactatgggt tgggcacag 39

<210> SEQ ID NO 631
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 631
cagagtgatg gcaccgggac tactacgggg tgggcacag 39

<210> SEQ ID NO 632
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 632
cagagtgatg gcaccggtac tacggtgggg tgggcacag 39

<210> SEQ ID NO 633
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 633
cagagtgatg gcaccgggac gacgtatggt tgggcacag 39

<210> SEQ ID NO 634
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 634
cagagtgatg gcaccggtac ggttcatggt tgggcacag 39

<210> SEQ ID NO 635
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 635
cagagtgatg gcaccgggac tgtgcagggg tgggcacag 39

<210> SEQ ID NO 636
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 636
cagagtgatg gcaccggtac tgtttctggt tgggcacag 39

<210> SEQ ID NO 637
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 637
cagagtgatg gcaccggtac tgttactggg tgggcacag 39

<210> SEQ ID NO 638
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 638
cagagtgatg gcacccatgc gaggttgtct tcggcacag 39

<210> SEQ ID NO 639
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 639
cagagtgatg gcacccatgc ttatatggcg tctgcacag 39

<210> SEQ ID NO 640
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 640
cagagtgatg gcacccattt tgcgccgccg cgtgcacag 39

<210> SEQ ID NO 641
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 641
cagagtgatg gcacccatat tcatctgagt agtgcacag 39

<210> SEQ ID NO 642
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 642
cagagtgatg gcacccatat tagggctctg agtgcacag 39

<210> SEQ ID NO 643
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 643
cagagtgatg gcacccatat tcgtttggcg agtgcacag 39

<210> SEQ ID NO 644
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 644
cagagtgatg gcacccatct gcagccgttt agggcacag 39

<210> SEQ ID NO 645
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 645
cagagtgatg gcacccatag tttttatgat gcggcacag 39

<210> SEQ ID NO 646
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 646
cagagtgatg gcacccattc tactacgggt tgggcacag 39

<210> SEQ ID NO 647
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
cagagtgatg gcacccatac gcggacgggt tgggcacag 39

<210> SEQ ID NO 648
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
cagagtgatg gcacccatgt tagggcgttg tcggcacag 39

<210> SEQ ID NO 649
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
cagagtgatg gcacccatgt ttatatggct agtgcacag 39

<210> SEQ ID NO 650
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
cagagtgatg gcacccatgt gtatatgtct agtgcacag 39

<210> SEQ ID NO 651
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
cagagtgatg gcaccattgc gcttccgttt aaggcacag 39

<210> SEQ ID NO 652
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
cagagtgatg gcaccattgc tttgccgttt agggcacag 39

<210> SEQ ID NO 653
<211> LENGTH: 39
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 653
cagagtgatg gcaccattgc gacgcggtat gtggcacag 39

<210> SEQ ID NO 654
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 654
cagagtgatg gcaccattga gcggcctttt cgtgcacag 39

<210> SEQ ID NO 655
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 655
cagagtgatg gcaccattgg ttatgcgtat gttgcacag 39

<210> SEQ ID NO 656
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 656
cagagtgatg gcaccattca ggctccgttt aaggcacag 39

<210> SEQ ID NO 657
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 657
cagagtgatg gcaccattcg tcttcctttt aaggcacag 39

<210> SEQ ID NO 658
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 658
cagagtgatg gcaccatttc taaggaggtg ggggcacag 39

<210> SEQ ID NO 659
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 659
cagagtgatg gcaccatttc gcagcctttt aaggcacag 39

<210> SEQ ID NO 660
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 660
cagagtgatg gcaccaagat tcagctgtct agtgcacag 39

<210> SEQ ID NO 661
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 661
cagagtgatg gcaccaagat tcggttgtcg tctgcacag 39

<210> SEQ ID NO 662
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 662
cagagtgatg gcaccaagct gatgttgagt agtgcacag 39

<210> SEQ ID NO 663
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 663
cagagtgatg gcaccaagtt gaggcttagt tctgcacag 39

<210> SEQ ID NO 664
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 664
cagagtgatg gcaccaagat ggtgttgcag ctggcacag 39

<210> SEQ ID NO 665
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 665
cagagtgatg gcaccaagag tcttgtgcag cttgcacag 39

<210> SEQ ID NO 666
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 666
cagagtgatg gcaccaaggt gctggtgcag ttggcacag 39

<210> SEQ ID NO 667
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 667
cagagtgatg gcaccttggc tgctcctttt aaggcacag 39

<210> SEQ ID NO 668
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 668
cagagtgatg ggactttggc ggtgaatttt aaggcacag 39

<210> SEQ ID NO 669
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 669
cagagtgatg ggactttggc ggtgcctttt aaggcacag 39

<210> SEQ ID NO 670
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 670
cagagtgatg gcacccttgc gtatcctttt aaggcacag 39

<210> SEQ ID NO 671
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 671
cagagtgatg gcaccctgga gaggccgttt cgggcacag 39

<210> SEQ ID NO 672
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 672
cagagtgatg ggactttgga ggtgcatttt aaggcacag 39

<210> SEQ ID NO 673
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 673
cagagtgatg gcaccttgct gaggctgagt agtgcacag 39

<210> SEQ ID NO 674
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 674
cagagtgatg gcaccttgaa taatccgttt agggcacag 39

<210> SEQ ID NO 675
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 675
cagagtgatg gcaccttgca gcagccgttt cgggcacag 39

<210> SEQ ID NO 676
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 676
cagagtgatg gcaccctgtc tcagcctttt agggcacag 39

<210> SEQ ID NO 677
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 677
cagagtgatg gcaccttgtc gcgtacgctt tgggcacag 39

<210> SEQ ID NO 678
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 678
cagagtgatg gcaccctgtc tagtccgttt agggcacag 39

<210> SEQ ID NO 679
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 679
cagagtgatg gcaccttgac ggttcctttt cgggcacag 39

<210> SEQ ID NO 680
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 680
cagagtgatg gcacccttgt tgcgccgttt agggcacag 39

<210> SEQ ID NO 681
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 681
cagagtgatg gcacgatgga taagcctttt agggcacag 39

<210> SEQ ID NO 682
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 682
cagagtgatg gcaccatgga taggccgttt aaggcacag 39

<210> SEQ ID NO 683
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 683
cagagtgatg gcaccatgtt gcgtcttagt tcggcacag 39

<210> SEQ ID NO 684
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 684
cagagtgatg gcaccatgca gcttacgggg tgggcacag 39

<210> SEQ ID NO 685
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 685
cagagtgatg gcaccaatgg tctgaagggg tgggcacag 39

<210> SEQ ID NO 686
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 686
cagagtgatg gcaccaatag tattagtggg tgggcacag 39

<210> SEQ ID NO 687
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 687
cagagtgatg gcaccaattc tctgtcgggt tgggcacag 39

<210> SEQ ID NO 688
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 688
cagagtgatg gcaccaattc tacgacgggt tgggcacag 39

<210> SEQ ID NO 689
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 689
cagagtgatg gcaccaatag tgttacgggt tgggcacag 39

<210> SEQ ID NO 690
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 690
cagagtgatg gcaccaatac tattaatggg tgggcacag 39

<210> SEQ ID NO 691
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 691
cagagtgatg gcaccaatac gttggggggg tgggcacag 39

<210> SEQ ID NO 692
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 692
cagagtgatg gcaccaatac tactcatggg tgggcacag 39

<210> SEQ ID NO 693
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 693
cagagtgatg gcaccaatta taggctgtcg agtgcacag 39

<210> SEQ ID NO 694
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 694
cagagtgatg gcacccaggc gctgtcgggg tgggcacag 39

<210> SEQ ID NO 695
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 695
cagagtgatg gcacccagtt taggttgtct tcggcacag 39

<210> SEQ ID NO 696
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 696
cagagtgatg gcacccagtt tagtcctccg cgtgcacag 39

<210> SEQ ID NO 697
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 697
cagagtgatg gcacccaggg gctgaagggg tgggcacag 39

<210> SEQ ID NO 698
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 698
cagagtgatg gcacccagac tacgagtggg tgggcacag 39

<210> SEQ ID NO 699
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 699
cagagtgatg gcaccagggc tcttacgggt tgggcacag 39

<210> SEQ ID NO 700
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 700
cagagtgatg gcacccggtt ttcgctttcg agtgcacag 39

<210> SEQ ID NO 701
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 701
cagagtgatg gcaccagggg gttgtcgggg tgggcacag 39

<210> SEQ ID NO 702
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
cagagtgatg gcaccaggat tgggctgagt agtgcacag 39

<210> SEQ ID NO 703
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
cagagtgatg gcaccaggct tcatctggcg agtgcacag 39

<210> SEQ ID NO 704
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
cagagtgatg gcaccaggct tcatctgtcg tcggcacag 39

<210> SEQ ID NO 705
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
cagagtgatg gcacccgttt gctgctgtcg agtgcacag 39

<210> SEQ ID NO 706
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
cagagtgatg gcacccgttt gatgctttct agtgcacag 39

<210> SEQ ID NO 707
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
cagagtgatg gcacccgttt gaatcttagt tcggcacag 39

<210> SEQ ID NO 708

<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 708
cagagtgatg gcacccggat ggttgttcag cttgcacag 39

<210> SEQ ID NO 709
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 709
cagagtgatg gcacccgtaa tatgtatgag ggggcacag 39

<210> SEQ ID NO 710
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 710
cagagtgatg gcaccaggag tattacgggg tgggcacag 39

<210> SEQ ID NO 711
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 711
cagagtgatg gcaccaggag tttgcatggg tgggcacag 39

<210> SEQ ID NO 712
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 712
cagagtgatg gcacccggag tactacgggt tgggcacag 39

<210> SEQ ID NO 713
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 713
cagagtgatg gcacccgtac tacgacgggt tgggcacag 39

<210> SEQ ID NO 714
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 714
cagagtgatg gcacccggac ggtgactggt tgggcacag 39

<210> SEQ ID NO 715
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 715
cagagtgatg gcacccgtac tgtggtgcag ttggcacag 39

<210> SEQ ID NO 716
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 716
cagagtgatg gcacccgggt gcatctttct agtgcacag 39

<210> SEQ ID NO 717
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 717
cagagtgatg gcacctcgtt tccgtatgct cgggcacag 39

<210> SEQ ID NO 718
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 718
cagagtgatg gcacctcgtt tacgccgcct aaggcacag 39

<210> SEQ ID NO 719
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 719
cagagtgatg gcacctcgtt tactccgccg cgggcacag 39

<210> SEQ ID NO 720
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 720
cagagtgatg gcacctctgg gttgcatggg tgggcacag 39

<210> SEQ ID NO 721
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 721
cagagtgatg gcaccagtgg gcttaagggg tgggcacag 39

<210> SEQ ID NO 722
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 722
cagagtgatg gcacctcgat tcatttgagt agtgcacag 39

<210> SEQ ID NO 723
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 723
cagagtgatg gcacctcgat tatgttgagt tctgcacag 39

<210> SEQ ID NO 724
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 724
cagagtgatg gcacctcttt gcggctttct tctgcacag 39

<210> SEQ ID NO 725
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 725
cagagtgatg gcacctctaa ttatggggcg cgggcacag 39

<210> SEQ ID NO 726
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 726
cagagtgatg gcaccagttc gtattatgat gcggcacag 39

<210> SEQ ID NO 727
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 727
cagagtgatg gcacctcgag ttattatgat tctgcacag 39

<210> SEQ ID NO 728
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 728
cagagtgatg gcacctctac gatttctggt tgggcacag 39

<210> SEQ ID NO 729
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 729
cagagtgatg gcaccagtac tattacgggt tgggcacag 39

<210> SEQ ID NO 730
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 730
cagagtgatg gcacctcgac gttgcatggg tgggcacag 39

<210> SEQ ID NO 731
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 731
cagagtgatg gcacctctac tctgcgtggg tgggcacag 39

<210> SEQ ID NO 732
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 732
cagagtgatg gcacctcgac gctgtcgggg tgggcacag 39

<210> SEQ ID NO 733
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
cagagtgatg gcacctctta tgtgccgccg aaggcacag 39

<210> SEQ ID NO 734
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
cagagtgatg gcaccagtta tgtgccgcct cgggcacag 39

<210> SEQ ID NO 735
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
cagagtgatg gcaccacggc gacttattat aaggcacag 39

<210> SEQ ID NO 736
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
cagagtgatg gcaccacttt tactcctcct cgggcacag 39

<210> SEQ ID NO 737
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
cagagtgatg gcaccactct ggctcctttt agggcacag 39

<210> SEQ ID NO 738
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 738
cagagtgatg gcaccacttt ggttccgccg cgtgcacag 39

<210> SEQ ID NO 739
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 739
cagagtgatg gcaccacgag taagacgctt tgggcacag 39

<210> SEQ ID NO 740
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 740
cagagtgatg gcaccacttc taggactttg tgggcacag 39

<210> SEQ ID NO 741
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 741
cagagtgatg gcaccacgac tcgtagtttg tatgcacag 39

<210> SEQ ID NO 742
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 742
cagagtgatg gcaccactac gactacgggt tgggcacag 39

<210> SEQ ID NO 743
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 743
cagagtgatg gcaccactac gtatggggct cgtgcacag 39

<210> SEQ ID NO 744
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 744
cagagtgatg gcaccacttg gacgccgccg cgtgcacag 39

<210> SEQ ID NO 745
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 745
cagagtgatg gcaccacgta tatgcttagt agtgcacag 39

<210> SEQ ID NO 746
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 746
cagagtgatg gcaccacgta tgttcctccg cgggcacag 39

<210> SEQ ID NO 747
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 747
cagagtgatg gcaccgtggc gaatcctttt cgggcacag 39

<210> SEQ ID NO 748
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 748
cagagtgatg gcaccgtgga tcggcctttt aaggcacag 39

<210> SEQ ID NO 749
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 749
cagagtgatg gcaccgttat tcatctgagt agtgcacag 39

<210> SEQ ID NO 750
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 750
cagagtgatg gcaccgttat tctgttgtcg agtgcacag 39

<210> SEQ ID NO 751
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 751
cagagtgatg gcaccgtgat tatgctgtcg agtgcacag 39

<210> SEQ ID NO 752
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 752
cagagtgatg gcaccgtgct tcatttgtcg tctgcacag 39

<210> SEQ ID NO 753
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 753
cagagtgatg gcaccgtttt gatgctgagt agtgcacag 39

<210> SEQ ID NO 754
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 754
cagagtgatg gcaccgtgtt ggtgccgttt agggcacag 39

<210> SEQ ID NO 755
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 755
cagagtgatg gcaccgttcc gtatcttgct tctgcacag 39

<210> SEQ ID NO 756
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 756
cagagtgatg gcaccgtgcc gtatttgtct tcggcacag 39

<210> SEQ ID NO 757
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 757
cagagtgatg gcaccgttcg tgtgccgttt agggcacag 39

<210> SEQ ID NO 758
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 758
cagagtgatg gcaccgtgtc gatgccgttt aaggcacag 39

<210> SEQ ID NO 759
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 759
cagagtgatg gcaccgtgtc taatccgttt agggcacag 39

<210> SEQ ID NO 760
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 760
cagagtgatg gcaccgtttc tacgcgttgg gtggcacag 39

<210> SEQ ID NO 761
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 761
cagagtgatg gcaccgtgac gacgactggg tgggcacag 39

<210> SEQ ID NO 762
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 762
cagagtgatg gcaccgtgac ggttacgggg tgggcacag 39

<210> SEQ ID NO 763
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 763
cagagtgatg gcaccgtttg ggtgcctcct agggcacag 39

<210> SEQ ID NO 764
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 764
cagagtgatg gcaccgttta taggttgtcg agtgcacag 39

<210> SEQ ID NO 765
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 765
cagagtgatg gcacctatgc gcgtttgtct tctgcacag 39

<210> SEQ ID NO 766
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 766
cagagtgatg gcacctatgg taataagttg tgggcacag 39

<210> SEQ ID NO 767
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 767
cagagtgatg gcacctatat tcatctgtct tcggcacag 39

<210> SEQ ID NO 768
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 768
cagagtgatg gcacctattc gacgagtggg tgggcacag 39

<210> SEQ ID NO 769
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 769
cagagtgatg gcgtgcatcc tgggctttcg agtgcacag 39

<210> SEQ ID NO 770
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 770
cagagtgatg gcgtggttgc gttgcttgct agtgcacag 39

<210> SEQ ID NO 771
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 771
cagagtgatg gctatgtggg tgttggtagt ttggcacag 39

<210> SEQ ID NO 772
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 772
cagagtgccc aagcacag 18

<210> SEQ ID NO 773
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 773
cagagtgcac aagcaggagc aggaagcgaa agagcacag 39

<210> SEQ ID NO 774
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 774
cagagtgcac aagaccaaaa cccaggaaga tgggcacag 39

<210> SEQ ID NO 775
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 775
cagagtgcac aagaactcac aagaccattc ctcgcacag 39

<210> SEQ ID NO 776
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 776
cagagtgcac aagaagtccc aggatacaga tgggcacag 39

<210> SEQ ID NO 777
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 777
cagagtgcac aattcccaac aaactacgac agcgcacag 39

<210> SEQ ID NO 778
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 778
cagagtgcac aattcgtcgt cggacaacaa tacgcacag 39

<210> SEQ ID NO 779
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 779
cagagtgcac aaggagcaag cccaggaaga tgggcacag 39

<210> SEQ ID NO 780
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 780
cagagtgcac aaggagaaaa cccaggaaga tgggcacag 39

<210> SEQ ID NO 781
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 781
cagagtgcac aaggaggaaa cccaggaaga tgggcacag 39

<210> SEQ ID NO 782
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 782
cagagtgcac aaggaggaag cacaggaagc aacgcacag 39

<210> SEQ ID NO 783
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 783
cagagtgcac aaggaccaac aagaccattc ctcgcacag 39

<210> SEQ ID NO 784
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 784
cagagtgcac aaggaagaga cggatgggca gcagcacag 39

<210> SEQ ID NO 785
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 785
cagagtgcac aaggaagaat gacagacagc caagcacag 39

<210> SEQ ID NO 786
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 786
cagagtgcac aaggaagcga cgtcggaaga tgggcacag 39

<210> SEQ ID NO 787

<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 787
cagagtgcac aaggaagcaa cccaggaaga tgggcacag 39

<210> SEQ ID NO 788
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 788
cagagtgcac aaggaagcaa cagcccacaa gtcgcacag 39

<210> SEQ ID NO 789
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 789
cagagtgcac aaggaagctg gaacccacca gcagcacag 39

<210> SEQ ID NO 790
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 790
cagagtgcac aaggaacatg gaacccacca gcagcacag 39

<210> SEQ ID NO 791
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 791
cagagtgcac aaggagtctt catcccacca aaagcacag 39

<210> SEQ ID NO 792
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 792
cagagtgcac aacacgtcaa cgcaagccaa agcgcacag 39

<210> SEQ ID NO 793
<211> LENGTH: 39

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
cagagtgcac aaatcaaagc aggatgggca caagcacag 39

<210> SEQ ID NO 794
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
cagagtgcac aaatcatgag cggatacgca caagcacag 39

<210> SEQ ID NO 795
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
cagagtgcac aaaaaagcgt cggaagcgtc tacgcacag 39

<210> SEQ ID NO 796
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
cagagtgcac aactcgaaca cggattcgca caagcacag 39

<210> SEQ ID NO 797
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
cagagtgcac aactcggagg agtcctcagc gcagcacag 39

<210> SEQ ID NO 798
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
cagagtgcac aactcggact cagccaagga agagcacag 39

<210> SEQ ID NO 799
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 799
cagagtgcac aactcggata cggattcgca caagcacag 39

<210> SEQ ID NO 800
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 800
cagagtgcac aactcaaata cggactcgca caagcacag 39

<210> SEQ ID NO 801
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 801
cagagtgcac aactcagaat cggattcgca caagcacag 39

<210> SEQ ID NO 802
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 802
cagagtgcac aactcagaat gggatacagc caagcacag 39

<210> SEQ ID NO 803
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 803
cagagtgcac aactcagaca aggatacgca caagcacag 39

<210> SEQ ID NO 804
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 804
cagagtgcac aactcagagt cggattcgca caagcacag 39

<210> SEQ ID NO 805
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 805
cagagtgcac aactcagctg cagaagccaa atggcacag 39

<210> SEQ ID NO 806
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 806
cagagtgcac aactcacata cagccaaagc ctcgcacag 39

<210> SEQ ID NO 807
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 807
cagagtgcac aactctacaa aggatacagc caagcacag 39

<210> SEQ ID NO 808
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 808
cagagtgcac aaatgccaca aagaccattc ctcgcacag 39

<210> SEQ ID NO 809
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 809
cagagtgcac aaaacggaaa cccaggaaga tgggcacag 39

<210> SEQ ID NO 810
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 810
cagagtgcac aaccagaagg aagcgcaaga tgggcacag 39

<210> SEQ ID NO 811
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 811
cagagtgcac aaccactcgc agtctacgga gcagcacag 39

<210> SEQ ID NO 812
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
cagagtgcac aaccacaaag cagcagcatg agcgcacag 39

<210> SEQ ID NO 813
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
cagagtgcac aaccaagcgt cggaggatac tgggcacag 39

<210> SEQ ID NO 814
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
cagagtgcac aacaagcagt cggacaaagc tgggcacag 39

<210> SEQ ID NO 815
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
cagagtgcac aacaaagaag cctcgcaagc ggagcacag 39

<210> SEQ ID NO 816
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
cagagtgcac aacaagtcat gaacagccaa ggagcacag 39

<210> SEQ ID NO 817
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 817
cagagtgcac aaagaggagt cggactcagc caagcacag 39

<210> SEQ ID NO 818
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 818
cagagtgcac aaagacacga cgcagaagga agcgcacag 39

<210> SEQ ID NO 819
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 819
cagagtgcac aaagaaaagg agaaccacac tacgcacag 39

<210> SEQ ID NO 820
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 820
cagagtgcac aaagatacac aggagacagc agcgcacag 39

<210> SEQ ID NO 821
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 821
cagagtgcac aaagcgcaat ggcagcaaaa ggagcacag 39

<210> SEQ ID NO 822
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 822
cagagtgcac aaagcggagg actcacagga agcgcacag 39

<210> SEQ ID NO 823
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 823
cagagtgcac aaagcggagg agtcggacaa gtcgcacag 39

<210> SEQ ID NO 824
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 824
cagagtgcac aaagcctcgc aacaccattc agagcacag 39

<210> SEQ ID NO 825
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 825
cagagtgcac aaagcatgag cagaccattc ctcgcacag 39

<210> SEQ ID NO 826
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 826
cagagtgcac aaagccaact cagaccattc ctcgcacag 39

<210> SEQ ID NO 827
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 827
cagagtgcac aaagcgtcgc aaaaccattc ctcgcacag 39

<210> SEQ ID NO 828
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 828
cagagtgcac aaagcgtcag ccaaccattc agagcacag 39

<210> SEQ ID NO 829
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 829
cagagtgcac aaagcgtcgt cagaccattc ctcgcacag 39

<210> SEQ ID NO 830
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 830
cagagtgcac aaacagcact cagcagcagc acagcacag 39

<210> SEQ ID NO 831
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 831
cagagtgcac aaacagaaat gggaggaaga tgcgcacag 39

<210> SEQ ID NO 832
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 832
cagagtgcac aaacaggatt cgcaccacca agagcacag 39

<210> SEQ ID NO 833
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 833
cagagtgcac aaacaatcag aggatacagc agcgcacag 39

<210> SEQ ID NO 834
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 834
cagagtgcac aaacaatcag caactaccac acagcacag 39

<210> SEQ ID NO 835
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 835
cagagtgcac aaacactcgc aagaccattc gtcgcacag 39

<210> SEQ ID NO 836
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 836
cagagtgcac aaacactcgc agtcccattc aaagcacag 39

<210> SEQ ID NO 837
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 837
cagagtgcac aaacaccaga cagaccatgg ctcgcacag 39

<210> SEQ ID NO 838
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 838
cagagtgcac aaacaagagc aggatacgca caagcacag 39

<210> SEQ ID NO 839
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 839
cagagtgcac aaacaagagc aggatacagc caagcacag 39

<210> SEQ ID NO 840
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 840
cagagtgcac aaacaagaga atacctcctc ggagcacag 39

<210> SEQ ID NO 841
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 841
cagagtgcac aaacaagcgc aaaaccattc ctcgcacag 39

<210> SEQ ID NO 842
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 842
cagagtgcac aaacaagcgc aagaccattc ctcgcacag 39

<210> SEQ ID NO 843
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 843
cagagtgcac aaacaacaga cagaccattc ctcgcacag 39

<210> SEQ ID NO 844
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 844
cagagtgcac aaacaacaga aaaaccatgg ctcgcacag 39

<210> SEQ ID NO 845
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 845
cagagtgcac aaacagtcgc aagaccattc tacgcacag 39

<210> SEQ ID NO 846
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 846
cagagtgcac aaacagtcgc aacaccattc agagcacag 39

<210> SEQ ID NO 847
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 847
cagagtgcac aaacagtcac acaactcttc aaagcacag 39

<210> SEQ ID NO 848
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 848
cagagtgcac aagtccacgt cggaagcgtc tacgcacag 39

<210> SEQ ID NO 849
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 849
cagagtgcac aagtcctcgc aggatacaac atggcacag 39

<210> SEQ ID NO 850
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 850
cagagtgcac aagtcagcga agcaagagtc agagcacag 39

<210> SEQ ID NO 851
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 851
cagagtgcac aagtcgtcgt cggatacagc caagcacag 39

<210> SEQ ID NO 852
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 852
cagagtgcac aatgggcagc aggatacaac gtcgcacag 39

<210> SEQ ID NO 853
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 853
cagagtgcac aatgggaact cagcaacgga tacgcacag 39

<210> SEQ ID NO 854
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 854
cagagtgcac aatgggaagt caaaggagga tacgcacag 39

<210> SEQ ID NO 855
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 855
cagagtgcac aatgggaagt caaaagagga tacgcacag 39

<210> SEQ ID NO 856
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 856
cagagtgcac aatgggaagt ccaaagcgga ttcgcacag 39

<210> SEQ ID NO 857
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 857
cagagtgcac aatgggaagt cagaggagga tacgcacag 39

<210> SEQ ID NO 858
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 858
cagagtgcac aatgggaagt cacaagcgga tgggcacag 39

<210> SEQ ID NO 859
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 859
cagagtgcac aatggggagc accaagccac ggagcacag 39

<210> SEQ ID NO 860
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 860
cagagtgcac aatggatgga actcggaagc agcgcacag 39

<210> SEQ ID NO 861
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 861
cagagtgcac aatggatgtt cggaggaagc ggagcacag 39

<210> SEQ ID NO 862
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 862
cagagtgcac aatggatgct cggaggagca caagcacag 39

<210> SEQ ID NO 863
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 863
cagagtgcac aatggccaac agcatacgac gcagcacag 39

<210> SEQ ID NO 864
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 864
cagagtgcac aatggccaac aagctacgac gcagcacag 39

<210> SEQ ID NO 865
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 865
cagagtgcac aatggcaagt ccaaacagga ttcgcacag 39

<210> SEQ ID NO 866

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866

cagagtgcac aatggagcac agaaggagga tacgcacag                          39


<210> SEQ ID NO 867
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867

cagagtgcac aatggacagc agcaggagga tacgcacag                          39


<210> SEQ ID NO 868
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868

cagagtgcac aatggacaac agaaagcgga tacgcacag                          39


<210> SEQ ID NO 869
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869

cagagtgcac aatgggtcta cggaagcagc cacgcacag                          39


<210> SEQ ID NO 870
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870

cagagtgcac aatacctcgc aggatacaca gtcgcacag                          39


<210> SEQ ID NO 871
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871

cagagtgcac aatacctcaa aggatacagc gtcgcacag                          39


<210> SEQ ID NO 872
<211> LENGTH: 39
```

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 872
cagagtgcac aatacctcag cggatacaac acagcacag 39

<210> SEQ ID NO 873
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 873
cagagtgacg gagcagcagc aacaacagga tgggcacag 39

<210> SEQ ID NO 874
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 874
cagagtgacg gagcaggagg aacaagcgga tgggcacag 39

<210> SEQ ID NO 875
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 875
cagagtgacg gagcaggaac aacaagcgga tgggcacag 39

<210> SEQ ID NO 876
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 876
cagagtgacg gagcacacgg actcagcgga tgggcacag 39

<210> SEQ ID NO 877
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 877
cagagtgacg gagcacacgt cggactcagc agcgcacag 39

<210> SEQ ID NO 878
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 878
cagagtgacg gagcaagaac agtcctccaa ctcgcacag 39

<210> SEQ ID NO 879
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 879
cagagtgacg gagaatacca aaaaccattc agagcacag 39

<210> SEQ ID NO 880
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 880
cagagtgacg gaggaggaac aacaacagga tgggcacag 39

<210> SEQ ID NO 881
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 881
cagagtgacg gacacgcaac aagcatggga tgggcacag 39

<210> SEQ ID NO 882
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 882
cagagtgacg gaaaaggaag cacacaagga tgggcacag 39

<210> SEQ ID NO 883
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 883
cagagtgacg gaaaacaata ccaactcagc agcgcacag 39

<210> SEQ ID NO 884
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
cagagtgacg gaaacggagg actcaaagga tgggcacag 39

<210> SEQ ID NO 885
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
cagagtgacg gacaaggagg actcagcgga tgggcacag 39

<210> SEQ ID NO 886
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886
cagagtgacg gacaacactt cgcaccacca agagcacag 39

<210> SEQ ID NO 887
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
cagagtgacg gaagagcaac aaaaacactc tacgcacag 39

<210> SEQ ID NO 888
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
cagagtgacg gaagaaacgc actcacagga tgggcacag 39

<210> SEQ ID NO 889
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
cagagtgacg gaagaagaca agtcatccaa ctcgcacag 39

<210> SEQ ID NO 890
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 890
cagagtgacg gaagagtcta cggactcagc agcgcacag 39

<210> SEQ ID NO 891
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
cagagtgacg gaagcggaag aacaacagga tgggcacag 39

<210> SEQ ID NO 892
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
cagagtgacg gaagcggaac aacaagagga tgggcacag 39

<210> SEQ ID NO 893
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
cagagtgacg gaagcggaac agtcagcgga tgggcacag 39

<210> SEQ ID NO 894
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
cagagtgacg gaagcccaga aaaaccattc agagcacag 39

<210> SEQ ID NO 895
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
cagagtgacg gaagccaaag cacaacagga tgggcacag 39

<210> SEQ ID NO 896
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 896
cagagtgacg gaagcagctt ctacccacca aaagcacag 39

<210> SEQ ID NO 897
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 897
cagagtgacg gaagcagcag ctactacgac gcagcacag 39

<210> SEQ ID NO 898
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 898
cagagtgacg gaagcacaga aagaccattc agagcacag 39

<210> SEQ ID NO 899
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 899
cagagtgacg gaacagcagc aagactcagc agcgcacag 39

<210> SEQ ID NO 900
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 900
cagagtgacg gaacagcaga caaaccattc agagcacag 39

<210> SEQ ID NO 901
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 901
cagagtgacg gaacagcaga cagaccattc agagcacag 39

<210> SEQ ID NO 902
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 902
cagagtgacg gaacagcaga aagaccattc agagcacag 39

<210> SEQ ID NO 903
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 903
cagagtgacg gaacagcaat ccacctcagc agcgcacag 39

<210> SEQ ID NO 904
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 904
cagagtgacg gaacagcaat ctacctcagc agcgcacag 39

<210> SEQ ID NO 905
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 905
cagagtgacg gaacagcact catgctcagc agcgcacag 39

<210> SEQ ID NO 906
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 906
cagagtgacg gaacagcaag catcagcgga tgggcacag 39

<210> SEQ ID NO 907
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 907
cagagtgacg gaacagcaag cacaagcgga tgggcacag 39

<210> SEQ ID NO 908
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 908
cagagtgacg gaacagcaag cgtcacagga tgggcacag 39

<210> SEQ ID NO 909
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 909
cagagtgacg gaacagcaag ctactacgac agcgcacag 39

<210> SEQ ID NO 910
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 910
cagagtgacg gaacagcaac aacaatggga tgggcacag 39

<210> SEQ ID NO 911
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 911
cagagtgacg gaacagcaac aacaacagga tgggcacag 39

<210> SEQ ID NO 912
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 912
cagagtgacg gaacagcata cagactcagc agcgcacag 39

<210> SEQ ID NO 913
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 913
cagagtgacg gaacagacaa aatgtggagc atcgcacag 39

<210> SEQ ID NO 914
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 914
cagagtgacg gaacaggagg aatcaaagga tgggcacag 39

<210> SEQ ID NO 915
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 915
cagagtgacg gaacaggagg aatcatggga tgggcacag 39

<210> SEQ ID NO 916
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 916
cagagtgacg gaacaggagg aatcagcgga tgggcacag 39

<210> SEQ ID NO 917
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 917
cagagtgacg gaacaggagg actcgcagga tgggcacag 39

<210> SEQ ID NO 918
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 918
cagagtgacg gaacaggagg actccacgga tgggcacag 39

<210> SEQ ID NO 919
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 919
cagagtgacg gaacaggagg actccaagga tgggcacag 39

<210> SEQ ID NO 920
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 920
cagagtgacg gaacaggagg actcagagga tgggcacag 39

<210> SEQ ID NO 921
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 921
cagagtgacg gaacaggagg actcagcgga tgggcacag 39

<210> SEQ ID NO 922
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 922
cagagtgacg gaacaggagg actcacagga tgggcacag 39

<210> SEQ ID NO 923
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 923
cagagtgacg gaacaggagg aacaaaagga tgggcacag 39

<210> SEQ ID NO 924
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 924
cagagtgacg gaacaggagg aacaagcgga tgggcacag 39

<210> SEQ ID NO 925
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 925
cagagtgacg gaacaggagg agtccacgga tgggcacag 39

<210> SEQ ID NO 926
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 926
cagagtgacg gaacaggagg agtcatggga tgggcacag 39

<210> SEQ ID NO 927
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 927
cagagtgacg gaacaggagg agtcagcgga tgggcacag 39

<210> SEQ ID NO 928
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 928
cagagtgacg gaacaggagg agtcacagga tgggcacag 39

<210> SEQ ID NO 929
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 929
cagagtgacg gaacaggagg agtctacgga tgggcacag 39

<210> SEQ ID NO 930
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 930
cagagtgacg gaacaggaaa cctccaagga tgggcacag 39

<210> SEQ ID NO 931
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 931
cagagtgacg gaacaggaaa cctcagagga tgggcacag 39

<210> SEQ ID NO 932
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 932
cagagtgacg gaacaggaaa cctcagcgga tgggcacag 39

<210> SEQ ID NO 933
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 933
cagagtgacg gaacaggaaa cacacacgga tgggcacag 39

<210> SEQ ID NO 934
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 934
cagagtgacg gaacaggaaa cacaagagga tgggcacag 39

<210> SEQ ID NO 935
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 935
cagagtgacg gaacaggaaa cacaagcgga tgggcacag 39

<210> SEQ ID NO 936
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 936
cagagtgacg gaacaggaaa cgtcagcgga tgggcacag 39

<210> SEQ ID NO 937
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 937
cagagtgacg gaacaggaaa cgtcacagga tgggcacag 39

<210> SEQ ID NO 938
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 938
cagagtgacg gaacaggaca actcgtcgga tgggcacag 39

<210> SEQ ID NO 939
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 939
cagagtgacg gaacaggaca aacaatcgga tgggcacag 39

<210> SEQ ID NO 940
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 940
cagagtgacg gaacaggaca agtcacagga tgggcacag 39

<210> SEQ ID NO 941
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 941
cagagtgacg gaacaggaag actcacagga tgggcacag 39

<210> SEQ ID NO 942
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 942
cagagtgacg gaacaggaag aacagtcgga tgggcacag 39

<210> SEQ ID NO 943
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 943
cagagtgacg gaacaggaag cggaatgatg acagcacag 39

<210> SEQ ID NO 944
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 944
cagagtgacg gaacaggaag catcagcgga tgggcacag 39

<210> SEQ ID NO 945

<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
cagagtgacg gaacaggaag cctcgcagga tgggcacag 39

<210> SEQ ID NO 946
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
cagagtgacg gaacaggaag cctcaacgga tgggcacag 39

<210> SEQ ID NO 947
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
cagagtgacg gaacaggaag cctccaagga tgggcacag 39

<210> SEQ ID NO 948
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
cagagtgacg gaacaggaag cctcagcgga tgggcacag 39

<210> SEQ ID NO 949
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
cagagtgacg gaacaggaag cctcgtcgga tgggcacag 39

<210> SEQ ID NO 950
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
cagagtgacg gaacaggaag cacacacgga tgggcacag 39

<210> SEQ ID NO 951
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 951
cagagtgacg gaacaggaag cacaaaagga tgggcacag 39

<210> SEQ ID NO 952
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 952
cagagtgacg gaacaggaag cacaatggga tgggcacag 39

<210> SEQ ID NO 953
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 953
cagagtgacg gaacaggaag cacacaagga tgggcacag 39

<210> SEQ ID NO 954
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 954
cagagtgacg gaacaggaag cacaagcgga tgggcacag 39

<210> SEQ ID NO 955
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 955
cagagtgacg gaacaggaag cacaacagga tgggcacag 39

<210> SEQ ID NO 956
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 956
cagagtgacg gaacaggaag cgtcatggga tgggcacag 39

<210> SEQ ID NO 957
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 957
cagagtgacg gaacaggaag cgtcacagga tgggcacag 39

<210> SEQ ID NO 958
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 958
cagagtgacg gaacaggaac actcgcagga tgggcacag 39

<210> SEQ ID NO 959
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 959
cagagtgacg gaacaggaac actccacgga tgggcacag 39

<210> SEQ ID NO 960
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 960
cagagtgacg gaacaggaac actcaaagga tgggcacag 39

<210> SEQ ID NO 961
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 961
cagagtgacg gaacaggaac actcagcgga tgggcacag 39

<210> SEQ ID NO 962
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 962
cagagtgacg gaacaggaac aacactcgga tgggcacag 39

<210> SEQ ID NO 963
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 963
cagagtgacg gaacaggaac aacaatggga tgggcacag 39

<210> SEQ ID NO 964
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 964
cagagtgacg gaacaggaac aacaacagga tgggcacag 39

<210> SEQ ID NO 965
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 965
cagagtgacg gaacaggaac aacagtcgga tgggcacag 39

<210> SEQ ID NO 966
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 966
cagagtgacg gaacaggaac aacatacgga tgggcacag 39

<210> SEQ ID NO 967
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 967
cagagtgacg gaacaggaac agtccacgga tgggcacag 39

<210> SEQ ID NO 968
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 968
cagagtgacg gaacaggaac agtccaagga tgggcacag 39

<210> SEQ ID NO 969
<211> LENGTH: 39
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 969
cagagtgacg gaacaggaac agtcagcgga tgggcacag 39

<210> SEQ ID NO 970
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 970
cagagtgacg gaacaggaac agtcacagga tgggcacag 39

<210> SEQ ID NO 971
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 971
cagagtgacg gaacacacgc aagactcagc agcgcacag 39

<210> SEQ ID NO 972
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 972
cagagtgacg gaacacacgc atacatggca agcgcacag 39

<210> SEQ ID NO 973
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 973
cagagtgacg gaacacactt cgcaccacca agagcacag 39

<210> SEQ ID NO 974
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 974
cagagtgacg gaacacacat ccacctcagc agcgcacag 39

<210> SEQ ID NO 975
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 975
cagagtgacg gaacacacat cagagcactc agcgcacag 39

<210> SEQ ID NO 976
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 976
cagagtgacg gaacacacat cagactcgca agcgcacag 39

<210> SEQ ID NO 977
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 977
cagagtgacg gaacacacct ccaaccattc agagcacag 39

<210> SEQ ID NO 978
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 978
cagagtgacg gaacacacag cttctacgac gcagcacag 39

<210> SEQ ID NO 979
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 979
cagagtgacg gaacacacag cacaacagga tgggcacag 39

<210> SEQ ID NO 980
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 980
cagagtgacg gaacacacac aagaacagga tgggcacag 39

<210> SEQ ID NO 981
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 981
cagagtgacg gaacacacgt cagagcactc agcgcacag 39

<210> SEQ ID NO 982
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 982
cagagtgacg gaacacacgt ctacatggca agcgcacag 39

<210> SEQ ID NO 983
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 983
cagagtgacg gaacacacgt ctacatgagc agcgcacag 39

<210> SEQ ID NO 984
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 984
cagagtgacg gaacaatcgc actcccattc aaagcacag 39

<210> SEQ ID NO 985
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 985
cagagtgacg gaacaatcgc actcccattc agagcacag 39

<210> SEQ ID NO 986
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 986
cagagtgacg gaacaatcgc aacaagatac gtcgcacag 39

<210> SEQ ID NO 987
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 987
cagagtgacg gaacaatcga aagaccattc agagcacag 39

<210> SEQ ID NO 988
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 988
cagagtgacg gaacaatcgg atacgcatac gtcgcacag 39

<210> SEQ ID NO 989
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 989
cagagtgacg gaacaatcca agcaccattc aaagcacag 39

<210> SEQ ID NO 990
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 990
cagagtgacg gaacaatcag actcccattc aaagcacag 39

<210> SEQ ID NO 991
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 991
cagagtgacg gaacaatcag caaagaagtc ggagcacag 39

<210> SEQ ID NO 992
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 992
cagagtgacg gaacaatcag ccaaccattc aaagcacag 39

<210> SEQ ID NO 993
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 993
cagagtgacg gaacaaaaat ccaactcagc agcgcacag 39

<210> SEQ ID NO 994
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 994
cagagtgacg gaacaaaaat cagactcagc agcgcacag 39

<210> SEQ ID NO 995
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 995
cagagtgacg gaacaaaact catgctcagc agcgcacag 39

<210> SEQ ID NO 996
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 996
cagagtgacg gaacaaaact cagactcagc agcgcacag 39

<210> SEQ ID NO 997
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 997
cagagtgacg gaacaaaaat ggtcctccaa ctcgcacag 39

<210> SEQ ID NO 998
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 998
cagagtgacg gaacaaaaag cctcgtccaa ctcgcacag 39

<210> SEQ ID NO 999
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 999
cagagtgacg gaacaaaagt cctcgtccaa ctcgcacag 39

<210> SEQ ID NO 1000
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1000
cagagtgacg gaacactcgc agcaccattc aaagcacag 39

<210> SEQ ID NO 1001
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1001
cagagtgacg gaacactcgc agtcaacttc aaagcacag 39

<210> SEQ ID NO 1002
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1002
cagagtgacg gaacactcgc agtcccattc aaagcacag 39

<210> SEQ ID NO 1003
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1003
cagagtgacg gaacactcgc atacccattc aaagcacag 39

<210> SEQ ID NO 1004
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1004
cagagtgacg gaacactcga aagaccattc agagcacag 39

<210> SEQ ID NO 1005
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1005
cagagtgacg gaacactcga agtccacttc aaagcacag 39

<210> SEQ ID NO 1006
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1006
cagagtgacg gaacactcct cagactcagc agcgcacag 39

<210> SEQ ID NO 1007
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1007
cagagtgacg gaacactcaa caacccattc agagcacag 39

<210> SEQ ID NO 1008
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1008
cagagtgacg gaacactcca acaaccattc agagcacag 39

<210> SEQ ID NO 1009
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1009
cagagtgacg gaacactcag ccaaccattc agagcacag 39

<210> SEQ ID NO 1010
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1010
cagagtgacg gaacactcag cagaacactc tgggcacag 39

<210> SEQ ID NO 1011
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1011
cagagtgacg gaacactcag cagcccattc agagcacag 39

<210> SEQ ID NO 1012
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1012
cagagtgacg gaacactcac agtcccattc agagcacag 39

<210> SEQ ID NO 1013
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1013
cagagtgacg gaacactcgt cgcaccattc agagcacag 39

<210> SEQ ID NO 1014
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1014
cagagtgacg gaacaatgga caaaccattc agagcacag 39

<210> SEQ ID NO 1015
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1015
cagagtgacg gaacaatgga cagaccattc aaagcacag 39

<210> SEQ ID NO 1016
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1016
cagagtgacg gaacaatgct cagactcagc agcgcacag 39

<210> SEQ ID NO 1017
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1017
cagagtgacg gaacaatgca actcacagga tgggcacag 39

<210> SEQ ID NO 1018
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1018
cagagtgacg gaacaaacgg actcaaagga tgggcacag 39

<210> SEQ ID NO 1019
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1019
cagagtgacg gaacaaacag catcagcgga tgggcacag 39

<210> SEQ ID NO 1020
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1020
cagagtgacg gaacaaacag cctcagcgga tgggcacag 39

<210> SEQ ID NO 1021
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1021
cagagtgacg gaacaaacag cacaacagga tgggcacag 39

<210> SEQ ID NO 1022
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1022
cagagtgacg gaacaaacag cgtcacagga tgggcacag 39

<210> SEQ ID NO 1023
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1023
cagagtgacg gaacaaacac aatcaacgga tgggcacag 39

<210> SEQ ID NO 1024

<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1024
cagagtgacg gaacaaacac actcggagga tgggcacag 39

<210> SEQ ID NO 1025
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1025
cagagtgacg gaacaaacac aacacacgga tgggcacag 39

<210> SEQ ID NO 1026
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1026
cagagtgacg gaacaaacta cagactcagc agcgcacag 39

<210> SEQ ID NO 1027
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1027
cagagtgacg gaacacaagc actcagcgga tgggcacag 39

<210> SEQ ID NO 1028
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1028
cagagtgacg gaacacaatt cagactcagc agcgcacag 39

<210> SEQ ID NO 1029
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1029
cagagtgacg gaacacaatt cagcccacca agagcacag 39

<210> SEQ ID NO 1030
<211> LENGTH: 39

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1030
cagagtgacg gaacacaagg actcaaagga tgggcacag 39

<210> SEQ ID NO 1031
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1031
cagagtgacg gaacacaaac aacaagcgga tgggcacag 39

<210> SEQ ID NO 1032
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1032
cagagtgacg gaacaagagc actcacagga tgggcacag 39

<210> SEQ ID NO 1033
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1033
cagagtgacg gaacaagatt cagcctcagc agcgcacag 39

<210> SEQ ID NO 1034
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1034
cagagtgacg gaacaagagg actcagcgga tgggcacag 39

<210> SEQ ID NO 1035
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1035
cagagtgacg gaacaagaat cggactcagc agcgcacag 39

<210> SEQ ID NO 1036
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 1036
cagagtgacg gaacaagact ccacctcgca agcgcacag 39

<210> SEQ ID NO 1037
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1037
cagagtgacg gaacaagact ccacctcagc agcgcacag 39

<210> SEQ ID NO 1038
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1038
cagagtgacg gaacaagact cctcctcagc agcgcacag 39

<210> SEQ ID NO 1039
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1039
cagagtgacg gaacaagact catgctcagc agcgcacag 39

<210> SEQ ID NO 1040
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1040
cagagtgacg gaacaagact caacctcagc agcgcacag 39

<210> SEQ ID NO 1041
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1041
cagagtgacg gaacaagaat ggtcgtccaa ctcgcacag 39

<210> SEQ ID NO 1042
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1042
cagagtgacg gaacaagaaa catgtacgaa ggagcacag 39

<210> SEQ ID NO 1043
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1043
cagagtgacg gaacaagaag catcacagga tgggcacag 39

<210> SEQ ID NO 1044
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1044
cagagtgacg gaacaagaag cctccacgga tgggcacag 39

<210> SEQ ID NO 1045
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1045
cagagtgacg gaacaagaag cacaacagga tgggcacag 39

<210> SEQ ID NO 1046
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1046
cagagtgacg gaacaagaac aacaacagga tgggcacag 39

<210> SEQ ID NO 1047
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1047
cagagtgacg gaacaagaac agtcacagga tgggcacag 39

<210> SEQ ID NO 1048
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 1048
cagagtgacg gaacaagaac agtcgtccaa ctcgcacag 39

<210> SEQ ID NO 1049
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1049
cagagtgacg gaacaagagt ccacctcagc agcgcacag 39

<210> SEQ ID NO 1050
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1050
cagagtgacg gaacaagctt cccatacgca agagcacag 39

<210> SEQ ID NO 1051
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1051
cagagtgacg gaacaagctt cacaccacca aaagcacag 39

<210> SEQ ID NO 1052
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1052
cagagtgacg gaacaagctt cacaccacca agagcacag 39

<210> SEQ ID NO 1053
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1053
cagagtgacg gaacaagcgg actccacgga tgggcacag 39

<210> SEQ ID NO 1054
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1054
cagagtgacg gaacaagcgg actcaaagga tgggcacag 39

<210> SEQ ID NO 1055
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1055
cagagtgacg gaacaagcat ccacctcagc agcgcacag 39

<210> SEQ ID NO 1056
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1056
cagagtgacg gaacaagcat catgctcagc agcgcacag 39

<210> SEQ ID NO 1057
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1057
cagagtgacg gaacaagcct cagactcagc agcgcacag 39

<210> SEQ ID NO 1058
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1058
cagagtgacg gaacaagcaa ctacggagca agagcacag 39

<210> SEQ ID NO 1059
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1059
cagagtgacg gaacaagcag ctactacgac gcagcacag 39

<210> SEQ ID NO 1060
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1060
cagagtgacg gaacaagcag ctactacgac agcgcacag 39

<210> SEQ ID NO 1061
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1061
cagagtgacg gaacaagcac aatcagcgga tgggcacag 39

<210> SEQ ID NO 1062
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1062
cagagtgacg gaacaagcac aatcacagga tgggcacag 39

<210> SEQ ID NO 1063
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1063
cagagtgacg gaacaagcac actccacgga tgggcacag 39

<210> SEQ ID NO 1064
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1064
cagagtgacg gaacaagcac actcagagga tgggcacag 39

<210> SEQ ID NO 1065
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1065
cagagtgacg gaacaagcac actcagcgga tgggcacag 39

<210> SEQ ID NO 1066
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1066
cagagtgacg gaacaagcta cgtcccacca aaagcacag 39

<210> SEQ ID NO 1067
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1067
cagagtgacg gaacaagcta cgtcccacca agagcacag 39

<210> SEQ ID NO 1068
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1068
cagagtgacg gaacaacagc aacatactac aaagcacag 39

<210> SEQ ID NO 1069
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1069
cagagtgacg gaacaacatt cacaccacca agagcacag 39

<210> SEQ ID NO 1070
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1070
cagagtgacg gaacaacact cgcaccattc agagcacag 39

<210> SEQ ID NO 1071
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1071
cagagtgacg gaacaacact cgtcccacca agagcacag 39

<210> SEQ ID NO 1072
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1072
cagagtgacg gaacaacaag caaaacactc tgggcacag 39

<210> SEQ ID NO 1073
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1073
cagagtgacg gaacaacaag cagaacactc tgggcacag 39

<210> SEQ ID NO 1074
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1074
cagagtgacg gaacaacaac aagaagcctc tacgcacag 39

<210> SEQ ID NO 1075
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1075
cagagtgacg gaacaacaac aacaacagga tgggcacag 39

<210> SEQ ID NO 1076
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1076
cagagtgacg gaacaacaac atacggagca agagcacag 39

<210> SEQ ID NO 1077
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1077
cagagtgacg gaacaacatg gacaccacca agagcacag 39

<210> SEQ ID NO 1078
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1078
cagagtgacg gaacaacata catgctcagc agcgcacag 39

<210> SEQ ID NO 1079
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1079
cagagtgacg gaacaacata cgtcccacca agagcacag 39

<210> SEQ ID NO 1080
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1080
cagagtgacg gaacagtcgc aaacccattc agagcacag 39

<210> SEQ ID NO 1081
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1081
cagagtgacg gaacagtcga cagaccattc aaagcacag 39

<210> SEQ ID NO 1082
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1082
cagagtgacg gaacagtcat ccacctcagc agcgcacag 39

<210> SEQ ID NO 1083
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1083
cagagtgacg gaacagtcat cctcctcagc agcgcacag 39

<210> SEQ ID NO 1084
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1084
cagagtgacg gaacagtcat catgctcagc agcgcacag 39

<210> SEQ ID NO 1085
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1085
cagagtgacg gaacagtcct ccacctcagc agcgcacag 39

<210> SEQ ID NO 1086
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1086
cagagtgacg gaacagtcct catgctcagc agcgcacag 39

<210> SEQ ID NO 1087
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1087
cagagtgacg gaacagtcct cgtcccattc agagcacag 39

<210> SEQ ID NO 1088
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1088
cagagtgacg gaacagtccc atacctcgca agcgcacag 39

<210> SEQ ID NO 1089
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1089
cagagtgacg gaacagtccc atacctcagc agcgcacag 39

<210> SEQ ID NO 1090
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1090
cagagtgacg gaacagtcag agtcccattc agagcacag 39

<210> SEQ ID NO 1091
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1091
cagagtgacg gaacagtcag catgccattc aaagcacag 39

<210> SEQ ID NO 1092
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
cagagtgacg gaacagtcag caacccattc agagcacag 39

<210> SEQ ID NO 1093
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1093
cagagtgacg gaacagtcag cacaagatgg gtcgcacag 39

<210> SEQ ID NO 1094
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1094
cagagtgacg gaacagtcac aacaacagga tgggcacag 39

<210> SEQ ID NO 1095
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1095
cagagtgacg gaacagtcac agtcacagga tgggcacag 39

<210> SEQ ID NO 1096
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1096
cagagtgacg gaacagtctg ggtcccacca agagcacag 39

<210> SEQ ID NO 1097
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1097
cagagtgacg gaacagtcta cagactcagc agcgcacag 39

<210> SEQ ID NO 1098
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1098
cagagtgacg gaacatacgc aagactcagc agcgcacag 39

<210> SEQ ID NO 1099
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1099
cagagtgacg gaacatacgg aaacaaactc tgggcacag 39

<210> SEQ ID NO 1100
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1100
cagagtgacg gaacatacat ccacctcagc agcgcacag 39

<210> SEQ ID NO 1101
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1101
cagagtgacg gaacatacag cacaagcgga tgggcacag 39

<210> SEQ ID NO 1102
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1102
cagagtgacg gagtccaccc aggactcagc agcgcacag 39

<210> SEQ ID NO 1103

<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1103
cagagtgacg gagtcgtcgc actcctcgca agcgcacag 39

<210> SEQ ID NO 1104
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1104
cagagtgacg gatacgtcgg agtcggaagc ctcgcacag 39

<210> SEQ ID NO 1105
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1105
gcccaaggtt cgtggaatcc gccggcg 27

<210> SEQ ID NO 1106
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1106
gcccaaaatg gtaatccggg gcggtgg 27

<210> SEQ ID NO 1107
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1107
gcccaaacga ctgagaagcc gtggctg 27

<210> SEQ ID NO 1108
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1108
gatggcacgg cggatcgtcc ttttcgg 27

<210> SEQ ID NO 1109
<211> LENGTH: 27

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1109
gatggcacca tttcgcagcc ttttaag 27

<210> SEQ ID NO 1110
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1110
gatggcacct tggctgctcc ttttaag 27

<210> SEQ ID NO 1111
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1111
gatggcacct tgcagcagcc gtttcgg 27

<210> SEQ ID NO 1112
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1112
gatggcaccc tgtctcagcc ttttagg 27

<210> SEQ ID NO 1113
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1113
gatggcacca tggataggcc gtttaag 27

<210> SEQ ID NO 1114
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1114
gatggcaccc gtactacgac gggttgg 27

<210> SEQ ID NO 1115
<211> LENGTH: 27
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 1115
gatggcacca cttttactcc tcctcgg 27

<210> SEQ ID NO 1116
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1116
gatggcacca cgtatgttcc tccgcgg 27

<210> SEQ ID NO 1117
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1117
gcccaagggg agaatccggg taggtgg 27

<210> SEQ ID NO 1118
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1118
gcccaaggta cttggaatcc gccggct 27

<210> SEQ ID NO 1119
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1119
gcccaaacta ctgataggcc ttttttg 27

<210> SEQ ID NO 1120
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1120
gatggcaccg ctgataagcc gtttcgg 27

<210> SEQ ID NO 1121
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1121
gatggcaccg cggagaggcc ttttagg 27

<210> SEQ ID NO 1122
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1122
gatggcaccg gtggtattaa ggggtgg 27

<210> SEQ ID NO 1123
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1123
gatggcaccg ggaatactcg ggggtgg 27

<210> SEQ ID NO 1124
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1124
gatggcaccc atacgcggac gggttgg 27

<210> SEQ ID NO 1125
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1125
gatggcacca ttgagcggcc ttttcgt 27

<210> SEQ ID NO 1126
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1126
gatggcacct tgaataatcc gtttagg 27

<210> SEQ ID NO 1127
<211> LENGTH: 27
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 1127
gatggcacca atggtctgaa ggggtgg 27

<210> SEQ ID NO 1128
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
gatggcacct cgtttacgcc gcctaag 27

<210> SEQ ID NO 1129
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
gatggcacct cgtttactcc gccgcgg 27

<210> SEQ ID NO 1130
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
gatggcacca ctacgtatgg ggctcgt 27

<210> SEQ ID NO 1131
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
gatggcacca cttggacgcc gccgcgt 27

<210> SEQ ID NO 1132
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
gatggcacca gttatgttcc tccgagg 27

<210> SEQ ID NO 1133
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1133
gcccaatttc ctacgaatta tgattct 27

<210> SEQ ID NO 1134
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1134
gcccaacctg agggtagtgc gaggtgg 27

<210> SEQ ID NO 1135
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1135
gcccaatggc ctacgagtta tgatgct 27

<210> SEQ ID NO 1136
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1136
gatggcaccg cgattcatct ttcgtct 27

<210> SEQ ID NO 1137
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1137
gatggcaccg ggcaggtgac tgggtgg 27

<210> SEQ ID NO 1138
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1138
gatggcacga tggataagcc ttttagg 27

<210> SEQ ID NO 1139
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1139
gatggcacct cgagttatta tgattct 27

<210> SEQ ID NO 1140
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1140
gatggcagta gttcttatta tgatgcg 27

<210> SEQ ID NO 1141
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1141
gatggcaccg cgagttatta tgattct 27

<210> SEQ ID NO 1142
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1142
gatggcaccg gtaatgtgac ggggtgg 27

<210> SEQ ID NO 1143
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1143
gcacaaggaa gctggaaccc accagca 27

<210> SEQ ID NO 1144
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1144
gcacaaaacg gaaacccagg aagatgg 27

<210> SEQ ID NO 1145
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1145
gcacaaacaa cagaaaaacc atggctc 27

<210> SEQ ID NO 1146
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1146
gacggaacag cagacagacc attcaga 27

<210> SEQ ID NO 1147
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1147
gacggaacaa tcagccaacc attcaaa 27

<210> SEQ ID NO 1148
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1148
gacggaacac tcgcagcacc attcaaa 27

<210> SEQ ID NO 1149
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1149
gacggaacac tccaacaacc attcaga 27

<210> SEQ ID NO 1150
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1150
gacggaacac tcagccaacc attcaga 27

<210> SEQ ID NO 1151
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1151
gacggaacaa tggacagacc attcaaa 27

<210> SEQ ID NO 1152
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1152
gacggaacaa gaacaacaac aggatgg 27

<210> SEQ ID NO 1153
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1153
gacggaacaa cattcacacc accaaga 27

<210> SEQ ID NO 1154
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1154
gacggaacaa catacgtccc accaaga 27

<210> SEQ ID NO 1155
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1155
gcacaaggag aaaacccagg aagatgg 27

<210> SEQ ID NO 1156
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1156
gcacaaggaa catggaaccc accagca 27

<210> SEQ ID NO 1157
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1157
gcacaaacaa cagacagacc attcctc 27

<210> SEQ ID NO 1158
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1158
gacggaacag cagacaaacc attcaga 27

<210> SEQ ID NO 1159
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1159
gacggaacag cagaaagacc attcaga 27

<210> SEQ ID NO 1160
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1160
gacggaacag gaggaatcaa aggatgg 27

<210> SEQ ID NO 1161
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1161
gacggaacag gaaacacaag aggatgg 27

<210> SEQ ID NO 1162
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1162
gacggaacac acacaagaac aggatgg 27

<210> SEQ ID NO 1163
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1163
gacggaacaa tcgaaagacc attcaga 27

<210> SEQ ID NO 1164
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1164
gacggaacac tcaacaaccc attcaga 27

<210> SEQ ID NO 1165
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1165
gacggaacaa acggactcaa aggatgg 27

<210> SEQ ID NO 1166
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1166
gacggaacaa gcttcacacc accaaaa 27

<210> SEQ ID NO 1167
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1167
gacggaacaa gcttcacacc accaaga 27

<210> SEQ ID NO 1168
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1168
gacggaacaa caacatacgg agcaaga 27

<210> SEQ ID NO 1169
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1169
gacggaacaa catggacacc accaaga 27

<210> SEQ ID NO 1170
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1170
gacggaacaa gctacgtccc accaaga 27

<210> SEQ ID NO 1171
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1171
gcacaattcc caacaaacta cgacagc 27

<210> SEQ ID NO 1172
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1172
gcacaaccag aaggaagcgc aagatgg 27

<210> SEQ ID NO 1173
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1173
gcacaatggc caacaagcta cgacgca 27

<210> SEQ ID NO 1174
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1174
gacggaacag caatccacct cagcagc 27

<210> SEQ ID NO 1175
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1175
gacggaacag gacaagtcac aggatgg 27

<210> SEQ ID NO 1176
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1176
gacggaacaa tggacaaacc attcaga 27

<210> SEQ ID NO 1177
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1177
gacggaacaa gcagctacta cgacagc 27

<210> SEQ ID NO 1178
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1178
gacggaagca gcagctacta cgacgca 27

<210> SEQ ID NO 1179
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1179
gacggaacag caagctacta cgacagc 27

<210> SEQ ID NO 1180
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1180
gacggaacag gaaacgtcac aggatgg 27

<210> SEQ ID NO 1181
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (9)..(9)

<223> OTHER INFORMATION: Lys or Arg

<400> SEQUENCE: 1181

Asp Gly Thr Xaa Xaa Xaa Pro Phe Xaa
1 5

<210> SEQ ID NO 1182
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (9)..(9)
<223> OTHER INFORMATION: Ser or Ala

<400> SEQUENCE: 1182

Asp Gly Thr Xaa Xaa Xaa Tyr Asp Xaa
1 5

<210> SEQ ID NO 1183
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(7)
<223> OTHER INFORMATION: Any amino acid

<400> SEQUENCE: 1183

Asp Gly Thr Xaa Xaa Xaa Xaa Gly Trp
1 5

<210> SEQ ID NO 1184
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (9)..(9)
<223> OTHER INFORMATION: Arg or Lys

<400> SEQUENCE: 1184

Cys Gly Thr Xaa Xaa Xaa Pro Pro Xaa
1 5

<210> SEQ ID NO 1185
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES -continued

```
<222> LOCATION: (4)..(6)
<223> OTHER INFORMATION: Any amino acid

<400> SEQUENCE: 1185

Asp Gly Thr Xaa Xaa Xaa Pro Phe Arg
1               5
```